US008852861B2

(12) United States Patent
Ried et al.

(10) Patent No.: US 8,852,861 B2
(45) Date of Patent: Oct. 7, 2014

(54) COMPOSITION FOR DETECTING THE RESPONSE OF RECTAL ADENOCARCINOMAS TO RADIOCHEMOTHERAPY

(75) Inventors: Thomas Ried, Bethesda, MD (US); Michael J. Difilippantonio, Rockville, MD (US); Bijan-Michael Ghadimi, Bethesda, MD (US); Marian Grade, Goettingen (DE); Heinz Becker, Goettingen (DE); Torsten Liersch, Goettingen (DE)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 956 days.

(21) Appl. No.: 10/585,725

(22) PCT Filed: Jan. 12, 2005

(86) PCT No.: PCT/US2005/000891

§ 371 (c)(1), (2), (4) Date: Jul. 12, 2006

(87) PCT Pub. No.: WO2005/073411

PCT Pub. Date: Aug. 11, 2005

(65) Prior Publication Data

US 2008/0020373 A1 Jan. 24, 2008

Related U.S. Application Data

(60) Provisional application No. 60/535,491, filed on Jan. 12, 2004.

(51) Int. Cl.
*C12Q 1/68* (2006.01)
*C12N 15/01* (2006.01)

(52) U.S. Cl.
CPC ........ *C12Q 1/6886* (2013.01); *C12Q 2600/136* (2013.01); *C12Q 2600/106* (2013.01)
USPC ......... 435/6.1; 435/6.11; 435/6.12; 435/6.14; 435/442

(58) Field of Classification Search
None
See application file for complete search history.

(56) References Cited

FOREIGN PATENT DOCUMENTS

WO WO 03/053223 A 7/2003

OTHER PUBLICATIONS

Tockman et al (Cancer Res., 1992, 52:2711s-2718s).*
Drexler et al (Leukemia and Lymphoma, 1993, 9:1-25).*
Zellner et al (Clin. Can. Res., 1998, 4:1797-1802).*
Embleton et al (Immunol Ser, 1984, 23:181-207).*
Jiang et al (J. Biol. Chem. 2003, 278(7) 4763-4769).*
Matsushita et al (FEBS Letters, 1999, vol. 443, pp. 348-352).*
Singh et al (Glycobiology, 2001, vol. 11, pp. 587-592).*
Greenbaum et al. (Genome Biology, 2003, vol. 4, Issue 9, pp. 117.1-117.8).*
Brennan et al. (J. Autoimmunity, 1989, 2 (suppl.): 177-186).*
Zimmer (Cell Motility and the Cytoskeleton, 1991. 20:325-337).*
Hell et al. (Laboratory Investigation, 1995, 73: 492-496).*
Fu et al. (EMBO J., 1996, 15:43982-4401).*
Ginestier et al. (Amer. J. Path. Oct. 2002 161: 1223-1333).*
Ishisaki et al. (Genomics 2001 74:172-179).*
Hansson et al. (Curr. Diab. Rep. 2010 10: 444-451).*
,Le Bacquer et al. (Human Mol. Gen. 2011 20(10): 1906-1915).*
Clarke, Paul A. et al., "Molecular pharmacology of cancer therapy in human colorectal cancer by gene expression profiling," Cancer Research, Oct. 15, 2003, pp. 6855-6863, vol. 63, No. 20.
Esposito, G. et al., "P27kipl expression is associated with tumor response to preoperative chemoradiotherapy in rectal cancer," Annals of Surgical Oncology: The Official Journal of the Society of Surgical Oncology, May 2001, pp. 311-318, vol. 8, No. 4.
Ghadimi, Michael B. et al., "Effectiveness of gene expression profiling for response prediction of rectal adenocarcinomas to preoperative chemoradiotherapy," Journal of Clinical Oncology: Official Journal of the American Society of Clinical Oncology, Mar. 20, 2005, pp. 1826-1838, vol. 23. No. 9.
Risinger, John I. et al., "Microarray analysis reveals distinct gene expression profiles among different histologic types of endometrial cancer," Cancer Research, Jan. 1, 2003, pp. 6-11, vol. 63, No. 1.
Hanna et al., "A Novel Alternative Approach for Prediction of Radiation Response of Squamous Cell Carcinoma of Head and Neck," Cancer Research, 61, 2001, pp. 2376-2380.
Rödel, et al., "Spontaneous and Radiation-Induced Apoptosis in Colorectal Carcinoma Cells with Different Intrinsic Radiosensitivities: Survivin as a Radioresistance Factor," Int. J. Radiation Oncology Biol. Phys. 55(5); 2003, pp. 1341-1347.
Kim et al., "p53, BCL-2, and Ki-67 Expression According to Tumor Response After Concurrent Chemoradiotherapy for Advanced Rectal Cancer" Annals of Surgical Oncology, 8(5); pp. 418-424,2001.
Adlard et al., "Prediction of the response of colorectal cancer to systemic therapy," Oncoloogy, 3, 2002, pp. 75-82, 2002.
Spitz et al., "p53 Immunohistocheimcal Staining Predicts Residual Disease after Chemoradiation," Clinical Cancer Research, 3, 1997, pp. 1685-1690.

(Continued)

*Primary Examiner* — Peter J Reddig
(74) *Attorney, Agent, or Firm* — Edwards Wildman Palmer LLP; Peter F. Corless

(57) ABSTRACT

A cDNA array (9984 genes) was used for expression profiling in rectal adenocarcinoma. The expression data were correlated to responsiveness to chemotherapy followed by radiotherapy. A set of 54 genes was found that were differentially expressed in responders vs. non-responders. The genes may be used as prognostic markers for determining whether a rectal adenocarcinoma is responsive to radiochemotherapy.

15 Claims, 2 Drawing Sheets

(56) References Cited

OTHER PUBLICATIONS

Wheeler et al., "p53 Status and the Regression of Rectal Cancer Following Preoperative Chemoradiotherapy," Gut, 46, 2000, p. TH42 (Abstract Only).

Scott, et al., A histopathological assessment of the response of rectal adenocarcinoma to combination chemo-radiotherapy: relationship to apoptotic activity, p53 and bcl-2 expression, European J. Surg. Oncology, 24, 1998, pp. 169-173.

* cited by examiner

COMPOSITION FOR DETECTING THE RESPONSE OF RECTAL ADENOCARCINOMAS TO RADIOCHEMOTHERAPY

This application claims the benefit of the filing date of U.S. Provisional Application Ser. No. 60/535,491, filed Jan. 12, 2004, whose disclosure is entirely incorporated by reference herein.

The instant application contains a "lengthy" Sequence Listing which has been submitted via CD-R (CD-ROM) in lieu of a printed paper copy, and is hereby incorporated by reference in its entirety. Said CD-R, recorded on Jul. 10, 2006, are labeled "Copy 1" and "Copy 2", respectively, and each contains only one identical 588 Kb file (31978233.APP).

FIELD OF THE INVENTION

The present invention relates, e.g., to a composition comprising a plurality of nucleic acid probes for use in research and diagnostic applications.

BACKGROUND INFORMATION

Rectal adenocarcinomas are among the most frequent malignant tumors in the Western World. Surgery, including total mesorectal resection, is the primary treatment for rectal carcinomas. In locally advanced stages of this disease, radiation or combined radiochemotherapy is mandatory. Whether radiochemotherapy should be administered prior to surgery (neoadjuvant) or after resection of the primary tumor (adjuvant), however, is still a matter of controversy (Sauer R. (2002) *Pathol Oncol Res* 8, 7-17; Pahlman et al. (1998) *Eur J Cancer* 34, 438-48; Nelson et al. (2001) *N Engl J Med* 345, 690-2). The decision to administer neoadjuvant radiochemotherapy relies primarily on the depth of tumor infiltration, which, in specialized centers is determined pre-therapeutically by rectal ultrasound (Liersch et al. (2003) *Chirurg* 74, 224-34; Hunerbein et al. *Ann Surg* (1997) 225, 432-8; Adams et al. (1999) *Dis Colon Rectum* 42, 159-66; Glaser et al. (1990) *Br J Surg* 77, 883-7). Neoadjuvant regimens might be particularly attractive (i) because a priori not curatively resectable tumors can be down-sized to achieve the undisputed benefit of tumor cell free surgical margins (R0-resection), (ii) because preoperative treatment reduces tumor burden and, therefore, might increase the possibility for sphincter preservation, and (iii) because radiochemotherapy cannot be applied when postoperative clinical complications occur.

However, the response of individual tumors to radiochemotherapy is not uniform. This poses a considerable clinical dilemma because patients with a priori resistant tumors could be spared exposure to radiation and DNA-damaging drugs, treatments that are associated with substantial side effects. In such cases surgery could be scheduled without delay. Alternatively, different neoadjuvant treatment modalities including additional chemotherapeutics could be pursued. It would therefore be of significant clinical relevance to identify predictive markers of cancer response to neoadjuvant radiochemotherapy.

Accordingly, numerous groups have employed targeted approaches to correlate expression levels of candidate genes in response to radiation, different chemotherapeutic drugs, and combinations of radiation and chemotherapy (for review see Pasche et al. (2002) *Best Pract Res Clin Gastroenterol* 16, 331-45; Adlard et al. (2002) *Lancet Oncol* 3, 75-82). The selections of candidate genes primarily included genes required for drug metabolism, drug activation, drug resistance, and DNA damage repair, and oncogenes and tumor suppressor genes involved in cell cycle control. Unfortunately, these candidate gene approaches have not materialized into sound pre-therapeutic predictors of response to radiochemotherapy. See, e.g., Okonkwo et al. (2001) *Oncol Rep* 8, 497-500; Saw et al (2003) *Dis Colon Rectum* 46, 192-202; Spitz et al. (1997) *Clin Cancer Res* 3, 1685-90; Luna-Perez et al. (1998) *Ann Surg Oncol* 5, 203-8; Elsaleh et al. (2000) *Radiother Oncol* 56, 239-44; Diez et al (2003) *Oncology* 64, 213-9; Scott et al. (1998) *Eur J Surg Oncol* 24, 169-73. There remains a need to establish reliable, clinically useful, predictors of radiochemosensitivity of rectal adenocarcinomas.

Parallel profiling of global gene expression levels based on microarray technologies has emerged as a powerful tool to monitor the transcriptome of cancer cells for tumor classification and prognosis (Rosenwald et al. (2002) *N Engl J Med* 346, 1937-47; van't Veer et al. (2002) *Nature* 415, 530-6; Iizuka et al. (2003) *Lancet* 361, 923-9; Bertucci et al. (2001) *Lancet Oncol* 2, 674-82; Yeoh et al. (2002) *Cancer Cell* 1, 133-43). In addition, the power of gene expression profiling as a predictor of drug response has been explored in several model systems, including the NCI-60 cancer cell line panel (Staunton et al. (2001) *Proc Natl Acad Sci USA* 98, 10787-92; Scherf et al. (2000) *Nat Genet* 24, 236-44) and tumor xenografts (Zembutsu et al. (2002) *Cancer Res* 62, 518-27). The results of these studies provide evidence that at least for some tumors and a subset of drugs, pre-therapeutic gene expression profiles might predict treatment response.

The present inventors have analyzed gene expression profiles of rectal adenocarcinomas, and have identified genes whose expression is correlated with responsiveness of the tumors to radiochemotherapy (e.g., neoadjuvant radiochemotherapy). Combinations comprising probes specific for these genes can be used in, e.g., diagnostic and experimental methods.

DESCRIPTION OF THE INVENTION

Figure 1:
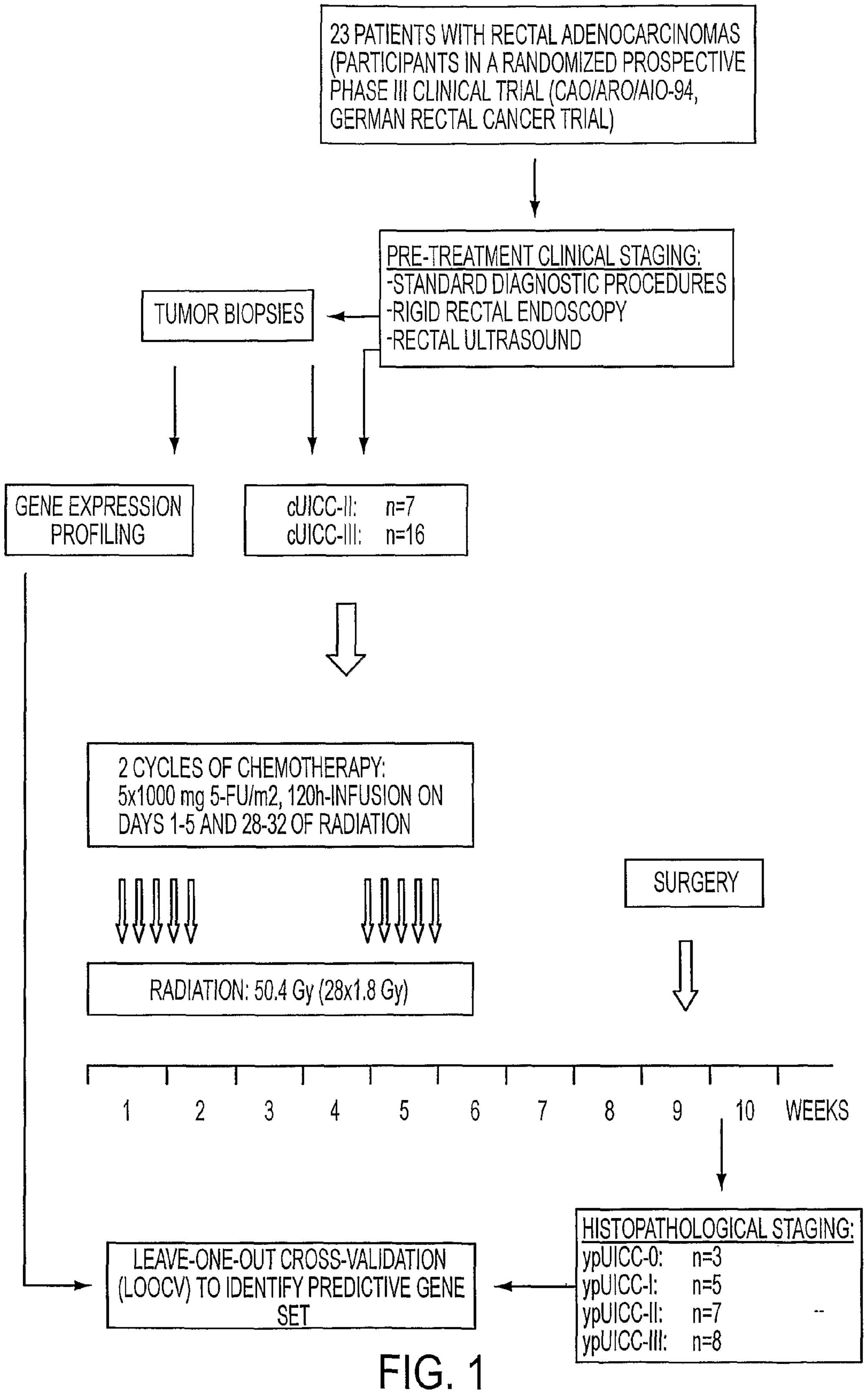
FIG. 1 is a pictorial presentation of specimen accrual, clinical diagnosis, and experimental design. cUICC refers to pre-therapeutic clinical staging of tumors based on rectal ultrasound and computed tomography. ypUICC refers to histological assessment of the resected specimen after neoadjuvant therapy.

The present invention relates, e.g., to the identification of genes and gene products (molecular markers, molecular signatures) from rectal adenocarcinomas whose expression, compared to a baseline value, is correlated with the responsiveness of the tumors to radiochemotherapy. As used herein, a "baseline value" includes, e.g., the expression in normal tissue, such as normal rectal tissue, e.g. from the subject or from a "pool" of normal subjects; or from a pool of different tissues from normal subjects. In a preferred embodiment, the expression is from a pool of cell lines (e.g. of carcinogenic origin), such as the universal human reference library available from Stratagene (catalogue no. 740000). The pooled values may be either commercially available or otherwise derived. Alternatively, the baseline value may be the expression in rectal carcinomas that are known to be "non-responders" to radiochemotherapy, e.g., the average value from a pool or compilation of such tumor samples. The baseline value may be available in a database compiled from any of such values.

About 54 molecular markers are identified herein that are expressed in a significantly altered amount in rectal carcinomas that are responsive to radiochemotherapy, compared to rectal adenocarcinomas that are not responsive. Of the 54 molecular markers, 13 are up-regulated, and 41 are down-regulated, in responders compared to non-responders. Of course, other genes, as well, may be differentially regulated in responders compared to non-responders.

These molecular markers can serve as the basis for diagnostic assays to determine the responsiveness of a rectal carcinoma to radiochemotherapy. For example, nucleic acid probes corresponding to one or more of the genes, and/or antibodies specific for proteins encoded by the genes, can be used to analyze a sample from a rectal tumor, in order to determine the responsiveness. Molecules (e.g. nucleic acid probes, antibodies, etc) corresponding to any number of the 54 identified genes, in any combination or permutation, can be used in compositions and methods of the invention. The genes and gene products can also aid in the identification of therapeutic agents, e.g. agents which can be administered in conjunction with radiochemotherapy, and which enhance the responsiveness of a rectal tumor to the radiochemotherapy. Furthermore, the identification of genes whose expression is correlated with responsiveness to radiochemotherapy can also provide a basis for explaining the different metabolic processes involved in such responsiveness, and thus can be used as research tools.

One aspect of the invention is a composition (combination) comprising one or a plurality of (preferably at least about 5, at least about 10, or at least about 15) isolated nucleic acids of at least about 8 contiguous nucleotides (e.g., at least about 12, 15, 25, 35, 50 or 75 contiguous nucleotides), selected from nucleic acids that correspond to genes 1-54 from Table 3, and comprising no more than about $1\times10^6$ (e.g., no more than about 500,000; 200,000; 100,000; 50,000; 25,000; 14,000; 13000; 12,000; 11,000; 10,000; 9,000; 8,000; 7,000; 6,000; 5,000, 4,000; 3,000; 2,000; 1,000; 500; 250; 150; 70 or 50) total isolated nucleic acids. In embodiments of the invention, the composition comprises at least about 5 (e.g., at least about 10, 15, 25, 50, 54, 60, 70 or 100 or more) nucleic acids that correspond to genes 1-54 from Table 3. In embodiments of the invention, at least one of the nucleic acids that correspond to genes 1-54 contains at least about 50 contiguous nucleotides, and/or is a cDNA. For example, the nucleic acids corresponding to genes 1-54 of Table 3 may be selected from:

(a) nucleic acids that comprise the sequences of SEQ ID NOs: 1-58 or 113-123;

(b) nucleic acids that comprise sequences that are at least about 85% (e.g., at least about 90%, 95%, or 98%) identical to the sequences of SEQ ID NOs: 1-58 or 113-123;

(c) nucleic acids that comprise sequences encoding polypeptides represented by SEQ ID NOs: 59-112;

(d) nucleic acids that comprise sequences of active fragments of the nucleic acids of (a), (b), or (c);

(e) nucleic acids that comprise sequences of active variants of the nucleic acids of (a), (b), or (c) and/or (f) nucleic acids that comprise complete complements of the sequences of any of the nucleic acids (a)-(e);

wherein the nucleic acids hybridize under conditions of high stringency to nucleic acids represented by SEQ ID NOs: 1-58 or 113-123, or to complements thereof.

The composition may be used, e.g., to determine the responsiveness of a rectal adenocarcinoma to radiochemotherapy.

As used herein, a "plurality" refers to two or more members, more preferably to a group of at least about 2, or at least about 5, or at least about 15, or at least about 54, etc., of the identified molecular markers.

As used herein, the term "isolated" nucleic acid (or polypeptide, or antibody) refers to a nucleic acid (or polypeptide, or antibody) that is in a form other than it occurs in nature, for example in a buffer, in a dry form awaiting reconstitution, as part of an array, a kit or a pharmaceutical composition, etc. The term an "isolated" nucleic acid or protein does not include a cell extract (e.g., a crude or semi-purified cell extract).

The majority of rectal tumors are carcinomas, and the majority of these rectal carcinomas are adenocarcinomas. The terms rectal tumor, carcinoma and adenocarcinoma are sometimes used interchangeably herein, with the understanding that the rectal tumors being discussed are preferably rectal adenocarcinomas. (It is noted that adenocarcinomas located in tissues other than the rectum may, under certain circumstances, also exhibit expression patterns similar to those discussed herein, with regard to responsiveness to radiochemotherapy.) A rectal adenocarcinoma that is "responsive to" radiochemotherapy is a tumor that is measurably more sensitive to such treatment than is a "non-responsive" tumor. The range of responsiveness of a responsive tumor may range widely. For example, in some cases, a responsive tumor may melt away, whereas in other cases, the reduction in size is not more than about 10%. Criteria for measuring responsiveness are known to skilled workers; some criteria are provided in the Examples.

The individual sequences of nucleic acids and proteins in the compositions and methods of the invention were publicly available at the time the invention was made. However, the relationship between expression of these sequences and the responsiveness of rectal adenocarcinomas to radiochemotherapy had not previously been observed; and the particular combinations of sequences in the compositions of the invention had not been disclosed or suggested.

The GenBank accession numbers and the sequences of some representative nucleic acids and proteins corresponding to genes 1-54 are provided in Table 3 (in Example II) and in the Sequence Listing attached hereto. Nucleic acids or proteins that "correspond to" a gene include nucleic acids or proteins that are expressed by the gene, or active fragments or variants of the expressed nucleic acids or proteins, or complements of the nucleic acids or fragments, etc. Only one strand of each nucleic acid is shown, but the complementary strand is understood to be included by any reference to the displayed strand. A "complement," as used herein, is a complete (full-length) complementary strand (with no mismatches) of a single strand nucleic acid.

As is discussed more fully below, probes from NCI-cDNA arrays (e.g., probes obtained from Incyte) were used in the experiments described herein to identify the 54 molecular markers of the invention. Some of those probes represent full-length coding sequences, and others (e.g., probes corresponding to genes 3, 6, 14, 19, 28, 30, 32, 44, 45, 48 and 51) are less than full-length. Full-length nucleic acid sequences (e.g., full-length coding sequences or genomic sequences)

that correspond to the less than full-length probes were obtained, using conventional methods to mine Genbank sequences. Both full-length and less than full-length sequences are listed in Table 3. Full-length SEQ ID NOs are listed in the first column of the table; and less than full-length coding sequences in the third column. The SEQ ID NOs listed in the second column of the table in general represent full length proteins. No protein sequences are listed for some of the short ESTs (e.g., genes 6, 28, 45 and 51); however, a skilled worker can readily identify open reading frames in these nucleic acid sequences and thus identify the corresponding protein sequences.

In a preferred embodiment, the nucleic acids corresponding to genes 1-54 of Table 3 are selected from the fifteen genes whose expression is most highly correlated in the study discussed herein with responsiveness of the tumors to radiochemotherapy [genes 1-12 (represented, e.g., by the nucleotide sequences of SEQ ID NOs: 1-15 and 113-114) and genes 42-44 (represented, e.g., by the nucleotide sequences of SEQ ID NOs: 46-48 and 120)]. That is, the nucleic acids in the composition (each having at least about 15 contiguous nucleotides) that correspond to genes in Table 3 may be selected from:

(a) nucleic acids that comprise sequences of SEQ ID NOs: 1-15, 113-114, 46-48, or 120;

(b) nucleic acids that comprise sequences that are at least about 85% (e.g., at least about 90%, 95%, or 98%) identical to SEQ ID NOs: 1-15, 113-114, 46-48, or 120;

(c) nucleic acids that comprise sequences encoding polypeptides represented by SEQ ID NOs 59-72 or 102-104;

(d) nucleic acids that comprise sequences of active fragments of the nucleic acids of (a), (b), or (c);

(e) nucleic acids that comprise sequences of active variants of the nucleic acids of (a), (b), or (c); and/or (f) nucleic acids that comprise complete complements of any of the sequences of nucleic acids (a)-(e);

wherein the nucleic acids hybridize under conditions of high stringency to nucleic acids represented by SEQ ID NOs: 11-15, 113-114, 46-48, or 120, or to complements thereof.

The nucleic acids discussed above, and derivatives thereof, can be used as probes to identify (e.g., by hybridization assays) polynucleotides whose expression is altered, compared to a baseline value, in rectal adenocarcinomas that are responsive to radiochemotherapy. As noted, some of the SEQ ID NOs represent full-length cDNAs, and others represent cDNAs or ESTs that are partial copies of gene coding sequences. The invention includes fragments containing sequential nucleotides of the partial or full-length cDNAs; preferably, these fragments are at least about 8, or at least about 15, nucleotides in length, and are specific for the genes from which the corresponding cDNAs were obtained. As discussed in more detail below, skilled workers will recognize how to select suitable fragments of a given nucleic acid that will hybridize specifically to a polynucleotide of interest.

Compositions of the invention may comprise any combination of, e.g., at least about 1, 2, 5, 10, 15, 20, 25, 50, 55, 60, 75 or 100 or more of the mentioned nucleic acids and/or fragments that correspond to genes from Table 3. A nucleic acid composition of the invention may comprise, consist essentially of, or consist of, a total of, e.g., about 1, 2, 5, 10, 15, 20, 25, 50, 60, 70, 100, 150, 250, 500, 750, 1,000, 2,000, 3,000, 5,000, 7,000; 8,000; 9,000; 10,000, 11,000; 12,000; 13,000; 14,000; 15,000; 25,000, 50,000, 100,000, 200,000, 500,000, $1\times10^6$, or more isolated nucleic acids. The term "consisting essentially of," in this context, refers to a value intermediate between the specific number of the mentioned elements (here, nucleic acids) encompassed by the term "consisting of" and the large number encompassed by the term "comprising." A nucleic acid composition of the invention preferably comprises no more than a total of, e.g., about $1\times10^6$ (e.g., no more than about 500,000; 200,000; 100,000; 50,000; 25,000; 14,000; 13,000; 12,000; 11,000; 10,000; 9,000; 8,000; 7,000; 6,000; 5,000, 4,000; 3,000; 2,000; 1,000; 750; 500; 250; 150; 100; 70; 60; 50; 25; 20; 15; 10; 5; 2; or 1) isolated nucleic acids.

Another embodiment of the invention is a composition of nucleic acids or fragments which hybridize specifically under conditions of high stringency to nucleic acids from the set represented by the SEQ ID NOs corresponding to genes 1-54 (e.g., SEQ ID NOs: 1-58 and 113-123), or to complements thereof.

The nucleic acid compositions of the invention may be in the form of an aqueous solution (e.g., for use in solution hybridization), or the nucleic acids in the composition may be immobilized on a substrate. In some compositions of the invention, the isolated nucleic acids are in an array or a microarray, e.g., they are hybridizable elements on an array, such as a microarray. A nucleic acid array may further comprise, bound (e.g., bound specifically) to one or more nucleic acids of the array, polynucleotides from a sample representing expressed genes. In general, as used herein, the term "nucleic acid" refers to a probe, whereas the term "polynucleotide" refers to an expression product of a gene, or a derivative of such an expression product. The sample may be, e.g., from an individual subject's rectal adenocarcinoma; from a normal tissue, such as a normal rectal tissue; from a tissue known to be non-responsive or known to be responsive to radiochemotherapy; or combinations thereof. In one embodiment, the nucleic acids in an array and the polynucleotides from a sample representing expressed genes have been subjected to nucleic acid hybridization under high stringency conditions (such that nucleic acids of the array that are specific for particular polynucleotides from the sample are specifically hybridized to those polynucleotides).

In the nucleic acid compositions of the invention, at least one phosphate, sugar and/or base moiety in the helix may be modified. For example, a phosphate may be modified as a phosphorothioate, a phosphoridothioate, a phosphoramidothioate, a phosphoramidate, a phosphordiimidate, a methylsphosphonate, an alkyl phosphotriester, 3'-aminopropyl, a formacetal, or an analogue thereof.

Another embodiment is a composition comprising one or a plurality of (e.g., at least about 5, 10 or 15) isolated nucleic acids, each of which hybridizes specifically under high stringency conditions to part or all of a coding sequence whose expression reflects (is indicative of, is correlated with) responsiveness of a rectal adenocarcinoma to radiochemotherapy. Examples of some such nucleic acids are nucleic acids corresponding to genes 1-54, as discussed above (e.g., nucleic acids represented by SEQ ID NOs: 1-58 or 113-123, or active fragments, variants, or complements thereof).

Sequences "corresponding to" a gene, or "specific for" a gene include sequences that are substantially similar to (e.g., hybridize under conditions of high stringency to) one of the strands of the double stranded form of that gene. By hybridizing "specifically" is meant herein that two components (e.g. an expressed gene or polynucleotide and a nucleic acid probe) bind selectively to each other and not generally to other components unintended for binding to the subject components. The parameters required to achieve specific interactions can be determined routinely, using conventional methods in the art.

Another aspect of the invention is a composition (combination) comprising polypeptides that are of a size and structure that can be recognized and/or bound by an antibody. That is, the polypeptides are antigenic. Specifically, the composition comprises one or a plurality of (e.g., at least about 5, 10 or 15) isolated, antigenic polypeptides selected from polypeptides that correspond to genes 1-54 from Table 3. For example, the composition may comprise polypeptides selected from:

(a) polypeptides comprising SEQ ID NOs: 59-112;

(b) polypeptides encoded by polynucleotides comprising SEQ ID NOs: 1-58 or 113-123;

(c) polypeptides whose sequences are at least about 85% (e.g., at least about 90%, 95%, or 98%) identical to SEQ ID NOs: 59-112;

(d) active variants of (a), (b) or (c); and/or (e) antigenic fragments of (a), (b) or (c), wherein the polypeptides, active variants or antigenic fragments are of a size and structure that can be recognized, or bound by, an antibody.

In a preferred embodiment, the polypeptides in the above composition that correspond to genes from Table 3 are selected from the fifteen polypeptides whose expression is most highly correlated in the study discussed herein with responsiveness of the tumors to radiochemotherapy [genes 1-12 (represented, e.g., by the amino acid sequences of SEQ ID NOs 59-72) and genes 42-44 (represented, e.g., by the amino acid sequences of SEQ ID NOs: 102-104)]. That is, the composition may comprise polypeptides selected from:

(a) polypeptides comprising SEQ ID NOs: 59-72 or 102-104;

(b) polypeptides encoded by polynucleotides comprising SEQ ID NOs: 1-15, 113-114, 46-48 or 120);

(c) polypeptides whose sequences are at least about 85% (e.g., at least about 90%, 95%, or 98%) identical to SEQ ID NOs: 59-72 or 102-104;

(d) active variants of (a), (b), or (c); and/or (e) antigenic fragments of (a), (b), or (c), wherein the polypeptides, active variants or antigenic fragments are of a size and structure that can be recognized and/or bound by an antibody.

One use of such compositions of polypeptides of the invention is as a source for generating antibodies that can be used to detect the responsiveness of a rectal adenocarcinoma to radiochemotherapy.

A composition of polypeptides of the invention may comprise any combination of, e.g., at least about 1, 2, 5, 10, 15, 25, 50, 55, 60, 75, 100 or more of the mentioned isolated polypeptides, variants or fragments that correspond to genes from Table 3. A polypeptide composition of the invention may comprise, consist essentially of, or consist of, e.g., at least about 1, 2, 5, 10, 15, 25, 50, 75, 100, 200, 500, 750, 1,000, 2,000, 3,000, 5,000, 10,000, 25,000, 50,000, 100,000, 200,000, 500,000, $1\times10^6$, $5\times10^6$ or more total isolated polypeptides.

Another embodiment is a composition comprising one or a plurality of (e.g., at least about 5, 10 or 15) isolated, antigenic, polypeptides for use in generating antibodies for detecting the response of a rectal adenocarcinoma to radiochemotherapy, wherein said polypeptides are polypeptides whose expression is correlated with responsiveness of the adenocarcinoma to radiochemotherapy.

Another aspect of the invention is a composition comprising antibodies specific for the polypeptides of the invention. As used herein, an antibody that is "specific for" a polypeptide includes an antibody that binds selectively to the polypeptide and not generally to other polypeptides unintended for binding to the antibody. The parameters required to achieve such specificity can be determined routinely, using conventional methods in the art.

One embodiment of the invention is a composition comprising selected numbers of such antibodies, which are in a form that permits their binding to the polypeptides for which they are specific. Specifically, the composition comprises one or a plurality of isolated antibodies (preferably at least about 5, 10 or 15 isolated antibodies), which are selected from antibodies that are specific for polypeptides corresponding to genes 1-54 from Table 3. Preferably, the antibodies are specific for polypeptides corresponding to genes 1-12 or 42-44 from Table 3. For example, the antibodies may be specific for polypeptides selected from:

(a) polypeptides comprising SEQ ID NOs: 59-112 (particularly SEQ ID NOs: 59-72 or 102-104);

(b) polypeptides encoded by polynucleotides comprising SEQ ID NOs: 1-58 or 113-123 (particularly SEQ ID NOs: 1-15, 46-48, 113-114, or 120);

(c) polypeptides that are at least about 85% (e.g., at least about 90%, 95%, or 98%) identical to SEQ ID NOs: 59-112 (particularly to SEQ ID NOs: 59-72 or 102-104);

(d) polypeptides that are active variants of (a), (b), or (c); and/or (e) polypeptides that are antigenic fragments of (a), (b) or (c).

Generally, the antigenic fragments comprise at least about 8 or at least about 12 contiguous amino acids of said polypeptide sequences.

The antibody compositions of the invention may be used, e.g., to determine the responsiveness of a rectal adenocarcinoma to radiochemotherapy.

The above compositions may comprise any combination of, e.g., at least about 1, 2, 5, 10, 15, 20, 25, 35, 45, 55, 65, 75, 100, 200, 300, 400, 500 or more of the mentioned isolated antibodies or antibody fragments specific for genes that correspond to genes from Table 3. An antibody composition of the invention may comprise, consist essentially of, or consist of a total of, e.g., at least about 1, 2, 5, 10, 15, 20, 25, 50, 60, 70, 100, 125, 150, 200, 250, 300, 400, 500, 750, 1,000, 2,000, 3,000, 5,000, 7,000; 8,000; 9,000; 10,000, 11,000; 12,000; 13,000; 14,000; 15,000; 25,000, 50,000, 100,000, 200,000, 500,000, $1\times10^6$ or more isolated antibodies. In embodiments of the invention, the composition comprises no more than about 1,000 (e.g., no more than about 500,000; 200,000; 100,000; 50,000; 25,000; 14,000; 13,000; 12,000; 11,000; 10,000; 9,000; 8,000; 7,000; 6,000; 5,000, 4,000; 3,000; 2,000; 1,000; 750; 500; 400; 300; 250; 200; 150; 125; 100; 70; 60; 50; 25; 20; 15; 10; 5; 2; or 1) total isolated antibodies.

The isolated antibodies in any of the above compositions may be in the form of an aqueous solution (e.g., in a form suitable for radioimmunoassay), or the isolated antibodies may be immobilized on a substrate. In embodiments of the invention, the isolated antibodies are in an array, e.g., a microarray; they may be reactive elements on an array, such as a microarray. By "reactive" elements is meant that the antibodies can react, e.g., bind, in a specific manner, with antigens for which they are specific.

Another aspect of the invention is a method for detecting (e.g., measuring, or quantitating) one or more polynucleotides or polypeptides of the invention in a sample, such as a sample from a rectal adenocarcinoma, compared to a baseline value. Generally, the detected polynucleotides or polypeptides correspond to a gene whose expression is correlated with responsiveness of the tumor to radiochemotherapy (e.g., genes 1-54 from Table 3). The method is generally a method for determining the responsiveness of the rectal adenocarcinoma to radiochemotherapy. In one embodiment, this method involves contacting the sample with a composition of nucleic acids, or of antibodies, of the invention, under conditions effective for specific binding of the nucleic acids to the polynucleotides in the sample (such as hybridization under conditions of high stringency), or effective for specific binding of the antibodies to the polypeptides in the sample. The method may further comprise detecting (e.g., determining the amount of) the polynucleotides in the sample which have bound to the nucleic acids, or detecting (e.g., determining the amount of) the polypeptides in the sample which have bound to the antibodies. Preferably, the polynucleotides or polypeptides that are detected reflect expression (either up-regulation or down-regulation) that is correlated with (indicative of) responsiveness of the adenocarcinoma to radiochemotherapy.

For example, a decrease in the amount (level of expression) of one or more of set #1 of 41 polynucleotides or polypeptides in a sample indicates that the adenocarcinoma is responsive to radiochemotherapy. Set #1 comprises nucleic acids corresponding to genes 1-41 (e.g., nucleic acids that comprise SEQ ID NOs: 1-45 or 113-119, or that can hybridize specifically (e.g., under conditions of high stringency) to those nucleic acids, or that are complements of those nucleic acids, etc.); and the corresponding polypeptides, which comprise sequences corresponding to genes 1-41 (e.g., polypeptides comprising SEQ ID NOs: 59-102, etc.).

An increase in the amount (level of expression) of one or more of set #2 of 13 polynucleotides or polypeptides in a sample indicates that the adenocarcinoma is responsive to radiochemotherapy. Set #2 comprises nucleic acids corresponding to genes 42-54 (e.g., nucleic acids that comprise SEQ ID NOs: 46-58 or 120-123, or that can hybridize specifically (e.g., under conditions of high stringency) to those nucleic acids, or that are complements of those nucleic acids, etc.); and the corresponding polypeptides, which comprise sequences corresponding to genes 42-54 (e.g., polypeptides comprising SEQ ID NOs: 102-112, etc.).

In assays described herein, a given polynucleotide or polypeptide may or may not be expressed in an increased or decreased amount in a sample from a rectal adenocarcinoma, compared to a baseline value. In a general sense, this invention relates to methods to determine if a gene product is expressed in an increased or decreased amount, irrespective of whether such increased or decreased expression is detected.

The rectal adenocarcinoma evaluated in this method is preferably from a human patient. The patient may not have been subjected to surgery, such as rectal resection, i.e., the patient is preoperative. In this case, the method can provide information as to whether preadjuvant therapy is advisable. Alternatively, the patient may have already been subjected to surgery, such as rectal resection, i.e., the patient is postoperative. In this case, the method can provide information as to whether adjuvant therapy is advisable.

In one embodiment, the method comprises determining in a polynucleotide sample which represents expressed genes in a rectal adenocarcinoma the amount (level of expression), compared to a baseline value, of one or a plurality of (e.g., at least about 5, 10 or 15) polynucleotides whose expression is correlated with the responsiveness of the adenocarcinoma to radiochemotherapy. For example, the expression of genes selected from genes 1-54 of Table 3 can be measured. As used herein, the term "polynucleotide" sample in general refers to expression products of genes, such as mRNA, or derivatives of such expression products, such as, e.g., cRNA, cDNA, or PCR amplification products. The term "nucleic acid" generally refers to a nucleic acid used as a probe to detect such polynucleotides.

In one embodiment of this method, each of the polynucleotides can hybridize specifically (e.g., under conditions of high stringency) to one of the nucleic acids noted above. For example, the nucleic acids may be selected from nucleic acids comprising SEQ ID NOs: 1-58 or 113-123 (in particular, SEQ ID NOs: 1-15, 46-48, 113-114, or 120), and/or the mentioned fragments or variants thereof (e.g., nucleic acids that are at least about 90%, 95% or 98% identical to those SEQ ID NOs; nucleic acids that encode polypeptides represented by SEQ ID NOs: 59-112 (in particular, SEQ ID NOs: 59-72 or 102-104); active fragments that comprise at least about 8 to 15 contiguous nucleotides of any of those nucleic acids; active variants of any of those nucleic acids; or complements of any of the above nucleic acids). In embodiments of this method, the amount (level of expression) of at least about 1, 2, 5, 10, 25, 50, or 54 of the polynucleotides corresponding to genes 1-54 from Table 3 is determined.

In one embodiment of the method, the amount (level of expression) of polynucleotides in a sample is determined by hybridizing polynucleotides in the sample to a nucleic acid composition of the invention, under conditions of high stringency, and comparing the amount of hybridization to a baseline value. In embodiments of this method, the nucleic acids are immobilized on a substrate, and/or are in an array, e.g. are hybridizable elements on an array, such as a microarray.

The amount of hybridization of a polynucleotide in the sample to a nucleic acid specific for it in the nucleic acid composition generally reflects the level of expression of the polynucleotide in the rectal adenocarcinoma.

The baseline value may be obtained, for example, by hybridizing a nucleic acid composition of the invention, under conditions of high stringency, to a control polynucleotide sample. For example, one can use a polynucleotide sample obtained from normal tissue, such as a normal rectal tissue, e.g. from the subject or from a "pool" of normal subjects; or to a polynucleotide obtained from a pool of different tissues of normal subjects. In a preferred embodiment, one uses a pool of cell lines of carcinogenic origin, such as the universal human reference library available from Stratagene (catalogue no. 740000). The pooled values may be either commercially available or otherwise derived. Alternatively, the baseline value may be the expression in rectal carcinomas that are known to be "non-responders" to radiochemotherapy, e.g., the average value from a pool or compilation of such tumor samples. Any of the above types of baseline values may available in a database compiled from such values.

In another embodiment of this method, the determination of the amount (level of expression) of polynucleotides in a sample is performed by quantitatively amplifying polynucleotides in the rectal adenocarcinoma sample with primers specific for those polynucleotides, and comparing the amount of amplified polynucleotide to a baseline value. For example, conventional methods of RT-PCR may be used. In one embodiment, the polynucleotides from the rectal adenocarcinoma sample (and, optionally, from controls) are labeled with a detectable label, e.g., a fluorescent label.

In another embodiment, the method comprises determining in a polypeptide sample from a rectal adenocarcinoma the amount (level of expression), compared to the amount (level of expression) of a baseline value, of each of one or a plurality of polypeptides whose expression is correlated with the responsiveness of the adenocarcinoma to radiochemotherapy (e.g., polypeptides corresponding to genes 1-54 of Table 3). The polypeptides may be selected from polypeptides that bind specifically to antibodies specific for polypeptides:

(a) comprising SEQ ID NOs: 59-112 particularly SEQ ID NOs: 59-72 or 102-104);

(b) encoded by polynucleotides comprising SEQ ID NOs: 1-58 and 113-123 (particularly SEQ ID NOs: 1-15, 46-48, 113-114, and 120);

(c) whose sequences are at least about 85% (e.g., at least about 90%, 95%, or 98%) identical to SEQ ID NOs: 59-112 (particularly to SEQ ID NOs: 59-72 and 102-104);

(d) that are active variants of (a), (b), or (c); and/or (e) that are antigenic fragments of (a), (b) or (c).

An altered amount (level of expression) of one or more of the polypeptides compared to a baseline value is correlated with the responsiveness of the rectal adenocarcinoma to radiochemotherapy. In embodiments of the invention, the amount of at least about 1, 2, 5, 10, 50 or 54 of the polypeptides is determined.

In one embodiment of this method, the determination is performed by:

contacting said polypeptide sample with an antibody composition containing one or a plurality of antibodies specific for polypeptides comprising polypeptides (a), (b), (c), (d) and/or (e) above, under conditions effective for at least one of said antibodies to bind specifically to the corresponding polypeptide (polypeptide for which it is specific), and comparing the amount (degree) of specific binding of to a baseline value.

The antibody composition may be in the form of an aqueous solution; the antibodies may be immobilized on a substrate or surface (e.g., a surface suitable for surface plasmon resonance (SPR)-based technology); and/or the antibodies may be in an array, e.g. they may be reactive elements on an array, such as a microarray.

The amount of binding of a polypeptide in the sample to an antibody specific for it in the antibody composition generally reflects the amount (level of expression) of the polypeptide in the rectal adenocarcinoma.

The baseline value may reflect the amount of the polypeptides expressed in normal tissue. For example, it may be obtained by contacting the antibody composition, under conditions as above, to a polypeptide sample obtained from normal rectal tissue, e.g., from the subject or a reference "pool" of normal subjects; or to a polypeptide sample obtained from a pool of different tissues of normal subjects. In a preferred embodiment, one uses a pool of cell lines of carcinogenic origin, such as the universal human reference library available from Stratagene (catalogue no. 740000). The pooled values may be either commercially available or otherwise derived. Alternatively, the baseline value may be determined with rectal carcinomas that are known to be "non-responders" to radiochemotherapy, e.g., the average value from a pool or compilation of such tumor samples. Any of the above types of baseline values may available in a compiled database.

Another aspect of the invention is a kit (e.g. for detecting the presence and/or amount of a polynucleotide in a sample from a rectal adenocarcinoma, which may indicate that the rectal adenocarcinoma is responsive to radiochemotherapy), comprising a composition of nucleic acids of the invention (e.g., in the form of an array) and, optionally, one or more reagents that facilitate hybridization of the nucleic acids in the composition to a test polynucleotide(s) of interest, and/or that facilitate detection of the hybridized polynucleotide(s), e.g., that facilitate detection of fluorescence. The kit may comprise a composition of nucleic acids of the invention (e.g., in the form of an array), means for carrying out hybridization of the nucleic acids in the composition to a test polynucleotide(s) of interest, and/or for means for reading hybridization results. Hybridization results may be units of fluorescence.

Another aspect is a kit (e.g. for detecting the presence and/or amount of a polypeptide in a sample from a rectal adenocarcinoma, which may indicate that the rectal adenocarcinoma is responsive to radiochemotherapy), comprising a composition of antibodies of the invention (e.g., in the form of an array) and, optionally, one or more reagents that facilitate binding of the antibodies in the composition with a test polypeptide(s) of interest, or that facilitate detection of bound antibody. The kit may comprise a composition of antibodies of the invention (e.g., in the form of an array), means for carrying out binding of the antibodies in the array to a test polynucleotide(s) of interest, and/or means for reading the binding results.

Another aspect of the invention is a method for identifying a candidate for an agent (e.g., a drug) that enhances (e.g., facilitates, increases, potentiates) the response of a rectal adenocarcinoma to radiochemotherapy. Such an agent would be particularly valuable if administered to a patient in conjunction with radiochemotherapy. One embodiment of this method comprises (a) contacting a rectal adenocarcinoma cell with a putative agent;

(b) hybridizing a sample of polynucleotides representing expressed genes obtained from the contacted adenocarcinoma cell to a nucleic acid composition of the invention, under conditions effective for specific hybridization of a nucleic acid probe of the invention to its corresponding polynucleotide target (e.g., under high stringency hybridization conditions); and (c) determining the amount (level of) of specific hybridization of one or more of the polynucleotides in the sample to one or more of the nucleic acids in the composition, compared to the amount in the absence of the putative agent, wherein the amount of specific hybridization of a polynucleotide reflects the amount (level) of its expression in the contacted adenocarcinoma cell, and wherein a putative agent that reduces the expression of one or more polynucleotides of the invention corresponding to genes 1-41, or that enhances the expression of one or more polynucleotides of the invention corresponding to genes 42-54, compared to the amount in the absence of the putative agent, is a candidate for an agent that enhances the response of a rectal adenocarcinoma to radiochemotherapy. The method may further comprise assessing the ability of the candidate agent to enhance responsiveness of an adenocarcinoma to radiochemotherapy in vivo.

Another aspect of the invention is a method for identifying a candidate for an agent (e.g., a drug) that enhances the response of a rectal adenocarcinoma to radiochemotherapy, comprising, (a) contacting a rectal adenocarcinoma cell with a putative agent;

(b) contacting a sample of polypeptides obtained from the contacted adenocarcinoma cell with an antibody composition of the invention, under conditions effective for specific binding of an antibody to its corresponding polypeptide; and (c) determining the amount (level of) of specific binding of one of more of the polypeptides in the sample to one of more of the antibodies of the composition, compared to the amount in the absence of the putative agent, wherein the amount of specific binding of a polypeptide reflects the amount (level) of its expression in the contacted adenocarcinoma, and wherein a putative agent that reduces the expression of one or more polypeptides of the invention corresponding to genes 1-41, or that enhances the expression of one or more polynucleotides of the invention corresponding to genes 42-54, compared to the amount in the absence of the putative agent, is a candidate for an agent that enhances the response of a rectal adenocarcinoma to radiochemotherapy. The method may further comprise assessing the ability of the candidate agent to enhance responsiveness of an adenocarcinoma to radiochemotherapy in vivo.

Another aspect of the invention is a method for identifying target genes for therapy of rectal adenocarcinomas.

One embodiment is a method for identifying a gene whose inhibition (of expression or activity) enhances the response of a rectal adenocarcinoma to radiochemotherapy, comprising (a) inhibiting in a rectal adenocarcinoma the expression and/or activity of a gene selected from genes 1 through 41, or the expression and/or activity of a gene product of one of those genes; and (b) determining if the rectal tumor exhibits an increased response to radiochemotherapy compared to a baseline value.

Another embodiment is a method for identifying a gene whose stimulation (of expression or activity) enhances the response of a rectal adenocarcinoma to radiochemotherapy, comprising (a) stimulating in a rectal adenocarcinoma the expression and/or activity of a gene selected from genes 42 through 54, or the expression and/or activity of a gene product of one of those genes; and (b) determining if the rectal tumor exhibits an increased response to radiochemotherapy compared to a baseline value.

In the present application, the term "nucleic acid" (e.g., with reference to probe molecules) refers both to DNA (including cDNA) and RNA, as well as DNA-like or RNA-like materials, such as branched DNAs, peptide nucleic acids (PNA) or locked nucleic acids (LNA). Nucleic acid probes for gene expression analysis include those comprising ribonucleotides, deoxyribonucleotides, both, and/or their analogues. Nucleic acids of the invention include double stranded and partially or completely single stranded molecules. In a preferred embodiment, probes for gene expression comprise single stranded nucleic acid molecules that are complementary to an mRNA target expressed by a gene of interest, or that are complementary to the opposite strand (e.g., complementary to a first strand cDNA generated from the mRNA).

Several nucleic acid probe sequences described herein are cDNAs complementary to genes or gene fragments; some are ESTs. For purposes of the analysis, it is not necessary that the full length sequence be known, as those of skill in the art will know how to obtain the full length sequence using the sequence of a given fragment or EST and known data mining, bioinformatic, and DNA sequencing methodologies without undue experimentation. If desired, the skilled artisan can subsequently select as a probe a nucleic acid that is longer than the initial gene fragment or EST, or a suitable fragment selected from that extended sequence. Many full length sequences (e.g., full-length coding sequences or genomic sequences) have been determined from less than full-length sequences used in the experiments described herein; these full length sequences are provided in Table 3. Again, a skilled worker can readily select suitable probe sequences, corresponding to coding sequences, using conventional procedures. Since some of the probe sequences are identified solely based on expression levels, it is not essential to know a priori the function of a particular gene.

The present invention includes a variety of active variants of nucleic acids. For example, nucleic acid probes can be sequence variants of the sequences described herein (e.g., they can include nucleotide substitutions, small insertions or deletions, nucleotide analogues, etc.); or they can be chemical variants (e.g., they can contain chemical derivatives); or they can be length variants. An "active variant," as used herein, is a variant that retains a measurable amount of an activity of the starting material. For example, an active variant of a nucleic acid probe retains an adequate ability to hybridize specifically to a complementary DNA strand (or mRNA) in a test sample. Preferably, an active variant of a nucleic acid probe also exhibits adequate resistance to nucleases and stability in the hybridization protocols employed. DNA or RNA may be made more resistant to nuclease degradation, e.g., by incorporating modified nucleosides (e.g., 2'-O-methylribose or 1'-α-anomers), or by modifying internucleoside linkages (e.g., methylphosphonates or phosphorothioates), as described below.

With regard to sequence variants, the invention includes nucleic acid probes which exhibit variations in sequence compared to the wild type sequence, provided the probe retains the ability to hybridize specifically to the polynucleotide to which it corresponds (e.g., to the nucleic acid from which it is derived, or a complement thereof). For example, small deletions, insertions, substitutions, rearrangements etc. are tolerated. The sequence changes may be introduced artificially, or they may be naturally occurring, e.g., changes reflecting degeneracy of the genetic code, allelic variants, species homologues, etc.

Nucleotide analogues can be incorporated into the nucleic acids by methods well known in the art. The only requirement is that the incorporated nucleotide analogues must serve to base pair with target polynucleotide sequences. For example, certain guanine nucleotides can be substituted with hypoxanthine which base pairs with cytosine residues. However, these base pairs are less stable than those between guanine and cytosine. Alternatively, adenine nucleotides can be substituted with 2,6-diaminopurine which can form stronger base pairs than those between adenine and thymidine.

The invention also relates to nucleic acid probes that are at least about 70%, 75%, 80%, 85%, 90%, 95%, 98% or 99% identical in sequence to a polynucleotide target of interest, or to a complement thereof. The invention also relates to nucleic acid probes that are at least about 70%, 75%, 80%, 85%, 90%, 95%, 98% or 99% identical or complementary to one of the nucleic acids of the invention corresponding to genes 1-54. Conventional algorithms can be used to determine the percent identity or complementarity, e.g., as described by Lipman and Pearson (*Proc. Natl Acad Sci* 80:726-730, 1983) or Martinez/Needleman-Wunsch (*Nucl Acid Research* 11:4629-4634, 1983).

The invention also relates to nucleic acid probes that hybridize specifically to corresponding target polunucleotides, e.g., under conditions of high stringency. Hybridization conditions are discussed elsewhere herein. Some nucleic acid probes may not hybridize effectively under hybridization conditions due to secondary structure. To optimize probe hybridization, the probe sequences may be examined using a computer algorithm to identify portions of genes without potential secondary structure. Such computer algorithms are well known in the art, such as OLIGO 4.06 Primer Analysis Software (National Biosciences, Plymouth, Minn.) or LASERGENE software (DNASTAR, Madison, Wis.); MACDASLS software (Hitachi Software Engineering Co, Std. South San Francisco, Calif.) and the like. These programs can search nucleotide sequences to identify stem loop structures and tandem repeats and to analyze G+C content of the sequence (those sequences with a G+C content greater than 60% are excluded). Alternatively, the probes can be optimized by trial and error. Experiments can be performed to determine whether probes and complementary target polynucleotides hybridize optimally under experimental conditions.

With regard to chemical variants, the nucleic acids can include nucleotides that have been derivatized chemically or enzymatically. Typical chemical modifications include derivatization with acyl, alkyl, aryl or amino groups. Suitable modified base moieties include, for example, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-ω-thiouridine, 5-carboxymethyl-aminomethyl uracil, dihydrouracil, β-D-galactosylqueosine, inosine, N6-isopentenyladenine, 1-methylguanine, 3-methyl-cytosine, 5-methylcytosine, N6-adenine, 7-methylguanine, 5-methylaminomethyluracil, 5-methoxyamino-methyl-2-thiouracil, β-D-mannosylqueosine, 5-methoxy-carboxymethyluracil, 5-methoxyuracil-2-methylthio-N6-iso-pentenyladenine, uracil-5-oxyacetic acid, butoxosine, pseudouracil, queuosine, 2-thio-cytosine, 5-methyl-2-thiouracil, 2-thiouracil, 4-thiouracil, 5-methyluracil, uracil-5-oxyacetic acid methylester, uracil-t-oxyacetic acid, 5-methyl-2-thiouracil, 3(3-amino-3-N-2-carboxypropyl) uracil and 2,6-diaminopurine.

The nucleic acid may comprise at least one modified sugar moiety including, but not limited, to arabinose, 2-fluoroarabinose, xylulose, and hexose.

The nucleic acid may comprise a modified phosphate backbone synthesized from one or more nucleotides having, for example, one of the following structures: a phosphorothioate, a phosphoridothioate, a phosphoramidothioate, a phosphoramidate, a phosphordiimidate, a methylphosphonate, an alkyl phosphotriester, 3'-aminopropyl and a formacetal or analog thereof.

The nucleic acid may be an α-anomeric oligonucleotide which forms specific double-stranded hybrids with complementary RNA in which, contrary to the usual β-units, the strands run parallel to each other (Gautier et al. (1987), *Nucl. Acids Res.* 15:6625-6641).

The nucleic acid may be conjugated to another molecule, e.g., a peptide, a hybridization-triggered cross-linking agent, a hybridization-triggered cleavage agent, etc., all of which are well-known in the art.

With regard to length variants (active fragments), those skilled in the art will appreciate that a probe of choice for a particular gene can be the full length coding sequence or any fragment thereof having generally at least about 8 or at least about 15 nucleotides. When the full length sequence is known, the practitioner can select any appropriate fragment of that sequence, using conventional methods. In some embodiments, multiple probes, corresponding to different portions of a given SEQ ID (molecular marker) of the invention, are used. For example, probes representing about 10 non-overlapping 20-mers can be selected from a 200-mer sequence. Thus, for example, if each of the 54 molecular markers of the invention is represented by 10 probes, the total number of the probes corresponding to the molecular markers in the composition (e.g., in a microarray) will be 540. A skilled worker can design a suitable selection of overlapping or non-overlapping probes corresponding to each expressed polynucleotide of interest, without undue experimentation.

A nucleic acid probe of the invention can be of any suitable length. The size of the DNA sequence of interest may vary, and is preferably from about 8 to about 10,000 nucleotides, e.g. from about 50 to about 3,500 nucleotides. In some embodiments, full-length coding sequences are preferred. In others, the nucleic acids range from about 50 to about 200 nucleotides, preferably from about 50 to about 80 nucleotides. All ranges provided herein include the end point values. Any nucleic acid that can uniquely identify a polynucleotide of the invention (e.g., that can hybridize to it specifically) is included in the invention. In general, a nucleic acid comprising at least about 8, 10, 15, 20 or 25 or more contiguous nucleotides contains sufficient information to specify uniquely a gene of a mammalian (e.g., human) genome. Practically, larger oligonucleotides are generally used as probes.

Nucleic acid probes (e.g., oligonucleotides) of this invention may be synthesized, in whole or in part, by standard synthetic methods known in the art. See, e.g., Caruthers et al. (1980) *Nucleic. Acids Symp*. Ser. (2) 215-233; Stein et al. (1998), *Nucl. Acids Res.* 16, 3209; and Sarin et al. (1988), *Proc. Natl. Acad. Sci. U.S.A* 85, 7448-7451. An automated synthesizer (such as those commercially available from Biosearch, Applied Biosystems) may be used. cDNA probes can be cloned and isolated by conventional methods; can be isolated from pre-existing clones, such as those from Incyte as described herein; or can be prepared by a combination of conventional synthetic methods.

A composition comprising nucleic acids of the invention can take any of a variety of forms. For example, the nucleic acids can be free in a solution (e.g., an aqueous solution), and can, e.g., be subjected to hybridization in solution to polynucleotides from a sample of interest. Methods of hybridization in solution are well-known in the art.

Alternatively, the nucleic acids can be in the form of an array. The term "array" as used herein means an ordered arrangement of addressable, accessible, spatially discrete or identifiable, molecules disposed on a surface. The molecules in the array can be hybridizable elements (e.g., nucleic acids) or reactive elements (e.g., antibodies). Arrays can comprise any number of sites that comprise probes, from about 5 to, in the case of a microarray, tens to hundreds of thousands or more.

Any of a variety of suitable, compatible surfaces can be used in conjunction with this invention. The surface (usually a solid, preferably a suitable rigid or semi-rigid support) can be any of a variety of organic or inorganic materials or combinations thereof, including, merely by way of example, plastics such as polypropylene or polystyrene; ceramic; silicon; (fused) silica, quartz or glass, which can have the thickness of, for example, a glass microscope slide or a glass cover slip; paper, such as filter paper; diazotized cellulose; nitrocellulose filters; nylon membrane; or polyacrylamide gel pad. Substrates that are transparent to light are useful when the method of performing an assay involves optical detection. Suitable surfaces include membranes, filters, chips, slides, wafers, fibers, magnetic or nonmagnetic beads, gels, tubing, plates, polymers, microparticles, capillaries, or the like. The substrate can have a variety of surface forms, such as wells, trenches, pins, channels and pores, to which the nucleic acid probes are bound. The shape of the surface is not critical. It can, for example, be a flat surface such as a square, rectangle, or circle; a curved surface; or a three dimensional surface such as a bead, particle, strand, precipitate, tube, sphere, etc. Microfluidic devises are also encompassed by the invention.

In a preferred embodiment, a composition of nucleic acids is in the form of a microarray (sometimes referred to as a DNA "chip"). Microarrays allow for massively parallel gene expression analysis. See, e.g., Lockhart et al (2002), *Nature* 405, 827-836 and Phimister (1999), *Nature Genetics* 21(supp), 1-60. In a microarray, the array elements are arranged so that there are preferably at least one or more different array elements, more preferably at least about 100 array elements, and most preferably at least about 1,000 array elements, on a 1 $cm^2$ substrate surface. The maximum number of array elements is unlimited, and can be at least 100,000 array elements. Furthermore, the hybridization signal from each of the array elements is individually distinguishable.

Methods of making DNA arrays, including microarrays are conventional. For example, the probes may be synthesized directly on the surface; or preformed molecules, such as oligonucleotides or cDNAs, may be introduced onto (e.g., bound to, or otherwise immobilized on) the surface. Among suitable fabrication methods are photolithography, pipetting, drop-touch, piezoelectric printing (ink-jet), or the like. For some typical methods, see Ekins et al. (1999), *Trends in Biotech* 17, 217-218; Healey et al. (1995) *Science* 269, 1078-80; WO95/251116; WO95/35505; and U.S. Pat. No. 5,605,662.

Furthermore, the probes do not have to be directly bound to the substrate, but rather can be bound to the substrate through a linker group. The linker groups are typically about 6 to 50 atoms long to provide exposure to the attached nucleic acid probe. Preferred linker groups include ethylene glycol oligomers, diamines, diacids and the like. Reactive groups on the substrate surface react with one of the terminal portions of the linker to bind the linker to the substrate. The other terminal portion of the linker is then functionalized for binding the nucleic acid probe.

A composition of the invention may comprise, optionally, nucleic acids (or polypeptides, or antibodies) that act as internal controls. The controls may be positive controls or negative controls, examples of which will be evident to the skilled worker.

In order to conduct an analysis of expressed genes, a sample representing expressed target genes (polynucleotides or polypeptides) is first derived from a rectal adenocarcinoma. As used herein, “polynucleotide” refers to a target whose expression is analyzed, whereas “nucleic acid” refers to a composition (of probes) used to analyze the expression of the polynucleotides. The sample can be derived from any bodily fluid (blood, urine, saliva, phlegm, gastric juices, etc.), from stool samples, or from cultured cells. Preferably, the sample is derived from rectal biopsy tissue. Because rectal adenocarcinoma cells can also be present in peripheral blood, blood samples may also be used.

DNA or RNA can be isolated according to any of a number of methods well known to those of skill in the art. For example, methods of purification of nucleic acids are described in Laboratory Techniques in Biochemistry and Molecular Biology: Hybridization With Nucleic Acid Probes, Part I. Theory and Nucleic Acid Preparation, P. Tijssen, ed. Elsevier, New York, N.Y. (1993). In one case, total RNA is isolated using the TRIZOL total RNA isolation reagent (Life Technologies, Gaithersburg, Md.) and mRNA is isolated using oligo d(T) column chromatography or glass beads. Alternatively, when target polynucleotides are derived from an mRNA, the target polynucleotide can be a cDNA reverse transcribed from an mRNA, an RNA transcribed from that cDNA, a DNA amplified from that cDNA, an RNA transcribed from the amplified DNA, or the like. When the target polynucleotide is derived from DNA, the target polynucleotide can be DNA amplified from DNA or RNA reverse transcribed from DNA. In yet another alternative, the targets are target polynucleotides prepared by more than one method. Accordingly, a polynucleotide sample “representing expressed genes” can comprise, e.g., mRNA, cRNA, cDNA, PCR products, or the like.

When target polynucleotides are amplified it is desirable to amplify the polynucleotide and maintain the relative abundances of the original sample, including low abundance transcripts. Total mRNA can be converted to cDNA and amplified by conventional procedures. For example, in one embodiment, mRNA is amplified by reverse transcription using a reverse transcriptase and a primer consisting of oligo d(T) and a sequence encoding the phage T7 promoter to provide a single stranded DNA template. The second cDNA strand is polymerized using a DNA polymerase and a RNAse which assists in breaking up the DNA/RNA hybrid. After synthesis of the double stranded cDNA, T7 RNA polymerase can be added and RNA transcribed from the second cDNA strand template (Van Gelder et al. U.S. Pat. No. 5,545,522). RNA can be amplified in vitro, in situ or in vivo (See Eberwine, U.S. Pat. No. 5,514,545). A cDNA may be amplified by any of a variety of conventional amplification procedures, including PCR. Suitable PCR primers can be selected using routine, any-recognized methods. For guidance with regard to designing suitable primers and other facets of PCR methodology, see Innes et al. eds. *PCR Protocols: a guide to methods and applications,* 1990, Academic Press, San Diego, Calif. or other standard references or manuals.

It is advantageous to include quantitation controls within the sample to assure that amplification and labeling procedures do not change the true distribution of target polynucleotides in a sample. For this purpose, a sample can be spiked with a known amount of a control target polynucleotide and the composition of nucleic acid probes can include reference nucleic acid probes which specifically hybridize with the control target polynucleotides. After hybridization and processing, the hybridization signals obtained should reflect accurately the amounts of control target polynucleotide added to the sample.

Prior to hybridization, it may be desirable to fragment the target polynucleotides. Fragmentation improves hybridization by minimizing secondary structure and cross-hybridization to other nucleic acid target polynucleotides in the sample or noncomplementary nucleic acid probes. Fragmentation can be performed by mechanical, enzymatic or chemical means.

The target polynucleotides may be labeled with one or more labeling moieties to allow for detection of hybridized probe/target polynucleotide complexes. The labeling moieties can include compositions that can be detected by spectroscopic, photochemical, biochemical, bioelectronic, immunochemical, electrical, optical or chemical means. The labeling moieties include radioisotopes, such as $^{32}P$, $^{33}P$ or $^{35}S$, chemilumninescent compounds, labeled binding proteins, heavy metal atoms, spectroscopic markers, such as fluorescent markers and dyes, magnetic labels, linked enzymes, mass spectrometry tags, spin labels, electron transfer donors and acceptors, and the like. In a preferred embodiment, a fluorescent dye is incorporated directly by using a fluorochrome conjugated nucleotide triphosphate (e.g. Cy3-dUTP) or through a secondary coupling reaction by first incorporating an amino allyl conjugated nucleotide triphosphate (e.g. amino allyl-dUTP) followed by chemical coupling of the fluorochrome (e.g. NHS-Cy3).

Exemplary dyes include quinoline dyes, triarylmethane dyes, phthaleins, azo dyes, cyanine dyes and the like. Preferably, fluorescent markers absorb light above about 300 nm, preferably above 400 nm, and usually emit light at wavelengths at least greater than 10 nm above the wavelength of the light absorbed. Specific preferred fluorescent markers include fluorescein, phycoerythrin, rhodamine, lissamine, and Cy3 and Cy5 available from Amersham Pharmacia Biotech (Piscataway, N.J.).

Labeling can be carried out during an amplification reaction, such as polymerase chain and in vitro transcription reactions, or by nick translation or 5' or 3'-end-labeling reactions. In one case, labeled nucleotides are used in an in vitro transcription reaction. When the label is incorporated after or without an amplification step, the label is incorporated by using terminal transferase or by kinasing the 5' end of the target polynucleotide and then incubating overnight with a labeled oligonucleotide in the presence of T4 RNA ligase.

Alternatively, the labeling moiety can be incorporated after hybridization once a probe/target complex has formed. In one case, biotin is first incorporated during an amplification step as described above. After the hybridization reaction, unbound polynucleotides are rinsed away so that the only biotin remaining bound to the substrate is that attached to target polynucleotides that are hybridized to the nucleic acid probes. Then, an avidin-conjugated fluorophore, such as avidin-phycoerythrin, that binds with high affinity to biotin is added. In another case, the labeling moiety is incorporated by intercalation into preformed target/polynucleotide probe complexes. In this case, an intercalating dye such as a psoralen-linked dye can be employed.

Under some circumstances it may be advantageous to immobilize the target polynucleotides on a substrate and have the nucleic acid probes bind to the immobilized target polynucleotides. In such cases the target polynucleotides can be attached to a substrate as described above.

Hybridization causes a denatured nucleic acid probe and a denatured complementary target polynucleotide to form a stable duplex through base pairing. Hybridization methods are well known to those skilled in the art (See, for example, Laboratory Techniques in Biochemistry and Molecular Biology, Vol. 24: Hybridization With Nucleic Acid Probes, P. Tijssen, ed. Elsevier, New York, N.Y. (1993)). Conditions can be selected for hybridization where exactly complementary target and nucleic acid probe can hybridize, i.e., each base pair must interact with its complementary base pair. Alternatively, conditions can be selected where target and probes have mismatches but are still able to hybridize. Suitable conditions can be selected, for example, by varying the concentrations of salt or formamide in the prehybridization, hybridization and wash solutions, or by varying the hybridization and wash temperatures.

Hybridization can be performed at low stringency with buffers, such as 6×SSPE with 0.005% Triton X-100 at 37° C., which permits hybridization between target and polynucleotide probes that contain some mismatches to form target polynucleotide/probe complexes. Subsequent washes are performed at higher stringency with buffers, such as 0.5× SSPE with 0.005% Triton X-100 at 50° C., to retain hybridization of only those target/probe complexes that contain exactly complementary sequences. Alternatively, hybridization can be performed with buffers, such as 5×SSC/0.2% SDS at 60° C., and washes performed in 2×SSC/0.2% SDS and then in 0.1×SSC. Stringency can also be increased by adding agents such as formamide. Background signals can be reduced by the use of detergent, such as sodium dodecyl sulfate, Sarcosyl or Triton X-100, or a blocking agent, such as sperm DNA or bovine serum albumin (BSA).

In a preferred embodiment, nucleic acid probes of the invention hybridize specifically to target polynucleotides of interest under conditions of high stringency. As used herein, "conditions of high stringency" or "high stringent hybridization conditions" means any conditions in which hybridization will occur when there is at least about 95%, preferably about 97 to 100%, nucleotide complementarity (identity) between the nucleic acids (e.g., a polynucleotide of interest and a nucleic acid probe). Generally, high stringency conditions are selected to be about 5° C. to 20° C. lower than the thermal melting point ($T_m$) for the specific sequence at a defined ionic strength and pH. Appropriate high stringent hybridization conditions include, e.g., hybridization in a buffer such as, for example, 6×SSPE-T (0.9 M NaCl, 60 mM $NaH_2PO_4$, 6 mM EDTA and 0.05% Triton X-100) for between about 10 minutes and about at least 3 hours (in a preferred embodiment, at least about 15 minutes) at a temperature ranging from about 4° C. to about 37° C.). In a most preferred embodiment, hybridization under high stringent conditions is carried out in 5×SSC, 50% dionized Formamide, 0.1% SDS at 42° C. overnight.

Hybridization specificity can be evaluated by comparing the hybridization of specificity-control nucleic acid probes to specificity-control target polynucleotides that are added to a sample in a known amount. The specificity-control target polynucleotides may have one or more sequence mismatches compared with the corresponding nucleic acid probes. In this manner, whether only complementary target polynucleotides are hybridizing to the nucleic acid probes or whether mismatched hybrid duplexes are forming is determined.

Hybridization reactions can be performed in absolute or differential hybridization formats. In the absolute hybridization format, target polynucleotides from one sample are hybridized to the probes in an array (e.g., in a microarray format) and signals detected after hybridization complex formation correlate to target polynucleotide levels in a sample. In the differential hybridization format, the differential expression of a set of genes in two biological samples is analyzed. For differential hybridization, target polynucleotides from both biological samples are prepared and labeled with different labeling moieties. A mixture of the two labeled target polynucleotides is added to an array (e.g., a microarray). The array is then examined under conditions in which the emissions from the two different labels are individually detectable. Probes in the array that are hybridized to substantially equal numbers of target polynucleotides derived from both biological samples give a distinct combined fluorescence (Shalon et al. PCT publication WO95/35505). In a preferred embodiment, the labels are fluorescent labels with distinguishable emission spectra, such as a lissamine conjugated nucleotide analog and a fluorescein conjugated nucleotide-analog. In another embodiment Cy3/Cy5 fluorophores (Amersham Pharmacia Biotech) are employed.

After hybridization, the array (e.g., microarray) is washed to remove nonhybridized polynucleotides and complex formation between the hybridizable array elements and the target polynucleotides is detected. Methods for detecting complex formation are well known to those skilled in the art. In a preferred embodiment, the target polynucleotides are labeled with a fluorescent label and levels and patterns of fluorescence indicative of complex formation are measured. In one embodiment, the measurement is accomplished by fluorescence microscopy, preferably confocal fluorescence microscopy. An argon ion laser excites the fluorescent label, emissions are directed to a photomultiplier and the amount of emitted light detected and quantitated. The detected signal should be proportional to the amount of probe/target polynucleotide complex at each position of the microarray. The fluorescence microscope can be associated with a computer-driven scanner device to generate a quantitative two-dimensional image of hybridization intensity. The scanned image is examined to determine the abundance/expression level of each hybridized target polynucleotide. In another embodiment, the measurement of levels and patterns of fluorescence is accomplished with a fluorescent imaging device, such as a microarray scanner (e.g., Axon scanner with GenePix Pro software). As with the previous measurement method, the measurements can be used to determine the abundance/expression level of each hybridized target polynucleotide.

In a differential hybridization experiment, target polynucleotides from two or more different biological samples are labeled with two or more different fluorescent labels with different emission wavelengths. Fluorescent signals are detected separately with different photomultipliers set to detect specific wavelengths. The relative abundances/expression levels of the target polynucleotides in two or more samples is obtained.

Typically, array fluorescence intensities can be normalized to take into account variations in hybridization intensities when more than one array is used under similar test conditions. In a preferred embodiment, individual probe/target complex hybridization intensities are normalized using the intensities derived from internal normalization controls contained on each microarray.

Other methods for quantitating the amount of an expressed nucleic acid (e.g., an expressed mRNA) corresponding to a molecular marker of interest of the invention will be evident to the skilled worker. For example, any of a variety of quantitative amplification procedures, such as quantitative PCR, can be carried out. Methods for selecting suitable amplification primers, based on the sequences disclosed herein, for optimizing amplification conditions, and for detecting and quantitating the amplified product, are conventional. Some such procedures are discussed herein with reference to amplifying nucleic acid samples in preparation for hybridization assays.

Other aspects of the invention relate to methods for determining the responsiveness of a rectal adenocarcinoma to radiochemotherapy, comprising detecting the presence of, and/or quantitating the amount of, one or more protein (polypeptide) products whose expression is correlated with the responsiveness. The terms “protein” and “polypeptide” are used interchangeably herein.

Polypeptides whose expression is measured include those comprising SEQ ID NOs: 59-112.

The presence or quantity of the protein product in a body fluid, a stool sample, or, preferably, in a tissue or cell sample from the subject, is determined, and compared to a baseline value.

Methods of preparing samples (e.g., from patients) for polypeptide analysis are conventional and well-known in the art, and a variety of methods known to skilled workers can be used to determine the amount of these proteins. For example, enzymatic activities of the proteins can be measured, using conventional procedures. Alternatively, the proteins can be detected by immunological methods such as, e.g., immunoassays (EIA), radioimmunoassay (RIA), immunofluorescence microscopy, or immunohistochemistry, all of which assay methods are fully conventional. See, e.g., U.S. Pat. No. 6,602,661.

The invention includes antibodies which are specific for polypeptides comprising SEQ ID NOs: 59-112, or for active variants or fragments of these polypeptides. An “active” variant or fragment of a polypeptide of the invention is one which is able to bind to, or to elicit, an antibody that is specific for a polypeptide corresponding to one of genes 1-54. For example, polypeptides comprising small substitutions, additions, deletions, etc, are tolerated provided they retain the ability to elicit a desired antibody, as are suitable antigenic fragments of the polypeptides. Antigens that exhibit at least about 90% (e.g., at least about 95%, or at least about 98%) sequence identity to a polypeptide comprising one of SEQ ID NOs: 59-112, or to a fragment thereof, are also tolerated. Methods for determining if a polypeptide exhibits a particular percent identity to a polypeptide comprising, e.g., one of SEQ ID NOs: 59-112 are conventional; algorithms such as those discussed elsewhere herein in regard to nucleic acids can be used.

In a preferred embodiment, antibodies of the invention are immobilized on a surface (e.g., are reactive elements on an array, such as a microarray, or are on another surface, such as used for surface plasmon resonance (SPR)-based technology [e.g., Biacore]), and polypeptides in the sample are detected by virtue of their ability to bind specifically to the antibodies. Methods of preparing the surfaces and performing the analyses are conventional.

Any of a variety of antibodies can be used in methods of the invention. Such antibodies include, e.g., polyclonal, monoclonal (mAbs), recombinant, humanized or partially humanized, single chain, Fab, and fragments thereof. The antibodies can be of any isotype, e.g., IgM, various IgG isotypes such as $IgG_1$, $IgG_{2a}$, etc., and they can be from any animal species that produces antibodies, including goat, rabbit, mouse, chicken or the like. An antibody “specific for” a polypeptide means that the antibody recognizes a defined sequence of amino acids, or epitope, either present in the full length polypeptide or in a peptide fragment thereof.

Antibodies can be prepared according to conventional method, which are well known, e.g. Green et al., Production of Polyclonal Antisera, in *Immunochemical Protocols* (Manson, ed.), (Humana Press 1992); Coligan et al., in *Current Protocols in Immunology*, Sec. 2.4.1 (1992); Kohler & Milstein (1975), *Nature* 256, 495; Coligan et al., sections 2.5.1-2.6.7; and Harlow et al., Antibodies: A Laboratory Manual, page 726 (Cold Spring Harbor Laboratory Pub. 1988). Methods of preparing humanized or partially humanized antibodies, and antibody fragments, and methods of purifying antibodies, are conventional.

The molecular profiling information described herein can be harnessed for the purpose of identifying agents (e.g., drugs) that can enhance (increase, facilitate, potentiate, etc.) the response of a rectal adenocarcinoma to radiochemotherapy. Such agents are particularly useful when administered, as therapeutic agents, in conjunction with radiochemotherapy, in order to enhance the effect of the radiochemotherapy. For example, the agents can be administered to a subject before, during or after radiochemotherapy is carried out. Agents are selected which enhance expression or activity of one or more genes whose up-regulation is correlated with the responsiveness, and/or which decrease expression and/or activity of one or more genes whose down-regulation is correlated with the responsiveness.

In assays to identify such agents, putative agents are introduced into cells, and either polynucleotide expression or activity levels, or polypeptide expression or activity levels, are measured. The expression and/or activity levels of polynucleotides or polypeptides corresponding to marker genes of the invention are determined. Preferably, the methods are carried out in vitro, with cultured cells or with tumor tissue, and employ high throughput procedures. Candidate agents selected in this manner can then be tested further in vivo.

In one embodiment, rectal adenocarcinoma cell lines are prepared from tumors that are either responsive or non-responsive to radiochemotherapy, using standard methods, and are profiled using the present methods. Preferred cell lines are those that maintain the expression profile of the primary tumor from which they were derived. One or several such cell lines may be used as a “general” panel; alternatively or additionally, cell lines from individual subjects may be prepared and used. In other embodiments, previously established rectal adenocarcinoma cell lines are used, or non-tumor rectal cells, or cells from other normal tissues, are used. A skilled worker can readily select a suitable cell line to use in the method.

The molecular alterations in cell line cells contacted with a putative modulatory agent can be measured at the mRNA level (gene expression) applying conventional methods, such as those disclosed herein. Alternatively, one can assay the protein product(s) or activities of the selected gene(s), using conventional procedures. For example, in the case of secreted or cell-surface proteins, expression can be assessed using immunoassay or other immunological methods including enzyme immunoassays (EIA), radioimmunoassay (RIA), immunofluorescence microscopy or flow cytometry. EIAs are described in greater detail in several references (Butler, J E, In: *Structure of Antigens*, Vol. 1 (Van Regenmortel, M., CRC Press, Boca Raton 1992, pp. 209-259; Butler, J E, "ELISA," In: van Oss, C. J. et al. (eds), *Immunochemistry*, Marcel Dekker, Inc., New York, 1994, pp. 759-803; Butler, J E (ed.), *Immunochemistry of Solid-Phase Immunoassay*, CRC Press, Boca Raton, 1991). RIAs are discussed in Kirkham and Hunter (eds.), *Radioimmune Assay Methods*, E. & S. Livingstone, Edinburgh, 1970. Preferably, polypeptide samples are contacted with antibody compositions of the invention that are in the form of an array, such as a microarray, and are analyzed as described elsewhere herein.

Without wishing to be bound by any particular mechanism, it is suggested that, among the types of agents that can be tested and identified as therapeutic agents are, e.g., agents that (1) act on a cellular pathway that inhibits or stimulates expression of a gene of interest, (2) act directly on the protein product, or (3) bypass the step in a cellular pathway mediated by the product of this gene.

A variety of types of agents can be tested and identified as the desired agents.

For example, one can utilize known properties of a target protein to devise agents to stimulate or inhibit its production or activity, as desired. That is, one can devise a means to inhibit the action of, or bind, block, remove or otherwise diminish the presence, activity and/or availability of, a protein whose down-regulation is associated with responsiveness to radiochemotherapy; or one can devise a means to stimulate the action of, or to potentiate or enhance the activity of or availability of, a protein whose up-regulation is associated with such responsiveness. For example, in the case of a cellular receptor, one could expose the receptor to an antagonist, a soluble form of the receptor or a "decoy" ligand binding site of a receptor (to compete for ligand) (Gershoni J M et al., (1988) *Proc Natl Acad Sci USA* 85, 4087-9; U.S. Pat. No. 5,770,572) to inhibit it.

Antibodies may be administered to a cell to bind and inactivate (or compete with), or to enhance the activity of, secreted protein products or expressed cell-surface products of genes of interest.

Another approach is to employ antisense oligonucleotides or nucleic acid constructs that inhibit expression of a gene whose down-regulation is desired, in a highly specific manner. Methods to select, test and optimize putative antisense sequences are routine. In one embodiment, nucleic acid constructs are used to express an antisense molecule of interest. Methods to operatively link appropriate antisense sequences to an appropriate regulatory element, e.g., a promoter, such as a strong promoter, an inducible strong promoter, or the like. Inducible promoters include, e.g., an estrogen inducible system (Braselmann et al. (1993) *Proc Natl Acad Sci USA* 90, 1657-1661). Also known are repressible systems driven by the conventional antibiotic, tetracycline (Gossen et al., (1992) *Proc. Natl. Acad. Sci. USA* 89, 5547-5551).

In another embodiment of inhibition by antisense, antisense oligonucleotides are administered to a cell. The oligonucleotides can be DNA or RNA or chimeric mixtures or derivatives or modified versions thereof, single-stranded or double-stranded. The oligonucleotides can be modified at the base moiety, sugar moiety, or phosphate backbone (as discussed above). The oligonucleotide may include other appending groups such as peptides, or agents facilitating transport across the cell membrane (see, e.g. Letsinger et al. (1989) *Proc. Natl. Acad. Sci. USA* 84, 684-652; PCT Publication WO 88/09810 (1988)), hybridization-triggered cleavage agents (e.g. Krol et al. (1988), *BioTechniques* 6, 958-976) or intercalating agents (e.g., Zon (1988), *Pharm. Res* 5, 539-549).

Multiple antisense constructs or oligonucleotides specific for different genes can be employed together. The sequences of the downregulated genes described herein can be used to design the antisense molecules (Hambor et al., (1988) *J. Exp. Med.* 168, 1237-1245; Holt et al., (1986) *Proc. Nat'l. Acad. Sci.* 83, 4794-4798; Izant et al., (1984) *Cell* 36, 1007-1015); Izant et al., (1985) *Science* 229, 345-352; De Benedetti et al., (1987) *Proc. Natl. Acad. Sci. USA,* 84, 658-662). The antisense sequences may range from about 6 to about 50 nucleotides, and may be as large as 100 or 200 nucleotides, or larger. They may correspond to full-length coding sequences and/or may be genomic sequences that comprise non-coding sequences.

Another approach is to use ribozymes that can specifically cleave nucleic acids encoding the overexpressed genes of the invention. Such methods are routine in the art and methods of making and using any of a variety of appropriate ribozymes are well known to the skilled worker. For reviews on ribozymes see e.g., Ohkawa et al. (1995) *J. Biochem.* 118, 251-258; Sigurdsson et al. (1995) *Trends Biotechnol.* 13, 286-289; Rossi, J. J. (1995) *Trends Biotechnol.* 13, 301-306; Kiehntopf et al. (1995) *J. Mol. Med.* 73, 65-71). A ribozyme having specificity for an mRNA of interest can be designed based upon the nucleotide sequence of, e.g., the corresponding cDNA. For example, a derivative of a Tetrahymena L-19 IVS RNA can be constructed in which the base sequence of the active site is complementary to the base sequence to be cleaved in an mRNA corresponding to one of the overexpressed genes of the invention. See for example U.S. Pat. Nos. 4,987,071 and 5,116,742, both by Cech et al. Alternatively, the sequence of an overexpressed gene of the invention can be used to select a catalytic RNA having a specific ribonuclease activity from a pool of RNA molecules. See for example Bartel et al. (1993) *Science* 261, 1411-1418.

Another approach involves double stranded RNAs called small interfering RNAs. An siRNA is a double-stranded RNA molecule comprising self-complementary sense and antisense regions, wherein the antisense region comprises nucleotide sequence that is complementary to nucleotide sequence in a target nucleic acid molecule or a portion thereof, and the sense region has a nucleotide sequence corresponding to the target nucleic acid sequence or a portion thereof. The siRNA can be assembled from two separate oligonucleotides, where one strand is the sense strand and the other is the antisense strand, wherein the antisense and sense strands are self-complementary. The siRNA can be assembled from a single oligonucleotide, where the self-complementary sense and antisense regions of the siRNA are linked by means of a nucleic acid based or non-nucleic acid-based linker(s). The siRNA can be a polynucleotide with a hairpin secondary structure, having self-complementary sense and antisense regions. The siRNA can be a circular single-stranded polynucleotide having two or more loop structures and a stem comprising self-complementary sense and antisense regions, wherein the circular polynucleotide can be processed either in vivo or in vitro to generate an active siNA molecule capable of mediating RNAi. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions.

RNAi molecules can be used to inhibit gene expression, using conventional procedures. Typical method to design, make and use interfering RNA molecules are described, e.g., in U.S. Pat. No. 6,506,559, Lau et al. (2003) *Scientific American*, pp. 34-41; McManus et al. (2002) *Nature Reviews Genetics* 3, 737-747; Dykxhoorn et al. (2003) *Nature Reviews Molecular Cell Biology* 4, 457-467; Allshire (2002) *Science* 297, 1818-1819; Volpe et al. (2002) *Science* 297, 1833-1837; Jenuwein (2002) *Science* 297, 2215-2218; Hall et al. (2002) *Science* 297 2232-2237; Hutvagner et al. (2002) *Science* 297, 2056-60; McManus et al. (2002) *RNA* 8, 842-850; Reinhart et al. (2002) *Gene & Dev.* 16, 1616-1626; Reinhart et al. (2002) *Science* 297, 1831; Fire et al. (1998) *Nature* 391, 806-811, Moss (2001) *Curr Biol* 11, R772-5, Brummelkamp et al. (2002) *Science* 296, 550-3; Bass (2001) *Nature* 411 428-429; and Elbashir et al. (2001) *Nature* 411, 494-498; U.S. Pat. No. 6,506,559; US patent application 20030206887; and PCT applications WO99/07409, WO99/32619, WO 00/01846, WO 00/44914, WO00/44895, WO01/29058, WO01/36646, WO01/75164, WO01/92513, WO 01/29058, WO01/89304, WO01/90401, WO02/16620, and WO02/29858.

For guidance on methods to design interfering RNA molecules, see, e.g., Vickers et al. (2003) *J Biol Chem* 278, 7108-7118 and Yang et al. (2003) *Proc Natl Acad Sci USA* 99, 9942-9947. For methods to make siRNAs, see e.g. Tuschl et al. (1999) *Genes & Dev.* 13, 3191-3197; Kawasaki et al. (2003) *Nucleic Acids Res* 31, 700-707; Miyagishi et al. (2003) *Nature Biotechnol* 20, 497-500; Lee et al. (2002) *Nature Biotechnol* 20, 500-505, Brummelkamp et al. (2002) *Science* 296, 550-553; McManus et al. (2002) *RNA* 8, 842-850; Paddison et al. (2002a) *Gene Dev* 16, 948-958; Paddison et al. (2002b) *Proc Natl Acad Sci USA* 99, 1443-1448); Paul et al. (2002) *Nature Biotechnol* 20, 505-508; Sui et al. (2002) *Proc Natl Acad Sci USA* 99, 5515-5520; and Yu et al. (2002) *Proc Natl Acad Sci USA* 99, 6047-6052. For methods to use siRNAs to inhibit expression, see e.g. Hannon (2002) *Nature* 418, 244-251; Bernstein et al. (2002) *RNA* 7, 1509-1521; Hutvagner et al., *Curr. Opin. Genetics & Development* 12, 225-232; Brummelkamp (2002) *Science* 296, 550-553; Lee et al. (2002) *Nature Biotechnol* 20, 500-505; Miyagishi et al. (2002) *Nature Biotechnol.* 20, 497-500; Paddison et al. (2002) *Genes & Dev* 16, 948-958; Paul et al. (2002) *Nature Biotechnol.* 20, 505-508; Sui et al. (2002) *Proc. Natl. Acad. Sci. USA* 99, 5515-5520; and Yu et al. (2002) *Proc. Natl. Acad. Sci. USA* 99, 6047-6052.

Another approach is to use small molecules (sometimes referred to herein as "compounds"). They may be isolated from natural sources or developed synthetically, e.g., by combinatorial chemistry. In general, such molecules are identified from large libraries of natural products or synthetic (or semi-synthetic) extracts or chemical libraries according to methods known in the art. Those skilled in the field of drug discovery and development will understand that the precise source of test extracts or compounds is not critical to the methods of the invention. Accordingly, virtually any number of chemical extracts or compounds can be used in the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon Associates (Merrimack, N.H.) and Aldrich Chemical (Milwaukee, Wis.).

Alternatively, libraries of natural compounds in the form of bacterial, fungal, plant, and animal extracts are commercially available from a number of sources, e.g., Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

Once a molecule has been identified in vitro as a candidate agent that increases the responsiveness of a rectal adenocarcinoma to radiochemotherapy, one can further determine in vivo if the candidate does, in fact, increase the responsiveness in a subject. Furthermore, if a candidate agent is shown to inhibit or stimulate expression or activity of several genes whose expression is correlated with the responsiveness, one can inhibit or stimulate the expression of each of the genes individually, in vivo, in order to determine those genes whose expression is correlated to the responsiveness.

The candidate agent(s) can be introduced into any suitable animal model for rectal carcinoma. Eventually, agents that have been shown to be safe and effective in animal models can be tested and used in human patients.

Methods for introducing agents into cells or animals are conventional. For example, methods of gene transfer can be used, wherein antisense molecules, ribozymes, or siRNAs are introduced into a rectal adenocarcinoma cell, tissue or organ of interest, or nucleic acids that encode proteins which modulate (up-regulate or down-regulate) the production or activity of one or more of the genes of the invention are so introduced. Methods of gene transfer are conventional, and include virus-mediated gene transfer, for example, with retroviruses (Nabel et al. (1989) *Science* 244, 1342), lentiviruses, and recombinant adenovirus vectors (Horowitz, M. S., In: *Virology*, Fields, B N et al, eds, Raven Press, New York, 1990, p. 1679, or current edition; Berkner (1988) *Biotechniques* 6, 616-29, Strauss, S E, In: *The Adenoviruses*, Ginsberg, H S, ed., Plenum Press, New York, 1984, or current edition). Adeno-associated virus (AAV) can also be used (Samulski et al. (1991) *EMBO J.* 10, 3941 (1991); Lebkowski et al. (1988) *Mol. Cell. Biol.* 8, 3988-3996; Kotin et al. (1990), *Proc. Natl. Acad. Sci. USA* 87, 2211-2215; Hermonat et al. (1984), *J. Virol.* 51, 329-339). Improved efficiency is attained by the use of promoter enhancer elements in the DNA constructs (Philip et al. (1993), *J. Biol. Chem.* 268, 16087-16090).

In addition to virus-mediated gene transfer, physical means well-known in the art can be used for direct gene transfer, including administration of plasmid DNA (Wolff et al., 1990, supra) and particle-bombardment mediated gene transfer, originally described in the transformation of plant tissue (Klein et al. (1987), *Nature* 327, 70 (1987); Christou, et al. (1990), *Trends Biotechnol.* 6, 145) but also applicable to mammalian tissues in vivo, ex vivo or in vitro (Yang et al. (1990), *Proc. Natl. Acad. Sci. USA* 87, 9568 (1990); Williams et al. (1991), *Proc. Natl. Acad. Sci. USA* 88, 2726; Zelenin et al. (1991), *FEBS Lett.* 280, 94; Zelenin et al. (1989), *FEBS Lett.* 244, 65; Johnston et al (1991), *In Vitro Cell. Dev. Biol.* 27, 11). Furthermore, electroporation or calcium phosphate transfection, both well-known means to transfer genes into cell in vitro, can also be used to transfer DNA molecules according to the present invention to tissues in vivo (Pear et al. (1993) *Proc. Natl. Acad. Sci. USA* 90, 8392; Titomirov et al. (1991), *Biochim. Biophys. Acta* 1088, 131).

Gene transfer can also be achieved using "carrier mediated gene transfer" (Wu et al. (1989), *J. Biol. Chem.* 264, 16985; Wu et al. (1988), *J. Biol. Chem.* 263, 14621; Soriano et al. (1983), *Proc. Natl. Acad. Sci. USA* 80, 7128; Wang et al. (1982), *Proc. Natl. Acad. Sci. USA* 84, 7851; Wilson et al. (1992), *J. Biol. Chem.* 267, 963). Preferred carriers are targeted liposomes (Nicolau et al. (1983), *Proc. Natl. Acad Sci. USA* 80, 1068 (1983); Soriano et al., supra) such as immunoliposomes, which can incorporate acylated monoclonal antibodies into the lipid bilayer (Wang et al., supra), or polycations such as asialoglycoprotein/polylysine (Wu et al., 1989, supra). Liposomes have been used to encapsulate and deliver a variety of materials to cells, including nucleic acids and viral particles (Faller et al (1984), *J. Virol.* 49, 269-272).

Preformed liposomes that contain synthetic cationic lipids form stable complexes with polyanionic DNA (Felgner et al. (1987), *Proc. Natl. Acad. Sci. USA* 84, 7413-7417). Cationic liposomes, liposomes comprising some cationic lipid, that contained a membrane fusion-promoting lipid dioctadecyldimethyl-ammonium-bromide (DDAB) have efficiently transferred heterologous genes into eukaryotic cells (Rose et al. (1991), *Biotechniques* 10, 520-525). Cationic liposomes can mediate high level cellular expression of transgenes, or mRNA, by delivering them into a variety of cultured cell lines (Malone et al. (1989), *Proc. Natl. Acad. Sci. USA* 86, 6077-6081).

Another embodiment of the invention is a method for identifying a gene whose inhibition (e.g., inhibition of nucleic acid expression or activity, or inhibition of polypeptide synthesis or activity) enhances the response of a rectal tumor to radiochemotherapy. For example, one can test one or more of the genes of the invention whose over-expression is correlated with responsiveness of a rectal adenocarcinoma to radiochemotherapy (e.g., genes 1-41). The method can be carried out in vitro, but is preferably carried out in vivo, in a suitable animal model. In one embodiment, the method comprises:

a. inhibiting (completely or partially, using agents such as those discussed elsewhere herein) in a rectal adenocarcinoma the expression and/or activity of a polynucleotide corresponding to one of genes 1-41 (e.g., a polynucleotide that hybridizes specifically to a nucleic acid comprising one of SEQ ID NOs: 1-41 or 113-119, and/or to a fragment that comprises at least about 15 contiguous nucleotides of one of those sequences; or to a complement of one of those fragments); or inhibiting the synthesis and/or activity of a polypeptide corresponding to one of genes 1-41 (e.g., a polypeptide that binds specifically to an antibody of the invention, such as an antibody specific for one of polypeptides comprising SEQ ID NOs: 59-101, and/or for an antigenic fragment of one of those polypeptides), and b. determining if the rectal adenocarcinoma exhibits an increased response to radiochemotherapy, compared to the response in the absence of the inhibition.

Another embodiment of the invention is a method for identifying a gene whose stimulation (e.g., stimulation of nucleic acid expression or activity, or stimulation of polypeptide synthesis or activity) enhances the response of a rectal tumor to radiochemotherapy, comprising:

a. stimulating (completely or partially, using agents such as those discussed elsewhere herein) in a rectal adenocarcinoma the expression and/or activity of a polynucleotide corresponding to one of genes 42-54 (e.g., a polynucleotide that hybridizes specifically to a nucleic acid comprising one of SEQ ID NOs: 46-58 or 120-123, and/or to a fragment that comprises at least about 15 contiguous nucleotides of one of those sequences, or to a complement of one of those nucleic acids or fragments); or inhibiting the synthesis and/or activity of a polypeptide corresponding to one of genes 42-54 (e.g., a polypeptide that binds specifically to an antibody of the invention, such as an antibody specific for a polypeptide comprising one of SEQ ID NOs: 102-112, and/or for an antigenic fragment of one of those polypeptides), and b. determining if the rectal adenocarcinoma exhibits an increased response to radiochemotherapy, compared to the response in the absence of the stimulation.

Other aspects of the invention are kits suitable for performing any of the methods of the invention.

One embodiment of the invention is a kit for detecting the presence and/or amount of a polynucleotide in a sample from a rectal adenocarcinoma, which may indicate that the rectal adenocarcinoma is responsive to radiochemotherapy, comprising a composition of nucleic acids of the invention (e.g., in the form of an array) and, optionally, one or more reagents that facilitate hybridization of the nucleic acids in the composition to a test polynucleotide of interest, and/or that facilitate detection of the hybridized polynucleotide(s), e.g., that facilitate detection of fluorescence. The kit may comprise a composition of nucleic acids of the invention (e.g., in the form of an array), means for carrying out hybridization of the nucleic acids in the array to a test polynucleotide(s) of interest, and means for reading hybridization results. Hybridization results may be units of fluorescence.

Another embodiment is a kit for detecting the presence and/or amount of a polypeptide in a sample from a rectal adenocarcinoma, which may indicate that the rectal adenocarcinoma is responsive to radiochemotherapy, comprising a composition of antibodies of the invention (e.g., in the form of an array) and, optionally, one or more reagents that facilitate binding of the antibodies in the composition with a test protein(s) of interest, or that facilitate detection of bound antibody. The kit may comprise a composition of antibodies of the invention (e.g., in the form of an array or a Biacore chip), means for carrying out binding of the antibodies in the array to a test polypeptide(s) of interest, and means for reading the binding results.

Kits of the invention may comprise instructions for performing a method, such as a diagnostic method. Other optional elements of a kit of the invention include suitable buffers, media components, or the like; a computer or computer-readable medium for storing and/or evaluating the assay results; containers; or packaging materials. Reagents for performing suitable controls may also be included. The reagents of the kit may be in containers in which the reagents are stable, e.g., in lyophilized form or stabilized liquids. The reagents may also be in single use form, e.g., in single reaction form for diagnostic use.

The present invention also relates to combinations of the invention in which the nucleic acid or protein sequences of the invention are represented, not by physical molecules, but by computer-implemented databases. For example, the present invention relates to electronic forms of polynucleotides, polypeptides, antibodies, etc., of the present invention, including a computer-readable medium (e.g., magnetic, optical, etc., stored in any suitable format, such as flat files or hierarchical files) which comprise such sequences, or fragments thereof, e-commerce-related means, etc. An investigator may, e.g., compare an expression profile exhibited by a rectal adenocarcinoma sample of interest to an electronic form of one of the expression profiles of the invention, and may thereby determine its responsiveness to radiochemotherapy.

Having now generally described the invention, the same will be more readily understood through reference to the following examples which are provided by way of illustration, and are not intended to be limiting of the present invention, unless specified. In the foregoing and in the following examples, all temperatures are set forth uncorrected in degrees Celsius; and, unless otherwise indicated, all parts and percentages are by weight.

EXAMPLES

Example I

Patients and Methods

A. Selection of Patients and Response Classification

All patients are participants in a multicenter, randomized prospective phase III clinical trial (CAO/ARO/AIO-94, German Rectal Cancer Trial) aimed at determining the relative benefits of preoperative (neoadjuvant) versus postoperative (adjuvant) radiochemotherapy (Sauer et al. (2001) Strahlenther Onkol 177, 173-81). For the study here, we collected biopsies from 23 patients between December 2001 to October 2002 who were assigned to the neoadjuvant treatment arm adhering to the guidelines set by the local ethical review board. Pre-therapeutic staging was performed including complete medical history and physical evaluation, digital rectal examination, endorectal ultrasound, rigid rectoscopy with two tumor biopsies, colonoscopy, abdominal ultrasound, abdominal and pelvic computed tomography and chest X-ray. Endoscopic ultrasound was performed by two experienced surgeons and was based on the degree of tumor infiltration through the rectal wall (T-level) according to standard criteria (Liersch et al. (2003) *Chirurg* 74, 224-34; Adams et al. (1999) *Dis Colon Rectum* 42, 159-66; Glaser et al. (1990) *Br J Surg* 77, 883-7; Hunerbein et al. (2001) *Eur J Ultrasound* 13, 17-23). Only patients with uT-level 3 (n=22) and uT-level 4 (n=1) carcinomas located within 16 cm from the anocutaneous verge were included. The majority of the patients were diagnosed with uUICC III (n=16) carcinomas, and only seven patients were diagnosed as uUICC II. Two pre-therapeutical biopsies were taken from representative, adjacent areas of the tumors one of which was examined by one pathologist. All rectal cancers were histologically diagnosed as adenocarcinomas. The second biopsy was used for RNA extraction. All 23 patients randomly assigned to the neoadjuvant arm received a total dose of 50.4 Gy of radiation accompanied by 5-fluorouracil (5-FU, 1000 mg per $m^2$, days 1-5 and days 28-33) intravenous application. Details of the preoperative treatment modalities were described previously (Sauer et al. (2001) *Strahlenther Onkol* 177, 173-81). Standardized surgery was performed including total mesorectal excision (TME, (Heald et al. (1986) *Lancet* 1, 1479-82)) after an interval of approximately five weeks after radiochemotherapy. The histological workup of surgical specimens was performed according to UICC standards (Sobin L H, Wittekind C. UICC: TNM classification of malignant tumors. 5 ed. New York: John Wiley & Sons, 1997). Tumor response was assessed based on T-level down-sizing (as performed by rectal ultrasound before radiochemotherapy and histomorphologically after surgery). Down-sizing was defined as the reduction of tumor infiltration for at least one T-level. The experimental design is summarized in FIG. 1. We have chosen the T-level classification as the international standard for rectal cancer staging. The clinical data and details of the response classification are summarized in Table 1. Additionally, three matched pairs of preoperative biopsies and resected tumor specimens from patients of the adjuvant treatment arm were analyzed to establish the degree of similarity of the bioptic material and resected specimen.

TABLE 1

| Tumor Samples | uT | ypT | uUICC | ypUICC | uN | ypN | ypN total | ypN infiltrated | M | ypGrading | R |
|---|---|---|---|---|---|---|---|---|---|---|---|
| P1 | 3 | 0 | II | 0 | 0 | 0 | 18 | 0 | 0 | x | 0 |
| P2 | 3 | 0 | III | 0 | 1 | 0 | 27 | 0 | 0 | x | 0 |
| P3 | 3 | 0 | II | 0 | 0 | 0 | 16 | 0 | 0 | x | 0 |
| P4 | 3 | 2 | III | I | 1 | 0 | 22 | 0 | 0 | 2 | 0 |
| P5 | 3 | 1 | II | I | 0 | 0 | 20 | 0 | 0 | 2 | 0 |
| P6 | 3 | 2 | III | I | 1 | 0 | 24 | 0 | 0 | 2 | 0 |
| P7 | 3 | 1 | II | II | 0 | 0 | 18 | 0 | 0 | 2 | 0 |
| P8 | 4 | 3c | III | III | 0 | 1 | 19 | 3 | 0 | 3 | 0 |
| P9 | 3 | 2 | II | I | 0 | 0 | 16 | 0 | 0 | 3 | 0 |
| P10 | 3 | 3b | III | III | 1 | 1 | 30 | 1 | 0 | 2 | 0 |
| P11 | 3 | 3b | III | II | 1 | 0 | 15 | 0 | 0 | 2 | 0 |
| P12 | 3 | 3b | II | III | 0 | 0 | 8 | 1 | 0 | 3 | 0 |
| P13 | 3 | 3b | III | III | 1 | 1 | 27 | 1 | 0 | 2 | 0 |
| P14 | 3 | 4a | III | III | 1 | 1 | 19 | 1 | 0 | 2 | 0 |
| P15 | 3 | 3b | III | II | 1 | 0 | 28 | 0 | 0 | 2 | 0 |
| P16 | 3 | 3a | III | II | 1 | 0 | 21 | 0 | 0 | 2 | 0 |
| P17 | 3 | 3b | III | III | 1 | 1 | 19 | 2 | 0 | 3 | 0 |
| P18 | 3 | 4a | III | III | 1 | 1 | 21 | 2 | 0 | 2 | 0 |
| P19 | 3 | 3c | III | II | 1 | 0 | 24 | 0 | 0 | 3 | 0 |
| P20 | 3 | 3c | II | II | 0 | 0 | 16 | 0 | 0 | 2 | 0 |
| P21 | 3 | 3c | III | II | 1 | 0 | 17 | 0 | 0 | 2 | 0 |
| P22 | 3 | 3a | III | II | 1 | 0 | 14 | 0 | 0 | 2 | 0 |
| P23 | 3 | 4a | III | III | 1 | 1 | 22 | 1 | 0 | 2 | 0 |

Therapy response and clinical data of 23 patients included in this study.

uT, T-level determined by rectal ultrasound; ypT, T-level by histopathological assessment; uUICC, UICC stage by ultrasound; ypUICC, UICC stage by histopathological assessment; uN, lymph node status by ultrasound; ypN, lymph node status by histopathological assessment; ypN total, complete number of analyzed lymph nodes; ypN infiltrated, number of affected lymph nodes; M, distant metastasis; ypGrading, tumor grading by histopathological assessment; R, resectability (O refers to histologically tumor free surgical margins). u: before any treatment, yp: histopathological assessment after neodadjuvant treatment.

B. RNA Isolation and Expression Profiling

Following rectal ultrasound, tumor biopsies were ascertained and stored for later isolation of RNA (Ambion, Austin, Tex.). Tumor material was in the range of 5 mg to 80 mg. RNA extraction was performed using TRIZOL (Invitrogen, Carlsbad, Calif.) following standard procedures. High-quality RNA could be successfully extracted from all samples. In order to generate enough RNA for repeat hybridizations, mRNA was amplified using the RiboAmp RNA amplification kit (Arcturus, Mountain View, Calif.), which resulted in antisense mRNA amounts that averaged 40 μg. cRNA was reverse transcribed into cDNA incorporating aminoallyl-dUTP. Labeled cDNA was purified using Qiagen columns (QIAquick, PCR purification kit, Qiagen, Los Angeles, Calif.), followed by chemical coupling of Cy3 (Amersham, Piscataway, N.J.). Control cRNA was generated by amplification of a universal human reference mRNA pool (Stratagene, La Jolla, Calif.; catalogue number 740000) and labeled as above using Cy5 (Amersham). RNA quantification and labeling efficiency was determined using the Nanodrop quantification device (Nanodrop, Rockland, Del.). Expression profiling was carried out on the NCI-cDNA arrays (9984 genes) as follows: 3.0 μg of Cy3 labeled test cDNA and 3.0 μg of Cy5 labeled control cDNA were hybridized at 42° C. overnight in specifically designed hybridization cassettes (TeleChem International, Inc., Sunnyvale, Calif.). After hybridization, slides were washed and scanned on an Axon scanner using GenePixPro (3.0) software (Axon Instruments, Inc., Union City, Calif.). Background subtraction and normalization was performed when submitting the data to the CIT/NIH-microarray database, mAdb (web site nciarray.nih.gov). Spot quality was assessed according to criteria in GenePixPro (3.0) software. Spots with a small size or low intensity in both the red and green channels were eliminated, as were genes with more than 50% of missing data. This a priori filtering to remove genes with unreliable signals resulted in a final tally of 9059 genes. For each patient sample two independent hybridizations were performed. Correlation coefficients of the technical repeat hybridizations were greater than 0.95, with one exception (P1, correlation coefficient of 0.87).

C. Statistical Analysis

All statistical analyses were done on the BRBArrayTools package for micro-array analysis developed at the Biometric Research Branch of the National Cancer Institute (Simon R, Peng A. BRB ArrayTools, 2003). BRBArrayTools can be obtained from the web site linus.nci.nih.gov/BRB-ArrayTools.html. Technical replicate expression profiles of the same tumor specimen were highly consistent and were averaged for analysis. A class comparison analysis was applied to determine which genes were differentially expressed between the two classes. For this we used a two-sample T-test with a randomized variance model (Wright G, Simon R. A random variance model for differential gene detection in small sample microarray experiments, 2003. Tech. Rep. 013, Biometric Research Branch, National Cancer Institute, at the web site linus.nci.nih.gov/~brb/TechReport.htm. The randomized variance model assumes that the variance of the expression of each gene is randomly drawn from an inverse-gamma distribution. For a small number of samples, this gives better results than assigning equal variance to all genes or attempting to estimate the variances separately for each gene.

We applied six different classification methods to predict response: Compound Covariate Predictor (Radmacher et al. (2002) *J Comput Biol* 9, 505-11), Diagonal Linear Discriminant Analysis (Dudoit et al. (2002) *Journal of the American Statistical Association,* 77-87), 1 and 3-Nearest Neighbor classifiers (Devroye, L, Gyorfi L, G. Lugosi. A probabilistic theory of pattern recognition. New York: Springer, 1996), Nearest Centroid classifier and Support Vector Machine (Vapnik V N. Statistical learning theory. New York: John Wiley & Sons, Inc., 1998). The genes that are differentially expressed at a $p<0.001$ level were used as predictive features in the classifiers. A leave-one-out cross-validation (LOOCV) was employed to estimate the prediction accuracy for each classification method. With LOOCV one sample is left out and the remaining samples are used to build a classifier, which would then be used to classify the left out sample. Both feature selection and classifier design was repeated each time a sample was left out. The fraction of samples that are classified correctly is an estimate of the classification accuracy.

The significance of the classification results are calculated by permuting the class labels of the samples and then finding the fraction of times this re-labeling resulted in higher LOOCV classification accuracy. The method is described in detail in Radmacher et al. (Radmacher et al. (2002) *J Comput Biol* 9, 505-11).

Example II

Identification of Genes Whose Expression is Correlated with Responsiveness to Radiochemotherapy In order to identify molecular signatures of responsiveness of rectal carcinomas to neoadjuvant, preoperative radiochemotherapy, we analyzed gene expression profiles of 23 tumor biopsies. The flow of sample collection, clinical diagnosis, and experimental design is depicted in FIG. 1. All patients participated in a randomized clinical trial aimed at comparing the relative benefits of adjuvant versus neoadjuvant radiochemotherapy of locally advanced rectal carcinoma. Since standardization of surgical procedure and evaluation of therapy response is critical, all patient samples were collected from a single clinic (University Medical Center Göttingen, Germany). Before biopsy sampling, initial tumor staging was performed by rectal ultrasound, a procedure that, in the experience of the inventors, shows concordance with the histomorphological classification of tumor resections in more than 85% of cases (Liersch et al. (2003) *Chirurg* 74, 224-34). In all instances, duplet biopsies were ascertained and submitted to either histopathological evaluation or for the purpose of expression profiling. Neoadjuvant treatment, the histological diagnosis, and surgical resection of carcinomas were standardized as part of the clinical trial.

To establish the degree of similarity of the bioptic samples and the surgically removed tumors, three matched pairs of biopsies and tumors of patients from the adjuvant treatment arm were compared using gene expression profiling. Average correlation coefficients were in the range of 84%, indicating that in general the tumor biopsies reflect the transcriptome of rectal carcinomas.

Gene expression profiles of the tumors from patients assigned to the neoadjuvant arm of the study were established using 10K cDNA arrays and then evaluated by class comparison analysis. In class comparison analysis, all samples were evaluated and genes that were differentially expressed in tumors with or without response were identified.

The clinical data and response classification are listed in Table 1. Response classification was based on T-level down-sizing. Nine patients were considered responders (P1-P9) and 14 patients showed no T-level response (P10-P23). T-level down-sizing was supported by 54 genes ($p<0.001$), which were differentially expressed between the two response classes. Classification results for T-level down-sizing were most accurate using the Compound Covariate Predictor and Diagonal Linear Discriminant analysis. Results are presented here for the Compound Covariate Predictor. Four patients were incorrectly classified, three of whom belonged to the non-response group but were classified as responders (P15, P21 and P23), while responder P1 was incorrectly placed in the non-response group. Class prediction using T-level down-sizing results in 83% correct assignment as to either responders or non-responders ($p=0.03$). Table 2 shows the classification accuracy obtained for the all six classifiers for the T-level down-sizing classification.

TABLE 2

Classification accuracy
Class label 1 refers to the group of responders, class label 0 to the group of non-responders.

| Tumor Samples | Class label | Number of genes in classifier | Compound Covariate Predictor Correct? | Linear Discriminant Analysis Correct? | 1-Nearest Neighbor Correct? | 3 Nearest Neighbor Correct? | Nearest Centroid Correct? | Support Vector Machine Correct? |
|---|---|---|---|---|---|---|---|---|
| P1 | 1 | 89 | NO | NO | NO | NO | NO | NO |
| P2 | 1 | 48 | YES | NO | NO | NO | YES | NO |
| P3 | 1 | 41 | YES | YES | YES | NO | NO | YES |
| P4 | 1 | 45 | YES | YES | NO | YES | YES | NO |
| P5 | 1 | 36 | YES | YES | YES | YES | YES | YES |
| P6 | 1 | 39 | YES | YES | YES | YES | YES | YES |
| P7 | 1 | 40 | YES | YES | NO | NO | NO | NO |
| P8 | 1 | 47 | YES | YES | NO | YES | YES | NO |
| P9 | 1 | 43 | YES | YES | NO | YES | NO | NO |
| P10 | 0 | 41 | YES | YES | NO | YES | NO | YES |
| P11 | 0 | 39 | YES | YES | YES | YES | YES | YES |
| P12 | 0 | 35 | YES | YES | YES | YES | YES | YES |
| P13 | 0 | 53 | YES | YES | YES | YES | YES | YES |
| P14 | 0 | 38 | YES | YES | YES | YES | YES | YES |
| P15 | 0 | 66 | NO | NO | NO | NO | NO | NO |
| P16 | 0 | 54 | YES | YES | YES | YES | YES | YES |
| P17 | 0 | 47 | YES | YES | YES | YES | YES | YES |
| P18 | 0 | 40 | YES | YES | YES | YES | YES | YES |
| P19 | 0 | 44 | YES | YES | YES | YES | YES | YES |
| P20 | 0 | 43 | YES | YES | YES | YES | NO | NO |
| P21 | 0 | 84 | NO | NO | NO | NO | NO | NO |
| P22 | 0 | 46 | YES | YES | YES | YES | YES | YES |
| P23 | 0 | 56 | NO | YES | NO | NO | NO | NO |
| Percent correctly classified | | | 83 | 83 | 57 | 70 | 61 | 57 |

The sensitivity of the test measured as the percentage of responders that were predicted correctly as responders is 89%. Specificity (i.e., patients that were correctly classified as non-responders to radiochemotherapy) was 79%. The positive predictive value (percentage of patients classified as responders who were true responders) is 73% and the negative predictive value (percentage of patients classified as non-responders who were true non-responders) is 92%.

Table 3 provides the annotation of the 54 most significantly changed genes in class comparison analysis. 41 genes were down-regulated and 13 genes showed higher expression values in the group of responders. This list of genes includes calmin, kinectin 1, copine III, villin-like, motilin, cdc42, myosin IA, cyclin T1, interleukin 12A, SMC1 (structural maintenance of chromosomes 1), platelet derived growth factor C and a number of genes that encode proteins involved in signaling, membrane transport and proteins with varying enzymatic properties (thiolase, lipase, peptidase and protease activity).

TABLE 3

| | DNA SEQ ID NO: | PRT SEQ ID NO: | Probe SEQ ID NO: | Description | Clone |
|---|---|---|---|---|---|
| 1 | 1 | 59 | | calmin (calponin-like, transmembrane) | IncytePD: 1464613 |
| 2 | 2-3 | 60-61 | | FK506 binding protein 1B, 12.6 kDa | IncytePD: 1288118 |
| 3 | 4 | 62 | 113 | kinectin 1 (kinesin receptor) | IncytePD: 3736760 |
| 4 | 5 | 63 | | copine III | IncytePD: 3444952 |
| 5 | 6 | 64 | | glutamic-pyruvate transaminase (alanine aminotransferase) | IncytePD: 1630709 |
| 6 | 7 | NO | 114 | Incyte EST | IncytePD: 1607471 |
| 7 | 8 | 65 | | filamin B, beta (actin binding protein 278) | IncytePD: 1871362 |
| 8 | 9 | 66 | | villin-like | IncytePD: 2804190 |
| 9 | 10 | 67 | | homeo box D9 | IncytePD: 2956581 |
| 10 | 11-12 | 68-69 | | CDC42 binding protein kinase alpha (DMPK-like) | IncytePD: 1602261 |
| 11 | 13-14 | 70-71 | | *Homo sapiens* cDNA FLJ30016 fis, clone 3NB692000429. | IncytePD: 1570161 |
| 12 | 15 | 72 | | monoglyceride lipase | IncytePD: 2174920 |
| 13 | 16 | 73 | | acetyl-Coenzyme A acyltransferase 1 (peroxisomal 3-oxoacyl-Coenzyme A thiolase) | IncytePD: 1926543 |
| 14 | 17 | 74 | 115 | regulator of G-protein signalling 19 interacting protein 1 | IncytePD: 1626914 |
| 15 | 18 | 75 | | p21/Cdc42/Rac1-activated kinase 1 (STE20 homolog, yeast) | IncytePD: 2632434 |
| 16 | 19 | 76 | | motilin | IncytePD: 237225 |
| 17 | 20 | 77 | | inositol 1,3,4-triphosphate 5/6 kinase | IncytePD: 1967095 |
| 18 | 21 | 78 | | myosin IA | IncytePD: 1502005 |
| 19 | 22 | 79 | 116 | S164 protein | IncytePD: 2047730 |
| 20 | 23 | 80 | | protein phosphatase 1, regulatory subunit 10 | IncytePD: 2314555 |
| 21 | 24 | 81 | | KIAA0138 gene product | IncytePD: 1731569 |
| 22 | 25 | 82 | | mucin 5, subtype B, tracheobronchial | IncytePD: 1737280 |
| 23 | 26 | 83 | | E74-like factor 1 (ets domain transcription factor) | IncytePD: 1312824 |
| 24 | 27 | 84 | | metal-regulatory transcription factor 1 | IncytePD: 2467743 |
| 25 | 28 | 85 | | small nuclear protein PRAC | IncytePD: 2231168 |
| 26 | 29 | 86 | | cyclin T1 | IncytePD: 2928577 |
| 27 | 30-31 | 87-88 | | hypothetical protein FLJ12949 | IncytePD: 1393595 |
| 28 | 32 | NO | 117 | ESTs, Moderately similar to TRY2__HUMAN Trypsin II precursor (Anionic trypsinogen) [*H. sapiens*] | IncytePD: 1222442 |
| 29 | 33 | 89 | | *Homo sapiens*, clone IMAGE: 4797596, mRNA | IncytePD: 475497 |
| 30 | 34 | 90 | 118 | ESTs | IncytePD: 1398814 |
| 31 | 35 | 91 | | *Homo sapiens*, clone IMAGE: 5587702, mRNA | IncytePD: 1964852 |
| 32 | 36 | 92 | 119 | WAS protein family, member 2 | IncytePD: 1448116 |
| 33 | 37 | 93 | | adaptor-related protein complex 3, delta 1 subunit | IncytePD: 1301192 |
| 34 | 38 | 94 | | protein expressed in thyroid | IncytePD: 1807085 |
| 35 | 39 | 95 | | sodium channel, nonvoltage-gated 1, beta (Liddle syndrome) | IncytePD: 2121687 |
| 36 | 40 | 96 | | KIAA0284 protein | IncytePD: 1890138 |
| 37 | 41 | 97 | | deltex homolog 2 (*Drosophila*) | IncytePD: 1691161 |
| 38 | 42 | 98 | | myeloid/lymphoid or mixed-lineage leukemia (trithorax homolog, *Drosophila*) | IncytePD: 1692195 |
| 39 | 43 | 99 | | chromosome 11 open reading frame 13 | IncytePD: 1919646 |
| 40 | 44 | 100 | | small nuclear RNA activating complex, polypeptide 2, 45 kDa | IncytePD: 1445203 |
| 41 | 45 | 101 | | SMC1 structural maintenance of chromosomes 1-like 1 (yeast) | IncytePD: 3074894 |
| 42 | 46 | 102 | | LIV-1 protein, estrogen regulated | IncytePD: 1402273 |
| 43 | 47 | 103 | | membrane-bound transcription factor protease, site 2 | IncytePD: 1302425 |
| 44 | 48 | 104 | 120 | ESTs, glutamate-cysteine ligase, modifier subunit | IncytePD: 1432207 |
| 45 | 49 | NO | 121 | ESTs | IncytePD: 4106720 |
| 46 | 50 | 105 | | hypothetical protein DKFZp762O076 | IncytePD: 1967206 |
| 47 | 51 | 106 | | guanylate cyclase 1, soluble, beta 3 | IncytePD: 1417408 |
| 48 | 52 | 107 | 122 | eukaryotic translation initiation factor 5A2 | IncytePD: 786494 |
| 49 | 53 | 108 | | interleukin 12A (natural killer cell stimulatory factor 1, cytotoxic lymphocyte maturation factor 1, p35) | IncytePD: 2760318 |
| 50 | 54 | 109 | | hypothetical protein MGC26706 | IncytePD: 2706048 |
| 51 | 55 | NO | 123 | Incyte EST | IncytePD: 2922438 |
| 52 | 56 | 110 | | solute carrier family 1 (glial high affinity glutamate transporter), member 3 | IncytePD: 3074077 |
| 53 | 57 | 111 | | serine/threonine kinase 18 | IncytePD: 2732630 |
| 54 | 58 | 112 | | platelet derived growth factor C | IncytePD: 943826 |

TABLE 3-continued

| | UG cluster | Gene symbol | Accession Number | Map |
|---|---|---|---|---|
| 1 | Hs.406099 | CLMN | NM_024734 | 14q32.2 |
| 2 | Hs.77643 | FKBP1B | NM_004116 | 2p24.1 |
| | | | NM_054033 | |
| 3 | | | AI916662 | |
| 4 | Hs.14158 | CPNE3 | NM_003909 | 8q21.13 |
| 5 | Hs.103502 | GPT | NM_005309 | 8q24.3 |
| 6 | | | | |
| 7 | Hs.81008 | FLNB | NM_001457 | 3p14.3 |
| 8 | Hs.103665 | VILL | NM_015873 | 3p21.3 |
| 9 | Hs.236646 | HOXD9 | NM_014213 | 2q31.1 |
| 10 | Hs.18586 | CDC42BPA | NM_003607 | 1q42.11 |
| | | | NM_014826 | |
| 11 | Hs.14931 | | NM_024880 | 10 |
| | | | NM_030756 | |
| 12 | Hs.6721 | MGLL | NM_007283 | 3q21.3 |
| 13 | Hs.166160 | ACAA1 | NM_001607 | 3p23-p22 |
| 14 | Hs.6454 | RGS19IP1 | AA740666 | 19p13.1 |
| 15 | Hs.64056 | PAK1 | NM_002576 | 11q13-q14 |
| 16 | Hs.2813 | MLN | NM_002418 | 6p21.3 |
| 17 | Hs.6453 | ITPK1 | NM_014216 | 14q31 |
| 18 | Hs.5394 | MYO1A | AF105424 | 12q13-q15 |
| 19 | Hs.180789 | S164 | AI400786 | 14q24.3 |
| 20 | Hs.106019 | PPP1R10 | NM_002714 | 6p21.3 |
| 21 | Hs.159384 | KIAA0138 | NM_014649 | 19p13.3 |
| 22 | Hs.102482 | MUC5B | XM_039877 | 11p15 |
| 23 | Hs.154365 | ELF1 | NM_172373 | 13q13 |
| 24 | Hs.211581 | MTF1 | NM_005955 | 1p33 |
| 25 | Hs.116467 | PRAC | BC_030950 | 17q21 |
| 26 | Hs.279906 | CCNT1 | NM_001240 | 12pter-qter |
| 27 | Hs.184519 | FLJ12949 | NM_178159 | 19p13.2 |
| | | | NM_023008 | |
| 28 | Hs.66915 | | AI934538 | 22 |
| 29 | Hs.355279 | | NM_022740 | 7 |
| 30 | Hs.355960 | | N41458 | 12 |
| 31 | Hs.427683 | | BC035712 | 10 |
| 32 | Hs.288908 | WASF2 | AI094497 | 1p36.11-p34.3 |
| 33 | Hs.75056 | AP3D1 | NM_003938 | 19p13.3 |
| 34 | Hs.7486 | YF13H12 | NM_014297 | 19q13.2 |
| 35 | Hs.37129 | SCNN1B | NM_001039 | 16p12.2-p12.1 |
| 36 | Hs.182536 | KIAA0284 | AB006622 | 14q32.33 |
| 37 | Hs.89135 | DTX2 | NM_020892 | 7q11.23 |
| 38 | Hs.199160 | MLL | BC_036089 | 11q23 |
| 39 | Hs.72925 | C11orf13 | NM_003475 | 11p15.5 |
| 40 | Hs.78403 | SNAPC2 | NM_003083 | 19p13.3-p13.2 |
| 41 | Hs.211602 | SMC1L1 | NM_006306 | Xp11.22-p11.21 |
| 42 | Hs.79136 | LIV-1 | NM_012319 | 18q12.1 |
| 43 | Hs.350970 | MBTPS2 | AF019612 | Xp22.1-p22.2 |
| 44 | Hs.315562 | GCLM | AA805202 | 1p22.11 |
| 45 | Hs.12876 | | AA845636 | 66 |
| 46 | Hs.21621 | DKFZp762O076 | NM_018710 | 8q21.3 |
| 47 | Hs.77890 | GUCY1B3 | BC_047620 | 4q31.3-q33 |
| 48 | Hs.104660 | EIF5A2 | AA134594 | 3q26.2 |
| 49 | Hs.673 | IL12A | NM_000882 | 3p12-q13.2 |
| 50 | Hs.65406 | MGC26706 | NM_152581 | Xp22.31 |
| 51 | | | — | |
| 52 | Hs.75379 | SLC1A3 | Z31713 | 5p13 |
| 53 | Hs.172052 | STK18 | NM_014264 | 4q27-q28 |
| 54 | Hs.43080 | PDGFC | NM_016205 | 4q32 |

List of 54 most significantly changed genes in the class-comparison analysis. UG cluster, unigene cluster.

Genes 1-41 are expressed at lower levels in the responders, and genes 42-54 are expressed at higher levels in the responders. Gene 1 is the most statistically significant down-regulated gene and gene 41 is the least statistically significant down-regulated gene. Gene 42 is the most statistically significant up-regulated gene and gene 54 is the least statistically significant up-regulated gene.

Figure 2:
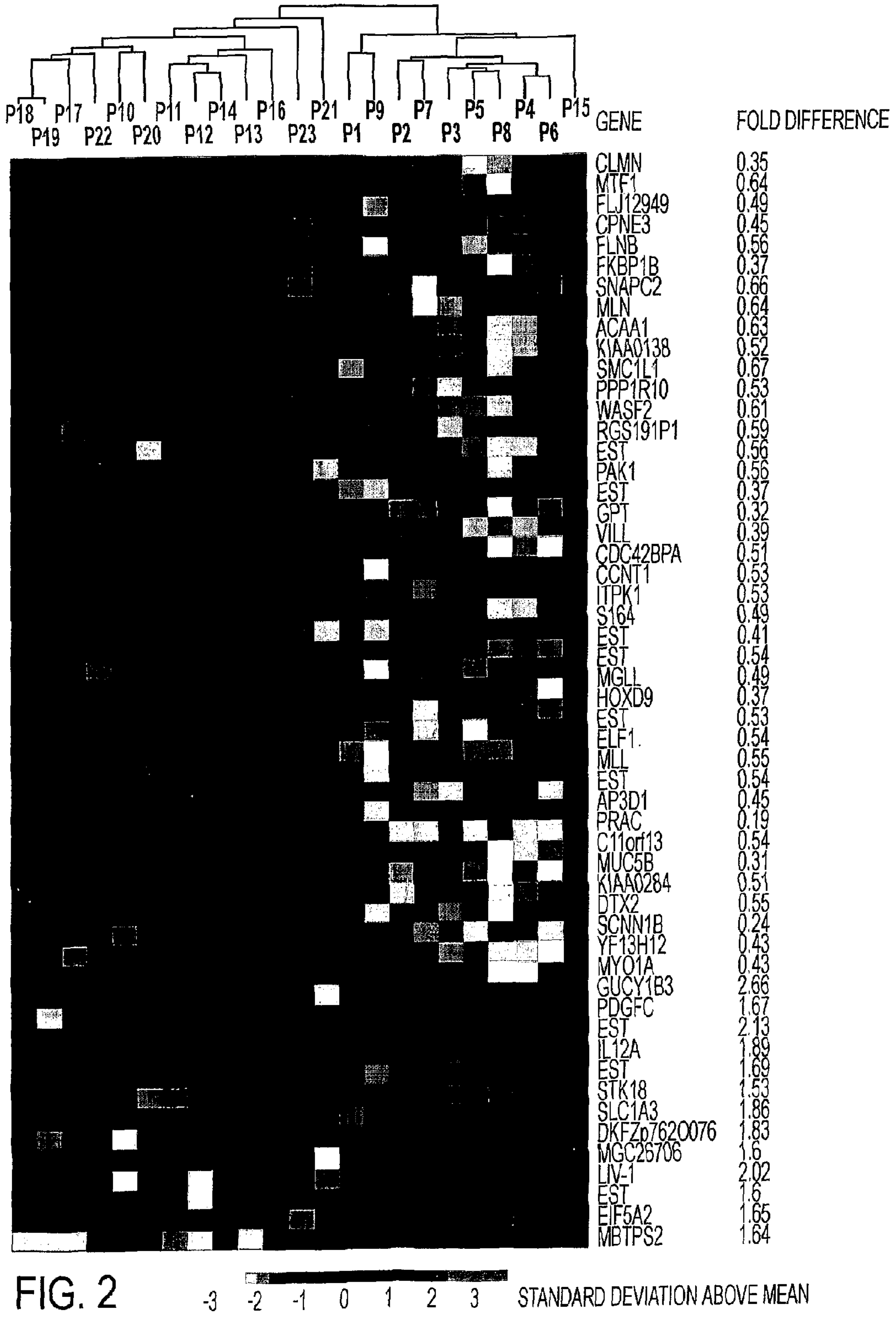
FIG. 2 shows a hierarchical cluster analysis of 23 patients based on the 54 most significantly changed genes ($p<0.001$) when using T-level-down-sizing. Note that in this cluster analysis, all but one patient (P15) were correctly assigned to the group of non-responders (13 patients on the left), while the 10 patients on the right were grouped as responders. Gene symbols and fold change between the groups are listed to the right. Values <1 reflect down-regulation (white) in the class of responders, whereas values >1 reflect up-regulation (grey).

The results of a hierarchical cluster analysis of the 54 genes are presented pictorially in FIG. 2. Fifteen of the 54 genes are particularly highly correlated with the degree of responsiveness to radiochemotherapy ($p<0.00032$). These genes are indicated as genes 1-12 (down-regulated) and 42-44 (up-regulated).

Several candidate genes have previously been analyzed by other groups for their potential to serve as predictors for response to radiation or chemotherapy. These include Ku70/80, ERCC1, TP53, DPYD (dihydropyrimidine dehydrogenase), and TYMS (thymidylate synthase). The expression levels of these genes in our analysis, however, were not significantly different in groups of responders or non-responders based on T-level down-sizing.

The 54 genes whose expression levels were most significantly changed represent members of several cellular pathways and map to multiple different chromosomes. Of particular interest are genes that encode proteins involved in DNA damage repair pathways, such as SMC1, which is involved in the S-phase checkpoint mediated by ATM (Yazdi et al. (2002) *Genes Dev* 16, 571-82; Kim et al. (2002) *Genes Dev* 16, 560-70). A number of genes were involved in microtubule organization. For instance, calmin has homology to calponin and dystrophin (Ishisaki et al. (2001) *Genomics* 74, 172-9). Cdc42 is a member of the Rho GTPase subfamily and triggers microtubule reorganization and cytoskeletal remodeling through GSK-3 and APC, two proteins involved in Wnt-signaling (Etienne-Manneville et al. (2003) *Nature;* 421, 753-6; Harwood et al. (2003) *Nat Cell Biol* 5, 275-7). Filamin B is an integrator of cell mechanics and signaling and acts in the Rho signaling apparatus (Stossel et al. (2001) *Nat Rev Mol Cell Biol* 2, 138-45); villin proteins are involved in actin metabolism (Athman et al. (2002) *Am J Physiol Gastrointest Liver Physiol* 283, G496-502); and kinectin 1 is a binding partner of kinesin, and belongs to a class of molecular motors involved in mitoses, axoplasmic transport and secretion (Karcher et al. (2002) *Trends Cell Biol* 12, 21-7). The preponderance of genes involved in microtubule organization cannot be explained by relative abundance of members of such gene families alone. Again, none of the previously used candidate genes were present in this list.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and in the figures are hereby incorporated in their entirety by reference.

We claim:

1. A method for determining if a rectal adenocarcinoma is responsive to therapy with 5-fluorouracil (5-FU) and radiation, comprising:

(a) providing a polynucleotide sample obtained from a rectal adenocarcinoma of a subject;

(b) detecting in the sample the amounts of a polynucleotides selected from the group consisting of a polynucleotide having at least 95% sequence identity to SEQ ID NO: 31, a polynucleotide having at least 95% sequence identity to SEQ ID NO: 14, a polynucleotide having at least 95% sequence identity to SEQ ID NO: 1 and a polynucleotide having at least 95% sequence identity to SEQ ID NO: 5;

(c) comparing the amounts of the polynucleotides to a baseline value that is indicative of the level of expression of the polynucleotide in a subject that is not responsive to therapy with 5-FU and radiation, wherein a decrease in the amount of the polynucleotides compared to the baseline value indicates that the rectal adenocarcinoma is responsive to therapy with 5-FU and radiation; and d) administering 5-FU and radiation therapy to the subject.

2. The method of claim 1, wherein the polynucleotides can hybridize specifically, under conditions of high stringency, to the complement of a nucleic acid selected from SEQ ID NO: 31, SEQ ID NO: 14, SEQ ID NO: 1 and SEQ ID NO: 5.

3. The method of claim 1, wherein a decrease in the level of expression of SEQ ID NO: 31, SEQ ID NO: 14, SEQ ID NO: 1 and SEQ ID NO: 5 indicates that the adenocarcinoma is responsive to therapy with 5-fluorouracil (5-FU) and radiation.

4. The method of claim 1, wherein the rectal adenocarcinoma is in a human patient.

5. The method of claim 4, wherein the patient is preoperative.

6. The method of claim 4, wherein the patient is postoperative.

7. The method of claim 1, wherein detecting the amount of the polynucleotides in the sample is carried out by hybridizing the polynucleotides in the sample to one or more polynucleotides that are the complement of SEQ ID NO: 31, SEQ ID NO: 14, SEQ ID NO: 1 or SEQ ID NO: 5 under stringent hybridization conditions, and comparing the amount of hybridization to a baseline value that is indicative of the degree of expression of the polynucleotide in a subject that is not responsive to therapy with 5-FU and radiation.

8. The method of wherein the polynucleotides that are the complement of SEQ ID NO: 31, SEQ ID NO: 14, SEQ ID NO: 1 or SEQ ID NO: 5 are immobilized on a substrate.

9. The method of claim 7, wherein the polynucleotides that are the complement of SEQ ID NO: 31, SEQ ID NO: 14, SEQ ID NO: 1 or SEQ ID NO: 5 are in an array.

10. The method of claim 7, wherein the polynucleotides that are the complement of SEQ ID NO: 31, SEQ ID NO: 14, SEQ ID NO: 1 or SEQ ID NO: 5 are hybridizable elements in a microarray.

11. The method of claim 7, wherein the polynucleotides in the sample are labeled with a detectable label.

12. The method of claim 11, wherein the detectable label is a fluorescent label.

13. The method of claim 1, wherein the detecting is performed by quantitatively amplifying polynucleotides in the rectal adenocarcinoma sample with primers specific for those polynucleotides, and comparing the amount of amplified polynucleotide to a baseline value.

14. The method of claim 1 wherein the detecting step comprises detecting in the sample the amount of a polynucleotide selected from the group consisting of a polynucleotide having at least 98% sequence identity to SEQ ID NO: 31, a polynucleotide having at least 98% sequence identity to SEQ ID NO: 14, a polynucleotide having at least 98% sequence identity to SEQ ID NO: 1 and a polynucleotide having at least 98% sequence identity to SEQ ID NO: 5.

15. The method of claim 1 wherein the detecting step comprises detecting the sample the amount of a polynucleotide selected from the group consisting of a polynucleotide having at least 99% sequence identity to SEQ ID NO: 31, a polynucleotide having at least 99% sequence identity to SEQ ID NO: 14, a polynucleotide having at least 99% sequence identity to SEQ ID NO: 1 and a polynucleotide having at least 99% sequence identity to SEQ ID NO: 5.

* * * * *

SEQUENCE LISTING

```
<160> NUMBER OF SEQ ID NOS: 123

<210> SEQ ID NO 1
<211> LENGTH: 3118
<212> TYPE: DNA
<213> ORGANISM: Homo sapiens

<400> SEQUENCE: 1

gcgcgcccgc cagccaggct ctccgcgccc gccgcccgcg ccgcgctggc ccgggctctc     60

ccgcccgcgc ttcatggctg cacacgagtg ggactggttc caacgcgagg agctcatcgg    120

gcagattagc gacatccgag tgcagaacct gcaagttgag agggaaaatg tgcagaagag    180

gacctttaca cgatggataa atctacatct agaaaagtgc aacccacctc tagaagttaa    240

agatttattc gtcgatatac aagatggcaa aatcctaatg gctttgttag aagtcctgtc    300

tgggcggaat ctgctgcacg aatacaaatc ctcgtcgcat cgtatttttc ggttgaacaa    360

catagcgaaa gcacttaagt ttttggaaga tagcaatgta aaactggtta gcattgatgc    420

agcagaaata gcagatggca acccttcttt ggttcttggg ctgatatgga acataatcct    480

cttcttccag attaaggagc tcacaggcaa cctcagcaga aactctccat cttccagctt    540

gtcccctggc tcagggggca cagactcaga ctcatccttc ccacccacac ccactgcaga    600

gaggagcgtg gcaatatcgg tgaaagacca gaggaaggct atcaaggccc tgttggcgtg    660

ggtgcagagg aaaacgagaa agtatggcgt ggcggtgcag gactttgcgg gcagttggag    720

gagtgggctg gctttcctgg cggtgatcaa ggccattgac cccagcctgg tggacatgaa    780

acaggccctg gaaaattcca cacgagaaaa tctagagaag gctttcagca tcgcacagga    840

tgccctgcac atccccaggc tcctggagcc agaagacatc atggttgaca caccagacga    900

gcagtctatc atgacttacg tggcacagtt tctagaacgt tttccggagt tggaagccga    960

agatattttc gattcagata aagaagttcc tatcgaatcc acttttgttc gcatcaaaga   1020

aactccttct gaacaggaga gcaaagtctt cgttctgact gaaaatgggg agcgtaccta   1080

cactgttaac catgaaacca gccacccacc accctccaaa gtctttgtct gtgacaagcc   1140

cgagagcatg aaggaattcc gcctggatgg tgtttccagc catgcgctgt cagacagctc   1200

caccgagttc atgcaccaga ttattgacca ggtcctgcaa gggggcccag gtaagaccag   1260

cgacatcagt gagccatctc cagaatcctc cattttatca tccagaaagg agaacgggag   1320
```

-continued

```
gtccaactct ttgccgatca agaaaacagt tcactttgag gctgacacct acaaggatcc   1380

tttctgcagt aagaacctgt ccctttgctt tgaagggagc ccaagagtgg caaaggaatc   1440

attgaggcag gatggacatg tcttggcagt tgaggttgct gaggaaaagg aacagaaaca   1500

ggaatcctcg aagattccag aatcctcctc tgacaaggtc gctggtgaca tttttttggt   1560

ggagggcaca aacaataatt ctcagtcttc ttcctgtaat ggtgctttag agagtacagc   1620

ccgccacgat gaagaaagtc actctctttc acccccagga gaaaatactg tgatggccga   1680

ttccttccag atcaaggtta acctgatgac tgtagaagct ttagaggagg gagactattt   1740

tgaagccatc ccattaaaag cctcaaaatt taacagcgac ctaatagatt ttgcttctac   1800

cagccaggct ttcaacaaag ttccttcacc tcatgagaca aaacctgacg aggatgctga   1860

ggcttttgag aatcatgctg aaaaactagg taaaaggagt attaaatctg ctcacaaaaa   1920

gaaggattcg ccagagcctc aagttaagat ggacaaacat gaacctcatc aggactccgg   1980

agaagaagct gaaggctgtc cttcagcccc agaagagaca ccagtggata aaaagccaga   2040

ggtgcatgaa aaggccaaga gaaagtccac ccgtcctcat tatgaggaag agggagaaga   2100

cgatgacctc cagggtgtgg gcgaggaatt atcttccagc cccccaagca gctgtgtcag   2160

cttggagacc cttgggagtc acagcgaaga aggcctggat ttcaagccct ccccacccct   2220

ctcaaaggtt tccgtcattc cccacgacct cttctatttc ccacactatg aggttcccct   2280

ggctgcagtt ttggaggctt atgtagaaga cccggaggat ctaaaaaatg aagaaatgga   2340

tctcgaagag ccagagggct atatgccaga cctggactcc agggaggagg aggccgatgg   2400

ctctcagagc agctccagtt cctcggtgcc aggagagagc ctccccagtg ccagcgacca   2460

ggtgctgtat ctcagcaggg gtggtgtggg taccacacca gcctcagaac ccgctccact   2520

ggccccccat gaggaccacc agcaaaggga gaccaaagag aatgacccca tggacagcca   2580

tcagtcccag gaatccccaa acctggaaaa catagcaaac cccctagaag aaaatgtaac   2640

gaaagaatca atcagtagta aaaaaaagga aaaaaggaaa catgtggacc acgtagaaag   2700

ttcactattt gtagcaccag gaagtgttca atcctcagat gacctagaag aagacagtag   2760

cgactacagc attccttcca ggactagtca cagtgactcc agcatttacc ttcgacgaca   2820

tactcatagg tcttcggaat cggatcattt tagctatgtt cagttgagga acgcagcaga   2880

tctggatgac agaagaaacc gaatattaac caggaaggcc aacagctcag gagaagccat   2940

gtcactgggg agccacagcc cgcagagtga ctccctgaca cagcttgtcc agcagccgga   3000

tatgatgtat tttattctct tcctgtggct cctggtgtac tgcttgctgc tcttcccaca   3060

actggatgtt agcaggctct gatacgtgtg tctggataat aaaaaagaca ggaccctg     3118
```

<210> SEQ ID NO 2
<211> LENGTH: 930
<212> TYPE: DNA
<213> ORGANISM: Homo sapiens

<400> SEQUENCE: 2

```
gcgagccgga gcgacggcgg ggctggggcc ggagccgagc cggggtcggg cagcagcagg     60

gaccccccag aggcggggcc tgtgggaccg ctatgggcgt ggagatcgag accatctccc    120

ccggagacgg aaggacattc cccaagaagg gccaaacgtg tgtggtgcac tacacaggaa    180

tgctccaaaa tgggaagaag tttgattcat ccagagacag aaacaaacct ttcaagttca    240

gaattggcaa acaggaagtc atcaaaggtt ttgaagaggg tgcagcccag atgagcttgg    300

ggcagagggc gaagctgacc tgcacccctg atgtggcata tggagccacg ggccaccccg    360
```

```
gtgtcatccc tcccaatgcc accctcatct ttgacgtgga gctgctcaac ttagagtgaa    420

ggcaggaagg aactcaaggt ggtggctgga gatggctgct gctcaccctc ctagcctgct    480

ctgccactgg gacggctcct gcttttgggg ctcttgatca gtgtgctaac ctcactgcct    540

catggcatca tccattctct ctgcccaagt tgctctgtat gtgttcgtca gtgttcatgc    600

gaattcttgc ttgaggaaac ttcggttgca gattgaagca tttcaggttg tgcattttgt    660

gtgatgcatg tagtagcctt tcctgatgac agaacacaga tctcttgttc gcacaatcta    720

cactgcctta ccttcactta aaccacacac acaaggtgct cagacatgaa atgtacatgg    780

cgtaccgtac acagagggac ttgagccagt tacctttgct gtcactttct ctcttataaa    840

ttctgttagc tgctcactta aacaatgtcc tctttgagaa aatgtaaaat aaaggctctg    900

tgcttgacaa aaaaaaaaaa aaaaaaaaaa                                     930
```

<210> SEQ ID NO 3
<211> LENGTH: 972
<212> TYPE: DNA
<213> ORGANISM: Homo sapiens

<400> SEQUENCE: 3

```
gcgagccgga gcgacggcgg ggctggggcc ggagccgagc cggggtcggg cagcagcagg     60

gaccccccag aggcggggcc tgtgggaccg ctatgggcgt ggagatcgag accatctccc    120

ccggagacgg aaggacattc cccaagaagg gccaaacgtg tgtggtgcac tacacaggaa    180

tgctccaaaa tgggaagaag tttgattcat ccagagacag aaacaaacct ttcaagttca    240

gaattggcaa acaggaagtc atcaaaggtt ttgaagaggg tgcagcccag ctgggtcctc    300

tttctcctct ccccatctgc cccccatccct gctagatgag cttggggcag agggcgaagc    360

tgacctgcac ccctgatgtg gcatatggag ccacgggcca ccccggtgtc atccctccca    420

atgccaccct catctttgac gtggagctgc tcaacttaga gtgaaggcag gaaggaactc    480

aaggtggctg gagatggctg ctgctcaccc tcctagcctg ctctgccact gggacggctc    540

ctgcttttgg ggctcttgat cagtgtgcta acctcactgc ctcatggcat catccattct    600

ctctgcccaa gttgctctgt atgtgttcgt cagtgttcat gcgaattctt gcttgaggaa    660

acttcggttg cagattgaag catttcaggt tgtgcatttt gtgtgatgca tgtagtagcc    720

tttcctgatg acagaacaca gatctcttgt tcgcacaatc tacactgcct taccttcact    780

taaaccacac acacaaggtg ctcagacatg aaatgtacat ggcgtaccgt acacagaggg    840

acttgagcca gttacctttg ctgtcacttt ctctcttata aattctgtta gctgctcact    900

taaacaatgt cctctttgag aaaatgtaaa ataaaggctc tgtgcttgac aaaaaaaaaa    960

aaaaaaaaaa aa                                                        972
```

<210> SEQ ID NO 4
<211> LENGTH: 4816
<212> TYPE: DNA
<213> ORGANISM: Homo sapiens

<400> SEQUENCE: 4

```
cgtcttcccg gtctcctttc ccggccgcac agggtagatt ttcgttccgt cacccaggct     60

ggagtgcagt ggtgtgacct tggcttgctg caaccctttg cctcctgggt tcaagtgatt    120

ctcattgcct cagcctccta agtagctggg attacaggtt ttataggatc acattgacaa    180

aagtaccatg gagttttatg agtcagcata ttttattgtt cttattcctt caatagttat    240
```

-continued

```
tacagtaatt ttcctcttct tctggctttt catgaaagaa acattatatg atgaagttct    300
tgcaaaacag aaaagagaac aaaagcttat tcctaccaaa acagataaaa agaaagcaga    360
aaagaaaaag aataaaaaga aagaaatcca gaatggaaac ctccatgaat ccgactctga    420
gagtgtacct cgagacttta aattatcaga tgctttggca gtagaagatg atcaagttgc    480
acctgttcca ttgaatgtcg ttgaaacttc aagtagtgtt agggaaagaa aaaagaagga    540
aaagaaacaa aagcctgtgc ttgaagagca ggtcatcaaa gaaagtgacg catcaaagat    600
tcctggcaaa aaagtagaac ctgtcccagt tactaaacag cccacccctc cctctgaagc    660
agctgcctcg aagaagaaac cagggcagaa gaagtctaaa aatggaagcg atgaccagga    720
taaaaaggtg gaaactctca tggtaccatc aaaaaggcaa gaagcattgc ccctccacca    780
agagactaaa caagaaagtg gatcagggaa gaagaaagct tcatcaaaga aacaaaagac    840
agaaaatgtc ttcgtagatg aacccettat tcatgcaact acttatattc ctttgatgga    900
taatgctgac tcaagtcctg tggtagataa gagagaggtt attgatttgc ttaaacctga    960
ccaagtagaa gggatccaga aatctgggac taaaaaactg aagaccgaaa ctgacaaaga   1020
aaatgctgaa gtgaagttta aagattttct tctgtccttg aagactatga tgttttctga   1080
agatgaggct ctttgtgttg tagacttgct aaaggagaag tctggtgtaa tacaagatgc   1140
tttaaagaag tcaagtaagg gagaattgac tacgcttata catcagcttc aagaaaagga   1200
caagttactc gctgctgtga aggaagatgc tgctgctaca aaggatcggt gtaagcagtt   1260
aacccaggaa atgatgacag agaaagaaag aagcaatgtg gttataacaa ggatgaaaga   1320
tcgaattgga acattagaaa aggaacataa tgtatttcaa aacaaaatac atgtcagtta   1380
tcaagagact caacagatgc agatgaagtt tcagcaagtt cgtgagcaga tggaggcaga   1440
gatagctcac ttgaagcagg aaaatggtat actgagagat gcagtcagca acactacaaa   1500
tcaactggaa agcaagcagt ctgcagaact aaataaacta cgccaggatt atgctaggtt   1560
ggtgaatgag ctgactgaga aaacaggaaa gctacagcaa gaggaagtcc aaaagaagaa   1620
tgctgagcaa gcagctactc agttgaaggt tcaactacaa gaagctgaga gaaggtggga   1680
agaagttcag agctacatca ggaagagaac agcggaacat gaggcagcac agcaagattt   1740
acagagtaaa tttgtggcca aagaaaatga agtacagagt ctgcatagta agcttacaga   1800
taccttggta tcaaaacaac agttggagca aagactaatg cagttaatgg aatcagagca   1860
gaaaagggtg aacaaagaag agtctctaca aatgcaggtt caggatattt tggagcagaa   1920
tgaggctttg aaagctcaaa ttcagcagtt ccattcccag atagcagccc agacctccgc   1980
ttcagttcta gcagaagaat tacataaagt gattgcagaa aaggataagc agataaaaca   2040
gactgaagat tctttagcaa gtgaacgtga tcgtttaaca agtaaagaag aggaacttaa   2100
ggatatacag aatatgaatt tcttattaaa agctgaagtg cagaaattac aggccctggc   2160
aaatgagcag gctgctgctg cacatgaatt ggagaagatg caacaaagtg tttatgttaa   2220
agatgataaa ataagattgc tggaagagca actacaacat gaaatttcaa acaaaatgga   2280
agaatttaag attctaaatg accaaaacaa agcattaaaa tcagaagttc agaagctaca   2340
gactcttgtt tctgaacagc ctaataagga tgttgtggaa caaatggaaa aatgcattca   2400
agaaaaagat gagaagttaa agactgtgga agaattactt gaaactggac ttattcaggt   2460
ggcaactaaa gaagaggagc tgaatgcaat aagaacagaa aattcatctc tgacaaaaga   2520
agttcaagac ttaaaagcta agcaaaatga tcaggtttct tttgcctctc tagttgaaga   2580
acttaagaaa gtgatccatg agaaagatgg aaagatcaag tctgtagaag agcttctgga   2640
```

-continued

```
ggcagaactt ctcaaagttg ctaacaagga gaaaactgtt caggatttga aacaggaaat   2700
aaaggctcta aaagaagaaa taggaaatgt ccagcttgaa aaggctcaac agttatctat   2760
cacttccaaa gttcaggagc ttcagaactt attaaaagga aaagaggaac agatgaatac   2820
catgaaggct gttttggaag agaaagagaa agacctagcc aatacaggga agtggttaca   2880
ggatcttcaa gaagaaaatg aatctttaaa agcacatgtt caggaagtag cacaacataa   2940
cttgaaagag gcctcttctg catcacagtt tgaagaactt gagattgtgt tgaaagaaaa   3000
ggaaaatgaa ttgaagaggt tagaagccat gctaaaagag agggagagtg atctttctag   3060
caaaacacag ctgttacagg atgtacaaga tgaaaacaaa ttgtttaagt cccaaattga   3120
gcagcttaaa caacaaaact accaacaggc atcttctttt ccccctcatg aagaattatt   3180
aaaagtaatt tcagaaagag agaaagaaat aagtggtctc tggaatgagt tagattcttt   3240
gaaggatgca gttgaacacc agaggaagaa aaacaatgac cttcgggaga aaaactggga   3300
agcaatggaa gcattggcat caactgaaaa aatgctgcag gacaaagtga acaagacttc   3360
caaggaaagg cagcaacagg tggaagctgt tgagttggag gctaaagaag ttctcaaaaa   3420
attatttcca aaggtgtctg tcccttctaa tttgagttat ggtgaatggt tgcatggatt   3480
tgaaaaaaag gcaaaagaat gtatggctgg aacttcaggg tcagaggagg ttaaggttct   3540
agagcacaag ttgaaagaag ctgatgaaat gcacacattg ttacagctag agtgtgaaaa   3600
atacaaatcc gtccttgcag aaacagaagg aattttacag aagctacaga gaagtgttga   3660
gcaagaagaa aataaatgga aagttaaggt cgatgaatca cacaagacta ttaaacagat   3720
gcagtcatca tttacatctt cagaacaaga gctagagcga ttaagaagcg aaaataagga   3780
tattgaaaat ctgagaagag aacgagaaca tttggaaatg gaactagaaa aggcagagat   3840
ggaacgatct acctatgtta cagaagtcag agagctgaaa gatctgttga ctgaattgca   3900
gaaaaaactt gatgattcat attctgaagc agtaagacag aatgaagagc taaatttgtt   3960
gaaggcacag ttaaatgaaa cactcacaaa acttagaact gaacaaaatg aaagacagaa   4020
ggtagctggt gatttgcata aggctcaaca gtcactggag cttatccagt caaaaatagt   4080
aaaagctgct ggagacacta ctgttattga aaatagtgat gtttccccag aaacggagtc   4140
ttctgagaag gagacaatgt ctgtaagtct aaatcagact gtaacacagt tacagcagtt   4200
gcttcaggcg gtaaaccaac agctcacaaa ggagaaagag cactaccagg tgttagagtg   4260
atcatcctct ggcctacctt gacacatgct ctccttcaaa atgctaattc agagtgaagt   4320
aattgggaaa ctgttcattt gaggataaaa aaggcattgt attatatttt gccaaattaa   4380
agccttattt atgttttcac cctttctact ttgtcagaaa cactgaacag agttttgtct   4440
tttctaatcc ttgttagact actgatttaa agaaggaaaa aaaaaagcca actctgtaga   4500
caccttcaga gtttagtttt ataataaaaa ctgtttgaat aattagacct ttacattcct   4560
gaagataaac atgtaatctt ttatcttatt ttgctcaata aaattgttca gaagatcaaa   4620
gtggtaaaga caatgtaaaa tttaacattt taatactgat gttgtacact gttttactta   4680
acattttggg aagtaactgc ctctgacttc aactcaagaa aacacttttt tgttgctaat   4740
gtaatcggtt tttgtaatgg cgtcagcaaa taaaaggatg cttattattc aaaaaaaaaa   4800
aaaaaaaaaa aaaaaa                                                   4816
```

<210> SEQ ID NO 5
<211> LENGTH: 4737
<212> TYPE: DNA

<213> ORGANISM: Homo sapiens

<400> SEQUENCE: 5
gtcccagcgt cgctccggac gctgccaacc tgttctccac cgtcgctcga cttccacctc 60
taagactccc acgaaactca ggttgaataa ttcatcaaat tacacaactg aactcaagac 120
atggctgccc agtgtgtcac aaaggtggcg ctgaatgttt cctgtgccaa tcttttggat 180
aaagatatag ggtcaaagtc agacccttta tgtgtgttgt ttttgaatac aagtggtcaa 240
cagtggtatg aggttgagcg cacagaaagg attaagaatt gcttgaatcc ccaattttcc 300
aagacattta ttattgatta ctactttgaa gtggttcaga aattgaaatt tggggtttat 360
gacatcgaca acaaaactat tgagctgagt gatgatgact tcttagggga atgtgaatgt 420
acccttggac aaattgtttc cagcaagaag ctaactcgac cactggtgat gaaaactggc 480
agacctgcag gaaaagggag cattacgatt tcagctgaag aaataaaaga taatagagtg 540
gtcttgtttg aaatggaagc cagaaaactg gataataagg atctatttgg aaagtcagac 600
ccatacctgg aattccacaa gcagacatct gatggaaact ggctaatggt tcatcggaca 660
gaggttgtta aaaacaactt gaatcctgtt tggaggcctt tcaagatctc tcttaactca 720
ctgtgttacg gagatatgga caaaaccatt aaggtggagt gttatgatta tgacaatgat 780
gggtcacatg atctcattgg aacatttcag accaccatga caaaactgaa agaagcctcc 840
agaagctcac ctgttgaatt tgaatgcata aatgagaaaa aaaggcaaaa gaaaaaaagc 900
tacaagaatt caggtgttat cagtgtgaaa cagtgtgaga ttacagtaga atgcacattc 960
cttgactata taatgggagg atgtcagctg aattttactg tgggagtgga cttcactggc 1020
tccaatggtg acccaaggtc tccagactcc cttcattaca tcagccccaa tggcgttaat 1080
gagtatttga ctgctctctg gtctgtggga ctggtcattc aagattatga tgctgataag 1140
atgtttccag cttttggttt tggcgctcag atacctcctc agtggcaggt atcacatgaa 1200
tttccaatga acttcaaccc atccaatccc tactgcaatg gaatccaagg cattgtagag 1260
gcgtatcggt cttgtcttcc tcagataaaa ctctatggac caactaattt ttctccaatc 1320
ataaatcacg tggccaggtt tgctgctgca gccacgcaac agcagacagc ttctcaatat 1380
tttgtgcttt tgattattac tgatggtgtg atcacagacc ttgatgaaac cagacaagct 1440
atagttaatg cctccaggct gcctatgtcc atcataattg ttggagttgg aggtgctgac 1500
ttcagcgcca tggagtttct ggatggtgat ggtggaagtc tccgctcccc attgggcgaa 1560
gtggccatca gagatattgt ccagtttgtg cctttcagac agttccagaa tgctccaaaa 1620
gaagcacttg ctcagtgtgt cttggcagag attccccagc aggtggtggg ctacttcaat 1680
acatacaaac tccttcctcc caagaaccca gccacgaaac aacagaagca gtgaccactt 1740
caacagaatt cttttgtgtt atgtggagca atgccatctc tcaccccaaa tcgtgtatct 1800
gtcattctac gtacttttta cccccagcat ttatgatgta aatctctttc tctatggatt 1860
atatctgttt aaagcattct ttctaggtta ttttgggggg acagtgccaa gtccatcttt 1920
gcccagtcaa ttcagtgatt gatagcaatt tacattaatt gcagtaaagc tctttggatt 1980
agaaattagt gtggggaaag cttattctgt tgttgttttt gtttactttc atatgatgaa 2040
aatgctgtgt ttaagtgttt gtcaatagga agaatggaaa actgttggga tgatgtggtt 2100
tgcaggttgc tgtgcctgat tcacagtgta tgttgtataa gccaatgtcc atacctgatt 2160
atgagagctt cttaaattat atgatatcaa atttgttcct gtaactctgt atacagtgct 2220
tttctgcaag gtaaaaataa cctgtctatg catctgatttt ttgctacagt ttagacactg 2280

-continued tggtttacaa aacagcatgc actcaacttg ggactttatg aaaagtactg aatgagcagg 2340
aaaaggcgca tactcagttt tttaaatgta caatcaacaa gtaaaaataa cctcatgtaa 2400
gtaagccatt tttatttgcc tttctagata ttttatttta ttgtggaaaa ctgtaaacat 2460
ggtcagattt ggcttttttt ttcattaact gagcaagact ttcaggatat tgtagatgca 2520
cagatggtag gttgtcctga attctacatt attagattac tttaattgag atttgttaaa 2580
acggttagga ctgttttgtc caggaaagat aagaggacca aacatataag gtgaaattca 2640
gaattccgtt tccttctaac taatgaaaaa ctgcttacta aaaaaaaatt ttatactttc 2700
cttgctaagg tcccatatat tgatttgtac agatccactt agtcattttc tcctttttt 2760 aagaaccatt ttcatctgat ttttaaactc acgataccag ttatctgtta atcaaaattg 2820
cattttacaa tttaataatg tgatatttcc tatgtctaca gcatacctta ttaggtataa 2880
aacctactgc aacttagaaa aaggaaagaa aaaagaagac ttttccaact gctgcattaa 2940
gatagggtgg attttatgtg cttttttttt ttaagagttg aatttctttt cctgactttt 3000
accttttaca gcgtattact tagtgaacat tacattttca gaatagatcc taatatttta 3060
ttgagggcct atgtgctaaa aactatgcat atctatatat tggccaatta tctttaataa 3120
tttacctttt gaaattgcat gtttatcata tatccttaag tggacacata cagtgccatg 3180
ttgatgtgcc tctcagtttt attgaaaagc tgccccacag cccatgtctc ttgttctctg 3240
caatgcctca agggagtgag ctctcaacca cagatagctg tggcttctca gaagcagctc 3300
attgccaagg ccaggctgag aggggacctg cttgctgtgg tggttgccta gcccagatga 3360
gcatttacct accaccttcc cacttggcta gctgtccttt ggatatgtgc tgttaactgg 3420
ggaaggcatc taactagtag cctgctactc catagtatgg ctcaatagat gacacatcat 3480
tttgacatta tcaataggag aaaagaaaac taacccttct tctgattgtt tggagccata 3540
gttgtctcag atgttctaat tctctttgta tgcttggaaa cagcatagat atgttgctgt 3600
ggttttcaga attttctctt ttaatcacaa gaagcctttt aaaaaatgac ttacacatat 3660
tctcaatgta cagtaaaaca gacagaagtg agcttatctg tttgatgctg tggcagggtc 3720
ccagtcactg ggcatatcct ccttctcctt aaccagcttc tcagcagccc ctgagtcacc 3780
tgcacaaggt gcttgggaac tgctggttat gagcattcct ggttttcttc agccaaataa 3840
caggtaatca ctgtcaattg gatttggtct tcattatttt atattctgat tttatcagaa 3900
ttattctatt ttaaaattgt tttaaaattt aaaaacattt aattcatgat catgttcatc 3960
agtagatgct attattcata agaactgtga ttccagcaaa ctagggtaat tggtgccttt 4020
ttacagtttt gaataaaagc atttacaatt tctaaattat cagttttcac agtttcagca 4080
ctcaacctca tcatacgctg atttaatatt gttttacatt aaaatagtcc ttttccctgt 4140
tgtgccacca ttcatttaag tgctgtttgt tcttaaaatg catttaaaga aaaattaccc 4200
atattgactt tcacacctca tataatcaga tctattacaa atatatatcg gagtgacggt 4260
gcccaggata gatgtaatat ttcttacaga tgctggcaca gaggaaataa tataccagct 4320
aatctagtca cctaaccttg tggttagaat tgcaatttta agaccagaaa aatttgaagt 4380
ctgatcagag atttacaact gttcattata gtggtgcctt aggcaatctt tccaaagtaa 4440
attcagggcc ccattgctac ttatgccata tttggacata cttttttttt cttcaatttt 4500
gtaaacttcc tggaaagctg tcttcactaa gtatccccta gtctctatat atgtggttag 4560
tagtcatgga aatgacacat aaagtacgcc agaagtttga tggaacgtgt tagaaactgt 4620

-continued

```
tttgtgcttt tatggatgtc atacttgaca atacatgtgt aagttactaa tatatgaatt   4680

gatgctaaat atatcttaca tttgaattcc ttttggataa agttatttct tgatgtg      4737
```

<210> SEQ ID NO 6
<211> LENGTH: 1924
<212> TYPE: DNA
<213> ORGANISM: Homo sapiens

<400> SEQUENCE: 6

```
ccccgccttc acccactgcc tctgcctccc tggggcagag ctgtttccca gacgggtggg     60

gcggggccca actgtcccag ctccttcagc cctttctgtc cctcccagtg aggccagctg    120

cggtgaagag ggtgctctct tgcctggcgt tccctctgca cggctgcccc ctcccaccct    180

gcccactaag ccagacccac tgtcgccatt cccacttctg gtcctgccac ctcctgagct    240

gccttcccgc ctggtctggg tagagtcatg gcctcgagca caggtgaccg gagccaggcg    300

gtgaggcatg gactgagggc gaaggtgctg acgctggacg gcatgaaccc gcgtgtgcgg    360

agagtggagt acgcagtgcg tggccccata gtgcagcgag ccttggagct ggagcaggag    420

ctgcgccagg gtgtgaagaa gcctttcacc gaggtcatcc gtgccaacat cggggacgca    480

caggctatgg ggcagaggcc catcaccttc ctgcgccagg tcttggccct ctgtgttaac    540

cctgatcttc tgagcagccc caacttccct gacgatgcca agaaaagggc ggagcgcatc    600

ttgcaggcgt gtgggggcca cagtctgggg gcctacagcg tcagctccgg catccagctg    660

atccgggagg acgtggcgcg gtacattgag aggcgtgacg gaggcatccc tgcggacccc    720

aacaacgtct tcctgtccac aggggccagc gatgccatcg tgacggtgct gaagctgctg    780

gtggccggcg agggccacac acgcacgggt gtgctcatcc ccatccccca gtacccactc    840

tactcggcca cgctggcaga gctgggcgca gtgcaggtgg attactacct ggacgaggag    900

cgtgcctggg cgctggacgt ggccgagctt caccgtgcac tgggccaggc gcgtgaccac    960

tgccgccctc gtgcgctctg tgtcatcaac cctggcaacc ccaccgggca ggtgcagacc   1020

cgcgagtgca tcgaggccgt gatccgcttc gccttcgaag agcggctctt tctgctggcg   1080

gacgaggtgt accaggacaa cgtgtacgcc gcgggttcgc agttccactc attcaagaag   1140

gtgctcatgg agatggggcc gccctacgcc gggcagcagg agcttgcctc cttccactcc   1200

acctccaagg gctacatggg cgagtgcggg ttccgcggcg gctatgtgga ggtggtgaac   1260

atggacgctg cagtgcagca gcagatgctg aagctgatga gtgtgcggct gtgcccgccg   1320

gtgccaggac aggccctgct ggacctggtg gtcagcccgc ccgcgcccac cgacccctcc   1380

tttgcgcagt tccaggctga gaagcaggca gtgctggcag agctggcggc caaggccaag   1440

ctcaccgagc aggtcttcaa tgaggctcct ggcatcagct gcaacccagt gcagggcgcc   1500

atgtactcct tcccgcgcgt gcagctgccc ccgcgggcgg tggagcgcgc tcaggagctg   1560

ggcctggccc ccgatatgtt cttctgcctg cgcctcctgg aggagaccgg catctgcgtg   1620

gtgccaggga gcggctttgg gcagcgggaa ggcacctacc acttccggat gaccattctg   1680

ccccccttgg agaaactgcg gctgctgctg gagaagctga gcaggttcca tgccaagttc   1740

accctcgagt actcctgagc accccagctg gggccaggct gggtcgccct ggactgtgtg   1800

ctcaggagcc ctgggaggct ctggagccca ctgtacttgc tcttgatgcc tggcggggtg   1860

gggtgggggg ggtgctgggc ccctgcctct ctgcaggtcc ctaataaagc tgtgtggcag   1920

tctg                                                                1924
```

<210> SEQ ID NO 7
<211> LENGTH: 1924
<212> TYPE: DNA
<213> ORGANISM: Homo sapiens

<400> SEQUENCE: 7

```
ccccgccttc acccactgcc tctgcctccc tggggcagag ctgtttccca gacgggtggg     60

gcggggccca actgtcccag ctccttcagc cctttctgtc cctcccagtg aggccagctg    120

cggtgaagag ggtgctctct tgcctggcgt tccctctgca cggctgcccc ctcccaccct    180

gcccactaag ccagacccac tgtcgccatt cccacttctg gtcctgccac ctcctgagct    240

gccttcccgc ctggtctggg tagagtcatg gcctcgagca caggtgaccg gagccaggcg    300

gtgaggcatg gactgagggc gaaggtgctg acgctggacg gcatgaaccc gcgtgtgcgg    360

agagtggagt acgcagtgcg tggccccata gtgcagcgag ccttggagct ggagcaggag    420

ctgcgccagg gtgtgaagaa gcctttcacc gaggtcatcc gtgccaacat cggggacgca    480

caggctatgg ggcagaggcc catcaccttc ctgcgccagg tcttggccct ctgtgttaac    540

cctgatcttc tgagcagccc caacttccct gacgatgcca agaaaagggc ggagcgcatc    600

ttgcaggcgt gtgggggcca cagtctgggg gcctacagcg tcagctccgg catccagctg    660

atccgggagg acgtggcgcg gtacattgag aggcgtgacg gaggcatccc tgcggacccc    720

aacaacgtct tcctgtccac aggggccagc gatgccatcg tgacggtgct gaagctgctg    780

gtggccggcg agggccacac acgcacgggt gtgctcatcc ccatcccccca gtacccactc    840

tactcggcca cgctggcaga gctgggcgca gtgcaggtgg attactacct ggacgaggag    900

cgtgcctggg cgctggacgt ggccgagctt caccgtgcac tgggccaggc gcgtgaccac    960

tgccgccctc gtgcgctctg tgtcatcaac cctggcaacc ccaccgggca ggtgcagacc   1020

cgcgagtgca tcgaggccgt gatccgcttc gccttcgaag agcggctctt tctgctggcg   1080

gacgaggtgt accaggacaa cgtgtacgcc gcgggttcgc agttccactc attcaagaag   1140

gtgctcatgg agatggggcc gccctacgcc gggcagcagg agcttgcctc cttccactcc   1200

acctccaagg gctacatggg cgagtgcggg ttccgcggcg gctatgtgga ggtggtgaac   1260

atggacgctg cagtgcagca gcagatgctg aagctgatga gtgtgcggct gtgcccgccg   1320

gtgccaggac aggccctgct ggacctggtg gtcagcccgc ccgcgcccac cgacccctcc   1380

tttgcgcagt tccaggctga gaagcaggca gtgctggcag agctggcggc caaggccaag   1440

ctcaccgagc aggtcttcaa tgaggctcct ggcatcagct gcaacccagt gcagggcgcc   1500

atgtactcct tcccgcgcgt gcagctgccc ccgcgggcgg tggagcgcgc tcaggagctg   1560

ggcctggccc ccgatatgtt cttctgcctg cgcctcctgg aggagaccgg catctgcgtg   1620

gtgccaggga gcggctttgg gcagcgggaa ggcacctacc acttccggat gaccattctg   1680

ccccccttgg agaaactgcg gctgctgctg gagaagctga gcaggttcca tgccaagttc   1740

accctcgagt actcctgagc accccagctg gggccaggct gggtcgccct ggactgtgtg   1800

ctcaggagcc ctgggaggct ctggagccca ctgtacttgc tcttgatgcc tggcggggtg   1860

gggtgggggg ggtgctgggc ccctgcctct ctgcaggtcc ctaataaagc tgtgtggcag   1920

tctg                                                                1924
```

<210> SEQ ID NO 8
<211> LENGTH: 9432
<212> TYPE: DNA
<213> ORGANISM: Homo sapiens -continued

<400> SEQUENCE: 8
gccgtggctc cggtagcagc aagttcgaac cccgctcccg ctccgcttcg gttctcgctc 60
cttcggccct tgggcctcca aacaccagtc cccggcagct cgttgcgcat tgcgctctcc 120
ccgccaccag gatgccggta accgagaagg atctagctga ggacgcgcct tggaagaaga 180
tccagcagaa cacgttcaca cgctggtgca acgagcacct caagtgcgtg aacaaacgca 240
tcggcaacct gcagaccgac ctgagcgacg ggctgcggct catcgcgctg ctcgaggtgc 300
tcagccagaa gcgcatgtac cgcaagtacc atcagcggcc cacctttcgc cagatgcagc 360
tcgagaatgt gtccgtggcg ctcgagttcc tggaccgtga gagcatcaag ctcgtgtcca 420
tcgatagcaa agccattgtg gatgggaacc tgaagctcat cttgggtctg gtgtggacgc 480
tgatcctcca ctactccatc tccatgcccg tgtgggagga tgaaggggat gatgatgcca 540
agaagcagac gccaaagcag aggctgctgg ggtggattca gaacaagatc ccctacttgc 600
ccatcaccaa ctttaaccag aactggcaag acggcaaagc cctgggagcc ctggtagaca 660
gctgtgctcc aggtctgtgc ccagactggg aatcctggga cccgcagaag cctgtggata 720
atgcacgaga agccatgcag caggcagatg actggctggg tgtcccacag gtcatcactc 780
ctgaagaaat cattcacccg gatgtggacg agcactcagt tatgacttac ctgtcccagt 840
tccccaaagc caagctcaag ccgggggctc ctctcaaacc caaactcaac ccgaagaaag 900
ccagggccta tggcagagga atcgagccca ctggaaacat ggtgaagcag ccagccaagt 960
tcactgtgga caccatcagc gccgggcaag gagacgtgat ggtgtttgtt gaggacccag 1020
aagggaacaa agaggaggca caagtgaccc ctgacagcga caagaacaag acatactctg 1080
tggagtatct gcccaaggtc accgggctac acaaagtcac agtcctcttt gcaggacagc 1140
acatctccaa gagcccattt gaagtgagtg ttgacaaggc ccagggagat gccagtaaag 1200
tcactgcaaa aggtccaggg ttggaagctg tagggaacat cgccaataag cccacctact 1260
ttgacatcta tacggcagga gctggtgtgg gtgacattgg tgtggaggtg gaagatcccc 1320
aggggaagaa caccgtggag ttgctcgtgg aagacaaagg aaaccaggtg tatcgatgtg 1380
tgtacaaacc catgcagcct ggccctcacg tggtcaagat cttctttgct ggggacacta 1440
ttcctaagag tcccttcgtt gtgcaggttg gggaagcctg caatccaaat gcctgccggg 1500
ccagtggccg aggcctacaa cccaaaggcg tccgtatccg ggagaccaca gatttcaagg 1560
ttgacaccaa agctgcagga agtggggagc tcggggtaac catgaagggt cctaagggtc 1620
tggaggagct ggtgaagcag aaagactttc tggatggggt ctacgcattc gagtattacc 1680
ccagcacccc ggggagatac agcattgcca tcacatgggg gggacaccac attccaaaga 1740
gcccctttga agttcaagtt ggccctgaag cgggtatgca gaaagtccgt gcttggggcc 1800
ctgggctcca tggtgggatt gtcgggcggt cagcggactt cgtggtagaa tccattggct 1860
ctgaagtggg gtctctgggg tttgccattg aaggcccctc tcaggcaaag attgagtaca 1920
acgaccagaa tgatggatcg tgtgatgtca aatactggcc caaggagcct ggcgaatatg 1980
ctgttcacat catgtgtgac gacgaagaca tcaaggacag cccgtacatg gccttcatcc 2040
acccagccac gggaggctac aaccctgatc tggttcgagc atacgggcca ggtttggaga 2100
aatctggatg cattgtcaac aacctggccg agttcactgt ggatcctaag gatgctggaa 2160
aagctccctt aaagatattt gctcaggatg gggaaggcca acgcattgac atccagatga 2220
agaaccggat ggacggcaca tatgcatgct catacacccc ggtgaaggcc atcaagcaca 2280
ccattgctgt ggtctgggga ggcgtgaaca tcccgcacag cccctacagg gtcaacatcg 2340

-continued

```
ggcaaggtag ccatcctcag aaggtcaaag tgtttgggcc aggtgtggag agaagtggtc   2400
tgaaggcaaa tgaacctaca cacttcacgg tggactgtac tgaggctggg gaaggtgatg   2460
tcagtgttgg cattaagtgt gatgcccggg tgttaagtga agatgaggaa gacgtggatt   2520
ttgacattat tcacaatgcc aatgatacgt tcacagtcaa atatgtgcct cctgctgctg   2580
ggcgatacac tatcaaagtt ctctttgcat ctcaggaaat ccccgccagc cctttcagag   2640
tcaaagttga cccttcccac gatgccagca aagtgaaggc agaaggccca gggctcagca   2700
aagcaggtgt ggaaaatggg aaaccgaccc acttcactgt ctacaccaag gggcctggga   2760
aagccccgct caacgtgcag ttcaacagcc ctcttcctgg cgatgcagtg aaggatttgg   2820
atatcatcga taattatgac tactctcaca cggttaaata tacacccacc caacagggca   2880
acatgcaggt tctggtgact tacggtggcg atcccatccc taaaagccct ttcactgtgg   2940
gtgttgctgc accgctggat ctgagcaaga taaaactcaa tgggctggaa aacagggtgg   3000
aagttgggaa ggatcaggag ttcaccgttg ataccagggg ggcaggaggc caggggaagc   3060
tggacgtgac aatcctcagc cctctcgga aggtcgtgcc atgcctagtg acacctgtga   3120
caggccggga gaacagcacg gccaagttca tccctcggga ggaggggctg tatgctgtag   3180
acgtgaccta cgatggacac cctgtgcccg ggagccccta cacagtggag gcctcgctgc   3240
caccagatcc cagcaaggtg aaggcccacg gtcccggcct cgaaggtggt ctcgtgggca   3300
agcctgccga gttcaccatc gataccaaag gagctggtac tggaggtctg ggcttaacgg   3360
tggaaggtcc gtgcgaggcc aaaatcgagt gctccgacaa tggtgatggg acctgctccg   3420
tctcttacct tcccacaaaa cccggggagt acttcgtcaa catcctcttt gaagaagtcc   3480
acatacctgg gtctcccttc aaagctgaca ttgaaatgcc ctttgacccc tctaaagtcg   3540
tggcatcggg gccaggtctc gagcacggga aggtgggtga agctggcctc cttagcgtca   3600
actgctcgga agcgggaccg ggggccctgg gcctggaagc tgtctcggac tcgggaacaa   3660
aagccgaagt cagtattcag aacaacaaag atggcaccta cgcggtgacc tacgtgcccc   3720
tgacggccgg catgtacacg ttgaccatga agtatggtgg cgaactcgtg ccacacttcc   3780
ccgcccgggt caaggtggag cccgccgtgg acaccagcag gatcaaagtc tttggaccag   3840
gaatagaagg gaaagatgtg ttccgggaag ctaccaccga ctttacagtt gactctcggc   3900
cgctgaccca ggttgggggt gaccacatca aggcccacat tgccaacccc tcaggggcct   3960
ccaccgagtg ctttgtcaca gacaatgcgg atgggaccta ccaggtggaa tacacaccct   4020
ttgagaaagg tctccatgta gtggaggtga catatgatga cgtgcctatc ccaaacagtc   4080
ccttcaaggt ggctgtcact gaaggctgcc agccatctag ggtgcaagcc caaggacctg   4140
gattgaaaga ggcctttacc aacaagccca atgtcttcac cgtggttacc agaggcgcag   4200
gaattggtgg gcttggcata actgttgagg gaccatcaga gtcgaagata aattgcagag   4260
acaacaagga tggcagctgc agtgctgagt acattccttt cgcgccgggg gattacgatg   4320
ttaatatcac atatggagga gcccacatcc ctggcagccc cttcagggtt cctgtgaagg   4380
atgttgtgga ccccagcaag gtcaagattg ccggccccgg gctgggctca ggcgtccgag   4440
cccgtgtcct gcagtccttc acggtggaca gcagcaaggc tggcctggct ccgctggaag   4500
tgagggttct gggcccacga ggcttggtgg agccagtgaa catggtggac aatggagatg   4560
gcacacacac agtaacctac accccatctc aggagggacc ttacatggtc tcagttaaat   4620
atgctgatga agagattcct cgcagtccct tcaaggtcaa ggtccttccc acatatgatg   4680
```

-continued

```
ccagcaaagt gactgccagt ggccccggcc ttagttccta tggtgtgcct gccagtctac   4740
ctgtggactt tgcaattgat gcccgagatg ccggggaagg cctgcttgct gttcaaataa   4800
cggaccaaga aggaaaaccc aaaagagcca ttgtccatga caataaagat ggcacgtatg   4860
ctgtcaccta catccccgac aagactgggc gctatatgat tggagtcacc tacgggggtg   4920
acgacatccc actttctcct tatcgcatcc gagccacaca gacgggtgat gccagcaagt   4980
gcctggccac gggtcctgga atcgcctcca ctgtgaaaac tggcgaagaa gtaggctttg   5040
tggttgatgc caagactgcc gggaagggta aagtgacctg cacggttctg accccagatg   5100
gcactgaggc cgaggccgat gtcattgaga atgaagatgg aacctatgac atcttctaca   5160
cagctgccaa gccgggcaca tatgtgatct atgtgcgctt cggtggtgtt gatattccta   5220
acagcccctt cactgtcatg gccacagatg gggaagtcac agccgtggag gaggcaccgg   5280
taaatgcatg tccccctgga ttcaggccct gggtgaccga agaggcctat gtcccagtga   5340
gtgacatgaa cggcctggga tttaagcctt ttgacctggt cattccgttt gctgtcagga   5400
aaggagaaat cactggagag gtccacatgc cttctgggaa gacagccaca cctgagattg   5460
tggacaacaa ggacggcacg gtcactgtta gatatgcccc cactgaggtc gggctccatg   5520
agatgcacat caaatacatg ggcagccaca tccctgagag cccactccag ttctacgtga   5580
actaccccaa cagtggaagt gtttctgcat acggtccagg cctcgtgtat ggagtggcca   5640
acaaaactgc caccttcacc atcgtcacag aggatgcagg agaaggtggt ctggacttgg   5700
ctattgaggg cccctcaaaa gcagaaatca gctgcattga caataaagat gggacatgca   5760
cagtgaccta cctgccgact ctgccaggcg actacagcat tctggtcaag tacaatgaca   5820
agcacatccc tggcagcccc ttcacagcca agatcacaga tgacagcagg cggtgctccc   5880
aggtgaagtt gggctcagcc gctgacttcc tgctcgacat cagtgagact gacctcagca   5940
gcctgacggc cagcattaag gccccatctg gccgagacga gccctgtctc ctgaagaggc   6000
tgcccaacaa ccacattggc atctccttca tcccccggga agtgggcgaa catctggtca   6060
gcatcaagaa aaatggcaac catgtggcca acagccccgt gtctatcatg gtggtccagt   6120
cggagattgg tgacgcccgc cgagccaaag tctatggccg cggcctgtca gaaggccgga   6180
ctttcgagat gtctgacttc atcgtggaca caagggatgc aggttatggt ggcatatcct   6240
tggcggtgga aggccccagc aaagtggaca tccagacgga ggacctggaa gatggcacct   6300
gcaaagtctc ctacttccct accgtgcctg ggtttatat cgtctccacc aaattcgctg   6360
acgagcacgt gcctgggagc ccatttaccg tgaagatcag tggggaggga agagtcaaag   6420
agagcatcac ccgcaccagt cgggccccgt ccgtggccac tgtcgggagc atttgtgacc   6480
tgaacctgaa aatcccagaa atcaacagca gtgatatgtc ggcccacgtc accagcccct   6540
ctggccgtgt gactgaggca gagattgtgc ccatggggaa gaactcacac tgcgtccggt   6600
ttgtgcccca ggagatgggc gtgcacacgg tcagcgtcaa gtaccgtggg cagcacgtca   6660
ccggcagccc cttccagttc accgtggggc cacttggtga aggaggcgcc cacaaggtgc   6720
gggcaggagg ccctggcctg gagagaggag aagcgggagt cccagctgag ttcagcattt   6780
ggacccggga agcaggcgct ggaggcctct ccatcgctgt tgagggcccc agtaaggccg   6840
agattacatt cgatgaccat aaaaatgggt cgtgcggtgt atcttatatt gcccaagagc   6900
ctggtaacta cgaggtgtcc atcaagttca atgatgagca catcccggaa agcccctacc   6960
tggtgccggt catcgcaccc tccgacgacg cccgccgcct cactgttatg agccttcagg   7020
aatcgggatt aaaagttaac cagccagcat cctttgctat aaggttgaat ggcgcaaaag   7080
```

gcaagattga tgcaaaggtg cacagcccct ctggagccgt ggaggagtgc cacgtgtctg 7140
agctggagcc agataagtat gctgttcgct tcatccctca tgagaatggt gtccacacca 7200
tcgatgtcaa gttcaatggg agccacgtgg ttggaagccc cttcaaagtg cgcgttgggg 7260
agcctggaca agcggggaac cctgccctgg tgtccgccta tggcacggga ctcgaagggg 7320
gcaccacagg tatccagtcg gaattcttta ttaacaccac ccgagcaggt ccagggacat 7380
tatccgtcac catcgaaggc ccatccaagg ttaaaatgga ttgccaggaa acacctgaag 7440
ggtacaaagt catgtacacc cccatggctc ctggtaacta cctgatcagt gtcaaatacg 7500
gtgggcccaa ccacatcgtg ggcagtccct tcaaggccaa ggtgacaggc cagcgtctag 7560
ttagccctgg ctcagccaac gagacctcat ccatcctggt ggagtcagtg accaggtcgt 7620
ctacagagac ctgctatagc gccattccca aggcatcctc ggacgccagc aaggtgacct 7680
ctaagggggc agggctctca aaggcctttg tgggccagaa gagttccttc ctggtggact 7740
gcagcaaagc tggctccaac atgctgctga tcggggtcca tgggcccacc accccctgcg 7800
aggaggtctc catgaagcat gtaggcaacc agcaatacaa cgtcacatac gtcgtcaagg 7860
agaggggcga ttatgtgctg gctgtgaagt gggggggagga acacatccct ggcagccctt 7920
ttcatgtcac agtgccttaa aacagttttc tcaaatcctg gagagagttc ttgtggttgc 7980
ttttgttgct tgtttgtaat tcattttata caaagccctc cagcctgttt gtggggctga 8040
aaccccatcc ctaaaatatt gctgttgtaa aatgccttca gaaataagtc ctagactgga 8100
ctcttgaggg acatattgga gaatcttaag aaatgcaagc ttgttcaggg ggctgagaag 8160
atcctgagta cactaggtgc aaaccagaac tcttggtgga acagaccagc cactgcagca 8220
gacagaccag gaacacaatg agactgacat ttcaaaaaaa caaaactggc tagcctgagc 8280
tgctggttca ctcttcagca tttatgaaac aaggctaggg gaagatgggc agagaaaaag 8340
gggacaccta gtttggttgt catttggcaa aggagatgac ttaaaatccg cttaatctct 8400
tccagtgtcc gtgttaatgt atttggctat tagatcacta gcactgcttt accgctcctc 8460
atcgccaaca cccccatgct ctgtggcctt cttacacttc tcagagggca gagtggcagc 8520
cgggcaccct acagaaactc agagggcaga gtggcagcca ggcccacatg tctctcaagt 8580
acctgtcccc tcgctctggt gattatttct tgcagaatca ccacacgaga ccatcccggc 8640
agtcatggtt ttgctttagt tttccaagtc cgtttcagtc ccttccttgg tctgaagaaa 8700
ttctgcagtg gcgagcagtt tcccacttgc caaagatccc ttttaaccaa cactagccct 8760
tgtttttaac acacgctcca gcccttcatc agcctgggca gtcttaccaa aatgtttaaa 8820
gtgatctcag aggggcccat ggattaacgc cctcatccca aggtccgtcc catgacataa 8880
cactccacac ccgccccagc caacttcatg ggtcactttt tctggaaaat aatgatctgt 8940
acagacagga cagaatgaaa ctcctgcggc tctttggcct gaaagttggg aatggttggg 9000
ggagagaagg gcagcagctt attggtggtc ttttcaccat tggcagaaac agtgagagct 9060
gtgtggtgca gaaatccaga aatgaggtgt agggaatttt gcctgccttc ctgcagacct 9120
gagctggctt tggaatgagg ttaaagtgtc agggacgttg cctgagccca aatgtgtagt 9180
gtggtctggg caggcagacc tttaggtttt gctgcttagt cctgaggaag tggccactct 9240
tgtggcaggt gtagtatctg gggcgagtgt tgggggtaaa agcccaccct acagaaagtg 9300
gaacagcccg gacctgatgt gaaaggacca cgggtgttgt aagctgggac cggaaccaaa 9360
ctggaatcaa acgcgactgt aaattgtatc ttataactta ttaaataaaa cattgctccg 9420

```
taaaaaaaaa aa                                                    9432


<210> SEQ ID NO 9
<211> LENGTH: 2193
<212> TYPE: DNA
<213> ORGANISM: Homo sapiens

<400> SEQUENCE: 9

cgatgatgat tcagtggaat gggcccaaga ccagcatttc tgagaaggct cgggggctgg     60

ctttgaccta cagcctccgg gacagggaac gtggtggtgg tcgtgcacag attggtgtgg    120

tggatgatga ggccaaagcc ccggacctca tgcagatcat ggaggctgtg ctgggctgca    180

gggtgggcag cctgcgtgcc gccacgccca gcaaggatat caaccagctg cagaaggcca    240

atgttcgcct gtaccatgtc tatgagaagg gcaaagacct ggtggtcctg gagttggcga    300

ccccccact gacccaggac ctgctgcagg aggaggactt ctacatcctg gaccagggtg    360

gcttcaagat ctatgtgtgg cagggacgca tgtctagcct ccaggagaga aaggctgcct    420

tcagccgggc tgtgggcttc atccaggcca agggctaccc gacctacacc aacgtggagg    480

tggtgaacga cggcgccgag tcggccgcgt tcaagcagct cttccggact tggtctgaga    540

agcggcgcag gaaccagaag ctcggcggga gggataaatc gattcatgta aagctggacg    600

tgggcaagct gcacacccag cctaagttag cggcccagct caggatggtg gacgacggct    660

ctgggaaggt ggaggtgtgg tgcatccagg acttacacag gcagcccgtg gaccccaagc    720

gtcatggaca gctgtgtgca ggcaactgct accttgtgct ctacacatac cagaggctgg    780

gccgtgttca gtacatcctg tacctatggc agggccacca ggccactgcg gatgagattg    840

aggccctgaa cagcaacgct gaggaactag atgtcatgta tggtggcgtc ctagtacagg    900

agcatgtgac catgggcagc gagcccccc acttcctcgc catcttccag ggccagctgg    960

tgatcttcca ggagagagct gggcaccatg gaaaggggca gtcagcatcc accacaaggc   1020

ttttccaagt gcaaggcact gacagccaca acaccaggac catggaggtg ccagcccgtg   1080

cctcatccct caactccagt gacatcttct tgctggtcac agccagcgtc tgctacctct   1140

ggtttgggaa gggctgtaat ggtgatcagc gtgagatggc acgggtggtg gtcactgtca   1200

tttccaggaa gaatgaggaa acggtgctgg agggtcagga gcctccccac ttctgggagg   1260

ccctgggagg ccgggccccc taccccagca acaagaggct ccctgaggag gtccccagct   1320

tccagccacg actgtttgag tgctccagcc acatgggctg cctggtcctc gcagaagtgg   1380

ggttcttcag ccaggaggac ctggacaagt atgacatcat gttactggac acctggcagg   1440

agatcttcct gtggcttggg gaagctgcaa gtgagtggaa ggaggcggtg gcctggggcc   1500

aggagtacct gaagactcac ccagcaggga ggagcccggc cacacccatc gtgctggtca   1560

agcagggcca tgagcctccc accttcattg gatggttctt cacttgggac ccctacaagt   1620

ggactagcca cccgtcccac aaggaagtgg tggatggcag cccggcagca gcatcaacca   1680

tctctgagat aacagcagaa gtcaacaact tgcggctatc cagatggccg ggcaatggca   1740

gggcaggtgc cgtggccctg caggccctca agggctccca ggacagctca gagaatgatc   1800

tggtgcgaag ccccaagtcg gctggcagca gaaccagcag ctccgtcagc agcaccagcg   1860

ccacgatcaa cgggggcctg cgccgggaac aactgatgca ccaggctgtt gaggacctgc   1920

cagagggcgt ggaccctgcc cgcagggagt tctatctctc agactctgac ttccaagata   1980

tctttgggaa atccaaggag gaattctaca gcatggccac gtggaggcag cggcaggaga   2040

aaaagcagct gggcttcttc tgaacccaag ccctctcgac tgcccctatc ccctggaccc   2100
```

-continued caacatacct acaatgctgg ggaggccctg cttccactcc cctcagaggc ttttggtcat 2160
cctctgcgtg tcagtaaaag caggcagccc ata 2193

<210> SEQ ID NO 10
<211> LENGTH: 2089
<212> TYPE: DNA
<213> ORGANISM: Homo sapiens

<400> SEQUENCE: 10
gcggccgctc cgtgtgccct ggactcgccg cccgcggctc ggaagctgga gagtcagcga 60
cggggcccga ctgcgggacc gagggctgca agaagaagcg aacaaatagt ccccagcgcc 120
tcctctggat gcggtcgcgt ctgtggtcct ggcagccgct gggcgggcca ggccaggtcg 180
ggccgggccg agccgggcac atggacctgg gcctgcgggc tctaattgcg gcgcttatgt 240
tgatgatttt ttttttaatc acagcagccc ccagtttagc ggactgattt actcccggta 300
ttggtaaata tgatcacgtg ggccgcgcga ccaatggtgg aggctgcagc ctgcgaacta 360
gtcggtggct cgggcgccgg cggggagctg ctcggcggcg gacagtgtaa tgttgggtgg 420
gagtgcggga cgcctcaaaa tgtcttccag tggcaccctc agcaactact acgtggactc 480
gcttataggc catgagggcg acgaggtgtt cgcgcgcgcgc ttcgggccgc cggggccagg 540
cgcgcagggc cggcctgcag gtgtggctga tggcccggcc gccaccgccg ccgagttcgc 600
ctcgtgtagt tttgccccca gatcggccgt gttctctgcc tcgtggtccg cggtgccctc 660
ccagcccccg gcagcggcgg cgatgagcgg cctctaccac ccgtacgttc ccccgccgcc 720
cctggccgcc tctgcctccg agcccggccg ctacgtgcgc tcctggatgg agccgctgcc 780
cggcttcccg ggcggtgcgg gcggtggcgg tggtggtgga ggcggcggtc cgggccgcgg 840
tcccagccct ggccccagcg gcccagccaa cgggcgccac tacgggatta agcctgaaac 900
ccgagcggcc ccggcccccg ccacggccgc ctccaccacc tcctcctcct ccacttcctt 960
atcctcctcc tccaaacgga ctgagtgctc cgtggcccgg gagtcccagg ggagcagcgg 1020
ccccgagttc tcgtgcaact cgttcctgca ggagaaggcg gcagcggcga cgggggggaac 1080 cgggcctggg gcagggatcg gggccgcgac tgggacgggc ggctcgtcgg agccctcagc 1140
ttgcagcgac cacccgatcc caggctgttc gctgaaggag gaggagaagc agcattcgca 1200
gccgcagcag cagcaacttg acccaaacaa ccccgccgcg aactggatcc acgctcgctc 1260
cacccggaaa aagcgctgtc cctacaccaa ataccagacg cttgagctgg agaaagaatt 1320
cctcttcaac atgtacctca cccgggaccg gcgctacgag gtggccagga ttctcaacct 1380
aacagagaga caggtcaaaa tctggtttca gaaccgtagg atgaaaatga aaaagatgag 1440
caaggagaaa tgccccaaag gagactgacc cggcgcggtg ctggcgggag cgctcaaggg 1500
cagcggattt gttgttgttg ctgttttcct ttgtgggtgt ttggtgcttg atttccagaa 1560
actctccagc gacttggact tcttcttctt tttttttttc tttttagata gaagtgactg 1620
tgtggttggt ctctgaggta tttgggggac tctgtatttg ctcgtttacg tgttggaaaa 1680
accaagtggc tttggggttt cgccctatcc cactccctct ctttcctgct ccattggttc 1740
cttaagaaat gctatatttt gtgagtgcaa gctggcttgg ggagccctct cttgtgtaaa 1800
tgtcccccat gtttctgaaa agtgctgtag tttagtcccc tcacccccag cactgcccaa 1860
acaggggcca agtgcgcccc aattccaaga atgaaggcag agcgacaaca gtgcggacac 1920
cccggctgct agcccacggt gaagcccggc ggggttgccc accagttgcg aaagccccct 1980

-continued

```
ttcctcaggg agcacgcggg acctcggtgg agatctccag tgaggcttag aggagcccag   2040

ggcctcgggc gggttggggt ttgtcctcag tgcattggac gcgctgctc              2089


<210> SEQ ID NO 11
<211> LENGTH: 8019
<212> TYPE: DNA
<213> ORGANISM: Homo sapiens

<400> SEQUENCE: 11

gcggcccggt gcgggtgtcg gggagaccgg gctctctgcc cggcgcggcg cggcgcggct     60

cggcccacga gcgaccaccg acatggagtg ggctcgggcg gccaagtagc cgcttctccg    120

gagcccggtg ccagtgccgc ccgcagcccg ccttccaccc ccggccgcgc cgccggtcag    180

gccctagggt gaagccggga ggaaaatgaa gagttttcac cggaatccgt tgaaaatagg    240

actgactgca aagccttaaa gaaagaagga cctcgggagg agaaacgaaa agccgcctcc    300

gggcaagact tggcgtgctc cgagccgagg ggctgcttca gggacctcgc cccctccctt    360

tcccgctgga gaaattgccg ctgatgcatt atccaagtgg tggttgggag gatttgcagc    420

aacatttttg gttttccctc ccccttctat gcattctgtt tttttcctcc cttttctgtt    480

tttcttcttc ccgggaagtg aattgctgat gcaaatcgga ctttattcat taatgatgca    540

accggattcg tttcaggatt acgttgcacg agttgaattt tgaatgaagg agaagagttt    600

tttttttttt ttttaaagaa gtgttgactc tctagttcgt tgtactttta attattattt    660

tatttaaata tacgacttaa ttgtattctt ttaaaaatgc attaagtata tattttatgg    720

taatttaccc tcaaaatata tgtatatggg tgaaattgaa gacgcttcag ttaagtgagg    780

ttactggtgt gttggatgtt taattcagca ccagcattgc atgacagttg tttgaataac    840

aagtggttta tttttaaaac catacctttt aaaatttagg ttcagataat agtaaaagtc    900

atcataataa tttaaaggaa aaccagcaga aatcgaagca aacatgtctg gagaagtgcg    960

tttgaggcag ttggagcagt ttattttgga cgggcccgct cagaccaatg ggcagtgctt   1020

cagtgtggag acattactgg atatactcat ctgcctttat gatgaatgca ataattctcc   1080

attgagaaga gagaagaaca ttctcgaata cctagaatgg gctaaaccat ttacttctaa   1140

agtgaaacaa atgcgattac atagagaaga ctttgaaata ttaaaggtga ttggtcgagg   1200

agcttttggg gaggttgctg tagtaaaact aaaaaatgca gataaagtgt ttgccatgaa   1260

aatattgaat aaatgggaaa tgctgaaaag agctgagaca gcatgttttc gtgaagaaag   1320

ggatgtatta gtgaatggag acaataaatg gattacaacc ttgcactatg ctttccagga   1380

tgacaataac ttatacctgg ttatggatta ttatgttggt ggggatttgc ttactctact   1440

cagcaaattt gaagatagat tgcctgaaga tatggctaga ttttacttgg ctgagatggt   1500

gatagcaatt gactcagttc atcagctaca ttatgtacac agagacatta aacctgacaa   1560

tatactgatg gatatgaatg gacatattcg gttagcagat tttggttctt gtctgaagct   1620

gatggaagat ggaacggttc agtcctcagt ggctgtagga actccagatt atatctctcc   1680

tgaaatcctt caagccatgg aagatggaaa agggagatat ggacctgaat gtgactggtg   1740

gtctttgggg gtctgtatgt atgaaatgct ttacggagaa acaccatttt atgcagaatc   1800

gctggtggag acatacggaa aaatcatgaa ccacaaagag aggtttcagt ttccagccca   1860

agtgactgat gtgtctgaaa atgctaagga tcttattcga aggctcattt gtagcagaga   1920

acatcgactt ggtcaaaatg gaatagaaga ctttaagaaa cacccatttt tcagtggaat   1980

tgattgggat aatattcgga actgtgaagc accttatatt ccagaagtta gtagcccaac   2040
```

```
agatacatcg aattttgatg tagatgatga ttgtttaaaa aattctgaaa cgatgccccc   2100
accaacacat actgcatttt ctggccacca tctgccattt gttggtttta catatactag   2160
tagctgtgta ctttctgatc ggagctgttt aagagttacg gctggtccca cctcactgga   2220
tcttgatgtt aatgttcaga ggactctaga caacaactta gcaactgaag cttatgaaag   2280
aagaattaag cgccttgagc aagaaaaact tgaactcagt agaaaacttc aagagtcaac   2340
acagactgtc caagctctgc agtattcaac tgttgatggt ccactaacag caagcaaaga   2400
tttagaaata aaaaacttaa aagaagaaat tgaaaaacta agaaaacaag taacagaatc   2460
aagtcatttg gaacagcaac ttgaagaagc taatgctgtg aggcaagaac tagatgatgc   2520
ttttagacaa atcaaggctt atgaaaaaca aatcaaaacg ttacaacaag aaagagaaga   2580
tctaaataag gaactagtcc aggctagtga gcgattaaaa aaccaatcca aagagctgaa   2640
agacgcacac tgtcagagga aactggccat gcaggaattc atggagatca atgagcggct   2700
aacagaattg cacacccaaa aacagaaact tgctcgccat gtccgagata aggaagaaga   2760
ggtggacctg gtgatgcaaa aagttgaaag cttaaggcaa gaactgcgca gaacagaaag   2820
agccaaaaaa gagctggaag ttcatacaga agctctagct gctgaagcat ctaaagacag   2880
gaagctacgt gaacagagtg agcactattc taagcaactg gaaaatgaat tggagggact   2940
gaagcaaaaa caaattagtt actcaccagg agtatgcagc atagaacatc agcaagagat   3000
aaccaaacta aagactgatt tggaaaagaa aagtatcttt tatgaagaag aattatctaa   3060
aagagaagga atacatgcaa atgaaataaa aaatcttaag aaagaactgc atgattcaga   3120
aggtcagcaa cttgctctca acaaagaaat tatgatttta aaagacaaat tggaaaaaac   3180
cagaagagaa agtcaaagtg aaagggagga atttgaaagt gagttcaaac aacaatatga   3240
acgagaaaaa gtgttgttaa ctgaagaaaa taaaaagctg acgagtgaac ttgataagct   3300
tactactttg tatgagaact taagtataca caaccagcag ttagaagaag aggttaaaga   3360
tctagcagac aagaaagaat cagttgcaca ttgggaagcc caaatcacag aaataattca   3420
gtgggtcagc gatgaaaagg atgcacgagg gtatcttcag gccttagctt ctaaaatgac   3480
tgaagaattg gaggcattaa gaaattccag cttgggtaca cgagcaacag atatgccctg   3540
gaaaatgcgt cgttttgcga aactggatat gtcagctaga ctggagttgc agtcggctct   3600
ggatgcagaa ataagagcca aacaggccat ccaagaagag ttgaataaag ttaaagcatc   3660
taatatcata acagaatgta aactaaaaga ttcagagaag aagaacttgg aactactctc   3720
agaaatcgaa cagctgataa aggacactga agagcttaga tctgaaaagg gtatagagca   3780
ccaagactca cagcattctt tcttggcatt tttgaatacg cctaccgatg ctctggatca   3840
atttgaaact gtagactcca ctccactttc agttcacaca ccaaccttaa ggaaaaaagg   3900
atgtcctggt tcaactggct ttccacctaa gcgcaagact caccagtttt ttgtaaaatc   3960
ttttactact cctaccaagt gtcatcagtg tacctccttg atggtgggtt taataagaca   4020
gggctgttca tgtgaagtgt gtggattctc atgccatata acttgtgtaa acaaagctcc   4080
aaccacttgt ccagttcctc ctgaacagac aaaaggtccc ctgggtatag atcctcagaa   4140
aggaatagga acagcatatg aaggtcatgt caggattcct aagccagctg gagtgaagaa   4200
agggtggcag agagcactgg ctatagtgtg tgacttcaaa ctctttctgt acgatattgc   4260
tgaaggaaaa gcatctcagc ccagtgttgt cattagtcaa gtgattgaca tgagggatga   4320
agaattttct gtgagttcag tcttggcttc tgatgttatc catgcaagtc ggaaagatat   4380
```

-continued

```
accctgtata tttagggtca cagcttccca gctctcagca tctaataaca aatgttcaat   4440
cctgatgcta gcagacactg agaatgagaa gaataagtgg gtgggagtgc tgagtgaatt   4500
gcacaagatt ttgaagaaaa acaaattcag agaccgctca gtctatgttc ccaaagaggc   4560
ttatgacagc actctacccc tcattaaaac aacccaggca gccgcaatca tagatcatga   4620
aagaattgct ttgggaaacg aagaagggtt atttgttgta catgtcacca aagatgaaat   4680
tattagagtt ggtgacaata agaagattca tcagattgaa ctcattccaa atgatcagct   4740
tgttgctgtg atctcaggac gaaatcgtca tgtacgactt tttcctatgt cagcattgga   4800
tgggcgagag accgattttt acaagctgtc agaaactaaa gggtgtcaaa ccgtaacttc   4860
tggaaaggtg cgccatggag ctctcacatg cctgtgtgtg gctatgaaaa ggcaggtcct   4920
ctgttatgaa ctatttcaga gcaagacccg tcacagaaaa tttaaagaaa ttcaagtccc   4980
atataatgtc cagtggatgg caatcttcag tgaacaactc tgtgtgggat tccagtcagg   5040
atttctaaga taccccttga atggagaagg aaatccatac agtatgctcc attcaaatga   5100
ccatacacta tcatttattg cacatcaacc aatggatgct atctgcgcag ttgagatctc   5160
cagtaaagaa tatctgctgt gttttaacag cattgggata tacactgact gccagggccg   5220
aagatctaga caacaggaat tgatgtggcc agcaaatcct tcctcttgtt gttacaatgc   5280
accatatctc tcggtgtaca gtgaaaatgc agttgatatc tttgatgtga actccatgga   5340
atggattcag actcttcctc tcaaaaaggt tcgaccctta aacaatgaag gatcattaaa   5400
tcttttaggg ttggagacca ttagattaat atatttcaaa aataagatgg cagaaggga    5460
cgaactggta gtacctgaaa catcagataa tagtcggaaa caaatggtta gaaacattaa   5520
caataagcgg cgttattcct tcagagtccc agaagaggaa aggatgcagc agaggaggga   5580
aatgctacga gatccagaaa tgagaaataa attaatttct aatccaacta attttaatca   5640
catagcacac atgggtcctg gagatggaat acagatcctg aaagatctgc ccatgaaccc   5700
tcggcctcag gaaagtcgga cagtattcag tggctcagtc agtattccat ctatcaccaa   5760
atcccgccct gagccaggcc gctccatgag tgctagcagt ggcttgtcag caaggtcatc   5820
cgcacagaat ggcagcgcat taaagaggga attctctgga ggaagctaca gtgccaagcg   5880
gcagcccatg ccctccccgt cagagggctc tttgtcctct ggaggcatgg accaaggaag   5940
tgatgcccca gcgagggact ttgacggaga ggactctgac tctccgaggc attccacagc   6000
ttccaacagt tccaacctaa gcagcccccc aagcccagct tcaccccgaa aaaccaagag   6060
cctctccctg gagagcactg accgcgggag ctgggacccg tgagctgcct cagcactggg   6120
acctctcgct ctccgctccc tgccactcgc ctcctctcac tttcatctct tccctccacc   6180
tcgcctgctc ggcctgaaag ccaccagggg ctggcagcag tagcaggaca gggattcagg   6240
agttctgacg acacgactct cagatccacg cccccagcct aacagcaaca acaaagacag   6300
actttccgta gcagcttaga ttaacgttga tttcattcca tgcacttaga gttgctttca   6360
gtaacatttt accccctactc ccaaaggtag cttaaataga cagattacac aaatgtaagt   6420
gataagaata agattagaca gattttgctt tcacagtaga gtctcattat agtcctaaaa   6480
tagctcatgg gcttctccgc atccagaagg gagaattggt ccctggagtg gctcactaag   6540
ctcttaatca gcaaacgcag tgagtatcaa cctgattgtt gccaggaaat ccttatgaat   6600
taaaacaatg catattttac tacagtacag agtttaaatg aatacataaa tgtagaagta   6660
ctgaatgtat atatttaaaa ggagcctctt gtattcaaca aaagatggat gcatatataa   6720
gagagatgat ttaatttaaa gaaatatgtt gtttcttgtc tgtaatgtaa tgtaaagggt   6780
```

ggaaaggcct caagctcaca tttgtagaga gagagcgaga gaaatcagag ttccctttat 6840
tgccctgtcc tcaaactggt cataggctct agtcacctgg ggagctgtag aaaacacttg 6900
cagagccagg ttttgctggt ttggggcatg ccctgggcac cagagcttta acatttgaag 6960
ccacttcagc agcagcagca aaaggcgaac tcatctctac ccaagatgtt tcttttccta 7020
gtggtggaat ttgaacactt ctcacttttt attgtatttt atcttccgca gataaatgta 7080
gaaatacacg attctgtcac ctctgatccc ttccatctga aaggttacaa ggagtgttgt 7140
agcttctgaa ggtgcagaaa acaatttcta aaaatgcttt tattcctggg ctaatcctgt 7200
ccctccctaa gtcacagcga ggtgtctgtc ccagggctgg agatgcttcc caaggaggag 7260
tctgttttgt tgagagtggg cgtgggcttc ttcacataag cctggggaag gaagaaaaaa 7320
cggctttcat taccaaataa tgtaaaacct caaaagcaag ggcttcaaca gccttaacca 7380
aatattattc cccatagcca gtggaaaatg gatgtgacaa ccccagtgcg caggccagag 7440
tgagtgagcc cagcacggcg ctccgactgg cttcctctct caggtgctgg attgtggggt 7500
tagtggcatt tccagctgga ttcctcctgt tgtagttgcc ataaggaaat gagatgcaga 7560
atcagaagga tctatttcta cagaatcatt tcaccagtta agcacatgag tagagaaaga 7620
gataaaaata aaagtatctc atgaaggaaa gagattttgc ctctctttta cttttcacct 7680
aagtttctct gagaaataga gacaggattc tctctttaaa attcagtgaa aatgaagaaa 7740
gttttcctgc agttgctaac ctgagttgca gtgtttaagg ccatcatttc actgctgctg 7800
tctgtgactc cacgtctgtg tcactgaggt gacctgcgtg tcactgaggt ggccaccatg 7860
ctggcctgcg gcatgtgcag ggagctgagg ctgtttccag gtgatgctgc tgtgtggaga 7920
aggttctgag atgcagtgag ggaagaaagg atcctgctgg ggattccatt gtaagcacct 7980
ataatcggga attttcatgt aacagctttg acatttaaa 8019

<210> SEQ ID NO 12
<211> LENGTH: 7776
<212> TYPE: DNA
<213> ORGANISM: Homo sapiens

<400> SEQUENCE: 12
gcggcccggt gcgggtgtcg gggagaccgg gctctctgcc cggcgcggcg cggcgcggct 60
cggcccacga gcgaccaccg acatggagtg ggctcgggcg gccaagtagc cgcttctccg 120
gagcccggtg ccagtgccgc ccgcagcccg ccttccaccc ccggccgcgc cgccggtcag 180
gccctagggt gaagccggga ggaaaatgaa gagttttcac cggaatccgt tgaaaatagg 240
actgactgca aagccttaaa gaaagaagga cctcgggagg agaaacgaaa agccgcctcc 300
gggcaagact tggcgtgctc cgagccgagg ggctgcttca gggacctcgc cccctccctt 360
tcccgctgga gaaattgccg ctgatgcatt atccaagtgg tggttgggag gatttgcagc 420
aacatttttg gttttccctc ccccttctat gcattctgtt tttttcctcc cttttctgtt 480
tttcttcttc ccgggaagtg aattgctgat gcaaatcgga ctttattcat taatgatgca 540
accggattcg tttcaggatt acgttgcacg agttgaattt tgaatgaagg agaagagttt 600
tttttttttt ttttaaagaa gtgttgactc tctagttcgt tgtactttta attattattt 660
tatttaaata tacgacttaa ttgtattctt ttaaaaatgc attaagtata tattttatgg 720
taatttaccc tcaaaatata tgtatatggg tgaaattgaa gacgcttcag ttaagtgagg 780
ttactggtgt gttggatgtt taattcagca ccagcattgc atgacagttg tttgaataac 840

-continued

```
aagtggttta tttttaaaac catacctttt aaaatttagg ttcagataat agtaaaagtc    900
atcataataa tttaaaggaa aaccagcaga aatcgaagca aacatgtctg gagaagtgcg    960
tttgaggcag ttggagcagt ttattttgga cgggcccgct cagaccaatg ggcagtgctt   1020
cagtgtggag acattactgg atatactcat ctgcctttat gatgaatgca ataattctcc   1080
attgagaaga gagaagaaca ttctcgaata cctagaatgg gctaaaccat ttacttctaa   1140
agtgaaacaa atgcgattac atagagaaga ctttgaaata ttaaaggtga ttggtcgagg   1200
agcttttggg gaggttgctg tagtaaaact aaaaaatgca gataaagtgt ttgccatgaa   1260
aatattgaat aaatgggaaa tgctgaaaag agctgagaca gcatgttttc gtgaagaaag   1320
ggatgtatta gtgaatggag acaataaatg gattacaacc ttgcactatg ctttccagga   1380
tgacaataac ttatacctgg ttatggatta ttatgttggt ggggatttgc ttactctact   1440
cagcaaattt gaagatagat tgcctgaaga tatggctaga ttttacttgg ctgagatggt   1500
gatagcaatt gactcagttc atcagctaca ttatgtacac agagacatta aacctgacaa   1560
tatactgatg gatatgaatg gacatattcg gttagcagat tttggttctt gtctgaagct   1620
gatggaagat ggaacggttc agtcctcagt ggctgtagga actccagatt atatctctcc   1680
tgaaatcctt caagccatgg aagatggaaa agggagatat ggacctgaat gtgactggtg   1740
gtctttgggg gtctgtatgt atgaaatgct ttacggagaa acaccatttt atgcagaatc   1800
gctggtggag acatacggaa aaatcatgaa ccacaaagag aggtttcagt ttccagccca   1860
agtgactgat gtgtctgaaa atgctaagga tcttattcga aggctcattt gtagcagaga   1920
acatcgactt ggtcaaaatg gaatagaaga ctttaagaaa cacccatttt tcagtggaat   1980
tgattgggat aatattcgga actgtgaagc accttatatt ccagaagtta gtagcccaac   2040
agatacatcg aattttgatg tagatgatga ttgtttaaaa aattctgaaa cgatgccccc   2100
accaacacat actgcatttt ctggccacca tctgccattt gttggtttta catatactag   2160
tagctgtgta ctttctgatc ggagctgttt aagagttacg gctggtccca cctcactgga   2220
tcttgatgtt aatgttcaga ggactctaga caacaactta gcaactgaag cttatgaaag   2280
aagaattaag cgccttgagc aagaaaaact tgaactcagt agaaaacttc aagagtcaac   2340
acagactgtc caagctctgc agtattcaac tgttgatggt ccactaacag caagcaaaga   2400
tttagaaata aaaaacttaa aagaagaaat tgaaaaacta agaaaacaag taacagaatc   2460
aagtcatttg gaacagcaac ttgaagaagc taatgctgtg aggcaagaac tagatgatgc   2520
ttttagacaa atcaaggctt atgaaaaaca aatcaaaacg ttacaacaag aaagagaaga   2580
tctaaataag ctggaagttc atacagaagc tctagctgct gaagcatcta aagacaggaa   2640
gctacgtgaa cagagtgagc actattctaa gcaactggaa aatgaattgg agggactgaa   2700
gcaaaaacaa attagttact caccaggagt atgcagcata gaacatcagc aagagataac   2760
caaactaaag actgatttgg aaaagaaaag tatcttttat gaagaagaat tatctaaaag   2820
agaaggaata catgcaaatg aaataaaaaa tcttaagaaa gaactgcatg attcagaagg   2880
tcagcaactt gctctcaaca aagaaattat gattttaaaa gacaaattgg aaaaaaccag   2940
aagagaaagt caaagtgaaa gggaggaatt tgaaagtgag ttcaaacaac aatatgaacg   3000
agaaaaagtg ttgttaactg aagaaaataa aaagctgacg agtgaacttg ataagcttac   3060
tactttgtat gagaacttaa gtatacacaa ccagcagtta gaagaagagg ttaaagatct   3120
agcagacaag aaagaatcag ttgcacattg ggaagcccaa atcacagaaa taattcagtg   3180
ggtcagcgat gaaaaggatg cacgagggta tcttcaggcc ttagcttcta aaatgactga   3240
```

-continued agaattggag gcattaagaa attccagctt gggtacacga gcaacagata tgccctggaa 3300
aatgcgtcgt tttgcgaaac tggatatgtc agctagactg gagttgcagt cggctctgga 3360
tgcagaaata agagccaaac aggccatcca agaagagttg aataaagtta aagcatctaa 3420
tatcataaca gaatgtaaac taaaagattc agagaagaag aacttggaac tactctcaga 3480
aatcgaacag ctgataaagg acactgaaga gcttagatct gaaaagggta tagagcacca 3540
agactcacag cattctttct tggcattttt gaatacgcct accgatgctc tggatcaatt 3600
tgaaactgta gactccactc cactttcagt tcacacacca accttaagga aaaaaggatg 3660
tcctggttca actggctttc cacctaagcg caagactcac cagtttttg taaaatcttt 3720
tactactcct accaagtgtc atcagtgtac ctccttgatg gtgggtttaa taagacaggg 3780
ctgttcatgt gaagtgtgtg gattctcatg ccatataact tgtgtaaaca aagctccaac 3840
cacttgtcca gttcctcctg aacagacaaa aggtcccctg ggtatagatc ctcagaaagg 3900
aataggaaca gcatatgaag gtcatgtcag gattcctaag ccagctggag tgaagaaagg 3960
gtggcagaga gcactggcta tagtgtgtga cttcaaactc tttctgtacg atattgctga 4020
aggaaaagca tctcagccca gtgttgtcat tagtcaagtg attgacatga gggatgaaga 4080
attttctgtg agttcagtct tggcttctga tgttatccat gcaagtcgga aagatatacc 4140
ctgtatattt agggtcacag cttcccagct ctcagcatct aataacaaat gttcaatcct 4200
gatgctagca gacactgaga atgagaagaa taagtgggtg ggagtgctga gtgaattgca 4260
caagattttg aagaaaaaca aattcagaga ccgctcagtc tatgttccca aagaggctta 4320
tgacagcact ctacccctca ttaaaacaac ccaggcagcc gcaatcatag atcatgaaag 4380
aattgctttg ggaaacgaag aagggttatt tgttgtacat gtcaccaaag atgaaattat 4440
tagagttggt gacaataaga agattcatca gattgaactc attccaaatg atcagcttgt 4500
tgctgtgatc tcaggacgaa atcgtcatgt acgacttttt cctatgtcag cattggatgg 4560
gcgagagacc gatttttaca agctgtcaga aactaaaggg tgtcaaaccg taacttctgg 4620
aaaggtgcgc catggagctc tcacatgcct gtgtgtggct atgaaaaggc aggtcctctg 4680
ttatgaacta tttcagagca agacccgtca cagaaaattt aaagaaattc aagtcccata 4740
taatgtccag tggatggcaa tcttcagtga acaactctgt gtgggattcc agtcaggatt 4800
tctaagatac cccttgaatg gagaaggaaa tccatacagt atgctccatt caaatgacca 4860
tacactatca tttattgcac atcaaccaat ggatgctatc tgcgcagttg agatctccag 4920
taaagaatat ctgctgtgtt ttaacagcat tgggatatac actgactgcc agggccgaag 4980
atctagacaa caggaattga tgtggccagc aaatccttcc tcttgttgtt acaatgcacc 5040
atatctctcg gtgtacagtg aaaatgcagt tgatatcttt gatgtgaact ccatggaatg 5100
gattcagact cttcctctca aaaaggttcg acccttaaac aatgaaggat cattaaatct 5160
tttagggttg gagaccatta gattaatata tttcaaaaat aagatggcag aaggggacga 5220
actggtagta cctgaaacat cagataatag tcggaaacaa atggttagaa acattaacaa 5280
taagcggcgt tattccttca gagtcccaga agaggaaagg atgcagcaga ggagggaaat 5340
gctacgagat ccagaaatga gaaataaatt aatttctaat ccaactaatt ttaatcacat 5400
agcacacatg ggtcctggag atggaataca gatcctgaaa gatctgccca tgaaccctcg 5460
gcctcaggaa agtcggacag tattcagtgg ctcagtcagt attccatcta tcaccaaatc 5520
ccgccctgag ccaggccgct ccatgagtgc tagcagtggc ttgtcagcaa ggtcatccgc 5580

-continued

```
acagaatggc agcgcattaa agagggaatt ctctggagga agctacagtg ccaagcggca   5640
gcccatgccc tccccgtcag agggctcttt gtcctctgga ggcatggacc aaggaagtga   5700
tgccccagcg agggactttg acggagagga ctctgactct ccgaggcatt ccacagcttc   5760
caacagttcc aacctaagca gcccccccaag cccagcttca ccccgaaaaa ccaagagcct   5820
ctccctggag agcactgacc gcgggagctg ggacccgtga gctgcctcag cactgggacc   5880
tctcgctctc cgctccctgc cactcgcctc ctctcacttt catctcttcc ctccacctcg   5940
cctgctcggc ctgaaagcca ccaggggctg gcagcagtag caggacaggg attcaggagt   6000
tctgacgaca cgactctcag atccacgccc ccagcctaac agcaacaaca aagacagact   6060
ttccgtagca gcttagatta acgttgattt cattccatgc acttagagtt gctttcagta   6120
acattttacc cctactccca aaggtagctt aaatagacag attacacaaa tgtaagtgat   6180
aagaataaga ttagacagat tttgctttca cagtagagtc tcattatagt cctaaaatag   6240
ctcatgggct tctccgcatc cagaagggag aattggtccc tggagtggct cactaagctc   6300
ttaatcagca aacgcagtga gtatcaacct gattgttgcc aggaaatcct tatgaattaa   6360
aacaatgcat attttactac agtacagagt ttaaatgaat acataaatgt agaagtactg   6420
aatgtatata tttaaaagga gcctcttgta ttcaacaaaa gatggatgca tatataagag   6480
agatgattta atttaaagaa atatgttgtt tcttgtctgt aatgtaatgt aaagggtgga   6540
aaggcctcaa gctcacattt gtagagagag agcgagagaa atcagagttc cctttattgc   6600
cctgtcctca aactggtcat aggctctagt cacctgggga gctgtagaaa acacttgcag   6660
agccaggttt tgctggtttg gggcatgccc tgggcaccag agctttaaca tttgaagcca   6720
cttcagcagc agcagcaaaa ggcgaactca tctctaccca agatgtttct tttcctagtg   6780
gtggaatttg aacacttctc actttttatt gtattttatc ttccgcagat aaatgtagaa   6840
atacacgatt ctgtcacctc tgatcccttc catctgaaag gttacaagga gtgttgtagc   6900
ttctgaaggt gcagaaaaca atttctaaaa atgcttttat tcctgggcta atcctgtccc   6960
tccctaagtc acagcgaggt gtctgtccca gggctggaga tgcttcccaa ggaggagtct   7020
gttttgttga gagtgggcgt gggcttcttc acataagcct ggggaaggaa gaaaaaacgg   7080
ctttcattac caaataatgt aaaacctcaa aagcaagggc ttcaacagcc ttaaccaaat   7140
attattcccc atagccagtg gaaaatggat gtgacaaccc cagtgcgcag gccagagtga   7200
gtgagcccag cacggcgctc cgactggctt cctctctcag gtgctggatt gtggggttag   7260
tggcatttcc agctggattc ctcctgttgt agttgccata aggaaatgag atgcagaatc   7320
agaaggatct atttctacag aatcatttca ccagttaagc acatgagtag agaaagagat   7380
aaaaataaaa gtatctcatg aaggaaagag attttgcctc tcttttactt ttcacctaag   7440
tttctctgag aaatagagac aggattctct ctttaaaatt cagtgaaaat gaagaaagtt   7500
ttcctgcagt tgctaacctg agttgcagtg tttaaggcca tcatttcact gctgctgtct   7560
gtgactccac gtctgtgtca ctgaggtgac ctgcgtgtca ctgaggtggc caccatgctg   7620
gcctgcggca tgtgcaggga gctgaggctg tttccaggtg atgctgctgt gtggagaagg   7680
ttctgagatg cagtgaggga agaaaggatc ctgctgggga ttccattgta agcacctata   7740
atcgggaatt ttcatgtaac agctttgaca tttaaa                             7776
```

<210> SEQ ID NO 13
<211> LENGTH: 2757
<212> TYPE: DNA
<213> ORGANISM: Homo sapiens

<400> SEQUENCE: 13

```
attgtaaact agtttttggt ttgcaaaaaa aaaaaaaaaa aaaaaaaaaa aaaaaaaaaa     60
aaaaaaaaaa aaggtctttt gtaactgact tctttcactt agcaaatgga agggtttttg    120
atggaatctt agctcagatg tcgccctagg cttggccttc tggaactcac tgttctcttg    180
cttccttcca ccctgcctcc ctacccgctt tgctacaaga agacagaatg tagaaacccc    240
cagttgactt tttgagtaga aatgagccat gttctattta gtggtagaat gtttgctggg    300
ttagcccagg acttcagatg gagtgcttcc tcctttttaa taccttgtga ctgctgtgtt    360
ggcaagcaga gggttaaatg ctgcaggagg acatgggaga gtttttgctt tgagggtcca    420
ctggagcaag agaagcttga gagtctgtct ctgagatccc agaacagaca tgaagatatg    480
gtaccgattc ccttggtgct aaaaggaact ccaggggaat ttcaggaaac ccctcctttt    540
ctcgtcttta ttctcacccc gtccccccgc cacctctctc cccaagttca cactcaggag    600
ggaggaatct tttacctttt ccgttctggg cagcagcctg tagggaatgt tatcagtgtt    660
gggactgggc acgggaccaa gccttcctgg tgcctggact gcaacctagc tgagagctga    720
catggcaggg cgagttgtgt gtgagttggc tgcccctagg ctcataggcc tagcacaata    780
gagaccctgt caatggaggg acactatcag gcaggtcact atcaatgtga cagacactat    840
caggcaggtc acattggtgc agatccttgg aggactcccc cccacccccc atgagtggat    900
tcctccaggt caggggctgg ctgggactgt ggatgctgga gtaagtggaa ttgtgggtgc    960
actctgcttc agcagtactc tccaaggaga atgattgttt taataaatta ctgttttaat   1020
aagggaggtg gaagagcttt ttaatcactt gctttttaaa aatttttaat tttattttaa   1080
ttaattagtt tatttatttt ttgagacgga gtcttgctct gtcgcccagg ctggagtgca   1140
gtggcacgat ctcggctcac tgcacctctg cctcctggat tcacaccatt ctcctgcctc   1200
agcctccaga gtagctggga ctacaggcac ccgccaccac gcccgactaa tttttttgtat   1260
ttttagcaga gacggggttt caccgtgtta gccaggatgg tgtagatctc ctgaccttgt   1320
gatcctcccg cctcagcctt ccaaagggag ggattactgg cgtgagtcac cgcgcctggc   1380
ctttatttt tatttctttt gagatggagt tttgctctgt cacccaggct ggagtaccgg   1440
tggtgggatc tcgcctcact gcaacttgcg cctcccgggt tcaagcgatt ctccagcctc   1500
agcctcctga gtagctggga ttacaggcgt gtgccaccgc ctccagctaa tttttgtatt   1560
tttagtagag accgggcttc accatgttgg ccaggctggt ctcgaactcc tgacctcagg   1620
tgagcgtcct gccttggcct cccaaagtgc tgggattaca ggcgtgagcc actacaccca   1680
gccaatcagt tgcttttaaa ctacttaaat aaaaagagcc aacccaaaat cttgtgcatg   1740
cttgggaaac tggcagtgga atatgagaag tttttatttg tggtgcacac aggtgactcg   1800
ggctgttgtg tattggttct tgcctcgatc tgtagcaagc aatctgttgt ttcttgcctg   1860
ccttttggga agaaatgaaa aaagaagcag cacgagtctc catacatcat gattgtgatg   1920
gcactgggcc tgagaccttt tctgctgtcc aggtaaaaat gtgaagacca tggttttgag   1980
gtttcttaat aaattcaggt gttaagtgcc aagtgatgct cccagcccct gagctagagc   2040
aactatgctg ttcatgtccc caggaatgga agtggaccct agttaggtgc tggtggccag   2100
ccatgtgtac ctagggcagg gccaggtcct gtgtgtgtgt gtgtgtgtgt gtgtgtgtgt   2160
gtgtgtgtgt gagagagaga gagagagaga gagagagaca gagagagaga tagagagaaa   2220
cataaaggtg atcggcactc agacatcctg tgtggtccac ctcacttctc aagcaggtgt   2280
```

-continued ctttccagtc tacaactcgt tgaccacagg tggaattcat aagctctgtt ccctgtcctg 2340
cttgggtcct ccagagaaag aaatgttgaa ttatcatctt ggtgatggtc aactctgaaa 2400
gcctaaattt tcatgatcac caaagtgttt ggatttaaaa gggtggctca ctccgtaatt 2460
ccggcacttt gggaggctga ggcagaagga tcacttgagc ccagaagttt cagactaggc 2520
tgggcaacaa agcaagaccc ggtctctccc aaaaaaaaaa aaaaaaaaaa aaaaaaaaaa 2580
tcaaaaaaat tagctggggg tggtggtgtg ctcctatagc tccagctact caggaggctg 2640
aggcgggagg atcgcttgag cccaggggtt tgcggctgca gtgagctgtg attgcaccac 2700
tgcactccag cctgggcgac tgtgagaccc cgtctttaag aaaaaaaaaa aaaaaaa 2757

<210> SEQ ID NO 14
<211> LENGTH: 2444
<212> TYPE: DNA
<213> ORGANISM: Homo sapiens

<400> SEQUENCE: 14 ggttttttt ttttacccc cttttttatt tattattttt ttgcacattg agcggatcct 60
tgggaacgag agaaaaaaga aacccaaact cacgcgtgca gaagatctcc cccccttcc 120 cctcccctcc tccctctttt cccctcccca ggagaaaaag acccccaagc agaaaaaagt 180
tcaccttgga ctcgtctttt tcttgcaata ttttttgggg gggcaaaact ttgagggggt 240
gatttttttt ggcttttctt cctccttcat ttttcttcca aaattgctgc tggtgggtga 300
aaaaaaaatg ccgcagctga acggcggtgg aggggatgac ctaggcgcca acgacgaact 360
gatttccttc aaagacgagg gcgaacagga ggagaagagc tccgaaaact cctcggcaga 420
gagggattta gctgatgtca aatcgtctct agtcaatgaa tcagaaacga atcaaaacag 480
ctcctccgat tccgaggcgg aaagacggcc tccgcctcgc tccgaaagtt tccgagacaa 540
atcccgggaa agtttggaag aagcggccaa gaggcaagat ggagggctct ttaaggggcc 600
accgtatccc ggctacccct tcatcatgat ccccgacctg acgagcccct acctccccaa 660
cggatcgctc tcgcccaccg cccgaaccta tctccagatg aaatggccac tgcttgatgt 720
ccaggcaggg agcctccaga gtagacaagc cctcaaggat gcccggtccc catcaccggc 780
acacattgtc tctaacaaag tgccagtggt gcagcaccct caccatgtcc accccctcac 840
gcctcttatc acgtacagca atgaacactt cacgccggga aacccacctc cacacttacc 900
agccgacgta gaccccaaaa caggaatccc acggcctccg caccctccag atatatcccc 960
gtattaccca ctatcgcctg gcaccgtagg acaaatcccc catccgctag gatggttagt 1020
accacagcaa ggtcaaccag tgtacccaat cacgacagga ggattcagac accccctaccc 1080 cacagctctg accgtcaatg cttccgtgtc caggttccct ccccatatgg tcccaccaca 1140
tcatacgcta cacacgacgg gcattccgca tccggccata gtcacaccaa cagtcaaaca 1200
ggaatcgtcc cagagtgatg tcggctcact ccatagttca aagcatcagg actccaaaaa 1260
ggaagaagaa aagaagaagc cccacataaa gaaacctctt aatgcattca tgttgtatat 1320
gaaggaaatg agagcaaagg tcgtagctga gtgcacgttg aaagaaagcg cggccatcaa 1380
ccagatcctt gggcggaggt ggcatgcact gtccagagaa gagcaagcga aatactacga 1440
gctggcccgg aaggagcgac agcttcatat gcaactgtac cccggctggt ccgcgcggga 1500
taactatgga aagaagaaga agaggaaaag ggacaagcag ccgggagaga ccaatgaaca 1560
cagcgaatgt ttcctaaatc cttgcctttc acttcctccg attacagacc tcagcgctcc 1620
taagaaatgc cgagcgcgct ttggccttga tcaacagaat aactggtgcg gcccttgcag 1680

```
gagaaaaaaa aagtgcgttc gctacataca aggtgaaggc agctgcctca gcccaccctc   1740
ttcagatgga agcttactag attcgcctcc cccctccccg aacctgctag gctcccctcc   1800
ccgagacgcc aagtcacaga ctgagcagac ccagcctctg tcgctgtccc tgaagcccga   1860
ccccctggcc cacctgtcca tgatgcctcc gccacccgcc ctcctgctcg ctgaggccac   1920
ccacaaggcc tccgccctct gtcccaacgg ggccctggac ctgcccccag ccgctttgca   1980
gcctgccgcc ccctcctcat caattgcaca gccgtcgact tcttggttac attcccacag   2040
ctccctggcc gggacccagc cccagccgct gtcgctcgtc accaagtctt tagaatagct   2100
ttagcgtcgt gaaccccgct gctttgttta tggttttgtt tcacttttct taatttgccc   2160
cccaccccca ccttgaaagg ttttgttttg tactctctta attttgtgcc atgtggctac   2220
attagttgat gtttatcgag ttcattggtc aatatttgac ccattcttat ttcaatttct   2280
ccttttaaat atgtagatga gagaagaacc tcatgattgg taccaaaatt tttatcaaca   2340
gctgtttaaa gtctttgtag cgtttaaaaa atatatatat atacataact gttatgtagt   2400
tcggatagct tagttttaaa agactgatta aaaaacaaaa aaaa                    2444
```

<210> SEQ ID NO 15
<211> LENGTH: 1573
<212> TYPE: DNA
<213> ORGANISM: Homo sapiens

<400> SEQUENCE: 15

```
cttccccggt gcagacaccc ggcgaagccc acccggtttt cccagcggca tttccgatga     60
cagcttcggg gctacgtgtc ctgtgctgtc ggagacgcac aggaagcaaa gtttgtgaga    120
agccttgggg gcgactttgc cttgggcacc cgcatttgtg cgtctgcgag gtgcctcggt    180
gtgcgcggag ctagtttccc agtttcccgg gcccctccct tctccgagcc cctctagcga    240
tttgtttagg aaaagtgatg acatgaacta gtagtggaga atcgcagcgc cgctccccgc    300
cctggggagg gaggggagcc ccggagagcc tgccggtggg agctggaagc aggctcccgg    360
ctgagcgccc cagcccgaaa ggcagggtct gggtgcggga agagggctcg gagctgcctt    420
cctgctgcct tggggccgcc cagatgaggg aacagcccga tttgcctggt tctgattctc    480
caggctgtcg tggttgtgga atgcaaacgc cagcacataa tggaaacagg acctgaagac    540
ccttccagca tgccagagga aagttccccc aggcggaccc cgcagagcat tccctaccag    600
gacctccctc acctggtcaa tgcagacgga cagtacctct tctgcaggta ctggaaaccc    660
acaggcacac ccaaggccct catctttgtg tcccatggag ccggagagca cagtggccgc    720
tatgaagagc tggctcggat gctgatgggg ctggacctgc tggtgttcgc ccacgaccat    780
gttggccacg gacagagcga aggggagagg atggtagtgt ctgacttcca cgttttcgtc    840
agggatgtgt tgcagcatgt ggattccatg cagaaagact accctgggct tcctgtcttc    900
cttctgggcc actccatggg aggcgccatc gccatcctca cggccgcaga gaggccgggc    960
cacttcgccg gcatggtact catttcgcct ctggttcttg ccaatcctga atctgcaaca   1020
actttcaagg tccttgctgc gaaagtgctc aaccttgtgc tgccaaactt gtccctcggg   1080
cccatcgact ccagcgtgct ctctcggaat aagacagagg tcgacattta taactcagac   1140
cccctgatct gccgggcagg gctgaaggtg tgcttcggca tccaactgct gaatgccgtc   1200
tcacgggtgg agcgcgccct ccccaagctg actgtgccct tcctgctgct ccagggctct   1260
gccgatcgcc tatgtgacag caaaggggcc tacctgctca tggagttagc caagagccag   1320
```

-continued

```
gacaagactc tcaagattta tgaaggtgcc taccatgttc tccacaagga gcttcctgaa   1380

gtcaccaact ccgtcttcca tgaaataaac atgtgggtct ctcaaaggac agccacggca   1440

ggaactgcgt ccccaccctg aatgcattgg ccggtgcccg gctcatggtc tgggggatgc   1500

aggcagggga agggcagaga tggcttctca gatatggctt gcaaaaaaaa aaaaaaaaaa   1560

aaaaaaaaaa aaa                                                      1573
```

<210> SEQ ID NO 16
<211> LENGTH: 1695
<212> TYPE: DNA
<213> ORGANISM: Homo sapiens

<400> SEQUENCE: 16

```
atgtggttct gcgcgtgtgc ggacggctgt ctgttaactc cgcggtcagt tcccggactg     60

gtggctggtc tgcagggttg acctgcgcaa tgcagaggct gcaggtagtg ctgggccacc    120

tgaggggtcc ggccgattcc ggctggatgc cgcaggccgc gccttgcctg agcggtgccc    180

cgcaggcctc ggccgcggac gtggtggtgg tgcacgggcg gcgcacggcc atctgccggg    240

cgggccgcgg cggcttcaag gacaccaccc ccgacgagct tctctcggca gtcatgaccg    300

cggttctcaa ggacgtgaat ctgaggccgg aacagctggg ggacatctgt gtcggaaatg    360

tgctgcagcc tggggccggg gcaatcatgg cccgaatcgc ccagtttctg agtgacatcc    420

cggagactgt gcctttgtcc actgtcaata gacagtgttc gtcggggcta caggcagtgg    480

ccagcatagc aggtggcatc agaaatgggt cttatgacat tggcatggcc tgtggggtgg    540

agtccatgtc cctggctgac agagggaacc ctggaaatat tacttcgcgc ttgatggaga    600

aggagaaggc cagagattgc ctgattccta tggggataac ctctgagaat gtggctgagc    660

ggtttggcat ttcacgggag aagcaggata cctttgccct ggcttcccag cagaaggcag    720

caagagccca gagcaagggc tgtttccaag ctgagattgt gcctgtgacc accacggtcc    780

atgatgacaa gggcaccaag aggagcatca ctgtgaccca ggatgagggt atccgcccca    840

gcaccaccat ggagggcctg gccaaactga agcctgcctt caagaaagat ggttctacca    900

cagctggaaa ctctagccag gtgagtgatg gggcagctgc catcctgctg gcccggaggt    960

ccaaggcaga agagttgggc cttcccatcc ttggggtcct gaggtcttat gcagtggttg   1020

gggtcccacc tgacatcatg ggcattggac ctgcctatgc catcccagta gctttgcaaa   1080

aagcagggct gacagtgagt gacgtggaca tcttcgagat caatgaggcc tttgcaagcc   1140

aggctgccta ctgtgtggag aagctacgac tccccccctga gaaggtgaac cccctggggg   1200

gtgcagtggc cttagggcac ccactgggct gcactggggc acgacaggtc atcacgctgc   1260

tcaatgagct gaagcgccgt gggaagaggg catacggagt ggtgtccatg tgcatcggga   1320

ctggaatggg agccgctgcc gtctttgaat accctgggaa ctgagtgagg tcccaggctg   1380

gaggcgctac gcagacagtc ctgctgctct agcagcaagg cagtaacacc acaaaagcaa   1440

aaccacatgg gaaaactcag cactggtggt ggtggcagtg gacagatcaa ggcacttcaa   1500

ctcatttgga aaatgtgaac actgatgaca tggtatagga gtgggtgggg tgttgagcca   1560

cccatcagac cctctttagc tgtgcaagat aaaagcagcc tgggtcaccc aggccacaag   1620

gccatggtta attcttaagg caaggcaaat ccatggatga gaagtgcaat gggcatagta   1680

aaagtgcatg aattt                                                    1695
```

<210> SEQ ID NO 17
<211> LENGTH: 1936

<212> TYPE: DNA
<213> ORGANISM: Homo sapiens

<400> SEQUENCE: 17
ctggagtttg cggagggccg agccgggtgc gcacggggag gcggaggcag cggcggcggc 60
ggcggcggcg gcggcggcgg agcagatgaa gaaactgagg ccctgtgatg tgaagtgact 120
tgccccccag ccacacagct ggaccattct ggctgctgtc tggacaagaa gtcgtagggg 180
gtgagggtgg aagctgggaa acccacagga ggcaaccaca ctagtttaga tcttctggtg 240
accccacttc tcgctgctca tgccgctggg actggggcgg cggaaaaagg cgcccccctct 300
agtggaaaat gaggaggctg agccaggccg tggagggctg ggcgtggggg agccagggcc 360
tctgggcgga ggtgggtcgg ggggccccca aatgggcttg ccccccccctc ccccagccct 420
gcggccccgc ctcgtgttcc acacccagct ggcccatggc agtcccactg gccgcatcga 480
gggcttcacc aacgtcaagg agctgtatgg caagatcgcc gaggccttcc gcctgccaac 540
tgccgaggtg atgttctgca ccctgaacac ccacaaagtg gacatggaca agctcctggg 600
gggccagatc gggctggagg acttcatctt cgcccacgtg aaggggcagc gcaaggaggt 660
ggaggtgttc aagtcggagg atgcactcgg gctcaccatc acggacaacg gggctggcta 720
cgccttcatc aagcgcatca aggagggcag cgtgatcgac cacatccacc tcatcagcgt 780
gggcgacatg atcgaggcca ttaacgggca gagcctgctg ggctgccggc actacgaggt 840
ggcccggctg ctcaaggagc tgccccgagg ccgtaccttc acgctgaagc tcacggagcc 900
tcgcaaggcc ttcgacatga tcagccagcg ttcagcgggt ggccgccctg gctctggccc 960
acaactgggc actggccgag ggaccctgcg gctccgatcc cggggccccg ccacggtgga 1020
ggatctgccc tctgcctttg aagagaaggc cattgagaag gtggatgacc tgctggagag 1080
ttacatgggt atcagggaca cggagctggc ggccaccatg gtggagctgg gaaaggacaa 1140
aaggaacccg gatgagctgg ccgaggccct ggacgaacgg ctgggtgact ttgccttccc 1200
tgacgagttc gtctttgacg tctggggcgc cattggggac gccaaggtcg gccgctacta 1260
ggactgcccc cggaccctgc gatgatgacc cgggcgcaac ctggtggggg cccccagcag 1320
ggacactgac gtcaggaccc gagcctccag cctgagccta gctcagcagc ccaaggacga 1380
tggtgagggg aggtggggcc aggccccctg ccccgctcca atcggtacca tcccctccct 1440
ggttcccagt ctggccgggg tccccggccc ccctgtgccc tgttccccac ctacctcagc 1500
tgggtcaggc acagggaggg gagggatcag ccaaattggg cggccacccc cgcctccacc 1560
actttccacc atcagctgcc aaactggtcc ctctgtctcc ctggggcctt gggttctgtt 1620
tgggggtcat gaccttccta gtttcctgac gcagggaata caggggagag ggttgtcctt 1680
ccccccagca aatgcaataa tgccctcacc cctcctgaga ggagccccct ccctgtggag 1740
cctgttacct ccgcatttga cacgagtctg ctgtgaaccc cgcaacctcc tccccacctc 1800
ccatctctcc ttccaggccc atccctggcc cagagcagga gggagggagg gacgatggcg 1860
gtgggttttt gtatctgaat ttgctgtctt gaacataaag aatctatctg ctgttaaaaa 1920
aaaaaaaaaa aaaaaa 1936

<210> SEQ ID NO 18
<211> LENGTH: 2318
<212> TYPE: DNA
<213> ORGANISM: Homo sapiens

<400> SEQUENCE: 18

-continued

```
gccacgaagg ccacagacgc cttccccctt ggactctcat tcccttttcc acggagcccc     60
gcgctttcgt gagccccctc gaggaacctg gtctccgcat ccagttacca cctcctgcct    120
cagaggccat ctgagccctt cgcacctcgc ccctcagtcc ccccttgccc ccccgcggag    180
atcgcctcgc tccctcccgc ccccccatca tcccttccct cgcagttccc ctgtcctgag    240
gggagccccg ccacggcagc gacagcgggc aggagggaga aagtgaaggt tgggcgacac    300
ttggcctcac tcccggctag gcgcacccac ggggaggaga ggaggagccg agagagctga    360
gcagcgcgga agtagctgct gctggtggtg acaatgtcaa ataacggcct agacattcaa    420
gacaaacccc cagcccctcc gatgagaaat accagcacta tgattggagt cggcagcaaa    480
gatgctggaa ccctaaacca tggttctaaa cctctgcctc caaacccaga ggagaagaaa    540
aagaaggacc gattttaccg atccatttta cctggagata aaacaaataa aaagaaagag    600
aaagagcggc cagagatttc tctcccttca gattttgaac acacaattca tgtcggtttt    660
gatgctgtca caggggagtt tacgggaatg ccagagcagt gggcccgctt gcttcagaca    720
tcaaatatca ctaagtcgga gcagaagaaa aacccgcagg ctgttctgga tgtgttggag    780
ttttacaact cgaagaagac atccaacagc cagaaataca tgagctttac agataagtca    840
gctgaggatt acaattcttc taatgccttg aatgtgaagg ctgtgtctga gactcctgca    900
gtgccaccag tttcagaaga tgaggatgat gatgatgatg atgctacccc accaccagtg    960
attgctccac gcccagagca cacaaaatct gtatacacac ggtctgtgat tgaaccactt   1020
cctgtcactc caactcggga cgtggctaca tctcccattt cacctactga aaataacacc   1080
actccaccag atgctttgac ccggaatact gagaagcaga agaagaagcc taaaatgtct   1140
gatgaggaga tcttggagaa attacgaagc atagtgagtg tgggcgatcc taagaagaaa   1200
tatacacggt ttgagaagat tggacaaggt gcttcaggca ccgtgtacac agcaatggat   1260
gtggccacag gacaggaggt ggccattaag cagatgaatc ttcagcagca gcccaagaaa   1320
gagctgatta ttaatgagat cctggtcatg agggaaaaca agaacccaaa cattgtgaat   1380
tacttggaca gttacctcgt gggagatgag ctgtgggttg ttatggaata cttggctgga   1440
ggctccttga cagatgtggt gacagaaact tgcatggatg aaggccaaat tgcagctgtg   1500
tgccgtgagt gtctgcaggc tctggagttc ttgcattcga accaggtcat tcacagagac   1560
atcaagagtg acaatattct gttgggaatg gatggctctg tcaagctaac tgactttgga   1620
ttctgtgcac agataacccc agagcagagc aaacggagca ccatggtagg aaccccatac   1680
tggatggcac cagaggttgt gacacgaaag gcctatgggc ccaaggttga catctggtcc   1740
ctgggcatca tggccatcga aatgattgaa ggggagcctc catacctcaa tgaaaaccct   1800
ctgagagcct tgtacctcat tgccaccaat gggaccccag aacttcagaa cccagagaag   1860
ctgtcagcta tcttccggga ctttctgaac cgctgtctcg atatggatgt ggagaagaga   1920
ggttcagcta aagagctgct acagcatcaa ttcctgaaga ttgccaagcc cctctccagc   1980
ctcactccac tgattgctgc agctaaggag gcaacaaaga acaatcacta aaaccacact   2040
caccccagcc tcattgtgcc aagctctgtg agataaatgc acatttcaga aattccaact   2100
cctgatgccc tcttctcctt gccttgcttc tcccatttcc tgatctagca ctcctcaaga   2160
ctttgatcct tggaaaccgt gtgtccagca ttgaagagaa ctgcaactga atgactaatc   2220
agatgatggc catttctaaa taaggaattt cctcccaatt catggatatg agggtggttt   2280
atgattaagg gtttatataa ataaatgttt ctagtctt                            2318
```

-continued

<210> SEQ ID NO 19
<211> LENGTH: 571
<212> TYPE: DNA
<213> ORGANISM: Homo sapiens

<400> SEQUENCE: 19
tcagccggac accagaagac aagcagagag actcctccag acccactcag accacgtgca 60
cgccctccaa gatggtatcc cgtaaggctg tggctgctct gctggtggtg catgtagctg 120
ccatgctggc ctcccagacg gaagccttcg tccccatctt cacctatggc gaactccaga 180
ggatgcagga aaggaacgg aataaagggc aaaagaaatc cctgagtgta tggcagaggt 240
ctggggagga aggtcctgta gaccctgcgg agcccatcag ggaagaagaa aacgaaatga 300
tcaagctgac tgctcctctg gaaattggaa tgaggatgaa ctccagacag ctggaaaagt 360
acccggccac cctggaaggg ctgctgagtg agatgcttcc ccagcatgca gccaagtgat 420
ggccacgctg gggagaaggt ggacagattt gggaggcccc tcctgcccaa gtgaggccct 480
gggaatttac agagcctgcc agctgggctt ggaaggaaaa cacctttcca aagcaaattc 540
ccctccagca aataaagcat gaaatataca g 571

<210> SEQ ID NO 20
<211> LENGTH: 3139
<212> TYPE: DNA
<213> ORGANISM: Homo sapiens

<400> SEQUENCE: 20
ggccgaggag gaagtggcgg cggcggcggc gggactgcgc gccccagctc cgatccccgt 60
tccgcgtccc cgccgccggg aggaggtgcc cactcgctcg cggcgcgcgc cggccgccag 120
actcggcctg tgggcgattt cctccggacc caggctcccc gcccgaggag gaagatgcag 180
acctttctga aagggaagag agttggctac tggctgagcg agaagaaaat caagaagctg 240
aatttccagg ccttcgccga gctgtgcagg aagcgaggga tggaggttgt gcagctgaac 300
cttagccggc cgatcgagga gcagggcccc ctggacgtca tcatccacaa gctgactgac 360
gtcatccttg aagccgacca gaatgatagc cagtccctgg agctggtgca caggttccag 420
gagtacatcg atgcccaccc tgagaccatc gtcctggacc cgctccctgc catcagaacc 480
ctgcttgacc gctccaagtc ctatgagctc atccggaaga ttgaggccta catggaagac 540
gacaggatct gctcgccacc cttcatggag ctcacgagcc tgtgcgggga tgacaccatg 600
cggctgctgg agaagaacgg cttgactttc ccattcattt gcaaaaccag agtggctcat 660
ggcaccaact ctcacgagat ggctatcgtg ttcaaccagg agggcctgaa cgccatccag 720
ccaccctgcg tggtccagaa tttcatcaac cacaacgccg tcctgtacaa ggtgttcgtg 780
gttggcgagt cctacaccgt ggtccagagg ccctcactca agaacttctc cgcaggcaca 840
tcagaccgtg agtccatctt cttcaacagc cacaacgtgt caaagccgga gtcgtcatcg 900
gtcctgacgg agctggacaa gatcgagggc gtgttcgagc ggccgagcga cgaggtcatc 960
cgggagctct cccgggccct gcggcaggca ctgggcgtgt cactcttcgg catcgacatc 1020
atcatcaaca accagacagg gcagcacgcc gtcattgaca tcaatgcctt cccaggctac 1080
gagggcgtga gcgagttctt cacagacctc ctgaaccaca tcgccactgt cctgcagggc 1140
cagagcacag ccatggcagc cacaggggac gtggccctgc tgaggcacag caagcttctg 1200
gccgagccgg cgggcggcct ggtgggcgag cggacatgca gcgccagccc cggctgctgc 1260
ggcagcatga tgggccagga cgcgccctgg aaggctgagg ccgacgcggg cggcaccgcc 1320

-continued aagctgccgc accagagact cggctgcaac gccggcgtgt cgcccagctt ccagcagcat 1380
tgtgtggcct ccctggccac caaggcctcc tcccagtagc cacggagccg ggacccagag 1440
gggcagcgca gggcgcagag cacacccgct gggccagcag ctcccaacgg cgatgctact 1500
actaagaatc cccagtgatc tgattcttct gttttttaat ttttaacctg attctctgat 1560
gtcatgatct aaatgagggg tagtggggga tggaagagag taccaggtgg tccaccgttg 1620
gggagtgggg ccgtccgcct gctctctact gtgcagacct cctaactgag tttacacacg 1680
cttgtgtttg caacactagg tctggatggg aggtgagggg tgtgcgtatg gctgccatgc 1740
cggtgtctgt gcacatccct gtctgttggt ctccatggcc actgtggacc gggacccttg 1800
ggggaagcct gcccatgtcg ggctgtggga ggctgatcgg tgcatgtgag agtggcttcc 1860
cttctgcctg actccccact ccctgacctg ccccttcctt gtttttcctc ctactggtct 1920
ccaccaaggc tttgttagcc cccaccctgc ctggtgtgca gctaacccct ccctccccac 1980
agccagagga ggccacagac ccctcagggg agttccgcgc tggtgtctgg gctgtgctcc 2040
ctcactaaag ggaaggaaag gaagctgggc gtcctctggg ccccccaaca cacgtcccat 2100
ttagccctgc acagcggtct ccttccccta agccagcact gctgctccct ggagcccggg 2160
aaggaggctg cctggctgga ggcccgagcc gatggcgcct gtgctgagga tttgtgctgt 2220
gatttgggca aatcattcca ggtctttggg cctccacccc cttgtctcta gtggacattt 2280
gagatcagag agcaccacag ggctggcttt gtgccctaac ccctgggatg cagcctgcct 2340
ttccataaag tcacctaggt gaggataggc gcgggagcct cggcatgaca ccatggagat 2400
cggggccctc ttcccagtgg gttcactcct tttcacacct gctgggtccc tcctcaccca 2460
gcaggcctgg tccacctctc attgcaagcc ccaagcactg agccagcagg tgccagggag 2520
ccacccgccc cccatcgctt ctgcacacct cagactcacc ccatcacctt ggcagcaaag 2580
cactggctct gccgtctgac ccctgatcca ggcagccccc tctgcagaga aaagggttgg 2640
ggagaagcct ctgcagtcct ggaagatgtg gggtgctggg tgagaggcat cagcccccac 2700
aagtatgttt ttgtgtctta agatagcagt ttactttgaa aaagtgaaaa aggcttccgg 2760
gctgtcctct gcccagtgag atggaggacg ctagagaaag tgctgagtgt cccgagagag 2820
gcccccgagc cagtgcatgg aggtccttcg gcctggctca gctgggctgc aggatgccca 2880
ctttgaggag ggaggcacag ggcttgggcg aggggcagag gccatcagaa ctgcccggct 2940
tttttggaaa ctgaggaccc aacaactaac cacgtttaca cgacttgagt tttgaacccc 3000
gattaatgtc tgtacgtcac ctttcctagt tctgaccctg agccctgggg aacaggaaag 3060
cgtggctggc ctcttgcact gctttgtctc caaaataaac tactgaaatc aaaccgcaaa 3120
aaaaaaaaaa aaaaaaaaa 3139

<210> SEQ ID NO 21
<211> LENGTH: 3590
<212> TYPE: DNA
<213> ORGANISM: Homo sapiens

<400> SEQUENCE: 21
aaaatcagaa gagtggacac tggcaagagg agggcagcct ttttcccagc ttccttgcac 60
catggacagc tcccattaag ccacctctcc atcctggggc caggactctt atgccccatt 120
cctgtcaaat tgagatttca tccaccattc tccaaggaca gtgaagttat accctagttc 180
cagtgttggg atcagtggcc cctctggaca tgcctctcct ggaaggttct gtgggggtgg 240
aggatcttgt cctcctggaa cccttggtgg aggagtcact gctcaagaat cttcagcttc 300

-continued

```
gctatgaaaa caaggagatt tatacctaca ttgggaatgt ggtgatctca gtgaatccct    360
atcaacagct tcccatctat gggccagagt tcattgccaa atatcaagac tatactttct    420
atgagctgaa gccccatatc tacgcattgg caaatgtggc gtaccagtca ctgagggaca    480
gggaccgaga ccagtgtatc ctcatcacag gcgagagtgg atcagggaag actgaggcca    540
gcaagctggt gatgtcttat gtggctgccg tctgtgggaa aggagagcag gtgaactctg    600
tgaaggagca gctgctacag tctaacccag tgctggaggc ttttggcaat gccaagacca    660
ttcgcaacaa caattcctcc cgatttggaa aatacatgga tattgaattt gacttcaagg    720
gatccccct cggtggtgtc atcacaaact atctgcttga gaaatcccga ttagtgaagc    780
agctcaaagg agaaaggaac ttccacatct tctatcagct gctggctgga gcagatgaac    840
agctgctgaa ggccctgaag cttgagcggg atacaactgg ctatgcctat ctgaatcatg    900
aagtatccag agtggatggc atggacgacg cctccagctt cagggctgta cagagtgcaa    960
tggcagtgat tgggttctcg gaggaggaga ttcgacaagt gctagaggtg acatccatgg   1020
tgctaaagct ggggaacgtg ttggtggctg atgagttcca ggccagtggg ataccagcaa   1080
gtggcatccg tgatgggaga ggtgttcggg agattgggga gatggtgggc ttgaattcag   1140
aagaagtaga gagagctttg tgctcgagga ccatggaaac agccaaggaa aaggtggtca   1200
ctgcactgaa tgttatgcag gctcagtatg ctcgggacgc cctggctaag aacatctaca   1260
gccgcctctt tgactggata gtgaatcgaa tcaatgagag catcaaggtg ggcatcgggg   1320
aaaagaagaa ggtaatggga gtccttgata tctacggttt tgagatatta gaggataata   1380
gctttgagca atttgtgatc aactactgca atgagaagct gcagcaggtg ttcatagaga   1440
tgaccctgaa agaagagcaa gaggaatata agagagaagg cataccgtgg acaaaggtgg   1500
actactttga taatggcatc atttgtaagc tcattgagca taatcagcga ggtatcctgg   1560
ccatgttgga tgaggagtgc ctgcggcctg gggtggtcag tgactccact ttcctagcaa   1620
agctgaacca gctcttctcc aagcatggcc actacgagag caaagtcacc cagaatgccc   1680
agcgtcagta tgaccacacc atgggcctca gctgcttccg catctgccac tatgcgggca   1740
aggtgacata caacgtgacc agctttattg acaagaataa tgacctactc ttccgagacc   1800
tgttgcaggc catgtggaag gcccagcacc ccctccttcg gtccttgttt cctgagggca   1860
atcctaagca ggcatctctc aaacgccccc cgactgctgg ggcccagttc aagagttctg   1920
tggccatcct catgaagaat ctgtattcca agagccccaa ctacatcagg tgcataaagc   1980
ccaatgagca tcagcagcga ggtcagttct cttcagacct ggtggcaacc caggctcggt   2040
acctgggact gctggagaac gtacgggtgc gacgggcagg ctatgcccac cgccagggtt   2100
atgggccctt cctggaaagg taccgattgc tgagccggag cacctggcct cactggaatg   2160
ggggagaccg ggaaggtgtt gagaaggtcc tgggggagct gagcatgtcc tcgggggagc   2220
tggcctttgg caagacaaag atcttcatta gaagccccaa gactcttttc tacctcgaag   2280
aacagaggcg cctgagactc cagcagctgg ccacactcat acagaagatt taccgaggct   2340
ggcgctgccg cacccactac caactgatgc gaaagagtca gatcctcatc tcctcttggt   2400
ttcggggaaa catgcaaaag aaatgctatg ggaagataaa ggcatccgtg ttattgatcc   2460
aggcttttgt gagagggtgg aaggcccgaa agaattatcg caaatatttc cggtcagagg   2520
ctgccctcac cttggcagat ttcatctaca agagcatggt acagaaattc ctactggggc   2580
tgaagaacaa tttgccatcc acaaacgtct tagacaagac atggccagcc gcccccctaca   2640
```

-continued agtgcctcag cacagcaaat caggagctgc agcagctctt ctaccagtgg aagtgcaaga 2700
ggttccggga tcagctgtcc ccgaagcagg tagagatcct gagggaaaag ctctgtgcca 2760
gtgaactgtt caagggcaag aaggcttcat atccccagag tgtccccatt ccattctgtg 2820
gtgactacat tgggctgcaa gggaacccca agctgcagaa gctgaaaggc ggggaggagg 2880
ggcctgttct gatggcagag gccgtgaaga aggtcaatcg tggcaatggc aagacttctt 2940
ctcggattct cctcctgacc aagggccatg tgattctcac agacaccaag aagtcccagg 3000
ccaaaattgt cattgggcta gacaatgtgg ctggggtgtc agtcaccagc ctcaaggatg 3060
ggctctttag cttgcatctg agtgagatgt catcggtggg ctccaagggg gacttcctgc 3120
tggtcagcga gcatgtgatt gaactgctga ccaaaatgta ccgggctgtg ctggatgcca 3180
cgcagaggca gcttacagtc accgtgactg agaagttctc agtgaggttc aaggagaaca 3240
gtgtggctgt caaggtcgtc cagggccctg caggtggtga caacagcaag ctacgctaca 3300
aaaaaaaggg gagtcattgc ttggaggtga ctgtgcagtg aggagggggc accatgcaga 3360
gatggcagtt gcttcctcct gaaccagcac taatccccct ctgccctcct gtgtgggagg 3420
atctctaacc cctctgatcg tggcgcatgg cttggggatt aaactaccct tgaagaggac 3480
ccttgtccca aacccttctt gttctctcct ccaaaagtag cttcctccaa cccgcagcct 3540
ctctgcacac taataaaaca tgtggcttgg aaaggtccaa aaaaaaaaaa 3590

<210> SEQ ID NO 22
<211> LENGTH: 3008
<212> TYPE: DNA
<213> ORGANISM: Homo sapiens

<400> SEQUENCE: 22
taagaatgtc ttttccacct catttgaatc gccctcccat gggaatccca gcactcccac 60
cagggatccc acccccgcag tttccaggat ttcctccacc tgtacctcca gggaccccaa 120
tgattcctgt accaatgagc attatggctc ctgctccaac tgtcttagta cccactgtgt 180
ctatggttgg aaagcatttg ggcgcaagaa aggatcatcc aggcttaaag gctaaagaaa 240
atgatgaaaa ttgtggtcct actaccactg tttttgttgg caacatttcc gagaaagctt 300
cagacatgct tataagacaa ctcttagctc cttcggattc tgtgagtaca aggagccaga 360
atctaccctc cgtgcactca gattattaca tgacctgcaa attggagaga aaaagctact 420
cgttaaagtt gatgcaaaga caaaggcaca gctggatgaa tggaaagcaa agaagaaagc 480
ttctaatggg gttgggatga aagtagtaag ggaggctgga caaggttaac ttgccagaga 540
aagcactggt acagactatt ccaaacagag ctaattcatt aaggcagctt tgtaaaatgc 600
aaggccagaa actgtcacta atgacgatga agaagccttg gatgaagaaa caaagaggag 660
agatcagatg attaaagggg ctattgaagt tttaattcgt gaatactcca gtgagctaaa 720
tgccccctca caggaatctg attctcaccc caggaagaag aagaaggaaa agaaggagga 780
cattttccgc agatttccag tggccccact gatcccttat ccactcatca ctaaggagga 840
tataaatgct atagaaatgg aagaagacaa aagagacctg atatctcgag agatcagcaa 900
attcagagac acacataaga aactggaaga agagaaaggc aaaaaggaaa aagaaagaca 960
ggaaattgag aaagaacgga gagaaagaga gagggagcgt gaaagggaac gagaaaggcg 1020
agaacgggaa cgagaaaggg aaagagaacg tgaacgagaa aaggagaaag aacgggagcg 1080
ggaacgagaa cgggataggg accgtgaccg gacaaaagag agagaccgag atcgggatcg 1140
agagagagat cgtgaccggg atagagaaag gagctcagat cgtaataagg atcgcagtcg 1200
atcaagagaa aaaagcagag atcgtgaaag ggaacgagag cgggaaagag agagagagag 1260
agaacgagag cgagaacgag aacgggagcg agagagagag cgagagaggg aacgggagcg 1320
agaaagagaa aaagacaaaa aacgggaccg agaagaagat gaagaagatg catacgaacg 1380
aagaaaactt gaaagaaaac tccgagagaa agaagctgct tatcaagagc gccttaagaa 1440
ttgggaaatc agagaacgaa agaaaacccg ggaatatgag aaagaagctg aaagagaaga 1500
agaaagaaga agagaaatgg ccaaagaagc taaacgacta aaagaattct tagaagacta 1560
tgatgatgat agagatgacc ccaaatatta cagaggaagt gctcttcaga aaaggttgcg 1620
tgatagagaa aaggaaatgg aagcagatga acgagatagg aagagagaga aggaggagct 1680
tgaggaaatc aggcagcgcc ttctggcaga agggcatcca gatccagatg cagagctcca 1740
gaggatggaa caagaggctg agaggcgcag gcagccacaa ataaagcaag agccagaatc 1800
agaagaggag gaagaagaaa agcaagaaaa agaagaaaaa cgagaagaac ccatggaaga 1860
ggaagaggag ccagagcaaa agccttgtct gaaacctact ctgaggccca tcagctctgc 1920
tccatctgtt tcctctgcca gtggcaatgc aacacctaac actcctgggg atgagtctcc 1980
ctgtggtatt attattcctc atgaaaactc accagatcaa cagcaacctg aggagcatag 2040
gccaaaaata ggactaagtc ttaaactggg tgcttccaat agtcctggtc agcctaattc 2100
tgtgaagaga aagaaactac ctgtagatag tgtctttaac aaatttgagg atgaagacag 2160
tgatgacgta ccccgaaaaa ggaaactggt tcccttggat tatggtgaag atgataaaaa 2220
tgcaaccaaa ggcactgtaa acactgaaga aaagcgtaaa cacattaaga gtctcattga 2280
gaaaatccct acagccaaac ctgagctctt cgcttatccc ctggattggt ctattgtgga 2340
ttctatactg atggaacgtc gaattagacc atggattaat aagaaaatca tagaatatat 2400
aggtgaagaa gaagctacat tagttgattt tgtttgttct aaggttatgg ctcatagttc 2460
accccagagc attttagatg atgttgccat ggtacttgat gaagaagcag aagtttttat 2520
agtcaaaatg tggagattat tgatatatga aacagaagcc aagaaaattg gtcttgtgaa 2580
gtaaaacttt ttatatttag agttccattt cagatttctt ctttgccacc cttttaagga 2640
ctttgaattt ttctttgtct ttgaagacat tgtgagatct gtaatttttt ttttttgtag 2700
aaaatgtgaa ttttttggtc ctctaatttg ttgttgccct gtgtactccc ttggttgtaa 2760
agtcatctga atccttggtt ctctttatac tcaccaggta caaattactg gtatgtttta 2820
taagccgcag ctactgtaca cagcctatct gatataatct tgttctgctg atttgtttct 2880
tgtaaatatt aaaacgactc cccaattatt ttgcagaatt gcacttaata ttgaaatgta 2940
ctgtatagga accaacatga acaattttaa ttgaaaacac cagtcataaa ctattaccac 3000
ccccactc 3008

<210> SEQ ID NO 23
<211> LENGTH: 4540
<212> TYPE: DNA
<213> ORGANISM: Homo sapiens

<400> SEQUENCE: 23
attctggggt tcgtttagag gtttgaattt tctcggagaa agacaggccg gccacgagga 60
aaacagaaac aagccgcagc aacatctaag cccttgaaag gatcctgaga gaggggggaa 120
agggaaaaca gcagccacca gcccaaccac ttgtgtcttc tgccccttcc cacctatctt 180
gcccacccca ccagcccacg ctgcttggga cttgaaatct gtggccgaag gaccgtcact 240
acataacttc aaaaataatc aaccaccctc ccttcccaaa ccacccaaat tcactcatcc 300
agcgtttact tttttgaatc cactcagaac ttttttctgc gacccccctc cctaaatgga 360
gttgggtggg ggggaaatga atactgagtt ggcctttatt ttttaaaaga ctttttgatc 420
caatgaggcc ccctaaataa ttgagttttg ggtcctggtt ggttgtttta ttttttttcc 480
tccaaaattt tacccctcc cccctgagcc cgaggtgctg acgtcgcaaa aaaattggat 540
aaaaccacca tcatgggttc gggtcccata gaccccaaag aacttctcaa gggcctggac 600
agcttcctta accgagatgg ggaagtcaaa agtgtggatg ggatttccaa gatcttcagt 660
ttgatgaagg aagcacgaaa gatggtgagt cgatgcactt acttgaacat tctcctgcag 720
acccgttcac cagaaatatt ggtcaaattt attgacgttg gcggctacaa acttcttaac 780
aattggctga cgtattcaaa gacaaccaac aacattcccc tcctccagca aattctactg 840
accctgcagc atctaccgct cactgtagac catctcaagc agaacaacac agctaaactg 900
gtgaagcagc tgagcaagtc aagtgaggat gaagagctcc ggaaattggc ctcagtcctt 960
gtcagcgact ggatggctgt catccgctct cagagcagta cccagcctgc tgagaaagat 1020
aagaagaaac gtaaagatga aggaaaaagt cgaactaccc ttcctgagcg acctttgaca 1080
gaggtgaagg ctgagacccg ggctgaggag gccccagaga agaagaggga gaagcccaag 1140
tctcttcgca ccacagcacc cagtcatgcc aagttccgtt ccactggact agagctggag 1200
acaccatcct tggtgcctgt gaagaagaat gccagcacag tggtggtttc tgacaagtac 1260
aaccttaaac ccatccccct caaacgtcag agcaacgtag ctgctccagg agatgccact 1320 cccccctgcag agaagaaata caagccactc aacacaacac ctaatgccac caaagagatc 1380
aaagtgaaga tcatcccgcc acagcctatg gagggcctgg gctttctgga tgctcttaat 1440
tcagcccctg ttccaggcat caaaattaag aagaaaaaaa aagtactgtc acctacggct 1500
gccaagccaa gcccctttga agggaaaacg agcacagaac caagcacagc caaaccttct 1560
tccccagaac cagcaccacc ttctgaggca atggacgcag accgtccagg cacccccggtt 1620 cccccctgttg aagtcccgga gctcatggat acagcctctt tggagccagg agctctggat 1680
gccaagccag tggagagtcc tggagatcct aaccaactga cccggaaagg caggaagaggg 1740 aaaagtgtga catggcctga ggaaggcaaa ctgagagaat atttctattt tgaattggat 1800
gaaactgaac gagtaaatgt gaataagatc aaggactttg gtgaggcggc taagcgagag 1860
atactgtcag accgacatgc atttgagaca gcgcggcgtc tgagccatga taacatggag 1920
gagaaggtgc cctgggtgtg cccccggccc ctggttctgc cctcacctct tgtcacccct 1980
ggaagcaata gtcaggagcg atatatccag gctgagcggg agaagggaat ccttcaggag 2040
ctcttcctga acaaggagag tcctcatgag cctgatcctg agccctacga gcccataccc 2100
cctaaactca tccccctaga tgaggagtgt tccatggatg agactccgta tgttgagact 2160
ctggaacctg gggggtcagg tggctcacct gatggggcag gaggctccaa gttgcctcca 2220
gttctggcca atcttatggg aagcatgggt gctggaaagg gcccccaagg ccctggagga 2280
ggaggcatta atgtccaaga gatcctcacc tccatcatgg gtagcccaaa cagtcatcct 2340
tcagaggaac tactgaaaca accagactat tcggacaaga tcaagcagat gctggtgcca 2400
catggactcc taggccctgg cccaatagcc aatggtttcc caccaggggg tcctgggggc 2460
cccaagggca tgcagcactt tccccctgga cctgggggac ctatgccagg tccccatgga 2520
ggccctggtg ggccagtggg tccacgtctt ctgggtcctc caccccctcc ccggggaggt 2580
gatcccttct gggatggccc gggcgaccct atgcggggtg gcccaatgcg ggggggtcca 2640
ggaccaggtc ctggaccata ccatagaggc cgaggtggcc gaggaggaaa cgaacctcct 2700
cctcctcctc ctccattccg aggcgccaga ggaggtcgct ctggaggagg acccccaaat 2760
ggacgagggg gccctggtgg gggcatggtt ggaggtggtg ggcatcgtcc tcacgaaggc 2820
cctggtgggg gcatgggcaa cagcagtgga catcgtcccc acgaaggccc tggcggtggc 2880
atgggaagtg ggcatcgccc ccatgaaggc cctggtggta gcatgggtgg gggtggagga 2940
catcgtcccc acgaaggccc tggcggtggc atcagtggtg gcagtggcca tcgtccccat 3000
gaaggccctg gcggaggaat gggtgccggt ggtggacatc gcccccacga aggccctggc 3060
ggaagcatgg gtggaagtgg tggacatcgt ccccatgaag gccctggaca cgggggggccc 3120 catggccacc ggcctcatga tgtccctggt caccgaggcc atgaccatcg agggccgcca 3180
cctcatgagc accgtggcca tgatggtcct ggccacgggg gagggggcca ccgagggcac 3240
gatggaggcc acagccatgg aggagacatg tcaaaccgcc ctgtctgccg acatttcatg 3300
atgaagggca actgccgcta tgagaacaac tgtgccttct accacccggg tgtcaatggg 3360
ccccccctgc cctagggacc atttgcctgc cctgttcaca caacccctgt ggactgcagc 3420
ctcgctcttt ccaccctgtt atggcttctg tgaggcccat tttccctttt ccccagctga 3480
tgaggagccg gccccctcag ttcccacttg cttgggttcc tgggggtttt ctgatcactg 3540
gtgcgcattg atgtacatat tttcctccag tctggggagg agagagactg gaaacgttcc 3600
tggactgctg aagaggagac ccagttggct tcactttttg agaagattcg ccctgtaccc 3660
caaacccctt tccagtatta cccttaatgc ttgagaacct aaagctggtt atcctggcga 3720
acacccctac ccttctattg cggtccccca catgcacaca gaactctgac acaggatcag 3780
ctgcacttaa gaaatcatcc cagctaagtt cattattcct catggggtgg ggagatgctg 3840
aaaggggtat tgtatatccc actgcactga gagggctcaa tcagctggat ttgagttctg 3900
gaacacacat catccccacc cctcccccag cgtgggctca ccattcttag tcctttctca 3960
agtgggacct tcaactttct gtgaacaccc agtctgcgtc ctgggtctgc taggttcgat 4020
gatggcgaac tcgtatctgc atccggtgca agttttagct ggcagaggtg agaccggtgg 4080
tgctggtctg cctttgccaa ctatagccag tctggagact tgataaaata cttcagtgag 4140
accagcttct catcaacttg ggcccggcgt gctgggcctg aaagtcacac tacatgcact 4200
gcctttggga gtcagctcac tccctgctcc cacctggaac cttgccagcg tgaaggaggc 4260
ttccaggtac ttcaccctgt caaccacctc tgaatcccca ccaggcgcct tcctgggtgg 4320
attcaacaag atgattttgc cctttcccag ttctctcctt cactttggca tcagttgttt 4380
tctatgaaaa cagtggattg gttgggtttt gtgcagggtc ttgggttaga gccaaaatgg 4440
atttgaggat gagtattttt ttttttggtt ttgtatattt tgtacattaa taataaacag 4500
tggaaagaga agcagcttaa aaaaaaaaaa aaaaaaaaaa 4540

<210> SEQ ID NO 24
<211> LENGTH: 3233
<212> TYPE: DNA
<213> ORGANISM: Homo sapiens

<400> SEQUENCE: 24
tgcgactgag tcggtggcga agacgggaac gcgacgatgg cggagactct gcccgggtcg 60
ggcgactcgg gccctggcac ggcttctctc ggcccgggcg ttgcggagac tgggacgagg 120
cggctcagcg agctgcgggt gatcgatctg cgggcggagc tgaagaagcg gaacctggac 180

-continued

```
acgggcggca acaagagcgt cctgatggag cggctcaaga aggcggttaa agaagagggg    240
caagatcctg atgaaattgg catcgagtta gaagccacca gcaagaagtc agccaagaga    300
tgtgttaaag gactgaagat ggaggaggaa ggcacagaag ataatggcct ggaagacgat    360
tccagagacg ggcaggagga catggaagca agtctggaga acctgcagaa tatgggcatg    420
atggacatga gtgtgctaga cgaaactgaa gtggcgaata gcagtgctcc agattttggg    480
gaggatggca cggacggcct tctcgattcc ttttgtgata gtaaagaata cgtggctgca    540
cagctgagac agctcccggc tcagccccca gagcatgctg tggatgggga aggatttaag    600
aacactttgg aaacttcatc gttgaacttc aaagtaactc cggacattga agaatccctt    660
ttggagccag aaaatgagaa aatactcgac attttggggg aaacttgtaa atctgagcca    720
gtaaaagaag aaagttccga gctggagcag ccatttgcac aggacacaag tagcgtgggg    780
ccagacagaa agcttgcgga ggaagaggac ctatttgaca gcgcccatcc ggaagagggt    840
gatttagatt tggccagcga gtcaacagca cacgctcagt cgagcaaggc agacagcctg    900
ttagcggtag tgaaaaggga gcccgcggag cagccaggcg atggcgagag gacggactgt    960
gagcctgtag ggctagagcc ggcagttgag cagagtagtg cggcctccga gctcgcggag   1020
gcctctagcg aggagctcgc agaagcaccc acggaagccc caagcccaga agccagagat   1080
agcaaagaag acgggaggaa gtttgatttt gacgcttgta atgaagtccc tccggctcct   1140
aaagagtcct caaccagtga gggcgctgat cagaaaatga gctcttttaa ggaagaaaaa   1200
gatataaagc caatcattaa agatgaaaaa ggtcgggtcg gcagcggttc tggtcggaac   1260
ctgtgggtca gcgggctgtc ctccacaaca cgcgctacgg atctcaagaa ccttttcagc   1320
aagtatggga aggttgtcgg ggccaaagtg gtaacgaacg cccgcagccc ggggggctcga   1380
tgctatggat tcgtcaccat gtcgacatct gacgaggcga ccaagtgcat cagccatctc   1440
cacagaactg agctgcatgg acgaatgatc tccgtagaga aggccaaaaa tgagcctgct   1500
gggaaaaagc tttccgacag aaaagagtgc gaagtgaaga aggaaaaatt atcgagtgtc   1560
gacagacatc attctgtgga gatcaaaatt gaaaaaactg taattaagaa ggaagagaag   1620
attgagaaga aggaggaaaa aaagcctgaa gacattaaga aggaagaaaa agaccaggat   1680
gagctgaaac ccggacctac aaatcggtct agagtcacca aatcaggaag cagaggaatg   1740
gagcggacgg tcgtgatgga taaatcgaaa ggagagcccg tcattagcgt gaaaaccaca   1800
agcaggtcca aagagagaag ctccaagagt caggatcgca agtcagaaag caaagaaaag   1860
agagacatct tgtcgtttga taaaatcaaa gaacaaaggg agagagagcg ccagaggcag   1920
cgggaacggg agatccgcga aacggagagg cggcgggagc gcgagcagcg ggagcgggag   1980
caacgcctcg aggccttcca tgagcggaag gagaaggccc ggctacagcg ggaacgcctg   2040
cagctcgagt gccagcgcca gcggctggag cgggagcgca tggagcggga gcggctggag   2100
cgcgagcgca tgcgcgtgga gcgtgagcgc aggaaggagc aggagcgcat ccaccgcgag   2160
cgcgaggagc tgcggcgcca gcaggagcag ctgcgttacg agcaggagcg gcggcccggg   2220
cggaggccct acgacctgga ccgacgagat gatgcctatt ggccagaagg aaagcgtgtg   2280
gcaatggagg accgatatcg tgcagacttt ccccggccag accaccgctt tcacgacttc   2340
gatcatcgag accggggcca gtaccaggac cacgccatcg acaggcggga gggttcgagg   2400
ccaatgatgg gagaccaccg ggatgggcag cactatggag atgaccgcca tggccacgga   2460
ggacccccag agcgccacgg ccgggactcc cgtgatggct gggggggcta cggctccgac   2520
aagaggctga gtgaaggccg gggctgccc cctcccccca ggggtggccg tgactgggga   2580
```

```
gagcacaacc agcggctaga ggagcaccag gcacgcgcct ggcagggtgc catggacgca   2640
ggcgcggcta gccgggagca cgccaggtgg caaggtggcg agaggggcct gtctgggccc   2700
tcggggccgg ggcacatggc aagccgcggt ggagtggcgg ggcgaggcgg ctttgcacaa   2760
ggtggacatt cccagggcca cgtggtgcca ggtggcggac tggaaggtgg cggagtggcc   2820
agccaggacc ggggcagcag agtccctcac ccacaccctc atcccccccc gtacccccac   2880
ttcacccgcc gctactaagt cccactcgct gtgagttttc gggtgggcag acgcactgtt   2940
gaatctggta gccagggttc cctcgaactt gggggatctt tttaaaagca aagtaaatcc   3000
tgccaccatg ttgtagctca atacaatgtg aactcacttt tttttttttt tttaataaat   3060
gtgttcttgt tctgccattt ttaaatcaag gtttctgtta acgaggcatt ccattttcca   3120
ttaataaagt ttaccattcg caaaaaaaaa atgtgttctt gttctgccat ttttaaatca   3180
aggtttctgt taacgaggca ttccattttc cattaataaa gtttaccatt cgc          3233
```

<210> SEQ ID NO 25
<211> LENGTH: 17847
<212> TYPE: DNA
<213> ORGANISM: Homo sapiens

<400> SEQUENCE: 25

```
atgggtgccc cgagcgcgtg ccggacgctg gtgttggctc tggcggccat gctcgtggtg     60
ccgcaggcag agtgcacggg cagatccccc tacgactccc tgagtgtcct ggatgggacc    120
ctacccgtcc ccaacacagg gctctggggc ccccacgggct cacagtgtca ggaaactcag   180
gggctggctt ggatggggtg tccaggagaa gagacccagg gccctgtgga gccgagctgg    240
gagaatgcag ggcacaccat ggatggcggt gccccgacgt cctcgcccac ccggcgcgtg    300
agctttgttc cacccgtcac tgtcttcccc agcctgagcc gtaagcagat gctgcccctg    360
ccagccggga agggggtgtt tgccagtccc aaaggtgggg gcccagatct aggggtgcag    420
ctgccaccag ccctgaaccc ggcgcacaat gggcgggtgt gcagcacctg gggtgacttc    480
cactacaaga ccttcgacgg cgacgtcttc cgcttccctg gcctttgcaa ctacgtgttc    540
tctgagcact gccgcgccgc ctacgaggac ttcaacgtcc agctacgccg aggcctagtg    600
ggctccaggc ctgtggtcac ccgtgttgtc atcaaggccc aggggctggt gctggaggcg    660
tccaacggct ccgtcctcat caatgggcag cgggaggagc tgccttacag ccgcactggc    720
ctcctggtgg agcagagcgg ggactacatc aaggtcagca tccggctggt gctgacattc    780
ctgtggaacg gagaggacag tgccctgctg gagctggatc ccaaatacgc caaccagacc    840
tgtggcctgt gtggggactt caacggcctc ccggccttca acgagttcta tgcccacaac    900
gccaggctga ccccgctcca gtttgggaac ctgcagaagt tggatgggcc cacggagcag    960
tgcccggacc cgctgccctt gccggccggc aactgcacgg acgagccccc atggatggca   1020
ggggtgccca gcctggccca ctgtgctccc caggagggca tctgccaccg caccctgctg   1080
gggccggcct ttgcggagtg ccacgcactg gtggacagca ctgcgtacct ggccgcctgc   1140
gcccaggacc tgtgccgctg ccccacctgc ccgtgtgcca cctttgtgga atactcacgc   1200
cagtgcgccc acgcgggggg ccagccgcgg aactggaggt gccctgagct ctgcccccgg   1260
acctgccccc tcaacatgca gcaccaggag tgtggctcac cctgcacgga cacctgctcc   1320
aacccccagc gcgcgcagct ctgcgaggac cactgtgtgg acggctgctt ctgcccccca   1380
ggcacggtgc tggatgacat cacgcactct ggctgcctgc ccctcgggca gtgcccctgc   1440
```

-continued

```
acccacggcg gccgcaccta cagcccgggc acctccttca acaccacctg cagctcctgc   1500
acctgctccg gggggctatg gcagtgccag gacctgccgt gccctggcac ctgctctgtg   1560
cagggcgggg cccacatctc cacctatgat gagaaactct acgacctgca tggtgactgc   1620
agctacgttc tgtccaagag ccacatcccc cacatgggca tccccagcac acttctgggg   1680
ggcaccccac atcatcgagc caggcccaat gcacgcgtgg gtccttctcc ccagaaatgt   1740
gccgacagca gcttcaccgt gctggctgag ctgcggaagt gcggcctgac ggacaacgag   1800
aactgcctga aagcggtgac gctcagcctg gacggcgggg acacggccat ccgggtccaa   1860
gcggacggcg gcgtgttcct caactccatc tacacgcagc tgcccctgtc ggcagccaac   1920
atcaccctgt tcacaccctc gagcttcttc atcgtggtgc agacaggcct ggggctgcag   1980
ctgctggtgc agctggtgcc actcatgcag gtgtttgtca ggctggaccc cgcccaccag   2040
ggccagatgt gcggcctgtg tgggaacttc aaccagaacc aggctgacga cttcacggcc   2100
ctcagcgggg tggtggaggc cacgggcgca gccttcgcca acacctggaa ggcccaggct   2160
gcctgtgcca atgccaggaa cagctttgag gacccctgct ccctcagtgt ggagaatgag   2220
aactacgccc ggcactggtg ctcgcgcctg accgatccca acagtgcctt ctcgcgctgc   2280
cactccatca tcaaccccaa gcccttccac tcgaactgca tgtttgacac ctgcaactgt   2340
gagcggagcg aggactgcct gtgcgccgcg ctgtcctcct atgtgcacgc ctgtgccgcc   2400
aagggcgtac agctcagcga ctggagggac ggcgtctgca ccaagtacat gcagaactgc   2460
cccaagtccc agcgctacgc ctacgtggtg gatgcctgcc agcccacttg ccgcggcctg   2520
agtgaggccg acgtcacctg cagcgtttcc ttcgtgcctg tggacggctg cacctgcccc   2580
gcgggcacct tcctcaatga cgcgggcgcc tgtgtgcccg cccaggagtg cccctgctac   2640
gctcacggca ccgtgctggc tcctggagag gtggtgcacg acgagggcgc cgtgtggtaa   2700
gggtctgggg ggaaagcagg ccccccaggg tgtgcagccc ccatggtgta cctggactgc   2760
agcaacagct cggcgggcac ccctggggcc gagtgcctcc ggagctgcca cacgctggac   2820
gtgggctgtt tcagcacaca ctgcgtgtcc ggctgtgtct gtcccccggg gctggtgtcg   2880
gatgggagtg gggctgcat tgccgaggag gactgcccct gtgtgcacaa cgaggccacc   2940
tacaagcctg gagagaccat cagggtcgac tgcaacacct gcacctgcag gaaccggagg   3000
tgggagtgca gccaccggct ctgcctgggc acctgcgtgg cctacgggga tggccacttc   3060
atcacctttg atggcgatcg ctacagcttt gaaggcagct gcgagtacat cttggcccag   3120
gactactgtg ggacaacac cacccacggg accttccgca tcgtcaccga gaacatcccc   3180
tgtgggacca ccggcaccac ctgctccaag gccatcaagc tcttcgtgga ggtgagaacg   3240
gccccagctg tgagcacccc cgaccctgca gccaacgagc cggcccccag ggaagcttcg   3300
gtcggcttcc ggcagcgtct gcctcccctg cagagctacg agctgatcct ccaagagggg   3360
acctttaagg cggtggcgag agggccgggt ggggacccac cctacaagat acgctacatg   3420
gggatcttcc tggtcatcga gacccacggg atggccgtgt cctgggaccg gaagaccagc   3480
gtgttcatcc gactgcacca ggactacaag ggcagggtct gcggcctgtg cgggaacttc   3540
gacgacaatg ccatcaatga ctttgccacg cgtagccggt ccgtggtggg ggacgcactg   3600
gagtttggga acagctggaa gctctccccc tcctgcccgg acgccctggc acccaaggac   3660
ccctgcacgg ccaacccctt ccgcaagtcc tgggcccaga agcagtgcag catcctccac   3720
ggccccacct tcgccgcctg ccgctcccag gttgactcca ccaagtacta cgaggcctgc   3780
gtgaacgacg cgtgtgcctg cgactcgggt ggcgactgcg agtgtttctg cacggctgtg   3840
```

-continued

```
gctgcctacg cccaggcctg ccacgacgcg ggcctgtgtg tgtcctggcg gactccggac   3900
acctgcccct tgttctgtga cttctacaac ccacatgggg gctgtgagtg gcactaccag   3960
ccctgcgggg caccctgcct aaaaacctgc cggaacccca gtgggcactg cctggtggac   4020
ctgcctggcc tggaaggctg ctacccgaag tgcccaccca gccagccctt cttcaatgag   4080
gaccagatga agtgcgtggc ccagtgtggc tgctacgaca aggacggaaa ctactatgac   4140
gtcggtgcaa gggtccccac agcggagaac tgccagagct gtaactgcac acccagtggc   4200
atccagtgcg ctcacagcct tgaggcctgc acctgcacct atgaggacag gacctacagc   4260
taccaggacg tcatctacaa caccaccgat gggcttggcg cctgcttgat cgccatctgc   4320
ggaagcaacg gcaccatcat caggaaggct gtggcatgtc ctggaactcc agccacaacg   4380
ccattcacct tcaccaccgc ctgggtcccc cactccacga caagcccggc cctcccggtc   4440
tccaccgtgt gtgtccgcga ggtctgccgc tggtccagct ggtacaatgg gcaccgccca   4500
gagcccggcc tgggaggcgg agactttgag acgtttgaaa acctgaggca gagagggtac   4560
caggtatgcc ctgtgctggc tgacatcgag tgccgggcgg cgcagcttcc cgacatgccg   4620
ctggaggagc tgggccagca ggtggactgt gaccgcatgc gggggctgat gtgcgccaac   4680
agccaacaga gtcccccgct ctgtcacgac tacgagctgc gggttctctg ctgcgaatac   4740
gtgccctgtg gcccctcccc ggccccaggc accagccctc agccctccct cagtgccagc   4800
acggagcctg ctgtgcctac cccaacccag accacagcaa ccgaaaagac caccctatgg   4860
gtgaccccga gcatccggtc gacggcggcc ctcacctcgc agactgggtc cagctcaggc   4920
cccgtgacgg tcacccccctc ggccccaggt accaccacct gccagccccg gtgtcagtgg   4980
acagagtggt ttgatgagga ctaccccaag tctgaacaac ttggagggga cgttgagtcc   5040
tacgataaga tcagggccgc tggagggcac ttatgccagc agcctaagga catagagtgc   5100
caggccgaga gcttccccaa ctggaccctg gcacaggtgg ggcagaaggt gcactgtgac   5160
gtccacttcg gcctggtgtg caggaactgg gagcaggagg gcgtcttcaa gatgtgctac   5220
aactacagga tccgggtcct ctgctgcagt gacgaccact gcaggggacg tgccacaacc   5280
ccgccaccga ccacagagct ggagacggcc accaccacca ccacccaggc cctgttctca   5340
acgccgcagc ctacgagtag cccggggctg accagggctc ccccggccag caccacagca   5400
gtccccaccc tctcagaagg actgacatcc cccagataca caagcaccct tggtacagcc   5460
accacgggag gccccacgac gcctgcaggc tccacagaac ccactgtccc aggggtggcc   5520
acatccaccc ttccaacacg ctcagccctt ccagggacga cggggagctt gggcacatgg   5580
cgcccctcac agccacccac gctggcccca acaacaatgg caacctccag agctcgcccg   5640
acaggcacag ccagcaccgc ttccaaagag ccgctgacca cgagcctggc gccaacactc   5700
acgagcgagc tgtccacctc tcaggccgag accagcacgc ccaggacaga gacgacaatg   5760
agccccttga ctaacaccac caccagccag ggcacgaccc gctgtcaacc gaagtgtgag   5820
tggacagagt ggtttgacgt ggacttccca acctcagggg ttgcaggcgg ggacatggaa   5880
acttttgaaa acatcagggc tgctgggggc aagatgtgct gggcaccaaa gagcatagag   5940
tgccgggcgg agaactaccc cgaggtaagc atcgaccagg tcgggcaggt gctgacctgc   6000
agcctggaga cggggctgac ctgcaagaac gaagaccaga caggcaggtt caacatgtgc   6060
ttcaactaca acgtgcgtgt gctttgctgt gacgactaca gccactgccc cagtacccca   6120
gccaccagct ccacggccac gccctcctca actccgggga cgacctggat cctcacaaag   6180
```

-continued

```
ccgaccacaa cagccactac gactgcgtcc actggatcca cggccacccc gacctccacc   6240
ctgagaacag ctccccctcc caaagtgctg accaccacgg ccaccacacc cacagtcacc   6300
agctccaaag ccactccctc ctccagtcca gggactgcaa ccgcccttcc agcactgaga   6360
agcacagcca ccacacccac agctaccagc gttacaccca tcccctcttc ctccctgggc   6420
accacctgga cccgcctatc acagaccacc acacccacgg ccaccatgtc cacagccaca   6480
ccctcctcca ctccagagac tgcccacacc tccacagtgc ttaccgccac ggccaccaca   6540
actggggcca ccggctctgt ggccaccccc tcctccaccc caggaacagc tcacactacc   6600
aaagtgccaa ctaccacaac cacgggcttc acagccaccc cctcctccag cccagggacg   6660
gcactcacgc ctccagtgtg gatcagcaca accaccacac ccacaaccag aggctccacg   6720
gtgacccccct cctccatccc ggggaccacc cacaccgcca cagtgctgac caccaccacc   6780
acaactgtgg ccactggttc tatggcaaca ccctcctcta gcacacagac cagtggtact   6840
cccccatcac tgaccaccac ggccactacg atcacggcca ccggctccac caccaacccc   6900
tcctcaactc ctgggacaac tcccatcccc ccagtgctga ccaccaccgc caccacacct   6960
gcagccacca gcaacacagt gactccctcc tctgccctag ggaccaccca cacaccccca   7020
gtgccgaaca ccatggccac cacacacggg cgatccctgc cccccagcag tccccacacg   7080
gtgcgcacag cctggacttc ggccacctcg ggcatcttgg gcaccaccca catcacagag   7140
ccttccacgg tgacttccca caccctagca gcaaccaccg gtaccaccca gcactcgact   7200
ccagcccttt ccagccctca ccctagcagc agaaccaccg agtcaccccc ttctccaggg   7260
acgaccaccc cgggccacac cacggccacc tccaggacca cagccacggc cacacccagc   7320
aagacccgca cctcgaccct gctgcccagc agccccacat cggcccccat aaccacggtg   7380
gtgaccatgg gctgtgagcc ccagtgtgcc tggtcagagt ggctggacta cagctacccc   7440
atgccggggc cctctggcgg ggactttgac acctactcca acatccgtgc ggccggaggg   7500
gccgtctgtg agcagcccct gggcctcgag tgccgtgccc aggcccagcc tggtgtcccc   7560
ctgcgggagt tgggccaggt cgtggaatgc agcctggact ttggcctggt ctgcaggaac   7620
cgtgagcagg tggggaagtt caagatgtgc ttcaactatg aaatccgtgt gttctgctgc   7680
aactacggcc actgccccag caccccggcc accagctcta cggccatgcc ctcctccact   7740
ccggggacga cctggatcct cacagagctg accacaacag ccactacgac tgagtccact   7800
ggatccacgg ccaccccgtc ctccacccca gggaccacct ggatcctcac agagccgagc   7860
actacagcca ccgtgacggt gcccaccgga tccacggcca ccgcctcctc cacccaggca   7920
actgctggca ccccacatgt gagcaccacg gccacgacac ccacagtcac cagctccaaa   7980
gccactccct tctccagtcc agggactgca accgcccttc cagcactgag aagcacagcc   8040
accacaccca cagctaccag ctttacagcc atcccctcct cctccctggg caccacctgg   8100
acccgcctat cacagaccac cacacccacg gccaccatgt ccacagccac accctcctcc   8160
actccagaga ctgtccacac ctccacagtg cttaccacca cggccaccac aaccggggcc   8220
accggctctg tggccacccc ctcctccacc ccaggaacag ctcacactac caaagtgctg   8280
actaccacaa ccacgggctt cacagccacc ccctcctcca gcccagggac ggcacgcacg   8340
cttccagtgt ggatcagcac aaccaccaca cccacaacca gaggttccac ggtgaccccc   8400
tcctccatcc cggggaccac ccacaccccc acagtgctga ccaccaccac cacaactgtg   8460
gccactggtt ctatggcaac accctcctct agcacacaga ccagtggtac tcccccatca   8520
ctgaccacca cggccactac gatcacggcc accggctcca ccaccaaccc ctcctcaact   8580
```

-continued

```
ccagggacaa cacctatccc cccagtgctg accaccaccg ccaccacacc tgcagccacc   8640
agcagcacag tgactccctc ctctgcccta gggaccaccc acacaccccc agtgccgaac   8700
accacggcca ccacacacgg gcgatccctg tcccccagca gtccccacac ggtgcgcaca   8760
gcctggactt cggccacctc aggcaccttg ggcaccaccc acatcacaga gccttccacg   8820
gggacttccc acaccccagc agcaaccacc ggtaccaccc agcactcgac tccagccctg   8880
tccagccctc accctagcag caggaccacc gagtcacccc cttctccagg gacgaccacc   8940
ccgggccaca ccagggccac ctccaggacc acggccacgg ccacacccag caagacccgc   9000
acctcgaccc tgctgcccag cagccccaca tcggccccaa taaccacggt ggtgaccatg   9060
ggctgtgagc cccagtgtgc ctggtcagag tggctggact acagctaccc catgccgggg   9120
ccctctggcg gggactttga cacctactcc aacatccgtg cggccggagg ggccgtctgt   9180
gagcagcccc tgggcctcga gtgccgtgcc caggcccagc ctggtgtccc cctgcgggag   9240
ttgggccagg tcgtggaatg cagcctggac tttggcctgg tctgcaggaa ccgtgagcag   9300
gtggggaagt tcaagatgtg cttcaactat gaaatccgtg tgttctgctg caactacggc   9360
cactgcccca gcaccccggc caccagctct acggccacgc cctcctccac tccagggacg   9420
acctggatcc tcacagagca gaccacagca gccactacga ccgcaaccac tggatccacg   9480
gccatcccgt cctccacccc gggaacagct cccccctccca aagtgctgac cagcacggcc   9540
accacaccca cagccaccag ttccaaagcc acttcctcct ccagtccaag gactgcaacc   9600
acccttccag tgctgacaag cacagccacc aaatccacag ctaccagctt tacacccatc   9660
ccctccttca cccttgggac caccgggacc ctcccagaac agaccaccac acccatggcc   9720
accatgtcca caatccaccc ctcctccact ccggagacca cccacacctc cacagtgctg   9780
accacgaagg ccaccacgac aagggccacc agttccatgt ccacccccctc ctccactccg   9840
gggacgacct ggatcctcac agagctgacc acagcagcca ctacaactgc agccactggc   9900
cccacggcca ccccgtcctc caccccaggg accacctgga tcctcacaga gcccagcact   9960
acagccaccg tgacggtgcc caccggatcc acggccaccg cctcctccac ccgggcaact  10020
gctggcaccc tcaaagtgct gaccagcacg gccaccacac ccacagtcat cagctccaga  10080
gccactccct cctccagtcc agggactgca accgcccttc cagcactgag aagcacagcc  10140
accacaccca cagctaccag cgttacagcc atcccctctt cctccctggg caccgcctgg  10200
acccgcctat cacagaccac cacacccacg gccaccatgt ccacagccac accctcctct  10260
actccagaga ctgtccacac ctccacagtg cttaccacca cgaccaccac aaccagggcc  10320
accggctctg tggccacccc ctcctccacc ccaggaacag ctcacactac caaagtgccg  10380
actaccacaa ccacgggctt cacagccacc ccctcctcca gcccagggac ggcactcacg  10440
cctccagtgt ggatcagcac aaccaccaca cccacaacca gaggctccac ggtgaccccc  10500
tcctccatcc cggggaccac ccacaccgcc acagtgctga ccaccaccac cacaactgtg  10560
gccactggtt ctatggcaac accctcctct agcacacaga ccagtgggac cacccacaca  10620
cccccagtgc cgaacaccac ggccaccaca cacgggcggt ccctgccccc cagcagtccc  10680
cacacggtgc gcacagcctg gacttcggcc acctcgggca tcttgggcac cacccacatc  10740
acagagcctt ccacggtgac ttcccacacc ccagcagcaa ccaccagtac cacccagcac  10800
tcgactccag ccctgtccag ccctcaccct agcagcagga ccaccgagtc accccccttct  10860
ccagggacga ccaccccggg ccacaccagg ggcacctcca ggaccacagc cacagccaca  10920
```

-continued

```
cccagcaaga cccgcacctc gaccctgctg cccagcagcc ccacatcggc ccccataacc  10980
acggtggtga ccacgggctg tgagccccag tgtgcctggt cagagtggct ggactacagc  11040
taccccatgc cggggccctc tggcggggac tttgacacct actccaacat ccgtgcggcc  11100
ggaggggcag tctgtgagca gcccctgggc ctcgagtgcc gtgcccaggc ccagcctggt  11160
gtccccctgc gggagttggg ccaggtcgtg gaatgcagcc tggactttgg cctggtctgc  11220
aggaaccgtg agcaggtggg gaagttcaag atgtgcttca actatgaaat ccgtgtgttc  11280
tgctgcaact acggccactg ccccagcacc ccggccacca gctctacggc cacgccctcc  11340
tcaactccgg ggacgacctg gatcctcaca aagctgacca caacagccac tacgactgag  11400
tccactggat ccacggccac cccgtcctcc accccaggga ccacctggat cctcacagag  11460
ccgagcacta cagccaccgt gacggtgccc accggatcca cggccaccgc ctcctccacc  11520
caggcaactg ctggcacccc acatgtgagc accacggcca cgacacccac agtcaccagc  11580
tccaaagcca ctcccttctc cagtccaggg actgcaaccg cccttccagc actgagaagc  11640
acagccacca cacccacagc taccagcttt acagccatcc cctcctcctc cctgggcacc  11700
acctggaccc gcctatcaca gaccaccaca cccacggcca ccatgtccac agccacaccc  11760
tcctccactc cagagactgc ccacacctcc acagtgctta ccaccacggc caccacaacc  11820
agggccaccg gctctgtggc cacccccctct tccaccccag gaacagctca cactaccaaa  11880
gtgccgacta ccacaaccac gggcttcaca gtcacccccct cctccagccc agggacggca  11940
cgcacgcctc cagtgtggat cagcacaacc accacaccca caaccagtgg ctccacggtg  12000
acccccctcct ccgtcccggg gaccacccac accccccacag tgctgaccac caccaccaca  12060
actgtggcca ctggttctat ggcaacaccc tcctctagca cacagaccag tggtactccc  12120
ccatcactga tcaccacggc cactacgatc acggccaccg gctccaccac caacccctcc  12180
tcaactccag ggacaacacc tatcccccca gtgctgacca ccaccgccac cacacctgca  12240
gccaccagca gcacagtgac tccctcctct gccctaggga ccacccacac acccccagtg  12300
ccgaacacca cggccaccac acacgggcga tccctgtccc ccagcagtcc ccacacggtg  12360
cgcacagcct ggacttcggc cacctcaggc accttgggca ccacccacat cacagagcct  12420
tccacgggga cttcccacac cccagcagca accaccggta ccacccagca ctcgactcca  12480
gccctgtcca gccctcaccc tagcagcagg accaccgagt cacccccttc cccagggacg  12540
accaccccgg gccacaccac ggccacctcc aggaccacgg ccacggccac acccagcaag  12600
acccgcacct cgaccctgct gcccagcagc cccacatcgg cccccataac cacggtggtg  12660
accacgggct gtgagcccca gtgtgcctgg tcagagtggc tggactacag ctaccccatg  12720
ccggggccct ctggcgggga ctttgacacc tactccaaca tccgtgcggc cggaggggcc  12780
gtctgtgagc agcccctggg cctcgagtgc cgtgcccagg cccagcctgg tgtccccctg  12840
ggggagttgg gccaggtcgt ggaatgcagc ctggactttg gcctggtctg caggaaccgt  12900
gagcaggtgg ggaagttcaa gatgtgcttc aactatgaaa tccgtgtgtt ctgctgcaac  12960
tacggccact gccccagcac cccggccacc agctctacgg ccatgccctc ctccactccg  13020
gggacgacct ggatcctcac agagctgacc acaacagcca ctacgactgc atccactgga  13080
tccacggcca ccccgtcctc caccccggga acagctcccc ctcccaaagt gctgaccagc  13140
ccggccacca cacccacagc caccagttcc aaagccactt cctcctccag tccaaggact  13200
gcaaccaccc ttccagtgct gacaagcaca gccaccaaat ccacagctac cagcgttaca  13260
cccatcccct cctccaccct tggaccacc gggaccctcc cagaacagac caccacaccc  13320
```

gtggccacca tgtccacaat ccacccctcc tccactccgg agaccaccca cacctccaca 13380
gtgctgacca cgaaggccac cacgacaagg gccaccagtt ccacgtccac cccctcctcc 13440
actccgggga cgacctggat cctcacagag ctgaccacag cagccactac aactgcagcc 13500
actggcccca cggccacccc gtcctccacc ccagggacca cctggatcct cacagagctg 13560
accacaacag ccactacgac tgcgtccact ggatccacgg ccaccccgtc ctccacccca 13620
gggaccacct ggatcctcac agagccgagc actacagcca ccgtgacggt gcccaccgga 13680
tccacggcca ccgcctcctc cacccaggca actgctggca ccccacatgt gagcaccacg 13740
gccacgacac ccacagtcac cagctccaaa gccactccct cctccagtcc agggactgca 13800
actgcccttc cagcactgag aagcacagcc accacaccca cagctaccag ctttacagcc 13860
atcccctcct cctccctggg caccacctgg acccgcctat cacagaccac cacacccacg 13920
gccaccatgt ccacagccac accctcctcc actccagaga ctgtccacac ctccacagtg 13980
cttaccgcca cggccaccac aaccggggcc accggctctg tggccacccc ctcctccacc 14040
ccaggaacag ctcacactac caaagtgccg actaccacaa ccacgggctt cacagccacc 14100
ccctcctcca gcccagggac ggcactcacg cctccagtgt ggatcagcac aaccaccaca 14160
cccacaacca ccacacccac aaccagtggc tccacggtga ccccctcctc catcccgggg 14220
accacccaca ccgccagagt gctgaccacc accaccacaa ctgtggccac tggttctatg 14280
gcaacaccct cctctagcac acagaccagt ggtactcccc catcactgac caccacggcc 14340
actacgatca cggccaccgg ctccaccacc aacccctcct caactccagg gacaacaccc 14400
atcaccccag tgctgaccag cacggccacc acacccgcag ccaccagctc caaagccact 14460
tcctcctcca gtccaaggac tgcaaccacc cttccagtgc tgacaagcac agccacaaaa 14520
tccacagcta ccagctttac acccatcccc tcctccaccc tgtggaccac gtggaccgtc 14580
ccagcacaga ccaccacacc catgtccacc atgtccacaa tccacacctc ctctactcca 14640
gagaccaccc acacctccac agtgctgacc accacagcca ccatgacaag ggccaccaat 14700
tccacggcca cacctcctc cactctgggg acgacccgga tcctcactga gctgaccaca 14760
acagccacta caactgcagc cactggatcc acggccaccc tgtcctccac cccagggacc 14820
acctggatcc tcacagagcc gagcactata gccaccgtga tggtgcccac cggttccacg 14880
gccaccgcct cctccactct gggaacagct cacaccccca aagtggtgac caccatggcc 14940
actatgccca cagccactgc ctccacggtt cccagctcgt ccaccgtggg gaccacccgc 15000
acccctgcag tgctccccag cagcctgcca accttcagcg tgtccactgt gtcctcctca 15060
gtcctcacca ccctgagacc cactggcttc cccagctccc acttctctac tccctgcttc 15120
tgcagggcat ttggacagtt tttctcgccc ggggaagtca tctacaataa gaccgaccga 15180
gccggctgcc atttctacgc agtgtgcaat cagcactgtg acattgaccg cttccagggc 15240
gcctgtccca cctccccacc gccagtgtcc tccgccccgc tgtcctcgcc ctcccctgcc 15300
cctggctgtg acaatgccat ccctctccgg caggtgaatg agacctggac cctggagaac 15360
tgcacggtgg ccaggtgcgt gggtgacaac cgtgtcgtcc tgctggaccc aaagcctgtg 15420
gccaacgtca cctgcgtgaa caagcacctg cccatcaaag tgtcggaccc gagccagccc 15480
tgtgacttcc actatgagtg cgagtgcatc tgcagcatgt ggggcggctc ccactattcc 15540
acctttgacg gcacctctta caccttccgg ggcaactgca cctatgtcct catgagagag 15600
atccatgcac gctttgggaa tctcagcctc tacctggaca accactactg cacggcctct 15660

-continued

```
gccactgccg ctgccgcccg ctgccccgc gccctcagca tccactacaa gtccatggat  15720
atcgtcctca ctgtcaccat ggtgcatggg aaggaggagg gcctgatcct gtttgaccaa  15780
attccggtga gcagcggttt cagcaagaac ggcgtgcttg tgtctgtgct ggggaccacc  15840
accatgcgtg tggacattcc tgccctgggc gtgagcgtca ccttcaatgg ccaagtcttc  15900
caggcccggc tgccctacag cctcttccac aacaacaccg agggccagtg cggcacctgc  15960
accaacaacc agagggacga ctgtctccag cgggacggaa ccactgccgc cagttgcaag  16020
gacatggcca agacgtggct ggtccccgac agcagaaagg atggctgctg ggccccgact  16080
ggcacacccc ccactgccag ccccgcagcc ccggtgtcta gcacacccac ccccacccca  16140
tgcccaccac agccgctctg tgatctgatg ctgagccagg tctttgctga gtgccacaac  16200
cttgtgcccc cgggcccatt cttcaacgcc tgcatcagcg accactgcag ggccgccctt  16260
gaggtgccct gccagagcct ggaggcttac gcagagctct gccgcgcccg gggagtgtgc  16320
agtgactggc gaggtgcaac cggtggcctg tgcgacctca cctgcccacc caccaaagtg  16380
tacaagccat gcggccccat acagcctgcc acctgcaact ctaggaacca gagcccacag  16440
ctggagggga tggcggaggg ctgcttctgc cctgaggacc agatcctctt caacgcacac  16500
atgggcatct gcgtgcaggc ctgcccctgc gtgggacccg atgggtttcc taaatttccc  16560
ggggagcggt gggtcagcaa ctgccagtcc tgcgtgtgtg acgagggttc agtgtcggtg  16620
cagtgcaagc cctgccctg tgacgcccag ggtcagcccc cgccgtgcaa ccgtcccggc  16680
ttcgtaaccg tgaccaggcc ccgggccgag aacccctgct gccccgagac ggtgtgcgtg  16740
tgcaacacaa ccacctgccc ccagagcctg cctgtgtgcc cgccagggca ggagtccatc  16800
tgcacccagg aggagggcga ctgctgtccc accttccgct gcagacctca gctgtgttcg  16860
tacaatggca ccttctacgg ggttggtgca accttcccag gcgcccttcc ctgccacatg  16920
tgtacctgcc tctctgggga cacccaggac ccaacggtgc aatgtcagga ggatgcctgc  16980
aacaatacta cctgtcccca gggctttgag tacaagagag tggccgggca gtgctgtggg  17040
gagtgcgtcc agaccgcctg cctcacgccc gatggccagc cagtccagct gaatgaaacc  17100
tgggtcaaca gccatgtgga caactgcacc gtgtacctct gtgaggctga gggtggagtc  17160
catttgctga ccccacagcc tgcatcctgc ccagatgtgt ccagctgcag gggggagcctc  17220
aggaaaaccg gctgctgcta ctcctgtgag gaggactcct gtcaagtccg catcaacacg  17280
accatcctgt ggcaccaggg ctgcgagacc gaggtcaaca tcaccttctg cgagggctcc  17340
tgccccggag cgtccaagta ctcagcagag gcccaggcca tgcagcacca gtgcacctgc  17400
tgccaggaga ggcgggtcca cgaggagacg gtgcccttgc actgtcctaa cggctcagcc  17460
atcctgcaca cctacaccca cgtggatgag tgtggctgca cgcccttctg tgtccctgcg  17520
cccatggctc ccccacacac ccgtggcttc ccggcccagg aggccactgc tgtctgagaa  17580
cgttctgcct ccatccccat gctctgtcca cctggagcca ggatgtgcat tgtctgatca  17640
tgaaaacctt gggcctcctc tgcggagccc cccggcctgt gtgtggcacc ccgcgctccg  17700
tgctcctgct gcccaccccg tgggtgaaac cggccccaga agggtgaggg gccagcagga  17760
cccctttcgg gagggcgcca ctcaggagtc ctaccctggg agagcctgtg gcccaccttg  17820
gccttgcccc tccctgatgt cactggg                                     17847
```

<210> SEQ ID NO 26
<211> LENGTH: 3499
<212> TYPE: DNA
<213> ORGANISM: Homo sapiens

<400> SEQUENCE: 26

```
gccaagaagc ttgagagaag aaaaatttca gaaaaattgt ctcaatttga ctagaatatc     60
aatgaaccag gaaaactgaa gcaccttccc taaagaaaac ttgggtatac aattactcca    120
cagacagagc tgagggtttt ttacccaaat cagtcactgg attttgctgc ctgatacgtg    180
aatcttcttg gaatttttct catgtggatc taaggggaat gctttattat ggctgctgtt    240
gtccaacaga acgacctagt atttgaattt gctagtaacg tcatggagga tgaacgacag    300
cttggtgatc cagctatttt tcctgccgta attgtggaac atgttcctgg tgctgatatt    360
ctcaatagtt atgccggtct agcctgtgtg gaagagccca atgacatgat tactgagagt    420
tcactggatg ttgctgaaga agaaatcata gacgatgatg atgatgacat cacccttaca    480
gttgaagctt cttgtcatga cggggatgaa acaattgaaa ctattgaggc tgctgaggca    540
ctcctcaata tggattcccc tggccctatg ctggatgaaa aacgaataaa taataatata    600
tttagttcac ctgaagatga catggttgtt gccccagtca cccatgtgtc cgtcacatta    660
gatgggattc ctgaagtgat ggaaacacag caggtgcaag aaaaatatgc agactcaccg    720
ggagcctcat caccagaaca gcctaagagg aaaaaaggaa gaaaaactaa accaccacga    780
ccagattccc cagccactac gccaaatata tctgtgaaga agaaaaacaa agatggaaag    840
ggaaacacaa tttatctttg ggagtttttta ctggcactgc tccaggacaa ggctacttgt    900
cctaaataca tcaagtggac ccagcgagag aaaggcattt ttaaattggt ggattctaaa    960
gcagtgtcca ggttgtgggg gaagcacaaa aacaaacctg atatgaatta tgagaccatg   1020
ggaagagcac tcaggtacta ttaccaaagg ggtattctgg caaaagtgga aggtcagcgc   1080
ttggtgtatc agtttaaaga aatgccaaaa gatcttatat atataaatga tgaggatcca   1140
agttccagca tagagtcttc agatccatca ctatcttcat cagccacttc aaataggaat   1200
caaaccagcc ggtcgagagt atcttcaagt ccaggggtaa aaggaggagc cactacagtt   1260
ctaaaaccag ggaattctaa agctgcaaaa cccaaagatc ctgtggaagt tgcacaacca   1320
tcagaagttt tgaggacagt gcagcccacg cagtctccat atcctaccca gctcttccgg   1380
actgttcatg tagtacagcc agtacaggct gtcccagagg gagaagcagc tagaaccagt   1440
accatgcagg atgaaacatt aaattcttcc gttcagagta ttaggactat acaggctcca   1500
acccaagttc cagtggttgt gtctcctagg aatcagcagt tgcatacagt aacactccaa   1560
acagtgccac tcacaacagt tatagccagc acagatccat cagcaggtac tggatctcag   1620
aagtttattt tacaagccat tccatcatca cagcccatga cagtactgaa agaaaatgtc   1680
atgctgcagt cacaaaaggc gggctctcct ccttcaattg tcttgggccc tgcccaggtt   1740
cagcaggtcc ttactagcaa tgttcagacc atttgcaatg gaaccgtcag tgtggcttcc   1800
tctccatcct tcagtgctac tgcacctgtg gtgacctttt ctcctcgcag ttcacagctg   1860
gttgctcacc cacctggcac tgtaatcact tcagttatca aaactcaaga aacaaaaact   1920
cttacacagg aagtagagaa aaaggaatct gaagatcatt tgaaagagaa cactgagaaa   1980
acggagcagc agccacagcc ttatgtgatg gtagtgtcca gttccaatgg atttacttct   2040
caggtagcta tgaaacaaaa cgaactgctg gaacccaact ctttttagtt aatataccaa   2100
agcttatgaa taattgtttg ttaattgaac attttcaatt atatgcagac tgactgattc   2160
taagataaat tctaaggagg tttctaattt tgtaattgtt aaaaatagag ttaattttga   2220
ctttgttaga tgagggagga aaactcaact gtttctcttt gttatctaaa tgtttcagaa   2280
```

-continued

```
ttcaatcgtg aaggaacagg cattttacac tatgaagaca ttcttttgag atttttattt   2340
cagttgctat atcataagca tttttaaagt ttcttttcta attttacatt gtattagatt   2400
ttctgattct tttgtaaata cagaacttaa atagaaggca acaggaaatt tatataggaa   2460
ctattttcat tccacttgtg taagttaagt cttgactctt tcaaatgcaa aaaacctatt   2520
ttatgctttg ttaaaattat ggtgtcactt agattgactt tagttgactg cactatataa   2580
tatagaacta tgaatatgta gaataacatg aaaaattgga ggtgctggtg gtatggctga   2640
ccctgtttca gaagcaggat agtataaaag catcagccta agaatggcac tcccactaac   2700
tagctatgta atcttgacct ctttgggctt tagttcctct cataaaagga agagatgtat   2760
tggattagac tagattatca ccactttctc ttctagttct aattttttta attctaatac   2820
ctatattttc aagttatgtc aattaaatca ttatcaggtt atttcctaat gtaagaatag   2880
ctaaaatgtt gcagagaaat aagtgaccca acaaaattta ttcatctgtt atgggtaaga   2940
tctgccataa attcttccta aataatttgt ttactaactc tttaggccac tgtgctttgc   3000
ggtccattag taaacttgtg ttgctaagtg ctaaacagaa tactgctatt ttgagagagt   3060
caagactctt tcttaagggc caagaaagca acttgagcct tgggctaatc tggctgagta   3120
gtcagttata aaagcataat tgctttatat tttggatcat tttttactgg gggcggactt   3180
ggggggggtt gcatacaaag ataacatata tatccaactt tctgaaatga aatgttttta   3240
gattactttt tcaactgtaa ataatgtaca tttaatgtca caagaaaaaa atgtcttctg   3300
caaattttct agtataacag aaatttttgt agatgaaaaa aatcattatg tttagaggtc   3360
taatgctatg ttttcatatt acagagtgaa tttgtattta aacaaaaatt taaattttgg   3420
aatcctctaa acatttttgt atctttaatt ggtttattat taaataaatc atataaaaat   3480
tctcaaaaaa aaaaaaaaa                                                 3499
```

<210> SEQ ID NO 27
<211> LENGTH: 3302
<212> TYPE: DNA
<213> ORGANISM: Homo sapiens

<400> SEQUENCE: 27

```
cggtgctgcc gccgttgccg ggagccgcgg agacaagtca ttacgttttc atttctcaca     60
actgggctga gcacaactga accatggggg aacacagtcc agacaacaac atcatctact    120
ttgaggcaga ggaagatgag ctgacccccg atgataaaat gctcaggttt gtggataaaa    180
acggactggt gccttcctca tctggaactg tttatgatag gaccactgtt cttattgagc    240
aggaccctgg cactttggag gatgaagatg acgacggaca gtgcggagaa cacttgcctt    300
ttctagtagg gggtgaagag ggctttcacc tgatagatca tgaagcaatg tcccagggtt    360
atgtgcagca cattatctca ccagatcaga ttcatttgac aataaaccct ggttccacac    420
ccatgccaag aaatattgaa ggtgcaaccc tcactctgca gtcggaatgt ccggaaacaa    480
aacgtaaaga agtaaagcgg taccaatgta cctttgaggg ctgtccccgc acctacagca    540
cagcaggcaa cctgcgaacc caccagaaga ctcaccgagg agagtacacc tttgtctgta    600
atcaggaggg ctgtggcaaa gccttcctta cctctcacag cctcaggatc cacgtgcgag    660
tgcacacgaa ggagaagcca tttgagtgtg acgtgcaggg ctgtgagaag gcattcaaca    720
cactgtacag gctgaaagca catcagaggc ttcacacagg gaaaacgttt aactgtgaat    780
ctgaaggctg cagcaaatac ttcaccacac tcagtgatct gaggaagcac attcgaactc    840
atacagggga aaagccattt cggtgcgatc acgatggctg tggaaaagca tttgcagcaa    900
```

-continued

```
gccaccacct taaaactcac gttcgtacac atactggtga aagacccttc ttctgcccca    960
gtaatggctg tgagaaaaca ttcagcactc aatacagtct caaaagtcac atgaaaggtc   1020
atgataacaa aggacactca tacaatgcac ttccacaaca caatggatca gaggatacaa   1080
atcactcact ttgtctaagt gacttgagcc ttctgtccac agattctgaa ttgcgagaaa   1140
attccagtac gacccagggc caggacctca gcacaatttc accagcaatc atctttgaat   1200
caatgttcca gaattcagat gatacggcaa ttcaggaaga tcctcaacag acagcttcct   1260
tgactgaaag ttttaatggt gatgcagagt cagtcagtga tgttccgcca tccacaggaa   1320
attcagcatc tttatctctt ccacttgtac tgcaacctgg cctctccgag ccaccccagc   1380
ctctactacc tgcctcagct ccgtctgctc ctccgcctgc tccctcccta ggacctggct   1440
cccagcaagc tgcatttggc aacccccctg ctctcttaca acctccagaa gtgcctgttc   1500
cccacagcac acagtttgct gctaatcatc aagagtttct tccgcacccc caggcaccgc   1560
agcccattgt accaggactt tctgttgttg ctggggcttc tgcatcagca gcggcagtgg   1620
catcagctgt ggcagcacca gccccaccac aaagtactac tgagcccctg ccagccatgg   1680
tccagactct gcccctgggt gccaactctg tcctaactaa taatcccaca ataaccatca   1740
ccccaactcc caacacagct atcctgcagt ccagcctagt catgggagaa cagaacttac   1800
aatggatatt aaatggtgcc accagttctc cacaaaacca agaacaaatt cagcaagcat   1860
ctaaagttga gaaggtgttt tttaccactg cagtaccagt agccagtagc ccagggagct   1920
ctgtccagca gattggcctc agtgttcctg tgatcatcat caaacaagaa gaggcatgtc   1980
agtgtcagtg tgcatgccgg gactctgcaa aggagcgggc atccagcagg agaaagggct   2040
gctcctcccc accccctcca gagccgagcc cccaggctcc tgatgggccc agcctgcagc   2100
tcccagcgca gactttctct tcagcccctg ttcccgggtc atcatcctct accttgccct   2160
cctcctgtga gcaaagccga caagcagaga ctccttcaga ccctcagaca gaaacattaa   2220
gtgccatgga tgtgtcagag tttctatccc tccagagcct ggacaccccg tccaatctga   2280
ttcccattga agcactactg caggggggagg aggagatggg cctcaccagc agcttctcca   2340
agtgaagggc ccatgtgtgc tcacctctgg gaaaagcggg tgagcaggag gcatgaggta   2400
caatgcctgc catcatgggt cagaaatttg aaggatgaag aaatctactg tttgaaatcc   2460
tcacctttca gacgtatttt ctttattcac atcccaggag catccatttt aaggaactat   2520
tctttggaaa aaaacaaaaa acaaaaaaaa caacaaaaaa agctaagtta taagtgaact   2580
gtttggctgc actgtatgtc acttttgctt gttgtcatgt gaacttggaa actaaggtta   2640
ctcgtgtgca taaaaattct aaatgaaagg gtgtggtttc catcaatctg atgctgccca   2700
tcgcttgcac tggggtcttt gtggatcggg caggagtttt cagtgtgttg ggtgttgctc   2760
cttcctatgt gtcttttgaa tctgaggctg acatttgctt ggaaggccag acccttgctc   2820
catcagagag ggcagtggca aaggccagtg aggcagctgt gagttggaca gggttcaggt   2880
gagatggtgt tgtcatttgt gcttagtgtt ggtggtgctc agggtggata acacgggtcg   2940
ttctgcagcc cgcttcagca caaataggca gcttaaggcc tggctcacag gctgtggggt   3000
tgatctggct ctgcagaggc cctaggcagc ttgttgactg ctgtctgttg atgacgtgtg   3060
tgcaaagcag gctctagcaa catgatcact gtccttgcct tcctggttct ttctctcggt   3120
tggttgccag ggcttgcaga tcgcagtgaa ttttccttgg ggaacatcgc tgttttgtcc   3180
tagagtgaac ttgtggctta tggccagtgc tgtttggtgg tctgccttct ttttaatggt   3240
```

attttcttcc tcagagcaga agggctgcat tttgcttatc agaagaaggt gcagatttaa 3300
gg 3302

<210> SEQ ID NO 28
<211> LENGTH: 390
<212> TYPE: DNA
<213> ORGANISM: Homo sapiens

<400> SEQUENCE: 28
ccttcctctc ctagcctaag gcgtgcaaac agagcgccac tgggaggctg aaacctttag 60
gccgatgctt gcttgcaagg tcaggcaagc tggattctgg tccccacctt tgcagagaga 120
acagcgatgt tgtgcgccca tttctcagat caaggaccgg cccatcttac tacctccaag 180
agtgcttttc tctctaataa gaaaacatct actttgaaac atctactggg cgagaccagg 240
agtgatggct cagcctgtaa ttctggaatt tcgggaggcc gaggcaggaa gattccttga 300
gcacaggagt tccagaccag cctgggcaat gtagcaagac gctgtctcta tttatacaat 360
aaaaaaaaaa aaaaaaaaaa aaaaaaaaaa 390

<210> SEQ ID NO 29
<211> LENGTH: 2564
<212> TYPE: DNA
<213> ORGANISM: Homo sapiens

<400> SEQUENCE: 29
agatacacgg tttttaagaa agaacttcta accccactcc accgcccaac ggtcacgtga 60
cgcgcctgcg tcctcgcctc aaggtttttt ctggtcgcat attggctgtt aactcggcta 120
cggggtgtag cgaggtgcat tccggaagta ggtcctttga cttttgcttc ctctacggag 180
gcaagtaaca acccggcggt cgacgcttag cggaagttcg tcaagtcgca gttgcccccg 240
cacagcggat gtgggtcgcc tcttaggtga cgctgggaag tgcctgcaac cttcgccgct 300
gccttctggt tgaagcacta tggagggaga gaggaagaac aacaacaaac ggtggtattt 360
cactcgagaa cagctggaaa atagcccatc ccgtcgtttt ggcgtggacc cagataaaga 420
actttcttat cgccagcagg cggccaatct gcttcaggac atggggcagc gtcttaacgt 480
ctcacaattg actatcaaca ctgctatagt atacatgcat cgattctaca tgattcagtc 540
cttcacacag ttccctggaa attctgtggc tccagcagcc ttgtttctag cagctaaagt 600
ggaggagcag cccaaaaaat tggaacatgt catcaaggta gcacatactt gtctccatcc 660
tcaggaatcc cttcctgata ctagaagtga ggcttatttg caacaagttc aagatctggt 720
cattttagaa agcataattt tgcagacttt aggctttgaa ctaacaattg atcacccaca 780
tactcatgta gtaaagtgca ctcaacttgt tcgagcaagc aaggacttag cacagacttc 840
ttacttcatg gcaaccaaca gcctgcattt gaccacattt agcctgcagt acacacctcc 900
tgtggtggcc tgtgtctgca ttcacctggc ttgcaagtgg tccaattggg agatcccagt 960
ctcaactgac gggaagcact ggtgggagta tgttgacgcc actgtgacct tggaactttt 1020
agatgaactg acacatgagt ttctacagat tttggagaaa actcccaaca ggctcaaacg 1080
catttggaat tggagggcat gcgaggctgc caagaaaaca aaagcagatg accgaggaac 1140
agatgaaaag acttcagagc agacaatcct caatatgatt tcccagagct cttcagacac 1200
aaccattgca ggtttaatga gcatgtcaac ttctaccaca agtgcagtgc cttccctgcc 1260
agtctccgaa gagtcatcca gcaacttaac cagtgtggag atgttgccgg gcaagcgttg 1320
gctgtcctcc caaccttctt tcaaactaga acctactcag ggtcatcgga ctagtgagaa 1380
tttagcactt acaggagttg atcattcctt accacaggat ggttcaaatg catttatttc 1440
ccagaagcag aatagtaaga gtgtgccatc agctaaagtg tcactgaaag aataccgcgc 1500
gaagcatgca gaagaattgg ctgcccagaa gaggcaactg gagaacatgg aagccaatgt 1560
gaagtcacaa tatgcatatg ctgcccagaa tctcctttct catcatgata gccattcttc 1620
agtcattcta aaaatgccca tagagggttc agaaaacccc gagcggcctt ttctggaaaa 1680
ggctgacaaa acagctctca aaatgagaat cccagtggca ggtggagata aagctgcgtc 1740
ttcaaaacca gaggagataa aaatgcgcat aaaagtccat gctgcagctg ataagcacaa 1800
ttctgtagag gacagtgtta caaagagccg agagcacaaa gaaaagcaca agactcaccc 1860
atctaatcat catcatcatc ataatcacca ctcacacaag cactctcatt cccaacttcc 1920
agttggtact gggaacaaac gtcctggtga tccaaaacat agtagccaga caagcaactt 1980
agcacataaa acctatagct tgtctagttc tttttcctct tccagttcta ctcgtaaaag 2040
gggaccctct gaagagactg gaggggctgt gtttgatcat ccagccaaga ttgccaagag 2100
tactaaatcc tcttccctaa atttctcctt cccttcactt cctacaatgg gtcagatgcc 2160
tgggcatagc tcagacacaa gtggcctttc cttttcacag cccagctgta aaactcgtgt 2220
ccctcattcg aaactggata aagggcccac tggggccaat ggtcacaaca cgacccagac 2280
aatagactat caagacactg tgaatatgct tcactccctg ctcagtgccc agggtgttca 2340
gcccactcag cccactgcat ttgaatttgt tcgtccttat agtgactatc tgaatcctcg 2400
gtctggtgga atctcctcga gatctggcaa tacagacaaa ccccggccac cacctctgcc 2460
atcagaacct cctccaccac ttccacccct tcctaagtaa aaaaagaaaa agaagaggag 2520
aaaaaaactt ctttaaaaaa acacataatt tttcttttt tttt 2564

<210> SEQ ID NO 30
<211> LENGTH: 2948
<212> TYPE: DNA
<213> ORGANISM: Homo sapiens

<400> SEQUENCE: 30
gcgtgcgcaa tgggccacag aaccgccatg ccggaaccgc gcgggtcgtc gcagctgcgg 60
gtgaacgcgg cgtttgccgc gcggtacaac cgctaccggg agcgcgagga actgcagcgg 120
cgaatttgat ccccagcagg agcgggactt ttacaaaacg ctctccttgt tgaagaagaa 180
ggacccccgc atttatcaga aagatgccac cttctataac agaacagcat cgtcatcaga 240
cagtgaggag gacccagaag ccttggagaa gcagaagaaa gtgcggccca tgtacctgaa 300
ggactacgag aggaaggtta tcttggagaa ggcaggcaaa tatgttgatg aggagaactc 360
agacggggag acttccaatc acagactcca ggagacatcg tcgcaaagtt atgtggagga 420
acagaaacag ctcaaggaaa gcttccgggc atttgtggag gacagtgagg acgaggacgg 480
cgctggggag ggcggctcca gtttgctgca gaaacgtgcc aaaaccaggc aggagaaggc 540
ccaggaggag gccgactaca tcgagtggct gaagggacag aaagagattc ggaacccaga 600
ttccctgaag gaactgacgc atctcaagga atactggaac gaccctgagt tggatgaagg 660
ggagcggttc ctgcgggatt acatcctcaa caaacgctat gaggaggagg aagaggagga 720
ggaagatgaa gaggaaatgg aggaagagaa gggggtccac ggtcccccag tccagctggc 780
tgtggacgac tcctcagacg aaggggagct gtttctgaag aaacaggagg actttgaaca 840
gaagtacaat ttccgtttcg aggagccgga ctcagcatcg gtcaagacct acccacgcag 900

-continued

```
catcgcgtcc tccgtgcgcc gtaaggatga gcgcagaaag gagaagaggg aagagactcg    960
ggagcgaaag aagagggaga aagcaaagaa gcaggaagag ctcaagcagc tgaagaacct   1020
gaagaggaag gagattctgg ccaagctgga gaagctgcgg aaagtaacag gcaacgagat   1080
gctgggcctc gaggaggggg accttgaaga cgacttcgac cctgcccagc acgaccagct   1140
catgcagaag tgctttgggg acgagtacta cggggccgtg gaggaggaga agccacaatt   1200
tgaggaagaa gaagggcttg aagacgactg gaactgggac acgtgggacg ggcctgagca   1260
ggagggagac tggagccagc aggagctgca ctgtgaggac cccaacttca acatggacgc   1320
cgactacgac cccagccagc cgaggaagaa aaagcgcgag gccccccttga cgggcaagaa   1380
gaagcgcaag tcgcccttcg ccgcggccgt ggggcaggag aagcccgtgt tcgaacccgg   1440
ggacaagacg ttcgaggagt acctggatga gtattaccgg ctggactacg aggacatcat   1500
cgacgacctg ccctgtcgct tcaagtaccg cacagtggtg ccctgtgact ttggcctcag   1560
cactgaggag atcctcgctg ctgacgataa ggagctgaac cggtggtgct ccctaaagaa   1620
gacctgcatg tacaggtcag agcaggagga gctgcgggac aagcgggcgt acagccagaa   1680
ggcccagaac tcatggaaaa agcggcaggt cttcaagtca ctctgccgag aagaggcaga   1740
gacacctgcg gaagccacag ggaagccaca gagagatgaa gccggcccac agaggcagct   1800
gccagcccctt gatggcagct tgatggggcc ggagagtccc ccagcacagg aagaggaagc   1860
ccctgtatca ccccacaaga agccagcccc ccagaagcgg aggagggcca agaaggcacg   1920
gctgctgggc cccactgtga tgcttggtgg atgcgagttc agccgccaga gactgcaggc   1980
ctttggcctc aaccccaaac ggctgcactt ccgccagctg ggccggcagc ggaggaaaca   2040
acaggggccc aagaacagct cctgagcacc agggagcagg caggggcctc aggctcctct   2100
cctcaaatca agccctggac aggtctcgca cccacaagta ctatctgctg cagagatcct   2160
ctcatctgtg gccaggcacg cctgtaatcc cagcactttg ggaggccgag gtgaaaggat   2220
cacttgagcc caggaattgg agaccagcgt gggcaactta gcgagactcc atctctacaa   2280
aatgtggtga cacatgcctg tagtcccagc tactcaggag gctggggaag gaagatcact   2340
taaggccatg agtttgaggc tacagagagc tatgattgca ccactgcact ccagcctggg   2400
caacaaagca agaccctgtc tcttgaaaaa aaaaaaaaaa ttaaaaaaca cgtgtagctg   2460
tgggtaagga agtcgtccca ttttatggat gtggaaactg aggctgactt aaacttcccg   2520
tgacttggag ctctcacctc gagacacctc ccagacccca catcccctca gaacgctgcg   2580
cccagccaca cccacgatca agttacacag ctttattggc cccagcagc cacagttccc    2640
ccaagggggc tttgggacag ggagggcccg ggcgtccagt gcaaactaca gtacgtgagt   2700
caggccctga ggggggtgcc cggggtcctc cttccctacc ctgccaggag ggccccgctg   2760
gtgggagaca ggtgtatggg ctctgtgggc tctgtccctg gctgaatggc cccagactgg   2820
ttgcagctgg gcttgagggg ctgacaacag gaagtaccat catcactgcc agagctcaag   2880
atcccacacc cgacatgaca taaataaaaa aataaatagt gttgtatctt taaaaaaaaa   2940
aaaaaaaa                                                            2948
```

<210> SEQ ID NO 31
<211> LENGTH: 3022
<212> TYPE: DNA
<213> ORGANISM: Homo sapiens

<400> SEQUENCE: 31

```
gcgtgcgcaa tgggccacag aaccgccatg ccggaaccgc gcgggtcgtc gcagctgcgg     60
```

-continued

```
gtgaacgcgg cgtttgccgc gcggtacaac cgctaccggg agcgcgagga actgcagcgg    120
ctgaaggatc gctacgggga ccgagacagc agcagcgact ccagctccga gtcggactca    180
agcgacgagc gcgtggaatt tgatccccag caggagcggg acttttacaa aacgctctcc    240
ttgttgaaga agaaggaccc ccgcatttat cagaaagatg ccaccttcta taacagaaca    300
gcatcgtcat cagacagtga ggaggaccca gaagccttgg agaagcagaa gaaagtgcgg    360
cccatgtacc tgaaggacta cgagaggaag gttatcttgg agaaggcagg caaatatgtt    420
gatgaggaga actcagacgg ggagacttcc aatcacagac tccaggagac atcgtcgcaa    480
agttatgtgg aggaacagaa acagctcaag gaaagcttcc gggcatttgt ggaggacagt    540
gaggacgagg acggcgctgg ggagggcggc tccagtttgc tgcagaaacg tgccaaaacc    600
aggcaggaga aggcccagga ggaggccgac tacatcgagt ggctgaaggg acagaaagag    660
attcggaacc cagattccct gaaggaactg acgcatctca aggaatactg gaacgaccct    720
gagttggatg aaggggagcg gttcctgcgg gattacatcc tcaacaaacg ctatgaggag    780
gaggaagagg aggaggaaga tgaagaggaa atggaggaag agaagggggt ccacggtccc    840
ccagtccagc tggctgtgga cgactcctca gacgaagggg agctgtttct gaagaaacag    900
gaggactttg aacagaagta caatttccgt ttcgaggagc cggactcagc atcggtcaag    960
acctacccac gcagcatcgc gtcctccgtg cgccgtaagg atgagcgcag aaaggagaag   1020
agggaagaga ctcgggagcg aaagaagagg gagaaagcaa agaagcagga agagctcaag   1080
cagctgaaga acctgaagag gaaggagatt ctggccaagc tggagaagct gcggaaagta   1140
acaggcaacg agatgctggg cctcgaggag ggggaccttg aagacgactt cgaccctgcc   1200
cagcacgacc agctcatgca gaagtgcttt ggggacgagt actacggggc cgtggaggag   1260
gagaagccac aatttgagga agaagaaggg cttgaagacg actggaactg ggacacgtgg   1320
gacgggcctg agcaggaggg agactggagc cagcaggagc tgcactgtga ggacccccaac  1380
ttcaacatgg acgccgacta cgaccccagc cagccgagga agaaaaagcg cgaggccccc   1440
ttgacgggca agaagaagcg caagtcgccc ttcgccgcgg ccgtggggca ggagaagccc   1500
gtgttcgaac ccggggacaa gacgttcgag gagtacctgg atgagtatta ccggctggac   1560
tacgaggaca tcatcgacga cctgccctgt cgcttcaagt accgcacagt ggtgccctgt   1620
gactttggcc tcagcactga ggagatcctc gctgctgacg ataaggagct gaaccggtgg   1680
tgctccctaa agaagacctg catgtacagg tcagagcagg aggagctgcg ggacaagcgg   1740
gcgtacagcc agaaggccca gaactcatgg aaaaagcggc aggtcttcaa gtcactctgc   1800
cgagaagagg cagagacacc tgcggaagcc acagggaagc cacagagaga tgaagccggc   1860
ccacagaggc agctgccagc ccttgatggc agcttgatgg ggccggagag tcccccagca   1920
caggaagagg aagcccctgt atcaccccac aagaagccag ccccccagaa gcggaggagg   1980
gccaagaagg cacggctgct gggccccact gtgatgcttg gtggatgcga gttcagccgc   2040
cagagactgc aggcctttgg cctcaacccc aaacggctgc acttccgcca gctgggccgg   2100
cagcggagga aacaacaggg gcccaagaac agctcctgag caccagggag caggcagggg   2160
cctcaggctc ctctcctcaa atcaagccct ggacaggtct cgcacccaca agtactatct   2220
gctgcagaga tcctctcatc tgtggccagg cacgcctgta atcccagcac tttgggaggc   2280
cgaggtgaaa ggatcacttg agcccaggaa ttggagacca gcgtgggcaa cttagcgaga   2340
ctccatctct acaaaatgtg gtgacacatg cctgtagtcc cagctactca ggaggctggg   2400
```

```
gaaggaagat cacttaaggc catgagtttg aggctacaga gagctatgat tgcaccactg   2460

cactccagcc tgggcaacaa agcaagaccc tgtctcttga aaaaaaaaaa aaaattaaaa   2520

aacacgtgta gctgtgggta aggaagtcgt cccattttat ggatgtggaa actgaggctg   2580

acttaaactt cccgtgactt ggagctctca cctcgagaca cctcccagac cccacatccc   2640

ctcagaacgc tgcgcccagc cacacccacg atcaagttac acagctttat tggcccccag   2700

cagccacagt tcccccaagg gggctttggg acagggaggg cccgggcgtc cagtgcaaac   2760

tacagtacgt gagtcaggcc ctgagggggg tgcccggggt cctccttccc taccctgcca   2820

ggagggcccc gctggtggga gacaggtgta tgggctctgt gggctctgtc cctggctgaa   2880

tggccccaga ctggttgcag ctgggcttga ggggctgaca acaggaagta ccatcatcac   2940

tgccagagct caagatccca cacccgacat gacataaata aaaaaataaa tagtgttgta   3000

tctttaaaaa aaaaaaaaaa aa                                             3022


<210> SEQ ID NO 32
<211> LENGTH: 2044
<212> TYPE: DNA
<213> ORGANISM: Homo sapiens

<400> SEQUENCE: 32

ctggacgagt ccgagcgcgt cacctcctca cgctgcggct gtcgcccgtg tcccgccggc     60

ccgttccgtg tcgccccgca gtgctgcggc cgccgcggca ccatggctgt gtttgtcgtg    120

ctcctggcgt tggtggcggg tgttttgggg aacgagttta gtatattaaa atcaccaggg    180

tctgttgttt tccgaaatgg aaattggcct ataccaggag agcggatccc agacgtggct    240

gcattgtcca tgggcttctc tgtgaaagaa gacctttctt ggccaggact cgcagtgggt    300

aacctgtttc atcgtcctcg ggctaccgtc atggtgatgg tgaagggagt gaacaaactg    360

gctctacccc caggcagtgt catttcgtac cctttggaga atgcagttcc ttttagtctt    420

gacagtgttg caaattccat tcactcctta ttttctgagg aaactcctgt tgttttgcag    480

ttggctccca gtgaggaaag agtgtatatg gtagggaagg caaactcagt gtttgaagac    540

ctttcagtca ccttgcgcca gctccgtaat cgcctgtttc aagaaaactc tgttctcagt    600

tcactccccc tcaattctct gagtaggaac aatgaagttg acctgctctt tctttctgaa    660

ctgcaagtgc tacatgatat ttcaagcttg ctgtctcgtc ataagcatct agccaaggat    720

cattctcctg atttatattc actggagctg gcaggtttgg atgaaattgg gaagcgttat    780

ggggaagact ctgaacaatt cagagatgct tctaagatcc ttgttgacgc tctgcaaaag    840

tttgcagatg acatgtacag tctttatggt gggaatgcag tggtagagtt agtcactgtc    900

aagtcatttg acacctccct cattaggaag acaaggacta tccttgaggc aaaacaagcg    960

aagaacccag caagtcccta taaccttgca tataagtata attttgaata ttccgtggtt   1020

ttcaacatgg tactttggat aatgatcgcc ttggccttgg ctgtgattat cacctcttac   1080

aatatttgga acatggatcc tggatatgat agcatcattt ataggatgac aaaccagaag   1140

attcgaatgg attgaatgtt acctgtgcca gaattagaaa agggggttgg aaattggctg   1200

ttttgttaaa atatatcttt tagtgtgctt taaagtagat agtatacttt acatttataa   1260

aaaaaaatca aattttgttc tttattttgt gtgtgcctgt gatgtttttc tagagtgaat   1320

tatagtattg acgtgaatcc cactgtggta tagattccat aatatgcttg aatattatga   1380

tatagccatt taataacatt gatttcattc tgtttaatga atttggaaat atgcactgaa   1440

agaaatgtaa aacatttaga atagctcgtg ttatggaaaa aagtgcactg aatttattag   1500
```

-continued acaaacttac gaatgcttaa cttctttaca cagcataggt gaaaatcata tttgggctat 1560
tgtatactat gaacaatttg taaatgtctt aatttgatgt aaataactct gaaacaagag 1620
aaaaggtttt taacttagag tagccctaaa atatggatgt gcttatataa tcgcttagtt 1680
ttggaactgt atctgagtaa cagaggacag ctgtttttta accctcttct gcaagtttgt 1740
tgacctacat gggctaatat ggatactaaa aatactacat tgatctaaga agaaactagc 1800
cttgtggagt atatagatgc ttttcattat acacacaaaa atccctgagg gacattttga 1860
ggcatgaata taaaacattt ttatttcagt aacttttccc cctgtgtaag ttactatggt 1920
ttgtggtaca acttcattct atagaatatt aagtggaagt gggtgaattc tactttttat 1980
gttggagtgg accaatgtct atcaagagtg acaaataaag ttaatgatga ttccaaaaaa 2040
aaaa 2044

<210> SEQ ID NO 33
<211> LENGTH: 4000
<212> TYPE: DNA
<213> ORGANISM: Homo sapiens

<400> SEQUENCE: 33
cggccgcttt tttctcaaga tggcagattc ccactgaggc tgagggggcc gagctcgcgc 60
gccgcgttcc cttctccgtt gccatgaacc gcggacaccc cggccccgat ggcccccgtg 120
tacgaaggta tggcctcaca tgtgcaagtt ttctcccctc acacccttca atcaagtgcc 180
ttctgtagtg tgaagaaact aaaagtagag ccaagttcca actgggacat gactgggtac 240
ggctcccaca gcaaagtgta cagccagagc aagaacatac caccttctca gccagcctcc 300
acaaccgtca gcacctcctt gccggtccca aacccaagcc taccttacga gcagaccatc 360
gtcttcccag gaagcaccgg gcacatcgtg gtcacctcag caagcagcac ttctgtcacc 420
gggcaagtcc tcggcggacc acacaaccta atgcgtcgaa gcactgtgag cctccttgat 480
acctaccaaa aatgtggact caagcgtaag agcgaggaga tcgagaacac aagcagcgtg 540
cagatcatcg aggagcatcc acccatgatt cagaataatg caagcggggc cactgtcgcc 600
actgccacca cgtctactgc cacctccaaa aacagcggct ccaacagcga gggcgactat 660
cagctggtgc agcatgaggt gctgtgctcc atgaccaaca cctacgaggt cttagagttc 720
ttgggccgag ggacgtttgg acaagtggtc aagtgctgga aacggggcac caatgagatc 780
gtagccatca agatcctgaa gaaccgccca tcctatgccc gacaaggtca gattgaagtg 840
agcatcctgg cccggttgag cacggagagt gccgatgact ataacttcgt ccgggcctac 900
gaatgcttcc agcacaagaa ccacacgtgc ttggtcttcg agatgttgga gcagaacctc 960
tatgactttc tgaagcaaaa caagtttagc cccttgcccc tcaaatacat tcgcccagtt 1020
ctccagcagg tagccacagc cctgatgaaa ctcaaaagcc taggtcttat ccacgctgac 1080
ctcaaaccag aaaacatcat gctggtggat ccatctagac aaccatacag agtcaaggtc 1140
atcgactttg gttcagccag ccacgtctcc aaggctgtgt gctccaccta cttgcagtcc 1200
agatattaca gggcccctga gatcatcctt ggtttaccat tttgtgaggc aattgacatg 1260
tggtccctgg gctgtgttat tgcagaattg ttcctgggtt ggccgttata tccaggagct 1320
tcggagtatg atcagattcg gtatatttca caaacacagg gtttgcctgc tgaatattta 1380
ttaagcgccg ggacaaagac aactaggttt ttcaaccgtg acacggactc accatatcct 1440
ttgtggagac tgaagacacc agatgaccat gaagcagaga cagggattaa gtcaaaagaa 1500

-continued

```
gcaagaaagt acattttcaa ctgtttagat gatatggccc aggtgaacat gacgacagat   1560
ttggaaggga gcgacatgtt ggtagaaaag gctgaccggc gggagttcat tgacctgttg   1620
aagaagatgc tgaccattga tgctgacaag agaatcactc caatcgaaac cctgaaccat   1680
ccctttgtca ccatgacaca cttactcgat tttccccaca gcacacacgt caaatcatgt   1740
ttccagaaca tggagatctg caagcgtcgg gtgaatatgt atgacacggt gaaccagagc   1800
aaaacccctt tcatcacgca cgtggccccc agcacgtcca ccaacctgac catgaccttt   1860
aacaaccagc tgaccactgt ccacaaccag gctccctcct ctaccagtgc cactatttcc   1920
ttagccaatc ccgaagtctc catactaaac tacccatcta cactctacca gccctcagcg   1980
gcatccatgg ctgcagtggc ccagcggagc atgcccctgc agacaggaac agcccagatt   2040
tgtgcccggc ctgacccgtt ccagcaagct ctcatcgtgt gtccccccgg cttccaaggc   2100
ttgcaggcct ctccctctaa gcacgctggc tactcggtgc gaatggaaaa tgcagttccc   2160
atcgtcactc aagccccagg agctcagcct cttcagatcc aaccaggtct gcttgcccag   2220
caggcttggc caagtgggac ccagcagatc ctgcttcccc cagcatggca gcaactgact   2280
ggagtggcca cccacacatc agtgcagcat gccaccgtga ttcccgagac catggcaggc   2340
acccagcagc tggcggactg gagaaatacg catgctcacg gaagccatta taatcccatc   2400
atgcagcagc ctgcactatt gaccggtcat gtgacccttc cagcagcaca gcccttaaat   2460
gtgggtgtgg cccacgtgat gcggcagcag ccaaccagca ccacctcctc ccggaagagt   2520
aagcagcacc agtcatctgt gagaaatgtc tccacctgtg aggtgtcctc ctctcaggcc   2580
atcagctccc cacagcgatc caagcgtgtc aaggagaaca cacctccccg ctgtgccatg   2640
gtgcacagta gcccggcctg cagcacctcg gtcacctgtg ggtggggcga cgtggcctcc   2700
agcaccaccc gggaacggca gcggcagaca attgtcattc ccgacactcc cagccccacg   2760
gtcagcgtca tcaccatcag cagtgacacg gacgaggagg aggaacagaa acacgccccc   2820
accagcactg tctccaagca aagaaaaaac gtcatcagct gtgtcacagt ccacgactcc   2880
ccctactccg actcctccag caacaccagc ccctactccg tgcagcagcg tgctgggcac   2940
aacaatgcca atgcctttga caccaagggg agcctggaga atcactgcac ggggaacccc   3000
cgaaccatca tcgtgccacc cctgaaaacc caggccagcg aagtattggt ggagtgtgat   3060
agcctggtgc cagtcaacac cagtcaccac tcgtcctcct acaagtccaa gtcctccagc   3120
aacgtgacct ccaccagcgg tcactcttca gggagctcat ctggagccat cacctaccgg   3180
cagcagcggc cgggccccca cttccagcag cagcagccac tcaatctcag ccaggctcag   3240
cagcacatca ccacggaccg cactgggagc caccgaaggc agcaggccta catcactccc   3300
accatggccc aggctccgta ctccttcccg cacaacagcc ccagccacgg cactgtgcac   3360
ccgcatctgg ctgcagccgc tgccgctgcc cacctcccca cccagcccca cctctacacc   3420
tacactgcgc cggcggccct gggctccacc ggcaccgtgg cccacctggt ggcctcgcaa   3480
ggctctgcgc gccacaccgt gcagcacact gcctacccag ccagcatcgt ccaccaggtc   3540
cccgtgagca tgggcccccg ggtcctgccc tcgcccacca tccacccgag tcagtatcca   3600
gcccaatttg cccaccagac ctacatcagc gcctcgccag cctccaccgt ctacactgga   3660
tacccactga gccccgccaa ggtcaaccag taccccttaca tataaacact ggaggggagg   3720
gagggaggga gggagggaga gaatggcccg agggaggagg gagagaagga gggaggcgct   3780
cctgggaccg tgggcgctgg ccttttatac tgaagatgcc gcacacaaac aatgcaaacg   3840
gggcaggggc gggggggggg ggggcagagg gcagggggac gggtcgggac accagtgaaa   3900
```

cttgaaccgg gaagtgggag gacgtagagc agagaagaga acatttttaa aaggaaggga 3960
ttaaagaggg tgggaaatct atggttttta ttttaaaaaa 4000

<210> SEQ ID NO 34
<211> LENGTH: 5652
<212> TYPE: DNA
<213> ORGANISM: Homo sapiens

<400> SEQUENCE: 34
cttgctgtta atgaacttgg ttaaacatgg tcaagtgtat gtatgtatat attatcagta 60
ctggccttct ctatctaaga ggaatagcaa gaaatttaga gacattattt ggacattgat 120
ttctactaac tccactgaat tagattcagc cttcactttt tgggaaatgc acggacactg 180
ggaaagatga aatgaagaag ttttccagca tgatgttctt gtctttggag cttagcctta 240
cttaggtctt agaacaaaaa caagtcggta gttattagtt actgtatctc attttccaaa 300
acacacgttt ctttgttaca gtcatttaca catatttttg catgccacat tttgctttt 360 gagcttttgc tgaatcacta aatgaccacc tttcatgttc ctaatgtatt aaaattatca 420
gaggattctt tgaggattaa atgtgtcagt aagggtatta ttttgaacaa tgcgtaaaag 480
gtgaaggcca gctgaagagg ccttttttgtt gtgaacagaa taatatactg gaatctgagg 540
actgcactgt tatgaatgga ttatttggct atggaaagaa gttattttta ggcacagcat 600
ccctataagc cctgaagcta tgtgttttac aaactagaaa ttatgcacta aataaaaatt 660
accagatgtc agtctctgta tgtgccaaat ggcaaatgtg taatggttca gagcctggaa 720
gaaatgatgc ttatttcttt gccattcaaa ctcaaaaggg atagctgagg tagagtgctg 780
ttgaaaaaat tgcagtgttt ccagctaccc aaagatgtta cgaattgtta tctgaaaggc 840
tttcattctt tcccctcatg gctcgttgtg tgtttgtggc attacaaatg taacccacat 900
atttattcta atttattaca ttctttcctg aggctcctct tgttctttta aagggtcagc 960
agataactta ttttaagaat caacctggac acagtattct aacaaaggtc caatacagag 1020
ctaaataaat aataggagtc atagccagac acagtgactc acgcctgtaa tcccaacatt 1080
ttgggaggcc aaggcgggtg gattacctgg tggtgcatgc ctgtagtctc agctactcag 1140
gaggctgagg caggagaatc acttgaaccc gggacgcaga ggttacagtg aaccgagatt 1200
gcgccactgc actccagcct gggcaacaga gcgagacctc tatctcaaaa ataaataaat 1260
aaatacattt aaaatatata tatatatata tatatatata tatatatata tatatatata 1320
tatatatata tttatatata tttcgtgact tatatcttgc acataccagc atacctcatt 1380
aattttaatg taaccatcca ttggcttctc ttctctcctt agaaattcga gctcaactgg 1440
tagaacaaca aaaatgcctg gagcagcaaa cggagatgcg agttcagctt ctccaggatc 1500
tgcaagattt cttccgaaaa aaagctgaaa ttgagacgga atattcccgg aatctagaga 1560
agttagcaga aaggttcatg gcaaaaacaa gaagcactaa ggatcatcaa caatacaaga 1620
aagaccagaa cctgttgtct ccagtgaact gctggtattt gctcctgaac caagtaagga 1680
gagaaagcaa agaccatgca accttgagtg acatctatct gaacaatgtg attatgcggt 1740
tcatgcagat aagtgaggat tctaccagga tgtttaaaaa gagcaaagag attgcattcc 1800
aacttcatga ggatttaatg aaggttctta atgagcttta tacggtgatg aaaacatacc 1860
atatgtatca tgcagagagc atcagtgcag agagcaagct gaaagaggcc gaaaaacaag 1920
aggaaaagca aattgggaga tctggtgatc cagtcttcca tattcgacta gaggagagac 1980

-continued

```
atcaacggcg aagctctgta aagaaaattg aaaaaatgaa agaaaaaaga caagcaaaat   2040
attcagaaaa taagctaaaa tcaattaagg cacggaacga atatctccta acacttgaag   2100
ccaccaatgc ctcagttttc aagtactata ttcatgatct ttctgattta attgattgct   2160
gtgatcttgg ctaccatgca agtctgaaca gagccctaag aacatatctg tctgcggagt   2220
acaaccttga aacctccaga catgagggct tagacattat tgagaatgca gttgataatt   2280
tagagcccag gagcgataag cagagattca tggagatgta ccctgctgcg ttctgtccac   2340
caatgaagtt tgagtttcag tctcacatgg gtgatgaggt gtgccaggtc agtgcccagc   2400
agccagtcca ggcagagctc atgctcaggt accaacagtt gcagtcccgc cttgccacgc   2460
tcaaaatcga gaatgaagag gttaagaaaa cgactgaagc caccttgcag acgatacaag   2520
atatggtcac catcgaggac tatgatgttt ctgaatgctt ccagcacagt cgttccacag   2580
aatcagtgaa gtccactgtc tctgaaacct acctgagtaa acccagcatc gccaagagaa   2640
gagccaacca gcaggaaact gaacagttct acttcatgaa actcagagaa tatttggaag   2700
gcagtaatct catcacaaaa cttcaagcca aacatgactt gctgcagagg accctgggag   2760
aaggtcatag agctgaatat atgactacaa gccgaggacg aagaaactcg cacacaagac   2820
atcaggactc aggacaggtt attcccctca ttgtggaaag ctgtattcgg ttcatcaatc   2880
tctatggtct tcagcatcag ggaattttca gagtgtctgg ttcccaggtg gaagtcaatg   2940
atattaaaaa ttcatttgag agaggtgaaa atcctttggc tgatgaccag agtaaccatg   3000
atattaactc agttgctggc gttctgaagc tctatttccg tgggctggaa aacccccctct   3060
ttcctaagga aagatttaac gatctgattt cttgtatcag aatagataat ctctatgaga   3120
gggcgcttca catccgcaaa ctcctcctga ctttgcccag gtcggtcctt atagtgatga   3180
ggtacctctt tgccttcctc aatcatctat cacagtacag cgatgagaat atgatggacc   3240
cttataacct ggccatttgc tttggcccaa cattgatgcc tgtcccagaa atacaggatc   3300
aagtgtcttg ccaggcacat gtgaatgaaa ttatcaaaac catcatcatc caccatgaga   3360
ctattttccc agatgctaaa gagctggatg gccctgttta tgagaaatgt atggctggag   3420
atgactattg cgacagccca tacagtgagc acggtacatt ggaggaagtg gaccaagatg   3480
ctggtacaga gccccacaca agtgaagatg aatgtgagcc aatagaagca atagccaagt   3540
ttgactatgt tgggcggtct gccagagaac tatccttcaa gaagggtgcc tccctgctgc   3600
tgtatcaccg tgcatctgag gactggtggg aaggcaggca caacgggatt gacgggctgg   3660
tgcctcacca gtatatagtg gtgcaggata tggatgatac gttttcagac actctgagcc   3720
aaaaagccga cagtgaggcc agcagtgggc cagtcacgga agacaagtcc tcatccaagg   3780
acatgaactc cccgacagac cgtcatcctg acggctattt agccaggcaa cgaaaaagag   3840
gagagccacc ccctccagta aggcgtcctg gcaggaccag tgatggccat tgcccgctcc   3900
accctccaca tgccctttct aactcctcag ttgacctagg gtccccaagc cttgccagtc   3960
acccccgggg cctgctgcag aaccgtggcc tcaacaatga cagtcctgag cggaggcgca   4020
ggcctggcca tggcagcctg accaacatca gccggcacga ctccctcaag aagatcgaca   4080
gccctcccat tagaaggtcc acgtcatcag ggcaatacac gggcttcaat gaccacaagc   4140
cactggaccc agagacaatt gctcaggata ttgaagaaac gatgaacaca gctttgaatg   4200
aactccgaga actggagaga cagagcacag caaagcatgc ccctgatgtg gtgctggata   4260
ccctggagca agtgaaaaac tctcccaccc ctgccacttc cacggaatct ctcagccctt   4320
tgcacaacgt tgccctcagg agctccgagc ctcagattcg acgtagcacg agctcctcca   4380
```

gtgacacaat gagtactttc aagcctatgg tggcacccag aatgggcgtg cagctgaagc 4440
ctccagccct taggccaaaa cctgctgttc ttccaaaaac aaatcctacc ataggacctg 4500
ccccacctcc ccagggtcca acagacaagt catgcacaat gtaaaaacca gccaagcaag 4560
gccataaagg gaggtgactt aaaaaagaaa atggattagt gacaaaagtc actgatccat 4620
aactttcctt agttttgtgc ttataactgg agatcttttg gcttttctat gttgtcgaat 4680
gtaatgtctg agactagcta aattaacacg ggcatttgta ttttgtaatt tttttaaata 4740
actggacata tgtcatttta aggacaatag aaacacttag acttacttga aaatccaatg 4800
ctgcaccact tgtaatgaag gcaacaccgc tctccacatt gtacagagct tcaggtttaa 4860
tgtagcccag ctgagtcaga aaggttgtga cctgaaggca gaagaacccg aatgccacac 4920
ctcattggag tatagccagt gttggtctgt ggcacttggg ctgaaaggtg ataatggcat 4980
tgcgtggtag ctgacaatga gcaccttcgg ttccatgtgg agcggggttt agctcatgca 5040
aaagacttgc aattgtctcc atgggacgat cccagtggga ctgtcagccc acagctcgag 5100
tgggttggat gcttgcctct ttcctaacag ttatttcccc gggtccagct taaagactcg 5160
atggaaggag gtagaacctc tgctgttact gcttgaactt aacctgggaa aggagaggaa 5220
gacaccatct ccaaagctat taatgtcact ccttttgcga gcatgattag gccccggaga 5280
tttccaagtc cccccatcta cacttacaaa cgattagaag ggtttaattt taaagacttt 5340
ctggttacac tactccacga actcctccaa agatccgtta ttcaataact gcctagaaaa 5400
tgtttccatc tcctctaaat ccctgtgttc tcctctgtgg aaatgaaggc agcaagaagc 5460
acctgaggcc ttggttcatg cagtgttctc ttttgactaa atcacctagg ttcctttaaa 5520
catgctacaa agcccaggca tggtggtgca cacctgtact cccagctact cgggtggttt 5580
acacaggagg atggctttgg gcctagtagt tcgagtccag cctgggcagc atagtgtgag 5640
accctgtctc tt 5652

<210> SEQ ID NO 35
<211> LENGTH: 2920
<212> TYPE: DNA
<213> ORGANISM: Homo sapiens

<400> SEQUENCE: 35
tgtcaaccag cactttttaa gatgaactgt aaccaactag cttctcacat gcttctcata 60
tggtaagagt taattttagc tcatgaaact tttggttctg tgaaacacct gctgaacaga 120
ctcctgggaa gggggtctgt gggagtcgac atttatacaa ccttccaggt gattctgagc 180
ttatcagagc tggagaggca cttgctaccc aggggcttgg tgtggaacgt gagatgccaa 240
agccaaattc aggcctctca gctcaaggca ccctgaagca cagctagtca ctccagcaca 300
tgttgaagct gtgcatgttt acttcatgtt gaactgttca tgttttattt ttggaacact 360
ggggattggc aaaaaaaaaa aaaacccatg tgaataaagc cttctagggc accactgtgc 420
cgattgtgaa ccacacgtgg acaaaacaag ccgcgcttga tagcaactac ctacatgacc 480
agcactcccc tggatgctga tgctgccatg cgagacggga cgttggcgca gcagcatgcc 540
agccacccat tgcttctcct gcttgccaac tcaaccgtgc tgctccctca gacaccatca 600
cttgcgcctc ccaagcaatg gaagccctgg cgatgctctc atgagcccct cactccagca 660
gagcccctga ccaagccagg ggagcaggac ttttccagcc aaggacacaa cggactggtg 720
gctgtgagta cctccccact tgatcccact tcactggccc tgggcgtgtg gctctcagca 780

-continued gcctgggaag gagtgtgaag aagcaggtgg gataagggcc ttgagagaga aggaaaaggc 840
agcctagtcg atgctctctg ctctccagtg ctgactgggg gctgggtcga atgctcatct 900
gcagccagct gtggacatca caggctcctt tcctcccctt cccctaatgg ggaaaggtgg 960
tttccccatg gcctgtgagg gagtcaggga gcttccagaa acaagctgac aaggtgggga 1020
agcatgtaac caacacagca tgagagcagg cagcgtacct gcagagactg ggggtgaaca 1080
ccgccgtctt cgagaggcgc catgtgatcg gggtgcagc tgtcactgag gagatcatcc 1140
cagggtttaa gttctcccgc gcgtcctacc tgctcagcct gctgaggccg cagatttaca 1200
ctgatctgga gctgaagaaa catgggctga ggcttcatct tcgaaacccc tactccttca 1260
cccccatgct ggaagagggt gcaggcagca aggtgcccag gtgccttctg ctgggcacag 1320
acatggcaga aaaccagaag cagatcgccc agttctccca gaaggatgcc caggtctttc 1380
ccaaatatga ggagttcatg catcgcttgg cattagccat tgaccctctg ctggatgcgg 1440
cccccgtgga catggcggcc ttccagcatg gctccttgct gcaaaggatg aggtcgctct 1500
ccaccctcaa gcccctgctg aaggcaggcc gcatcctggg agcccagctt ccccgatatt 1560
atgaggtcct cacagctccc attaccaagg tgctggatca gtggttcgag tctgagcctt 1620
taaaagccac tctagccaca gatgcagtga ttggagccat gacaagtccc cacactccgg 1680
ggagtgggta tgtgctgctg caccatgtga tgggggcct ggagggaatg caggggggcct 1740 ggggctacgt ccaggggggc atgggtgccc tctctgatgc gatcgcaagc tcagccacca 1800
cacatggagc aagcatcttc actgaaaaga cagtggcgaa ggtgcaggtg aacagtgaag 1860
gctgtgttca aggagttgtg ctggaagatg gcacagaggt gagaagcaaa atggtgctgt 1920
ccaacacatc accgcagatc accttcctga agctgacgcc acaggagtgg cttcctgagg 1980
agttcctgga gagaatctct cagctggaca cccggtcgcc tgtcaccaag atcaatggta 2040
agaggcacac cacattgcag cactgtctcc tttgacccat ctgagtgaga aacctccagg 2100
ctgggggcag ctgaactcag tcatcatctc cattcccgga cctccagcct gtgtccccct 2160
gcagcctggt cagaagtggc cgtagacagg ctgcccagct tcctggcggc ccccaatgct 2220
cccaggggcc agccgctgcc ccatcaccaa tgctccatcc acctgaactg tgaagacacc 2280
ctcctccttc atcaggcctt tgaagatgcc atggatggcc tgccttccca cagtgtttga 2340
ttgcatcgag gtctatgccc ctggcttcaa ggactctgtg gttggcagag acatcctcac 2400
accaccagat ttggagagaa tcttcgggct tcctggaggg aacatattcc actgcgccat 2460
gtccctggac cagctctact tcgcccgccc cgtgcccctg cattctggct accgctgccc 2520
tctccagggc ctgtatctct gtggaagtgg ggctcatcct ggaggaggtg tgatgggagc 2580
tgctgggcga aatgcagcac atgtggcctt tagggacctc aagagcatgt gaccctgaac 2640
cagctctgac ccaggaagaa gactccaccc ctgaattcca agtgctccat tggatcagct 2700
tcccaggaag ttcagcttcg ggttagtaca taaggccacc acaatgctca agaaattatt 2760
ttagaaaaaa cgtacgagtt acatttagtg caagttgacc ttatgcccat gcctccatac 2820
atggactggt tctgttttat taaaactaat atttcataca aaaaaaaaaa aaaaaaaaaa 2880
aaaaaaaaaa aaaaaaaaaa aaaaaaaaaa aaaaaaaaaa 2920

<210> SEQ ID NO 36
<211> LENGTH: 2129
<212> TYPE: DNA
<213> ORGANISM: Homo sapiens

<400> SEQUENCE: 36

-continued

```
cgtaatggcg gacacaggca gggcgagcgc ggctgggggc gtagcgcgct gagggggtcc     60
ggccgtttgg cagcccgcga ggcggtccgc gggagcacac tctgtgcgga gactgggcgg    120
ccggccgacc cttcctgtcg ctgacggcga ctgcgggagg ccaggttgtt tttcaccatt    180
cagaacattg cctgaagcag gtccaccatg ccgttagtaa cgaggaacat cgagccaagg    240
cacctgtgcc gtcagacgtt gcctagcgtt agaagcgagc tggaatgcgt gaccaacatc    300
accctggcaa atgtcatccg acagctgggc agcctgagta aatatgcaga ggacattttt    360
ggagagctct ttactcaggc aaataccttt gcctctcggg taagctccct tgctgagagg    420
gtcgaccgac tacaggttaa agtcactcag ctggatccca aggaagaaga agtgtcactg    480
caaggaatca acacccgaaa agccttcaga agttccacca ttcaagacca gaagcttttt    540
gacagaaact ctctcccagt gcctgtctta gaaacataca atacctgtga tactcctccc    600
cctctcaaca atcttacccc ttacagggac gatggaaaag aggcactcaa attctacaca    660
gacccttcat acttctttga tctttggaag gagaagatgc tgcaggacac caaggatatc    720
atgaaagaga agagaaagca taggaaagaa aagaaagata atccaaatcg agggaatgta    780
aacccacgta aaatcaagac acgtaaggaa gagtgggaga aaatgaagat ggggcaagaa    840
tttgtggagt ccaaagaaaa gctggggact tctgggtatc cacccacttt ggtgtaccag    900
aatggcagca ttggctgtgt tgaaaacgtg gatgcaagta gctatccgcc accaccacag    960
tcagactctg cttcttcacc ttctccttcc ttctccgagg acaacttgcc tcctccacca   1020
gcagaattca gttacccagt ggacaaccaa agaggatctg gtttggctgg acccaaaaga   1080
tccagtgtgg tcagcccaag ccatccacca ccagctcctc ctctaggctc tccaccaggc   1140
cctaaacccg ggtttgctcc accacctgcc cctccgccac ctccgcctcc aatgataggc   1200
atcccacctc caccaccgcc tgtaggattt gggtctccag ggacgcctcc accaccctca   1260
cccccatctt tcccacctca ccctgatttt gctgcccctc cacctcctcc tccaccacca   1320
gcagctgact acccaactct gccaccacct ccccttgtcc agccaacagg aggagcacct   1380
cctcctcccc ctcctcctcc tcctccgggg ccccctcctc cccctttcac tggtgcagat   1440
ggccaacctg ctataccacc accgctttct gataccacca agcccaagtc ctccttgcct   1500
gccgtgagcg atgcccgtag cgacctgctt tcagccatcc gtcaaggttt tcagctgcgc   1560
agggttgagg agcagcggga acaagagaag cgggatgttg tgggcaatga cgtggccacc   1620
atcttgtctc gtcgcattgc tgttgagtac agtgactcag aagatgactc ctctgaattt   1680
gatgaggacg actggtccga ttaactcttt ctgcctgctg cccaccttct ttttctttcc   1740
ttcctacctg ccttctttga tgccaacccc aacagacccg taggggggaga aaagggagga   1800
aaaaagtaat tttaaggggc caaagctttc cctgaagcaa ccaaagatat atccaagtgc   1860
ttcctccaag tcaacatgta tttcctctcc ccattttcag gccctgtggg gctcctgagg   1920
ttcagtagct gggatgttcc ctctttcctt caagtgcctg ttgcatattg aaaggaagga   1980
gaaatcccaa agcagattcc tttgatcggg tttctgttgg agatggggct tcccttagga   2040
gccatattca actacagcct tctaaaacct gtgccctcag ccactttaaa aaaaaaaaaa   2100
aaaaaaaaaa aaaaaaaaaa aaaaaaaaa                                      2129
```

<210> SEQ ID NO 37
<211> LENGTH: 4878
<212> TYPE: DNA
<213> ORGANISM: Homo sapiens

<400> SEQUENCE: 37

```
gtccgccatt tgcaaggggc ccggagcggg atcgcggcac ctgccgagcg ggtcgccgcc     60
tctgccgcgg tccttggacc ccgccgccgc cctggcctgg gagcttgccc cgccgcagcg    120
gccggcagcg cggcgctccg cgggcggcag gcacgggccc cgggcccccct cacggcgccc    180
agccgcgggc ctcccgaggc aaaagcccgt gggccgccgc gatggccctc aagatggtga    240
agggcagcat cgaccgcatg ttcgacaaga atctgcagga cttggtccgc ggcatccgta    300
accacaagga ggacgaggca aaatacatat ctcagtgcat tgatgagatc aagcaggagc    360
tgaagcagga caacatagcg gtgaaggcga acgcggtctg caagctgacg tatttacaga    420
tgttgggata cgacatcagc tgggccgcct tcaacatcat agaagtgatg agtgcctcca    480
agttcacctt caagcgaatt ggctacctcg ctgcttccca gagctttcac gaaggcaccg    540
acgtcatcat gctgaccacc aatcagatcc gtaaggactt gagcagcccc agccagtacg    600
acacaggtgt tgcactgacg ggtctgtcct gcttcgtcac cccagacctt gccagagacc    660
tggcaaatga catcatgaca ctgatgtcac acaccaagcc ctacatcagg aagaaggctg    720
tgctgatcat gtacaaggtg ttcctgaagt accccgagtc gctgcgccct gcctttcccc    780
ggctgaagga gaagctggag gaccccgacc ccggggttca gtcggctgcc gtcaatgtca    840
tctgcgagct ggccagacgc aaccctaaga actacctgtc cctggccccg ctctttttca    900
agctgatgac gtcctccacc aacaactggg tcctcatcaa gatcatcaag ctgttcggtg    960
ctcttactcc tttggaaccg cggctgggca agaagctgat cgagcccctc accaatctca   1020
tccacagcac gtctgccatg tctctcctct atgaatgtgt gaacaccgtg attgcagtgc   1080
tcatctcgct gtcctccggc atgcccaacc acagcgccag catccagctt tgtgttcaga   1140
aattaaggat attgatcgag gactccgatc agaacttgaa gtacctgggg ctgctggcaa   1200
tgtccaagat cctgaagacc caccccaagt ccgtgcagtc ccacaaggac ctcatcctgc   1260
agtgcctgga cgacaaggac gagtccatcc ggctgcgggc cctggacctg ctctatggga   1320
tggtgtccaa gaagaacctg atggagatcg tgaagaagct gatgacccac gtagacaagg   1380
cagagggtac cacctaccgt gacgagctgc tcaccaagat cattgacatc tgcagccagt   1440
ccaactacca gtacatcacc aacttcgagt ggtacatcag catcctggtg gagctgaccc   1500
ggctggaggg cacacggcac ggccacctca tcgccgccca aatgctggac gtggccatcc   1560
gcgtgaaggc catccgcaag ttcgccgtgt cccagatgtc tgcgctgctt gacagtgcac   1620
acctgctggc cagcagcacc cagcggaacg ggatctgtga ggtgctgtac gctgccgcct   1680
ggatctgcgg ggagttctca gagcatctgc aggaaccaca ccacactttg gaggccatgc   1740
tgcggcccag agtcaccacg ctgccaggcc acatccaggc cgtgtatgtg cagaacgtgg   1800
tcaagctcta cgcctccatc ctgcagcaga aggagcaggc cggggaggca gagggcgctc   1860
aggccgtcac ccagctcatg gtggaccggc tgccccagtt tgtgcagagc gcagacctgg   1920
aggtgcagga gcgggcgtcc tgcatcctgc agctggtcaa gcacatccag aagcttcagg   1980
ccaaggacgt gcctgtggca gaggaggtca gcgctctctt tgctggggag ctgaacccag   2040
tggcccccaa ggcccagaag aaggttccag tccccgaagg cctggacctg gacgcctgga   2100
tcaatgagcc actctcggac agcgagtcag aggacgagag gcccagggcc gtcttccacg   2160
aggaggagca gcggcgtccc aagcaccggc cgtcggaggc ggacgaggaa gagctggctc   2220
ggcgccgaga ggcccggaag caggagcagg ccaacaaccc cttctacatc aagagctcgc   2280
catcgccaca gaagcggtac caggacaccc cgggcgtgga gcacattccc gtggtgcaga   2340
```

-continued

```
ttgacctctc cgtccccttg aaggttccag ggctgcctat gtcagatcag tatgtgaagc   2400
tggaggagga gcggcggcac cggcagaagc tggagaagga caagaggagg aaaaagagga   2460
aggagaagga gaagaagggc aagcgccgcc acagctcgct gcccacggag agcgacgagg   2520
acatcgcccc tgcccagcag gtggacatcg tcacagagga gatgcctgag aatgctctgc   2580
ccagcgacga ggatgacaaa gaccccaacg acccctacag ggctctggat attgacctgg   2640
ataagccctt agccgacagc gagaaactgc ctattcagaa acacagaaac accgagacct   2700
caaaatcccc tgagaaggac gttcccatgg tagaaaagaa gagcaagaaa cccaagaaga   2760
aagagaaaaa acacaaagag aaagagagag acaaggagaa gaagaaggag aaggagaaga   2820
agaaatctcc caagcctaag aagaagaagc acaggaagga gaaggaggag cggaccaaag   2880
gcaagaagaa gtccaagaag cagcctccag gcagcgagga ggcagcgggg gagccggtgc   2940
agaatggcgc gccagaggag gagcagctcc cgcctgagtc cagctactcc ctcctcgctg   3000
aaaattccta tgttaaaatg acctgtgaca tccggggcag tctgcaggag gacagccagg   3060
tcactgtggc catcgtgctg gagaacagga gcagcagcat cctcaagggc atggagctca   3120
gcgtgctgga ctcactcaat gccaggatgg cccggccgca gggctcctcc gtccacgatg   3180
gcgtccccgt gcctttccag ctgcccccag gcgtctccaa cgaagcccag tatgtgttca   3240
ccatccagag catcgtcatg gcgcagaagc tcaaggggac cctgtccttc attgccaaga   3300
atgacgaggg tgcgacccac gagaagctgg acttcaggct gcacttcagc tgcagctcct   3360
acttgatcac cactccctgc tacagtgacg cctttgctaa gttgctggag tctggggact   3420
tgagcatgag ctcaatcaaa gtcgatggca ttcggatgtc cttccagaat cttctggcga   3480
agatctgttt tcaccaccat ttttccgttg tggagcgagt ggactcctgc gcctccatgt   3540
acagccgctc catccagggc caccatgtct gcctcctggt gaaaaaggtg agaactctgt   3600
ctcagtcgac gggaagtgca gtgactccac gctactgagc aacttgttag aagagatgaa   3660
ggcgacgctg gccaagtgtt gagagctgcc tgcgagcccc gcaccacccc gcggagcacg   3720
tacccaggga ccgcagccct gacgtgtctc gcctctcctc agtcgtgtgt actgtaccca   3780
agcctgagtg ttaatttaac tctatgttgt ccgccgtgta gacatccgag gtcatttgtt   3840
gcgttgaatt atctgaccat cctttttac tgtgactctt cccattctct ttggcaagaa   3900
gtccccttct cgcccccaaa ccagcaaggg actcccccac ctgggtctgt gccctgcccc   3960
gcgctggggg ccgagtcctt gaatgtggct tcaggggctc ctgtcctggg ccagggcctg   4020
atgggcacca cgtgaggggc acttggtgga cagggcgggg ctgacgtggc ctcctctggg   4080
gtcgcctgct tttgacccaa aggtcctgac ggttgcgtcc gggggagggg aaggaagggc   4140
cgctgtcgcc aaggttttct ctcccagaac ccacagtggg aaagcggtct tgccaggcgt   4200
tgtccattgt cagtgtgctc gtgggctggt gactgggtct tgggatccca ggccacgcgc   4260
cagccaggct gtgggcaggg cggggccagg gacgccaaag agaggttgca gtcagaaccg   4320
tggacggggt gggttgaggc ctctctgcca cccgtcttcc tggtcagcag aagtgcatct   4380
cggcttgggt ttggggtggt ccgcatcccc tgcttgccac tatgcgcacc aaggtttccc   4440
cacatccttc ccagcaccct taggaaggcc caggcagggc ctggaagcag cggacctggg   4500
ctgttctgtg ttgaaggagt gtgcccagtg cccttgggca ggacctgtga gagccacctc   4560
acaggcagag cccccaccag gcagggcaag gagactccgc tcactcccca cggccagcgt   4620
gggcacagga ctgacccttc ttcagagata atgacatttt atcttctcct tttgatgaaa   4680
```

actgtcactt tagcatgtaa tccattacag aatcccatgc agtgattcca ggatttgaaa 4740
ttgtatgatg tgttacataa gaatttattt gctatcgaca ttcccgtata aagagagaga 4800
catatcacgc tgctgtcatg attttgtgtc aagatgatcc aataaagttg taaaacaggc 4860
atttccaaaa aaaaaaaa 4878

<210> SEQ ID NO 38
<211> LENGTH: 964
<212> TYPE: DNA
<213> ORGANISM: Homo sapiens

<400> SEQUENCE: 38
gagtgccgta gcgcccggct cctgcagacg ctcggcctcc gctcattcct gaccccgcag 60
tgggcgcgat ggcggaggct gtactgaggg tcgcccggcg gcagctgagc cagcgcggcg 120
ggtctggagc cccatcctc ctgcggcaga tgttcgagcc tgtgagctgc accttcacgt 180
acctgctggg tgacggagag tcccgggagg ccgttctgat cgacccagtc ctggaaacag 240
cgcctcggga tgcccagctg atcaaggagc tggggctgcg gctgctctat gctgtgaata 300
cccactgcca cgcggaccac attacaggct cggggctgct ccgttccctc ctccctggct 360
gccagtctgt catctcccgc cttagtgggg cccaggctga cttacacatt gaggatggag 420
actccatccg cttcgggcgc ttcgcgttgg agaccagggc cagccctggc cacaccccag 480
gctgtgtcac cttcgtcctg aatgaccaca gcatggcctt cactggagat gccctgttga 540
tccgtgggtg tgggcggaca gacttccagc aaggctgtgc caagaccttg taccactcgg 600
tccatgaaaa gatcttcaca cttccaggag actgtctgat ctaccctgct cacgattacc 660
atgggttcac agtgtccacc gtggaggagg agaggactct gaaccctcgg ctcaccctca 720
gctgtgagga gtttgtcaaa atcatgggca acctgaactt gcctaaacct cagcagatag 780
actttgctgt tccagccaac atgcgctgtg ggtgcagac acccactgcc tgatctcact 840
tctgtcagat gctcccatcc actattaatg cactaggtgg gaggagaggg cggcaatgac 900
actgcacctc tcctttccca ccgcattccc tggagctccc taaataaaac ttttttttaac 960 gtga 964

<210> SEQ ID NO 39
<211> LENGTH: 3384
<212> TYPE: DNA
<213> ORGANISM: Homo sapiens

<400> SEQUENCE: 39
atggcccccg gggagaagat caaagccaaa atcaagaaga atctgcccgt gacgggccct 60
caggcgccga ccattaaaga gctgatgcgg tggtactgcc tcaacaccaa cacccatggc 120
tgtcgccgca tcgtggtgtc ccgcggccgt ctgcgccgcc tcctctggat cgggttcaca 180
ctgactgccg tggccctcat cctctggcag tgcgccctcc tcgtcttctc cttctatact 240
gtctcagttt ccatcaaagt ccacttccgg aagctggatt ttcctgcagt caccatctgc 300
aacatcaacc cctacaagta cagcaccgtt cgccaccttc tagctgactt ggaacaggag 360
accagagagg ccctgaagtc cctgtatggc tttccagagt cccggaagcg ccgagaggcg 420
gagtcctgga actccgtctc agagggaaag cagcctagat tctcccaccg gattccgctg 480
ctgatctttg atcaggatga gaagggcaag gccagggact tcttcacagg gaggaagcgg 540
aaagtcggcg gtagcatcat tcacaaggct tcaaatgtca tgcacatcga gtccaagcaa 600
gtggtgggat tccaactgtg ctcaaatgac acctccgact gtgccaccta caccttcagc 660

-continued

```
tcgggaatca atgccattca ggagtggtat aagctacact acatgaacat catggcacag    720
gtgcctctgg agaagaaaat caacatgagc tattctgctg aggagctgct ggtgacctgc    780
ttctttgatg gagtgtcctg tgatgccagg aatttcacgc ttttccacca cccgatgcat    840
gggaattgct atactttcaa caacagagaa aatgagacca ttctcagcac ctccatgggg    900
ggcagcgaat atgggctgca agtcattttg tacataaacg aagaggaata caacccattc    960
ctcgtgtcct ccactggagc taaggtgatc atccatcggc aggatgagta tccctccgtc   1020
gaagatgtgg gaacagagat tgagacaaca atggtcacct ctataggaat gcacctgaca   1080
gagtccttca agctgagtga gccctccagt cagtgcacgg agggcgggag tgacgtgcca   1140
atcaggaaca tctacaacgc tgcctactcg ctccagatct gccttcattc atgcttccag   1200
acaaagatgg tggagaaatg tgggtgtgcc cagtacagcc agcctctacc tcctgcagcc   1260
aactactgca actaccagca gcaccccaac tggatgtatt gttactacca actgcatcga   1320
gcctttgtcc aggaagagct gggctgccag tctgtgtgca aggaagcctg ccgctttaaa   1380
gagtggacac taaccacaag cctggcacaa tggccatctg tggtttcgga gaagtggttg   1440
ctgcctgttc tcacttggga ccaaggccgg caagtaaaca aaaagctcaa caagacagac   1500
ttggccaaac tcttgatatt ctacaaagac ctgaaccaga gatccatcat ggagagccca   1560
gccaacagta ttgagatgct tctgtccaac ttcggcggtc agctgggcct gtggatgagc   1620
tgctctgttg tctgcgtcat cgagatcatc gaggtcttct tcattgactt cttctctatc   1680
attgcccgcc gccagtggca gaaagccaag gagtggtggg cctggaaaca ggctccccca   1740
tgtccagaag ctccccgtag cccacagggc caggacaatc cagccctgga tatagacgat   1800
gacctaccca ctttcaactc tgctttgcac ctgcctccag ccctaggaac ccaagtgccc   1860
ggcacaccgc cccccaaata caatacccttg cgcttggaga gggccttttc caaccagctc   1920
acagataccc agatgctgga tgagctctga ggcagggttg agaagacaga tctagtcagg   1980
accaccagcc atggtctaag gacatggatc gggtgccccc agacgtgtgc acaggggacc   2040
ctctgcccca ctctgggctt ttcagatact ctgaccaaaa agcctgcttt aaaccgcaag   2100
atggggcctg ggcatgcgca ggaggagcca tcgggtacta cgcagcaaca ctcacaactg   2160
tccaggctga gataaatccc gggacctgaa ctattagcac gtcactagag actgggagcc   2220
gaggcagtgg tgctggccca agtgaaggcc agagtgagga ctgatgcagc tctttacggg   2280
tcttgagagg gaaggactct tccaaagccc caaagccgag ggtttcaccc acactgccag   2340
cctgggttgg ggcccaagga tgtgaccttg agtgtcaagg ctggacagct actgccagat   2400
gccaaagata ggagaaagtg ccagccctga agctggagcc gcttgtgaat aaactgttct   2460
tcatcattga cactggagaa aggtgtcctc catgccctca ggcagcagag aactggccca   2520
gagcccttgg agtgttggtg gagatcagag tgccgtggtg gaggtctggg actatgtcag   2580
agtgtcctca ctttggggca tgggtggctc caggagatgg atttagttat tcaattttgt   2640
ggatgaataa attgaggcac agaaagatta agttaccggc ccaaggtgac acagtgagga   2700
ggtggcagag ctaggatttg accccagaca atctgacttc atgattgtgg catccaattc   2760
gtgtctgtgc ctcaatttgt gcaaacgact gtgtcacttt gcttggggag ggggagcatc   2820
ccacccacat gccctgggca ggtgacccaa gacagagctg acccctccac caccaaaggc   2880
ctgtctctca ccaacaagcc aactgctcac agatgaccca cttcatacca cattcacatc   2940
tggccacctg actccagcta tcaggtatta agtcccgggc agcgataagc ccccccacaa   3000
```

```
cagtgtgtta gctctgtctt agcaacctga taggttagca taggggctgc aaatgttgtt   3060

ccgccacacc aaatccctgt ttttgtccat gaactaagaa ttttatttta ttttattttt   3120

tattttttgt agaaatagga tctcactatg ttgcccaggc tgttcttgaa ctcctggcct   3180

caaatgatct tcccacttca gcctcccaaa gtgcagggat tacaggcaca agccaccgtg   3240

cccagccaag aatttttatt tttgctttta aatacccaaa gaagaagatt ctgtgactca   3300

tggaaatgat atgagattcg aattccagtg tctataaata aagttttatt ggtacacagc   3360

cccaaaaaaa aaaaaaaaaa aaaa                                          3384
```

<210> SEQ ID NO 40
<211> LENGTH: 6280
<212> TYPE: DNA
<213> ORGANISM: Homo sapiens

<400> SEQUENCE: 40

```
ggtgaaggac ctgggcagcc tcaatgggac gtttgtgaat gacatgcgca tcccggacca     60

gaagtacgtc acgctgaagc tcaacgatgt catccgcttt ggctacgatt ccaacatgta    120

tgtgctggag cgtgtgcagc accgagtccc ggaggaggca ctcaagcatg aaaagtacac    180

cagccagctg caggtgagcg tgaagggttt ggcgcccaag aggagcgagg cactgccgga    240

acacacacca tactgcgagg cctcgaaccc caggccggag aagggggacc ggagaccagg    300

aacagaggca gcctcttacc gcacacccct gtatgggcag ccctcctggt ggggtgagga    360

cgatggtagc acgctgcctg atgcccagcg ccagggagag ccctacccag agcgccccaa    420

gggacccgtg cagcaggacg gggagctcca cggcttccgc gcccctgctg agcctcaggg    480

ctgctcgttc cggcgggagc ccagctactt cgagatcccc acgaaggaga ccccgcagcc    540

gtcgcagccc cccgaggtgc cggcacacga gatgcccacg aaggatgcag aggcaggtgg    600

gggcggagcg gcccctgtgg tgcagagcca cgcctccttc accatcgagt ttgatgactg    660

cagccctggc aagatgaaga tcaaggacca tatcaccaag ttttccctgc gccagcggcg    720

gcccccgggc aaggaggcca cacctggcga gatggtgtcg gctgagacca aggtggccga    780

ctggctggtg cagaatgacc cgagcctgct gcaccgggtt ggccctgggg atgaccgcca    840

cagcaccaag agcgacctgc ctgtccacac ccgcaccctg aagggccaca agcacgagga    900

cggcacgcag agtgactcag aggaccccct ggccaaggcg gcctcggccg ctggggtgcc    960

cttggaggcc agcgggggc aggtgcggct gcagaggcag atcaagcggg acccccagga   1020

gctactacat aaccagcagg cctttgtcat cgagttcttc gacgaggaca cgccccgaaa   1080

gaagcgctcc cagtccttca cgcacagccc gtccggggac cccaaggccg acaagcgccg   1140

tggcccaacg ccggccgata gggaccgccc cagtgtccca gccccagtcc aggcaggggg   1200

ccgcagctcg gggccacaga gggccggctc gctcaagcgg gagaagacag aggaacggct   1260

gggcagcccc tcgcccgcct cccgaacccc tgcccgcccc ttcggaagcg tggggcgccg   1320

ctcccgcctg gcccaggact tcatggccca gtgtctgcgg gagagctccc cggccgcccg   1380

gcccagcccc gagaaggttc ctccggtgct gcccgctccc ctgacacccc atgggaccag   1440

ccccgtgggc cccccgaccc caccgcccgc ccccacggac ccccagctga ccaaggcacg   1500

gaaacaggag gaggatgaca gcctcagtga cgcagggaca tacaccatcg agaccgaggc   1560

gcaggacacg gaggtggagg aggctcggaa gatgatcgac caggtctttg ggtgttgga    1620

gtcccctgaa ctctccaggg catcttcggc cacctttcgc ccagtcatca gaggggacag   1680

agatgagtct gatgacgggg gcgtggccca gcggatggcg ctactgcagg agtttgcctc   1740
```

-continued

```
ccggccactg ggtgcggccc cccaggcgga gcaccagggc ctcccggtgc cgggctcccc   1800
tgggggtcag aagtgggtgt cccgctgggc cagcctggct gacagctact cagacccggg   1860
cctcacagag gatggcctgg gacgtagagg cggggagccg gaggggtccc tgcctgtgcg   1920
catgcggcga cggctccctc agctgcccag tgagagggct gacagccctg cgggcccaga   1980
gagcagcagg aggagtgggc ctgggccacc ggagctggac agtgagcagc ccagccgcct   2040
cttcggccag gaggagttgg atcctgacag cctcagcgat gccagtgggt cggacggggg   2100
ccgaggcccc gagccagggg tggagccaca ggacagcaga cgcaggagcc cccaggaggg   2160
gcccacgtgg agcaggggtc ggcgctcacc aagggccccc ggggagccaa ctcccgcctc   2220
tttcttcatt ggggaccaga atggggacgc tgtgttatct aggaaactgc ttgcggctcc   2280
aggggatggg gagggcctag ggcagacagc ccagcccagc cccccagcac gggatggcgt   2340
ctatgtcagt gccaatggga gaatggtcat ccagctacgg cctggacggt ccccagaacc   2400
cgacggccct gccccagcct ttctccggca agagagcttc actaaggagc cagccagtgg   2460
tcccccagcg cccggcaagc ccccccacat ctccagccac ccgcttctac aggacctggc   2520
cgctacccgg gccgcacgca tggacttcca ctcccaggac acccacctga tcttgaagga   2580
gacggagacg gccctggcgg ccctggaggc ccgactcctc tctaattctg tggatgccga   2640
gtgtgagggg ggcagcaccc cgaggccgcc ggaggacgcc ctgtctgggg actcggacgt   2700
ggacacagcc agcaccgtca gcctgcgtag tggcaagagc gggcccagcc ccacaacccc   2760
ccagcctctg cgggcacaga aggagatgtc gccatccccg ccagctgcac aggacccggg   2820
aggcaccgcc ctggtcagtg cccgtgagca gtcctcagag aggcagcatc acccacttgg   2880
cccgacggac atgggccgtg gagagccggt acggcgctca gccataaggc gtggccacag   2940
gccccgaggg tccctggatt ggcccagtga ggagcgtggc cctgtcctcg cccacctacc   3000
cagctcagat gtgatggcct ccaaccacga aacccctgag gccaccgggg caggacggct   3060
aggttctcgc cggaaaccag cggccccacc gccatcccca gctgcccggg aggagcagag   3120
ccgtagctca gccagctccc agaaggggcc gcaggccttg acccgctcca acagcctgtc   3180
cacccctcgc cccacacggg cctcccggct gaggcgggcc cggctggggg acgcttcaga   3240
cactgaggct gcggatggtg agcgggggtc cctgggcaac cctgagcccg tgggccggcc   3300
agctgctgag caggccaaga agctgtcacg cctggacatc ctggccatgc cccggaagcg   3360
ggccggctcc ttcacaggga ctagtgaccc cgaggcagcc cctgcccgca ccagcttctc   3420
tggccgcagt gtggagttgt gctgtgccag ccgcaagccc accatggccg aagcacgggc   3480
tgtctccagg aaggctgcca acacagccac caccacgggt ccccgccagc ccttcagcag   3540
ggcccgctcg ggcagtgccc gatacacctc caccactcag accccgaggg ctggcagctc   3600
cagccgggct cgttcccggg cccccggccc ccgggacacg gacgacgatg aggaggagcc   3660
tgacccttat ggtttcatcg tgcagacggc agagattgcg gagattgcca ggctgagcca   3720
gacgctggtg aaggacgtgg ccatcctagc ccaggagatc cacgatgtgg ctggggacgg   3780
tgacacactg ggctcctcgg agcctgccca cagcgcctcc ctcagcaaca tgcccagcac   3840
ccccgcctcg accatctctg cccgggagga gctggtgcag cgcatccccg aggccagcct   3900
caacttccag aaggtgccgc ccggctcgct gaactctcgg gactttgacc agaacatgaa   3960
cgacagctgt gaggacgccc tggccaacaa gacgcggcct cggaaccgag aggaggtgat   4020
cttcgataac ctgatgctga acccggtgtc ccagctgtcg caggccatcc gtgagaacac   4080
```

-continued

```
agagcacctt gccgagaaga tgaagatcct ctttcagaac acagggagag cttgggagga   4140
cctggaagcc aggatcaacg ccgagaacga ggtgcccatc ctgaagacat ctaacaagga   4200
aatcagctcc atcctgaagg aactgaggcg ggtgcagaaa cagctggaag ttatcaatgc   4260
catcgtggac cccagtggga gcctggacct gctcacagga aacaggagct tggccagctc   4320
tgcacagccg gggctgggga agggccgcgt ggctgcccag agcccaccct cacccgcctc   4380
agccgaggcc ctgctgccag ccctgcccct gaggaatttc ccacagcggg ccagctgtgg   4440
gcctcccagc ctcccggacc ccaccttcct ccctgatgcc gagaggttcc tgatctaggc   4500
cccagacctg gccaggccag cctccctgtg cgtgtgcgtc tctgccttcc gtccgccgca   4560
cacccgcctg cctggccgca ggtggttctc cctgaagacc cccacatgtg ccatatccct   4620
gtgggcgggt gcctcccacg cccttgcccc ctcgtcagct cccagccagc accctactca   4680
ccctgtccag ccccatggcc acccccaccc ctgcctcgcc ccctacaggc ctctgggccc   4740
agctcctggc caggctgctg ccaaggtcaa gccctcaagg gcattacccc gcctcctctt   4800
catcactgtt atttttgtct ttagctttaa aggaaagagt tgttggtgcc attgcaggtg   4860
cccccctccag gcctgactgg ctccgccagg cactaacctg ccataaccct ttgtgctggc   4920
ctgcggccag gcagaggaag agaggtcgac tgtggggtca tttggtgcca aacatggagg   4980
tgggcaggct cacctgttcc tgggactgtc tgagatggca gggcacttgc cctggtggct   5040
cccacctgac cccaggcctt ttataggcag gagccccact gcttccagcc tctggtgcca   5100
acacagttgc caaacccatt gagcttgggg ctgccccgtg gaggcctcct gggtatggac   5160
caggggcttg ttgagagctg agccatgcac acaggtgcag acacccccca actcccatgc   5220
acacggctag tccaggcgcc tccacgctgc accgtgagga ctgcagggca tgtccccgtg   5280
aggggctatg ggcctctgta ggtgggcttc caaggtcctg ggtgcagccg ggtgcatggc   5340
agcccttctg gcgggggtga gcgcacgacc aaagtcactg gaagccgggt ttccggaagc   5400
tcgcagcttg gcctgcacca cacgccctcc ccttttggct tcacgccatc aggcctcaag   5460
tgggcatggg ggcagggacg ggcccaggaa ctgttgtttt ctcaggattc tttcagctgg   5520
gaacatggca ggtgagcaga gcttggtgcc tctgccgtgg cccctgctgg ggcagcccgt   5580
gttgccggag cctctaagcc aaagagcccg ttggccgtgg ttggtggggg tggacgtggg   5640
ggtgtcccac ctggaccaga ctggcgtggg tgagctccac accctgcctg gcaatggtat   5700
gagagtcgga cctggacagg gccagctgct gggggagcgg cactggggac tggaggctgg   5760
aagcgggtgg tgtgtgtccc ctgtttactt ttagctgagc tggggttggg tgtacgggtt   5820
ctgttcctct gagccctgcg gcccacctga tgtttacgtg tgtgtgtgag ggggggcggg   5880
ggtggcaggt gtccccccct ggtccccgcc ccaagagcct gctgtctgta tggaggaggt   5940
gctagcccgg tccaccgggc tgctgcccac ccctgcatgc cccagttgcc caccccgcct   6000
gcccctggac atgaagtggt cacgcttcat ccacggctcc ttcccacccc tcggcagtgg   6060
ctgtgcaatg ttttaagttc acaagttcct gctcctcccc acactgagct cctttgttcc   6120
tcccccctcca gcctttgcct gggaactggt ccttgtttgc cgggcttctc ggagggttca   6180
ctgtacattc gttctcaggt ggtcttgtgg ctgtctttcg gaaaatggtt attttatatg   6240
atttgtcatg gaatttgttc taataaatca ttcttctatc                         6280
```

<210> SEQ ID NO 41
<211> LENGTH: 2782
<212> TYPE: DNA
<213> ORGANISM: Homo sapiens

<400> SEQUENCE: 41
gcgacgccga gtttcactct ggctgccttc tcctgagagt cggagccaca gccagagccc 60
tgcccaggcc gagccggagc tgcagcccga gcgcggtggt gccctcagcc ccgtcctctt 120
gtcctcctca gcctcggtgc cttggaattt gtgtcgctga gtcagcaagc ctttcagatt 180
tgcccggttt ttgttgtttg tggtttgtat caagatggga actcaaacaa gtcattcctc 240
ctaaggagct ggtgtcttca tccagaaggg acagtttgtg ccagctctcc agagagaaaa 300
ggatctggta ctgttctgga gtggcctgta gcagacactg aaccaccagc cagctgcatt 360
tgttgtcctg gaagtcattg ccaactctgc cagtcacact ggggtcccca aagaagtcaa 420
gatctgccgg aggcgctggg caatgacccc gggactccag gccagagggg tctgaagctg 480
tttgggaaag cagcgggact ccttgggaag atggccatgg ccccaagccc ttccctggtg 540
caggtgtaca ccagccccgc ggctgtggcc gtgtgggaat ggcaggacgg gctgggcacc 600
tggcacccct acagtgccac cgtctgcagc ttcatcgagc agcagtttgt ccagcagaag 660
ggccaacgtt ttgggcttgg gagcctggcc cacagcatcc ccttgggcca ggcagacccc 720
tcgctggccc cttacattat tgacctcccc agctggaccc agttccgcca ggacaccggc 780
accatgcggg ctgtgcggag acacctgttc ccccagcact cagcccctgg ccgaggtgtc 840
gtctgggagt ggctgagcga cgatggctcc tggactgcct atgaagccag cgtctgtgac 900
tatctggagc agcaggtggc caggggcaac cagctcgtgg acttggcccc cctggggtac 960
aactacactg tcaactacac cacccacacg cagaccaaca agacttccag cttttgccgc 1020
agcgtgcggc gccaagcagg gccgccttac ccggtgacca ccatcatcgc tccgccgggc 1080
cacacaggcg tcgcctgctc ttgccaccag tgcctcagtg gcagcagaac tggccccgtg 1140
tcaggccgct accgccactc catgaccaac ctccctgcat accccgtccc ccagcacccc 1200
ccacacagga ccgcttctgt gtttgggacc caccaggcct ttgcaccgta caacaaaccc 1260
tcactctccg gggcccggtc tgcgcccagg ctgaacacca ccaacgcctg gggcgcagct 1320
cctccttccc tggggagcca gcccctctac cgctccagcc tctcccacct gggaccgcag 1380
cacctgcccc caggatcctc cacctccggt gcagtcagtg cctccctccc cagcggtccc 1440
tcaagcagcc cagggagcgt ccctgccact gtgcccatgc agatgccaaa gcccagcaga 1500
gtccagcagg cgctcgcagg catgacgagt gttctgatgt cagccattgg actccctgtg 1560
tgtcttagcc gcgcacccca gcccaccagc cctcccgcct cccgtctggc ttccaaaagt 1620
cacggctcag ttaagagatt gaggaaaatg tccgtgaaag gagcgacccc gaagccagag 1680
ccagagccag agcaggtcat aaaaaactac acggaagagc tgaaagtgcc cccagatgag 1740
gactgcatca tctgcatgga gaagctgtcc gcagcgtctg gatacagcga tgtgactgac 1800
agcaaggcaa tcgggtccct agctgtgggc cacctcacca agtgcagcca tgccttccac 1860
ctgctgtgcc tcctggccat gtactgcaac ggcaataagg atggaagtct gcagtgtccc 1920
tcctgcaaaa ccatctatgg agagaagacg gggacccagc cccagggaaa gatggaggta 1980
ttacggttcc agatgtcgct ccccggccac gaggactgcg ggaccatcct catagtttac 2040
agcattcccc atggtatcca gggccctgag caccccaatc ccggaaagcc gttcactgcc 2100
agagggtttc cccgccagtg ctaccttcca gacaacgccc agggccgcaa ggtcctagag 2160
ctcctgaagg tggcctggaa gaggcggctc atcttcacag tgggcacgtc cagcaccacg 2220
ggtgagacgg acaccgtggt atggaacgag atccaccaca agacagagat ggaccgcaac 2280

-continued

```
attacgggcc acggctatcc cgaccccaac tacctgcaga acgtgctggc tgagctggct   2340

gcccaggggg tgaccgagga ctgcctggag cagcagtgac ctcgcacccc agcacgcccg   2400

cctctggtgg ccaccccgct gccccatggc tggctgggtg gccaggcagg aagtgcccag   2460

cccgagaggc tgggaggttt gttgagggtg tggggtgtgc cccacctgaa gccggggctc   2520

cccctgcctg cctctctctc ctcctcccct ctgggaattg ggcagccctg ggcagttgta   2580

ctcatggggg cttaggatgc agctacctca gtgcgcaggg cccgtctgtc ctctgggggc   2640

tgcttcgggc ccgcggtgct cggggcctgg tgtggggcga gtagagactt ccccagcctg   2700

gacgggcgtg ggttctgggt cagcttcttt tacctcaatt ttgtttgcaa taaatgctct   2760

atagccaaaa aaaaaaaaaa aa                                            2782
```

<210> SEQ ID NO 42
<211> LENGTH: 2124
<212> TYPE: DNA
<213> ORGANISM: Homo sapiens

<400> SEQUENCE: 42

```
gctccgcaat catcttcttt accctggagc tgctgctgct gctgctgctt ttgcttttgg     60

ggctgagttt aataagcgag cgagcgagca agcgagcgcg gggggaaaaa ggcagagaat    120

gtccgccatc taccctccgc tcctgggcgc gctctcattc atagcagcct cttcatgaat    180

tacagctgag ggggggcgga ggaggggggg gtaccacaca acaccccagc aaacctccgg    240

gcccccaggc atggctagct cgtgtgccgt gcaggtgaag ctggagctgg ggcaccgcgc    300

ccaggtgagg aaaaaaccca ccgtggaggg cttcacccac gactggatgg tgttcgtacg    360

cggtccggag cacagtaaca tacagcactt tgtggagaaa gtcgtcttcc acttgcacga    420

aagctttcct aggccaaaaa gagtgtgcaa agatccacct tacaaagtag aagaatctgg    480

gtatgctggt ttcattttgc caattgaagt ttattttaaa aacaaggaag aacctaggaa    540

agtccgcttt gattatgact tattcctgca tcttgaaggc catccaccag tgaatcacct    600

ccgctgtgaa aagctaactt tcaacaaccc cacagaggac tttaggagaa agttgctgaa    660

ggcaggaggg gaccctaata ggagtattca taccagcagc agcagcagca gcagcagtag    720

cagcagcagc agcagcagca gcagcagcag tagcagcagc agcagcggca gcagcagcag    780

cagtagcagc agcagtagca gcagcagcag cagcagtagt accagttttt caaagcctca    840

caaattaatg aaggagcaca aggaaaaacc ttctaaagac tccagagaac ataaaagtgc    900

cttcaaagaa ccttccaggg atcacaacaa atcttccaaa gaatcctcta agaaacccaa    960

agaaaataaa ccactgaaag aagagaaaat agttcctaag atggccttca aggaacctaa   1020

acccatgtca aaagagccaa aaccagatag taacttactc accatcacca gtggacaaga   1080

taagaaggct cctagtaaaa ggccgcccat ttcagattct gaagaactct cagccaaaaa   1140

aaggaaaaag agtagctcag aggctttatt taaaagtttt tctagcgcac caccactgat   1200

actcacttgt tctgctgaca aaaaacagat aaaagataaa tctcatgtca agatgggaaa   1260

ggtcaaaatt gaaagtgaga catcagagaa gaagaaatca acgttaccgc catttgatga   1320

tattgtggat cccaatgatt cagatgtgga ggagaatata tcctctaaat ctgattctga   1380

acaacccagt cctgccagct ccagctccag ctccagctcc agcttcacac catcccagac   1440

caggcaacaa ggtcctttga ggtctataat gaaagatctg cattctgatg acaatgagga   1500

ggaatcagat gaagtggagg ataacgacaa tgactctgaa atggagaggc ctgtaaatag   1560

aggaggcagc cgaagtcgca gagttagctt aagtgatggc agcgatagtg aaagcagttc   1620
```

```
tgcttcttca cccctacatc acgaacctcc accaccctta ctaaaaacca acaacaacca   1680

gattcttgaa gtgaaaagtc caataaagca aagcaaatca gataagcaaa taaagaatgg   1740

tgaatgtgac aaggcatacc tagatgaact ggtagagctt cacagaaggt taatgacatt   1800

gagagaaaga cacattctgc agcagatcgt gaaccttata gaagaaactg gacactttca   1860

tatcacaaac acaacatttg attttgatct ttgctcgctg gacaaaacca cagtccgtaa   1920

actacagagt tacctggaaa catctggaac atcctgagga tataacaact ggatgcatca   1980

agaactattg tgtttttttt ttttggtttt tttttttttt tggttgtgat tttttgttct   2040

tgttgtttat atgaaaacac tcaaaatgat gcaaccaaaa gggaaaaaat aaaaatcaaa   2100

caacctccaa aaaaaaaaaa aaaa                                          2124
```

```
<210> SEQ ID NO 43
<211> LENGTH: 1539
<212> TYPE: DNA
<213> ORGANISM: Homo sapiens

<400> SEQUENCE: 43

gaattcgggg ggaggggcca gtgtcctccg agccaggaca ggcatgttgt tgggactggc     60

ggccatggag ctgaaggtgt gggtggatgg catccagcgt gtggtctgtg gggtctcaga    120

gcagaccacc tgccaggaag tggtcatcgc actagcccaa gcaataggcc agactggccg    180

ctttgtgctt gtgcagcggc ttcgggagaa ggagcggcag ttgctgccac aagagtgtcc    240

agtgggcgcc caggccacct gcggacagtt tgccagcgat gtccagtttg tcctgaggcg    300

cacagggccc agcctagctg ggaggccctc ctcagacagc tgtccacccc cggaacgctg    360

cctaattcgt gccagcctcc ctgtaaagcc acgggctgcg ctgggctgtg agccccgcaa    420

aacactgacc cccgagccag cccccagcct ctcacgccct gggcctgcgg cccctgtgac    480

acccacacca ggctgctgca cagacctgcg gggcctggag ctcagggtgc agaggaatgc    540

tgaggagctg ggccatgagg ccttctggga gcaagagctg cgccgggagc aggcccggga    600

gcgagaggga caggcacgcc tgcaggcact aagtgcggcc actgctgagc atgccgcccg    660

gctgcaggcc ctggacgctc aggcccgtgc cctggaggct gagctgcagc tggcagcgga    720

ggcccctggg ccccccctcac ctatggcatc tgccactgag cgcctgcacc aggacctggc    780

tgttcaggag cggcagagtg cggaggtgca gggcagcctg gctctggtga gccgggccct    840

ggaggcagca gagcgagcct tgcaggctca ggctcaggag ctggaggagc tgaaccgaga    900

gctccgtcag tgcaacctgc agcagttcat ccagcagacc ggggctgcgc tgccaccgcc    960

cccacggcct gacaggggcc ctcctggcac tcagggccct ctgcctccag ccagagagga   1020

gtccctcctg ggcgctccct ctgagtccca tgctggtgcc cagcctaggc cccgaggtgg   1080

cccccatgac gcagaactcc tggaggtagc agcagctcct gccccagagt ggtgtcctct   1140

ggcagcccag ccccaggctc tgtgacagcc tagtgagggc tgcaagacca tcctgcccgg   1200

accacagaag gagagttggc ggtcacagag ggctcctctg ccaggcagtg ggaagccctg   1260

ggtttggcct caggagctgg gggtgcagtg ggggactgcc ctagtccttg ccaggtcgcc   1320

cagcaccctg gagaagcatg gggcgtagcc agctcggaac ttgccaggcc ccaaaggcca   1380

cgactgcctg ttggggacag gagatgcatg gacagtgtgc tcaagctgtg ggcatgtgct   1440

tgcctgcggg agaggtcctt cactgtgtgt acacagcaag agcatgtgtg tgccacttcc   1500

cctaccccaa cgtgaaaacc tcaataaact gcccgaagc                          1539
```

<210> SEQ ID NO 44
<211> LENGTH: 1514
<212> TYPE: DNA
<213> ORGANISM: Homo sapiens

<400> SEQUENCE: 44
cgcgcctgcc tctttctgag cggcatgaag ccacctccca ggcggcgagc ggccccggcg 60
cgctatctgg gcgaggtgac cggtcccgcg acctggagcg ctcgcgagaa gcggcagcta 120
gtgcgactcc tgcaggcgcg gcagggccag ccggagccgg acgccaccga gctggcccgg 180
gagctgcggg gccggagcga ggctgagatc cgggtcttcc tccagcagct caagggccgc 240
gtagcccggg aggccattca gaaagtgcat ccgggtggcc ttcagggacc aaggcgccgg 300
gaggcacagc cccagcccc catagaggtc tggacggatc tggctgagaa gataacaggg 360
ccactggaag aagccctggc agtggctttc tcgcaggtgc tcaccatcgc ggccacggaa 420
ccggtcaccc tcctgcactc caagcccccc aagcccacgc aggcccgtgg aaagcctttg 480
ctcctgagcg cccctggagg acaggaagac cccgcccctg aaatacctag ctctgcccct 540
gctgcaccta gctccgcacc caggactcct gaccctgccc ctgagaaacc ttctgagtcg 600
tcggctggtc cctccactga agaagacttt gctgtggact ttgagaagat ctacaagtac 660
ttgtcctctg tctcccgaag tggccgcagc cccgagctct cagcagctga gtccgctgtg 720
gtcctcgacc tgctcatgtc acttccagag gagctgccac tcctgccctg cacagccctg 780
gttgagcata tgacggagac gtacctacgc ctgacagccc cccagcccat tcccgctgga 840
gggagcctgg ggcctgcagc agaaggggat ggggctggct ccaaggcacc agaggagacc 900
cccccagcca ccgagaaggc cgagcacagc gaactgaaat cgccttggca agcagctggg 960
atctgtcccc tgaacccgtt cctggtgccc ctggagcttc tgggtcgggc agccacccct 1020
gccaggtgag gggcatggcg ggcaggaggc cacaccaggc cccccgccct gcccctcggt 1080
tctgctcggc tggccctggc tctttctgag gatcccgtca tgggggaagg tccttgagat 1140
gatgctcagc tgtggggcgg gcctctaaga tgccccatac tttgggggtc tcagaaatgg 1200
aacccccgtt gtacaggggt tgggtggggg ttgcaggact ccactcacaa gcctcctgat 1260
gtcaaggaca ggcggacagg gctggcctcc cccagtcccc aagccccact gtgccttgtt 1320
gtctgctggg gggccatagc tggcactgcc caccgtaaag gccctcgcac attttccccc 1380
ttcctgtaca cctcggggcc agcatcctca ccttcttcaa ctgaccagtc gtggttactc 1440
cctgctgcca ggtccttccc cttcccgggg gtattctgtg accatgaata aagttaccat 1500
tctctttctc tttc 1514

<210> SEQ ID NO 45

<400> SEQUENCE: 45

000

<210> SEQ ID NO 46
<211> LENGTH: 2744
<212> TYPE: DNA
<213> ORGANISM: Homo sapiens

<400> SEQUENCE: 46
ctcgtgccga attcggcacg agaccgcgtg ttcgcgcctg gtagagattt ctcgaagaca 60
ccagtgggcc cgtgtggaac caaacctgcg cgcgtggccg ggccgtggga caacgaggcc 120

-continued

```
gcggagacga aggcgcaatg gcgaggaagt tatctgtaat cttgatcctg acctttgccc    180
tctctgtcac aaatcccctt catgaactaa aagcagctgc tttcccccag accactgaga    240
aaattagtcc gaattgggaa tctggcatta atgttgactt ggcaatttcc acacggcaat    300
atcatctaca acagcttttc taccgctatg gagaaaataa ttctttgtca gttgaagggt    360
tcagaaaatt acttcaaaat ataggcatag ataagattaa aagaatccat atacaccatg    420
accacgacca tcactcagac cacgagcatc actcagacca tgagcgtcac tcagaccatg    480
agcatcactc agaccacgag catcactctg accataatca tgctgcttct ggtaaaaata    540
agcgaaaagc tctttgccca gaccatgact cagatagttc aggtaaagat cctagaaaca    600
gccaggggaa aggagctcac cgaccagaac atgccagtgg tagaaggaat gtcaaggaca    660
gtgttagtgc tagtgaagtg acctcaactg tgtacaacac tgtctctgaa ggaactcact    720
ttctagagac aatagagact ccaagacctg gaaaactctt ccccaaagat gtaagcagct    780
ccactccacc cagtgtcaca tcaaagagcc gggtgagccg gctggctggt aggaaaacaa    840
atgaatctgt gagtgagccc cgaaaaggct ttatgtattc cagaaacaca aatgaaaatc    900
ctcaggagtg tttcaatgca tcaaagctac tgacatctca tggcatgggc atccaggttc    960
cgctgaatgc aacagagttc aactatctct gtccagccat catcaaccaa attgatgcta   1020
gatcttgtct gattcataca agtgaaaaga aggctgaaat ccctccaaag acctattcat   1080
tacaaatagc ctgggttggt ggttttatag ccatttccat catcagtttc ctgtctctgc   1140
tgggggttat cttagtgcct ctcatgaatc gggtgttttt caaatttctc ctgagtttcc   1200
ttgtggcact ggccgttggg actttgagtg gtgatgcttt tttacacctt cttccacatt   1260
ctcatgcaag tcaccaccat agtcatagcc atgaagaacc agcaatggaa atgaaaagag   1320
gaccactttt cagtcatctg tcttctcaaa acatagaaga aagtgcctat tttgattcca   1380
cgtggaaggg tctaacagct ctaggaggcc tgtatttcat gtttcttgtt gaacatgtcc   1440
tcacattgat caaacaattt aaagataaga agaaaaagaa tcagaagaaa cctgaaaatg   1500
atgatgatgt ggagattaag aagcagttgt ccaagtatga atctcaactt tcaacaaatg   1560
aggagaaagt agatacagat gatcgaactg aaggctattt acgagcagac tcacaagagc   1620
cctcccactt tgattctcag cagcctgcag tcttggaaga agaagaggtc atgatagctc   1680
atgctcatcc acaggaagtc tacaatgaat atgtacccag agggtgcaag aataaatgcc   1740
attcacattt ccacgataca ctcggccagt cagacgatct cattcaccac catcatgact   1800
accatcatat tctccatcat caccaccacc aaaaccacca tcctcacagt cacagccagc   1860
gctactctcg ggaggagctg aaagatgccg gcgtcgccac tttggcctgg atggtgataa   1920
tgggtgatgg cctgcacaat ttcagcgatg gcctagcaat tggtgctgct tttactgaag   1980
gcttatcaag tggtttaagt acttctgttg ctgtgttctg tcatgagttg cctcatgaat   2040
taggtgactt tgctgttcta ctaaaggctg gcatgaccgt taagcaggct gtcctttata   2100
atgcattgtc agccatgctg gcgtatcttg gaatggcaac aggaattttc attggtcatt   2160
atgctgaaaa tgtttctatg tggatatttg cacttactgc tggcttattc atgtatgttg   2220
ctctggttga tatggtacct gaaatgctgc acaatgatgc tagtgaccat ggatgtagcc   2280
gctgggggta tttcttttta cagaatgctg ggatgctttt gggttttgga attatgttac   2340
ttatttccat atttgaacat aaaatcgtgt ttcgtataaa tttctagtta aggtttaaat   2400
gctagagtag cttaaaaagt tgtcatagtt tcagtaggtc atagggagat gagtttgtat   2460
gctgtactat gcagcgttta aagttagtgg gttttgtgat tttgtattg aatattgctg   2520
```

-continued

```
tctgttacaa agtcagttaa aggtacgttt taatatttaa gttattctat cttggagata   2580

aaatctgtat gtgcaattca ccggtattac cagtttatta tgtaaacaag agatttggca   2640

tgacatgttc tgtatgtttc agggaaaaat gtctttaatg ctttttcaag aactaacaca   2700

gttattccta tactggattt taggtctctg aagaactgct ggtg                    2744
```

```
<210> SEQ ID NO 47
<211> LENGTH: 1759
<212> TYPE: DNA
<213> ORGANISM: Homo sapiens

<400> SEQUENCE: 47

agcggatgct ggggctgtaa ggcgcgcgcg gtcagctgtt ggcggtgcag ggaggaggac     60

gccggggctc gccttccctc ctctgccgcc gctgccgcca tgattccggt gtcgctggtg    120

gtggtggtgg tgggtggctg gactgtcgtc tacctgaccg acttggtgct gaagtcatct    180

gtctatttta aacattctta tgaagactgg ctggaaaaca acggactgag catctcccct    240

ttccacataa gatggcaaac tgctgttttc aatcgtgcct tttacagttg gggacggcgg    300

aaagcaagga tgctttacca atggttcaat tttggaatgg tgtttggcgt aattgccatg    360

tttagctcat tttttctcct tggaaaaacg ctgatgcaga ctttggcaca aatgatggct    420

gactctccct cttcttattc ttcctcctct tcttcctctt cctcctcttc ttcctcttcc    480

tcttcttcat cttcttcctc ttcctcgctt cacaatgaac aggtgttaca agttgtggtt    540

cctggtataa atttacccgt caatcaactg acctatttct tcacggcagt tctcattagt    600

ggtgttgtac atgaaattgg acatgggata gcagctatta gggaacaagt tcgatttaat    660

ggctttggga tttttctctt cattatttat cctggagcat ttgttgatct gttcaccact    720

catttgcaac ttatatcgcc agtccagcag ctaaggatat tttgtgcagg tatctggcat    780

aattttgtcc ttgcactctt gggtatttta gctcttgttc tcctcccagt aattctcttg    840

ccattttact acactggagt tggggtgctc atcactgaag ttgctgagga ctctcctgcc    900

attggaccca gaggcctttt tgtgggagac cttgtcaccc atctacagga ttgtcctgtt    960

actaatgtgc aagattggaa tgaatgttta gataccatcg cctatgagcc ccaaattggt   1020

tactgtataa gtgcatcaac tttacagcag ttaagtttcc cagttagagc atacaaacga   1080

ctagatggtt caactgaatg ctgtaacaat cacagcctca cagatgtgtg cttttcctac   1140

agaaataatt ttaataagcg tttgcataca tgtcttcctg cccggaaagc agttgaagca   1200

actcaagttt gcagaaccaa taaagactgt aaaaaaagct caagttcaag tttctgtata   1260

ataccttctt tggaaactca cactcgctta ataaaagtaa aacacccacc tcagattgat   1320

atgttatacg taggacatcc tctgcatctt cactacacag tgagcatcac cagttttatc   1380

ccacgtttta actttctaag catagatctg ccagtggttg tggagacatt tgtcaagtac   1440

ctgatttccc tctcaggagc tctggctatt gttaatgcag taccctgctt tgctttggat   1500

ggacaatgga ttctaaactc tttcttggat gccaccctta cctcagtgat tggagacaat   1560

gatgtcaaag atctaatagg gtttttcatc ttgctgggtg gcagtgtact tttggctgcc   1620

aatgtgaccc tgggactctg gatggttaca gcacggtaat gtttgcactc atctgacaga   1680

atccctgagt tacagtatac agctatgtgg taatattcat tgccattgaa attcttactt   1740

ggtatgaaat ataaagtgt                                                1759

<210> SEQ ID NO 48
```

<211> LENGTH: 1610
<212> TYPE: DNA
<213> ORGANISM: Homo sapiens

<400> SEQUENCE: 48
ggcacgaggc tgcggccgca gtagccggag ccggagccgc agccaccggt gccttccttt 60
cccgccgccg cccagccgcc gtccggcctc cctcgggccc gagcgcagac caggctccag 120
ccgcgcggcg ccggcagcct cgcgctccct ctcgggtctc tctcgggcct cgggcaccgc 180
gtcctgtggg cggccgcctg cctgcccgcc cgcccgcagc cccttgcctg ccggcccctg 240
ggcggcccgt gccatgggca ccgacagccg cgcggccaag gcgctcctgg cgcgggcccg 300
caccctgcac ctgcagacgg ggaacctgct gaactggggc cgcctgcgga agaagtgccc 360
gtccacgcac agcgaggagc ttcatgattg tatccaaaaa accttgaatg aatggagttc 420
ccaaatcaac ccagatttgg tcagggagtt tccagatgtc ttggaatgca ctgtatctca 480
tgcagtagaa aagataaatc ctgatgaaag agaagaaatg aaagtttctg caaaactgtt 540
cattgtagaa tcaaactctt catcatcaac tagaagtgca gttgacatgg cctgttcagt 600
ccttggagtt gcacagctgg attctgtgat cattgcttca cctcctattg aagatggagt 660
taatctttcc ttggagcatt tacagcctta ctgggaggaa ttagaaaact tagttcagag 720
caaaaagatt gttgccatag gtacctctga tctagacaaa acacagttgg aacagctgta 780
tcagtgggca caggtaaaac caaatagtaa ccaagttaat cttgcctcct gctgtgtgat 840
gccaccagat ttgactgcat ttgctaaaca atttgacata cagctgttga ctcacaatga 900
tccaaaagaa ctgctttctg aagcaagttt ccaagaagct cttcaggaaa gcattcctga 960
cattcaagcg cacgagtggg tgccgctgtg gctactgcgg tattcggtca ttgtgaaaag 1020
tagaggaatt atcaaatcaa aaggctacat tttacaagct aaaagaaggg gttcttaact 1080
gacttaggag cataacttac ctgtaatttc cttcaatatg agagaaaatt gagatgtgta 1140
aaatctagtt actgcctgta aatggtgtca ttgaggcaga tattctttcg tcatatttga 1200
cagtatgttg tctgtcaagt tttaaatact tatcttgcct ccatatcaat ccattctcat 1260
gaacctctgt attgctttcc ttaaactatt gttttctaat tgaaattgtc tataaagaaa 1320
atacttgcaa tatatttttc ctttattttt atgactaata taaatcaaga aaatttgttg 1380
ttagatatat tttggcctag gtatcagggt aatgtatata catatttttt atttccaaaa 1440
aaaattcatt aattgcttct taactcttat tataaccaag caatttaatt acaattgtta 1500
aaactgaaat actggaagaa gatatttttc ctgtcattga tgagatatat cagagtaact 1560
ggagtagctg ggatttacta gtagtgtaaa taaaattcac tcttcaatac 1610

<210> SEQ ID NO 49
<211> LENGTH: 2044
<212> TYPE: DNA
<213> ORGANISM: Homo sapiens

<400> SEQUENCE: 49
ctggacgagt ccgagcgcgt cacctcctca cgctgcggct gtcgcccgtg tcccgccggc 60
ccgttccgtg tcgccccgca gtgctgcggc cgccgcggca ccatggctgt gtttgtcgtg 120
ctcctggcgt tggtggcggg tgttttgggg aacgagttta gtatattaaa atcaccaggg 180
tctgttgttt tccgaaatgg aaattggcct ataccaggag agcggatccc agacgtggct 240
gcattgtcca tgggcttctc tgtgaaagaa gacctttctt ggccaggact cgcagtgggt 300
aacctgtttc atcgtcctcg ggctaccgtc atggtgatgg tgaagggagt gaacaaactg 360
gctctacccc caggcagtgt catttcgtac cctttggaga atgcagttcc ttttagtctt 420
gacagtgttg caaattccat tcactcctta ttttctgagg aaactcctgt tgttttgcag 480
ttggctccca gtgaggaaag agtgtatatg gtagggaagg caaactcagt gtttgaagac 540
ctttcagtca ccttgcgcca gctccgtaat cgcctgtttc aagaaaactc tgttctcagt 600
tcactccccc tcaattctct gagtaggaac aatgaagttg acctgctctt tctttctgaa 660
ctgcaagtgc tacatgatat ttcaagcttg ctgtctcgtc ataagcatct agccaaggat 720
cattctcctg atttatattc actggagctg gcaggtttgg atgaaattgg gaagcgttat 780
ggggaagact ctgaacaatt cagagatgct tctaagatcc ttgttgacgc tctgcaaaag 840
tttgcagatg acatgtacag tctttatggt gggaatgcag tggtagagtt agtcactgtc 900
aagtcatttg acacctccct cattaggaag acaaggacta tccttgaggc aaaacaagcg 960
aagaacccag caagtcccta taaccttgca tataagtata attttgaata ttccgtggtt 1020
ttcaacatgg tactttggat aatgatcgcc ttggccttgg ctgtgattat cacctcttac 1080
aatatttgga acatggatcc tggatatgat agcatcattt ataggatgac aaaccagaag 1140
attcgaatgg attgaatgtt acctgtgcca gaattagaaa agggggttgg aaattggctg 1200
ttttgttaaa atatatcttt tagtgtgctt taaagtagat agtatacttt acatttataa 1260
aaaaaaatca aattttgttc tttattttgt gtgtgcctgt gatgtttttc tagagtgaat 1320
tatagtattg acgtgaatcc cactgtggta tagattccat aatatgcttg aatattatga 1380
tatagccatt taataacatt gatttcattc tgtttaatga atttggaaat atgcactgaa 1440
agaaatgtaa aacatttaga atagctcgtg ttatggaaaa aagtgcactg aatttattag 1500
acaaacttac gaatgcttaa cttctttaca cagcataggt gaaaatcata tttgggctat 1560
tgtatactat gaacaatttg taaatgtctt aatttgatgt aaataactct gaaacaagag 1620
aaaaggtttt taacttagag tagccctaaa atatggatgt gcttatataa tcgcttagtt 1680
ttggaactgt atctgagtaa cagaggacag ctgtttttta accctcttct gcaagtttgt 1740
tgacctacat gggctaatat ggatactaaa aatactacat tgatctaaga agaaactagc 1800
cttgtggagt atatagatgc ttttcattat acacacaaaa atccctgagg gacattttga 1860
ggcatgaata taaaacattt ttatttcagt aacttttccc cctgtgtaag ttactatggt 1920
ttgtggtaca acttcattct atagaatatt aagtggaagt gggtgaattc tactttttat 1980
gttggagtgg accaatgtct atcaagagtg acaaataaag ttaatgatga ttccaaaaaa 2040
aaaa 2044

<210> SEQ ID NO 50
<211> LENGTH: 2266
<212> TYPE: DNA
<213> ORGANISM: Homo sapiens

<400> SEQUENCE: 50
agcggagcag tagccaccac tccgccgagg ccgcaacccc ggctcggcct ccccaggccc 60
cgccgctgcc gcagtcatgg ctgctgatgg ggtggacgaa cgctcgcctc tgctgtcagc 120
atcccactcc ggaaatgtca ctcccaccgc cccaccgtac ttgcaagaaa gcagccccag 180
agcggagctc ccacctccat atacagccat tgccagtcca gacgccagtg gtattccagt 240
aataaactgc cgtgtgtgcc aatcactaat caatttggat ggcaagcttc accagcatgt 300
ggttaagtgc acagtttgca atgaagctac gccaatcaaa aaccccccaa caggcaagaa 360

-continued

```
atatgttaga tgcccttgta attgtcttct catttgtaag gacacatctc ggcgaatagg    420
atgcccaaga cccaactgta gacggataat taaccttggc ccagtaatgc ttatttctga    480
agaacaacca gctcagcctg cattgccaat ccaaccagaa ggtacaaggg tcgtgtgtgg    540
gcactgtgga aacacattcc tgtggatgga actgaggttc aacactctgg caaaatgccc    600
acactgcaaa aaaatctcct cagtgggtag tgcacttcca cgaagacgct gctgtgcata    660
tattaccatt ggaatgatat gtattttcat tggagttggg ttaactgttg gcaccccaga    720
ttttgcaagg cgatttcgag caacctatgt ttcttgggca attgcttatc tcctaggatt    780
gatctgcctt atccgagctt gttattgggg agccataaga gtcagttatc cagaacacag    840
ttttgcataa gcttgtttat gattcagtaa tgcaggtgag agtgtctagc agttcttggt    900
aagctactct ggacatcttt aaattattta tcctaatgga ttccattctg gtttatgtat    960
aatcgtttca agactttggg agtcttttat gaacaaatgc tcattgcact atattatatg   1020
caaattgttt tgctgctagg ttttcaaaat ttgaataata aagccttttc atgttctttt   1080
acatctctta tagatatttt tggatttgtt accaaacatt acatttactc tcaccctttt   1140
attattttta aataagttat ttcattactt gctgatacat gagtattcct aagtgtttat   1200
aaatatttct ataatagttt cacatttata tttacatttt aattaaacag tatcaaaatt   1260
gcttgcttaa aacctaagca atatgcattt tgcttgaact gcttactgta actttaacct   1320
aagattatag tgaccttatt caggaaaaaa aaaaaattta gtgtaacttc aaagacttga   1380
cattcttgtc agaggaaaaa aaatttctag atactgtttg cttgtttttt gttgtttgta   1440
gaaagataaa atattttggt aataatttaa aatacaagaa cgaatattta tttgtccaca   1500
gttggagatg ttggataaat gtcttttctc aaagatcaca ggacttttgt ctttcatttt   1560
tgccttttta tttaccattt ataaaagatc tggtctggat tatggaattt aatgtttatc   1620
agctctatgt attcctttat agaggcttga ggaagtattt cacataacat gttttataat   1680
acttaaccat ttatccaaag atatatttac attgggttgt gccccttttcc cttagatcat   1740
ggtaaatttt tcttattgag gtaattatgt actacttata tttgaaggaa gcttatgaca   1800
ttttacagta gctaaaatgt tgagattaga ggtactttta ctattcttct caaaggtaac   1860
tgatcagata attacccaaa ttattcaaga aaatagatca gaaataaaga acaacataat   1920
tttctaagaa ttcattgaaa tttatggaat cagctctcgc actgcccatc tttgcagttt   1980
tgaaaaagaa attgcttaat cacaaatgtt ctacagtctt taaatgtagt agaattagac   2040
agtgagatca tctgagtaaa ttgattggtg attccagaga taagactaat attttaaatt   2100
atttatgata ctgattagta taaaaacgta ctcatcacag aatttgaagc aaaatacatg   2160
tacacttcaa agagtaaatg acaaatgtat aaatgctgta gctcaggatt atatgtacct   2220
ttaaaaatac actaataaag attattgttc aaaaaaaaaa aaaaaa                  2266
```

<210> SEQ ID NO 51
<211> LENGTH: 3142
<212> TYPE: DNA
<213> ORGANISM: Homo sapiens

<400> SEQUENCE: 51

```
gtggccgctg ccgcctctgc ctgggtccct tcggccgtac ctctgcgtgg gggctgcctc     60
cccggctccc ggtgcagaca ccatgtacgg atttgtgaat cacgccctgg agttgctggt    120
gatccgcaat tacggccccg aggtgtggga agacatcaaa aaagaggcac agttagatga    180
agaaggacag tttcttgtca gaataatata tgatgactcc aaaacttatg atttggttgc    240
```

-continued

```
tgctgcaagc aaagtcctca atctcaatgc tggagaaatc ctccaaatgt ttgggaagat    300
gtttttcgtc ttttgccaag aatctggtta tgatacaatc ttgcgtgtcc tgggctctaa    360
tgtcagagaa tttctacaga accttgatgc tctgcacgac caccttgcta ccatctaccc    420
aggaatgcgt gcaccttcct ttaggtgcac tgatgcagaa aagggcaaag gactcatttt    480
gcactactac tcagagagag aaggacttca ggatattgtc attggaatca tcaaaacagt    540
ggcacaacaa atccatggca ctgaaataga catgaaggtt attcagcaaa gaaatgaaga    600
atgtgatcat actcaatttt taattgaaga aaaagagtca aaagaagagg atttttatga    660
agatcttgac agatttgaag aaaatggtac ccaggaatca cgcatcagcc catatacatt    720
ctgcaaagct ttcctttttc atataatatt tgaccgggac ctagtggtca ctcagtgtgg    780
caatgctata tacagagttc tcccccagct ccagcctggg aattgcagcc ttctgtctgt    840
cttctcgctg gttcgtcctc atattgatat tagtttccat gggatccttt ctcacatcaa    900
tactgttttt gtattgagaa gcaaggaagg attgttggat gtggagaaat tagaatgtga    960
ggatgaactg actgggactg agatcagctg cttacgtctc aagggtcaaa tgatctactt   1020
acctgaagca gatagcatac tttttctatg ttcaccaagt gtcatgaacc tggacgattt   1080
gacaaggaga gggctgtatc taagtgacat ccctctgcat gatgccacac gcgatcttgt   1140
tcttttggga gaacaattta gagaggaata caaactcacc caagaactgg aaatcctcac   1200
tgacaggcta cagctcacgt taagagccct ggaagatgaa aagaaaaaga cagacacatt   1260
gctgtattct gtccttcctc cgtctgttgc caatgagctg cggcacaagc gtccagtgcc   1320
tgccaaaaga tatgacaatg tgaccatcct ctttagtggc attgtgggct tcaatgcttt   1380
ctgtagcaag catgcatctg gagaaggagc catgaagatc gtcaacctcc tcaacgacct   1440
ctacaccaga tttgacacac tgactgattc ccggaaaaac ccatttgttt ataaggtgga   1500
gactgttggt gacaagtata tgacagtgag tggtttacca gagccatgca ttcaccatgc   1560
acgatccatc tgccacctgg ccttggacat gatggaaatt gctggccagg ttcaagtaga   1620
tggtgaatct gttcagataa caatagggat acacactgga gaggtagtta caggtgtcat   1680
aggacagcgg atgcctcgat actgtctttt tgggaatact gtcaacctca caagccgaac   1740
agaaaccaca ggagaaaagg gaaaaataaa tgtgtctgaa tatacataca gatgtcttat   1800
gtctccagaa aattcagatc cacaattcca cttggagcac agaggcccag tgtccatgaa   1860
gggcaaaaaa gaaccaatgc aagtttggtt tctatccaga aaaaatacag gaacagagga   1920
aacaaagcag gatgatgact gaatcttgga ttgtggggtg aagaggagta cagactaggt   1980
tccagttttc tcctaacacg tgccaagccc aggagcagtt cttccctatg gatacagatt   2040
ttcttttgtc cttgtccatt accccaagac tttcttctag atatatctct cactatccgt   2100
tattcaacct tagctctgct ttctattact ttttaggctt tagtatatta tctaaagttt   2160
ggcttttgat gtggatgatg tgagcttcat gtgtcttaaa atctactaca agcattacct   2220
aacatggtga tctgcaagta gtaggcaccc aataaatatt tgttgaattt agttaaatga   2280
aactgaacag tgtttggcca tgtgtatatt tatatcatgt ttaccaaatc tgtttagtgt   2340
tccacatata tgtatatgta tattttaatg actataatgt aataaagttt atatcatgtt   2400
ggtgtatatc attatagaaa tcattttcta aaggagtgaa ttctaagttt taggggaaaa   2460
aatgcaattt attttcagac tcccaaagta agaattaaca tatcatgcta agaaaatagt   2520
gactattttg aagtatgcta cttccctttc agaaatatag aatacacgtt tctgttatta   2580
```

-continued

```
aagtatttga ttactaattc aaatcatatg gcaattataa ttcttctaaa atgctatcat   2640

ttgtaactgt atcccctgta ttaaatctca ttaaccacag gcagctgtta cagaaagctg   2700

cattgtttca cattgagctg ttacattagt tcaggctaaa tgttgggcgc tccaaccaca   2760

tccaagaata aatctggaaa cacactgctg ggatactgct gttagagccc ttcttggcct   2820

tgtattccca gaaatgagct ccctttcctt agcttagaag aatgtgatta tatccaggac   2880

atcatgttca gaaaacttag tttactttca gcatagaatg cattactgtt ggaataattg   2940

gcctctagct cttaaatgtc tctgataact tattaatatc tatctttata aaatagagtg   3000

caactacttt tgtgtaaaaa tgtttgcctt taaatttagt atttcatatc agcacatcga   3060

tatatgtata aatgttccat gttaatgtgt aaaagagtct gtaataaatt atttttttca   3120

cgtgtcaaaa aaaaaaaaaa aa                                            3142
```

<210> SEQ ID NO 52
<211> LENGTH: 5537
<212> TYPE: DNA
<213> ORGANISM: Homo sapiens

<400> SEQUENCE: 52

```
ggaactgccg cggccgccac cgccgctgcc ggcgccgctg ctgtagggga ccagcgcggg     60

tgcgcagacg aaaggcgctc tttgccagct gaaagttccc acggaaaaac taccatctcc    120

cctgcccacc atggcagacg aaattgattt cactactgga gatgccgggg cttccagcac    180

ttaccctatg cagtgctcgg ccttgcgcaa aaacggcttc gtggtgctca aaggacgacc    240

atgcaaaata gtggagatgt caacttccaa aactggaaag catggtcatg ccaaggttca    300

ccttgttgga attgatattt tcacgggcaa aaaatatgaa gatatttgtc cttctactca    360

caacatggat gttccaaata ttaagagaaa tgattatcaa ctgatatgca ttcaagatgg    420

ttacctttcc ctgctgacag aaactggtga agttcgtgag gatcttaaac tgccagaagg    480

tgaactaggc aaagaaatag agggaaaata caatgcaggt gaagatgtac aggtgtctgt    540

catgtgtgca atgagtgaag aatatgctgt agccataaaa ccctgcaaat aaacggaaac    600

atcaggcatg aacactgttt atgtctgaat caactgcaga tctaatttgg ttctaagttg    660

tcaccaaagc tatagccttc ataagcaacc tcatttcttt ttttaattgt tttcagattg    720

tgctgggtta gttttgcaag caattgataa tttttaaaaa attatcaata tgtataattt    780

tttttgaatt ttgtagatat gtttcctata atattcctgt ggttttcagt atgtcagtcc    840

aagaaacaaa caagatagct tcagcagatg tgatttgtct gagcaaatca ttcctgtgtt    900

ttagttagat gataaaccag ggttttaaat caaacaatgt agcataaagt ggtattgaag    960

taccatattt aagttgaact gctctgcatt aattacagat ttaatataaa atgaactgat   1020

tatatattgg aattgttgca ctttcagcct gtgtagggca aacacaaatc cttaaacaaa   1080

aatcatgtta tcaaaaactg tcagttattt tggtggccac atgcaaccat gtgattactt   1140

tggtcatact atttaccaaa ttgttggcaa acttgatgta accttatatg gtggttttag   1200

tcccttctta tggttggcag aagggcactg aactgttggg tgaaagttag ttagcaagta   1260

agattataag gaagacacaa aagacagtgg caaagagggt tgattaaatc tataagtttt   1320

tatgtgagga ctttgtaagt cagcataaaa atgaaaagtt gtttctcagt tgtttttgct   1380

tttaactttg cccccaacgt ttaaagggag tgatctgctt tacatgatac tatgcaatgc   1440

ttgttttcca actatgttga ataaatagta atatttatca gtaaatactc ctttccaact   1500

tcctttttttt ttttttttt tttgagactg agtctcactc catcagccag gctggagtgc   1560
```

-continued

```
agtggtgcaa tctcggctca ctgcaacctc tgcctcccga gttcaagcaa ttctcctgcc   1620
tcagcctccc aagtagctgg gactacaggt gcatgccacc acgcccagct actttttttgt   1680
gtattttagt agagatgggg tttcaccatg ttgtctaggc tggtcttgaa ctcctgacct   1740
caggtgatcc acctgcctca gcctcccaaa gtgctgggat tacaggcatg agccaccaca   1800
cccagcccct ttccaaccat ttctaagtag attttttgac attaatgtat ttattaaaca   1860
aaaactgaga attccttaaa ttgatttgga atttttgtta attttatgtc cttttttttcc   1920
taaagtgaat taaagtgaat catggaagca gcattacttt atatgaatat tattatttaa   1980
gttaagttat tttaagtata tgcatttttt ctgattgttg tgtgacttaa ttcagttgct   2040
ggtgtgaact ataactagca aataattcta taaactgaat tattttaaaa ggtattttag   2100
gtgacaccac tgcatttcta tttcatcttt tgagtcatat gtatattatt tccagaattt   2160
tagacattat tacagggttt gtgaggacct ttgactcagt gacaatcatc atattggagc   2220
aaaacataga acaaaatcac tatctcagaa ataccttaat tctctaagac tggctcttag   2280
acctctccca tcatgccttg acctctaaaa agccctttgt tcctatcttc taaaggaaag   2340
tatatcatat atgatgatgt aactgatcta atcagtgact ggaaatagca ttagtaacag   2400
aagatcccaa gttttagttg cttaatttgt acacactttt aaatattgtc ttagcctcgg   2460
caaaccaatt tggggaagaa gcaagatact ttaagagaaa tacaaaggaa atttctaaag   2520
cacaagaaat agtgaggtag tagttagtcg tctttcctac aacattttag cttttgccca   2580
tctaaagcac aattaaaatt aggctacatt ctttccagta ttctatttaa gtacctacta   2640
catactgctc tagtttctta gtactctgta atgtgtatct taattgctac tggttggcat   2700
tgtaactcat aggaattcca gaaaattatt aatccgtgct gcttgcagtt cattcatatg   2760
gcccctctta accatgctgg tgttatgatt cagtattaac tctcaattag catgcccctg   2820
ttcttcctaa cttgtaaaat ttcacataaa tatattttca attgtgtaca aattaagggt   2880
gtacaaatta taataatgca tctctatctt catactttga atggcaaacg ctatttatgc   2940
ataaatattt tcattttaag taatatatga agtgtaaata ctcgatatat aagtatagat   3000
tttaaagata tgggacttta ttttcacata agtcaataga tgtttctcta gaacaaaata   3060
tttagtaaag ctttataaat tatattaaaa ggaagcgggg aacatgtatt ttttaacata   3120
gaacagaagt gacttcattc tttttagaca tcagaaatgt taaagttgat tcccaatatt   3180
tgttgtactt ttttgtagca aatgttaaaa atcacgagtt accatgtata gaatgtggac   3240
tgtcatgttg atatcattgt acagtgataa gccattttta tctgtataca tttcaccaat   3300
ttattaacag gttgaatatt tgtttctttt tagaacattt tatttatact gtgaagactt   3360
tgttatacct tatttgctac aacatagatc atatcattgc tactttgact tagcatttgc   3420
atcataaaca taattatgat gttttttttca tgctcccttc caggggctca gtcacttgaa   3480
gaaactgttg ctaaccaagc tcttgactct gtttccctta atgatacaag tctctgtacc   3540
agcgctttat gttaattacc aaaactctcc tgcatcagag catgatatct ataataggag   3600
atactgcaat aaaatgatta ggctgtaaaa tttggagaca caatttttca ttacaatgca   3660
atttgcatgt gcacatgtgc gcacataact ttatatgtta gttctttttt ccaaactccc   3720
aactcttaaa agtattgtag tctgttggtg cctcaactgt tggtaacttt tttttttaa   3780
atttacaact ttccacaact tgtttttgta ctttaaggtt tctcaattag aatatttcta   3840
gttgagctgt aatttgaatg cattgttctc agggctattt gtgctaaaag ctgaaatttc   3900
```

-continued attattttaa agctaattgc ctgaaaatat attggcagaa ttttcccaaa ttgtaataac 3960
tgtgatacat gcatataaaa aaatccttaa tgtcaacaca cttaaactac atgctaaata 4020
gtcaagaaaa aaatggaaac agtagcatcc atactggaat cttgccatat ttttttcatt 4080
ttagaataga ttttggcagt ctcatcttag aatcctatcc ttaggataca tctgaaagca 4140
ttcctttggc atggacccca gagatagttt tggagccagg cattgatgta gaggttcacc 4200
aaacatattt agggataata gataaattca taatgctttt ttgggtacac tgaaatgttt 4260
acatactgaa ttctgtaata tgaactagga acgcatttac tatgagaaaa tatggctctt 4320
aagcagtgta agagtgaaaa tataagcata tttccattaa cagtatattg tactgatcag 4380
cagctctcat tttaacatca gttaggcata atatttcata gttttcaagc cttttttttc 4440
tgctaacatt cagacaagta acaggcaaca aagatttaag aaaaatttat ggtggaaaac 4500
cttaaaaatt gagacaattc aatctattta atctattaaa tttttctct gaattgggta 4560 tatggcatca ttatttgatt ttagcaggga acatttggat ttagcttatg aaacacagat 4620
gttctatggg aacatggctt gaagccaata tgtaatttaa tgtttttcca ttaaacaaac 4680
atctgaacac caacttagct accaagtgag gtcaagtgcc tgaaaagtac tgtatacatc 4740
taataagcat gttttcctta tgtaaaagat gcactttatg gcaatgcata ccaggctttc 4800
acctgctaga aacatacttg ttgccaactt tgccatctac cactattctc ctccttagaa 4860
caggtagaaa cctattttac aaaaaaaaaa aaaaaaaaaa aaagacaggt tattgtattt 4920
atatgaagtc cctaaaactg tttcttggta ttgatagact taagtttatc ttagttcaag 4980
attgcacttt ttaaaaaact ctggactatt ttcagcaatg accgaacagc ttgtcacaca 5040
tcatagttgt gatctttttt gaggagttat ttattgtggt taatatctac tataaataag 5100
cattcttgtg cttgttacaa agcataatgc aaattactag ttctatacta gtataatgaa 5160
aatgactagt tctatactgt tatgtacttt tgtcttcctc cccaaaaagg aaacagttta 5220
gcattgtcta aattcagtgg cactttttta gtaatacatt ttttttcttt agatacagga 5280
gaactattgc ttttacctgc agaaactcaa atgttttcgc taaaacttta aaattctaaa 5340
atacgtagta tgggtattac taattgtaca ttttacattt caaaaatagt taaaattcaa 5400
atgttaagtc tttgacttaa aaaaccttta aatatagata ataccttaac aattataact 5460
ttgtgatatt attaaaatat atttgtctgt taacttcatc agttgtatta aataaaaata 5520
gttaacagct tgcacta 5537

<210> SEQ ID NO 53
<211> LENGTH: 1444
<212> TYPE: DNA
<213> ORGANISM: Homo sapiens

<400> SEQUENCE: 53
tttcattttg ggccgagctg gaggcggcgg ggccgtcccg gaacggctgc ggccgggcac 60
cccgggagtt aatccgaaag cgccgcaagc cccgcgggcc ggccgcaccg cacgtgtcac 120
cgagaagctg atgtagagag agacacagaa ggagacagaa agcaagagac cagagtcccg 180
ggaaagtcct gccgcgcctc gggacaatta taaaaatgtg gccccctggg tcagcctccc 240
agccaccgcc ctcacctgcc gcggccacag gtctgcatcc agcggctcgc cctgtgtccc 300
tgcagtgccg gctcagcatg tgtccagcgc gcagcctcct ccttgtggct accctggtcc 360
tcctggacca cctcagtttg gccagaaacc tccccgtggc cactccagac ccaggaatgt 420
tcccatgcct tcaccactcc caaaacctgc tgagggccgt cagcaacatg ctccagaagg 480

```
ccagacaaac tctagaattt taccccttgca cttctgaaga gattgatcat gaagatatca    540
caaaagataa aaccagcaca gtggaggcct gtttaccatt ggaattaacc aagaatgaga    600
gttgcctaaa ttccagagag acctctttca taactaatgg gagttgcctg gcctccagaa    660
agacctcttt tatgatggcc ctgtgcctta gtagtattta tgaagacttg aagatgtacc    720
aggtggagtt caagaccatg aatgcaaagc ttctgatgga tcctaagagg cagatctttc    780
tagatcaaaa catgctggca gttattgatg agctgatgca ggccctgaat ttcaacagtg    840
agactgtgcc acaaaaatcc tcccttgaag aaccggattt ttataaaact aaaatcaagc    900
tctgcatact tcttcatgct ttcagaattc gggcagtgac tattgataga gtgatgagct    960
atctgaatgc ttcctaaaaa gcgaggtccc tccaaaccgt tgtcattttt ataaaacttt   1020
gaaatgagga aactttgata ggatgtggat taagaactag ggaggggggaa agaaggatgg   1080
gactattaca tccacatgat acctctgatc aagtattttt gacatttact gtggataaat   1140
tgtttttaag ttttcatgaa tgaattgcta agaagggaaa atatccatcc tgaaggtgtt   1200
tttcattcac tttaatagaa gggcaaatat ttataagcta tttctgtacc aaagtgtttg   1260
tggaaacaaa catgtaagca taacttattt taaaatattt atttatataa cttggtaatc   1320
atgaaagcat ctgagctaac ttatatttat ttatgttata tttattaaat tatttatcaa   1380
gtgtatttga aaaatatttt taagtgttct aaaaataaaa gtattgaatt aaagtgaaaa   1440
aaaa                                                                1444
```

<210> SEQ ID NO 54
<211> LENGTH: 3189
<212> TYPE: DNA
<213> ORGANISM: Homo sapiens

<400> SEQUENCE: 54

```
agcgggcggg actgccgggt gatgagatac tcggtcggcg acggtagaac gggcgacggc     60
gacaaccgca atcacatcca cgacggtgat catggcagag aatcacgccc agaataaagc    120
caagctcatc tctgagaccc ggaggaggtt cgaagctgag tatgtgacag ataagtcaga    180
taaatatgat gcacgtgatg ttgaaaggct acaacaagat gataactggg ttgaaagtta    240
cttatcttgg agacataata ttgtagatga aacactgaag atgctcgatg agagttttca    300
gtggaggaaa gaaatttctg tcaatgacct taatgaatcc tccattccca gatggttatt    360
ggaaattggt gttatttatc tccatggtta tgacaaagaa ggtaacaaat tgttctggat    420
cagggtgaag tatcatgtaa aagaccagaa aaccatattg gacaaaaaga agctcatagc    480
attctggttg gaacgttatg ctaagaggga aaatgggaaa cctgtaacag tgatgtttga    540
cctgtcagaa actggaataa atagcattga catggacttt gtacgcttta tcatcaactg    600
ctttaaggtt tattacccta aatacctctc aaaaatagtg atctttgata tgccttggtt    660
aatgaatgct gctttcaaaa ttgtgaaaac ctggcttggt ccagaagcag tgagcttgtt    720
gaagtttaca agcaaaaatg aagtccagga ctatgtcagt gtagaatacc tgcctcccca    780
catgggtgga actgatcctt tcaagtatag ctatccacca ctagtagatg atgacttcca    840
gaccccactg tgtgagaatg ggcctattac cagtgaggat gaaacttcaa gtaaagaaga    900
catagaaagt gatggcaaag aaacattgga aacaatttct aatgaagaac aaacacctct    960
tcttaaaaag attaacccaa ccgaatctac ttccaaagca gaagaaaatg aaaaagttga   1020
ttcaaaagtg aaagctttca agaaaccatt gagtgtattt aaaggcccct tactacacat   1080
```

-continued

```
cagcccagca gaagaactgt actttggaag tacagaatcc ggagagaaga aaaccttaat   1140

agtgttgaca aatgtaacta aaaatatagt ggcatttaag gtgagaacaa cagctccaga   1200

aaaatacaga gtcaagccaa gcaatagcag ctgtgacccg ggtgcatcag tggatatagt   1260

tgtgtctccc catgggggtt taacagtctc tgcccaagac cgttttctga taatggctgc   1320

agaaatggaa cagtcatctg gcacaggccc agcagaatta actcagtttt ggaaagaagt   1380

tcccagaaac aaagtgatgg aacataggtt aagatgccat actgttgaaa gcagtaaacc   1440

aaacactctt acgttaaaag acaatgcttt caatatgtca gataaaacca gtgaagatat   1500

atgtctacaa ctcagtcgtt tactagaaag caataggaag cttgaagacc aagttcagcg   1560

ttgtatctgg ttccagcagc tgctgctttc cttaacaatg ctcttgcttg cttttgtcac   1620

ctctttcttc tatttattgt acagttaaag aagtggtgcc gggtaggaac cacggttcct   1680

tcgtccatta gttggaaaaa gtaacagacc taaaactcta ccaagctact aaaaacattg   1740

cacatctgtg cttcctaaaa ggaaatatgc agcacgtgga ggggaacaca tacatgtctt   1800

gaaaataaac tgctagaata aagaaatgct ggagaaattg attataagag actatagcta   1860

tttagtaaag taagtaaagg catatccatt gtgtaaatta atagtttaaa tataatttat   1920

tttttccttt tgatctgaat acttttaaag cttaagtttt atcgtgtaaa tacattagct   1980

aaactgaaaa gtataagtaa catgctttgt tgcagccaaa aaatgtaatc tgcttttta    2040

tgacagaatt attatagctg agctgactta ctagcttttc tatactatgt atatagaaga   2100

acatgtatat tgagaaagaa aacatactta tatagaggaa tttatgtaac catgactttg   2160

taattttgag aattcctccc agtgatggtc agtattcttt tggaatgtaa accgatttaa   2220

tgccaaacca ccttaacctt tgtttctcag tgttccttaa cagcctgcct tttattaatc   2280

tcaggttttt ttatgaacac tctcatttca gtagaatttg gaaaactaag cgtggttgga   2340

atttctttga attctgttag taatgcccaa aagaaaagtc tcaagcagtc cccctatcca   2400

gtcattttta tggagtttca tgttgtccac tatagctgga cactgaacct tttgcctaat   2460

ttattataaa ggcctgaccc tctattgtcc catcttcacc cccattccag agcagaggag   2520

tctctgtgga ccatgaattg cactgtctcc ctcctcattt ctaaatgaaa ggtattagat   2580

ataaattttt ttgaaaggtt agttgtttga gatgctaagc aggataataa atttagattt   2640

taaaatgttc cctgtaaaag tcagcccatg acaaggaaat ttacaaaata ctagagtatc   2700

tagaagggtg aaaacaaaaa aaaataaaaa gaaacacaga cgcccaggtg tcagctctcc   2760

gtttaaagaa tgaaaaatgt aactcatgat gatctgtgaa accttcaaac taggaccaat   2820

tgacttactt gatattctgc ctttgatatg gtagtaccca cccggtattc ctaaaatcct   2880

aaaaagatac accttgcagt agcagaggca atgacatgag tttgttttct cattaatatg   2940

accagtttgg gtctatgttg gttcacatgt acatctactt tatatgaaag aaaaaacagt   3000

tgtctgcctg taaaatgttg agtttcgatt gagccatgtt tggagatttt attactattc   3060

tgaagggtag tgttgttggt tttcatcttc aagaagttga ttccaaaact gagttatgaa   3120

gaatgatata acagttcctt caaaattggc ctaggaaata aaaccttaaa aggaaaaaaa   3180

aaaaaaaaa                                                            3189
```

<210> SEQ ID NO 55
<211> LENGTH: 2266
<212> TYPE: DNA
<213> ORGANISM: Homo sapiens

<400> SEQUENCE: 55

-continued

```
agcggagcag tagccaccac tccgccgagg ccgcaacccc ggctcggcct ccccaggccc     60
cgccgctgcc gcagtcatgg ctgctgatgg ggtggacgaa cgctcgcctc tgctgtcagc    120
atcccactcc ggaaatgtca ctcccaccgc cccaccgtac ttgcaagaaa gcagccccag    180
agcggagctc ccacctccat atacagccat tgccagtcca gacgccagtg gtattccagt    240
aataaactgc cgtgtgtgcc aatcactaat caatttggat ggcaagcttc accagcatgt    300
ggttaagtgc acagtttgca atgaagctac gccaatcaaa aaccccccaa caggcaagaa    360
atatgttaga tgcccttgta attgtcttct catttgtaag gacacatctc ggcgaatagg    420
atgcccaaga cccaactgta gacggataat taaccttggc ccagtaatgc ttatttctga    480
agaacaacca gctcagcctg cattgccaat ccaaccagaa ggtacaaggg tcgtgtgtgg    540
gcactgtgga aacacattcc tgtggatgga actgaggttc aacactctgg caaaatgccc    600
acactgcaaa aaaatctcct cagtgggtag tgcacttcca cgaagacgct gctgtgcata    660
tattaccatt ggaatgatat gtattttcat tggagttggg ttaactgttg gcaccccaga    720
ttttgcaagg cgatttcgag caacctatgt ttcttgggca attgcttatc tcctaggatt    780
gatctgcctt atccgagctt gttattgggg agccataaga gtcagttatc cagaacacag    840
ttttgcataa gcttgtttat gattcagtaa tgcaggtgag agtgtctagc agttcttggt    900
aagctactct ggacatcttt aaattattta tcctaatgga ttccattctg gtttatgtat    960
aatcgtttca agactttggg agtcttttat gaacaaatgc tcattgcact atattatatg   1020
caaattgttt tgctgctagg ttttcaaaat ttgaataata aagccttttc atgttctttt   1080
acatctctta tagatatttt tggatttgtt accaaacatt acatttactc tcaccctttt   1140
attattttta aataagttat ttcattactt gctgatacat gagtattcct aagtgtttat   1200
aaatatttct ataatagttt cacatttata tttacatttt aattaaacag tatcaaaatt   1260
gcttgcttaa aacctaagca atatgcattt tgcttgaact gcttactgta actttaacct   1320
aagattatag tgaccttatt caggaaaaaa aaaaaattta gtgtaacttc aaagacttga   1380
cattcttgtc agaggaaaaa aaatttctag atactgtttg cttgtttttt gttgtttgta   1440
gaaagataaa atattttggt aataatttaa aatacaagaa cgaatattta tttgtccaca   1500
gttggagatg ttggataaat gtcttttctc aaagatcaca ggacttttgt ctttcatttt   1560
tgccttttta tttaccattt ataaaagatc tggtctggat tatggaattt aatgtttatc   1620
agctctatgt attcctttat agaggcttga ggaagtattt cacataacat gttttataat   1680
acttaaccat ttatccaaag atatatttac attgggttgt gccccttcc cttagatcat    1740
ggtaaatttt tcttattgag gtaattatgt actacttata tttgaaggaa gcttatgaca   1800
ttttacagta gctaaaatgt tgagattaga ggtactttta ctattcttct caaaggtaac   1860
tgatcagata attacccaaa ttattcaaga aaatagatca gaaataaaga acaacataat   1920
tttctaagaa ttcattgaaa tttatggaat cagctctcgc actgcccatc tttgcagttt   1980
tgaaaaagaa attgcttaat cacaaatgtt ctacagtctt taaatgtagt agaattagac   2040
agtgagatca tctgagtaaa ttgattggtg attccagaga taagactaat attttaaatt   2100
atttatgata ctgattagta taaaaacgta ctcatcacag aatttgaagc aaaatacatg   2160
tacacttcaa agagtaaatg acaaatgtat aaatgctgta gctcaggatt atatgtacct   2220
ttaaaaatac actaataaag attattgttc aaaaaaaaaa aaaaaa                  2266
```

<210> SEQ ID NO 56

<211> LENGTH: 3234
<212> TYPE: DNA
<213> ORGANISM: Homo sapiens

<400> SEQUENCE: 56
gtttgcattt ctaatgacag tgaactgaca aagcgtgaaa gtggtctaag gagcaaaaca 60
aagccagcaa gcctgcttct ggtgtgccaa gattaatcaa tattccagaa acctcgggtt 120
tcccctcctc cctgtgcggt ttccattccc cactcctcct ttcccgggca cagactcctc 180
cctctcttct taagttgccc tgatagtaac ttgcagtttc agagcacatg cacactgtca 240
ggctagcctg cctgcttacg cgcgctgcgg attgttgctc cgttgtacct gctgggaatt 300
cacctcgtta ctgcttgata tcttccaccc cttacaaaat cagaaaaggt aagtgtcaca 360
ttctgtgttc ctgctgggtt taatttctcc tttcacttct ctgccgatgt atttgccttc 420
caagcagagg agtagcctga atcaaggcta gccattttgg tagataaagt ccttgttagt 480
catctcacgt cgtgagagtg tggtgctgtt tatgccggtc gctgttaatt cggagttgag 540
tcattcgggg tggattgggg gcagattgtg gcgcgagatc tagaaaaagg atcaaggttg 600
agcggatctg cttaaaagtg actggtaaga ggaatcagag ctattagttt aaaaaaaaaa 660
aaattccttg ggtccttcct tcccttattt cccggtcttc cacttctccc taagcattta 720
atccagtgtg aagtcttaaa caaattagaa gtcttagtat cactgacccc aacttgcaat 780
tttatttaaa aggcaaactg ttaagacaag tctttttttt tcctgcactg ggattgcgag 840
aagtcatttg cgaggagtcc tttggtttcc agttacctcc ccacaggcgc acacgctggc 900
tgcttgcgtt ggcagcgaca cacatccatg gtacggctgg ttttcactcg gattgattat 960
gggaagggct atggattaga gctcctgtaa agcaccaagg aggaatccct tgatttttca 1020
gaacagctga tttccaccag gaaagagatt tactgaaatg tagttaaata gcgtgagtgc 1080
tttaaagaaa ccagaaacca caagctgtaa tgtttggaat gaaaattggt ttcatctcat 1140
ctgttctaga aatcctaaat tttaaaacgc taaaaagtca gcgatagttt ctcggaagat 1200
tccagcatgt gtgtcacaaa gaaaaacact acttcatact tctacttgtg ataaacgaag 1260
ctgaattgtg atttcagatg atttatagat gtgcccagag cactttgctt atttcatgga 1320
aaaaaaatga aaaaattacc ctgtaaaata gtcacatgta tttcccatgt actgtgggca 1380
cttgtgttct ttttatgacc atatttacta gtagatatta ttatattttt tcttaatgaa 1440
gaaaatagct ggttacttta ctgcatgtaa cagagacaac tcccacctat cagtatctta 1500
attattttta ttgacctggt tatgctttca accatgtata cagcataatt tgtcaagtaa 1560
tgattgaata ctttctgtgc attcagttca attggacatt tactgattgt gtacgttgtg 1620
caaggcatca gctgggttct gcgggggagg gtgggaatag gggttctcag tcagatctag 1680
ctctgaagaa ccccttttata gcctcattgg aaggggaagg acggattttt aaaaagaaaa 1740
tagaatatat tccgaattta tgcacatttc tcacacgtgg tccactaaaa tatgcacact 1800
gcaaccttga ggtctggtat tgtggctctc cagtccttga ttcctgctga gattatgcaa 1860
tttgccaaga gcttgcctgg tgtggagcag cactgatttc tcacccctgg aggctataac 1920
tcatgtctct ttttctccca ttctagttgt gttttctaat accaaagagg aggtttggct 1980
ttctgtgggt gattcccaga cactgaagtg caaagaagag accctcctag aaaagtaaaa 2040
tatgactaaa agcaatggag aagagcccaa gatggggggc aggatggaga gattccagca 2100
gggagtccgt aaacgcacac ttttggccaa gaagaaagtg cagaacatta caaaggagga 2160
tgttaaaagt tacctgtttc ggaatgcttt tgtgctgctc acagtcaccg ctgtcattgt 2220

-continued

```
gggtgagtca tttgattaaa aacaaaaaaa cctgtatctt gtttctctgg ggcatctggc   2280

tgcccgggga atattatcag atgaactagt tgtaggtatc aaaatggtag cctaggcttt   2340

cctctgaact tgatgatttt tctccataaa aatgactgtt ttggcttgtt tggagcaata   2400

tatagtaaac acatcattag gcatcattag gcatcattag gcattatgca aatcaattgt   2460

gtgaggaaga aaataaataa aatattttcc catttcatgt aaggataagg aagtgatcat   2520

ttaatcatta ggcatgacaa agcaagcatg ctagatttgg ccaaaatgta attatataca   2580

atgtcagttg cacttaaaac taatttatac aattagtaca cctaaaatga catgttggtt   2640

ccaaatagta attatattct aactggtgct gacttgaagc tgagtatcaa cgcttaggca   2700

cagagaccga atattttatg tgtttgcact ctctcaccca gcaactggga aaggtagatt   2760

ggggaaaatg ttaacacaga tctctttcat tcattgcttt gcagagcctg ccataaccag   2820

ctatacettt ttttgaatca tttccatctc ttactaattt agcagggttg acagcaatct   2880

gtactaataa aatattattg ttttgttttg tttattgatc ttaaaagtta tagtttatta   2940

cttatgggtg gcattgatcc tactttaaaa tatagctgaa aaaacctact tatttggaat   3000

tttgaccaac caatacagaa tccttagatt gacaacatat acgccaatgc caggttgtaa   3060

atattccaac ttaacctacc aatttgccac caaaaaagag gcattcagta ccgttttaat   3120

ctctactttg gagtttgcca agatttccat caactttaaa gaggtaatga tttaataaag   3180

attaagaaaa ttctgtagtg tgtaaatata actttttca agaaaattga attc          3234
```

<210> SEQ ID NO 57
<211> LENGTH: 3331
<212> TYPE: DNA
<213> ORGANISM: Homo sapiens

<400> SEQUENCE: 57

```
cagagggcac cgcccaggcc tcggaaggtg tcagggagaa ctttccgtgg tttcagcgtc     60

gtcgcctgga gcggcggttt agagagccga gcctgatggg cgccaaggcc ggctggctgc    120

ttggagcgct gcctcgaagg gactgcgtaa ggaagctaat ccggagaacc caggccagag    180

cctgaaatat ggcgacctgc atcggggaga agatcgagga ttttaaagtt ggaaatctgc    240

ttggtaaagg atcatttgct ggtgtctaca gagctgagtc cattcacagt ggtttggaag    300

ttgcaatcaa aatgatagat aagaaagcca tgtacaaagc aggaatggta cagagagtcc    360

aaaatgaggt gaaaatacat tgccaattga aacatccttc tatcttggag ctttataact    420

attttgaaga tagcaattat gtgtatctgg tattagaaat gtgccataat ggagaaatga    480

acaggtatct aaagaataga gtgaaaccct tctcagaaaa tgaagctcga cacttcatgc    540

accagatcat cacagggatg ttgtatcttc attctcatgg tatactacac cgggacctca    600

cactttctaa cctcctactg actcgtaata tgaacatcaa gattgctgat tttgggctgg    660

caactcaact gaaaatgcca catgaaaagc actatacatt atgtggaact cctaactaca    720

tttcaccaga aattgccact cgaagtgcac atggccttga atctgatgtt tggtccctgg    780

gctgtatgtt ttatacatta cttatcggga gaccaccctt cgacactgac acagtcaaga    840

acacattaaa taaagtagta ttggcagatt atgaaatgcc aactttttttg tcaatagagg    900

ccaaggacct tattcaccag ttacttcgta gaaatccagc agatcgttta agtctgtctt    960

cagtattgga ccatcctttt atgtcccgaa attcttcaac aaaaagtaaa gatttaggaa   1020

ctgtggaaga ctcaattgat agtgggcatg ccacaatttc tactgcaatt acagcttctt   1080
```

-continued

```
ccagtaccag tataagtggt agtttatttg acaaaagaag acttttgatt ggtcagccac   1140
tcccaaataa aatgactgta tttccaaaga ataaaagttc aactgatttt tcttcttcag   1200
gagatggaaa cagtttttat actcagtggg gaaatcaaga aaccagtaat agtggaaggg   1260
gaagagtaat tcaagatgca gaagaaaggc cacattctcg ataccttcgt agagcttatt   1320
cctctgatag atctggcact tctaatagac agtctcaagc aaaaacatat acaatggaac   1380
gatgtcactc agcagaaatg ctttcagtgt ccaaaagatc aggaggaggt gaaaatgaag   1440
agaggtactc acccacagac aacaatgcca acatttttaa cttctttaaa gaaaagacat   1500
ccagtagttc tggatctttt gaaagacctg ataacaatca agcactctcc aatcatcttt   1560
gtccaggaaa aactcctttt ccatttgcag acccgacacc tcagactgaa accgtacaac   1620
agtggtttgg gaatctgcaa ataaatgctc atttaagaaa aactactgaa tatgacagca   1680
tcagcccaaa ccgggacttc cagggccatc cagatttgca gaaggacaca tcaaaaaatg   1740
cctggactga tacaaaagtc aaaaagaact ctgatgcttc tgataatgca cattctgtaa   1800
aacagcaaaa taccatgaaa tatatgactg cacttcacag taaacctgag ataatccaac   1860
aagaatgtgt ttttggctca gatcctcttt ctgaacagag caagactagg ggtatggagc   1920
caccatgggg ttatcagaat cgtacattaa gaagcattac atctccgttg gttgctcaca   1980
ggttaaaacc aatcagacag aaaaccaaaa aggctgtggt gagcatactt gattcagagg   2040
aggtgtgtgt ggagcttgta aaggagtatg catctcaaga atatgtgaaa gaagttcttc   2100
agatatctag tgatggaaat acgatcacta tttattatcc aaatggtggt agaggttttc   2160
ctcttgctga tagaccaccc tcacctactg acaacatcag taggtacagc tttgacaatt   2220
taccagaaaa atactggcga aaatatcaat atgcttccag gtttgtacag cttctaagat   2280
ctaaatctcc caaaatcact tattttacaa gatatgctaa atgcattttg atggagaatt   2340
ctcctggtgc tgattttgag gtttggtttt atgatggggt aaaaatacac aaaacagaag   2400
atttcattca ggtgattgaa aagacaggga agtcttacac tttaaaaagt gaaagtgaag   2460
ttaatagctt gaaagaggag ataaaaatgt atatggacca tgctaatgag ggtcatcgta   2520
tttgtttagc actggaatcc ataatttcag aagaggaaag gaaaactagg agtgctccct   2580
ttttcccaat aatcatagga agaaaacctg gtagtactag ttcacctaag gccttatcac   2640
ctcctccttc tgtggattca aattacccaa cgagagatag agcatctttc aacagaatgg   2700
tcatgcatag tgatgcttct ccaacacagg caccaatcct taatccctct atggttacaa   2760
atgaaggact tggtcttaca actacagctt ctggaacaga catctcttct aatagtctaa   2820
aagattgtct tcctaaatca gcacaacttt tgaaatctgt ttttgtgaaa aatgttggtt   2880
gggctacaca gttaactagt ggagctgtgt gggttcagtt taatgatggg tcccagttgg   2940
ttgtgcaggc aggagtgtct tctatcagtt atacctcacc aaatggtcaa acaactaggt   3000
atggagaaaa tgaaaaatta ccagactaca tcaaacagaa attacagtgt ctgtcttcca   3060
tccttttgat gttttctaat ccgactccta attttcattg attaaaactc ctttcagaca   3120
tataagttta ataaataact tttttgttga ctttcaagta aagtgatttt ttttaattta   3180
acataaagtc ttcagaaagc ctttctatga aagaatttta acctataatg taaaccatgt   3240
atctgagata acaaagcaga atgaaacttg agtcacttac taaatatagt ggatataaaa   3300
tagaacacct gactttgctc ttagaccata a                                  3331
```

<210> SEQ ID NO 58
<211> LENGTH: 3007

<212> TYPE: DNA
<213> ORGANISM: Homo sapiens

<400> SEQUENCE: 58

```
gcccggagag ccgcatctat tggcagcttt gttattgatc agaaactgct cgccgccgac     60
ttggcttcca gtctggctgc gggcaaccct tgagttttcg cctctgtcct gtcccccgaa    120
ctgacaggtg ctcccagcaa cttgctgggg acttctcgcc gctcccccgc gtccccaccc    180
cctcattcct ccctcgcctt cacccccacc cccaccactt cgccacagct caggatttgt    240
ttaaaccttg ggaaactggt tcaggtccag gttttgcttt gatccttttc aaaaactgga    300
gacacagaag agggctctag gaaaaagttt tggatgggat tatgtggaaa ctaccctgcg    360
attctctgct gccagagcag gctcggcgct tccaccccag tgcagccttc ccctggcggt    420
ggtgaaagag actcgggagt cgctgcttcc aaagtgcccg ccgtgagtga gctctcaccc    480
cagtcagcca aatgagcctc ttcgggcttc tcctgctgac atctgccctg gccggccaga    540
gacaggggac tcaggcggaa tccaacctga gtagtaaatt ccagttttcc agcaacaagg    600
aacagaacgg agtacaagat cctcagcatg agagaattat tactgtgtct actaatggaa    660
gtattcacag cccaaggttt cctcatactt atccaagaaa tacggtcttg gtatggagat    720
tagtagcagt agaggaaaat gtatggatac aacttacgtt tgatgaaaga tttgggcttg    780
aagacccaga agatgacata tgcaagtatg attttgtaga agttgaggaa cccagtgatg    840
gaactatatt agggcgctgg tgtggttctg gtactgtacc aggaaaacag atttctaaag    900
gaaatcaaat taggataaga tttgtatctg atgaatattt tccttctgaa ccagggttct    960
gcatccacta caacattgtc atgccacaat tcacagaagc tgtgagtcct tcagtgctac   1020
ccccttcagc tttgccactg gacctgctta ataatgctat aactgccttt agtaccttgg   1080
aagaccttat tcgatatctt gaaccagaga gatggcagtt ggacttagaa gatctatata   1140
ggccaacttg gcaacttctt ggcaaggctt ttgtttttgg aagaaaatcc agagtggtgg   1200
atctgaacct tctaacagag gaggtaagat tatacagctg cacacctcgt aacttctcag   1260
tgtccataag ggaagaacta aagagaaccg ataccatttt ctggccaggt tgtctcctgg   1320
ttaaacgctg tggtgggaac tgtgcctgtt gtctccacaa ttgcaatgaa tgtcaatgtg   1380
tcccaagcaa agttactaaa aaataccacg aggtccttca gttgagacca aagaccggtg   1440
tcaggggatt gcacaaatca ctcaccgacg tggccctgga gcaccatgag gagtgtgact   1500
gtgtgtgcag agggagcaca ggaggatagc cgcatcacca ccagcagctc ttgcccagag   1560
ctgtgcagtg cagtggctga ttctattaga gaacgtatgc gttatctcca tccttaatct   1620
cagttgtttg cttcaaggac ctttcatctt caggatttac agtgcattct gaaagaggag   1680
acatcaaaca gaattaggag ttgtgcaaca gctcttttga gaggaggcct aaaggacagg   1740
agaaaaggtc ttcaatcgtg gaaagaaaat taaatgttgt attaaataga tcaccagcta   1800
gtttcagagt taccatgtac gtattccact agctgggttc tgtatttcag ttctttcgat   1860
acggcttagg gtaatgtcag tacaggaaaa aaactgtgca agtgagcacc tgattccgtt   1920
gccttgctta actctaaagc tccatgtcct gggcctaaaa tcgtataaaa tctggatttt   1980
tttttttttt tttgctcata ttcacatatg taaaccagaa cattctatgt actacaaacc   2040
tggtttttaa aaaggaacta tgttgctatg aattaaactt gtgtcgtgct gataggacag   2100
actggatttt tcatatttct tattaaaatt tctgccattt agaagaagag aactacattc   2160
atggtttgga agagataaac ctgaaaagaa gagtggcctt atcttcactt tatcgataag   2220
```

-continued

```
tcagtttatt tgtttcattg tgtacatttt tatattctcc ttttgacatt ataactgttg   2280

gcttttctaa tcttgttaaa tatatctatt tttaccaaag gtatttaata ttcttttta    2340

tgacaactta gatcaactat ttttagcttg gtaaattttt ctaaacacaa ttgttatagc   2400

cagaggaaca aagatgatat aaaatattgt tgctctgaca aaaatacatg tatttcattc   2460

tcgtatggtg ctagagttag attaatctgc attttaaaaa actgaattgg aatagaattg   2520

gtaagttgca aagacttttt gaaaataatt aaattatcat atcttccatt cctgttattg   2580

gagatgaaaa taaaaagcaa cttatgaaag tagacattca gatccagcca ttactaacct   2640

attccttttt tggggaaatc tgagcctagc tcagaaaaac ataaagcacc ttgaaaaaga   2700

cttggcagct tcctgataaa gcgtgctgtg ctgtgcagta ggaacacatc ctatttattg   2760

tgatgttgtg gttttattat cttaaactct gttccataca cttgtataaa tacatggata   2820

tttttatgta cagaagtatg tctcttaacc agttcactta ttgtactctg gcaatttaaa   2880

agaaaatcag taaaatattt tgcttgtaaa atgcttaata tcgtgcctag gttatgtggt   2940

gactatttga atcaaaaatg tattgaatca tcaaataaaa gaatgtggct attttgggga   3000

gaaaatt                                                             3007
```

<210> SEQ ID NO 59
<211> LENGTH: 1002
<212> TYPE: PRT
<213> ORGANISM: Homo sapiens

<400> SEQUENCE: 59

```
Met Ala Ala His Glu Trp Asp Trp Phe Gln Arg Glu Glu Leu Ile Gly
 1               5                  10                  15

Gln Ile Ser Asp Ile Arg Val Gln Asn Leu Gln Val Glu Arg Glu Asn
            20                  25                  30

Val Gln Lys Arg Thr Phe Thr Arg Trp Ile Asn Leu His Leu Glu Lys
        35                  40                  45

Cys Asn Pro Pro Leu Glu Val Lys Asp Leu Phe Val Asp Ile Gln Asp
    50                  55                  60

Gly Lys Ile Leu Met Ala Leu Leu Glu Val Leu Ser Gly Arg Asn Leu
65                  70                  75                  80

Leu His Glu Tyr Lys Ser Ser Ser His Arg Ile Phe Arg Leu Asn Asn
                85                  90                  95

Ile Ala Lys Ala Leu Lys Phe Leu Glu Asp Ser Asn Val Lys Leu Val
            100                 105                 110

Ser Ile Asp Ala Ala Glu Ile Ala Asp Gly Asn Pro Ser Leu Val Leu
        115                 120                 125

Gly Leu Ile Trp Asn Ile Ile Leu Phe Phe Gln Ile Lys Glu Leu Thr
    130                 135                 140

Gly Asn Leu Ser Arg Asn Ser Pro Ser Ser Ser Leu Ser Pro Gly Ser
145                 150                 155                 160

Gly Gly Thr Asp Ser Asp Ser Ser Phe Pro Pro Thr Pro Thr Ala Glu
                165                 170                 175

Arg Ser Val Ala Ile Ser Val Lys Asp Gln Arg Lys Ala Ile Lys Ala
            180                 185                 190

Leu Leu Ala Trp Val Gln Arg Lys Thr Arg Lys Tyr Gly Val Ala Val
        195                 200                 205

Gln Asp Phe Ala Gly Ser Trp Arg Ser Gly Leu Ala Phe Leu Ala Val
    210                 215                 220

Ile Lys Ala Ile Asp Pro Ser Leu Val Asp Met Lys Gln Ala Leu Glu
```

```
225                 230                 235                 240

Asn Ser Thr Arg Glu Asn Leu Glu Lys Ala Phe Ser Ile Ala Gln Asp
                245                 250                 255

Ala Leu His Ile Pro Arg Leu Leu Glu Pro Glu Asp Ile Met Val Asp
            260                 265                 270

Thr Pro Asp Glu Gln Ser Ile Met Thr Tyr Val Ala Gln Phe Leu Glu
        275                 280                 285

Arg Phe Pro Glu Leu Glu Ala Glu Asp Ile Phe Asp Ser Asp Lys Glu
    290                 295                 300

Val Pro Ile Glu Ser Thr Phe Val Arg Ile Lys Glu Thr Pro Ser Glu
305                 310                 315                 320

Gln Glu Ser Lys Val Phe Val Leu Thr Glu Asn Gly Glu Arg Thr Tyr
                325                 330                 335

Thr Val Asn His Glu Thr Ser His Pro Pro Pro Ser Lys Val Phe Val
            340                 345                 350

Cys Asp Lys Pro Glu Ser Met Lys Glu Phe Arg Leu Asp Gly Val Ser
        355                 360                 365

Ser His Ala Leu Ser Asp Ser Ser Thr Glu Phe Met His Gln Ile Ile
    370                 375                 380

Asp Gln Val Leu Gln Gly Gly Pro Gly Lys Thr Ser Asp Ile Ser Glu
385                 390                 395                 400

Pro Ser Pro Glu Ser Ser Ile Leu Ser Ser Arg Lys Glu Asn Gly Arg
                405                 410                 415

Ser Asn Ser Leu Pro Ile Lys Lys Thr Val His Phe Glu Ala Asp Thr
            420                 425                 430

Tyr Lys Asp Pro Phe Cys Ser Lys Asn Leu Ser Leu Cys Phe Glu Gly
        435                 440                 445

Ser Pro Arg Val Ala Lys Glu Ser Leu Arg Gln Asp Gly His Val Leu
    450                 455                 460

Ala Val Glu Val Ala Glu Glu Lys Glu Gln Lys Gln Glu Ser Ser Lys
465                 470                 475                 480

Ile Pro Glu Ser Ser Ser Asp Lys Val Ala Gly Asp Ile Phe Leu Val
                485                 490                 495

Glu Gly Thr Asn Asn Asn Ser Gln Ser Ser Ser Cys Asn Gly Ala Leu
            500                 505                 510

Glu Ser Thr Ala Arg His Asp Glu Glu Ser His Ser Leu Ser Pro Pro
        515                 520                 525

Gly Glu Asn Thr Val Met Ala Asp Ser Phe Gln Ile Lys Val Asn Leu
    530                 535                 540

Met Thr Val Glu Ala Leu Glu Glu Gly Asp Tyr Phe Glu Ala Ile Pro
545                 550                 555                 560

Leu Lys Ala Ser Lys Phe Asn Ser Asp Leu Ile Asp Phe Ala Ser Thr
                565                 570                 575

Ser Gln Ala Phe Asn Lys Val Pro Ser Pro His Glu Thr Lys Pro Asp
            580                 585                 590

Glu Asp Ala Glu Ala Phe Glu Asn His Ala Glu Lys Leu Gly Lys Arg
        595                 600                 605

Ser Ile Lys Ser Ala His Lys Lys Lys Asp Ser Pro Glu Pro Gln Val
    610                 615                 620

Lys Met Asp Lys His Glu Pro His Gln Asp Ser Gly Glu Glu Ala Glu
625                 630                 635                 640

Gly Cys Pro Ser Ala Pro Glu Glu Thr Pro Val Asp Lys Lys Pro Glu
                645                 650                 655
```

-continued

```
Val His Glu Lys Ala Lys Arg Lys Ser Thr Arg Pro His Tyr Glu Glu
            660                 665                 670

Glu Gly Glu Asp Asp Asp Leu Gln Gly Val Gly Glu Glu Leu Ser Ser
        675                 680                 685

Ser Pro Pro Ser Ser Cys Val Ser Leu Glu Thr Leu Gly Ser His Ser
    690                 695                 700

Glu Glu Gly Leu Asp Phe Lys Pro Ser Pro Pro Leu Ser Lys Val Ser
705                 710                 715                 720

Val Ile Pro His Asp Leu Phe Tyr Phe Pro His Tyr Glu Val Pro Leu
                725                 730                 735

Ala Ala Val Leu Glu Ala Tyr Val Glu Asp Pro Glu Asp Leu Lys Asn
            740                 745                 750

Glu Glu Met Asp Leu Glu Glu Pro Glu Gly Tyr Met Pro Asp Leu Asp
        755                 760                 765

Ser Arg Glu Glu Glu Ala Asp Gly Ser Gln Ser Ser Ser Ser Ser Ser
    770                 775                 780

Val Pro Gly Glu Ser Leu Pro Ser Ala Ser Asp Gln Val Leu Tyr Leu
785                 790                 795                 800

Ser Arg Gly Gly Val Gly Thr Thr Pro Ala Ser Glu Pro Ala Pro Leu
                805                 810                 815

Ala Pro His Glu Asp His Gln Gln Arg Glu Thr Lys Glu Asn Asp Pro
            820                 825                 830

Met Asp Ser His Gln Ser Gln Glu Ser Pro Asn Leu Glu Asn Ile Ala
        835                 840                 845

Asn Pro Leu Glu Glu Asn Val Thr Lys Glu Ser Ile Ser Ser Lys Lys
    850                 855                 860

Lys Glu Lys Arg Lys His Val Asp His Val Glu Ser Ser Leu Phe Val
865                 870                 875                 880

Ala Pro Gly Ser Val Gln Ser Ser Asp Asp Leu Glu Glu Asp Ser Ser
                885                 890                 895

Asp Tyr Ser Ile Pro Ser Arg Thr Ser His Ser Asp Ser Ser Ile Tyr
            900                 905                 910

Leu Arg Arg His Thr His Arg Ser Ser Glu Ser Asp His Phe Ser Tyr
        915                 920                 925

Val Gln Leu Arg Asn Ala Ala Asp Leu Asp Asp Arg Arg Asn Arg Ile
    930                 935                 940

Leu Thr Arg Lys Ala Asn Ser Ser Gly Glu Ala Met Ser Leu Gly Ser
945                 950                 955                 960

His Ser Pro Gln Ser Asp Ser Leu Thr Gln Leu Val Gln Gln Pro Asp
                965                 970                 975

Met Met Tyr Phe Ile Leu Phe Leu Trp Leu Leu Val Tyr Cys Leu Leu
            980                 985                 990

Leu Phe Pro Gln Leu Asp Val Ser Arg Leu
        995                 1000
```

<210> SEQ ID NO 60
<211> LENGTH: 108
<212> TYPE: PRT
<213> ORGANISM: Homo sapiens

<400> SEQUENCE: 60

```
Met Gly Val Glu Ile Glu Thr Ile Ser Pro Gly Asp Gly Arg Thr Phe
 1               5                  10                  15

Pro Lys Lys Gly Gln Thr Cys Val Val His Tyr Thr Gly Met Leu Gln
```

-continued

```
            20                  25                  30

Asn Gly Lys Lys Phe Asp Ser Ser Arg Asp Arg Asn Lys Pro Phe Lys
        35                  40                  45

Phe Arg Ile Gly Lys Gln Glu Val Ile Lys Gly Phe Glu Glu Gly Ala
    50                  55                  60

Ala Gln Met Ser Leu Gly Gln Arg Ala Lys Leu Thr Cys Thr Pro Asp
65                  70                  75                  80

Val Ala Tyr Gly Ala Thr Gly His Pro Gly Val Ile Pro Pro Asn Ala
                85                  90                  95

Thr Leu Ile Phe Asp Val Glu Leu Leu Asn Leu Glu
            100                 105


<210> SEQ ID NO 61
<211> LENGTH: 80
<212> TYPE: PRT
<213> ORGANISM: Homo sapiens

<400> SEQUENCE: 61

Met Gly Val Glu Ile Glu Thr Ile Ser Pro Gly Asp Gly Arg Thr Phe
 1               5                  10                  15

Pro Lys Lys Gly Gln Thr Cys Val Val His Tyr Thr Gly Met Leu Gln
            20                  25                  30

Asn Gly Lys Lys Phe Asp Ser Ser Arg Asp Arg Asn Lys Pro Phe Lys
        35                  40                  45

Phe Arg Ile Gly Lys Gln Glu Val Ile Lys Gly Phe Glu Glu Gly Ala
    50                  55                  60

Ala Gln Leu Gly Pro Leu Ser Pro Leu Pro Ile Cys Pro His Pro Cys
65                  70                  75                  80


<210> SEQ ID NO 62
<211> LENGTH: 1357
<212> TYPE: PRT
<213> ORGANISM: Homo sapiens

<400> SEQUENCE: 62

Met Glu Phe Tyr Glu Ser Ala Tyr Phe Ile Val Leu Ile Pro Ser Ile
 1               5                  10                  15

Val Ile Thr Val Ile Phe Leu Phe Phe Trp Leu Phe Met Lys Glu Thr
            20                  25                  30

Leu Tyr Asp Glu Val Leu Ala Lys Gln Lys Arg Glu Gln Lys Leu Ile
        35                  40                  45

Pro Thr Lys Thr Asp Lys Lys Lys Ala Glu Lys Lys Lys Asn Lys Lys
    50                  55                  60

Lys Glu Ile Gln Asn Gly Asn Leu His Glu Ser Asp Ser Glu Ser Val
65                  70                  75                  80

Pro Arg Asp Phe Lys Leu Ser Asp Ala Leu Ala Val Glu Asp Asp Gln
                85                  90                  95

Val Ala Pro Val Pro Leu Asn Val Val Glu Thr Ser Ser Ser Val Arg
            100                 105                 110

Glu Arg Lys Lys Lys Glu Lys Lys Gln Lys Pro Val Leu Glu Glu Gln
        115                 120                 125

Val Ile Lys Glu Ser Asp Ala Ser Lys Ile Pro Gly Lys Lys Val Glu
   130                 135                 140

Pro Val Pro Val Thr Lys Gln Pro Thr Pro Pro Ser Glu Ala Ala Ala
145                 150                 155                 160

Ser Lys Lys Lys Pro Gly Gln Lys Lys Ser Lys Asn Gly Ser Asp Asp
```

-continued

```
                165                 170                 175

Gln Asp Lys Lys Val Glu Thr Leu Met Val Pro Ser Lys Arg Gln Glu
            180                 185                 190

Ala Leu Pro Leu His Gln Glu Thr Lys Gln Glu Ser Gly Ser Gly Lys
        195                 200                 205

Lys Lys Ala Ser Ser Lys Lys Gln Lys Thr Glu Asn Val Phe Val Asp
    210                 215                 220

Glu Pro Leu Ile His Ala Thr Thr Tyr Ile Pro Leu Met Asp Asn Ala
225                 230                 235                 240

Asp Ser Ser Pro Val Val Asp Lys Arg Glu Val Ile Asp Leu Leu Lys
                245                 250                 255

Pro Asp Gln Val Glu Gly Ile Gln Lys Ser Gly Thr Lys Lys Leu Lys
            260                 265                 270

Thr Glu Thr Asp Lys Glu Asn Ala Glu Val Lys Phe Lys Asp Phe Leu
        275                 280                 285

Leu Ser Leu Lys Thr Met Met Phe Ser Glu Asp Glu Ala Leu Cys Val
    290                 295                 300

Val Asp Leu Leu Lys Glu Lys Ser Gly Val Ile Gln Asp Ala Leu Lys
305                 310                 315                 320

Lys Ser Ser Lys Gly Glu Leu Thr Thr Leu Ile His Gln Leu Gln Glu
                325                 330                 335

Lys Asp Lys Leu Leu Ala Ala Val Lys Glu Asp Ala Ala Ala Thr Lys
            340                 345                 350

Asp Arg Cys Lys Gln Leu Thr Gln Glu Met Met Thr Glu Lys Glu Arg
        355                 360                 365

Ser Asn Val Val Ile Thr Arg Met Lys Asp Arg Ile Gly Thr Leu Glu
    370                 375                 380

Lys Glu His Asn Val Phe Gln Asn Lys Ile His Val Ser Tyr Gln Glu
385                 390                 395                 400

Thr Gln Gln Met Gln Met Lys Phe Gln Gln Val Arg Glu Gln Met Glu
                405                 410                 415

Ala Glu Ile Ala His Leu Lys Gln Glu Asn Gly Ile Leu Arg Asp Ala
            420                 425                 430

Val Ser Asn Thr Thr Asn Gln Leu Glu Ser Lys Gln Ser Ala Glu Leu
        435                 440                 445

Asn Lys Leu Arg Gln Asp Tyr Ala Arg Leu Val Asn Glu Leu Thr Glu
    450                 455                 460

Lys Thr Gly Lys Leu Gln Gln Glu Glu Val Gln Lys Lys Asn Ala Glu
465                 470                 475                 480

Gln Ala Ala Thr Gln Leu Lys Val Gln Leu Gln Glu Ala Glu Arg Arg
                485                 490                 495

Trp Glu Glu Val Gln Ser Tyr Ile Arg Lys Arg Thr Ala Glu His Glu
            500                 505                 510

Ala Ala Gln Gln Asp Leu Gln Ser Lys Phe Val Ala Lys Glu Asn Glu
        515                 520                 525

Val Gln Ser Leu His Ser Lys Leu Thr Asp Thr Leu Val Ser Lys Gln
    530                 535                 540

Gln Leu Glu Gln Arg Leu Met Gln Leu Met Glu Ser Glu Gln Lys Arg
545                 550                 555                 560

Val Asn Lys Glu Glu Ser Leu Gln Met Gln Val Gln Asp Ile Leu Glu
                565                 570                 575

Gln Asn Glu Ala Leu Lys Ala Gln Ile Gln Gln Phe His Ser Gln Ile
            580                 585                 590
```

-continued

```
Ala Ala Gln Thr Ser Ala Ser Val Leu Ala Glu Glu Leu His Lys Val
        595                 600                 605

Ile Ala Glu Lys Asp Lys Gln Ile Lys Gln Thr Glu Asp Ser Leu Ala
    610                 615                 620

Ser Glu Arg Asp Arg Leu Thr Ser Lys Glu Glu Glu Leu Lys Asp Ile
625                 630                 635                 640

Gln Asn Met Asn Phe Leu Leu Lys Ala Glu Val Gln Lys Leu Gln Ala
                645                 650                 655

Leu Ala Asn Glu Gln Ala Ala Ala Ala His Glu Leu Glu Lys Met Gln
            660                 665                 670

Gln Ser Val Tyr Val Lys Asp Asp Lys Ile Arg Leu Leu Glu Glu Gln
        675                 680                 685

Leu Gln His Glu Ile Ser Asn Lys Met Glu Glu Phe Lys Ile Leu Asn
    690                 695                 700

Asp Gln Asn Lys Ala Leu Lys Ser Glu Val Gln Lys Leu Gln Thr Leu
705                 710                 715                 720

Val Ser Glu Gln Pro Asn Lys Asp Val Val Glu Gln Met Glu Lys Cys
                725                 730                 735

Ile Gln Glu Lys Asp Glu Lys Leu Lys Thr Val Glu Glu Leu Leu Glu
            740                 745                 750

Thr Gly Leu Ile Gln Val Ala Thr Lys Glu Glu Glu Leu Asn Ala Ile
        755                 760                 765

Arg Thr Glu Asn Ser Ser Leu Thr Lys Glu Val Gln Asp Leu Lys Ala
    770                 775                 780

Lys Gln Asn Asp Gln Val Ser Phe Ala Ser Leu Val Glu Glu Leu Lys
785                 790                 795                 800

Lys Val Ile His Glu Lys Asp Gly Lys Ile Lys Ser Val Glu Glu Leu
                805                 810                 815

Leu Glu Ala Glu Leu Leu Lys Val Ala Asn Lys Glu Lys Thr Val Gln
            820                 825                 830

Asp Leu Lys Gln Glu Ile Lys Ala Leu Lys Glu Glu Ile Gly Asn Val
        835                 840                 845

Gln Leu Glu Lys Ala Gln Gln Leu Ser Ile Thr Ser Lys Val Gln Glu
    850                 855                 860

Leu Gln Asn Leu Leu Lys Gly Lys Glu Glu Gln Met Asn Thr Met Lys
865                 870                 875                 880

Ala Val Leu Glu Glu Lys Glu Lys Asp Leu Ala Asn Thr Gly Lys Trp
                885                 890                 895

Leu Gln Asp Leu Gln Glu Glu Asn Glu Ser Leu Lys Ala His Val Gln
            900                 905                 910

Glu Val Ala Gln His Asn Leu Lys Glu Ala Ser Ser Ala Ser Gln Phe
        915                 920                 925

Glu Glu Leu Glu Ile Val Leu Lys Glu Lys Glu Asn Glu Leu Lys Arg
    930                 935                 940

Leu Glu Ala Met Leu Lys Glu Arg Glu Ser Asp Leu Ser Ser Lys Thr
945                 950                 955                 960

Gln Leu Leu Gln Asp Val Gln Asp Glu Asn Lys Leu Phe Lys Ser Gln
                965                 970                 975

Ile Glu Gln Leu Lys Gln Gln Asn Tyr Gln Gln Ala Ser Ser Phe Pro
            980                 985                 990

Pro His Glu Glu Leu Leu Lys Val Ile Ser Glu Arg Glu Lys Glu Ile
        995                 1000                1005
```

-continued

```
Ser Gly Leu Trp Asn Glu Leu Asp Ser Leu Lys Asp Ala Val Glu His
   1010                1015                1020

Gln Arg Lys Lys Asn Asn Asp Leu Arg Glu Lys Asn Trp Glu Ala Met
1025                1030                1035                1040

Glu Ala Leu Ala Ser Thr Glu Lys Met Leu Gln Asp Lys Val Asn Lys
                1045                1050                1055

Thr Ser Lys Glu Arg Gln Gln Gln Val Glu Ala Val Glu Leu Glu Ala
            1060                1065                1070

Lys Glu Val Leu Lys Lys Leu Phe Pro Lys Val Ser Val Pro Ser Asn
        1075                1080                1085

Leu Ser Tyr Gly Glu Trp Leu His Gly Phe Glu Lys Lys Ala Lys Glu
   1090                1095                1100

Cys Met Ala Gly Thr Ser Gly Ser Glu Glu Val Lys Val Leu Glu His
1105                1110                1115                1120

Lys Leu Lys Glu Ala Asp Glu Met His Thr Leu Leu Gln Leu Glu Cys
                1125                1130                1135

Glu Lys Tyr Lys Ser Val Leu Ala Glu Thr Glu Gly Ile Leu Gln Lys
            1140                1145                1150

Leu Gln Arg Ser Val Glu Gln Glu Glu Asn Lys Trp Lys Val Lys Val
        1155                1160                1165

Asp Glu Ser His Lys Thr Ile Lys Gln Met Gln Ser Ser Phe Thr Ser
 1170                1175                1180

Ser Glu Gln Glu Leu Glu Arg Leu Arg Ser Glu Asn Lys Asp Ile Glu
1185                1190                1195                1200

Asn Leu Arg Arg Glu Arg Glu His Leu Glu Met Glu Leu Glu Lys Ala
                1205                1210                1215

Glu Met Glu Arg Ser Thr Tyr Val Thr Glu Val Arg Glu Leu Lys Asp
            1220                1225                1230

Leu Leu Thr Glu Leu Gln Lys Lys Leu Asp Asp Ser Tyr Ser Glu Ala
        1235                1240                1245

Val Arg Gln Asn Glu Glu Leu Asn Leu Leu Lys Ala Gln Leu Asn Glu
   1250                1255                1260

Thr Leu Thr Lys Leu Arg Thr Glu Gln Asn Glu Arg Gln Lys Val Ala
1265                1270                1275                1280

Gly Asp Leu His Lys Ala Gln Gln Ser Leu Glu Leu Ile Gln Ser Lys
                1285                1290                1295

Ile Val Lys Ala Ala Gly Asp Thr Thr Val Ile Glu Asn Ser Asp Val
            1300                1305                1310

Ser Pro Glu Thr Glu Ser Ser Glu Lys Glu Thr Met Ser Val Ser Leu
        1315                1320                1325

Asn Gln Thr Val Thr Gln Leu Gln Gln Leu Leu Gln Ala Val Asn Gln
   1330                1335                1340

Gln Leu Thr Lys Glu Lys Glu His Tyr Gln Val Leu Glu
1345                1350                1355
```

<210> SEQ ID NO 63
<211> LENGTH: 537
<212> TYPE: PRT
<213> ORGANISM: Homo sapiens

<400> SEQUENCE: 63

```
Met Ala Ala Gln Cys Val Thr Lys Val Ala Leu Asn Val Ser Cys Ala
 1               5                  10                  15

Asn Leu Leu Asp Lys Asp Ile Gly Ser Lys Ser Asp Pro Leu Cys Val
            20                  25                  30
```

-continued

```
Leu Phe Leu Asn Thr Ser Gly Gln Gln Trp Tyr Glu Val Glu Arg Thr
        35                  40                  45

Glu Arg Ile Lys Asn Cys Leu Asn Pro Gln Phe Ser Lys Thr Phe Ile
    50                  55                  60

Ile Asp Tyr Tyr Phe Glu Val Val Gln Lys Leu Lys Phe Gly Val Tyr
65                  70                  75                  80

Asp Ile Asp Asn Lys Thr Ile Glu Leu Ser Asp Asp Asp Phe Leu Gly
                85                  90                  95

Glu Cys Glu Cys Thr Leu Gly Gln Ile Val Ser Ser Lys Lys Leu Thr
            100                 105                 110

Arg Pro Leu Val Met Lys Thr Gly Arg Pro Ala Gly Lys Gly Ser Ile
        115                 120                 125

Thr Ile Ser Ala Glu Glu Ile Lys Asp Asn Arg Val Val Leu Phe Glu
    130                 135                 140

Met Glu Ala Arg Lys Leu Asp Asn Lys Asp Leu Phe Gly Lys Ser Asp
145                 150                 155                 160

Pro Tyr Leu Glu Phe His Lys Gln Thr Ser Asp Gly Asn Trp Leu Met
                165                 170                 175

Val His Arg Thr Glu Val Val Lys Asn Asn Leu Asn Pro Val Trp Arg
            180                 185                 190

Pro Phe Lys Ile Ser Leu Asn Ser Leu Cys Tyr Gly Asp Met Asp Lys
        195                 200                 205

Thr Ile Lys Val Glu Cys Tyr Asp Tyr Asp Asn Asp Gly Ser His Asp
    210                 215                 220

Leu Ile Gly Thr Phe Gln Thr Thr Met Thr Lys Leu Lys Glu Ala Ser
225                 230                 235                 240

Arg Ser Ser Pro Val Glu Phe Glu Cys Ile Asn Glu Lys Lys Arg Gln
                245                 250                 255

Lys Lys Lys Ser Tyr Lys Asn Ser Gly Val Ile Ser Val Lys Gln Cys
            260                 265                 270

Glu Ile Thr Val Glu Cys Thr Phe Leu Asp Tyr Ile Met Gly Gly Cys
        275                 280                 285

Gln Leu Asn Phe Thr Val Gly Val Asp Phe Thr Gly Ser Asn Gly Asp
    290                 295                 300

Pro Arg Ser Pro Asp Ser Leu His Tyr Ile Ser Pro Asn Gly Val Asn
305                 310                 315                 320

Glu Tyr Leu Thr Ala Leu Trp Ser Val Gly Leu Val Ile Gln Asp Tyr
                325                 330                 335

Asp Ala Asp Lys Met Phe Pro Ala Phe Gly Phe Gly Ala Gln Ile Pro
            340                 345                 350

Pro Gln Trp Gln Val Ser His Glu Phe Pro Met Asn Phe Asn Pro Ser
        355                 360                 365

Asn Pro Tyr Cys Asn Gly Ile Gln Gly Ile Val Glu Ala Tyr Arg Ser
    370                 375                 380

Cys Leu Pro Gln Ile Lys Leu Tyr Gly Pro Thr Asn Phe Ser Pro Ile
385                 390                 395                 400

Ile Asn His Val Ala Arg Phe Ala Ala Ala Ala Thr Gln Gln Gln Thr
                405                 410                 415

Ala Ser Gln Tyr Phe Val Leu Leu Ile Ile Thr Asp Gly Val Ile Thr
            420                 425                 430

Asp Leu Asp Glu Thr Arg Gln Ala Ile Val Asn Ala Ser Arg Leu Pro
        435                 440                 445
```

```
Met Ser Ile Ile Ile Val Gly Val Gly Gly Ala Asp Phe Ser Ala Met
    450                 455                 460

Glu Phe Leu Asp Gly Asp Gly Gly Ser Leu Arg Ser Pro Leu Gly Glu
465                 470                 475                 480

Val Ala Ile Arg Asp Ile Val Gln Phe Val Pro Phe Arg Gln Phe Gln
                485                 490                 495

Asn Ala Pro Lys Glu Ala Leu Ala Gln Cys Val Leu Ala Glu Ile Pro
            500                 505                 510

Gln Gln Val Val Gly Tyr Phe Asn Thr Tyr Lys Leu Leu Pro Pro Lys
        515                 520                 525

Asn Pro Ala Thr Lys Gln Gln Lys Gln
    530                 535


<210> SEQ ID NO 64
<211> LENGTH: 496
<212> TYPE: PRT
<213> ORGANISM: Homo sapiens

<400> SEQUENCE: 64

Met Ala Ser Ser Thr Gly Asp Arg Ser Gln Ala Val Arg His Gly Leu
 1               5                  10                  15

Arg Ala Lys Val Leu Thr Leu Asp Gly Met Asn Pro Arg Val Arg Arg
            20                  25                  30

Val Glu Tyr Ala Val Arg Gly Pro Ile Val Gln Arg Ala Leu Glu Leu
        35                  40                  45

Glu Gln Glu Leu Arg Gln Gly Val Lys Lys Pro Phe Thr Glu Val Ile
    50                  55                  60

Arg Ala Asn Ile Gly Asp Ala Gln Ala Met Gly Gln Arg Pro Ile Thr
65                  70                  75                  80

Phe Leu Arg Gln Val Leu Ala Leu Cys Val Asn Pro Asp Leu Leu Ser
                85                  90                  95

Ser Pro Asn Phe Pro Asp Asp Ala Lys Lys Arg Ala Glu Arg Ile Leu
            100                 105                 110

Gln Ala Cys Gly Gly His Ser Leu Gly Ala Tyr Ser Val Ser Ser Gly
        115                 120                 125

Ile Gln Leu Ile Arg Glu Asp Val Ala Arg Tyr Ile Glu Arg Arg Asp
    130                 135                 140

Gly Gly Ile Pro Ala Asp Pro Asn Asn Val Phe Leu Ser Thr Gly Ala
145                 150                 155                 160

Ser Asp Ala Ile Val Thr Val Leu Lys Leu Leu Val Ala Gly Glu Gly
                165                 170                 175

His Thr Arg Thr Gly Val Leu Ile Pro Ile Pro Gln Tyr Pro Leu Tyr
            180                 185                 190

Ser Ala Thr Leu Ala Glu Leu Gly Ala Val Gln Val Asp Tyr Tyr Leu
      195                   200                 205

Asp Glu Glu Arg Ala Trp Ala Leu Asp Val Ala Glu Leu His Arg Ala
  210                   215                 220

Leu Gly Gln Ala Arg Asp His Cys Arg Pro Arg Ala Leu Cys Val Ile
225                 230                 235                 240

Asn Pro Gly Asn Pro Thr Gly Gln Val Gln Thr Arg Glu Cys Ile Glu
                245                 250                 255

Ala Val Ile Arg Phe Ala Phe Glu Glu Arg Leu Phe Leu Leu Ala Asp
            260                 265                 270

Glu Val Tyr Gln Asp Asn Val Tyr Ala Ala Gly Ser Gln Phe His Ser
        275                 280                 285
```

Phe Lys Lys Val Leu Met Glu Met Gly Pro Pro Tyr Ala Gly Gln Gln
290 295 300

Glu Leu Ala Ser Phe His Ser Thr Ser Lys Gly Tyr Met Gly Glu Cys
305 310 315 320

Gly Phe Arg Gly Gly Tyr Val Glu Val Val Asn Met Asp Ala Ala Val
325 330 335

Gln Gln Gln Met Leu Lys Leu Met Ser Val Arg Leu Cys Pro Pro Val
340 345 350

Pro Gly Gln Ala Leu Leu Asp Leu Val Val Ser Pro Pro Ala Pro Thr
355 360 365

Asp Pro Ser Phe Ala Gln Phe Gln Ala Glu Lys Gln Ala Val Leu Ala
370 375 380

Glu Leu Ala Ala Lys Ala Lys Leu Thr Glu Gln Val Phe Asn Glu Ala
385 390 395 400

Pro Gly Ile Ser Cys Asn Pro Val Gln Gly Ala Met Tyr Ser Phe Pro
405 410 415

Arg Val Gln Leu Pro Pro Arg Ala Val Glu Arg Ala Gln Glu Leu Gly
420 425 430

Leu Ala Pro Asp Met Phe Phe Cys Leu Arg Leu Leu Glu Glu Thr Gly
435 440 445

Ile Cys Val Val Pro Gly Ser Gly Phe Gly Gln Arg Glu Gly Thr Tyr
450 455 460

His Phe Arg Met Thr Ile Leu Pro Pro Leu Glu Lys Leu Arg Leu Leu
465 470 475 480

Leu Glu Lys Leu Ser Arg Phe His Ala Lys Phe Thr Leu Glu Tyr Ser
485 490 495

<210> SEQ ID NO 65
<211> LENGTH: 2602
<212> TYPE: PRT
<213> ORGANISM: Homo sapiens

<400> SEQUENCE: 65

Met Pro Val Thr Glu Lys Asp Leu Ala Glu Asp Ala Pro Trp Lys Lys
1 5 10 15

Ile Gln Gln Asn Thr Phe Thr Arg Trp Cys Asn Glu His Leu Lys Cys
20 25 30

Val Asn Lys Arg Ile Gly Asn Leu Gln Thr Asp Leu Ser Asp Gly Leu
35 40 45

Arg Leu Ile Ala Leu Leu Glu Val Leu Ser Gln Lys Arg Met Tyr Arg
50 55 60

Lys Tyr His Gln Arg Pro Thr Phe Arg Gln Met Gln Leu Glu Asn Val
65 70 75 80

Ser Val Ala Leu Glu Phe Leu Asp Arg Glu Ser Ile Lys Leu Val Ser
85 90 95

Ile Asp Ser Lys Ala Ile Val Asp Gly Asn Leu Lys Leu Ile Leu Gly
100 105 110

Leu Val Trp Thr Leu Ile Leu His Tyr Ser Ile Ser Met Pro Val Trp
115 120 125

Glu Asp Glu Gly Asp Asp Asp Ala Lys Lys Gln Thr Pro Lys Gln Arg
130 135 140

Leu Leu Gly Trp Ile Gln Asn Lys Ile Pro Tyr Leu Pro Ile Thr Asn
145 150 155 160

Phe Asn Gln Asn Trp Gln Asp Gly Lys Ala Leu Gly Ala Leu Val Asp

-continued

```
                165                 170                 175

Ser Cys Ala Pro Gly Leu Cys Pro Asp Trp Glu Ser Trp Asp Pro Gln
            180                 185                 190

Lys Pro Val Asp Asn Ala Arg Glu Ala Met Gln Gln Ala Asp Asp Trp
        195                 200                 205

Leu Gly Val Pro Gln Val Ile Thr Pro Glu Glu Ile Ile His Pro Asp
    210                 215                 220

Val Asp Glu His Ser Val Met Thr Tyr Leu Ser Gln Phe Pro Lys Ala
225                 230                 235                 240

Lys Leu Lys Pro Gly Ala Pro Leu Lys Pro Lys Leu Asn Pro Lys Lys
                245                 250                 255

Ala Arg Ala Tyr Gly Arg Gly Ile Glu Pro Thr Gly Asn Met Val Lys
            260                 265                 270

Gln Pro Ala Lys Phe Thr Val Asp Thr Ile Ser Ala Gly Gln Gly Asp
        275                 280                 285

Val Met Val Phe Val Glu Asp Pro Glu Gly Asn Lys Glu Glu Ala Gln
    290                 295                 300

Val Thr Pro Asp Ser Asp Lys Asn Lys Thr Tyr Ser Val Glu Tyr Leu
305                 310                 315                 320

Pro Lys Val Thr Gly Leu His Lys Val Thr Val Leu Phe Ala Gly Gln
                325                 330                 335

His Ile Ser Lys Ser Pro Phe Glu Val Ser Val Asp Lys Ala Gln Gly
            340                 345                 350

Asp Ala Ser Lys Val Thr Ala Lys Gly Pro Gly Leu Glu Ala Val Gly
        355                 360                 365

Asn Ile Ala Asn Lys Pro Thr Tyr Phe Asp Ile Tyr Thr Ala Gly Ala
    370                 375                 380

Gly Val Gly Asp Ile Gly Val Glu Val Glu Asp Pro Gln Gly Lys Asn
385                 390                 395                 400

Thr Val Glu Leu Leu Val Glu Asp Lys Gly Asn Gln Val Tyr Arg Cys
                405                 410                 415

Val Tyr Lys Pro Met Gln Pro Gly Pro His Val Val Lys Ile Phe Phe
            420                 425                 430

Ala Gly Asp Thr Ile Pro Lys Ser Pro Phe Val Val Gln Val Gly Glu
        435                 440                 445

Ala Cys Asn Pro Asn Ala Cys Arg Ala Ser Gly Arg Gly Leu Gln Pro
    450                 455                 460

Lys Gly Val Arg Ile Arg Glu Thr Thr Asp Phe Lys Val Asp Thr Lys
465                 470                 475                 480

Ala Ala Gly Ser Gly Glu Leu Gly Val Thr Met Lys Gly Pro Lys Gly
                485                 490                 495

Leu Glu Glu Leu Val Lys Gln Lys Asp Phe Leu Asp Gly Val Tyr Ala
            500                 505                 510

Phe Glu Tyr Tyr Pro Ser Thr Pro Gly Arg Tyr Ser Ile Ala Ile Thr
        515                 520                 525

Trp Gly Gly His His Ile Pro Lys Ser Pro Phe Glu Val Gln Val Gly
    530                 535                 540

Pro Glu Ala Gly Met Gln Lys Val Arg Ala Trp Gly Pro Gly Leu His
545                 550                 555                 560

Gly Gly Ile Val Gly Arg Ser Ala Asp Phe Val Val Glu Ser Ile Gly
                565                 570                 575

Ser Glu Val Gly Ser Leu Gly Phe Ala Ile Glu Gly Pro Ser Gln Ala
            580                 585                 590
```

-continued

```
Lys Ile Glu Tyr Asn Asp Gln Asn Asp Gly Ser Cys Asp Val Lys Tyr
        595                 600                 605

Trp Pro Lys Glu Pro Gly Glu Tyr Ala Val His Ile Met Cys Asp Asp
    610                 615                 620

Glu Asp Ile Lys Asp Ser Pro Tyr Met Ala Phe Ile His Pro Ala Thr
625                 630                 635                 640

Gly Gly Tyr Asn Pro Asp Leu Val Arg Ala Tyr Gly Pro Gly Leu Glu
                645                 650                 655

Lys Ser Gly Cys Ile Val Asn Asn Leu Ala Glu Phe Thr Val Asp Pro
            660                 665                 670

Lys Asp Ala Gly Lys Ala Pro Leu Lys Ile Phe Ala Gln Asp Gly Glu
        675                 680                 685

Gly Gln Arg Ile Asp Ile Gln Met Lys Asn Arg Met Asp Gly Thr Tyr
    690                 695                 700

Ala Cys Ser Tyr Thr Pro Val Lys Ala Ile Lys His Thr Ile Ala Val
705                 710                 715                 720

Val Trp Gly Gly Val Asn Ile Pro His Ser Pro Tyr Arg Val Asn Ile
                725                 730                 735

Gly Gln Gly Ser His Pro Gln Lys Val Lys Val Phe Gly Pro Gly Val
            740                 745                 750

Glu Arg Ser Gly Leu Lys Ala Asn Glu Pro Thr His Phe Thr Val Asp
        755                 760                 765

Cys Thr Glu Ala Gly Glu Gly Asp Val Ser Val Gly Ile Lys Cys Asp
    770                 775                 780

Ala Arg Val Leu Ser Glu Asp Glu Glu Asp Val Asp Phe Asp Ile Ile
785                 790                 795                 800

His Asn Ala Asn Asp Thr Phe Thr Val Lys Tyr Val Pro Pro Ala Ala
                805                 810                 815

Gly Arg Tyr Thr Ile Lys Val Leu Phe Ala Ser Gln Glu Ile Pro Ala
            820                 825                 830

Ser Pro Phe Arg Val Lys Val Asp Pro Ser His Asp Ala Ser Lys Val
        835                 840                 845

Lys Ala Glu Gly Pro Gly Leu Ser Lys Ala Gly Val Glu Asn Gly Lys
    850                 855                 860

Pro Thr His Phe Thr Val Tyr Thr Lys Gly Ala Gly Lys Ala Pro Leu
865                 870                 875                 880

Asn Val Gln Phe Asn Ser Pro Leu Pro Gly Asp Ala Val Lys Asp Leu
                885                 890                 895

Asp Ile Ile Asp Asn Tyr Asp Tyr Ser His Thr Val Lys Tyr Thr Pro
            900                 905                 910

Thr Gln Gln Gly Asn Met Gln Val Leu Val Thr Tyr Gly Gly Asp Pro
        915                 920                 925

Ile Pro Lys Ser Pro Phe Thr Val Gly Val Ala Ala Pro Leu Asp Leu
    930                 935                 940

Ser Lys Ile Lys Leu Asn Gly Leu Glu Asn Arg Val Glu Val Gly Lys
945                 950                 955                 960

Asp Gln Glu Phe Thr Val Asp Thr Arg Gly Ala Gly Gly Gln Gly Lys
                965                 970                 975

Leu Asp Val Thr Ile Leu Ser Pro Ser Arg Lys Val Val Pro Cys Leu
            980                 985                 990

Val Thr Pro Val Thr Gly Arg Glu Asn Ser Thr Ala Lys Phe Ile Pro
        995                 1000                1005
```

-continued

```
Arg Glu Glu Gly Leu Tyr Ala Val Asp Val Thr Tyr Asp Gly His Pro
   1010                1015                1020

Val Pro Gly Ser Pro Tyr Thr Val Glu Ala Ser Leu Pro Pro Asp Pro
1025                1030                1035                1040

Ser Lys Val Lys Ala His Gly Pro Gly Leu Glu Gly Gly Leu Val Gly
                1045                1050                1055

Lys Pro Ala Glu Phe Thr Ile Asp Thr Lys Gly Ala Gly Thr Gly Gly
            1060                1065                1070

Leu Gly Leu Thr Val Glu Gly Pro Cys Glu Ala Lys Ile Glu Cys Ser
       1075                1080                1085

Asp Asn Gly Asp Gly Thr Cys Ser Val Ser Tyr Leu Pro Thr Lys Pro
   1090                1095                1100

Gly Glu Tyr Phe Val Asn Ile Leu Phe Glu Glu Val His Ile Pro Gly
1105                1110                1115                1120

Ser Pro Phe Lys Ala Asp Ile Glu Met Pro Phe Asp Pro Ser Lys Val
                1125                1130                1135

Val Ala Ser Gly Pro Gly Leu Glu His Gly Lys Val Gly Glu Ala Gly
            1140                1145                1150

Leu Leu Ser Val Asn Cys Ser Glu Ala Gly Pro Gly Ala Leu Gly Leu
       1155                1160                1165

Glu Ala Val Ser Asp Ser Gly Thr Lys Ala Glu Val Ser Ile Gln Asn
   1170                1175                1180

Asn Lys Asp Gly Thr Tyr Ala Val Thr Tyr Val Pro Leu Thr Ala Gly
1185                1190                1195                1200

Met Tyr Thr Leu Thr Met Lys Tyr Gly Gly Glu Leu Val Pro His Phe
                1205                1210                1215

Pro Ala Arg Val Lys Val Glu Pro Ala Val Asp Thr Ser Arg Ile Lys
            1220                1225                1230

Val Phe Gly Pro Gly Ile Glu Gly Lys Asp Val Phe Arg Glu Ala Thr
       1235                1240                1245

Thr Asp Phe Thr Val Asp Ser Arg Pro Leu Thr Gln Val Gly Gly Asp
   1250                1255                1260

His Ile Lys Ala His Ile Ala Asn Pro Ser Gly Ala Ser Thr Glu Cys
1265                1270                1275                1280

Phe Val Thr Asp Asn Ala Asp Gly Thr Tyr Gln Val Glu Tyr Thr Pro
                1285                1290                1295

Phe Glu Lys Gly Leu His Val Val Glu Val Thr Tyr Asp Asp Val Pro
            1300                1305                1310

Ile Pro Asn Ser Pro Phe Lys Val Ala Val Thr Glu Gly Cys Gln Pro
       1315                1320                1325

Ser Arg Val Gln Ala Gln Gly Pro Gly Leu Lys Glu Ala Phe Thr Asn
   1330                1335                1340

Lys Pro Asn Val Phe Thr Val Val Thr Arg Gly Ala Gly Ile Gly Gly
1345                1350                1355                1360

Leu Gly Ile Thr Val Glu Gly Pro Ser Glu Ser Lys Ile Asn Cys Arg
                1365                1370                1375

Asp Asn Lys Asp Gly Ser Cys Ser Ala Glu Tyr Ile Pro Phe Ala Pro
            1380                1385                1390

Gly Asp Tyr Asp Val Asn Ile Thr Tyr Gly Gly Ala His Ile Pro Gly
       1395                1400                1405

Ser Pro Phe Arg Val Pro Val Lys Asp Val Val Asp Pro Ser Lys Val
   1410                1415                1420

Lys Ile Ala Gly Pro Gly Leu Gly Ser Gly Val Arg Ala Arg Val Leu
```

-continued

```
1425                1430                1435                1440

Gln Ser Phe Thr Val Asp Ser Ser Lys Ala Gly Leu Ala Pro Leu Glu
                1445                1450                1455

Val Arg Val Leu Gly Pro Arg Gly Leu Val Glu Pro Val Asn Met Val
            1460                1465                1470

Asp Asn Gly Asp Gly Thr His Thr Val Thr Tyr Thr Pro Ser Gln Glu
        1475                1480                1485

Gly Pro Tyr Met Val Ser Val Lys Tyr Ala Asp Glu Glu Ile Pro Arg
    1490                1495                1500

Ser Pro Phe Lys Val Lys Val Leu Pro Thr Tyr Asp Ala Ser Lys Val
1505                1510                1515                1520

Thr Ala Ser Gly Pro Gly Leu Ser Ser Tyr Gly Val Pro Ala Ser Leu
                1525                1530                1535

Pro Val Asp Phe Ala Ile Asp Ala Arg Asp Ala Gly Glu Gly Leu Leu
            1540                1545                1550

Ala Val Gln Ile Thr Asp Gln Glu Gly Lys Pro Lys Arg Ala Ile Val
        1555                1560                1565

His Asp Asn Lys Asp Gly Thr Tyr Ala Val Thr Tyr Ile Pro Asp Lys
    1570                1575                1580

Thr Gly Arg Tyr Met Ile Gly Val Thr Tyr Gly Gly Asp Asp Ile Pro
1585                1590                1595                1600

Leu Ser Pro Tyr Arg Ile Arg Ala Thr Gln Thr Gly Asp Ala Ser Lys
                1605                1610                1615

Cys Leu Ala Thr Gly Pro Gly Ile Ala Ser Thr Val Lys Thr Gly Glu
            1620                1625                1630

Glu Val Gly Phe Val Val Asp Ala Lys Thr Ala Gly Lys Gly Lys Val
        1635                1640                1645

Thr Cys Thr Val Leu Thr Pro Asp Gly Thr Glu Ala Glu Ala Asp Val
    1650                1655                1660

Ile Glu Asn Glu Asp Gly Thr Tyr Asp Ile Phe Tyr Thr Ala Ala Lys
1665                1670                1675                1680

Pro Gly Thr Tyr Val Ile Tyr Val Arg Phe Gly Gly Val Asp Ile Pro
                1685                1690                1695

Asn Ser Pro Phe Thr Val Met Ala Thr Asp Gly Glu Val Thr Ala Val
            1700                1705                1710

Glu Glu Ala Pro Val Asn Ala Cys Pro Pro Gly Phe Arg Pro Trp Val
        1715                1720                1725

Thr Glu Glu Ala Tyr Val Pro Val Ser Asp Met Asn Gly Leu Gly Phe
    1730                1735                1740

Lys Pro Phe Asp Leu Val Ile Pro Phe Ala Val Arg Lys Gly Glu Ile
1745                1750                1755                1760

Thr Gly Glu Val His Met Pro Ser Gly Lys Thr Ala Thr Pro Glu Ile
                1765                1770                1775

Val Asp Asn Lys Asp Gly Thr Val Thr Val Arg Tyr Ala Pro Thr Glu
            1780                1785                1790

Val Gly Leu His Glu Met His Ile Lys Tyr Met Gly Ser His Ile Pro
        1795                1800                1805

Glu Ser Pro Leu Gln Phe Tyr Val Asn Tyr Pro Asn Ser Gly Ser Val
    1810                1815                1820

Ser Ala Tyr Gly Pro Gly Leu Val Tyr Gly Val Ala Asn Lys Thr Ala
1825                1830                1835                1840

Thr Phe Thr Ile Val Thr Glu Asp Ala Gly Glu Gly Gly Leu Asp Leu
                1845                1850                1855
```

```
Ala Ile Glu Gly Pro Ser Lys Ala Glu Ile Ser Cys Ile Asp Asn Lys
           1860                1865                1870

Asp Gly Thr Cys Thr Val Thr Tyr Leu Pro Thr Leu Pro Gly Asp Tyr
       1875                1880                1885

Ser Ile Leu Val Lys Tyr Asn Asp Lys His Ile Pro Gly Ser Pro Phe
   1890                1895                1900

Thr Ala Lys Ile Thr Asp Asp Ser Arg Arg Cys Ser Gln Val Lys Leu
1905                1910                1915                1920

Gly Ser Ala Ala Asp Phe Leu Leu Asp Ile Ser Glu Thr Asp Leu Ser
               1925                1930                1935

Ser Leu Thr Ala Ser Ile Lys Ala Pro Ser Gly Arg Asp Glu Pro Cys
           1940                1945                1950

Leu Leu Lys Arg Leu Pro Asn Asn His Ile Gly Ile Ser Phe Ile Pro
       1955                1960                1965

Arg Glu Val Gly Glu His Leu Val Ser Ile Lys Lys Asn Gly Asn His
   1970                1975                1980

Val Ala Asn Ser Pro Val Ser Ile Met Val Val Gln Ser Glu Ile Gly
1985                1990                1995                2000

Asp Ala Arg Arg Ala Lys Val Tyr Gly Arg Gly Leu Ser Glu Gly Arg
               2005                2010                2015

Thr Phe Glu Met Ser Asp Phe Ile Val Asp Thr Arg Asp Ala Gly Tyr
           2020                2025                2030

Gly Gly Ile Ser Leu Ala Val Glu Gly Pro Ser Lys Val Asp Ile Gln
       2035                2040                2045

Thr Glu Asp Leu Glu Asp Gly Thr Cys Lys Val Ser Tyr Phe Pro Thr
   2050                2055                2060

Val Pro Gly Val Tyr Ile Val Ser Thr Lys Phe Ala Asp Glu His Val
2065                2070                2075                2080

Pro Gly Ser Pro Phe Thr Val Lys Ile Ser Gly Glu Gly Arg Val Lys
               2085                2090                2095

Glu Ser Ile Thr Arg Thr Ser Arg Ala Pro Ser Val Ala Thr Val Gly
           2100                2105                2110

Ser Ile Cys Asp Leu Asn Leu Lys Ile Pro Glu Ile Asn Ser Ser Asp
       2115                2120                2125

Met Ser Ala His Val Thr Ser Pro Ser Gly Arg Val Thr Glu Ala Glu
   2130                2135                2140

Ile Val Pro Met Gly Lys Asn Ser His Cys Val Arg Phe Val Pro Gln
2145                2150                2155                2160

Glu Met Gly Val His Thr Val Ser Val Lys Tyr Arg Gly Gln His Val
               2165                2170                2175

Thr Gly Ser Pro Phe Gln Phe Thr Val Gly Pro Leu Gly Glu Gly Gly
           2180                2185                2190

Ala His Lys Val Arg Ala Gly Gly Pro Gly Leu Glu Arg Gly Glu Ala
       2195                2200                2205

Gly Val Pro Ala Glu Phe Ser Ile Trp Thr Arg Glu Ala Gly Ala Gly
   2210                2215                2220

Gly Leu Ser Ile Ala Val Glu Gly Pro Ser Lys Ala Glu Ile Thr Phe
2225                2230                2235                2240

Asp Asp His Lys Asn Gly Ser Cys Gly Val Ser Tyr Ile Ala Gln Glu
               2245                2250                2255

Pro Gly Asn Tyr Glu Val Ser Ile Lys Phe Asn Asp Glu His Ile Pro
           2260                2265                2270
```

-continued

```
Glu Ser Pro Tyr Leu Val Pro Val Ile Ala Pro Ser Asp Asp Ala Arg
       2275                2280                2285

Arg Leu Thr Val Met Ser Leu Gln Glu Ser Gly Leu Lys Val Asn Gln
   2290                2295                2300

Pro Ala Ser Phe Ala Ile Arg Leu Asn Gly Ala Lys Gly Lys Ile Asp
2305                2310                2315                2320

Ala Lys Val His Ser Pro Ser Gly Ala Val Glu Glu Cys His Val Ser
               2325                2330                2335

Glu Leu Glu Pro Asp Lys Tyr Ala Val Arg Phe Ile Pro His Glu Asn
           2340                2345                2350

Gly Val His Thr Ile Asp Val Lys Phe Asn Gly Ser His Val Val Gly
       2355                2360                2365

Ser Pro Phe Lys Val Arg Val Gly Glu Pro Gly Gln Ala Gly Asn Pro
   2370                2375                2380

Ala Leu Val Ser Ala Tyr Gly Thr Gly Leu Glu Gly Gly Thr Thr Gly
2385                2390                2395                2400

Ile Gln Ser Glu Phe Phe Ile Asn Thr Thr Arg Ala Gly Pro Gly Thr
               2405                2410                2415

Leu Ser Val Thr Ile Glu Gly Pro Ser Lys Val Lys Met Asp Cys Gln
           2420                2425                2430

Glu Thr Pro Glu Gly Tyr Lys Val Met Tyr Thr Pro Met Ala Pro Gly
       2435                2440                2445

Asn Tyr Leu Ile Ser Val Lys Tyr Gly Gly Pro Asn His Ile Val Gly
   2450                2455                2460

Ser Pro Phe Lys Ala Lys Val Thr Gly Gln Arg Leu Val Ser Pro Gly
2465                2470                2475                2480

Ser Ala Asn Glu Thr Ser Ser Ile Leu Val Glu Ser Val Thr Arg Ser
               2485                2490                2495

Ser Thr Glu Thr Cys Tyr Ser Ala Ile Pro Lys Ala Ser Ser Asp Ala
           2500                2505                2510

Ser Lys Val Thr Ser Lys Gly Ala Gly Leu Ser Lys Ala Phe Val Gly
       2515                2520                2525

Gln Lys Ser Ser Phe Leu Val Asp Cys Ser Lys Ala Gly Ser Asn Met
   2530                2535                2540

Leu Leu Ile Gly Val His Gly Pro Thr Thr Pro Cys Glu Glu Val Ser
2545                2550                2555                2560

Met Lys His Val Gly Asn Gln Gln Tyr Asn Val Thr Tyr Val Val Lys
               2565                2570                2575

Glu Arg Gly Asp Tyr Val Leu Ala Val Lys Trp Gly Glu Glu His Ile
           2580                2585                2590

Pro Gly Ser Pro Phe His Val Thr Val Pro
       2595                2600
```

<210> SEQ ID NO 66
<211> LENGTH: 686
<212> TYPE: PRT
<213> ORGANISM: Homo sapiens

<400> SEQUENCE: 66

```
Met Met Ile Gln Trp Asn Gly Pro Lys Thr Ser Ile Ser Glu Lys Ala
 1               5                  10                  15

Arg Gly Leu Ala Leu Thr Tyr Ser Leu Arg Asp Arg Glu Arg Gly Gly
            20                  25                  30

Gly Arg Ala Gln Ile Gly Val Val Asp Asp Glu Ala Lys Ala Pro Asp
        35                  40                  45
```

```
Leu Met Gln Ile Met Glu Ala Val Leu Gly Cys Arg Val Gly Ser Leu
    50                  55                  60

Arg Ala Ala Thr Pro Ser Lys Asp Ile Asn Gln Leu Gln Lys Ala Asn
65                  70                  75                  80

Val Arg Leu Tyr His Val Tyr Glu Lys Gly Lys Asp Leu Val Val Leu
                85                  90                  95

Glu Leu Ala Thr Pro Pro Leu Thr Gln Asp Leu Leu Gln Glu Glu Asp
            100                 105                 110

Phe Tyr Ile Leu Asp Gln Gly Gly Phe Lys Ile Tyr Val Trp Gln Gly
        115                 120                 125

Arg Met Ser Ser Leu Gln Glu Arg Lys Ala Ala Phe Ser Arg Ala Val
    130                 135                 140

Gly Phe Ile Gln Ala Lys Gly Tyr Pro Thr Tyr Thr Asn Val Glu Val
145                 150                 155                 160

Val Asn Asp Gly Ala Glu Ser Ala Ala Phe Lys Gln Leu Phe Arg Thr
                165                 170                 175

Trp Ser Glu Lys Arg Arg Arg Asn Gln Lys Leu Gly Gly Arg Asp Lys
            180                 185                 190

Ser Ile His Val Lys Leu Asp Val Gly Lys Leu His Thr Gln Pro Lys
        195                 200                 205

Leu Ala Ala Gln Leu Arg Met Val Asp Asp Gly Ser Gly Lys Val Glu
    210                 215                 220

Val Trp Cys Ile Gln Asp Leu His Arg Gln Pro Val Asp Pro Lys Arg
225                 230                 235                 240

His Gly Gln Leu Cys Ala Gly Asn Cys Tyr Leu Val Leu Tyr Thr Tyr
                245                 250                 255

Gln Arg Leu Gly Arg Val Gln Tyr Ile Leu Tyr Leu Trp Gln Gly His
            260                 265                 270

Gln Ala Thr Ala Asp Glu Ile Glu Ala Leu Asn Ser Asn Ala Glu Glu
        275                 280                 285

Leu Asp Val Met Tyr Gly Gly Val Leu Val Gln Glu His Val Thr Met
    290                 295                 300

Gly Ser Glu Pro Pro His Phe Leu Ala Ile Phe Gln Gly Gln Leu Val
305                 310                 315                 320

Ile Phe Gln Glu Arg Ala Gly His His Gly Lys Gly Gln Ser Ala Ser
                325                 330                 335

Thr Thr Arg Leu Phe Gln Val Gln Gly Thr Asp Ser His Asn Thr Arg
            340                 345                 350

Thr Met Glu Val Pro Ala Arg Ala Ser Ser Leu Asn Ser Ser Asp Ile
        355                 360                 365

Phe Leu Leu Val Thr Ala Ser Val Cys Tyr Leu Trp Phe Gly Lys Gly
    370                 375                 380

Cys Asn Gly Asp Gln Arg Glu Met Ala Arg Val Val Val Thr Val Ile
385                 390                 395                 400

Ser Arg Lys Asn Glu Glu Thr Val Leu Glu Gly Gln Glu Pro Pro His
                405                 410                 415

Phe Trp Glu Ala Leu Gly Gly Arg Ala Pro Tyr Pro Ser Asn Lys Arg
            420                 425                 430

Leu Pro Glu Glu Val Pro Ser Phe Gln Pro Arg Leu Phe Glu Cys Ser
        435                 440                 445

Ser His Met Gly Cys Leu Val Leu Ala Glu Val Gly Phe Phe Ser Gln
    450                 455                 460
```

```
Glu Asp Leu Asp Lys Tyr Asp Ile Met Leu Leu Asp Thr Trp Gln Glu
465                 470                 475                 480

Ile Phe Leu Trp Leu Gly Glu Ala Ala Ser Glu Trp Lys Glu Ala Val
                485                 490                 495

Ala Trp Gly Gln Glu Tyr Leu Lys Thr His Pro Ala Gly Arg Ser Pro
            500                 505                 510

Ala Thr Pro Ile Val Leu Val Lys Gln Gly His Glu Pro Pro Thr Phe
        515                 520                 525

Ile Gly Trp Phe Phe Thr Trp Asp Pro Tyr Lys Trp Thr Ser His Pro
    530                 535                 540

Ser His Lys Glu Val Val Asp Gly Ser Pro Ala Ala Ala Ser Thr Ile
545                 550                 555                 560

Ser Glu Ile Thr Ala Glu Val Asn Asn Leu Arg Leu Ser Arg Trp Pro
                565                 570                 575

Gly Asn Gly Arg Ala Gly Ala Val Ala Leu Gln Ala Leu Lys Gly Ser
            580                 585                 590

Gln Asp Ser Ser Glu Asn Asp Leu Val Arg Ser Pro Lys Ser Ala Gly
        595                 600                 605

Ser Arg Thr Ser Ser Ser Val Ser Ser Thr Ser Ala Thr Ile Asn Gly
    610                 615                 620

Gly Leu Arg Arg Glu Gln Leu Met His Gln Ala Val Glu Asp Leu Pro
625                 630                 635                 640

Glu Gly Val Asp Pro Ala Arg Arg Glu Phe Tyr Leu Ser Asp Ser Asp
                645                 650                 655

Phe Gln Asp Ile Phe Gly Lys Ser Lys Glu Glu Phe Tyr Ser Met Ala
            660                 665                 670

Thr Trp Arg Gln Arg Gln Glu Lys Lys Gln Leu Gly Phe Phe
        675                 680                 685


<210> SEQ ID NO 67
<211> LENGTH: 342
<212> TYPE: PRT
<213> ORGANISM: Homo sapiens

<400> SEQUENCE: 67

Met Ser Ser Ser Gly Thr Leu Ser Asn Tyr Tyr Val Asp Ser Leu Ile
 1               5                  10                  15

Gly His Glu Gly Asp Glu Val Phe Ala Ala Arg Phe Gly Pro Pro Gly
            20                  25                  30

Pro Gly Ala Gln Gly Arg Pro Ala Gly Val Ala Asp Gly Pro Ala Ala
        35                  40                  45

Thr Ala Ala Glu Phe Ala Ser Cys Ser Phe Ala Pro Arg Ser Ala Val
    50                  55                  60

Phe Ser Ala Ser Trp Ser Ala Val Pro Ser Gln Pro Pro Ala Ala Ala
65                  70                  75                  80

Ala Met Ser Gly Leu Tyr His Pro Tyr Val Pro Pro Pro Pro Leu Ala
                85                  90                  95

Ala Ser Ala Ser Glu Pro Gly Arg Tyr Val Arg Ser Trp Met Glu Pro
            100                 105                 110

Leu Pro Gly Phe Pro Gly Gly Ala Gly Gly Gly Gly Gly Gly Gly Gly
        115                 120                 125

Gly Gly Pro Gly Arg Gly Pro Ser Pro Gly Pro Ser Gly Pro Ala Asn
    130                 135                 140

Gly Arg His Tyr Gly Ile Lys Pro Glu Thr Arg Ala Ala Pro Ala Pro
145                 150                 155                 160
```

```
Ala Thr Ala Ala Ser Thr Thr Ser Ser Ser Ser Thr Ser Leu Ser Ser
                165                 170                 175

Ser Ser Lys Arg Thr Glu Cys Ser Val Ala Arg Glu Ser Gln Gly Ser
            180                 185                 190

Ser Gly Pro Glu Phe Ser Cys Asn Ser Phe Leu Gln Glu Lys Ala Ala
        195                 200                 205

Ala Ala Thr Gly Gly Thr Gly Pro Gly Ala Gly Ile Gly Ala Ala Thr
    210                 215                 220

Gly Thr Gly Gly Ser Ser Glu Pro Ser Ala Cys Ser Asp His Pro Ile
225                 230                 235                 240

Pro Gly Cys Ser Leu Lys Glu Glu Glu Lys Gln His Ser Gln Pro Gln
                245                 250                 255

Gln Gln Gln Leu Asp Pro Asn Asn Pro Ala Ala Asn Trp Ile His Ala
            260                 265                 270

Arg Ser Thr Arg Lys Lys Arg Cys Pro Tyr Thr Lys Tyr Gln Thr Leu
        275                 280                 285

Glu Leu Glu Lys Glu Phe Leu Phe Asn Met Tyr Leu Thr Arg Asp Arg
    290                 295                 300

Arg Tyr Glu Val Ala Arg Ile Leu Asn Leu Thr Glu Arg Gln Val Lys
305                 310                 315                 320

Ile Trp Phe Gln Asn Arg Arg Met Lys Met Lys Lys Met Ser Lys Glu
                325                 330                 335

Lys Cys Pro Lys Gly Asp
            340


<210> SEQ ID NO 68
<211> LENGTH: 1719
<212> TYPE: PRT
<213> ORGANISM: Homo sapiens

<400> SEQUENCE: 68

Met Ser Gly Glu Val Arg Leu Arg Gln Leu Glu Gln Phe Ile Leu Asp
 1               5                  10                  15

Gly Pro Ala Gln Thr Asn Gly Gln Cys Phe Ser Val Glu Thr Leu Leu
            20                  25                  30

Asp Ile Leu Ile Cys Leu Tyr Asp Glu Cys Asn Asn Ser Pro Leu Arg
        35                  40                  45

Arg Glu Lys Asn Ile Leu Glu Tyr Leu Glu Trp Ala Lys Pro Phe Thr
    50                  55                  60

Ser Lys Val Lys Gln Met Arg Leu His Arg Glu Asp Phe Glu Ile Leu
65                  70                  75                  80

Lys Val Ile Gly Arg Gly Ala Phe Gly Glu Val Ala Val Val Lys Leu
                85                  90                  95

Lys Asn Ala Asp Lys Val Phe Ala Met Lys Ile Leu Asn Lys Trp Glu
            100                 105                 110

Met Leu Lys Arg Ala Glu Thr Ala Cys Phe Arg Glu Glu Arg Asp Val
        115                 120                 125

Leu Val Asn Gly Asp Asn Lys Trp Ile Thr Thr Leu His Tyr Ala Phe
    130                 135                 140

Gln Asp Asp Asn Asn Leu Tyr Leu Val Met Asp Tyr Tyr Val Gly Gly
145                 150                 155                 160

Asp Leu Leu Thr Leu Leu Ser Lys Phe Glu Asp Arg Leu Pro Glu Asp
                165                 170                 175

Met Ala Arg Phe Tyr Leu Ala Glu Met Val Ile Ala Ile Asp Ser Val
```

-continued

```
            180                 185                 190

His Gln Leu His Tyr Val His Arg Asp Ile Lys Pro Asp Asn Ile Leu
        195                 200                 205

Met Asp Met Asn Gly His Ile Arg Leu Ala Asp Phe Gly Ser Cys Leu
    210                 215                 220

Lys Leu Met Glu Asp Gly Thr Val Gln Ser Ser Val Ala Val Gly Thr
225                 230                 235                 240

Pro Asp Tyr Ile Ser Pro Glu Ile Leu Gln Ala Met Glu Asp Gly Lys
                245                 250                 255

Gly Arg Tyr Gly Pro Glu Cys Asp Trp Trp Ser Leu Gly Val Cys Met
            260                 265                 270

Tyr Glu Met Leu Tyr Gly Glu Thr Pro Phe Tyr Ala Glu Ser Leu Val
        275                 280                 285

Glu Thr Tyr Gly Lys Ile Met Asn His Lys Glu Arg Phe Gln Phe Pro
    290                 295                 300

Ala Gln Val Thr Asp Val Ser Glu Asn Ala Lys Asp Leu Ile Arg Arg
305                 310                 315                 320

Leu Ile Cys Ser Arg Glu His Arg Leu Gly Gln Asn Gly Ile Glu Asp
                325                 330                 335

Phe Lys Lys His Pro Phe Phe Ser Gly Ile Asp Trp Asp Asn Ile Arg
            340                 345                 350

Asn Cys Glu Ala Pro Tyr Ile Pro Glu Val Ser Ser Pro Thr Asp Thr
        355                 360                 365

Ser Asn Phe Asp Val Asp Asp Asp Cys Leu Lys Asn Ser Glu Thr Met
    370                 375                 380

Pro Pro Pro Thr His Thr Ala Phe Ser Gly His His Leu Pro Phe Val
385                 390                 395                 400

Gly Phe Thr Tyr Thr Ser Ser Cys Val Leu Ser Asp Arg Ser Cys Leu
                405                 410                 415

Arg Val Thr Ala Gly Pro Thr Ser Leu Asp Leu Asp Val Asn Val Gln
            420                 425                 430

Arg Thr Leu Asp Asn Asn Leu Ala Thr Glu Ala Tyr Glu Arg Arg Ile
        435                 440                 445

Lys Arg Leu Glu Gln Glu Lys Leu Glu Leu Ser Arg Lys Leu Gln Glu
    450                 455                 460

Ser Thr Gln Thr Val Gln Ala Leu Gln Tyr Ser Thr Val Asp Gly Pro
465                 470                 475                 480

Leu Thr Ala Ser Lys Asp Leu Glu Ile Lys Asn Leu Lys Glu Glu Ile
                485                 490                 495

Glu Lys Leu Arg Lys Gln Val Thr Glu Ser Ser His Leu Glu Gln Gln
            500                 505                 510

Leu Glu Glu Ala Asn Ala Val Arg Gln Glu Leu Asp Asp Ala Phe Arg
        515                 520                 525

Gln Ile Lys Ala Tyr Glu Lys Gln Ile Lys Thr Leu Gln Gln Glu Arg
    530                 535                 540

Glu Asp Leu Asn Lys Glu Leu Val Gln Ala Ser Glu Arg Leu Lys Asn
545                 550                 555                 560

Gln Ser Lys Glu Leu Lys Asp Ala His Cys Gln Arg Lys Leu Ala Met
                565                 570                 575

Gln Glu Phe Met Glu Ile Asn Glu Arg Leu Thr Glu Leu His Thr Gln
            580                 585                 590

Lys Gln Lys Leu Ala Arg His Val Arg Asp Lys Glu Glu Glu Val Asp
        595                 600                 605
```

-continued

```
Leu Val Met Gln Lys Val Glu Ser Leu Arg Gln Glu Leu Arg Arg Thr
    610                 615                 620

Glu Arg Ala Lys Lys Glu Leu Glu Val His Thr Glu Ala Leu Ala Ala
625                 630                 635                 640

Glu Ala Ser Lys Asp Arg Lys Leu Arg Glu Gln Ser Glu His Tyr Ser
                645                 650                 655

Lys Gln Leu Glu Asn Glu Leu Glu Gly Leu Lys Gln Lys Gln Ile Ser
            660                 665                 670

Tyr Ser Pro Gly Val Cys Ser Ile Glu His Gln Gln Glu Ile Thr Lys
        675                 680                 685

Leu Lys Thr Asp Leu Glu Lys Lys Ser Ile Phe Tyr Glu Glu Glu Leu
    690                 695                 700

Ser Lys Arg Glu Gly Ile His Ala Asn Glu Ile Lys Asn Leu Lys Lys
705                 710                 715                 720

Glu Leu His Asp Ser Glu Gly Gln Gln Leu Ala Leu Asn Lys Glu Ile
                725                 730                 735

Met Ile Leu Lys Asp Lys Leu Glu Lys Thr Arg Arg Glu Ser Gln Ser
            740                 745                 750

Glu Arg Glu Glu Phe Glu Ser Glu Phe Lys Gln Gln Tyr Glu Arg Glu
        755                 760                 765

Lys Val Leu Leu Thr Glu Glu Asn Lys Lys Leu Thr Ser Glu Leu Asp
    770                 775                 780

Lys Leu Thr Thr Leu Tyr Glu Asn Leu Ser Ile His Asn Gln Gln Leu
785                 790                 795                 800

Glu Glu Glu Val Lys Asp Leu Ala Asp Lys Lys Glu Ser Val Ala His
                805                 810                 815

Trp Glu Ala Gln Ile Thr Glu Ile Ile Gln Trp Val Ser Asp Glu Lys
            820                 825                 830

Asp Ala Arg Gly Tyr Leu Gln Ala Leu Ala Ser Lys Met Thr Glu Glu
        835                 840                 845

Leu Glu Ala Leu Arg Asn Ser Ser Leu Gly Thr Arg Ala Thr Asp Met
    850                 855                 860

Pro Trp Lys Met Arg Arg Phe Ala Lys Leu Asp Met Ser Ala Arg Leu
865                 870                 875                 880

Glu Leu Gln Ser Ala Leu Asp Ala Glu Ile Arg Ala Lys Gln Ala Ile
                885                 890                 895

Gln Glu Glu Leu Asn Lys Val Lys Ala Ser Asn Ile Ile Thr Glu Cys
            900                 905                 910

Lys Leu Lys Asp Ser Glu Lys Lys Asn Leu Glu Leu Leu Ser Glu Ile
        915                 920                 925

Glu Gln Leu Ile Lys Asp Thr Glu Glu Leu Arg Ser Glu Lys Gly Ile
    930                 935                 940

Glu His Gln Asp Ser Gln His Ser Phe Leu Ala Phe Leu Asn Thr Pro
945                 950                 955                 960

Thr Asp Ala Leu Asp Gln Phe Glu Thr Val Asp Ser Thr Pro Leu Ser
                965                 970                 975

Val His Thr Pro Thr Leu Arg Lys Lys Gly Cys Pro Gly Ser Thr Gly
            980                 985                 990

Phe Pro Pro Lys Arg Lys Thr His Gln Phe Phe Val Lys Ser Phe Thr
        995                 1000                1005

Thr Pro Thr Lys Cys His Gln Cys Thr Ser Leu Met Val Gly Leu Ile
   1010                1015                1020
```

-continued

Arg Gln Gly Cys Ser Cys Glu Val Cys Gly Phe Ser Cys His Ile Thr
1025 1030 1035 1040

Cys Val Asn Lys Ala Pro Thr Thr Cys Pro Val Pro Pro Glu Gln Thr
1045 1050 1055

Lys Gly Pro Leu Gly Ile Asp Pro Gln Lys Gly Ile Gly Thr Ala Tyr
1060 1065 1070

Glu Gly His Val Arg Ile Pro Lys Pro Ala Gly Val Lys Lys Gly Trp
1075 1080 1085

Gln Arg Ala Leu Ala Ile Val Cys Asp Phe Lys Leu Phe Leu Tyr Asp
1090 1095 1100

Ile Ala Glu Gly Lys Ala Ser Gln Pro Ser Val Val Ile Ser Gln Val
1105 1110 1115 1120

Ile Asp Met Arg Asp Glu Glu Phe Ser Val Ser Ser Val Leu Ala Ser
1125 1130 1135

Asp Val Ile His Ala Ser Arg Lys Asp Ile Pro Cys Ile Phe Arg Val
1140 1145 1150

Thr Ala Ser Gln Leu Ser Ala Ser Asn Asn Lys Cys Ser Ile Leu Met
1155 1160 1165

Leu Ala Asp Thr Glu Asn Glu Lys Asn Lys Trp Val Gly Val Leu Ser
1170 1175 1180

Glu Leu His Lys Ile Leu Lys Lys Asn Lys Phe Arg Asp Arg Ser Val
1185 1190 1195 1200

Tyr Val Pro Lys Glu Ala Tyr Asp Ser Thr Leu Pro Leu Ile Lys Thr
1205 1210 1215

Thr Gln Ala Ala Ala Ile Ile Asp His Glu Arg Ile Ala Leu Gly Asn
1220 1225 1230

Glu Glu Gly Leu Phe Val Val His Val Thr Lys Asp Glu Ile Ile Arg
1235 1240 1245

Val Gly Asp Asn Lys Lys Ile His Gln Ile Glu Leu Ile Pro Asn Asp
1250 1255 1260

Gln Leu Val Ala Val Ile Ser Gly Arg Asn Arg His Val Arg Leu Phe
1265 1270 1275 1280

Pro Met Ser Ala Leu Asp Gly Arg Glu Thr Asp Phe Tyr Lys Leu Ser
1285 1290 1295

Glu Thr Lys Gly Cys Gln Thr Val Thr Ser Gly Lys Val Arg His Gly
1300 1305 1310

Ala Leu Thr Cys Leu Cys Val Ala Met Lys Arg Gln Val Leu Cys Tyr
1315 1320 1325

Glu Leu Phe Gln Ser Lys Thr Arg His Arg Lys Phe Lys Glu Ile Gln
1330 1335 1340

Val Pro Tyr Asn Val Gln Trp Met Ala Ile Phe Ser Glu Gln Leu Cys
1345 1350 1355 1360

Val Gly Phe Gln Ser Gly Phe Leu Arg Tyr Pro Leu Asn Gly Glu Gly
1365 1370 1375

Asn Pro Tyr Ser Met Leu His Ser Asn Asp His Thr Leu Ser Phe Ile
1380 1385 1390

Ala His Gln Pro Met Asp Ala Ile Cys Ala Val Glu Ile Ser Ser Lys
1395 1400 1405

Glu Tyr Leu Leu Cys Phe Asn Ser Ile Gly Ile Tyr Thr Asp Cys Gln
1410 1415 1420

Gly Arg Arg Ser Arg Gln Gln Glu Leu Met Trp Pro Ala Asn Pro Ser
1425 1430 1435 1440

Ser Cys Cys Tyr Asn Ala Pro Tyr Leu Ser Val Tyr Ser Glu Asn Ala

```
                1445                1450                1455

Val Asp Ile Phe Asp Val Asn Ser Met Glu Trp Ile Gln Thr Leu Pro
            1460                1465                1470

Leu Lys Lys Val Arg Pro Leu Asn Asn Glu Gly Ser Leu Asn Leu Leu
        1475                1480                1485

Gly Leu Glu Thr Ile Arg Leu Ile Tyr Phe Lys Asn Lys Met Ala Glu
    1490                1495                1500

Gly Asp Glu Leu Val Val Pro Glu Thr Ser Asp Asn Ser Arg Lys Gln
1505                1510                1515                1520

Met Val Arg Asn Ile Asn Asn Lys Arg Arg Tyr Ser Phe Arg Val Pro
                1525                1530                1535

Glu Glu Glu Arg Met Gln Gln Arg Arg Glu Met Leu Arg Asp Pro Glu
            1540                1545                1550

Met Arg Asn Lys Leu Ile Ser Asn Pro Thr Asn Phe Asn His Ile Ala
        1555                1560                1565

His Met Gly Pro Gly Asp Gly Ile Gln Ile Leu Lys Asp Leu Pro Met
    1570                1575                1580

Asn Pro Arg Pro Gln Glu Ser Arg Thr Val Phe Ser Gly Ser Val Ser
1585                1590                1595                1600

Ile Pro Ser Ile Thr Lys Ser Arg Pro Glu Pro Gly Arg Ser Met Ser
                1605                1610                1615

Ala Ser Ser Gly Leu Ser Ala Arg Ser Ser Ala Gln Asn Gly Ser Ala
            1620                1625                1630

Leu Lys Arg Glu Phe Ser Gly Gly Ser Tyr Ser Ala Lys Arg Gln Pro
        1635                1640                1645

Met Pro Ser Pro Ser Glu Gly Ser Leu Ser Ser Gly Gly Met Asp Gln
    1650                1655                1660

Gly Ser Asp Ala Pro Ala Arg Asp Phe Asp Gly Glu Asp Ser Asp Ser
1665                1670                1675                1680

Pro Arg His Ser Thr Ala Ser Asn Ser Ser Asn Leu Ser Ser Pro Pro
                1685                1690                1695

Ser Pro Ala Ser Pro Arg Lys Thr Lys Ser Leu Ser Leu Glu Ser Thr
            1700                1705                1710

Asp Arg Gly Ser Trp Asp Pro
        1715


<210> SEQ ID NO 69
<211> LENGTH: 1638
<212> TYPE: PRT
<213> ORGANISM: Homo sapiens

<400> SEQUENCE: 69

Met Ser Gly Glu Val Arg Leu Arg Gln Leu Glu Gln Phe Ile Leu Asp
 1               5                  10                  15

Gly Pro Ala Gln Thr Asn Gly Gln Cys Phe Ser Val Glu Thr Leu Leu
            20                  25                  30

Asp Ile Leu Ile Cys Leu Tyr Asp Glu Cys Asn Asn Ser Pro Leu Arg
        35                  40                  45

Arg Glu Lys Asn Ile Leu Glu Tyr Leu Glu Trp Ala Lys Pro Phe Thr
    50                  55                  60

Ser Lys Val Lys Gln Met Arg Leu His Arg Glu Asp Phe Glu Ile Leu
65                  70                  75                  80

Lys Val Ile Gly Arg Gly Ala Phe Gly Glu Val Ala Val Val Lys Leu
                85                  90                  95
```

```
Lys Asn Ala Asp Lys Val Phe Ala Met Lys Ile Leu Asn Lys Trp Glu
            100                 105                 110

Met Leu Lys Arg Ala Glu Thr Ala Cys Phe Arg Glu Glu Arg Asp Val
        115                 120                 125

Leu Val Asn Gly Asp Asn Lys Trp Ile Thr Thr Leu His Tyr Ala Phe
    130                 135                 140

Gln Asp Asp Asn Asn Leu Tyr Leu Val Met Asp Tyr Tyr Val Gly Gly
145                 150                 155                 160

Asp Leu Leu Thr Leu Leu Ser Lys Phe Glu Asp Arg Leu Pro Glu Asp
                165                 170                 175

Met Ala Arg Phe Tyr Leu Ala Glu Met Val Ile Ala Ile Asp Ser Val
            180                 185                 190

His Gln Leu His Tyr Val His Arg Asp Ile Lys Pro Asp Asn Ile Leu
        195                 200                 205

Met Asp Met Asn Gly His Ile Arg Leu Ala Asp Phe Gly Ser Cys Leu
    210                 215                 220

Lys Leu Met Glu Asp Gly Thr Val Gln Ser Ser Val Ala Val Gly Thr
225                 230                 235                 240

Pro Asp Tyr Ile Ser Pro Glu Ile Leu Gln Ala Met Glu Asp Gly Lys
                245                 250                 255

Gly Arg Tyr Gly Pro Glu Cys Asp Trp Trp Ser Leu Gly Val Cys Met
            260                 265                 270

Tyr Glu Met Leu Tyr Gly Glu Thr Pro Phe Tyr Ala Glu Ser Leu Val
        275                 280                 285

Glu Thr Tyr Gly Lys Ile Met Asn His Lys Glu Arg Phe Gln Phe Pro
    290                 295                 300

Ala Gln Val Thr Asp Val Ser Glu Asn Ala Lys Asp Leu Ile Arg Arg
305                 310                 315                 320

Leu Ile Cys Ser Arg Glu His Arg Leu Gly Gln Asn Gly Ile Glu Asp
                325                 330                 335

Phe Lys Lys His Pro Phe Phe Ser Gly Ile Asp Trp Asp Asn Ile Arg
            340                 345                 350

Asn Cys Glu Ala Pro Tyr Ile Pro Glu Val Ser Ser Pro Thr Asp Thr
        355                 360                 365

Ser Asn Phe Asp Val Asp Asp Asp Cys Leu Lys Asn Ser Glu Thr Met
    370                 375                 380

Pro Pro Pro Thr His Thr Ala Phe Ser Gly His His Leu Pro Phe Val
385                 390                 395                 400

Gly Phe Thr Tyr Thr Ser Ser Cys Val Leu Ser Asp Arg Ser Cys Leu
                405                 410                 415

Arg Val Thr Ala Gly Pro Thr Ser Leu Asp Leu Asp Val Asn Val Gln
            420                 425                 430

Arg Thr Leu Asp Asn Asn Leu Ala Thr Glu Ala Tyr Glu Arg Arg Ile
        435                 440                 445

Lys Arg Leu Glu Gln Glu Lys Leu Glu Leu Ser Arg Lys Leu Gln Glu
    450                 455                 460

Ser Thr Gln Thr Val Gln Ala Leu Gln Tyr Ser Thr Val Asp Gly Pro
465                 470                 475                 480

Leu Thr Ala Ser Lys Asp Leu Glu Ile Lys Asn Leu Lys Glu Glu Ile
                485                 490                 495

Glu Lys Leu Arg Lys Gln Val Thr Glu Ser Ser His Leu Glu Gln Gln
            500                 505                 510

Leu Glu Glu Ala Asn Ala Val Arg Gln Glu Leu Asp Asp Ala Phe Arg
```

```
        515                 520                 525

Gln Ile Lys Ala Tyr Glu Lys Gln Ile Lys Thr Leu Gln Gln Glu Arg
    530                 535                 540

Glu Asp Leu Asn Lys Leu Glu Val His Thr Glu Ala Leu Ala Ala Glu
545                 550                 555                 560

Ala Ser Lys Asp Arg Lys Leu Arg Glu Gln Ser Glu His Tyr Ser Lys
                565                 570                 575

Gln Leu Glu Asn Glu Leu Glu Gly Leu Lys Gln Lys Gln Ile Ser Tyr
            580                 585                 590

Ser Pro Gly Val Cys Ser Ile Glu His Gln Gln Glu Ile Thr Lys Leu
        595                 600                 605

Lys Thr Asp Leu Glu Lys Lys Ser Ile Phe Tyr Glu Glu Glu Leu Ser
    610                 615                 620

Lys Arg Glu Gly Ile His Ala Asn Glu Ile Lys Asn Leu Lys Lys Glu
625                 630                 635                 640

Leu His Asp Ser Glu Gly Gln Gln Leu Ala Leu Asn Lys Glu Ile Met
                645                 650                 655

Ile Leu Lys Asp Lys Leu Glu Lys Thr Arg Arg Glu Ser Gln Ser Glu
            660                 665                 670

Arg Glu Glu Phe Glu Ser Glu Phe Lys Gln Gln Tyr Glu Arg Glu Lys
        675                 680                 685

Val Leu Leu Thr Glu Glu Asn Lys Lys Leu Thr Ser Glu Leu Asp Lys
    690                 695                 700

Leu Thr Thr Leu Tyr Glu Asn Leu Ser Ile His Asn Gln Gln Leu Glu
705                 710                 715                 720

Glu Glu Val Lys Asp Leu Ala Asp Lys Lys Glu Ser Val Ala His Trp
                725                 730                 735

Glu Ala Gln Ile Thr Glu Ile Ile Gln Trp Val Ser Asp Glu Lys Asp
            740                 745                 750

Ala Arg Gly Tyr Leu Gln Ala Leu Ala Ser Lys Met Thr Glu Glu Leu
        755                 760                 765

Glu Ala Leu Arg Asn Ser Ser Leu Gly Thr Arg Ala Thr Asp Met Pro
    770                 775                 780

Trp Lys Met Arg Arg Phe Ala Lys Leu Asp Met Ser Ala Arg Leu Glu
785                 790                 795                 800

Leu Gln Ser Ala Leu Asp Ala Glu Ile Arg Ala Lys Gln Ala Ile Gln
                805                 810                 815

Glu Glu Leu Asn Lys Val Lys Ala Ser Asn Ile Ile Thr Glu Cys Lys
            820                 825                 830

Leu Lys Asp Ser Glu Lys Lys Asn Leu Glu Leu Leu Ser Glu Ile Glu
        835                 840                 845

Gln Leu Ile Lys Asp Thr Glu Glu Leu Arg Ser Glu Lys Gly Ile Glu
    850                 855                 860

His Gln Asp Ser Gln His Ser Phe Leu Ala Phe Leu Asn Thr Pro Thr
865                 870                 875                 880

Asp Ala Leu Asp Gln Phe Glu Thr Val Asp Ser Thr Pro Leu Ser Val
                885                 890                 895

His Thr Pro Thr Leu Arg Lys Lys Gly Cys Pro Gly Ser Thr Gly Phe
            900                 905                 910

Pro Pro Lys Arg Lys Thr His Gln Phe Phe Val Lys Ser Phe Thr Thr
        915                 920                 925

Pro Thr Lys Cys His Gln Cys Thr Ser Leu Met Val Gly Leu Ile Arg
    930                 935                 940
```

```
Gln Gly Cys Ser Cys Glu Val Cys Gly Phe Ser Cys His Ile Thr Cys
945                 950                 955                 960

Val Asn Lys Ala Pro Thr Thr Cys Pro Val Pro Pro Glu Gln Thr Lys
                965                 970                 975

Gly Pro Leu Gly Ile Asp Pro Gln Lys Gly Ile Gly Thr Ala Tyr Glu
            980                 985                 990

Gly His Val Arg Ile Pro Lys Pro Ala Gly Val Lys Lys Gly Trp Gln
        995                 1000                1005

Arg Ala Leu Ala Ile Val Cys Asp Phe Lys Leu Phe Leu Tyr Asp Ile
   1010                 1015                1020

Ala Glu Gly Lys Ala Ser Gln Pro Ser Val Val Ile Ser Gln Val Ile
1025                1030                1035                1040

Asp Met Arg Asp Glu Glu Phe Ser Val Ser Ser Val Leu Ala Ser Asp
               1045                1050                1055

Val Ile His Ala Ser Arg Lys Asp Ile Pro Cys Ile Phe Arg Val Thr
           1060                1065                1070

Ala Ser Gln Leu Ser Ala Ser Asn Asn Lys Cys Ser Ile Leu Met Leu
       1075                1080                1085

Ala Asp Thr Glu Asn Glu Lys Asn Lys Trp Val Gly Val Leu Ser Glu
   1090                1095                1100

Leu His Lys Ile Leu Lys Lys Asn Lys Phe Arg Asp Arg Ser Val Tyr
1105                1110                1115                1120

Val Pro Lys Glu Ala Tyr Asp Ser Thr Leu Pro Leu Ile Lys Thr Thr
               1125                1130                1135

Gln Ala Ala Ala Ile Ile Asp His Glu Arg Ile Ala Leu Gly Asn Glu
           1140                1145                1150

Glu Gly Leu Phe Val Val His Val Thr Lys Asp Glu Ile Ile Arg Val
       1155                1160                1165

Gly Asp Asn Lys Lys Ile His Gln Ile Glu Leu Ile Pro Asn Asp Gln
   1170                1175                1180

Leu Val Ala Val Ile Ser Gly Arg Asn Arg His Val Arg Leu Phe Pro
1185                1190                1195                1200

Met Ser Ala Leu Asp Gly Arg Glu Thr Asp Phe Tyr Lys Leu Ser Glu
               1205                1210                1215

Thr Lys Gly Cys Gln Thr Val Thr Ser Gly Lys Val Arg His Gly Ala
           1220                1225                1230

Leu Thr Cys Leu Cys Val Ala Met Lys Arg Gln Val Leu Cys Tyr Glu
       1235                1240                1245

Leu Phe Gln Ser Lys Thr Arg His Arg Lys Phe Lys Glu Ile Gln Val
   1250                1255                1260

Pro Tyr Asn Val Gln Trp Met Ala Ile Phe Ser Glu Gln Leu Cys Val
1265                1270                1275                1280

Gly Phe Gln Ser Gly Phe Leu Arg Tyr Pro Leu Asn Gly Glu Gly Asn
               1285                1290                1295

Pro Tyr Ser Met Leu His Ser Asn Asp His Thr Leu Ser Phe Ile Ala
           1300                1305                1310

His Gln Pro Met Asp Ala Ile Cys Ala Val Glu Ile Ser Ser Lys Glu
       1315                1320                1325

Tyr Leu Leu Cys Phe Asn Ser Ile Gly Ile Tyr Thr Asp Cys Gln Gly
   1330                1335                1340

Arg Arg Ser Arg Gln Gln Glu Leu Met Trp Pro Ala Asn Pro Ser Ser
1345                1350                1355                1360
```

```
Cys Cys Tyr Asn Ala Pro Tyr Leu Ser Val Tyr Ser Glu Asn Ala Val
                1365                1370                1375

Asp Ile Phe Asp Val Asn Ser Met Glu Trp Ile Gln Thr Leu Pro Leu
            1380                1385                1390

Lys Lys Val Arg Pro Leu Asn Asn Glu Gly Ser Leu Asn Leu Leu Gly
        1395                1400                1405

Leu Glu Thr Ile Arg Leu Ile Tyr Phe Lys Asn Lys Met Ala Glu Gly
    1410                1415                1420

Asp Glu Leu Val Val Pro Glu Thr Ser Asp Asn Ser Arg Lys Gln Met
1425                1430                1435                1440

Val Arg Asn Ile Asn Asn Lys Arg Arg Tyr Ser Phe Arg Val Pro Glu
                1445                1450                1455

Glu Glu Arg Met Gln Gln Arg Arg Glu Met Leu Arg Asp Pro Glu Met
            1460                1465                1470

Arg Asn Lys Leu Ile Ser Asn Pro Thr Asn Phe Asn His Ile Ala His
        1475                1480                1485

Met Gly Pro Gly Asp Gly Ile Gln Ile Leu Lys Asp Leu Pro Met Asn
    1490                1495                1500

Pro Arg Pro Gln Glu Ser Arg Thr Val Phe Ser Gly Ser Val Ser Ile
1505                1510                1515                1520

Pro Ser Ile Thr Lys Ser Arg Pro Glu Pro Gly Arg Ser Met Ser Ala
                1525                1530                1535

Ser Ser Gly Leu Ser Ala Arg Ser Ser Ala Gln Asn Gly Ser Ala Leu
            1540                1545                1550

Lys Arg Glu Phe Ser Gly Gly Ser Tyr Ser Ala Lys Arg Gln Pro Met
        1555                1560                1565

Pro Ser Pro Ser Glu Gly Ser Leu Ser Ser Gly Gly Met Asp Gln Gly
    1570                1575                1580

Ser Asp Ala Pro Ala Arg Asp Phe Asp Gly Glu Asp Ser Asp Ser Pro
1585                1590                1595                1600

Arg His Ser Thr Ala Ser Asn Ser Ser Asn Leu Ser Ser Pro Pro Ser
                1605                1610                1615

Pro Ala Ser Pro Arg Lys Thr Lys Ser Leu Ser Leu Glu Ser Thr Asp
            1620                1625                1630

Arg Gly Ser Trp Asp Pro
        1635


<210> SEQ ID NO 70
<211> LENGTH: 152
<212> TYPE: PRT
<213> ORGANISM: Homo sapiens

<400> SEQUENCE: 70

Met Ser His Val Leu Phe Ser Gly Arg Met Phe Ala Gly Leu Ala Gln
 1               5                  10                  15

Asp Phe Arg Trp Ser Ala Ser Ser Phe Leu Ile Pro Cys Asp Cys Cys
            20                  25                  30

Val Gly Lys Gln Arg Val Lys Cys Cys Arg Arg Thr Trp Glu Ser Phe
        35                  40                  45

Cys Phe Glu Gly Pro Leu Glu Gln Glu Lys Leu Glu Ser Leu Ser Leu
    50                  55                  60

Arg Ser Gln Asn Arg His Glu Asp Met Val Pro Ile Pro Leu Val Leu
65                  70                  75                  80

Lys Gly Thr Pro Gly Glu Phe Gln Glu Thr Pro Pro Phe Leu Val Phe
                85                  90                  95
```

```
Ile Leu Thr Pro Ser Pro Arg His Leu Ser Pro Gln Val His Thr Gln
            100                 105                 110

Glu Gly Gly Ile Phe Tyr Leu Phe Arg Ser Gly Gln Gln Pro Val Gly
        115                 120                 125

Asn Val Ile Ser Val Gly Thr Gly His Gly Thr Lys Pro Ser Trp Cys
    130                 135                 140

Leu Asp Cys Asn Leu Ala Glu Ser
145                 150


<210> SEQ ID NO 71
<211> LENGTH: 596
<212> TYPE: PRT
<213> ORGANISM: Homo sapiens

<400> SEQUENCE: 71

Met Pro Gln Leu Asn Gly Gly Gly Gly Asp Asp Leu Gly Ala Asn Asp
 1               5                  10                  15

Glu Leu Ile Ser Phe Lys Asp Glu Gly Glu Gln Glu Glu Lys Ser Ser
            20                  25                  30

Glu Asn Ser Ser Ala Glu Arg Asp Leu Ala Asp Val Lys Ser Ser Leu
        35                  40                  45

Val Asn Glu Ser Glu Thr Asn Gln Asn Ser Ser Ser Asp Ser Glu Ala
    50                  55                  60

Glu Arg Arg Pro Pro Pro Arg Ser Glu Ser Phe Arg Asp Lys Ser Arg
65                  70                  75                  80

Glu Ser Leu Glu Glu Ala Ala Lys Arg Gln Asp Gly Gly Leu Phe Lys
                85                  90                  95

Gly Pro Pro Tyr Pro Gly Tyr Pro Phe Ile Met Ile Pro Asp Leu Thr
            100                 105                 110

Ser Pro Tyr Leu Pro Asn Gly Ser Leu Ser Pro Thr Ala Arg Thr Tyr
        115                 120                 125

Leu Gln Met Lys Trp Pro Leu Leu Asp Val Gln Ala Gly Ser Leu Gln
    130                 135                 140

Ser Arg Gln Ala Leu Lys Asp Ala Arg Ser Pro Ser Pro Ala His Ile
145                 150                 155                 160

Val Ser Asn Lys Val Pro Val Val Gln His Pro His His Val His Pro
                165                 170                 175

Leu Thr Pro Leu Ile Thr Tyr Ser Asn Glu His Phe Thr Pro Gly Asn
            180                 185                 190

Pro Pro Pro His Leu Pro Ala Asp Val Asp Pro Lys Thr Gly Ile Pro
        195                 200                 205

Arg Pro Pro His Pro Pro Asp Ile Ser Pro Tyr Tyr Pro Leu Ser Pro
    210                 215                 220

Gly Thr Val Gly Gln Ile Pro His Pro Leu Gly Trp Leu Val Pro Gln
225                 230                 235                 240

Gln Gly Gln Pro Val Tyr Pro Ile Thr Thr Gly Gly Phe Arg His Pro
                245                 250                 255

Tyr Pro Thr Ala Leu Thr Val Asn Ala Ser Val Ser Arg Phe Pro Pro
            260                 265                 270

His Met Val Pro Pro His His Thr Leu His Thr Thr Gly Ile Pro His
        275                 280                 285

Pro Ala Ile Val Thr Pro Thr Val Lys Gln Glu Ser Ser Gln Ser Asp
    290                 295                 300

Val Gly Ser Leu His Ser Ser Lys His Gln Asp Ser Lys Lys Glu Glu
```

305 310 315 320

Glu Lys Lys Lys Pro His Ile Lys Lys Pro Leu Asn Ala Phe Met Leu
325 330 335

Tyr Met Lys Glu Met Arg Ala Lys Val Val Ala Glu Cys Thr Leu Lys
340 345 350

Glu Ser Ala Ala Ile Asn Gln Ile Leu Gly Arg Arg Trp His Ala Leu
355 360 365

Ser Arg Glu Glu Gln Ala Lys Tyr Tyr Glu Leu Ala Arg Lys Glu Arg
370 375 380

Gln Leu His Met Gln Leu Tyr Pro Gly Trp Ser Ala Arg Asp Asn Tyr
385 390 395 400

Gly Lys Lys Lys Lys Arg Lys Arg Asp Lys Gln Pro Gly Glu Thr Asn
405 410 415

Glu His Ser Glu Cys Phe Leu Asn Pro Cys Leu Ser Leu Pro Pro Ile
420 425 430

Thr Asp Leu Ser Ala Pro Lys Lys Cys Arg Ala Arg Phe Gly Leu Asp
435 440 445

Gln Gln Asn Asn Trp Cys Gly Pro Cys Arg Arg Lys Lys Lys Cys Val
450 455 460

Arg Tyr Ile Gln Gly Glu Gly Ser Cys Leu Ser Pro Pro Ser Ser Asp
465 470 475 480

Gly Ser Leu Leu Asp Ser Pro Pro Pro Ser Pro Asn Leu Leu Gly Ser
485 490 495

Pro Pro Arg Asp Ala Lys Ser Gln Thr Glu Gln Thr Gln Pro Leu Ser
500 505 510

Leu Ser Leu Lys Pro Asp Pro Leu Ala His Leu Ser Met Met Pro Pro
515 520 525

Pro Pro Ala Leu Leu Leu Ala Glu Ala Thr His Lys Ala Ser Ala Leu
530 535 540

Cys Pro Asn Gly Ala Leu Asp Leu Pro Pro Ala Ala Leu Gln Pro Ala
545 550 555 560

Ala Pro Ser Ser Ser Ile Ala Gln Pro Ser Thr Ser Trp Leu His Ser
565 570 575

His Ser Ser Leu Ala Gly Thr Gln Pro Gln Pro Leu Ser Leu Val Thr
580 585 590

Lys Ser Leu Glu
595

<210> SEQ ID NO 72
<211> LENGTH: 313
<212> TYPE: PRT
<213> ORGANISM: Homo sapiens

<400> SEQUENCE: 72

Met Glu Thr Gly Pro Glu Asp Pro Ser Ser Met Pro Glu Glu Ser Ser
1 5 10 15

Pro Arg Arg Thr Pro Gln Ser Ile Pro Tyr Gln Asp Leu Pro His Leu
20 25 30

Val Asn Ala Asp Gly Gln Tyr Leu Phe Cys Arg Tyr Trp Lys Pro Thr
35 40 45

Gly Thr Pro Lys Ala Leu Ile Phe Val Ser His Gly Ala Gly Glu His
50 55 60

Ser Gly Arg Tyr Glu Glu Leu Ala Arg Met Leu Met Gly Leu Asp Leu
65 70 75 80

```
Leu Val Phe Ala His Asp His Val Gly His Gly Gln Ser Glu Gly Glu
                85                  90                  95

Arg Met Val Val Ser Asp Phe His Val Phe Val Arg Asp Val Leu Gln
            100                 105                 110

His Val Asp Ser Met Gln Lys Asp Tyr Pro Gly Leu Pro Val Phe Leu
        115                 120                 125

Leu Gly His Ser Met Gly Gly Ala Ile Ala Ile Leu Thr Ala Ala Glu
    130                 135                 140

Arg Pro Gly His Phe Ala Gly Met Val Leu Ile Ser Pro Leu Val Leu
145                 150                 155                 160

Ala Asn Pro Glu Ser Ala Thr Thr Phe Lys Val Leu Ala Ala Lys Val
                165                 170                 175

Leu Asn Leu Val Leu Pro Asn Leu Ser Leu Gly Pro Ile Asp Ser Ser
            180                 185                 190

Val Leu Ser Arg Asn Lys Thr Glu Val Asp Ile Tyr Asn Ser Asp Pro
        195                 200                 205

Leu Ile Cys Arg Ala Gly Leu Lys Val Cys Phe Gly Ile Gln Leu Leu
    210                 215                 220

Asn Ala Val Ser Arg Val Glu Arg Ala Leu Pro Lys Leu Thr Val Pro
225                 230                 235                 240

Phe Leu Leu Leu Gln Gly Ser Ala Asp Arg Leu Cys Asp Ser Lys Gly
                245                 250                 255

Ala Tyr Leu Leu Met Glu Leu Ala Lys Ser Gln Asp Lys Thr Leu Lys
            260                 265                 270

Ile Tyr Glu Gly Ala Tyr His Val Leu His Lys Glu Leu Pro Glu Val
        275                 280                 285

Thr Asn Ser Val Phe His Glu Ile Asn Met Trp Val Ser Gln Arg Thr
    290                 295                 300

Ala Thr Ala Gly Thr Ala Ser Pro Pro
305                 310


<210> SEQ ID NO 73
<211> LENGTH: 424
<212> TYPE: PRT
<213> ORGANISM: Homo sapiens

<400> SEQUENCE: 73

Met Gln Arg Leu Gln Val Val Leu Gly His Leu Arg Gly Pro Ala Asp
 1               5                  10                  15

Ser Gly Trp Met Pro Gln Ala Ala Pro Cys Leu Ser Gly Ala Pro Gln
            20                  25                  30

Ala Ser Ala Ala Asp Val Val Val Val His Gly Arg Arg Thr Ala Ile
        35                  40                  45

Cys Arg Ala Gly Arg Gly Gly Phe Lys Asp Thr Thr Pro Asp Glu Leu
    50                  55                  60

Leu Ser Ala Val Met Thr Ala Val Leu Lys Asp Val Asn Leu Arg Pro
65                  70                  75                  80

Glu Gln Leu Gly Asp Ile Cys Val Gly Asn Val Leu Gln Pro Gly Ala
                85                  90                  95

Gly Ala Ile Met Ala Arg Ile Ala Gln Phe Leu Ser Asp Ile Pro Glu
            100                 105                 110

Thr Val Pro Leu Ser Thr Val Asn Arg Gln Cys Ser Ser Gly Leu Gln
        115                 120                 125

Ala Val Ala Ser Ile Ala Gly Gly Ile Arg Asn Gly Ser Tyr Asp Ile
    130                 135                 140
```

```
Gly Met Ala Cys Gly Val Glu Ser Met Ser Leu Ala Asp Arg Gly Asn
145                 150                 155                 160

Pro Gly Asn Ile Thr Ser Arg Leu Met Glu Lys Glu Lys Ala Arg Asp
                165                 170                 175

Cys Leu Ile Pro Met Gly Ile Thr Ser Glu Asn Val Ala Glu Arg Phe
            180                 185                 190

Gly Ile Ser Arg Glu Lys Gln Asp Thr Phe Ala Leu Ala Ser Gln Gln
        195                 200                 205

Lys Ala Ala Arg Ala Gln Ser Lys Gly Cys Phe Gln Ala Glu Ile Val
    210                 215                 220

Pro Val Thr Thr Thr Val His Asp Asp Lys Gly Thr Lys Arg Ser Ile
225                 230                 235                 240

Thr Val Thr Gln Asp Glu Gly Ile Arg Pro Ser Thr Thr Met Glu Gly
                245                 250                 255

Leu Ala Lys Leu Lys Pro Ala Phe Lys Lys Asp Gly Ser Thr Thr Ala
            260                 265                 270

Gly Asn Ser Ser Gln Val Ser Asp Gly Ala Ala Ala Ile Leu Leu Ala
        275                 280                 285

Arg Arg Ser Lys Ala Glu Glu Leu Gly Leu Pro Ile Leu Gly Val Leu
    290                 295                 300

Arg Ser Tyr Ala Val Val Gly Val Pro Pro Asp Ile Met Gly Ile Gly
305                 310                 315                 320

Pro Ala Tyr Ala Ile Pro Val Ala Leu Gln Lys Ala Gly Leu Thr Val
                325                 330                 335

Ser Asp Val Asp Ile Phe Glu Ile Asn Glu Ala Phe Ala Ser Gln Ala
            340                 345                 350

Ala Tyr Cys Val Glu Lys Leu Arg Leu Pro Pro Glu Lys Val Asn Pro
        355                 360                 365

Leu Gly Gly Ala Val Ala Leu Gly His Pro Leu Gly Cys Thr Gly Ala
    370                 375                 380

Arg Gln Val Ile Thr Leu Leu Asn Glu Leu Lys Arg Arg Gly Lys Arg
385                 390                 395                 400

Ala Tyr Gly Val Val Ser Met Cys Ile Gly Thr Gly Met Gly Ala Ala
                405                 410                 415

Ala Val Phe Glu Tyr Pro Gly Asn
            420
```

<210> SEQ ID NO 74
<211> LENGTH: 333
<212> TYPE: PRT
<213> ORGANISM: Homo sapiens

<400> SEQUENCE: 74

```
Met Pro Leu Gly Leu Gly Arg Arg Lys Lys Ala Pro Pro Leu Val Glu
 1               5                  10                  15

Asn Glu Glu Ala Glu Pro Gly Arg Gly Gly Leu Gly Val Gly Glu Pro
            20                  25                  30

Gly Pro Leu Gly Gly Gly Gly Ser Gly Gly Pro Gln Met Gly Leu Pro
        35                  40                  45

Pro Pro Pro Pro Ala Leu Arg Pro Arg Leu Val Phe His Thr Gln Leu
    50                  55                  60

Ala His Gly Ser Pro Thr Gly Arg Ile Glu Gly Phe Thr Asn Val Lys
65                  70                  75                  80

Glu Leu Tyr Gly Lys Ile Ala Glu Ala Phe Arg Leu Pro Thr Ala Glu
```

```
                85                  90                  95

Val Met Phe Cys Thr Leu Asn Thr His Lys Val Asp Met Asp Lys Leu
            100                 105                 110

Leu Gly Gly Gln Ile Gly Leu Glu Asp Phe Ile Phe Ala His Val Lys
        115                 120                 125

Gly Gln Arg Lys Glu Val Glu Val Phe Lys Ser Glu Asp Ala Leu Gly
    130                 135                 140

Leu Thr Ile Thr Asp Asn Gly Ala Gly Tyr Ala Phe Ile Lys Arg Ile
145                 150                 155                 160

Lys Glu Gly Ser Val Ile Asp His Ile His Leu Ile Ser Val Gly Asp
                165                 170                 175

Met Ile Glu Ala Ile Asn Gly Gln Ser Leu Leu Gly Cys Arg His Tyr
            180                 185                 190

Glu Val Ala Arg Leu Leu Lys Glu Leu Pro Arg Gly Arg Thr Phe Thr
        195                 200                 205

Leu Lys Leu Thr Glu Pro Arg Lys Ala Phe Asp Met Ile Ser Gln Arg
    210                 215                 220

Ser Ala Gly Gly Arg Pro Gly Ser Gly Pro Gln Leu Gly Thr Gly Arg
225                 230                 235                 240

Gly Thr Leu Arg Leu Arg Ser Arg Gly Pro Ala Thr Val Glu Asp Leu
                245                 250                 255

Pro Ser Ala Phe Glu Glu Lys Ala Ile Glu Lys Val Asp Asp Leu Leu
            260                 265                 270

Glu Ser Tyr Met Gly Ile Arg Asp Thr Glu Leu Ala Ala Thr Met Val
        275                 280                 285

Glu Leu Gly Lys Asp Lys Arg Asn Pro Asp Glu Leu Ala Glu Ala Leu
    290                 295                 300

Asp Glu Arg Leu Gly Asp Phe Ala Phe Pro Asp Glu Phe Val Phe Asp
305                 310                 315                 320

Val Trp Gly Ala Ile Gly Asp Ala Lys Val Gly Arg Tyr
                325                 330


<210> SEQ ID NO 75
<211> LENGTH: 545
<212> TYPE: PRT
<213> ORGANISM: Homo sapiens

<400> SEQUENCE: 75

Met Ser Asn Asn Gly Leu Asp Ile Gln Asp Lys Pro Pro Ala Pro Pro
 1               5                  10                  15

Met Arg Asn Thr Ser Thr Met Ile Gly Val Gly Ser Lys Asp Ala Gly
            20                  25                  30

Thr Leu Asn His Gly Ser Lys Pro Leu Pro Pro Asn Pro Glu Glu Lys
        35                  40                  45

Lys Lys Lys Asp Arg Phe Tyr Arg Ser Ile Leu Pro Gly Asp Lys Thr
    50                  55                  60

Asn Lys Lys Lys Glu Lys Glu Arg Pro Glu Ile Ser Leu Pro Ser Asp
65                  70                  75                  80

Phe Glu His Thr Ile His Val Gly Phe Asp Ala Val Thr Gly Glu Phe
                85                  90                  95

Thr Gly Met Pro Glu Gln Trp Ala Arg Leu Leu Gln Thr Ser Asn Ile
            100                 105                 110

Thr Lys Ser Glu Gln Lys Lys Asn Pro Gln Ala Val Leu Asp Val Leu
        115                 120                 125
```

```
Glu Phe Tyr Asn Ser Lys Lys Thr Ser Asn Ser Gln Lys Tyr Met Ser
    130                 135                 140

Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Pro Val Ser Glu Asp
                165                 170                 175

Glu Asp Asp Asp Asp Asp Asp Ala Thr Pro Pro Pro Val Ile Ala Pro
            180                 185                 190

Arg Pro Glu His Thr Lys Ser Val Tyr Thr Arg Ser Val Ile Glu Pro
        195                 200                 205

Leu Pro Val Thr Pro Thr Arg Asp Val Ala Thr Ser Pro Ile Ser Pro
    210                 215                 220

Thr Glu Asn Asn Thr Thr Pro Pro Asp Ala Leu Thr Arg Asn Thr Glu
225                 230                 235                 240

Lys Gln Lys Lys Lys Pro Lys Met Ser Asp Glu Glu Ile Leu Glu Lys
                245                 250                 255

Leu Arg Ser Ile Val Ser Val Gly Asp Pro Lys Lys Lys Tyr Thr Arg
            260                 265                 270

Phe Glu Lys Ile Gly Gln Gly Ala Ser Gly Thr Val Tyr Thr Ala Met
        275                 280                 285

Asp Val Ala Thr Gly Gln Glu Val Ala Ile Lys Gln Met Asn Leu Gln
    290                 295                 300

Gln Gln Pro Lys Lys Glu Leu Ile Ile Asn Glu Ile Leu Val Met Arg
305                 310                 315                 320

Glu Asn Lys Asn Pro Asn Ile Val Asn Tyr Leu Asp Ser Tyr Leu Val
                325                 330                 335

Gly Asp Glu Leu Trp Val Val Met Glu Tyr Leu Ala Gly Gly Ser Leu
            340                 345                 350

Thr Asp Val Val Thr Glu Thr Cys Met Asp Glu Gly Gln Ile Ala Ala
        355                 360                 365

Val Cys Arg Glu Cys Leu Gln Ala Leu Glu Phe Leu His Ser Asn Gln
    370                 375                 380

Val Ile His Arg Asp Ile Lys Ser Asp Asn Ile Leu Leu Gly Met Asp
385                 390                 395                 400

Gly Ser Val Lys Leu Thr Asp Phe Gly Phe Cys Ala Gln Ile Thr Pro
                405                 410                 415

Glu Gln Ser Lys Arg Ser Thr Met Val Gly Thr Pro Tyr Trp Met Ala
            420                 425                 430

Pro Glu Val Val Thr Arg Lys Ala Tyr Gly Pro Lys Val Asp Ile Trp
        435                 440                 445

Ser Leu Gly Ile Met Ala Ile Glu Met Ile Glu Gly Glu Pro Pro Tyr
    450                 455                 460

Leu Asn Glu Asn Pro Leu Arg Ala Leu Tyr Leu Ile Ala Thr Asn Gly
465                 470                 475                 480

Thr Pro Glu Leu Gln Asn Pro Glu Lys Leu Ser Ala Ile Phe Arg Asp
                485                 490                 495

Phe Leu Asn Arg Cys Leu Asp Met Asp Val Glu Lys Arg Gly Ser Ala
            500                 505                 510

Lys Glu Leu Leu Gln His Gln Phe Leu Lys Ile Ala Lys Pro Leu Ser
        515                 520                 525

Ser Leu Thr Pro Leu Ile Ala Ala Ala Lys Glu Ala Thr Lys Asn Asn
    530                 535                 540

His
```

545

<210> SEQ ID NO 76
<211> LENGTH: 115
<212> TYPE: PRT
<213> ORGANISM: Homo sapiens

<400> SEQUENCE: 76

Met Val Ser Arg Lys Ala Val Ala Ala Leu Leu Val Val His Val Ala
1 5 10 15

Ala Met Leu Ala Ser Gln Thr Glu Ala Phe Val Pro Ile Phe Thr Tyr
20 25 30

Gly Glu Leu Gln Arg Met Gln Glu Lys Glu Arg Asn Lys Gly Gln Lys
35 40 45

Lys Ser Leu Ser Val Trp Gln Arg Ser Gly Glu Glu Gly Pro Val Asp
50 55 60

Pro Ala Glu Pro Ile Arg Glu Glu Glu Asn Glu Met Ile Lys Leu Thr
65 70 75 80

Ala Pro Leu Glu Ile Gly Met Arg Met Asn Ser Arg Gln Leu Glu Lys
85 90 95

Tyr Pro Ala Thr Leu Glu Gly Leu Leu Ser Glu Met Leu Pro Gln His
100 105 110

Ala Ala Lys
115

<210> SEQ ID NO 77
<211> LENGTH: 414
<212> TYPE: PRT
<213> ORGANISM: Homo sapiens

<400> SEQUENCE: 77

Met Gln Thr Phe Leu Lys Gly Lys Arg Val Gly Tyr Trp Leu Ser Glu
1 5 10 15

Lys Lys Ile Lys Lys Leu Asn Phe Gln Ala Phe Ala Glu Leu Cys Arg
20 25 30

Lys Arg Gly Met Glu Val Val Gln Leu Asn Leu Ser Arg Pro Ile Glu
35 40 45

Glu Gln Gly Pro Leu Asp Val Ile Ile His Lys Leu Thr Asp Val Ile
50 55 60

Leu Glu Ala Asp Gln Asn Asp Ser Gln Ser Leu Glu Leu Val His Arg
65 70 75 80

Phe Gln Glu Tyr Ile Asp Ala His Pro Glu Thr Ile Val Leu Asp Pro
85 90 95

Leu Pro Ala Ile Arg Thr Leu Leu Asp Arg Ser Lys Ser Tyr Glu Leu
100 105 110

Ile Arg Lys Ile Glu Ala Tyr Met Glu Asp Asp Arg Ile Cys Ser Pro
115 120 125

Pro Phe Met Glu Leu Thr Ser Leu Cys Gly Asp Asp Thr Met Arg Leu
130 135 140

Leu Glu Lys Asn Gly Leu Thr Phe Pro Phe Ile Cys Lys Thr Arg Val
145 150 155 160

Ala His Gly Thr Asn Ser His Glu Met Ala Ile Val Phe Asn Gln Glu
165 170 175

Gly Leu Asn Ala Ile Gln Pro Pro Cys Val Val Gln Asn Phe Ile Asn
180 185 190

His Asn Ala Val Leu Tyr Lys Val Phe Val Val Gly Glu Ser Tyr Thr

```
        195                 200                 205

Val Val Gln Arg Pro Ser Leu Lys Asn Phe Ser Ala Gly Thr Ser Asp
    210                 215                 220

Arg Glu Ser Ile Phe Phe Asn Ser His Asn Val Ser Lys Pro Glu Ser
225                 230                 235                 240

Ser Ser Val Leu Thr Glu Leu Asp Lys Ile Glu Gly Val Phe Glu Arg
                245                 250                 255

Pro Ser Asp Glu Val Ile Arg Glu Leu Ser Arg Ala Leu Arg Gln Ala
            260                 265                 270

Leu Gly Val Ser Leu Phe Gly Ile Asp Ile Ile Ile Asn Asn Gln Thr
        275                 280                 285

Gly Gln His Ala Val Ile Asp Ile Asn Ala Phe Pro Gly Tyr Glu Gly
    290                 295                 300

Val Ser Glu Phe Phe Thr Asp Leu Leu Asn His Ile Ala Thr Val Leu
305                 310                 315                 320

Gln Gly Gln Ser Thr Ala Met Ala Ala Thr Gly Asp Val Ala Leu Leu
                325                 330                 335

Arg His Ser Lys Leu Leu Ala Glu Pro Ala Gly Gly Leu Val Gly Glu
            340                 345                 350

Arg Thr Cys Ser Ala Ser Pro Gly Cys Cys Gly Ser Met Met Gly Gln
        355                 360                 365

Asp Ala Pro Trp Lys Ala Glu Ala Asp Ala Gly Gly Thr Ala Lys Leu
    370                 375                 380

Pro His Gln Arg Leu Gly Cys Asn Ala Gly Val Ser Pro Ser Phe Gln
385                 390                 395                 400

Gln His Cys Val Ala Ser Leu Ala Thr Lys Ala Ser Ser Gln
                405                 410


<210> SEQ ID NO 78
<211> LENGTH: 1043
<212> TYPE: PRT
<213> ORGANISM: Homo sapiens

<400> SEQUENCE: 78

Met Pro Leu Leu Glu Gly Ser Val Gly Val Glu Asp Leu Val Leu Leu
 1               5                  10                  15

Glu Pro Leu Val Glu Glu Ser Leu Leu Lys Asn Leu Gln Leu Arg Tyr
            20                  25                  30

Glu Asn Lys Glu Ile Tyr Thr Tyr Ile Gly Asn Val Val Ile Ser Val
        35                  40                  45

Asn Pro Tyr Gln Gln Leu Pro Ile Tyr Gly Pro Glu Phe Ile Ala Lys
    50                  55                  60

Tyr Gln Asp Tyr Thr Phe Tyr Glu Leu Lys Pro His Ile Tyr Ala Leu
65                  70                  75                  80

Ala Asn Val Ala Tyr Gln Ser Leu Arg Asp Arg Asp Arg Asp Gln Cys
                85                  90                  95

Ile Leu Ile Thr Gly Glu Ser Gly Ser Gly Lys Thr Glu Ala Ser Lys
            100                 105                 110

Leu Val Met Ser Tyr Val Ala Ala Val Cys Gly Lys Gly Glu Gln Val
        115                 120                 125

Asn Ser Val Lys Glu Gln Leu Leu Gln Ser Asn Pro Val Leu Glu Ala
    130                 135                 140

Phe Gly Asn Ala Lys Thr Ile Arg Asn Asn Asn Ser Ser Arg Phe Gly
145                 150                 155                 160
```

-continued

```
Lys Tyr Met Asp Ile Glu Phe Asp Phe Lys Gly Ser Pro Leu Gly Gly
                165                 170                 175

Val Ile Thr Asn Tyr Leu Leu Glu Lys Ser Arg Leu Val Lys Gln Leu
            180                 185                 190

Lys Gly Glu Arg Asn Phe His Ile Phe Tyr Gln Leu Leu Ala Gly Ala
        195                 200                 205

Asp Glu Gln Leu Leu Lys Ala Leu Lys Leu Glu Arg Asp Thr Thr Gly
    210                 215                 220

Tyr Ala Tyr Leu Asn His Glu Val Ser Arg Val Asp Gly Met Asp Asp
225                 230                 235                 240

Ala Ser Ser Phe Arg Ala Val Gln Ser Ala Met Ala Val Ile Gly Phe
                245                 250                 255

Ser Glu Glu Glu Ile Arg Gln Val Leu Glu Val Thr Ser Met Val Leu
            260                 265                 270

Lys Leu Gly Asn Val Leu Val Ala Asp Glu Phe Gln Ala Ser Gly Ile
        275                 280                 285

Pro Ala Ser Gly Ile Arg Asp Gly Arg Gly Val Arg Glu Ile Gly Glu
    290                 295                 300

Met Val Gly Leu Asn Ser Glu Glu Val Glu Arg Ala Leu Cys Ser Arg
305                 310                 315                 320

Thr Met Glu Thr Ala Lys Glu Lys Val Val Thr Ala Leu Asn Val Met
                325                 330                 335

Gln Ala Gln Tyr Ala Arg Asp Ala Leu Ala Lys Asn Ile Tyr Ser Arg
            340                 345                 350

Leu Phe Asp Trp Ile Val Asn Arg Ile Asn Glu Ser Ile Lys Val Gly
        355                 360                 365

Ile Gly Glu Lys Lys Lys Val Met Gly Val Leu Asp Ile Tyr Gly Phe
    370                 375                 380

Glu Ile Leu Glu Asp Asn Ser Phe Glu Gln Phe Val Ile Asn Tyr Cys
385                 390                 395                 400

Asn Glu Lys Leu Gln Gln Val Phe Ile Glu Met Thr Leu Lys Glu Glu
                405                 410                 415

Gln Glu Glu Tyr Lys Arg Glu Gly Ile Pro Trp Thr Lys Val Asp Tyr
            420                 425                 430

Phe Asp Asn Gly Ile Ile Cys Lys Leu Ile Glu His Asn Gln Arg Gly
        435                 440                 445

Ile Leu Ala Met Leu Asp Glu Glu Cys Leu Arg Pro Gly Val Val Ser
    450                 455                 460

Asp Ser Thr Phe Leu Ala Lys Leu Asn Gln Leu Phe Ser Lys His Gly
465                 470                 475                 480

His Tyr Glu Ser Lys Val Thr Gln Asn Ala Gln Arg Gln Tyr Asp His
                485                 490                 495

Thr Met Gly Leu Ser Cys Phe Arg Ile Cys His Tyr Ala Gly Lys Val
            500                 505                 510

Thr Tyr Asn Val Thr Ser Phe Ile Asp Lys Asn Asn Asp Leu Leu Phe
        515                 520                 525

Arg Asp Leu Leu Gln Ala Met Trp Lys Ala Gln His Pro Leu Leu Arg
    530                 535                 540

Ser Leu Phe Pro Glu Gly Asn Pro Lys Gln Ala Ser Leu Lys Arg Pro
545                 550                 555                 560

Pro Thr Ala Gly Ala Gln Phe Lys Ser Ser Val Ala Ile Leu Met Lys
                565                 570                 575

Asn Leu Tyr Ser Lys Ser Pro Asn Tyr Ile Arg Cys Ile Lys Pro Asn
```

-continued

```
            580                 585                 590

Glu His Gln Gln Arg Gly Gln Phe Ser Ser Asp Leu Val Ala Thr Gln
        595                 600                 605

Ala Arg Tyr Leu Gly Leu Leu Glu Asn Val Arg Val Arg Arg Ala Gly
    610                 615                 620

Tyr Ala His Arg Gln Gly Tyr Gly Pro Phe Leu Glu Arg Tyr Arg Leu
625                 630                 635                 640

Leu Ser Arg Ser Thr Trp Pro His Trp Asn Gly Gly Asp Arg Glu Gly
                645                 650                 655

Val Glu Lys Val Leu Gly Glu Leu Ser Met Ser Ser Gly Glu Leu Ala
            660                 665                 670

Phe Gly Lys Thr Lys Ile Phe Ile Arg Ser Pro Lys Thr Leu Phe Tyr
        675                 680                 685

Leu Glu Glu Gln Arg Arg Leu Arg Leu Gln Gln Leu Ala Thr Leu Ile
    690                 695                 700

Gln Lys Ile Tyr Arg Gly Trp Arg Cys Arg Thr His Tyr Gln Leu Met
705                 710                 715                 720

Arg Lys Ser Gln Ile Leu Ile Ser Ser Trp Phe Arg Gly Asn Met Gln
                725                 730                 735

Lys Lys Cys Tyr Gly Lys Ile Lys Ala Ser Val Leu Leu Ile Gln Ala
            740                 745                 750

Phe Val Arg Gly Trp Lys Ala Arg Lys Asn Tyr Arg Lys Tyr Phe Arg
        755                 760                 765

Ser Glu Ala Ala Leu Thr Leu Ala Asp Phe Ile Tyr Lys Ser Met Val
    770                 775                 780

Gln Lys Phe Leu Leu Gly Leu Lys Asn Asn Leu Pro Ser Thr Asn Val
785                 790                 795                 800

Leu Asp Lys Thr Trp Pro Ala Ala Pro Tyr Lys Cys Leu Ser Thr Ala
                805                 810                 815

Asn Gln Glu Leu Gln Gln Leu Phe Tyr Gln Trp Lys Cys Lys Arg Phe
            820                 825                 830

Arg Asp Gln Leu Ser Pro Lys Gln Val Glu Ile Leu Arg Glu Lys Leu
        835                 840                 845

Cys Ala Ser Glu Leu Phe Lys Gly Lys Lys Ala Ser Tyr Pro Gln Ser
    850                 855                 860

Val Pro Ile Pro Phe Cys Gly Asp Tyr Ile Gly Leu Gln Gly Asn Pro
865                 870                 875                 880

Lys Leu Gln Lys Leu Lys Gly Gly Glu Glu Gly Pro Val Leu Met Ala
                885                 890                 895

Glu Ala Val Lys Lys Val Asn Arg Gly Asn Gly Lys Thr Ser Ser Arg
            900                 905                 910

Ile Leu Leu Leu Thr Lys Gly His Val Ile Leu Thr Asp Thr Lys Lys
        915                 920                 925

Ser Gln Ala Lys Ile Val Ile Gly Leu Asp Asn Val Ala Gly Val Ser
    930                 935                 940

Val Thr Ser Leu Lys Asp Gly Leu Phe Ser Leu His Leu Ser Glu Met
945                 950                 955                 960

Ser Ser Val Gly Ser Lys Gly Asp Phe Leu Leu Val Ser Glu His Val
                965                 970                 975

Ile Glu Leu Leu Thr Lys Met Tyr Arg Ala Val Leu Asp Ala Thr Gln
            980                 985                 990

Arg Gln Leu Thr Val Thr Val Thr Glu Lys Phe Ser Val Arg Phe Lys
        995                 1000                1005
```

Glu Asn Ser Val Ala Val Lys Val Val Gln Gly Pro Ala Gly Gly Asp
1010 1015 1020

Asn Ser Lys Leu Arg Tyr Lys Lys Lys Gly Ser His Cys Leu Glu Val
1025 1030 1035 1040

Thr Val Gln

<210> SEQ ID NO 79
<211> LENGTH: 638
<212> TYPE: PRT
<213> ORGANISM: Homo sapiens

<400> SEQUENCE: 79

Met Ile Lys Gly Ala Ile Glu Val Leu Ile Arg Glu Tyr Ser Ser Glu
1 5 10 15

Leu Asn Ala Pro Ser Gln Glu Ser Asp Ser His Pro Arg Lys Lys Lys
20 25 30

Lys Glu Lys Lys Glu Asp Ile Phe Arg Arg Phe Pro Val Ala Pro Leu
35 40 45

Ile Pro Tyr Pro Leu Ile Thr Lys Glu Asp Ile Asn Ala Ile Glu Met
50 55 60

Glu Glu Asp Lys Arg Asp Leu Ile Ser Arg Glu Ile Ser Lys Phe Arg
65 70 75 80

Asp Thr His Lys Lys Leu Glu Glu Glu Lys Gly Lys Lys Glu Lys Glu
85 90 95

Arg Gln Glu Ile Glu Lys Glu Arg Arg Glu Arg Glu Arg Glu Arg Glu
100 105 110

Arg Glu Arg Glu Arg Arg Glu Arg Glu Arg Glu Arg Glu Arg Glu Arg
115 120 125

Glu Arg Glu Lys Glu Lys Glu Arg Glu Arg Glu Arg Glu Arg Asp Arg
130 135 140

Asp Arg Asp Arg Thr Lys Glu Arg Asp Arg Asp Arg Asp Arg Glu Arg
145 150 155 160

Asp Arg Asp Arg Asp Arg Glu Arg Ser Ser Asp Arg Asn Lys Asp Arg
165 170 175

Ser Arg Ser Arg Glu Lys Ser Arg Asp Arg Glu Arg Glu Arg Glu Arg
180 185 190

Glu Arg Glu Arg Glu Arg Glu Arg Glu Arg Glu Arg Glu Arg Glu Arg
195 200 205

Glu Arg Glu Arg Glu Arg Glu Arg Glu Arg Glu Arg Glu Lys Asp Lys
210 215 220

Lys Arg Asp Arg Glu Glu Asp Glu Glu Asp Ala Tyr Glu Arg Arg Lys
225 230 235 240

Leu Glu Arg Lys Leu Arg Glu Lys Glu Ala Ala Tyr Gln Glu Arg Leu
245 250 255

Lys Asn Trp Glu Ile Arg Glu Arg Lys Lys Thr Arg Glu Tyr Glu Lys
260 265 270

Glu Ala Glu Arg Glu Glu Glu Arg Arg Arg Glu Met Ala Lys Glu Ala
275 280 285

Lys Arg Leu Lys Glu Phe Leu Glu Asp Tyr Asp Asp Asp Arg Asp Asp
290 295 300

Pro Lys Tyr Tyr Arg Gly Ser Ala Leu Gln Lys Arg Leu Arg Asp Arg
305 310 315 320

Glu Lys Glu Met Glu Ala Asp Glu Arg Asp Arg Lys Arg Glu Lys Glu
325 330 335

Glu Leu Glu Glu Ile Arg Gln Arg Leu Leu Ala Glu Gly His Pro Asp
340 345 350

Pro Asp Ala Glu Leu Gln Arg Met Glu Gln Glu Ala Glu Arg Arg Arg
355 360 365

Gln Pro Gln Ile Lys Gln Glu Pro Glu Ser Glu Glu Glu Glu Glu Glu
370 375 380

Lys Gln Glu Lys Glu Glu Lys Arg Glu Glu Pro Met Glu Glu Glu Glu
385 390 395 400

Glu Pro Glu Gln Lys Pro Cys Leu Lys Pro Thr Leu Arg Pro Ile Ser
405 410 415

Ser Ala Pro Ser Val Ser Ser Ala Ser Gly Asn Ala Thr Pro Asn Thr
420 425 430

Pro Gly Asp Glu Ser Pro Cys Gly Ile Ile Ile Pro His Glu Asn Ser
435 440 445

Pro Asp Gln Gln Gln Pro Glu Glu His Arg Pro Lys Ile Gly Leu Ser
450 455 460

Leu Lys Leu Gly Ala Ser Asn Ser Pro Gly Gln Pro Asn Ser Val Lys
465 470 475 480

Arg Lys Lys Leu Pro Val Asp Ser Val Phe Asn Lys Phe Glu Asp Glu
485 490 495

Asp Ser Asp Asp Val Pro Arg Lys Arg Lys Leu Val Pro Leu Asp Tyr
500 505 510

Gly Glu Asp Asp Lys Asn Ala Thr Lys Gly Thr Val Asn Thr Glu Glu
515 520 525

Lys Arg Lys His Ile Lys Ser Leu Ile Glu Lys Ile Pro Thr Ala Lys
530 535 540

Pro Glu Leu Phe Ala Tyr Pro Leu Asp Trp Ser Ile Val Asp Ser Ile
545 550 555 560

Leu Met Glu Arg Arg Ile Arg Pro Trp Ile Asn Lys Lys Ile Ile Glu
565 570 575

Tyr Ile Gly Glu Glu Glu Ala Thr Leu Val Asp Phe Val Cys Ser Lys
580 585 590

Val Met Ala His Ser Ser Pro Gln Ser Ile Leu Asp Asp Val Ala Met
595 600 605

Val Leu Asp Glu Glu Ala Glu Val Phe Ile Val Lys Met Trp Arg Leu
610 615 620

Leu Ile Tyr Glu Thr Glu Ala Lys Lys Ile Gly Leu Val Lys
625 630 635

<210> SEQ ID NO 80
<211> LENGTH: 940
<212> TYPE: PRT
<213> ORGANISM: Homo sapiens

<400> SEQUENCE: 80

Met Gly Ser Gly Pro Ile Asp Pro Lys Glu Leu Leu Lys Gly Leu Asp
1 5 10 15

Ser Phe Leu Asn Arg Asp Gly Glu Val Lys Ser Val Asp Gly Ile Ser
20 25 30

Lys Ile Phe Ser Leu Met Lys Glu Ala Arg Lys Met Val Ser Arg Cys
35 40 45

Thr Tyr Leu Asn Ile Leu Leu Gln Thr Arg Ser Pro Glu Ile Leu Val
50 55 60

Lys Phe Ile Asp Val Gly Gly Tyr Lys Leu Leu Asn Asn Trp Leu Thr

```
65                  70                  75                  80

Tyr Ser Lys Thr Thr Asn Asn Ile Pro Leu Leu Gln Gln Ile Leu Leu
                85                  90                  95

Thr Leu Gln His Leu Pro Leu Thr Val Asp His Leu Lys Gln Asn Asn
            100                 105                 110

Thr Ala Lys Leu Val Lys Gln Leu Ser Lys Ser Ser Glu Asp Glu Glu
        115                 120                 125

Leu Arg Lys Leu Ala Ser Val Leu Val Ser Asp Trp Met Ala Val Ile
    130                 135                 140

Arg Ser Gln Ser Ser Thr Gln Pro Ala Glu Lys Asp Lys Lys Lys Arg
145                 150                 155                 160

Lys Asp Glu Gly Lys Ser Arg Thr Thr Leu Pro Glu Arg Pro Leu Thr
                165                 170                 175

Glu Val Lys Ala Glu Thr Arg Ala Glu Glu Ala Pro Glu Lys Lys Arg
            180                 185                 190

Glu Lys Pro Lys Ser Leu Arg Thr Thr Ala Pro Ser His Ala Lys Phe
        195                 200                 205

Arg Ser Thr Gly Leu Glu Leu Glu Thr Pro Ser Leu Val Pro Val Lys
    210                 215                 220

Lys Asn Ala Ser Thr Val Val Val Ser Asp Lys Tyr Asn Leu Lys Pro
225                 230                 235                 240

Ile Pro Leu Lys Arg Gln Ser Asn Val Ala Ala Pro Gly Asp Ala Thr
                245                 250                 255

Pro Pro Ala Glu Lys Lys Tyr Lys Pro Leu Asn Thr Thr Pro Asn Ala
            260                 265                 270

Thr Lys Glu Ile Lys Val Lys Ile Ile Pro Pro Gln Pro Met Glu Gly
        275                 280                 285

Leu Gly Phe Leu Asp Ala Leu Asn Ser Ala Pro Val Pro Gly Ile Lys
    290                 295                 300

Ile Lys Lys Lys Lys Lys Val Leu Ser Pro Thr Ala Ala Lys Pro Ser
305                 310                 315                 320

Pro Phe Glu Gly Lys Thr Ser Thr Glu Pro Ser Thr Ala Lys Pro Ser
                325                 330                 335

Ser Pro Glu Pro Ala Pro Pro Ser Glu Ala Met Asp Ala Asp Arg Pro
            340                 345                 350

Gly Thr Pro Val Pro Pro Val Glu Val Pro Glu Leu Met Asp Thr Ala
        355                 360                 365

Ser Leu Glu Pro Gly Ala Leu Asp Ala Lys Pro Val Glu Ser Pro Gly
    370                 375                 380

Asp Pro Asn Gln Leu Thr Arg Lys Gly Arg Lys Arg Lys Ser Val Thr
385                 390                 395                 400

Trp Pro Glu Glu Gly Lys Leu Arg Glu Tyr Phe Tyr Phe Glu Leu Asp
                405                 410                 415

Glu Thr Glu Arg Val Asn Val Asn Lys Ile Lys Asp Phe Gly Glu Ala
            420                 425                 430

Ala Lys Arg Glu Ile Leu Ser Asp Arg His Ala Phe Glu Thr Ala Arg
        435                 440                 445

Arg Leu Ser His Asp Asn Met Glu Glu Lys Val Pro Trp Val Cys Pro
    450                 455                 460

Arg Pro Leu Val Leu Pro Ser Pro Leu Val Thr Pro Gly Ser Asn Ser
465                 470                 475                 480

Gln Glu Arg Tyr Ile Gln Ala Glu Arg Glu Lys Gly Ile Leu Gln Glu
                485                 490                 495
```

-continued

```
Leu Phe Leu Asn Lys Glu Ser Pro His Glu Pro Asp Pro Glu Pro Tyr
            500                 505                 510

Glu Pro Ile Pro Pro Lys Leu Ile Pro Leu Asp Glu Glu Cys Ser Met
        515                 520                 525

Asp Glu Thr Pro Tyr Val Glu Thr Leu Glu Pro Gly Gly Ser Gly Gly
    530                 535                 540

Ser Pro Asp Gly Ala Gly Gly Ser Lys Leu Pro Pro Val Leu Ala Asn
545                 550                 555                 560

Leu Met Gly Ser Met Gly Ala Gly Lys Gly Pro Gln Gly Pro Gly Gly
                565                 570                 575

Gly Gly Ile Asn Val Gln Glu Ile Leu Thr Ser Ile Met Gly Ser Pro
            580                 585                 590

Asn Ser His Pro Ser Glu Glu Leu Leu Lys Gln Pro Asp Tyr Ser Asp
        595                 600                 605

Lys Ile Lys Gln Met Leu Val Pro His Gly Leu Leu Gly Pro Gly Pro
    610                 615                 620

Ile Ala Asn Gly Phe Pro Pro Gly Gly Pro Gly Gly Pro Lys Gly Met
625                 630                 635                 640

Gln His Phe Pro Pro Gly Pro Gly Gly Pro Met Pro Gly Pro His Gly
                645                 650                 655

Gly Pro Gly Gly Pro Val Gly Pro Arg Leu Leu Gly Pro Pro Pro Pro
            660                 665                 670

Pro Arg Gly Gly Asp Pro Phe Trp Asp Gly Pro Gly Asp Pro Met Arg
        675                 680                 685

Gly Gly Pro Met Arg Gly Gly Pro Gly Pro Gly Pro Gly Pro Tyr His
    690                 695                 700

Arg Gly Arg Gly Gly Arg Gly Gly Asn Glu Pro Pro Pro Pro Pro Pro
705                 710                 715                 720

Pro Phe Arg Gly Ala Arg Gly Gly Arg Ser Gly Gly Gly Pro Pro Asn
                725                 730                 735

Gly Arg Gly Gly Pro Gly Gly Gly Met Val Gly Gly Gly Gly His Arg
            740                 745                 750

Pro His Glu Gly Pro Gly Gly Gly Met Gly Asn Ser Ser Gly His Arg
        755                 760                 765

Pro His Glu Gly Pro Gly Gly Gly Met Gly Ser Gly His Arg Pro His
    770                 775                 780

Glu Gly Pro Gly Gly Ser Met Gly Gly Gly Gly Gly His Arg Pro His
785                 790                 795                 800

Glu Gly Pro Gly Gly Gly Ile Ser Gly Gly Ser Gly His Arg Pro His
                805                 810                 815

Glu Gly Pro Gly Gly Gly Met Gly Ala Gly Gly Gly His Arg Pro His
            820                 825                 830

Glu Gly Pro Gly Gly Ser Met Gly Gly Ser Gly Gly His Arg Pro His
        835                 840                 845

Glu Gly Pro Gly His Gly Gly Pro His Gly His Arg Pro His Asp Val
    850                 855                 860

Pro Gly His Arg Gly His Asp His Arg Gly Pro Pro Pro His Glu His
865                 870                 875                 880

Arg Gly His Asp Gly Pro Gly His Gly Gly Gly Gly His Arg Gly His
                885                 890                 895

Asp Gly Gly His Ser His Gly Gly Asp Met Ser Asn Arg Pro Val Cys
            900                 905                 910
```

Arg His Phe Met Met Lys Gly Asn Cys Arg Tyr Glu Asn Asn Cys Ala
915 920 925

Phe Tyr His Pro Gly Val Asn Gly Pro Pro Leu Pro
930 935 940

<210> SEQ ID NO 81
<211> LENGTH: 953
<212> TYPE: PRT
<213> ORGANISM: Homo sapiens

<400> SEQUENCE: 81

Met Ala Glu Thr Leu Pro Gly Ser Gly Asp Ser Gly Pro Gly Thr Ala
1 5 10 15

Ser Leu Gly Pro Gly Val Ala Glu Thr Gly Thr Arg Arg Leu Ser Glu
20 25 30

Leu Arg Val Ile Asp Leu Arg Ala Glu Leu Lys Lys Arg Asn Leu Asp
35 40 45

Thr Gly Gly Asn Lys Ser Val Leu Met Glu Arg Leu Lys Lys Ala Val
50 55 60

Lys Glu Glu Gly Gln Asp Pro Asp Glu Ile Gly Ile Glu Leu Glu Ala
65 70 75 80

Thr Ser Lys Lys Ser Ala Lys Arg Cys Val Lys Gly Leu Lys Met Glu
85 90 95

Glu Glu Gly Thr Glu Asp Asn Gly Leu Glu Asp Asp Ser Arg Asp Gly
100 105 110

Gln Glu Asp Met Glu Ala Ser Leu Glu Asn Leu Gln Asn Met Gly Met
115 120 125

Met Asp Met Ser Val Leu Asp Glu Thr Glu Val Ala Asn Ser Ser Ala
130 135 140

Pro Asp Phe Gly Glu Asp Gly Thr Asp Gly Leu Leu Asp Ser Phe Cys
145 150 155 160

Asp Ser Lys Glu Tyr Val Ala Ala Gln Leu Arg Gln Leu Pro Ala Gln
165 170 175

Pro Pro Glu His Ala Val Asp Gly Glu Gly Phe Lys Asn Thr Leu Glu
180 185 190

Thr Ser Ser Leu Asn Phe Lys Val Thr Pro Asp Ile Glu Glu Ser Leu
195 200 205

Leu Glu Pro Glu Asn Glu Lys Ile Leu Asp Ile Leu Gly Glu Thr Cys
210 215 220

Lys Ser Glu Pro Val Lys Glu Glu Ser Ser Glu Leu Glu Gln Pro Phe
225 230 235 240

Ala Gln Asp Thr Ser Ser Val Gly Pro Asp Arg Lys Leu Ala Glu Glu
245 250 255

Glu Asp Leu Phe Asp Ser Ala His Pro Glu Glu Gly Asp Leu Asp Leu
260 265 270

Ala Ser Glu Ser Thr Ala His Ala Gln Ser Ser Lys Ala Asp Ser Leu
275 280 285

Leu Ala Val Val Lys Arg Glu Pro Ala Glu Gln Pro Gly Asp Gly Glu
290 295 300

Arg Thr Asp Cys Glu Pro Val Gly Leu Glu Pro Ala Val Glu Gln Ser
305 310 315 320

Ser Ala Ala Ser Glu Leu Ala Glu Ala Ser Ser Glu Glu Leu Ala Glu
325 330 335

Ala Pro Thr Glu Ala Pro Ser Pro Glu Ala Arg Asp Ser Lys Glu Asp
340 345 350

-continued

```
Gly Arg Lys Phe Asp Phe Asp Ala Cys Asn Glu Val Pro Pro Ala Pro
        355                 360                 365

Lys Glu Ser Ser Thr Ser Glu Gly Ala Asp Gln Lys Met Ser Ser Phe
    370                 375                 380

Lys Glu Glu Lys Asp Ile Lys Pro Ile Ile Lys Asp Glu Lys Gly Arg
385                 390                 395                 400

Val Gly Ser Gly Ser Gly Arg Asn Leu Trp Val Ser Gly Leu Ser Ser
                405                 410                 415

Thr Thr Arg Ala Thr Asp Leu Lys Asn Leu Phe Ser Lys Tyr Gly Lys
            420                 425                 430

Val Val Gly Ala Lys Val Val Thr Asn Ala Arg Ser Pro Gly Ala Arg
        435                 440                 445

Cys Tyr Gly Phe Val Thr Met Ser Thr Ser Asp Glu Ala Thr Lys Cys
    450                 455                 460

Ile Ser His Leu His Arg Thr Glu Leu His Gly Arg Met Ile Ser Val
465                 470                 475                 480

Glu Lys Ala Lys Asn Glu Pro Ala Gly Lys Lys Leu Ser Asp Arg Lys
                485                 490                 495

Glu Cys Glu Val Lys Lys Glu Lys Leu Ser Ser Val Asp Arg His His
            500                 505                 510

Ser Val Glu Ile Lys Ile Glu Lys Thr Val Ile Lys Lys Glu Glu Lys
        515                 520                 525

Ile Glu Lys Lys Glu Glu Lys Lys Pro Glu Asp Ile Lys Lys Glu Glu
    530                 535                 540

Lys Asp Gln Asp Glu Leu Lys Pro Gly Pro Thr Asn Arg Ser Arg Val
545                 550                 555                 560

Thr Lys Ser Gly Ser Arg Gly Met Glu Arg Thr Val Val Met Asp Lys
                565                 570                 575

Ser Lys Gly Glu Pro Val Ile Ser Val Lys Thr Thr Ser Arg Ser Lys
            580                 585                 590

Glu Arg Ser Ser Lys Ser Gln Asp Arg Lys Ser Glu Ser Lys Glu Lys
        595                 600                 605

Arg Asp Ile Leu Ser Phe Asp Lys Ile Lys Glu Gln Arg Glu Arg Glu
    610                 615                 620

Arg Gln Arg Gln Arg Glu Arg Glu Ile Arg Glu Thr Glu Arg Arg Arg
625                 630                 635                 640

Glu Arg Glu Gln Arg Glu Arg Glu Gln Arg Leu Glu Ala Phe His Glu
                645                 650                 655

Arg Lys Glu Lys Ala Arg Leu Gln Arg Glu Arg Leu Gln Leu Glu Cys
            660                 665                 670

Gln Arg Gln Arg Leu Glu Arg Glu Arg Met Glu Arg Glu Arg Leu Glu
        675                 680                 685

Arg Glu Arg Met Arg Val Glu Arg Glu Arg Arg Lys Glu Gln Glu Arg
    690                 695                 700

Ile His Arg Glu Arg Glu Glu Leu Arg Arg Gln Gln Glu Gln Leu Arg
705                 710                 715                 720

Tyr Glu Gln Glu Arg Arg Pro Gly Arg Arg Pro Tyr Asp Leu Asp Arg
                725                 730                 735

Arg Asp Asp Ala Tyr Trp Pro Glu Gly Lys Arg Val Ala Met Glu Asp
            740                 745                 750

Arg Tyr Arg Ala Asp Phe Pro Arg Pro Asp His Arg Phe His Asp Phe
        755                 760                 765
```

```
Asp His Arg Asp Arg Gly Gln Tyr Gln Asp His Ala Ile Asp Arg Arg
    770                 775                 780

Glu Gly Ser Arg Pro Met Met Gly Asp His Arg Asp Gly Gln His Tyr
785                 790                 795                 800

Gly Asp Asp Arg His Gly His Gly Gly Pro Pro Glu Arg His Gly Arg
                805                 810                 815

Asp Ser Arg Asp Gly Trp Gly Gly Tyr Gly Ser Asp Lys Arg Leu Ser
            820                 825                 830

Glu Gly Arg Gly Leu Pro Pro Pro Pro Arg Gly Gly Arg Asp Trp Gly
        835                 840                 845

Glu His Asn Gln Arg Leu Glu Glu His Gln Ala Arg Ala Trp Gln Gly
    850                 855                 860

Ala Met Asp Ala Gly Ala Ala Ser Arg Glu His Ala Arg Trp Gln Gly
865                 870                 875                 880

Gly Glu Arg Gly Leu Ser Gly Pro Ser Gly Pro Gly His Met Ala Ser
                885                 890                 895

Arg Gly Gly Val Ala Gly Arg Gly Gly Phe Ala Gln Gly Gly His Ser
            900                 905                 910

Gln Gly His Val Val Pro Gly Gly Gly Leu Glu Gly Gly Gly Val Ala
        915                 920                 925

Ser Gln Asp Arg Gly Ser Arg Val Pro His Pro His Pro His Pro Pro
    930                 935                 940

Pro Tyr Pro His Phe Thr Arg Arg Tyr
945                 950


<210> SEQ ID NO 82
<211> LENGTH: 5858
<212> TYPE: PRT
<213> ORGANISM: Homo sapiens
<220> FEATURE:
<221> NAME/KEY: MOD_RES
<222> LOCATION: (900)..(900)
<223> OTHER INFORMATION: Xaa can be any naturally occurring amino acid

<400> SEQUENCE: 82

Met Gly Ala Pro Ser Ala Cys Arg Thr Leu Val Leu Ala Leu Ala Ala
 1               5                  10                  15

Met Leu Val Val Pro Gln Ala Glu Cys Thr Gly Arg Ser Pro Tyr Asp
            20                  25                  30

Ser Leu Ser Val Leu Asp Gly Thr Leu Pro Val Pro Asn Thr Gly Leu
        35                  40                  45

Trp Gly Pro Thr Gly Ser Gln Cys Gln Glu Thr Gln Gly Leu Ala Trp
    50                  55                  60

Met Gly Cys Pro Gly Glu Glu Thr Gln Gly Pro Val Glu Pro Ser Trp
65                  70                  75                  80

Glu Asn Ala Gly His Thr Met Asp Gly Gly Ala Pro Thr Ser Ser Pro
                85                  90                  95

Thr Arg Arg Val Ser Phe Val Pro Pro Val Thr Val Phe Pro Ser Leu
            100                 105                 110

Ser Arg Lys Gln Met Leu Pro Leu Pro Ala Gly Lys Gly Val Phe Ala
        115                 120                 125

Ser Pro Lys Gly Gly Gly Pro Asp Leu Gly Val Gln Leu Pro Pro Ala
    130                 135                 140

Leu Asn Pro Ala His Asn Gly Arg Val Cys Ser Thr Trp Gly Asp Phe
145                 150                 155                 160

His Tyr Lys Thr Phe Asp Gly Asp Val Phe Arg Phe Pro Gly Leu Cys
```

```
                165                 170                 175

Asn Tyr Val Phe Ser Glu His Cys Arg Ala Ala Tyr Glu Asp Phe Asn
            180                 185                 190

Val Gln Leu Arg Arg Gly Leu Val Gly Ser Arg Pro Val Val Thr Arg
        195                 200                 205

Val Val Ile Lys Ala Gln Gly Leu Val Leu Glu Ala Ser Asn Gly Ser
    210                 215                 220

Val Leu Ile Asn Gly Gln Arg Glu Glu Leu Pro Tyr Ser Arg Thr Gly
225                 230                 235                 240

Leu Leu Val Glu Gln Ser Gly Asp Tyr Ile Lys Val Ser Ile Arg Leu
                245                 250                 255

Val Leu Thr Phe Leu Trp Asn Gly Glu Asp Ser Ala Leu Leu Glu Leu
            260                 265                 270

Asp Pro Lys Tyr Ala Asn Gln Thr Cys Gly Leu Cys Gly Asp Phe Asn
        275                 280                 285

Gly Leu Pro Ala Phe Asn Glu Phe Tyr Ala His Asn Ala Arg Leu Thr
    290                 295                 300

Pro Leu Gln Phe Gly Asn Leu Gln Lys Leu Asp Gly Pro Thr Glu Gln
305                 310                 315                 320

Cys Pro Asp Pro Leu Pro Leu Pro Ala Gly Asn Cys Thr Asp Glu Pro
                325                 330                 335

Pro Trp Met Ala Gly Val Pro Ser Leu Ala His Cys Ala Pro Gln Glu
            340                 345                 350

Gly Ile Cys His Arg Thr Leu Leu Gly Pro Ala Phe Ala Glu Cys His
        355                 360                 365

Ala Leu Val Asp Ser Thr Ala Tyr Leu Ala Ala Cys Ala Gln Asp Leu
    370                 375                 380

Cys Arg Cys Pro Thr Cys Pro Cys Ala Thr Phe Val Glu Tyr Ser Arg
385                 390                 395                 400

Gln Cys Ala His Ala Gly Gly Gln Pro Arg Asn Trp Arg Cys Pro Glu
                405                 410                 415

Leu Cys Pro Arg Thr Cys Pro Leu Asn Met Gln His Gln Glu Cys Gly
            420                 425                 430

Ser Pro Cys Thr Asp Thr Cys Ser Asn Pro Gln Arg Ala Gln Leu Cys
        435                 440                 445

Glu Asp His Cys Val Asp Gly Cys Phe Cys Pro Pro Gly Thr Val Leu
    450                 455                 460

Asp Asp Ile Thr His Ser Gly Cys Leu Pro Leu Gly Gln Cys Pro Cys
465                 470                 475                 480

Thr His Gly Gly Arg Thr Tyr Ser Pro Gly Thr Ser Phe Asn Thr Thr
                485                 490                 495

Cys Ser Ser Cys Thr Cys Ser Gly Gly Leu Trp Gln Cys Gln Asp Leu
            500                 505                 510

Pro Cys Pro Gly Thr Cys Ser Val Gln Gly Gly Ala His Ile Ser Thr
        515                 520                 525

Tyr Asp Glu Lys Leu Tyr Asp Leu His Gly Asp Cys Ser Tyr Val Leu
    530                 535                 540

Ser Lys Ser His Ile Pro His Met Gly Ile Pro Ser Thr Leu Leu Gly
545                 550                 555                 560

Gly Thr Pro His His Arg Ala Arg Pro Asn Ala Arg Val Gly Pro Ser
                565                 570                 575

Pro Gln Lys Cys Ala Asp Ser Ser Phe Thr Val Leu Ala Glu Leu Arg
            580                 585                 590
```

```
Lys Cys Gly Leu Thr Asp Asn Glu Asn Cys Leu Lys Ala Val Thr Leu
        595                 600                 605

Ser Leu Asp Gly Gly Asp Thr Ala Ile Arg Val Gln Ala Asp Gly Gly
    610                 615                 620

Val Phe Leu Asn Ser Ile Tyr Thr Gln Leu Pro Leu Ser Ala Ala Asn
625                 630                 635                 640

Ile Thr Leu Phe Thr Pro Ser Ser Phe Phe Ile Val Val Gln Thr Gly
                645                 650                 655

Leu Gly Leu Gln Leu Leu Val Gln Leu Val Pro Leu Met Gln Val Phe
            660                 665                 670

Val Arg Leu Asp Pro Ala His Gln Gly Gln Met Cys Gly Leu Cys Gly
        675                 680                 685

Asn Phe Asn Gln Asn Gln Ala Asp Asp Phe Thr Ala Leu Ser Gly Val
    690                 695                 700

Val Glu Ala Thr Gly Ala Ala Phe Ala Asn Thr Trp Lys Ala Gln Ala
705                 710                 715                 720

Ala Cys Ala Asn Ala Arg Asn Ser Phe Glu Asp Pro Cys Ser Leu Ser
                725                 730                 735

Val Glu Asn Glu Asn Tyr Ala Arg His Trp Cys Ser Arg Leu Thr Asp
            740                 745                 750

Pro Asn Ser Ala Phe Ser Arg Cys His Ser Ile Ile Asn Pro Lys Pro
        755                 760                 765

Phe His Ser Asn Cys Met Phe Asp Thr Cys Asn Cys Glu Arg Ser Glu
    770                 775                 780

Asp Cys Leu Cys Ala Ala Leu Ser Ser Tyr Val His Ala Cys Ala Ala
785                 790                 795                 800

Lys Gly Val Gln Leu Ser Asp Trp Arg Asp Gly Val Cys Thr Lys Tyr
                805                 810                 815

Met Gln Asn Cys Pro Lys Ser Gln Arg Tyr Ala Tyr Val Val Asp Ala
            820                 825                 830

Cys Gln Pro Thr Cys Arg Gly Leu Ser Glu Ala Asp Val Thr Cys Ser
        835                 840                 845

Val Ser Phe Val Pro Val Asp Gly Cys Thr Cys Pro Ala Gly Thr Phe
    850                 855                 860

Leu Asn Asp Ala Gly Ala Cys Val Pro Ala Gln Glu Cys Pro Cys Tyr
865                 870                 875                 880

Ala His Gly Thr Val Leu Ala Pro Gly Glu Val Val His Asp Glu Gly
                885                 890                 895

Ala Val Trp Xaa Gly Ser Gly Gly Lys Ala Gly Pro Pro Gly Cys Ala
            900                 905                 910

Ala Pro Met Val Tyr Leu Asp Cys Ser Asn Ser Ser Ala Gly Thr Pro
        915                 920                 925

Gly Ala Glu Cys Leu Arg Ser Cys His Thr Leu Asp Val Gly Cys Phe
    930                 935                 940

Ser Thr His Cys Val Ser Gly Cys Val Cys Pro Pro Gly Leu Val Ser
945                 950                 955                 960

Asp Gly Ser Gly Gly Cys Ile Ala Glu Glu Asp Cys Pro Cys Val His
                965                 970                 975

Asn Glu Ala Thr Tyr Lys Pro Gly Glu Thr Ile Arg Val Asp Cys Asn
            980                 985                 990

Thr Cys Thr Cys Arg Asn Arg Arg Trp Glu Cys Ser His Arg Leu Cys
        995                 1000                1005
```

```
Leu Gly Thr Cys Val Ala Tyr Gly Asp Gly His Phe Ile Thr Phe Asp
   1010                1015                1020

Gly Asp Arg Tyr Ser Phe Glu Gly Ser Cys Glu Tyr Ile Leu Ala Gln
1025                1030                1035                1040

Asp Tyr Cys Gly Asp Asn Thr Thr His Gly Thr Phe Arg Ile Val Thr
               1045                1050                1055

Glu Asn Ile Pro Cys Gly Thr Thr Gly Thr Thr Cys Ser Lys Ala Ile
           1060                1065                1070

Lys Leu Phe Val Glu Val Arg Thr Ala Pro Ala Val Ser Thr Pro Asp
       1075                1080                1085

Pro Ala Ala Asn Glu Pro Ala Pro Arg Glu Ala Ser Val Gly Phe Arg
   1090                1095                1100

Gln Arg Leu Pro Pro Leu Gln Ser Tyr Glu Leu Ile Leu Gln Glu Gly
1105                1110                1115                1120

Thr Phe Lys Ala Val Ala Arg Gly Pro Gly Gly Asp Pro Pro Tyr Lys
               1125                1130                1135

Ile Arg Tyr Met Gly Ile Phe Leu Val Ile Glu Thr His Gly Met Ala
           1140                1145                1150

Val Ser Trp Asp Arg Lys Thr Ser Val Phe Ile Arg Leu His Gln Asp
       1155                1160                1165

Tyr Lys Gly Arg Val Cys Gly Leu Cys Gly Asn Phe Asp Asp Asn Ala
   1170                1175                1180

Ile Asn Asp Phe Ala Thr Arg Ser Arg Ser Val Val Gly Asp Ala Leu
1185                1190                1195                1200

Glu Phe Gly Asn Ser Trp Lys Leu Ser Pro Ser Cys Pro Asp Ala Leu
               1205                1210                1215

Ala Pro Lys Asp Pro Cys Thr Ala Asn Pro Phe Arg Lys Ser Trp Ala
           1220                1225                1230

Gln Lys Gln Cys Ser Ile Leu His Gly Pro Thr Phe Ala Ala Cys Arg
       1235                1240                1245

Ser Gln Val Asp Ser Thr Lys Tyr Tyr Glu Ala Cys Val Asn Asp Ala
   1250                1255                1260

Cys Ala Cys Asp Ser Gly Gly Asp Cys Glu Cys Phe Cys Thr Ala Val
1265                1270                1275                1280

Ala Ala Tyr Ala Gln Ala Cys His Asp Ala Gly Leu Cys Val Ser Trp
               1285                1290                1295

Arg Thr Pro Asp Thr Cys Pro Leu Phe Cys Asp Phe Tyr Asn Pro His
           1300                1305                1310

Gly Gly Cys Glu Trp His Tyr Gln Pro Cys Gly Ala Pro Cys Leu Lys
       1315                1320                1325

Thr Cys Arg Asn Pro Ser Gly His Cys Leu Val Asp Leu Pro Gly Leu
   1330                1335                1340

Glu Gly Cys Tyr Pro Lys Cys Pro Pro Ser Gln Pro Phe Phe Asn Glu
1345                1350                1355                1360

Asp Gln Met Lys Cys Val Ala Gln Cys Gly Cys Tyr Asp Lys Asp Gly
               1365                1370                1375

Asn Tyr Tyr Asp Val Gly Ala Arg Val Pro Thr Ala Glu Asn Cys Gln
           1380                1385                1390

Ser Cys Asn Cys Thr Pro Ser Gly Ile Gln Cys Ala His Ser Leu Glu
       1395                1400                1405

Ala Cys Thr Cys Thr Tyr Glu Asp Arg Thr Tyr Ser Tyr Gln Asp Val
   1410                1415                1420

Ile Tyr Asn Thr Thr Asp Gly Leu Gly Ala Cys Leu Ile Ala Ile Cys
```

-continued

```
1425                1430                1435                1440

Gly Ser Asn Gly Thr Ile Ile Arg Lys Ala Val Ala Cys Pro Gly Thr
                1445                1450                1455

Pro Ala Thr Thr Pro Phe Thr Phe Thr Thr Ala Trp Val Pro His Ser
            1460                1465                1470

Thr Thr Ser Pro Ala Leu Pro Val Ser Thr Val Cys Val Arg Glu Val
        1475                1480                1485

Cys Arg Trp Ser Ser Trp Tyr Asn Gly His Arg Pro Glu Pro Gly Leu
    1490                1495                1500

Gly Gly Gly Asp Phe Glu Thr Phe Glu Asn Leu Arg Gln Arg Gly Tyr
1505                1510                1515                1520

Gln Val Cys Pro Val Leu Ala Asp Ile Glu Cys Arg Ala Ala Gln Leu
                1525                1530                1535

Pro Asp Met Pro Leu Glu Glu Leu Gly Gln Gln Val Asp Cys Asp Arg
            1540                1545                1550

Met Arg Gly Leu Met Cys Ala Asn Ser Gln Gln Ser Pro Pro Leu Cys
        1555                1560                1565

His Asp Tyr Glu Leu Arg Val Leu Cys Cys Glu Tyr Val Pro Cys Gly
    1570                1575                1580

Pro Ser Pro Ala Pro Gly Thr Ser Pro Gln Pro Ser Leu Ser Ala Ser
1585                1590                1595                1600

Thr Glu Pro Ala Val Pro Thr Pro Thr Gln Thr Thr Ala Thr Glu Lys
                1605                1610                1615

Thr Thr Leu Trp Val Thr Pro Ser Ile Arg Ser Thr Ala Ala Leu Thr
            1620                1625                1630

Ser Gln Thr Gly Ser Ser Ser Gly Pro Val Thr Val Thr Pro Ser Ala
        1635                1640                1645

Pro Gly Thr Thr Thr Cys Gln Pro Arg Cys Gln Trp Thr Glu Trp Phe
    1650                1655                1660

Asp Glu Asp Tyr Pro Lys Ser Glu Gln Leu Gly Gly Asp Val Glu Ser
1665                1670                1675                1680

Tyr Asp Lys Ile Arg Ala Ala Gly Gly His Leu Cys Gln Gln Pro Lys
                1685                1690                1695

Asp Ile Glu Cys Gln Ala Glu Ser Phe Pro Asn Trp Thr Leu Ala Gln
            1700                1705                1710

Val Gly Gln Lys Val His Cys Asp Val His Phe Gly Leu Val Cys Arg
        1715                1720                1725

Asn Trp Glu Gln Glu Gly Val Phe Lys Met Cys Tyr Asn Tyr Arg Ile
    1730                1735                1740

Arg Val Leu Cys Cys Ser Asp Asp His Cys Arg Gly Arg Ala Thr Thr
1745                1750                1755                1760

Pro Pro Pro Thr Thr Glu Leu Glu Thr Ala Thr Thr Thr Thr Thr Gln
                1765                1770                1775

Ala Leu Phe Ser Thr Pro Gln Pro Thr Ser Ser Pro Gly Leu Thr Arg
            1780                1785                1790

Ala Pro Pro Ala Ser Thr Thr Ala Val Pro Thr Leu Ser Glu Gly Leu
        1795                1800                1805

Thr Ser Pro Arg Tyr Thr Ser Thr Leu Gly Thr Ala Thr Thr Gly Gly
    1810                1815                1820

Pro Thr Thr Pro Ala Gly Ser Thr Glu Pro Thr Val Pro Gly Val Ala
1825                1830                1835                1840

Thr Ser Thr Leu Pro Thr Arg Ser Ala Leu Pro Gly Thr Thr Gly Ser
                1845                1850                1855
```

-continued

```
Leu Gly Thr Trp Arg Pro Ser Gln Pro Pro Thr Leu Ala Pro Thr Thr
            1860                1865                1870

Met Ala Thr Ser Arg Ala Arg Pro Thr Gly Thr Ala Ser Thr Ala Ser
        1875                1880                1885

Lys Glu Pro Leu Thr Thr Ser Leu Ala Pro Thr Leu Thr Ser Glu Leu
    1890                1895                1900

Ser Thr Ser Gln Ala Glu Thr Ser Thr Pro Arg Thr Glu Thr Thr Met
1905                1910                1915                1920

Ser Pro Leu Thr Asn Thr Thr Thr Ser Gln Gly Thr Thr Arg Cys Gln
                1925                1930                1935

Pro Lys Cys Glu Trp Thr Glu Trp Phe Asp Val Asp Phe Pro Thr Ser
            1940                1945                1950

Gly Val Ala Gly Gly Asp Met Glu Thr Phe Glu Asn Ile Arg Ala Ala
        1955                1960                1965

Gly Gly Lys Met Cys Trp Ala Pro Lys Ser Ile Glu Cys Arg Ala Glu
    1970                1975                1980

Asn Tyr Pro Glu Val Ser Ile Asp Gln Val Gly Gln Val Leu Thr Cys
1985                1990                1995                2000

Ser Leu Glu Thr Gly Leu Thr Cys Lys Asn Glu Asp Gln Thr Gly Arg
                2005                2010                2015

Phe Asn Met Cys Phe Asn Tyr Asn Val Arg Val Leu Cys Cys Asp Asp
            2020                2025                2030

Tyr Ser His Cys Pro Ser Thr Pro Ala Thr Ser Ser Thr Ala Thr Pro
        2035                2040                2045

Ser Ser Thr Pro Gly Thr Thr Trp Ile Leu Thr Lys Pro Thr Thr Thr
    2050                2055                2060

Ala Thr Thr Thr Ala Ser Thr Gly Ser Thr Ala Thr Pro Thr Ser Thr
2065                2070                2075                2080

Leu Arg Thr Ala Pro Pro Pro Lys Val Leu Thr Thr Thr Ala Thr Thr
                2085                2090                2095

Pro Thr Val Thr Ser Ser Lys Ala Thr Pro Ser Ser Ser Pro Gly Thr
            2100                2105                2110

Ala Thr Ala Leu Pro Ala Leu Arg Ser Thr Ala Thr Thr Pro Thr Ala
        2115                2120                2125

Thr Ser Val Thr Pro Ile Pro Ser Ser Ser Leu Gly Thr Thr Trp Thr
    2130                2135                2140

Arg Leu Ser Gln Thr Thr Thr Pro Thr Ala Thr Met Ser Thr Ala Thr
2145                2150                2155                2160

Pro Ser Ser Thr Pro Glu Thr Ala His Thr Ser Thr Val Leu Thr Ala
                2165                2170                2175

Thr Ala Thr Thr Thr Gly Ala Thr Gly Ser Val Ala Thr Pro Ser Ser
            2180                2185                2190

Thr Pro Gly Thr Ala His Thr Thr Lys Val Pro Thr Thr Thr Thr Thr
        2195                2200                2205

Gly Phe Thr Ala Thr Pro Ser Ser Ser Pro Gly Thr Ala Leu Thr Pro
    2210                2215                2220

Pro Val Trp Ile Ser Thr Thr Thr Thr Pro Thr Thr Arg Gly Ser Thr
2225                2230                2235                2240

Val Thr Pro Ser Ser Ile Pro Gly Thr Thr His Thr Ala Thr Val Leu
                2245                2250                2255

Thr Thr Thr Thr Thr Thr Val Ala Thr Gly Ser Met Ala Thr Pro Ser
            2260                2265                2270
```

-continued

```
Ser Ser Thr Gln Thr Ser Gly Thr Pro Pro Ser Leu Thr Thr Thr Ala
       2275                2280                2285

Thr Thr Ile Thr Ala Thr Gly Ser Thr Thr Asn Pro Ser Ser Thr Pro
   2290                2295                2300

Gly Thr Thr Pro Ile Pro Pro Val Leu Thr Thr Thr Ala Thr Thr Pro
2305               2310                2315                2320

Ala Ala Thr Ser Asn Thr Val Thr Pro Ser Ser Ala Leu Gly Thr Thr
               2325                2330                2335

His Thr Pro Pro Val Pro Asn Thr Met Ala Thr Thr His Gly Arg Ser
           2340                2345                2350

Leu Pro Pro Ser Ser Pro His Thr Val Arg Thr Ala Trp Thr Ser Ala
       2355                2360                2365

Thr Ser Gly Ile Leu Gly Thr Thr His Ile Thr Glu Pro Ser Thr Val
   2370                2375                2380

Thr Ser His Thr Leu Ala Ala Thr Thr Gly Thr Thr Gln His Ser Thr
2385               2390                2395                2400

Pro Ala Leu Ser Ser Pro His Pro Ser Ser Arg Thr Thr Glu Ser Pro
               2405                2410                2415

Pro Ser Pro Gly Thr Thr Thr Pro Gly His Thr Thr Ala Thr Ser Arg
           2420                2425                2430

Thr Thr Ala Thr Ala Thr Pro Ser Lys Thr Arg Thr Ser Thr Leu Leu
       2435                2440                2445

Pro Ser Ser Pro Thr Ser Ala Pro Ile Thr Thr Val Val Thr Met Gly
   2450                2455                2460

Cys Glu Pro Gln Cys Ala Trp Ser Glu Trp Leu Asp Tyr Ser Tyr Pro
2465               2470                2475                2480

Met Pro Gly Pro Ser Gly Gly Asp Phe Asp Thr Tyr Ser Asn Ile Arg
               2485                2490                2495

Ala Ala Gly Gly Ala Val Cys Glu Gln Pro Leu Gly Leu Glu Cys Arg
           2500                2505                2510

Ala Gln Ala Gln Pro Gly Val Pro Leu Arg Glu Leu Gly Gln Val Val
       2515                2520                2525

Glu Cys Ser Leu Asp Phe Gly Leu Val Cys Arg Asn Arg Glu Gln Val
   2530                2535                2540

Gly Lys Phe Lys Met Cys Phe Asn Tyr Glu Ile Arg Val Phe Cys Cys
2545               2550                2555                2560

Asn Tyr Gly His Cys Pro Ser Thr Pro Ala Thr Ser Ser Thr Ala Met
               2565                2570                2575

Pro Ser Ser Thr Pro Gly Thr Thr Trp Ile Leu Thr Glu Leu Thr Thr
           2580                2585                2590

Thr Ala Thr Thr Thr Glu Ser Thr Gly Ser Thr Ala Thr Pro Ser Ser
       2595                2600                2605

Thr Pro Gly Thr Thr Trp Ile Leu Thr Glu Pro Ser Thr Thr Ala Thr
   2610                2615                2620

Val Thr Val Pro Thr Gly Ser Thr Ala Thr Ala Ser Ser Thr Gln Ala
2625               2630                2635                2640

Thr Ala Gly Thr Pro His Val Ser Thr Thr Ala Thr Thr Pro Thr Val
               2645                2650                2655

Thr Ser Ser Lys Ala Thr Pro Phe Ser Ser Pro Gly Thr Ala Thr Ala
           2660                2665                2670

Leu Pro Ala Leu Arg Ser Thr Ala Thr Thr Pro Thr Ala Thr Ser Phe
       2675                2680                2685

Thr Ala Ile Pro Ser Ser Ser Leu Gly Thr Thr Trp Thr Arg Leu Ser
```

```
                2690                2695                2700

Gln Thr Thr Thr Pro Thr Ala Thr Met Ser Thr Ala Thr Pro Ser Ser
2705                2710                2715                2720

Thr Pro Glu Thr Val His Thr Ser Thr Val Leu Thr Thr Thr Ala Thr
                2725                2730                2735

Thr Thr Gly Ala Thr Gly Ser Val Ala Thr Pro Ser Ser Thr Pro Gly
            2740                2745                2750

Thr Ala His Thr Thr Lys Val Leu Thr Thr Thr Thr Thr Gly Phe Thr
        2755                2760                2765

Ala Thr Pro Ser Ser Ser Pro Gly Thr Ala Arg Thr Leu Pro Val Trp
    2770                2775                2780

Ile Ser Thr Thr Thr Thr Pro Thr Thr Arg Gly Ser Thr Val Thr Pro
2785                2790                2795                2800

Ser Ser Ile Pro Gly Thr Thr His Thr Pro Thr Val Leu Thr Thr Thr
                2805                2810                2815

Thr Thr Thr Val Ala Thr Gly Ser Met Ala Thr Pro Ser Ser Ser Thr
            2820                2825                2830

Gln Thr Ser Gly Thr Pro Pro Ser Leu Thr Thr Thr Ala Thr Thr Ile
        2835                2840                2845

Thr Ala Thr Gly Ser Thr Thr Asn Pro Ser Ser Thr Pro Gly Thr Thr
    2850                2855                2860

Pro Ile Pro Pro Val Leu Thr Thr Thr Ala Thr Thr Pro Ala Ala Thr
2865                2870                2875                2880

Ser Ser Thr Val Thr Pro Ser Ser Ala Leu Gly Thr Thr His Thr Pro
                2885                2890                2895

Pro Val Pro Asn Thr Thr Ala Thr Thr His Gly Arg Ser Leu Ser Pro
            2900                2905                2910

Ser Ser Pro His Thr Val Arg Thr Ala Trp Thr Ser Ala Thr Ser Gly
        2915                2920                2925

Thr Leu Gly Thr Thr His Ile Thr Glu Pro Ser Thr Gly Thr Ser His
    2930                2935                2940

Thr Pro Ala Ala Thr Thr Gly Thr Thr Gln His Ser Thr Pro Ala Leu
2945                2950                2955                2960

Ser Ser Pro His Pro Ser Ser Arg Thr Thr Glu Ser Pro Pro Ser Pro
                2965                2970                2975

Gly Thr Thr Thr Pro Gly His Thr Arg Ala Thr Ser Arg Thr Thr Ala
            2980                2985                2990

Thr Ala Thr Pro Ser Lys Thr Arg Thr Ser Thr Leu Leu Pro Ser Ser
        2995                3000                3005

Pro Thr Ser Ala Pro Ile Thr Thr Val Val Thr Met Gly Cys Glu Pro
    3010                3015                3020

Gln Cys Ala Trp Ser Glu Trp Leu Asp Tyr Ser Tyr Pro Met Pro Gly
3025                3030                3035                3040

Pro Ser Gly Gly Asp Phe Asp Thr Tyr Ser Asn Ile Arg Ala Ala Gly
                3045                3050                3055

Gly Ala Val Cys Glu Gln Pro Leu Gly Leu Glu Cys Arg Ala Gln Ala
            3060                3065                3070

Gln Pro Gly Val Pro Leu Arg Glu Leu Gly Gln Val Val Glu Cys Ser
        3075                3080                3085

Leu Asp Phe Gly Leu Val Cys Arg Asn Arg Glu Gln Val Gly Lys Phe
    3090                3095                3100

Lys Met Cys Phe Asn Tyr Glu Ile Arg Val Phe Cys Cys Asn Tyr Gly
3105                3110                3115                3120
```

His Cys Pro Ser Thr Pro Ala Thr Ser Ser Thr Ala Thr Pro Ser Ser
3125 3130 3135

Thr Pro Gly Thr Thr Trp Ile Leu Thr Glu Gln Thr Thr Ala Ala Thr
3140 3145 3150

Thr Thr Ala Thr Thr Gly Ser Thr Ala Ile Pro Ser Ser Thr Pro Gly
3155 3160 3165

Thr Ala Pro Pro Pro Lys Val Leu Thr Ser Thr Ala Thr Thr Pro Thr
3170 3175 3180

Ala Thr Ser Ser Lys Ala Thr Ser Ser Ser Ser Pro Arg Thr Ala Thr
3185 3190 3195 3200

Thr Leu Pro Val Leu Thr Ser Thr Ala Thr Lys Ser Thr Ala Thr Ser
3205 3210 3215

Phe Thr Pro Ile Pro Ser Phe Thr Leu Gly Thr Thr Gly Thr Leu Pro
3220 3225 3230

Glu Gln Thr Thr Thr Pro Met Ala Thr Met Ser Thr Ile His Pro Ser
3235 3240 3245

Ser Thr Pro Glu Thr Thr His Thr Ser Thr Val Leu Thr Thr Lys Ala
3250 3255 3260

Thr Thr Thr Arg Ala Thr Ser Ser Met Ser Thr Pro Ser Ser Thr Pro
3265 3270 3275 3280

Gly Thr Thr Trp Ile Leu Thr Glu Leu Thr Thr Ala Ala Thr Thr Thr
3285 3290 3295

Ala Ala Thr Gly Pro Thr Ala Thr Pro Ser Ser Thr Pro Gly Thr Thr
3300 3305 3310

Trp Ile Leu Thr Glu Pro Ser Thr Thr Ala Thr Val Thr Val Pro Thr
3315 3320 3325

Gly Ser Thr Ala Thr Ala Ser Ser Thr Arg Ala Thr Ala Gly Thr Leu
3330 3335 3340

Lys Val Leu Thr Ser Thr Ala Thr Thr Pro Thr Val Ile Ser Ser Arg
3345 3350 3355 3360

Ala Thr Pro Ser Ser Ser Pro Gly Thr Ala Thr Ala Leu Pro Ala Leu
3365 3370 3375

Arg Ser Thr Ala Thr Thr Pro Thr Ala Thr Ser Val Thr Ala Ile Pro
3380 3385 3390

Ser Ser Ser Leu Gly Thr Ala Trp Thr Arg Leu Ser Gln Thr Thr Thr
3395 3400 3405

Pro Thr Ala Thr Met Ser Thr Ala Thr Pro Ser Ser Thr Pro Glu Thr
3410 3415 3420

Val His Thr Ser Thr Val Leu Thr Thr Thr Thr Thr Thr Thr Arg Ala
3425 3430 3435 3440

Thr Gly Ser Val Ala Thr Pro Ser Ser Thr Pro Gly Thr Ala His Thr
3445 3450 3455

Thr Lys Val Pro Thr Thr Thr Thr Thr Gly Phe Thr Ala Thr Pro Ser
3460 3465 3470

Ser Ser Pro Gly Thr Ala Leu Thr Pro Pro Val Trp Ile Ser Thr Thr
3475 3480 3485

Thr Thr Pro Thr Thr Arg Gly Ser Thr Val Thr Pro Ser Ser Ile Pro
3490 3495 3500

Gly Thr Thr His Thr Ala Thr Val Leu Thr Thr Thr Thr Thr Thr Val
3505 3510 3515 3520

Ala Thr Gly Ser Met Ala Thr Pro Ser Ser Ser Thr Gln Thr Ser Gly
3525 3530 3535

```
Thr Thr His Thr Pro Pro Val Pro Asn Thr Thr Ala Thr Thr His Gly
            3540                3545                3550

Arg Ser Leu Pro Pro Ser Ser Pro His Thr Val Arg Thr Ala Trp Thr
        3555                3560                3565

Ser Ala Thr Ser Gly Ile Leu Gly Thr Thr His Ile Thr Glu Pro Ser
    3570                3575                3580

Thr Val Thr Ser His Thr Pro Ala Ala Thr Thr Ser Thr Thr Gln His
3585                3590                3595                3600

Ser Thr Pro Ala Leu Ser Ser Pro His Pro Ser Ser Arg Thr Thr Glu
                3605                3610                3615

Ser Pro Pro Ser Pro Gly Thr Thr Thr Pro Gly His Thr Arg Gly Thr
            3620                3625                3630

Ser Arg Thr Thr Ala Thr Ala Thr Pro Ser Lys Thr Arg Thr Ser Thr
        3635                3640                3645

Leu Leu Pro Ser Ser Pro Thr Ser Ala Pro Ile Thr Thr Val Val Thr
    3650                3655                3660

Thr Gly Cys Glu Pro Gln Cys Ala Trp Ser Glu Trp Leu Asp Tyr Ser
3665                3670                3675                3680

Tyr Pro Met Pro Gly Pro Ser Gly Gly Asp Phe Asp Thr Tyr Ser Asn
                3685                3690                3695

Ile Arg Ala Ala Gly Gly Ala Val Cys Glu Gln Pro Leu Gly Leu Glu
            3700                3705                3710

Cys Arg Ala Gln Ala Gln Pro Gly Val Pro Leu Arg Glu Leu Gly Gln
        3715                3720                3725

Val Val Glu Cys Ser Leu Asp Phe Gly Leu Val Cys Arg Asn Arg Glu
    3730                3735                3740

Gln Val Gly Lys Phe Lys Met Cys Phe Asn Tyr Glu Ile Arg Val Phe
3745                3750                3755                3760

Cys Cys Asn Tyr Gly His Cys Pro Ser Thr Pro Ala Thr Ser Ser Thr
                3765                3770                3775

Ala Thr Pro Ser Ser Thr Pro Gly Thr Thr Trp Ile Leu Thr Lys Leu
            3780                3785                3790

Thr Thr Thr Ala Thr Thr Thr Glu Ser Thr Gly Ser Thr Ala Thr Pro
        3795                3800                3805

Ser Ser Thr Pro Gly Thr Thr Trp Ile Leu Thr Glu Pro Ser Thr Thr
    3810                3815                3820

Ala Thr Val Thr Val Pro Thr Gly Ser Thr Ala Thr Ala Ser Ser Thr
3825                3830                3835                3840

Gln Ala Thr Ala Gly Thr Pro His Val Ser Thr Thr Ala Thr Thr Pro
                3845                3850                3855

Thr Val Thr Ser Ser Lys Ala Thr Pro Phe Ser Ser Pro Gly Thr Ala
            3860                3865                3870

Thr Ala Leu Pro Ala Leu Arg Ser Thr Ala Thr Thr Pro Thr Ala Thr
        3875                3880                3885

Ser Phe Thr Ala Ile Pro Ser Ser Ser Leu Gly Thr Thr Trp Thr Arg
    3890                3895                3900

Leu Ser Gln Thr Thr Thr Pro Thr Ala Thr Met Ser Thr Ala Thr Pro
3905                3910                3915                3920

Ser Ser Thr Pro Glu Thr Ala His Thr Ser Thr Val Leu Thr Thr Thr
                3925                3930                3935

Ala Thr Thr Thr Arg Ala Thr Gly Ser Val Ala Thr Pro Ser Ser Thr
            3940                3945                3950

Pro Gly Thr Ala His Thr Thr Lys Val Pro Thr Thr Thr Thr Thr Gly
```

```
        3955                3960                3965

Phe Thr Val Thr Pro Ser Ser Ser Pro Gly Thr Ala Arg Thr Pro Pro
    3970                3975                3980

Val Trp Ile Ser Thr Thr Thr Thr Pro Thr Thr Ser Gly Ser Thr Val
3985                3990                3995                4000

Thr Pro Ser Ser Val Pro Gly Thr Thr His Thr Pro Thr Val Leu Thr
                4005                4010                4015

Thr Thr Thr Thr Thr Val Ala Thr Gly Ser Met Ala Thr Pro Ser Ser
            4020                4025                4030

Ser Thr Gln Thr Ser Gly Thr Pro Pro Ser Leu Ile Thr Thr Ala Thr
        4035                4040                4045

Thr Ile Thr Ala Thr Gly Ser Thr Thr Asn Pro Ser Ser Thr Pro Gly
    4050                4055                4060

Thr Thr Pro Ile Pro Pro Val Leu Thr Thr Thr Ala Thr Thr Pro Ala
4065                4070                4075                4080

Ala Thr Ser Ser Thr Val Thr Pro Ser Ser Ala Leu Gly Thr Thr His
                4085                4090                4095

Thr Pro Pro Val Pro Asn Thr Thr Ala Thr Thr His Gly Arg Ser Leu
            4100                4105                4110

Ser Pro Ser Ser Pro His Thr Val Arg Thr Ala Trp Thr Ser Ala Thr
        4115                4120                4125

Ser Gly Thr Leu Gly Thr Thr His Ile Thr Glu Pro Ser Thr Gly Thr
    4130                4135                4140

Ser His Thr Pro Ala Ala Thr Thr Gly Thr Thr Gln His Ser Thr Pro
4145                4150                4155                4160

Ala Leu Ser Ser Pro His Pro Ser Ser Arg Thr Thr Glu Ser Pro Pro
                4165                4170                4175

Ser Pro Gly Thr Thr Thr Pro Gly His Thr Thr Ala Thr Ser Arg Thr
            4180                4185                4190

Thr Ala Thr Ala Thr Pro Ser Lys Thr Arg Thr Ser Thr Leu Leu Pro
        4195                4200                4205

Ser Ser Pro Thr Ser Ala Pro Ile Thr Thr Val Val Thr Thr Gly Cys
    4210                4215                4220

Glu Pro Gln Cys Ala Trp Ser Glu Trp Leu Asp Tyr Ser Tyr Pro Met
4225                4230                4235                4240

Pro Gly Pro Ser Gly Gly Asp Phe Asp Thr Tyr Ser Asn Ile Arg Ala
                4245                4250                4255

Ala Gly Gly Ala Val Cys Glu Gln Pro Leu Gly Leu Glu Cys Arg Ala
            4260                4265                4270

Gln Ala Gln Pro Gly Val Pro Leu Gly Glu Leu Gly Gln Val Val Glu
        4275                4280                4285

Cys Ser Leu Asp Phe Gly Leu Val Cys Arg Asn Arg Glu Gln Val Gly
    4290                4295                4300

Lys Phe Lys Met Cys Phe Asn Tyr Glu Ile Arg Val Phe Cys Cys Asn
4305                4310                4315                4320

Tyr Gly His Cys Pro Ser Thr Pro Ala Thr Ser Ser Thr Ala Met Pro
                4325                4330                4335

Ser Ser Thr Pro Gly Thr Thr Trp Ile Leu Thr Glu Leu Thr Thr Thr
            4340                4345                4350

Ala Thr Thr Thr Ala Ser Thr Gly Ser Thr Ala Thr Pro Ser Ser Thr
        4355                4360                4365

Pro Gly Thr Ala Pro Pro Pro Lys Val Leu Thr Ser Pro Ala Thr Thr
    4370                4375                4380
```

-continued

```
Pro Thr Ala Thr Ser Ser Lys Ala Thr Ser Ser Ser Ser Pro Arg Thr
4385                4390                4395                4400

Ala Thr Thr Leu Pro Val Leu Thr Ser Thr Ala Thr Lys Ser Thr Ala
                4405                4410                4415

Thr Ser Val Thr Pro Ile Pro Ser Ser Thr Leu Gly Thr Thr Gly Thr
            4420                4425                4430

Leu Pro Glu Gln Thr Thr Thr Pro Val Ala Thr Met Ser Thr Ile His
        4435                4440                4445

Pro Ser Ser Thr Pro Glu Thr Thr His Thr Ser Thr Val Leu Thr Thr
    4450                4455                4460

Lys Ala Thr Thr Thr Arg Ala Thr Ser Ser Thr Ser Thr Pro Ser Ser
4465                4470                4475                4480

Thr Pro Gly Thr Thr Trp Ile Leu Thr Glu Leu Thr Thr Ala Ala Thr
                4485                4490                4495

Thr Thr Ala Ala Thr Gly Pro Thr Ala Thr Pro Ser Ser Thr Pro Gly
            4500                4505                4510

Thr Thr Trp Ile Leu Thr Glu Leu Thr Thr Thr Ala Thr Thr Thr Ala
        4515                4520                4525

Ser Thr Gly Ser Thr Ala Thr Pro Ser Ser Thr Pro Gly Thr Thr Trp
    4530                4535                4540

Ile Leu Thr Glu Pro Ser Thr Thr Ala Thr Val Thr Val Pro Thr Gly
4545                4550                4555                4560

Ser Thr Ala Thr Ala Ser Ser Thr Gln Ala Thr Ala Gly Thr Pro His
                4565                4570                4575

Val Ser Thr Thr Ala Thr Thr Pro Thr Val Thr Ser Ser Lys Ala Thr
            4580                4585                4590

Pro Ser Ser Ser Pro Gly Thr Ala Thr Ala Leu Pro Ala Leu Arg Ser
        4595                4600                4605

Thr Ala Thr Thr Pro Thr Ala Thr Ser Phe Thr Ala Ile Pro Ser Ser
    4610                4615                4620

Ser Leu Gly Thr Thr Trp Thr Arg Leu Ser Gln Thr Thr Thr Pro Thr
4625                4630                4635                4640

Ala Thr Met Ser Thr Ala Thr Pro Ser Ser Thr Pro Glu Thr Val His
                4645                4650                4655

Thr Ser Thr Val Leu Thr Ala Thr Ala Thr Thr Thr Gly Ala Thr Gly
            4660                4665                4670

Ser Val Ala Thr Pro Ser Ser Thr Pro Gly Thr Ala His Thr Thr Lys
        4675                4680                4685

Val Pro Thr Thr Thr Thr Thr Gly Phe Thr Ala Thr Pro Ser Ser Ser
    4690                4695                4700

Pro Gly Thr Ala Leu Thr Pro Pro Val Trp Ile Ser Thr Thr Thr Thr
4705                4710                4715                4720

Pro Thr Thr Thr Thr Pro Thr Thr Ser Gly Ser Thr Val Thr Pro Ser
                4725                4730                4735

Ser Ile Pro Gly Thr Thr His Thr Ala Arg Val Leu Thr Thr Thr Thr
            4740                4745                4750

Thr Thr Val Ala Thr Gly Ser Met Ala Thr Pro Ser Ser Ser Thr Gln
        4755                4760                4765

Thr Ser Gly Thr Pro Pro Ser Leu Thr Thr Thr Ala Thr Thr Ile Thr
    4770                4775                4780

Ala Thr Gly Ser Thr Thr Asn Pro Ser Ser Thr Pro Gly Thr Thr Pro
4785                4790                4795                4800
```

-continued

```
Ile Thr Pro Val Leu Thr Ser Thr Ala Thr Thr Pro Ala Ala Thr Ser
                4805                4810                4815

Ser Lys Ala Thr Ser Ser Ser Ser Pro Arg Thr Ala Thr Thr Leu Pro
            4820                4825                4830

Val Leu Thr Ser Thr Ala Thr Lys Ser Thr Ala Thr Ser Phe Thr Pro
        4835                4840                4845

Ile Pro Ser Ser Thr Leu Trp Thr Thr Trp Thr Val Pro Ala Gln Thr
    4850                4855                4860

Thr Thr Pro Met Ser Thr Met Ser Thr Ile His Thr Ser Ser Thr Pro
4865                4870                4875                4880

Glu Thr Thr His Thr Ser Thr Val Leu Thr Thr Thr Ala Thr Met Thr
                4885                4890                4895

Arg Ala Thr Asn Ser Thr Ala Thr Pro Ser Ser Thr Leu Gly Thr Thr
            4900                4905                4910

Arg Ile Leu Thr Glu Leu Thr Thr Thr Ala Thr Thr Thr Ala Ala Thr
        4915                4920                4925

Gly Ser Thr Ala Thr Leu Ser Ser Thr Pro Gly Thr Thr Trp Ile Leu
    4930                4935                4940

Thr Glu Pro Ser Thr Ile Ala Thr Val Met Val Pro Thr Gly Ser Thr
4945                4950                4955                4960

Ala Thr Ala Ser Ser Thr Leu Gly Thr Ala His Thr Pro Lys Val Val
                4965                4970                4975

Thr Thr Met Ala Thr Met Pro Thr Ala Thr Ala Ser Thr Val Pro Ser
            4980                4985                4990

Ser Ser Thr Val Gly Thr Thr Arg Thr Pro Ala Val Leu Pro Ser Ser
        4995                5000                5005

Leu Pro Thr Phe Ser Val Ser Thr Val Ser Ser Ser Val Leu Thr Thr
    5010                5015                5020

Leu Arg Pro Thr Gly Phe Pro Ser Ser His Phe Ser Thr Pro Cys Phe
5025                5030                5035                5040

Cys Arg Ala Phe Gly Gln Phe Phe Ser Pro Gly Glu Val Ile Tyr Asn
                5045                5050                5055

Lys Thr Asp Arg Ala Gly Cys His Phe Tyr Ala Val Cys Asn Gln His
            5060                5065                5070

Cys Asp Ile Asp Arg Phe Gln Gly Ala Cys Pro Thr Ser Pro Pro Pro
        5075                5080                5085

Val Ser Ser Ala Pro Leu Ser Ser Pro Ser Pro Ala Pro Gly Cys Asp
    5090                5095                5100

Asn Ala Ile Pro Leu Arg Gln Val Asn Glu Thr Trp Thr Leu Glu Asn
5105                5110                5115                5120

Cys Thr Val Ala Arg Cys Val Gly Asp Asn Arg Val Val Leu Leu Asp
                5125                5130                5135

Pro Lys Pro Val Ala Asn Val Thr Cys Val Asn Lys His Leu Pro Ile
            5140                5145                5150

Lys Val Ser Asp Pro Ser Gln Pro Cys Asp Phe His Tyr Glu Cys Glu
        5155                5160                5165

Cys Ile Cys Ser Met Trp Gly Gly Ser His Tyr Ser Thr Phe Asp Gly
    5170                5175                5180

Thr Ser Tyr Thr Phe Arg Gly Asn Cys Thr Tyr Val Leu Met Arg Glu
5185                5190                5195                5200

Ile His Ala Arg Phe Gly Asn Leu Ser Leu Tyr Leu Asp Asn His Tyr
                5205                5210                5215

Cys Thr Ala Ser Ala Thr Ala Ala Ala Ala Arg Cys Pro Arg Ala Leu
```

-continued

```
            5220                5225                5230

Ser Ile His Tyr Lys Ser Met Asp Ile Val Leu Thr Val Thr Met Val
        5235                5240                5245

His Gly Lys Glu Glu Gly Leu Ile Leu Phe Asp Gln Ile Pro Val Ser
    5250                5255                5260

Ser Gly Phe Ser Lys Asn Gly Val Leu Val Ser Val Leu Gly Thr Thr
5265                5270                5275                5280

Thr Met Arg Val Asp Ile Pro Ala Leu Gly Val Ser Val Thr Phe Asn
                5285                5290                5295

Gly Gln Val Phe Gln Ala Arg Leu Pro Tyr Ser Leu Phe His Asn Asn
            5300                5305                5310

Thr Glu Gly Gln Cys Gly Thr Cys Thr Asn Asn Gln Arg Asp Asp Cys
        5315                5320                5325

Leu Gln Arg Asp Gly Thr Thr Ala Ala Ser Cys Lys Asp Met Ala Lys
    5330                5335                5340

Thr Trp Leu Val Pro Asp Ser Arg Lys Asp Gly Cys Trp Ala Pro Thr
5345                5350                5355                5360

Gly Thr Pro Pro Thr Ala Ser Pro Ala Ala Pro Val Ser Ser Thr Pro
                5365                5370                5375

Thr Pro Thr Pro Cys Pro Pro Gln Pro Leu Cys Asp Leu Met Leu Ser
            5380                5385                5390

Gln Val Phe Ala Glu Cys His Asn Leu Val Pro Pro Gly Pro Phe Phe
        5395                5400                5405

Asn Ala Cys Ile Ser Asp His Cys Arg Gly Arg Leu Glu Val Pro Cys
    5410                5415                5420

Gln Ser Leu Glu Ala Tyr Ala Glu Leu Cys Arg Ala Arg Gly Val Cys
5425                5430                5435                5440

Ser Asp Trp Arg Gly Ala Thr Gly Gly Leu Cys Asp Leu Thr Cys Pro
                5445                5450                5455

Pro Thr Lys Val Tyr Lys Pro Cys Gly Pro Ile Gln Pro Ala Thr Cys
            5460                5465                5470

Asn Ser Arg Asn Gln Ser Pro Gln Leu Glu Gly Met Ala Glu Gly Cys
        5475                5480                5485

Phe Cys Pro Glu Asp Gln Ile Leu Phe Asn Ala His Met Gly Ile Cys
    5490                5495                5500

Val Gln Ala Cys Pro Cys Val Gly Pro Asp Gly Phe Pro Lys Phe Pro
5505                5510                5515                5520

Gly Glu Arg Trp Val Ser Asn Cys Gln Ser Cys Val Cys Asp Glu Gly
                5525                5530                5535

Ser Val Ser Val Gln Cys Lys Pro Leu Pro Cys Asp Ala Gln Gly Gln
            5540                5545                5550

Pro Pro Pro Cys Asn Arg Pro Gly Phe Val Thr Val Thr Arg Pro Arg
        5555                5560                5565

Ala Glu Asn Pro Cys Cys Pro Glu Thr Val Cys Val Cys Asn Thr Thr
    5570                5575                5580

Thr Cys Pro Gln Ser Leu Pro Val Cys Pro Pro Gly Gln Glu Ser Ile
5585                5590                5595                5600

Cys Thr Gln Glu Glu Gly Asp Cys Cys Pro Thr Phe Arg Cys Arg Pro
                5605                5610                5615

Gln Leu Cys Ser Tyr Asn Gly Thr Phe Tyr Gly Val Gly Ala Thr Phe
            5620                5625                5630

Pro Gly Ala Leu Pro Cys His Met Cys Thr Cys Leu Ser Gly Asp Thr
        5635                5640                5645
```

Gln Asp Pro Thr Val Gln Cys Gln Glu Asp Ala Cys Asn Asn Thr Thr
5650 5655 5660

Cys Pro Gln Gly Phe Glu Tyr Lys Arg Val Ala Gly Gln Cys Cys Gly
5665 5670 5675 5680

Glu Cys Val Gln Thr Ala Cys Leu Thr Pro Asp Gly Gln Pro Val Gln
5685 5690 5695

Leu Asn Glu Thr Trp Val Asn Ser His Val Asp Asn Cys Thr Val Tyr
5700 5705 5710

Leu Cys Glu Ala Glu Gly Gly Val His Leu Leu Thr Pro Gln Pro Ala
5715 5720 5725

Ser Cys Pro Asp Val Ser Ser Cys Arg Gly Ser Leu Arg Lys Thr Gly
5730 5735 5740

Cys Cys Tyr Ser Cys Glu Glu Asp Ser Cys Gln Val Arg Ile Asn Thr
5745 5750 5755 5760

Thr Ile Leu Trp His Gln Gly Cys Glu Thr Glu Val Asn Ile Thr Phe
5765 5770 5775

Cys Glu Gly Ser Cys Pro Gly Ala Ser Lys Tyr Ser Ala Glu Ala Gln
5780 5785 5790

Ala Met Gln His Gln Cys Thr Cys Cys Gln Glu Arg Arg Val His Glu
5795 5800 5805

Glu Thr Val Pro Leu His Cys Pro Asn Gly Ser Ala Ile Leu His Thr
5810 5815 5820

Tyr Thr His Val Asp Glu Cys Gly Cys Thr Pro Phe Cys Val Pro Ala
5825 5830 5835 5840

Pro Met Ala Pro Pro His Thr Arg Gly Phe Pro Ala Gln Glu Ala Thr
5845 5850 5855

Ala Val

<210> SEQ ID NO 83
<211> LENGTH: 619
<212> TYPE: PRT
<213> ORGANISM: Homo sapiens

<400> SEQUENCE: 83

Met Ala Ala Val Val Gln Gln Asn Asp Leu Val Phe Glu Phe Ala Ser
1 5 10 15

Asn Val Met Glu Asp Glu Arg Gln Leu Gly Asp Pro Ala Ile Phe Pro
20 25 30

Ala Val Ile Val Glu His Val Pro Gly Ala Asp Ile Leu Asn Ser Tyr
35 40 45

Ala Gly Leu Ala Cys Val Glu Glu Pro Asn Asp Met Ile Thr Glu Ser
50 55 60

Ser Leu Asp Val Ala Glu Glu Glu Ile Ile Asp Asp Asp Asp Asp Asp
65 70 75 80

Ile Thr Leu Thr Val Glu Ala Ser Cys His Asp Gly Asp Glu Thr Ile
85 90 95

Glu Thr Ile Glu Ala Ala Glu Ala Leu Leu Asn Met Asp Ser Pro Gly
100 105 110

Pro Met Leu Asp Glu Lys Arg Ile Asn Asn Asn Ile Phe Ser Ser Pro
115 120 125

Glu Asp Asp Met Val Val Ala Pro Val Thr His Val Ser Val Thr Leu
130 135 140

Asp Gly Ile Pro Glu Val Met Glu Thr Gln Gln Val Gln Glu Lys Tyr
145 150 155 160

```
Ala Asp Ser Pro Gly Ala Ser Ser Pro Glu Gln Pro Lys Arg Lys Lys
                165                 170                 175

Gly Arg Lys Thr Lys Pro Pro Arg Pro Asp Ser Pro Ala Thr Thr Pro
            180                 185                 190

Asn Ile Ser Val Lys Lys Lys Asn Lys Asp Gly Lys Gly Asn Thr Ile
        195                 200                 205

Tyr Leu Trp Glu Phe Leu Leu Ala Leu Leu Gln Asp Lys Ala Thr Cys
    210                 215                 220

Pro Lys Tyr Ile Lys Trp Thr Gln Arg Glu Lys Gly Ile Phe Lys Leu
225                 230                 235                 240

Val Asp Ser Lys Ala Val Ser Arg Leu Trp Gly Lys His Lys Asn Lys
                245                 250                 255

Pro Asp Met Asn Tyr Glu Thr Met Gly Arg Ala Leu Arg Tyr Tyr Tyr
            260                 265                 270

Gln Arg Gly Ile Leu Ala Lys Val Glu Gly Gln Arg Leu Val Tyr Gln
        275                 280                 285

Phe Lys Glu Met Pro Lys Asp Leu Ile Tyr Ile Asn Asp Glu Asp Pro
    290                 295                 300

Ser Ser Ser Ile Glu Ser Ser Asp Pro Ser Leu Ser Ser Ser Ala Thr
305                 310                 315                 320

Ser Asn Arg Asn Gln Thr Ser Arg Ser Arg Val Ser Ser Ser Pro Gly
                325                 330                 335

Val Lys Gly Gly Ala Thr Thr Val Leu Lys Pro Gly Asn Ser Lys Ala
            340                 345                 350

Ala Lys Pro Lys Asp Pro Val Glu Val Ala Gln Pro Ser Glu Val Leu
        355                 360                 365

Arg Thr Val Gln Pro Thr Gln Ser Pro Tyr Pro Thr Gln Leu Phe Arg
    370                 375                 380

Thr Val His Val Val Gln Pro Val Gln Ala Val Pro Glu Gly Glu Ala
385                 390                 395                 400

Ala Arg Thr Ser Thr Met Gln Asp Glu Thr Leu Asn Ser Ser Val Gln
                405                 410                 415

Ser Ile Arg Thr Ile Gln Ala Pro Thr Gln Val Pro Val Val Val Ser
            420                 425                 430

Pro Arg Asn Gln Gln Leu His Thr Val Thr Leu Gln Thr Val Pro Leu
        435                 440                 445

Thr Thr Val Ile Ala Ser Thr Asp Pro Ser Ala Gly Thr Gly Ser Gln
    450                 455                 460

Lys Phe Ile Leu Gln Ala Ile Pro Ser Ser Gln Pro Met Thr Val Leu
465                 470                 475                 480

Lys Glu Asn Val Met Leu Gln Ser Gln Lys Ala Gly Ser Pro Pro Ser
                485                 490                 495

Ile Val Leu Gly Pro Ala Gln Val Gln Gln Val Leu Thr Ser Asn Val
            500                 505                 510

Gln Thr Ile Cys Asn Gly Thr Val Ser Val Ala Ser Ser Pro Ser Phe
        515                 520                 525

Ser Ala Thr Ala Pro Val Val Thr Phe Ser Pro Arg Ser Ser Gln Leu
    530                 535                 540

Val Ala His Pro Pro Gly Thr Val Ile Thr Ser Val Ile Lys Thr Gln
545                 550                 555                 560

Glu Thr Lys Thr Leu Thr Gln Glu Val Glu Lys Lys Glu Ser Glu Asp
                565                 570                 575
```

His Leu Lys Glu Asn Thr Glu Lys Thr Glu Gln Gln Pro Gln Pro Tyr
580 585 590

Val Met Val Val Ser Ser Ser Asn Gly Phe Thr Ser Gln Val Ala Met
595 600 605

Lys Gln Asn Glu Leu Leu Glu Pro Asn Ser Phe
610 615

<210> SEQ ID NO 84
<211> LENGTH: 753
<212> TYPE: PRT
<213> ORGANISM: Homo sapiens

<400> SEQUENCE: 84

Met Gly Glu His Ser Pro Asp Asn Asn Ile Ile Tyr Phe Glu Ala Glu
1 5 10 15

Glu Asp Glu Leu Thr Pro Asp Asp Lys Met Leu Arg Phe Val Asp Lys
20 25 30

Asn Gly Leu Val Pro Ser Ser Ser Gly Thr Val Tyr Asp Arg Thr Thr
35 40 45

Val Leu Ile Glu Gln Asp Pro Gly Thr Leu Glu Asp Glu Asp Asp Asp
50 55 60

Gly Gln Cys Gly Glu His Leu Pro Phe Leu Val Gly Gly Glu Glu Gly
65 70 75 80

Phe His Leu Ile Asp His Glu Ala Met Ser Gln Gly Tyr Val Gln His
85 90 95

Ile Ile Ser Pro Asp Gln Ile His Leu Thr Ile Asn Pro Gly Ser Thr
100 105 110

Pro Met Pro Arg Asn Ile Glu Gly Ala Thr Leu Thr Leu Gln Ser Glu
115 120 125

Cys Pro Glu Thr Lys Arg Lys Glu Val Lys Arg Tyr Gln Cys Thr Phe
130 135 140

Glu Gly Cys Pro Arg Thr Tyr Ser Thr Ala Gly Asn Leu Arg Thr His
145 150 155 160

Gln Lys Thr His Arg Gly Glu Tyr Thr Phe Val Cys Asn Gln Glu Gly
165 170 175

Cys Gly Lys Ala Phe Leu Thr Ser His Ser Leu Arg Ile His Val Arg
180 185 190

Val His Thr Lys Glu Lys Pro Phe Glu Cys Asp Val Gln Gly Cys Glu
195 200 205

Lys Ala Phe Asn Thr Leu Tyr Arg Leu Lys Ala His Gln Arg Leu His
210 215 220

Thr Gly Lys Thr Phe Asn Cys Glu Ser Glu Gly Cys Ser Lys Tyr Phe
225 230 235 240

Thr Thr Leu Ser Asp Leu Arg Lys His Ile Arg Thr His Thr Gly Glu
245 250 255

Lys Pro Phe Arg Cys Asp His Asp Gly Cys Gly Lys Ala Phe Ala Ala
260 265 270

Ser His His Leu Lys Thr His Val Arg Thr His Thr Gly Glu Arg Pro
275 280 285

Phe Phe Cys Pro Ser Asn Gly Cys Glu Lys Thr Phe Ser Thr Gln Tyr
290 295 300

Ser Leu Lys Ser His Met Lys Gly His Asp Asn Lys Gly His Ser Tyr
305 310 315 320

Asn Ala Leu Pro Gln His Asn Gly Ser Glu Asp Thr Asn His Ser Leu
325 330 335

```
Cys Leu Ser Asp Leu Ser Leu Leu Ser Thr Asp Ser Glu Leu Arg Glu
            340                 345                 350

Asn Ser Ser Thr Thr Gln Gly Gln Asp Leu Ser Thr Ile Ser Pro Ala
        355                 360                 365

Ile Ile Phe Glu Ser Met Phe Gln Asn Ser Asp Asp Thr Ala Ile Gln
    370                 375                 380

Glu Asp Pro Gln Gln Thr Ala Ser Leu Thr Glu Ser Phe Asn Gly Asp
385                 390                 395                 400

Ala Glu Ser Val Ser Asp Val Pro Pro Ser Thr Gly Asn Ser Ala Ser
                405                 410                 415

Leu Ser Leu Pro Leu Val Leu Gln Pro Gly Leu Ser Glu Pro Pro Gln
            420                 425                 430

Pro Leu Leu Pro Ala Ser Ala Pro Ser Ala Pro Pro Pro Ala Pro Ser
        435                 440                 445

Leu Gly Pro Gly Ser Gln Gln Ala Ala Phe Gly Asn Pro Pro Ala Leu
    450                 455                 460

Leu Gln Pro Pro Glu Val Pro Val Pro His Ser Thr Gln Phe Ala Ala
465                 470                 475                 480

Asn His Gln Glu Phe Leu Pro His Pro Gln Ala Pro Gln Pro Ile Val
                485                 490                 495

Pro Gly Leu Ser Val Val Ala Gly Ala Ser Ala Ser Ala Ala Ala Val
            500                 505                 510

Ala Ser Ala Val Ala Ala Pro Ala Pro Pro Gln Ser Thr Thr Glu Pro
        515                 520                 525

Leu Pro Ala Met Val Gln Thr Leu Pro Leu Gly Ala Asn Ser Val Leu
    530                 535                 540

Thr Asn Asn Pro Thr Ile Thr Ile Thr Pro Thr Pro Asn Thr Ala Ile
545                 550                 555                 560

Leu Gln Ser Ser Leu Val Met Gly Glu Gln Asn Leu Gln Trp Ile Leu
                565                 570                 575

Asn Gly Ala Thr Ser Ser Pro Gln Asn Gln Glu Gln Ile Gln Gln Ala
            580                 585                 590

Ser Lys Val Glu Lys Val Phe Phe Thr Thr Ala Val Pro Val Ala Ser
        595                 600                 605

Ser Pro Gly Ser Ser Val Gln Gln Ile Gly Leu Ser Val Pro Val Ile
    610                 615                 620

Ile Ile Lys Gln Glu Glu Ala Cys Gln Cys Gln Cys Ala Cys Arg Asp
625                 630                 635                 640

Ser Ala Lys Glu Arg Ala Ser Ser Arg Arg Lys Gly Cys Ser Ser Pro
                645                 650                 655

Pro Pro Pro Glu Pro Ser Pro Gln Ala Pro Asp Gly Pro Ser Leu Gln
            660                 665                 670

Leu Pro Ala Gln Thr Phe Ser Ser Ala Pro Val Pro Gly Ser Ser Ser
        675                 680                 685

Ser Thr Leu Pro Ser Ser Cys Glu Gln Ser Arg Gln Ala Glu Thr Pro
    690                 695                 700

Ser Asp Pro Gln Thr Glu Thr Leu Ser Ala Met Asp Val Ser Glu Phe
705                 710                 715                 720

Leu Ser Leu Gln Ser Leu Asp Thr Pro Ser Asn Leu Ile Pro Ile Glu
                725                 730                 735

Ala Leu Leu Gln Gly Glu Glu Glu Met Gly Leu Thr Ser Ser Phe Ser
            740                 745                 750
```

Lys

<210> SEQ ID NO 85
<211> LENGTH: 57
<212> TYPE: PRT
<213> ORGANISM: Homo sapiens

<400> SEQUENCE: 85

```
Met Leu Cys Ala His Phe Ser Asp Gln Gly Pro Ala His Leu Thr Thr
 1               5                  10                  15

Ser Lys Ser Ala Phe Leu Ser Asn Lys Lys Thr Ser Thr Leu Lys His
            20                  25                  30

Leu Leu Gly Glu Thr Arg Ser Asp Gly Ser Ala Cys Asn Ser Gly Ile
        35                  40                  45

Ser Gly Gly Arg Gly Arg Lys Ile Pro
    50                  55
```

<210> SEQ ID NO 86
<211> LENGTH: 726
<212> TYPE: PRT
<213> ORGANISM: Homo sapiens

<400> SEQUENCE: 86

```
Met Glu Gly Glu Arg Lys Asn Asn Asn Lys Arg Trp Tyr Phe Thr Arg
 1               5                  10                  15

Glu Gln Leu Glu Asn Ser Pro Ser Arg Arg Phe Gly Val Asp Pro Asp
            20                  25                  30

Lys Glu Leu Ser Tyr Arg Gln Gln Ala Ala Asn Leu Leu Gln Asp Met
        35                  40                  45

Gly Gln Arg Leu Asn Val Ser Gln Leu Thr Ile Asn Thr Ala Ile Val
    50                  55                  60

Tyr Met His Arg Phe Tyr Met Ile Gln Ser Phe Thr Gln Phe Pro Gly
65                  70                  75                  80

Asn Ser Val Ala Pro Ala Ala Leu Phe Leu Ala Ala Lys Val Glu Glu
                85                  90                  95

Gln Pro Lys Lys Leu Glu His Val Ile Lys Val Ala His Thr Cys Leu
            100                 105                 110

His Pro Gln Glu Ser Leu Pro Asp Thr Arg Ser Glu Ala Tyr Leu Gln
        115                 120                 125

Gln Val Gln Asp Leu Val Ile Leu Glu Ser Ile Ile Leu Gln Thr Leu
    130                 135                 140

Gly Phe Glu Leu Thr Ile Asp His Pro His Thr His Val Val Lys Cys
145                 150                 155                 160

Thr Gln Leu Val Arg Ala Ser Lys Asp Leu Ala Gln Thr Ser Tyr Phe
                165                 170                 175

Met Ala Thr Asn Ser Leu His Leu Thr Thr Phe Ser Leu Gln Tyr Thr
            180                 185                 190

Pro Pro Val Val Ala Cys Val Cys Ile His Leu Ala Cys Lys Trp Ser
        195                 200                 205

Asn Trp Glu Ile Pro Val Ser Thr Asp Gly Lys His Trp Trp Glu Tyr
    210                 215                 220

Val Asp Ala Thr Val Thr Leu Glu Leu Leu Asp Glu Leu Thr His Glu
225                 230                 235                 240

Phe Leu Gln Ile Leu Glu Lys Thr Pro Asn Arg Leu Lys Arg Ile Trp
                245                 250                 255

Asn Trp Arg Ala Cys Glu Ala Ala Lys Lys Thr Lys Ala Asp Asp Arg
```

-continued

```
            260                 265                 270

Gly Thr Asp Glu Lys Thr Ser Glu Gln Thr Ile Leu Asn Met Ile Ser
        275                 280                 285

Gln Ser Ser Ser Asp Thr Thr Ile Ala Gly Leu Met Ser Met Ser Thr
    290                 295                 300

Ser Thr Thr Ser Ala Val Pro Ser Leu Pro Val Ser Glu Glu Ser Ser
305                 310                 315                 320

Ser Asn Leu Thr Ser Val Glu Met Leu Pro Gly Lys Arg Trp Leu Ser
                325                 330                 335

Ser Gln Pro Ser Phe Lys Leu Glu Pro Thr Gln Gly His Arg Thr Ser
            340                 345                 350

Glu Asn Leu Ala Leu Thr Gly Val Asp His Ser Leu Pro Gln Asp Gly
        355                 360                 365

Ser Asn Ala Phe Ile Ser Gln Lys Gln Asn Ser Lys Ser Val Pro Ser
    370                 375                 380

Ala Lys Val Ser Leu Lys Glu Tyr Arg Ala Lys His Ala Glu Glu Leu
385                 390                 395                 400

Ala Ala Gln Lys Arg Gln Leu Glu Asn Met Glu Ala Asn Val Lys Ser
                405                 410                 415

Gln Tyr Ala Tyr Ala Ala Gln Asn Leu Leu Ser His His Asp Ser His
            420                 425                 430

Ser Ser Val Ile Leu Lys Met Pro Ile Glu Gly Ser Glu Asn Pro Glu
        435                 440                 445

Arg Pro Phe Leu Glu Lys Ala Asp Lys Thr Ala Leu Lys Met Arg Ile
    450                 455                 460

Pro Val Ala Gly Gly Asp Lys Ala Ala Ser Ser Lys Pro Glu Glu Ile
465                 470                 475                 480

Lys Met Arg Ile Lys Val His Ala Ala Ala Asp Lys His Asn Ser Val
                485                 490                 495

Glu Asp Ser Val Thr Lys Ser Arg Glu His Lys Glu Lys His Lys Thr
            500                 505                 510

His Pro Ser Asn His His His His His Asn His His Ser His Lys His
        515                 520                 525

Ser His Ser Gln Leu Pro Val Gly Thr Gly Asn Lys Arg Pro Gly Asp
    530                 535                 540

Pro Lys His Ser Ser Gln Thr Ser Asn Leu Ala His Lys Thr Tyr Ser
545                 550                 555                 560

Leu Ser Ser Ser Phe Ser Ser Ser Ser Ser Thr Arg Lys Arg Gly Pro
                565                 570                 575

Ser Glu Glu Thr Gly Gly Ala Val Phe Asp His Pro Ala Lys Ile Ala
            580                 585                 590

Lys Ser Thr Lys Ser Ser Ser Leu Asn Phe Ser Phe Pro Ser Leu Pro
        595                 600                 605

Thr Met Gly Gln Met Pro Gly His Ser Ser Asp Thr Ser Gly Leu Ser
    610                 615                 620

Phe Ser Gln Pro Ser Cys Lys Thr Arg Val Pro His Ser Lys Leu Asp
625                 630                 635                 640

Lys Gly Pro Thr Gly Ala Asn Gly His Asn Thr Thr Gln Thr Ile Asp
                645                 650                 655

Tyr Gln Asp Thr Val Asn Met Leu His Ser Leu Leu Ser Ala Gln Gly
            660                 665                 670

Val Gln Pro Thr Gln Pro Thr Ala Phe Glu Phe Val Arg Pro Tyr Ser
        675                 680                 685
```

```
Asp Tyr Leu Asn Pro Arg Ser Gly Gly Ile Ser Ser Arg Ser Gly Asn
    690                 695                 700

Thr Asp Lys Pro Arg Pro Pro Pro Leu Pro Ser Glu Pro Pro Pro Pro
705                 710                 715                 720

Leu Pro Pro Leu Pro Lys
                725


<210> SEQ ID NO 87
<211> LENGTH: 591
<212> TYPE: PRT
<213> ORGANISM: Homo sapiens

<400> SEQUENCE: 87

Met Tyr Leu Lys Asp Tyr Glu Arg Lys Val Ile Leu Glu Lys Ala Gly
 1               5                  10                  15

Lys Tyr Val Asp Glu Glu Asn Ser Asp Gly Glu Thr Ser Asn His Arg
            20                  25                  30

Leu Gln Glu Thr Ser Ser Gln Ser Tyr Val Glu Glu Gln Lys Gln Leu
        35                  40                  45

Lys Glu Ser Phe Arg Ala Phe Val Glu Asp Ser Glu Asp Glu Asp Gly
    50                  55                  60

Ala Gly Glu Gly Gly Ser Ser Leu Leu Gln Lys Arg Ala Lys Thr Arg
65                  70                  75                  80

Gln Glu Lys Ala Gln Glu Glu Ala Asp Tyr Ile Glu Trp Leu Lys Gly
                85                  90                  95

Gln Lys Glu Ile Arg Asn Pro Asp Ser Leu Lys Glu Leu Thr His Leu
            100                 105                 110

Lys Glu Tyr Trp Asn Asp Pro Glu Leu Asp Glu Gly Glu Arg Phe Leu
        115                 120                 125

Arg Asp Tyr Ile Leu Asn Lys Arg Tyr Glu Glu Glu Glu Glu Glu Glu
    130                 135                 140

Glu Asp Glu Glu Glu Met Glu Glu Glu Lys Gly Val His Gly Pro Pro
145                 150                 155                 160

Val Gln Leu Ala Val Asp Asp Ser Ser Asp Glu Gly Glu Leu Phe Leu
                165                 170                 175

Lys Lys Gln Glu Asp Phe Glu Gln Lys Tyr Asn Phe Arg Phe Glu Glu
            180                 185                 190

Pro Asp Ser Ala Ser Val Lys Thr Tyr Pro Arg Ser Ile Ala Ser Ser
        195                 200                 205

Val Arg Arg Lys Asp Glu Arg Arg Lys Glu Lys Arg Glu Glu Thr Arg
    210                 215                 220

Glu Arg Lys Lys Arg Glu Lys Ala Lys Lys Gln Glu Glu Leu Lys Gln
225                 230                 235                 240

Leu Lys Asn Leu Lys Arg Lys Glu Ile Leu Ala Lys Leu Glu Lys Leu
                245                 250                 255

Arg Lys Val Thr Gly Asn Glu Met Leu Gly Leu Glu Glu Gly Asp Leu
            260                 265                 270

Glu Asp Asp Phe Asp Pro Ala Gln His Asp Gln Leu Met Gln Lys Cys
        275                 280                 285

Phe Gly Asp Glu Tyr Tyr Gly Ala Val Glu Glu Glu Lys Pro Gln Phe
    290                 295                 300

Glu Glu Glu Glu Gly Leu Glu Asp Asp Trp Asn Trp Asp Thr Trp Asp
305                 310                 315                 320

Gly Pro Glu Gln Glu Gly Asp Trp Ser Gln Gln Glu Leu His Cys Glu
```

-continued

```
                325                 330                 335

Asp Pro Asn Phe Asn Met Asp Ala Asp Tyr Asp Pro Ser Gln Pro Arg
            340                 345                 350

Lys Lys Lys Arg Glu Ala Pro Leu Thr Gly Lys Lys Lys Arg Lys Ser
        355                 360                 365

Pro Phe Ala Ala Ala Val Gly Gln Glu Lys Pro Val Phe Glu Pro Gly
    370                 375                 380

Asp Lys Thr Phe Glu Glu Tyr Leu Asp Glu Tyr Tyr Arg Leu Asp Tyr
385                 390                 395                 400

Glu Asp Ile Ile Asp Asp Leu Pro Cys Arg Phe Lys Tyr Arg Thr Val
                405                 410                 415

Val Pro Cys Asp Phe Gly Leu Ser Thr Glu Glu Ile Leu Ala Ala Asp
            420                 425                 430

Asp Lys Glu Leu Asn Arg Trp Cys Ser Leu Lys Lys Thr Cys Met Tyr
        435                 440                 445

Arg Ser Glu Gln Glu Glu Leu Arg Asp Lys Arg Ala Tyr Ser Gln Lys
    450                 455                 460

Ala Gln Asn Ser Trp Lys Lys Arg Gln Val Phe Lys Ser Leu Cys Arg
465                 470                 475                 480

Glu Glu Ala Glu Thr Pro Ala Glu Ala Thr Gly Lys Pro Gln Arg Asp
                485                 490                 495

Glu Ala Gly Pro Gln Arg Gln Leu Pro Ala Leu Asp Gly Ser Leu Met
            500                 505                 510

Gly Pro Glu Ser Pro Pro Ala Gln Glu Glu Glu Ala Pro Val Ser Pro
        515                 520                 525

His Lys Lys Pro Ala Pro Gln Lys Arg Arg Arg Ala Lys Lys Ala Arg
    530                 535                 540

Leu Leu Gly Pro Thr Val Met Leu Gly Gly Cys Glu Phe Ser Arg Gln
545                 550                 555                 560

Arg Leu Gln Ala Phe Gly Leu Asn Pro Lys Arg Leu His Phe Arg Gln
                565                 570                 575

Leu Gly Arg Gln Arg Arg Lys Gln Gln Gly Pro Lys Asn Ser Ser
            580                 585                 590


<210> SEQ ID NO 88
<211> LENGTH: 709
<212> TYPE: PRT
<213> ORGANISM: Homo sapiens

<400> SEQUENCE: 88

Met Gly His Arg Thr Ala Met Pro Glu Pro Arg Gly Ser Ser Gln Leu
 1               5                  10                  15

Arg Val Asn Ala Ala Phe Ala Ala Arg Tyr Asn Arg Tyr Arg Glu Arg
            20                  25                  30

Glu Glu Leu Gln Arg Leu Lys Asp Arg Tyr Gly Asp Arg Asp Ser Ser
        35                  40                  45

Ser Asp Ser Ser Ser Glu Ser Asp Ser Ser Asp Glu Arg Val Glu Phe
    50                  55                  60

Asp Pro Gln Gln Glu Arg Asp Phe Tyr Lys Thr Leu Ser Leu Leu Lys
65                  70                  75                  80

Lys Lys Asp Pro Arg Ile Tyr Gln Lys Asp Ala Thr Phe Tyr Asn Arg
                85                  90                  95

Thr Ala Ser Ser Ser Asp Ser Glu Glu Asp Pro Glu Ala Leu Glu Lys
            100                 105                 110
```

```
Gln Lys Lys Val Arg Pro Met Tyr Leu Lys Asp Tyr Glu Arg Lys Val
        115                 120                 125

Ile Leu Glu Lys Ala Gly Lys Tyr Val Asp Glu Glu Asn Ser Asp Gly
    130                 135                 140

Glu Thr Ser Asn His Arg Leu Gln Glu Thr Ser Ser Gln Ser Tyr Val
145                 150                 155                 160

Glu Glu Gln Lys Gln Leu Lys Glu Ser Phe Arg Ala Phe Val Glu Asp
                165                 170                 175

Ser Glu Asp Glu Asp Gly Ala Gly Glu Gly Gly Ser Ser Leu Leu Gln
            180                 185                 190

Lys Arg Ala Lys Thr Arg Gln Glu Lys Ala Gln Glu Glu Ala Asp Tyr
        195                 200                 205

Ile Glu Trp Leu Lys Gly Gln Lys Glu Ile Arg Asn Pro Asp Ser Leu
    210                 215                 220

Lys Glu Leu Thr His Leu Lys Glu Tyr Trp Asn Asp Pro Glu Leu Asp
225                 230                 235                 240

Glu Gly Glu Arg Phe Leu Arg Asp Tyr Ile Leu Asn Lys Arg Tyr Glu
                245                 250                 255

Glu Glu Glu Glu Glu Glu Glu Asp Glu Glu Glu Met Glu Glu Glu Lys
            260                 265                 270

Gly Val His Gly Pro Pro Val Gln Leu Ala Val Asp Asp Ser Ser Asp
        275                 280                 285

Glu Gly Glu Leu Phe Leu Lys Lys Gln Glu Asp Phe Glu Gln Lys Tyr
    290                 295                 300

Asn Phe Arg Phe Glu Glu Pro Asp Ser Ala Ser Val Lys Thr Tyr Pro
305                 310                 315                 320

Arg Ser Ile Ala Ser Ser Val Arg Arg Lys Asp Glu Arg Arg Lys Glu
                325                 330                 335

Lys Arg Glu Glu Thr Arg Glu Arg Lys Lys Arg Glu Lys Ala Lys Lys
            340                 345                 350

Gln Glu Glu Leu Lys Gln Leu Lys Asn Leu Lys Arg Lys Glu Ile Leu
        355                 360                 365

Ala Lys Leu Glu Lys Leu Arg Lys Val Thr Gly Asn Glu Met Leu Gly
    370                 375                 380

Leu Glu Glu Gly Asp Leu Glu Asp Asp Phe Asp Pro Ala Gln His Asp
385                 390                 395                 400

Gln Leu Met Gln Lys Cys Phe Gly Asp Glu Tyr Tyr Gly Ala Val Glu
                405                 410                 415

Glu Glu Lys Pro Gln Phe Glu Glu Glu Glu Gly Leu Glu Asp Asp Trp
            420                 425                 430

Asn Trp Asp Thr Trp Asp Gly Pro Glu Gln Glu Gly Asp Trp Ser Gln
        435                 440                 445

Gln Glu Leu His Cys Glu Asp Pro Asn Phe Asn Met Asp Ala Asp Tyr
    450                 455                 460

Asp Pro Ser Gln Pro Arg Lys Lys Lys Arg Glu Ala Pro Leu Thr Gly
465                 470                 475                 480

Lys Lys Lys Arg Lys Ser Pro Phe Ala Ala Ala Val Gly Gln Glu Lys
                485                 490                 495

Pro Val Phe Glu Pro Gly Asp Lys Thr Phe Glu Glu Tyr Leu Asp Glu
            500                 505                 510

Tyr Tyr Arg Leu Asp Tyr Glu Asp Ile Ile Asp Asp Leu Pro Cys Arg
        515                 520                 525

Phe Lys Tyr Arg Thr Val Val Pro Cys Asp Phe Gly Leu Ser Thr Glu
```

530 535 540

Glu Ile Leu Ala Ala Asp Asp Lys Glu Leu Asn Arg Trp Cys Ser Leu
545 550 555 560

Lys Lys Thr Cys Met Tyr Arg Ser Glu Gln Glu Glu Leu Arg Asp Lys
565 570 575

Arg Ala Tyr Ser Gln Lys Ala Gln Asn Ser Trp Lys Lys Arg Gln Val
580 585 590

Phe Lys Ser Leu Cys Arg Glu Glu Ala Glu Thr Pro Ala Glu Ala Thr
595 600 605

Gly Lys Pro Gln Arg Asp Glu Ala Gly Pro Gln Arg Gln Leu Pro Ala
610 615 620

Leu Asp Gly Ser Leu Met Gly Pro Glu Ser Pro Pro Ala Gln Glu Glu
625 630 635 640

Glu Ala Pro Val Ser Pro His Lys Lys Pro Ala Pro Gln Lys Arg Arg
645 650 655

Arg Ala Lys Lys Ala Arg Leu Leu Gly Pro Thr Val Met Leu Gly Gly
660 665 670

Cys Glu Phe Ser Arg Gln Arg Leu Gln Ala Phe Gly Leu Asn Pro Lys
675 680 685

Arg Leu His Phe Arg Gln Leu Gly Arg Gln Arg Arg Lys Gln Gln Gly
690 695 700

Pro Lys Asn Ser Ser
705

<210> SEQ ID NO 89
<211> LENGTH: 1198
<212> TYPE: PRT
<213> ORGANISM: Homo sapiens

<400> SEQUENCE: 89

Met Ala Pro Val Tyr Glu Gly Met Ala Ser His Val Gln Val Phe Ser
1 5 10 15

Pro His Thr Leu Gln Ser Ser Ala Phe Cys Ser Val Lys Lys Leu Lys
20 25 30

Val Glu Pro Ser Ser Asn Trp Asp Met Thr Gly Tyr Gly Ser His Ser
35 40 45

Lys Val Tyr Ser Gln Ser Lys Asn Ile Pro Pro Ser Gln Pro Ala Ser
50 55 60

Thr Thr Val Ser Thr Ser Leu Pro Val Pro Asn Pro Ser Leu Pro Tyr
65 70 75 80

Glu Gln Thr Ile Val Phe Pro Gly Ser Thr Gly His Ile Val Val Thr
85 90 95

Ser Ala Ser Ser Thr Ser Val Thr Gly Gln Val Leu Gly Gly Pro His
100 105 110

Asn Leu Met Arg Arg Ser Thr Val Ser Leu Leu Asp Thr Tyr Gln Lys
115 120 125

Cys Gly Leu Lys Arg Lys Ser Glu Glu Ile Glu Asn Thr Ser Ser Val
130 135 140

Gln Ile Ile Glu Glu His Pro Pro Met Ile Gln Asn Asn Ala Ser Gly
145 150 155 160

Ala Thr Val Ala Thr Ala Thr Thr Ser Thr Ala Thr Ser Lys Asn Ser
165 170 175

Gly Ser Asn Ser Glu Gly Asp Tyr Gln Leu Val Gln His Glu Val Leu
180 185 190

```
Cys Ser Met Thr Asn Thr Tyr Glu Val Leu Glu Phe Leu Gly Arg Gly
        195                 200                 205

Thr Phe Gly Gln Val Val Lys Cys Trp Lys Arg Gly Thr Asn Glu Ile
    210                 215                 220

Val Ala Ile Lys Ile Leu Lys Asn Arg Pro Ser Tyr Ala Arg Gln Gly
225                 230                 235                 240

Gln Ile Glu Val Ser Ile Leu Ala Arg Leu Ser Thr Glu Ser Ala Asp
                245                 250                 255

Asp Tyr Asn Phe Val Arg Ala Tyr Glu Cys Phe Gln His Lys Asn His
            260                 265                 270

Thr Cys Leu Val Phe Glu Met Leu Glu Gln Asn Leu Tyr Asp Phe Leu
        275                 280                 285

Lys Gln Asn Lys Phe Ser Pro Leu Pro Leu Lys Tyr Ile Arg Pro Val
    290                 295                 300

Leu Gln Gln Val Ala Thr Ala Leu Met Lys Leu Lys Ser Leu Gly Leu
305                 310                 315                 320

Ile His Ala Asp Leu Lys Pro Glu Asn Ile Met Leu Val Asp Pro Ser
                325                 330                 335

Arg Gln Pro Tyr Arg Val Lys Val Ile Asp Phe Gly Ser Ala Ser His
            340                 345                 350

Val Ser Lys Ala Val Cys Ser Thr Tyr Leu Gln Ser Arg Tyr Tyr Arg
        355                 360                 365

Ala Pro Glu Ile Ile Leu Gly Leu Pro Phe Cys Glu Ala Ile Asp Met
    370                 375                 380

Trp Ser Leu Gly Cys Val Ile Ala Glu Leu Phe Leu Gly Trp Pro Leu
385                 390                 395                 400

Tyr Pro Gly Ala Ser Glu Tyr Asp Gln Ile Arg Tyr Ile Ser Gln Thr
                405                 410                 415

Gln Gly Leu Pro Ala Glu Tyr Leu Leu Ser Ala Gly Thr Lys Thr Thr
            420                 425                 430

Arg Phe Phe Asn Arg Asp Thr Asp Ser Pro Tyr Pro Leu Trp Arg Leu
        435                 440                 445

Lys Thr Pro Asp Asp His Glu Ala Glu Thr Gly Ile Lys Ser Lys Glu
    450                 455                 460

Ala Arg Lys Tyr Ile Phe Asn Cys Leu Asp Asp Met Ala Gln Val Asn
465                 470                 475                 480

Met Thr Thr Asp Leu Glu Gly Ser Asp Met Leu Val Glu Lys Ala Asp
                485                 490                 495

Arg Arg Glu Phe Ile Asp Leu Leu Lys Lys Met Leu Thr Ile Asp Ala
            500                 505                 510

Asp Lys Arg Ile Thr Pro Ile Glu Thr Leu Asn His Pro Phe Val Thr
        515                 520                 525

Met Thr His Leu Leu Asp Phe Pro His Ser Thr His Val Lys Ser Cys
    530                 535                 540

Phe Gln Asn Met Glu Ile Cys Lys Arg Arg Val Asn Met Tyr Asp Thr
545                 550                 555                 560

Val Asn Gln Ser Lys Thr Pro Phe Ile Thr His Val Ala Pro Ser Thr
                565                 570                 575

Ser Thr Asn Leu Thr Met Thr Phe Asn Asn Gln Leu Thr Thr Val His
            580                 585                 590

Asn Gln Ala Pro Ser Ser Thr Ser Ala Thr Ile Ser Leu Ala Asn Pro
        595                 600                 605

Glu Val Ser Ile Leu Asn Tyr Pro Ser Thr Leu Tyr Gln Pro Ser Ala
```

```
    610                 615                 620

Ala Ser Met Ala Ala Val Ala Gln Arg Ser Met Pro Leu Gln Thr Gly
625                 630                 635                 640

Thr Ala Gln Ile Cys Ala Arg Pro Asp Pro Phe Gln Gln Ala Leu Ile
                645                 650                 655

Val Cys Pro Pro Gly Phe Gln Gly Leu Gln Ala Ser Pro Ser Lys His
            660                 665                 670

Ala Gly Tyr Ser Val Arg Met Glu Asn Ala Val Pro Ile Val Thr Gln
        675                 680                 685

Ala Pro Gly Ala Gln Pro Leu Gln Ile Gln Pro Gly Leu Leu Ala Gln
    690                 695                 700

Gln Ala Trp Pro Ser Gly Thr Gln Gln Ile Leu Leu Pro Pro Ala Trp
705                 710                 715                 720

Gln Gln Leu Thr Gly Val Ala Thr His Thr Ser Val Gln His Ala Thr
                725                 730                 735

Val Ile Pro Glu Thr Met Ala Gly Thr Gln Gln Leu Ala Asp Trp Arg
            740                 745                 750

Asn Thr His Ala His Gly Ser His Tyr Asn Pro Ile Met Gln Gln Pro
        755                 760                 765

Ala Leu Leu Thr Gly His Val Thr Leu Pro Ala Ala Gln Pro Leu Asn
    770                 775                 780

Val Gly Val Ala His Val Met Arg Gln Gln Pro Thr Ser Thr Thr Ser
785                 790                 795                 800

Ser Arg Lys Ser Lys Gln His Gln Ser Ser Val Arg Asn Val Ser Thr
                805                 810                 815

Cys Glu Val Ser Ser Ser Gln Ala Ile Ser Ser Pro Gln Arg Ser Lys
            820                 825                 830

Arg Val Lys Glu Asn Thr Pro Pro Arg Cys Ala Met Val His Ser Ser
        835                 840                 845

Pro Ala Cys Ser Thr Ser Val Thr Cys Gly Trp Gly Asp Val Ala Ser
    850                 855                 860

Ser Thr Thr Arg Glu Arg Gln Arg Gln Thr Ile Val Ile Pro Asp Thr
865                 870                 875                 880

Pro Ser Pro Thr Val Ser Val Ile Thr Ile Ser Ser Asp Thr Asp Glu
                885                 890                 895

Glu Glu Glu Gln Lys His Ala Pro Thr Ser Thr Val Ser Lys Gln Arg
            900                 905                 910

Lys Asn Val Ile Ser Cys Val Thr Val His Asp Ser Pro Tyr Ser Asp
        915                 920                 925

Ser Ser Ser Asn Thr Ser Pro Tyr Ser Val Gln Gln Arg Ala Gly His
    930                 935                 940

Asn Asn Ala Asn Ala Phe Asp Thr Lys Gly Ser Leu Glu Asn His Cys
945                 950                 955                 960

Thr Gly Asn Pro Arg Thr Ile Ile Val Pro Pro Leu Lys Thr Gln Ala
                965                 970                 975

Ser Glu Val Leu Val Glu Cys Asp Ser Leu Val Pro Val Asn Thr Ser
            980                 985                 990

His His Ser Ser Ser Tyr Lys Ser Lys Ser Ser Ser Asn Val Thr Ser
        995                 1000                1005

Thr Ser Gly His Ser Ser Gly Ser Ser Ser Gly Ala Ile Thr Tyr Arg
   1010                 1015                1020

Gln Gln Arg Pro Gly Pro His Phe Gln Gln Gln Gln Pro Leu Asn Leu
1025                1030                1035                1040
```

```
Ser Gln Ala Gln Gln His Ile Thr Thr Asp Arg Thr Gly Ser His Arg
                1045                1050                1055

Arg Gln Gln Ala Tyr Ile Thr Pro Thr Met Ala Gln Ala Pro Tyr Ser
            1060                1065                1070

Phe Pro His Asn Ser Pro Ser His Gly Thr Val His Pro His Leu Ala
        1075                1080                1085

Ala Ala Ala Ala Ala Ala His Leu Pro Thr Gln Pro His Leu Tyr Thr
    1090                1095                1100

Tyr Thr Ala Pro Ala Ala Leu Gly Ser Thr Gly Thr Val Ala His Leu
1105                1110                1115                1120

Val Ala Ser Gln Gly Ser Ala Arg His Thr Val Gln His Thr Ala Tyr
                1125                1130                1135

Pro Ala Ser Ile Val His Gln Val Pro Val Ser Met Gly Pro Arg Val
            1140                1145                1150

Leu Pro Ser Pro Thr Ile His Pro Ser Gln Tyr Pro Ala Gln Phe Ala
        1155                1160                1165

His Gln Thr Tyr Ile Ser Ala Ser Pro Ala Ser Thr Val Tyr Thr Gly
    1170                1175                1180

Tyr Pro Leu Ser Pro Ala Lys Val Asn Gln Tyr Pro Tyr Ile
1185                1190                1195


<210> SEQ ID NO 90
<211> LENGTH: 1022
<212> TYPE: PRT
<213> ORGANISM: Homo sapiens

<400> SEQUENCE: 90

Met Arg Val Gln Leu Leu Gln Asp Leu Gln Asp Phe Phe Arg Lys Lys
1               5                   10                  15

Ala Glu Ile Glu Thr Glu Tyr Ser Arg Asn Leu Glu Lys Leu Ala Glu
            20                  25                  30

Arg Phe Met Ala Lys Thr Arg Ser Thr Lys Asp His Gln Gln Tyr Lys
        35                  40                  45

Lys Asp Gln Asn Leu Leu Ser Pro Val Asn Cys Trp Tyr Leu Leu Leu
    50                  55                  60

Asn Gln Val Arg Arg Glu Ser Lys Asp His Ala Thr Leu Ser Asp Ile
65                  70                  75                  80

Tyr Leu Asn Asn Val Ile Met Arg Phe Met Gln Ile Ser Glu Asp Ser
                85                  90                  95

Thr Arg Met Phe Lys Lys Ser Lys Glu Ile Ala Phe Gln Leu His Glu
            100                 105                 110

Asp Leu Met Lys Val Leu Asn Glu Leu Tyr Thr Val Met Lys Thr Tyr
        115                 120                 125

His Met Tyr His Ala Glu Ser Ile Ser Ala Glu Ser Lys Leu Lys Glu
    130                 135                 140

Ala Glu Lys Gln Glu Glu Lys Gln Ile Gly Arg Ser Gly Asp Pro Val
145                 150                 155                 160

Phe His Ile Arg Leu Glu Glu Arg His Gln Arg Arg Ser Ser Val Lys
                165                 170                 175

Lys Ile Glu Lys Met Lys Glu Lys Arg Gln Ala Lys Tyr Ser Glu Asn
            180                 185                 190

Lys Leu Lys Ser Ile Lys Ala Arg Asn Glu Tyr Leu Leu Thr Leu Glu
        195                 200                 205

Ala Thr Asn Ala Ser Val Phe Lys Tyr Tyr Ile His Asp Leu Ser Asp
```

-continued

```
    210                 215                 220

Leu Ile Asp Cys Cys Asp Leu Gly Tyr His Ala Ser Leu Asn Arg Ala
225                 230                 235                 240

Leu Arg Thr Tyr Leu Ser Ala Glu Tyr Asn Leu Glu Thr Ser Arg His
                245                 250                 255

Glu Gly Leu Asp Ile Ile Glu Asn Ala Val Asp Asn Leu Glu Pro Arg
            260                 265                 270

Ser Asp Lys Gln Arg Phe Met Glu Met Tyr Pro Ala Ala Phe Cys Pro
        275                 280                 285

Pro Met Lys Phe Glu Phe Gln Ser His Met Gly Asp Glu Val Cys Gln
    290                 295                 300

Val Ser Ala Gln Gln Pro Val Gln Ala Glu Leu Met Leu Arg Tyr Gln
305                 310                 315                 320

Gln Leu Gln Ser Arg Leu Ala Thr Leu Lys Ile Glu Asn Glu Glu Val
                325                 330                 335

Lys Lys Thr Thr Glu Ala Thr Leu Gln Thr Ile Gln Asp Met Val Thr
            340                 345                 350

Ile Glu Asp Tyr Asp Val Ser Glu Cys Phe Gln His Ser Arg Ser Thr
        355                 360                 365

Glu Ser Val Lys Ser Thr Val Ser Glu Thr Tyr Leu Ser Lys Pro Ser
    370                 375                 380

Ile Ala Lys Arg Arg Ala Asn Gln Gln Glu Thr Glu Gln Phe Tyr Phe
385                 390                 395                 400

Met Lys Leu Arg Glu Tyr Leu Glu Gly Ser Asn Leu Ile Thr Lys Leu
                405                 410                 415

Gln Ala Lys His Asp Leu Leu Gln Arg Thr Leu Gly Glu Gly His Arg
            420                 425                 430

Ala Glu Tyr Met Thr Thr Ser Arg Gly Arg Arg Asn Ser His Thr Arg
        435                 440                 445

His Gln Asp Ser Gly Gln Val Ile Pro Leu Ile Val Glu Ser Cys Ile
    450                 455                 460

Arg Phe Ile Asn Leu Tyr Gly Leu Gln His Gln Gly Ile Phe Arg Val
465                 470                 475                 480

Ser Gly Ser Gln Val Glu Val Asn Asp Ile Lys Asn Ser Phe Glu Arg
                485                 490                 495

Gly Glu Asn Pro Leu Ala Asp Asp Gln Ser Asn His Asp Ile Asn Ser
            500                 505                 510

Val Ala Gly Val Leu Lys Leu Tyr Phe Arg Gly Leu Glu Asn Pro Leu
        515                 520                 525

Phe Pro Lys Glu Arg Phe Asn Asp Leu Ile Ser Cys Ile Arg Ile Asp
    530                 535                 540

Asn Leu Tyr Glu Arg Ala Leu His Ile Arg Lys Leu Leu Leu Thr Leu
545                 550                 555                 560

Pro Arg Ser Val Leu Ile Val Met Arg Tyr Leu Phe Ala Phe Leu Asn
                565                 570                 575

His Leu Ser Gln Tyr Ser Asp Glu Asn Met Met Asp Pro Tyr Asn Leu
            580                 585                 590

Ala Ile Cys Phe Gly Pro Thr Leu Met Pro Val Pro Glu Ile Gln Asp
        595                 600                 605

Gln Val Ser Cys Gln Ala His Val Asn Glu Ile Ile Lys Thr Ile Ile
    610                 615                 620

Ile His His Glu Thr Ile Phe Pro Asp Ala Lys Glu Leu Asp Gly Pro
625                 630                 635                 640
```

```
Val Tyr Glu Lys Cys Met Ala Gly Asp Asp Tyr Cys Asp Ser Pro Tyr
                645                 650                 655

Ser Glu His Gly Thr Leu Glu Glu Val Asp Gln Asp Ala Gly Thr Glu
            660                 665                 670

Pro His Thr Ser Glu Asp Glu Cys Glu Pro Ile Glu Ala Ile Ala Lys
        675                 680                 685

Phe Asp Tyr Val Gly Arg Ser Ala Arg Glu Leu Ser Phe Lys Lys Gly
    690                 695                 700

Ala Ser Leu Leu Leu Tyr His Arg Ala Ser Glu Asp Trp Trp Glu Gly
705                 710                 715                 720

Arg His Asn Gly Ile Asp Gly Leu Val Pro His Gln Tyr Ile Val Val
                725                 730                 735

Gln Asp Met Asp Asp Thr Phe Ser Asp Thr Leu Ser Gln Lys Ala Asp
            740                 745                 750

Ser Glu Ala Ser Ser Gly Pro Val Thr Glu Asp Lys Ser Ser Ser Lys
        755                 760                 765

Asp Met Asn Ser Pro Thr Asp Arg His Pro Asp Gly Tyr Leu Ala Arg
    770                 775                 780

Gln Arg Lys Arg Gly Glu Pro Pro Pro Pro Val Arg Arg Pro Gly Arg
785                 790                 795                 800

Thr Ser Asp Gly His Cys Pro Leu His Pro Pro His Ala Leu Ser Asn
                805                 810                 815

Ser Ser Val Asp Leu Gly Ser Pro Ser Leu Ala Ser His Pro Arg Gly
            820                 825                 830

Leu Leu Gln Asn Arg Gly Leu Asn Asn Asp Ser Pro Glu Arg Arg Arg
        835                 840                 845

Arg Pro Gly His Gly Ser Leu Thr Asn Ile Ser Arg His Asp Ser Leu
    850                 855                 860

Lys Lys Ile Asp Ser Pro Pro Ile Arg Arg Ser Thr Ser Ser Gly Gln
865                 870                 875                 880

Tyr Thr Gly Phe Asn Asp His Lys Pro Leu Asp Pro Glu Thr Ile Ala
                885                 890                 895

Gln Asp Ile Glu Glu Thr Met Asn Thr Ala Leu Asn Glu Leu Arg Glu
            900                 905                 910

Leu Glu Arg Gln Ser Thr Ala Lys His Ala Pro Asp Val Val Leu Asp
        915                 920                 925

Thr Leu Glu Gln Val Lys Asn Ser Pro Thr Pro Ala Thr Ser Thr Glu
    930                 935                 940

Ser Leu Ser Pro Leu His Asn Val Ala Leu Arg Ser Ser Glu Pro Gln
945                 950                 955                 960

Ile Arg Arg Ser Thr Ser Ser Ser Ser Asp Thr Met Ser Thr Phe Lys
                965                 970                 975

Pro Met Val Ala Pro Arg Met Gly Val Gln Leu Lys Pro Pro Ala Leu
            980                 985                 990

Arg Pro Lys Pro Ala Val Leu Pro Lys Thr Asn Pro Thr Ile Gly Pro
        995                 1000                1005

Ala Pro Pro Pro Gln Gly Pro Thr Asp Lys Ser Cys Thr Met
   1010                1015                1020
```

<210> SEQ ID NO 91
<211> LENGTH: 581
<212> TYPE: PRT
<213> ORGANISM: Homo sapiens -continued

<400> SEQUENCE: 91

```
Met Ala Ala Ser Gly Arg Gly Leu Cys Lys Ala Val Ala Ala Ser Pro
1               5                   10                  15

Phe Pro Ala Trp Arg Arg Asp Asn Thr Glu Ala Arg Gly Gly Leu Lys
            20                  25                  30

Pro Glu Tyr Asp Ala Val Val Ile Gly Ala Gly His Asn Gly Leu Val
        35                  40                  45

Ala Ala Ala Tyr Leu Gln Arg Leu Gly Val Asn Thr Ala Val Phe Glu
    50                  55                  60

Arg Arg His Val Ile Gly Gly Ala Ala Val Thr Glu Glu Ile Ile Pro
65                  70                  75                  80

Gly Phe Lys Phe Ser Arg Ala Ser Tyr Leu Leu Ser Leu Leu Arg Pro
                85                  90                  95

Gln Ile Tyr Thr Asp Leu Glu Leu Lys Lys His Gly Leu Arg Leu His
            100                 105                 110

Leu Arg Asn Pro Tyr Ser Phe Thr Pro Met Leu Glu Glu Gly Ala Gly
        115                 120                 125

Ser Lys Val Pro Arg Cys Leu Leu Leu Gly Thr Asp Met Ala Glu Asn
    130                 135                 140

Gln Lys Gln Ile Ala Gln Phe Ser Gln Lys Asp Ala Gln Val Phe Pro
145                 150                 155                 160

Lys Tyr Glu Glu Phe Met His Arg Leu Ala Leu Ala Ile Asp Pro Leu
                165                 170                 175

Leu Asp Ala Ala Pro Val Asp Met Ala Ala Phe Gln His Gly Ser Leu
            180                 185                 190

Leu Gln Arg Met Arg Ser Leu Ser Thr Leu Lys Pro Leu Leu Lys Ala
        195                 200                 205

Gly Arg Ile Leu Gly Ala Gln Leu Pro Arg Tyr Tyr Glu Val Leu Thr
    210                 215                 220

Ala Pro Ile Thr Lys Val Leu Asp Gln Trp Phe Glu Ser Glu Pro Leu
225                 230                 235                 240

Lys Ala Thr Leu Ala Thr Asp Ala Val Ile Gly Ala Met Thr Ser Pro
                245                 250                 255

His Thr Pro Gly Ser Gly Tyr Val Leu Leu His His Val Met Gly Gly
            260                 265                 270

Leu Glu Gly Met Gln Gly Ala Trp Gly Tyr Val Gln Gly Gly Met Gly
        275                 280                 285

Ala Leu Ser Asp Ala Ile Ala Ser Ser Ala Thr Thr His Gly Ala Ser
    290                 295                 300

Ile Phe Thr Glu Lys Thr Val Ala Lys Val Gln Val Asn Ser Glu Gly
305                 310                 315                 320

Cys Val Gln Gly Val Val Leu Glu Asp Gly Thr Glu Val Arg Ser Lys
                325                 330                 335

Met Val Leu Ser Asn Thr Ser Pro Gln Ile Thr Phe Leu Lys Leu Thr
            340                 345                 350

Pro Gln Glu Trp Leu Pro Glu Glu Phe Leu Glu Arg Ile Ser Gln Leu
        355                 360                 365

Asp Thr Arg Ser Pro Val Thr Lys Ile Asn Val Ala Val Asp Arg Leu
    370                 375                 380

Pro Ser Phe Leu Ala Ala Pro Asn Ala Pro Arg Gly Gln Pro Leu Pro
385                 390                 395                 400

His His Gln Cys Ser Ile His Leu Asn Cys Glu Asp Thr Leu Leu Leu
                405                 410                 415
```

His Gln Ala Phe Glu Asp Ala Met Asp Gly Leu Ser Ser His Arg Pro
420 425 430

Val Ile Glu Leu Cys Ile Pro Ser Ser Leu Asp Pro Thr Leu Ala Pro
435 440 445

Pro Gly Cys His Val Val Ser Leu Phe Thr Gln Tyr Thr Pro Tyr Thr
450 455 460

Leu Ala Gly Gly Lys Ala Trp Asp Glu Gln Glu Arg Asp Ala Tyr Ala
465 470 475 480

Asp Arg Val Phe Asp Cys Ile Glu Val Tyr Ala Pro Gly Phe Lys Asp
485 490 495

Ser Val Val Gly Arg Asp Ile Leu Thr Pro Pro Asp Leu Glu Arg Ile
500 505 510

Phe Gly Leu Pro Gly Gly Asn Ile Phe His Cys Ala Met Ser Leu Asp
515 520 525

Gln Leu Tyr Phe Ala Arg Pro Val Pro Leu His Ser Gly Tyr Arg Cys
530 535 540

Pro Leu Gln Gly Leu Tyr Leu Cys Gly Ser Gly Ala His Pro Gly Gly
545 550 555 560

Gly Val Met Gly Ala Ala Gly Arg Asn Ala Ala His Val Ala Phe Arg
565 570 575

Asp Leu Lys Ser Met
580

<210> SEQ ID NO 92
<211> LENGTH: 498
<212> TYPE: PRT
<213> ORGANISM: Homo sapiens

<400> SEQUENCE: 92

Met Pro Leu Val Thr Arg Asn Ile Glu Pro Arg His Leu Cys Arg Gln
1 5 10 15

Thr Leu Pro Ser Val Arg Ser Glu Leu Glu Cys Val Thr Asn Ile Thr
20 25 30

Leu Ala Asn Val Ile Arg Gln Leu Gly Ser Leu Ser Lys Tyr Ala Glu
35 40 45

Asp Ile Phe Gly Glu Leu Phe Thr Gln Ala Asn Thr Phe Ala Ser Arg
50 55 60

Val Ser Ser Leu Ala Glu Arg Val Asp Arg Leu Gln Val Lys Val Thr
65 70 75 80

Gln Leu Asp Pro Lys Glu Glu Glu Val Ser Leu Gln Gly Ile Asn Thr
85 90 95

Arg Lys Ala Phe Arg Ser Ser Thr Ile Gln Asp Gln Lys Leu Phe Asp
100 105 110

Arg Asn Ser Leu Pro Val Pro Val Leu Glu Thr Tyr Asn Thr Cys Asp
115 120 125

Thr Pro Pro Pro Leu Asn Asn Leu Thr Pro Tyr Arg Asp Asp Gly Lys
130 135 140

Glu Ala Leu Lys Phe Tyr Thr Asp Pro Ser Tyr Phe Phe Asp Leu Trp
145 150 155 160

Lys Glu Lys Met Leu Gln Asp Thr Lys Asp Ile Met Lys Glu Lys Arg
165 170 175

Lys His Arg Lys Glu Lys Lys Asp Asn Pro Asn Arg Gly Asn Val Asn
180 185 190

Pro Arg Lys Ile Lys Thr Arg Lys Glu Glu Trp Glu Lys Met Lys Met

```
        195                 200                 205

Gly Gln Glu Phe Val Glu Ser Lys Glu Lys Leu Gly Thr Ser Gly Tyr
    210                 215                 220

Pro Pro Thr Leu Val Tyr Gln Asn Gly Ser Ile Gly Cys Val Glu Asn
225                 230                 235                 240

Val Asp Ala Ser Ser Tyr Pro Pro Pro Pro Gln Ser Asp Ser Ala Ser
                245                 250                 255

Ser Pro Ser Pro Ser Phe Ser Glu Asp Asn Leu Pro Pro Pro Pro Ala
            260                 265                 270

Glu Phe Ser Tyr Pro Val Asp Asn Gln Arg Gly Ser Gly Leu Ala Gly
        275                 280                 285

Pro Lys Arg Ser Ser Val Val Ser Pro Ser His Pro Pro Pro Ala Pro
    290                 295                 300

Pro Leu Gly Ser Pro Pro Gly Pro Lys Pro Gly Phe Ala Pro Pro Pro
305                 310                 315                 320

Ala Pro Pro Pro Pro Pro Pro Pro Met Ile Gly Ile Pro Pro Pro Pro
                325                 330                 335

Pro Pro Val Gly Phe Gly Ser Pro Gly Thr Pro Pro Pro Pro Ser Pro
            340                 345                 350

Pro Ser Phe Pro Pro His Pro Asp Phe Ala Ala Pro Pro Pro Pro Pro
        355                 360                 365

Pro Pro Pro Ala Ala Asp Tyr Pro Thr Leu Pro Pro Pro Pro Leu Ser
    370                 375                 380

Gln Pro Thr Gly Gly Ala Pro Pro Pro Pro Pro Pro Pro Pro Pro Pro
385                 390                 395                 400

Gly Pro Pro Pro Pro Pro Phe Thr Gly Ala Asp Gly Gln Pro Ala Ile
                405                 410                 415

Pro Pro Pro Leu Ser Asp Thr Thr Lys Pro Lys Ser Ser Leu Pro Ala
            420                 425                 430

Val Ser Asp Ala Arg Ser Asp Leu Leu Ser Ala Ile Arg Gln Gly Phe
        435                 440                 445

Gln Leu Arg Arg Val Glu Glu Gln Arg Glu Gln Glu Lys Arg Asp Val
    450                 455                 460

Val Gly Asn Asp Val Ala Thr Ile Leu Ser Arg Arg Ile Ala Val Glu
465                 470                 475                 480

Tyr Ser Asp Ser Glu Asp Asp Ser Ser Glu Phe Asp Glu Asp Asp Trp
                485                 490                 495

Ser Asp


<210> SEQ ID NO 93
<211> LENGTH: 1138
<212> TYPE: PRT
<213> ORGANISM: Homo sapiens

<400> SEQUENCE: 93

Met Ala Leu Lys Met Val Lys Gly Ser Ile Asp Arg Met Phe Asp Lys
 1               5                  10                  15

Asn Leu Gln Asp Leu Val Arg Gly Ile Arg Asn His Lys Glu Asp Glu
            20                  25                  30

Ala Lys Tyr Ile Ser Gln Cys Ile Asp Glu Ile Lys Gln Glu Leu Lys
        35                  40                  45

Gln Asp Asn Ile Ala Val Lys Ala Asn Ala Val Cys Lys Leu Thr Tyr
    50                  55                  60

Leu Gln Met Leu Gly Tyr Asp Ile Ser Trp Ala Ala Phe Asn Ile Ile
```

-continued

```
65                  70                  75                  80

Glu Val Met Ser Ala Ser Lys Phe Thr Phe Lys Arg Ile Gly Tyr Leu
                85                  90                  95

Ala Ala Ser Gln Ser Phe His Glu Gly Thr Asp Val Ile Met Leu Thr
            100                 105                 110

Thr Asn Gln Ile Arg Lys Asp Leu Ser Ser Pro Ser Gln Tyr Asp Thr
        115                 120                 125

Gly Val Ala Leu Thr Gly Leu Ser Cys Phe Val Thr Pro Asp Leu Ala
    130                 135                 140

Arg Asp Leu Ala Asn Asp Ile Met Thr Leu Met Ser His Thr Lys Pro
145                 150                 155                 160

Tyr Ile Arg Lys Lys Ala Val Leu Ile Met Tyr Lys Val Phe Leu Lys
                165                 170                 175

Tyr Pro Glu Ser Leu Arg Pro Ala Phe Pro Arg Leu Lys Glu Lys Leu
            180                 185                 190

Glu Asp Pro Asp Pro Gly Val Gln Ser Ala Ala Val Asn Val Ile Cys
        195                 200                 205

Glu Leu Ala Arg Arg Asn Pro Lys Asn Tyr Leu Ser Leu Ala Pro Leu
    210                 215                 220

Phe Phe Lys Leu Met Thr Ser Ser Thr Asn Asn Trp Val Leu Ile Lys
225                 230                 235                 240

Ile Ile Lys Leu Phe Gly Ala Leu Thr Pro Leu Glu Pro Arg Leu Gly
                245                 250                 255

Lys Lys Leu Ile Glu Pro Leu Thr Asn Leu Ile His Ser Thr Ser Ala
            260                 265                 270

Met Ser Leu Leu Tyr Glu Cys Val Asn Thr Val Ile Ala Val Leu Ile
        275                 280                 285

Ser Leu Ser Ser Gly Met Pro Asn His Ser Ala Ser Ile Gln Leu Cys
    290                 295                 300

Val Gln Lys Leu Arg Ile Leu Ile Glu Asp Ser Asp Gln Asn Leu Lys
305                 310                 315                 320

Tyr Leu Gly Leu Leu Ala Met Ser Lys Ile Leu Lys Thr His Pro Lys
                325                 330                 335

Ser Val Gln Ser His Lys Asp Leu Ile Leu Gln Cys Leu Asp Asp Lys
            340                 345                 350

Asp Glu Ser Ile Arg Leu Arg Ala Leu Asp Leu Leu Tyr Gly Met Val
        355                 360                 365

Ser Lys Lys Asn Leu Met Glu Ile Val Lys Lys Leu Met Thr His Val
    370                 375                 380

Asp Lys Ala Glu Gly Thr Thr Tyr Arg Asp Glu Leu Leu Thr Lys Ile
385                 390                 395                 400

Ile Asp Ile Cys Ser Gln Ser Asn Tyr Gln Tyr Ile Thr Asn Phe Glu
                405                 410                 415

Trp Tyr Ile Ser Ile Leu Val Glu Leu Thr Arg Leu Glu Gly Thr Arg
            420                 425                 430

His Gly His Leu Ile Ala Ala Gln Met Leu Asp Val Ala Ile Arg Val
        435                 440                 445

Lys Ala Ile Arg Lys Phe Ala Val Ser Gln Met Ser Ala Leu Leu Asp
    450                 455                 460

Ser Ala His Leu Leu Ala Ser Ser Thr Gln Arg Asn Gly Ile Cys Glu
465                 470                 475                 480

Val Leu Tyr Ala Ala Ala Trp Ile Cys Gly Glu Phe Ser Glu His Leu
                485                 490                 495
```

-continued

```
Gln Glu Pro His His Thr Leu Glu Ala Met Leu Arg Pro Arg Val Thr
            500                 505                 510

Thr Leu Pro Gly His Ile Gln Ala Val Tyr Val Gln Asn Val Val Lys
        515                 520                 525

Leu Tyr Ala Ser Ile Leu Gln Gln Lys Glu Gln Ala Gly Glu Ala Glu
    530                 535                 540

Gly Ala Gln Ala Val Thr Gln Leu Met Val Asp Arg Leu Pro Gln Phe
545                 550                 555                 560

Val Gln Ser Ala Asp Leu Glu Val Gln Glu Arg Ala Ser Cys Ile Leu
                565                 570                 575

Gln Leu Val Lys His Ile Gln Lys Leu Gln Ala Lys Asp Val Pro Val
            580                 585                 590

Ala Glu Glu Val Ser Ala Leu Phe Ala Gly Glu Leu Asn Pro Val Ala
        595                 600                 605

Pro Lys Ala Gln Lys Lys Val Pro Val Pro Glu Gly Leu Asp Leu Asp
    610                 615                 620

Ala Trp Ile Asn Glu Pro Leu Ser Asp Ser Glu Ser Glu Asp Glu Arg
625                 630                 635                 640

Pro Arg Ala Val Phe His Glu Glu Glu Gln Arg Arg Pro Lys His Arg
                645                 650                 655

Pro Ser Glu Ala Asp Glu Glu Glu Leu Ala Arg Arg Arg Glu Ala Arg
            660                 665                 670

Lys Gln Glu Gln Ala Asn Asn Pro Phe Tyr Ile Lys Ser Ser Pro Ser
        675                 680                 685

Pro Gln Lys Arg Tyr Gln Asp Thr Pro Gly Val Glu His Ile Pro Val
    690                 695                 700

Val Gln Ile Asp Leu Ser Val Pro Leu Lys Val Pro Gly Leu Pro Met
705                 710                 715                 720

Ser Asp Gln Tyr Val Lys Leu Glu Glu Glu Arg Arg His Arg Gln Lys
                725                 730                 735

Leu Glu Lys Asp Lys Arg Arg Lys Lys Arg Lys Glu Lys Glu Lys Lys
            740                 745                 750

Gly Lys Arg Arg His Ser Ser Leu Pro Thr Glu Ser Asp Glu Asp Ile
        755                 760                 765

Ala Pro Ala Gln Gln Val Asp Ile Val Thr Glu Glu Met Pro Glu Asn
    770                 775                 780

Ala Leu Pro Ser Asp Glu Asp Asp Lys Asp Pro Asn Asp Pro Tyr Arg
785                 790                 795                 800

Ala Leu Asp Ile Asp Leu Asp Lys Pro Leu Ala Asp Ser Glu Lys Leu
                805                 810                 815

Pro Ile Gln Lys His Arg Asn Thr Glu Thr Ser Lys Ser Pro Glu Lys
            820                 825                 830

Asp Val Pro Met Val Glu Lys Lys Ser Lys Lys Pro Lys Lys Lys Glu
        835                 840                 845

Lys Lys His Lys Glu Lys Glu Arg Asp Lys Glu Lys Lys Lys Glu Lys
    850                 855                 860

Glu Lys Lys Lys Ser Pro Lys Pro Lys Lys Lys Lys His Arg Lys Glu
865                 870                 875                 880

Lys Glu Glu Arg Thr Lys Gly Lys Lys Lys Ser Lys Lys Gln Pro Pro
                885                 890                 895

Gly Ser Glu Glu Ala Ala Gly Glu Pro Val Gln Asn Gly Ala Pro Glu
            900                 905                 910
```

```
Glu Glu Gln Leu Pro Pro Glu Ser Ser Tyr Ser Leu Leu Ala Glu Asn
        915                 920                 925

Ser Tyr Val Lys Met Thr Cys Asp Ile Arg Gly Ser Leu Gln Glu Asp
    930                 935                 940

Ser Gln Val Thr Val Ala Ile Val Leu Glu Asn Arg Ser Ser Ser Ile
945                 950                 955                 960

Leu Lys Gly Met Glu Leu Ser Val Leu Asp Ser Leu Asn Ala Arg Met
                965                 970                 975

Ala Arg Pro Gln Gly Ser Ser Val His Asp Gly Val Pro Val Pro Phe
            980                 985                 990

Gln Leu Pro Pro Gly Val Ser Asn Glu Ala Gln Tyr Val Phe Thr Ile
        995                 1000                1005

Gln Ser Ile Val Met Ala Gln Lys Leu Lys Gly Thr Leu Ser Phe Ile
   1010                 1015                1020

Ala Lys Asn Asp Glu Gly Ala Thr His Glu Lys Leu Asp Phe Arg Leu
1025                1030                1035                1040

His Phe Ser Cys Ser Ser Tyr Leu Ile Thr Thr Pro Cys Tyr Ser Asp
               1045                1050                1055

Ala Phe Ala Lys Leu Leu Glu Ser Gly Asp Leu Ser Met Ser Ser Ile
           1060                1065                1070

Lys Val Asp Gly Ile Arg Met Ser Phe Gln Asn Leu Leu Ala Lys Ile
       1075                1080                1085

Cys Phe His His His Phe Ser Val Val Glu Arg Val Asp Ser Cys Ala
   1090                1095                1100

Ser Met Tyr Ser Arg Ser Ile Gln Gly His His Val Cys Leu Leu Val
1105                1110                1115                1120

Lys Lys Val Arg Thr Leu Ser Gln Ser Thr Gly Ser Ala Val Thr Pro
               1125                1130                1135

Arg Tyr


<210> SEQ ID NO 94
<211> LENGTH: 227
<212> TYPE: PRT
<213> ORGANISM: Homo sapiens

<400> SEQUENCE: 94

Met Phe Glu Pro Val Ser Cys Thr Phe Thr Tyr Leu Leu Gly Asp Gly
 1               5                  10                  15

Glu Ser Arg Glu Ala Val Leu Ile Asp Pro Val Leu Glu Thr Ala Pro
            20                  25                  30

Arg Asp Ala Gln Leu Ile Lys Glu Leu Gly Leu Arg Leu Leu Tyr Ala
        35                  40                  45

Val Asn Thr His Cys His Ala Asp His Ile Thr Gly Ser Gly Leu Leu
    50                  55                  60

Arg Ser Leu Leu Pro Gly Cys Gln Ser Val Ile Ser Arg Leu Ser Gly
65                  70                  75                  80

Ala Gln Ala Asp Leu His Ile Glu Asp Gly Asp Ser Ile Arg Phe Gly
                85                  90                  95

Arg Phe Ala Leu Glu Thr Arg Ala Ser Pro Gly His Thr Pro Gly Cys
            100                 105                 110

Val Thr Phe Val Leu Asn Asp His Ser Met Ala Phe Thr Gly Asp Ala
        115                 120                 125

Leu Leu Ile Arg Gly Cys Gly Arg Thr Asp Phe Gln Gln Gly Cys Ala
    130                 135                 140
```

```
Lys Thr Leu Tyr His Ser Val His Glu Lys Ile Phe Thr Leu Pro Gly
145                 150                 155                 160

Asp Cys Leu Ile Tyr Pro Ala His Asp Tyr His Gly Phe Thr Val Ser
                165                 170                 175

Thr Val Glu Glu Glu Arg Thr Leu Asn Pro Arg Leu Thr Leu Ser Cys
            180                 185                 190

Glu Glu Phe Val Lys Ile Met Gly Asn Leu Asn Leu Pro Lys Pro Gln
        195                 200                 205

Gln Ile Asp Phe Ala Val Pro Ala Asn Met Arg Cys Gly Val Gln Thr
    210                 215                 220

Pro Thr Ala
225


<210> SEQ ID NO 95
<211> LENGTH: 640
<212> TYPE: PRT
<213> ORGANISM: Homo sapiens

<400> SEQUENCE: 95

Met His Val Lys Lys Tyr Leu Leu Lys Gly Leu His Arg Leu Gln Lys
 1               5                  10                  15

Gly Pro Gly Tyr Thr Tyr Lys Glu Leu Leu Val Trp Tyr Cys Asp Asn
            20                  25                  30

Thr Asn Thr His Gly Pro Lys Arg Ile Ile Cys Glu Gly Pro Lys Lys
        35                  40                  45

Lys Ala Met Trp Phe Leu Leu Thr Leu Leu Phe Ala Ala Leu Val Cys
    50                  55                  60

Trp Gln Trp Gly Ile Phe Ile Arg Thr Tyr Leu Ser Trp Glu Val Ser
65                  70                  75                  80

Val Ser Leu Ser Val Gly Phe Lys Thr Met Asp Phe Pro Ala Val Thr
                85                  90                  95

Ile Cys Asn Ala Ser Pro Phe Lys Tyr Ser Lys Ile Lys His Leu Leu
            100                 105                 110

Lys Asp Leu Asp Glu Leu Met Glu Ala Val Leu Glu Arg Ile Leu Ala
        115                 120                 125

Pro Glu Leu Ser His Ala Asn Ala Thr Arg Asn Leu Asn Phe Ser Ile
    130                 135                 140

Trp Asn His Thr Pro Leu Val Leu Ile Asp Glu Arg Asn Pro His His
145                 150                 155                 160

Pro Met Val Leu Asp Leu Phe Gly Asp Asn His Asn Gly Leu Thr Ser
                165                 170                 175

Ser Ser Ala Ser Glu Lys Ile Cys Asn Ala His Gly Cys Lys Met Ala
            180                 185                 190

Met Arg Leu Cys Ser Leu Asn Arg Thr Gln Cys Thr Phe Arg Asn Phe
        195                 200                 205

Thr Ser Ala Thr Gln Ala Leu Thr Glu Trp Tyr Ile Leu Gln Ala Thr
    210                 215                 220

Asn Ile Phe Ala Gln Val Pro Gln Gln Glu Leu Val Glu Met Ser Tyr
225                 230                 235                 240

Pro Gly Glu Gln Met Ile Leu Ala Cys Leu Phe Gly Ala Glu Pro Cys
                245                 250                 255

Asn Tyr Arg Asn Phe Thr Ser Ile Phe Tyr Pro His Tyr Gly Asn Cys
            260                 265                 270

Tyr Ile Phe Asn Trp Gly Met Thr Glu Lys Ala Leu Pro Ser Ala Asn
        275                 280                 285
```

Pro Gly Thr Glu Phe Gly Leu Lys Leu Ile Leu Asp Ile Gly Gln Glu
    290                 295                 300

Asp Tyr Val Pro Phe Leu Ala Ser Thr Gly Gly Val Arg Leu Met Leu
305                 310                 315                 320

His Glu Gln Arg Ser Tyr Pro Phe Ile Arg Asp Glu Gly Ile Tyr Ala
                325                 330                 335

Met Ser Gly Thr Glu Thr Ser Ile Gly Val Leu Val Asp Lys Leu Gln
            340                 345                 350

Arg Met Gly Glu Pro Tyr Ser Pro Cys Thr Val Asn Gly Ser Glu Val
        355                 360                 365

Pro Val Gln Asn Phe Tyr Ser Asp Tyr Asn Thr Thr Tyr Ser Ile Gln
    370                 375                 380

Ala Cys Leu Arg Ser Cys Phe Gln Asp His Met Ile Arg Asn Cys Asn
385                 390                 395                 400

Cys Gly His Tyr Leu Tyr Pro Leu Pro Arg Gly Glu Lys Tyr Cys Asn
                405                 410                 415

Asn Arg Asp Phe Pro Asp Trp Ala His Cys Tyr Ser Asp Leu Gln Met
            420                 425                 430

Ser Val Ala Gln Arg Glu Thr Cys Ile Gly Met Cys Lys Glu Ser Cys
        435                 440                 445

Asn Asp Thr Gln Tyr Lys Met Thr Ile Ser Met Ala Asp Trp Pro Ser
    450                 455                 460

Glu Ala Ser Glu Asp Trp Ile Phe His Val Leu Ser Gln Glu Arg Asp
465                 470                 475                 480

Gln Ser Thr Asn Ile Thr Leu Ser Arg Lys Gly Ile Val Lys Leu Asn
                485                 490                 495

Ile Tyr Phe Gln Glu Phe Asn Tyr Arg Thr Ile Glu Glu Ser Ala Ala
            500                 505                 510

Asn Asn Ile Val Trp Leu Leu Ser Asn Leu Gly Gly Gln Phe Gly Phe
        515                 520                 525

Trp Met Gly Gly Ser Val Leu Cys Leu Ile Glu Phe Gly Glu Ile Ile
    530                 535                 540

Ile Asp Phe Val Trp Ile Thr Ile Ile Lys Leu Val Ala Leu Ala Lys
545                 550                 555                 560

Ser Leu Arg Gln Arg Arg Ala Gln Ala Ser Tyr Ala Gly Pro Pro Pro
                565                 570                 575

Thr Val Ala Glu Leu Val Glu Ala His Thr Asn Phe Gly Phe Gln Pro
            580                 585                 590

Asp Thr Ala Pro Arg Ser Pro Asn Thr Gly Pro Tyr Pro Ser Glu Gln
        595                 600                 605

Ala Leu Pro Ile Pro Gly Thr Pro Pro Pro Asn Tyr Asp Ser Leu Arg
    610                 615                 620

Leu Gln Pro Leu Asp Val Ile Glu Ser Asp Ser Glu Gly Asp Ala Ile
625                 630                 635                 640

<210> SEQ ID NO 96
<211> LENGTH: 1498
<212> TYPE: PRT
<213> ORGANISM: Homo sapiens

<400> SEQUENCE: 96

Val Lys Asp Leu Gly Ser Leu Asn Gly Thr Phe Val Asn Asp Met Arg
 1               5                  10                  15

Ile Pro Asp Gln Lys Tyr Val Thr Leu Lys Leu Asn Asp Val Ile Arg

-continued

```
            20                  25                  30

Phe Gly Tyr Asp Ser Asn Met Tyr Val Leu Glu Arg Val Gln His Arg
        35                  40                  45

Val Pro Glu Glu Ala Leu Lys His Glu Lys Tyr Thr Ser Gln Leu Gln
    50                  55                  60

Val Ser Val Lys Gly Leu Ala Pro Lys Arg Ser Glu Ala Leu Pro Glu
65                  70                  75                  80

His Thr Pro Tyr Cys Glu Ala Ser Asn Pro Arg Pro Glu Lys Gly Asp
                85                  90                  95

Arg Arg Pro Gly Thr Glu Ala Ala Ser Tyr Arg Thr Pro Leu Tyr Gly
            100                 105                 110

Gln Pro Ser Trp Trp Gly Glu Asp Asp Gly Ser Thr Leu Pro Asp Ala
        115                 120                 125

Gln Arg Gln Gly Glu Pro Tyr Pro Glu Arg Pro Lys Gly Pro Val Gln
    130                 135                 140

Gln Asp Gly Glu Leu His Gly Phe Arg Ala Pro Ala Glu Pro Gln Gly
145                 150                 155                 160

Cys Ser Phe Arg Arg Glu Pro Ser Tyr Phe Glu Ile Pro Thr Lys Glu
                165                 170                 175

Thr Pro Gln Pro Ser Gln Pro Pro Glu Val Pro Ala His Glu Met Pro
            180                 185                 190

Thr Lys Asp Ala Glu Ala Gly Gly Gly Gly Ala Ala Pro Val Val Gln
        195                 200                 205

Ser His Ala Ser Phe Thr Ile Glu Phe Asp Asp Cys Ser Pro Gly Lys
    210                 215                 220

Met Lys Ile Lys Asp His Ile Thr Lys Phe Ser Leu Arg Gln Arg Arg
225                 230                 235                 240

Pro Pro Gly Lys Glu Ala Thr Pro Gly Glu Met Val Ser Ala Glu Thr
                245                 250                 255

Lys Val Ala Asp Trp Leu Val Gln Asn Asp Pro Ser Leu Leu His Arg
            260                 265                 270

Val Gly Pro Gly Asp Asp Arg His Ser Thr Lys Ser Asp Leu Pro Val
        275                 280                 285

His Thr Arg Thr Leu Lys Gly His Lys His Glu Asp Gly Thr Gln Ser
    290                 295                 300

Asp Ser Glu Asp Pro Leu Ala Lys Ala Ala Ser Ala Ala Gly Val Pro
305                 310                 315                 320

Leu Glu Ala Ser Gly Gly Gln Val Arg Leu Gln Arg Gln Ile Lys Arg
                325                 330                 335

Asp Pro Gln Glu Leu Leu His Asn Gln Gln Ala Phe Val Ile Glu Phe
            340                 345                 350

Phe Asp Glu Asp Thr Pro Arg Lys Lys Arg Ser Gln Ser Phe Thr His
        355                 360                 365

Ser Pro Ser Gly Asp Pro Lys Ala Asp Lys Arg Arg Gly Pro Thr Pro
    370                 375                 380

Ala Asp Arg Asp Arg Pro Ser Val Pro Ala Pro Val Gln Ala Gly Gly
385                 390                 395                 400

Arg Ser Ser Gly Pro Gln Arg Ala Gly Ser Leu Lys Arg Glu Lys Thr
                405                 410                 415

Glu Glu Arg Leu Gly Ser Pro Ser Pro Ala Ser Arg Thr Pro Ala Arg
            420                 425                 430

Pro Phe Gly Ser Val Gly Arg Arg Ser Arg Leu Ala Gln Asp Phe Met
        435                 440                 445
```

```
Ala Gln Cys Leu Arg Glu Ser Ser Pro Ala Ala Arg Pro Ser Pro Glu
    450                 455                 460

Lys Val Pro Pro Val Leu Pro Ala Pro Leu Thr Pro His Gly Thr Ser
465                 470                 475                 480

Pro Val Gly Pro Pro Thr Pro Pro Pro Ala Pro Thr Asp Pro Gln Leu
                485                 490                 495

Thr Lys Ala Arg Lys Gln Glu Glu Asp Asp Ser Leu Ser Asp Ala Gly
            500                 505                 510

Thr Tyr Thr Ile Glu Thr Glu Ala Gln Asp Thr Glu Val Glu Glu Ala
        515                 520                 525

Arg Lys Met Ile Asp Gln Val Phe Gly Val Leu Glu Ser Pro Glu Leu
    530                 535                 540

Ser Arg Ala Ser Ser Ala Thr Phe Arg Pro Val Ile Arg Gly Asp Arg
545                 550                 555                 560

Asp Glu Ser Asp Asp Gly Gly Val Ala Gln Arg Met Ala Leu Leu Gln
                565                 570                 575

Glu Phe Ala Ser Arg Pro Leu Gly Ala Ala Pro Gln Ala Glu His Gln
            580                 585                 590

Gly Leu Pro Val Pro Gly Ser Pro Gly Gly Gln Lys Trp Val Ser Arg
        595                 600                 605

Trp Ala Ser Leu Ala Asp Ser Tyr Ser Asp Pro Gly Leu Thr Glu Asp
    610                 615                 620

Gly Leu Gly Arg Arg Gly Gly Glu Pro Glu Gly Ser Leu Pro Val Arg
625                 630                 635                 640

Met Arg Arg Arg Leu Pro Gln Leu Pro Ser Glu Arg Ala Asp Ser Pro
                645                 650                 655

Ala Gly Pro Glu Ser Ser Arg Arg Ser Gly Pro Gly Pro Pro Glu Leu
            660                 665                 670

Asp Ser Glu Gln Pro Ser Arg Leu Phe Gly Gln Glu Glu Leu Asp Pro
        675                 680                 685

Asp Ser Leu Ser Asp Ala Ser Gly Ser Asp Gly Gly Arg Gly Pro Glu
    690                 695                 700

Pro Gly Val Glu Pro Gln Asp Ser Arg Arg Arg Ser Pro Gln Glu Gly
705                 710                 715                 720

Pro Thr Trp Ser Arg Gly Arg Arg Ser Pro Arg Ala Pro Gly Glu Pro
                725                 730                 735

Thr Pro Ala Ser Phe Phe Ile Gly Asp Gln Asn Gly Asp Ala Val Leu
            740                 745                 750

Ser Arg Lys Leu Leu Ala Ala Pro Gly Asp Gly Glu Gly Leu Gly Gln
        755                 760                 765

Thr Ala Gln Pro Ser Pro Pro Ala Arg Asp Gly Val Tyr Val Ser Ala
    770                 775                 780

Asn Gly Arg Met Val Ile Gln Leu Arg Pro Gly Arg Ser Pro Glu Pro
785                 790                 795                 800

Asp Gly Pro Ala Pro Ala Phe Leu Arg Gln Glu Ser Phe Thr Lys Glu
                805                 810                 815

Pro Ala Ser Gly Pro Pro Ala Pro Gly Lys Pro Pro His Ile Ser Ser
            820                 825                 830

His Pro Leu Leu Gln Asp Leu Ala Ala Thr Arg Ala Ala Arg Met Asp
        835                 840                 845

Phe His Ser Gln Asp Thr His Leu Ile Leu Lys Glu Thr Glu Thr Ala
    850                 855                 860
```

```
Leu Ala Ala Leu Glu Ala Arg Leu Leu Ser Asn Ser Val Asp Ala Glu
865                 870                 875                 880

Cys Glu Gly Gly Ser Thr Pro Arg Pro Pro Glu Asp Ala Leu Ser Gly
                885                 890                 895

Asp Ser Asp Val Asp Thr Ala Ser Thr Val Ser Leu Arg Ser Gly Lys
            900                 905                 910

Ser Gly Pro Ser Pro Thr Thr Pro Gln Pro Leu Arg Ala Gln Lys Glu
        915                 920                 925

Met Ser Pro Ser Pro Pro Ala Ala Gln Asp Pro Gly Gly Thr Ala Leu
    930                 935                 940

Val Ser Ala Arg Glu Gln Ser Ser Glu Arg Gln His His Pro Leu Gly
945                 950                 955                 960

Pro Thr Asp Met Gly Arg Gly Glu Pro Val Arg Arg Ser Ala Ile Arg
                965                 970                 975

Arg Gly His Arg Pro Arg Gly Ser Leu Asp Trp Pro Ser Glu Glu Arg
            980                 985                 990

Gly Pro Val Leu Ala His Leu Pro Ser Ser Asp Val Met Ala Ser Asn
        995                 1000                1005

His Glu Thr Pro Glu Ala Thr Gly Ala Gly Arg Leu Gly Ser Arg Arg
   1010                1015                1020

Lys Pro Ala Ala Pro Pro Pro Ser Pro Ala Ala Arg Glu Glu Gln Ser
1025                1030                1035                1040

Arg Ser Ser Ala Ser Ser Gln Lys Gly Pro Gln Ala Leu Thr Arg Ser
               1045                1050                1055

Asn Ser Leu Ser Thr Pro Arg Pro Thr Arg Ala Ser Arg Leu Arg Arg
           1060                1065                1070

Ala Arg Leu Gly Asp Ala Ser Asp Thr Glu Ala Ala Asp Gly Glu Arg
       1075                1080                1085

Gly Ser Leu Gly Asn Pro Glu Pro Val Gly Arg Pro Ala Ala Glu Gln
   1090                1095                1100

Ala Lys Lys Leu Ser Arg Leu Asp Ile Leu Ala Met Pro Arg Lys Arg
1105                1110                1115                1120

Ala Gly Ser Phe Thr Gly Thr Ser Asp Pro Glu Ala Ala Pro Ala Arg
               1125                1130                1135

Thr Ser Phe Ser Gly Arg Ser Val Glu Leu Cys Cys Ala Ser Arg Lys
           1140                1145                1150

Pro Thr Met Ala Glu Ala Arg Ala Val Ser Arg Lys Ala Ala Asn Thr
       1155                1160                1165

Ala Thr Thr Thr Gly Pro Arg Gln Pro Phe Ser Arg Ala Arg Ser Gly
   1170                1175                1180

Ser Ala Arg Tyr Thr Ser Thr Thr Gln Thr Pro Arg Ala Gly Ser Ser
1185                1190                1195                1200

Ser Arg Ala Arg Ser Arg Ala Pro Gly Pro Arg Asp Thr Asp Asp Asp
               1205                1210                1215

Glu Glu Glu Pro Asp Pro Tyr Gly Phe Ile Val Gln Thr Ala Glu Ile
           1220                1225                1230

Ala Glu Ile Ala Arg Leu Ser Gln Thr Leu Val Lys Asp Val Ala Ile
       1235                1240                1245

Leu Ala Gln Glu Ile His Asp Val Ala Gly Asp Gly Asp Thr Leu Gly
   1250                1255                1260

Ser Ser Glu Pro Ala His Ser Ala Ser Leu Ser Asn Met Pro Ser Thr
1265                1270                1275                1280

Pro Ala Ser Thr Ile Ser Ala Arg Glu Glu Leu Val Gln Arg Ile Pro
```

```
                1285                1290                1295

Glu Ala Ser Leu Asn Phe Gln Lys Val Pro Pro Gly Ser Leu Asn Ser
            1300                1305                1310

Arg Asp Phe Asp Gln Asn Met Asn Asp Ser Cys Glu Asp Ala Leu Ala
        1315                1320                1325

Asn Lys Thr Arg Pro Arg Asn Arg Glu Glu Val Ile Phe Asp Asn Leu
    1330                1335                1340

Met Leu Asn Pro Val Ser Gln Leu Ser Gln Ala Ile Arg Glu Asn Thr
1345                1350                1355                1360

Glu His Leu Ala Glu Lys Met Lys Ile Leu Phe Gln Asn Thr Gly Arg
                1365                1370                1375

Ala Trp Glu Asp Leu Glu Ala Arg Ile Asn Ala Glu Asn Glu Val Pro
            1380                1385                1390

Ile Leu Lys Thr Ser Asn Lys Glu Ile Ser Ser Ile Leu Lys Glu Leu
        1395                1400                1405

Arg Arg Val Gln Lys Gln Leu Glu Val Ile Asn Ala Ile Val Asp Pro
    1410                1415                1420

Ser Gly Ser Leu Asp Leu Leu Thr Gly Asn Arg Ser Leu Ala Ser Ser
1425                1430                1435                1440

Ala Gln Pro Gly Leu Gly Lys Gly Arg Val Ala Ala Gln Ser Pro Pro
                1445                1450                1455

Ser Pro Ala Ser Ala Glu Ala Leu Leu Pro Ala Leu Pro Leu Arg Asn
            1460                1465                1470

Phe Pro Gln Arg Ala Ser Cys Gly Pro Pro Ser Leu Pro Asp Pro Thr
        1475                1480                1485

Phe Leu Pro Asp Ala Glu Arg Phe Leu Ile
    1490                1495


<210> SEQ ID NO 97
<211> LENGTH: 622
<212> TYPE: PRT
<213> ORGANISM: Homo sapiens

<400> SEQUENCE: 97

Met Ala Met Ala Pro Ser Pro Ser Leu Val Gln Val Tyr Thr Ser Pro
 1               5                  10                  15

Ala Ala Val Ala Val Trp Glu Trp Gln Asp Gly Leu Gly Thr Trp His
            20                  25                  30

Pro Tyr Ser Ala Thr Val Cys Ser Phe Ile Glu Gln Gln Phe Val Gln
        35                  40                  45

Gln Lys Gly Gln Arg Phe Gly Leu Gly Ser Leu Ala His Ser Ile Pro
    50                  55                  60

Leu Gly Gln Ala Asp Pro Ser Leu Ala Pro Tyr Ile Ile Asp Leu Pro
65                  70                  75                  80

Ser Trp Thr Gln Phe Arg Gln Asp Thr Gly Thr Met Arg Ala Val Arg
                85                  90                  95

Arg His Leu Phe Pro Gln His Ser Ala Pro Gly Arg Gly Val Val Trp
            100                 105                 110

Glu Trp Leu Ser Asp Asp Gly Ser Trp Thr Ala Tyr Glu Ala Ser Val
        115                 120                 125

Cys Asp Tyr Leu Glu Gln Gln Val Ala Arg Gly Asn Gln Leu Val Asp
    130                 135                 140

Leu Ala Pro Leu Gly Tyr Asn Tyr Thr Val Asn Tyr Thr Thr His Thr
145                 150                 155                 160
```

```
Gln Thr Asn Lys Thr Ser Ser Phe Cys Arg Ser Val Arg Arg Gln Ala
                165                 170                 175

Gly Pro Pro Tyr Pro Val Thr Thr Ile Ile Ala Pro Pro Gly His Thr
            180                 185                 190

Gly Val Ala Cys Ser Cys His Gln Cys Leu Ser Gly Ser Arg Thr Gly
        195                 200                 205

Pro Val Ser Gly Arg Tyr Arg His Ser Met Thr Asn Leu Pro Ala Tyr
    210                 215                 220

Pro Val Pro Gln His Pro Pro His Arg Thr Ala Ser Val Phe Gly Thr
225                 230                 235                 240

His Gln Ala Phe Ala Pro Tyr Asn Lys Pro Ser Leu Ser Gly Ala Arg
                245                 250                 255

Ser Ala Pro Arg Leu Asn Thr Thr Asn Ala Trp Gly Ala Ala Pro Pro
            260                 265                 270

Ser Leu Gly Ser Gln Pro Leu Tyr Arg Ser Ser Leu Ser His Leu Gly
        275                 280                 285

Pro Gln His Leu Pro Pro Gly Ser Ser Thr Ser Gly Ala Val Ser Ala
    290                 295                 300

Ser Leu Pro Ser Gly Pro Ser Ser Ser Pro Gly Ser Val Pro Ala Thr
305                 310                 315                 320

Val Pro Met Gln Met Pro Lys Pro Ser Arg Val Gln Gln Ala Leu Ala
                325                 330                 335

Gly Met Thr Ser Val Leu Met Ser Ala Ile Gly Leu Pro Val Cys Leu
            340                 345                 350

Ser Arg Ala Pro Gln Pro Thr Ser Pro Pro Ala Ser Arg Leu Ala Ser
        355                 360                 365

Lys Ser His Gly Ser Val Lys Arg Leu Arg Lys Met Ser Val Lys Gly
    370                 375                 380

Ala Thr Pro Lys Pro Glu Pro Glu Pro Glu Gln Val Ile Lys Asn Tyr
385                 390                 395                 400

Thr Glu Glu Leu Lys Val Pro Pro Asp Glu Asp Cys Ile Ile Cys Met
                405                 410                 415

Glu Lys Leu Ser Ala Ala Ser Gly Tyr Ser Asp Val Thr Asp Ser Lys
            420                 425                 430

Ala Ile Gly Ser Leu Ala Val Gly His Leu Thr Lys Cys Ser His Ala
        435                 440                 445

Phe His Leu Leu Cys Leu Leu Ala Met Tyr Cys Asn Gly Asn Lys Asp
    450                 455                 460

Gly Ser Leu Gln Cys Pro Ser Cys Lys Thr Ile Tyr Gly Glu Lys Thr
465                 470                 475                 480

Gly Thr Gln Pro Gln Gly Lys Met Glu Val Leu Arg Phe Gln Met Ser
                485                 490                 495

Leu Pro Gly His Glu Asp Cys Gly Thr Ile Leu Ile Val Tyr Ser Ile
            500                 505                 510

Pro His Gly Ile Gln Gly Pro Glu His Pro Asn Pro Gly Lys Pro Phe
        515                 520                 525

Thr Ala Arg Gly Phe Pro Arg Gln Cys Tyr Leu Pro Asp Asn Ala Gln
    530                 535                 540

Gly Arg Lys Val Leu Glu Leu Leu Lys Val Ala Trp Lys Arg Arg Leu
545                 550                 555                 560

Ile Phe Thr Val Gly Thr Ser Ser Thr Thr Gly Glu Thr Asp Thr Val
                565                 570                 575

Val Trp Asn Glu Ile His His Lys Thr Glu Met Asp Arg Asn Ile Thr
```

580 585 590

Gly His Gly Tyr Pro Asp Pro Asn Tyr Leu Gln Asn Val Leu Ala Glu
595 600 605

Leu Ala Ala Gln Gly Val Thr Glu Asp Cys Leu Glu Gln Gln
610 615 620

<210> SEQ ID NO 98
<211> LENGTH: 568
<212> TYPE: PRT
<213> ORGANISM: Homo sapiens

<400> SEQUENCE: 98

Met Ala Ser Ser Cys Ala Val Gln Val Lys Leu Glu Leu Gly His Arg
1 5 10 15

Ala Gln Val Arg Lys Lys Pro Thr Val Glu Gly Phe Thr His Asp Trp
20 25 30

Met Val Phe Val Arg Gly Pro Glu His Ser Asn Ile Gln His Phe Val
35 40 45

Glu Lys Val Val Phe His Leu His Glu Ser Phe Pro Arg Pro Lys Arg
50 55 60

Val Cys Lys Asp Pro Pro Tyr Lys Val Glu Glu Ser Gly Tyr Ala Gly
65 70 75 80

Phe Ile Leu Pro Ile Glu Val Tyr Phe Lys Asn Lys Glu Glu Pro Arg
85 90 95

Lys Val Arg Phe Asp Tyr Asp Leu Phe Leu His Leu Glu Gly His Pro
100 105 110

Pro Val Asn His Leu Arg Cys Glu Lys Leu Thr Phe Asn Asn Pro Thr
115 120 125

Glu Asp Phe Arg Arg Lys Leu Leu Lys Ala Gly Gly Asp Pro Asn Arg
130 135 140

Ser Ile His Thr Ser Ser Ser Ser Ser Ser Ser Ser Ser Ser Ser Ser
145 150 155 160

Ser Ser Ser Ser Ser Ser Ser Ser Ser Ser Ser Ser Gly Ser Ser Ser
165 170 175

Ser Ser Ser Ser Ser Ser Ser Ser Ser Ser Ser Ser Ser Ser Thr Ser
180 185 190

Phe Ser Lys Pro His Lys Leu Met Lys Glu His Lys Glu Lys Pro Ser
195 200 205

Lys Asp Ser Arg Glu His Lys Ser Ala Phe Lys Glu Pro Ser Arg Asp
210 215 220

His Asn Lys Ser Ser Lys Glu Ser Ser Lys Lys Pro Lys Glu Asn Lys
225 230 235 240

Pro Leu Lys Glu Glu Lys Ile Val Pro Lys Met Ala Phe Lys Glu Pro
245 250 255

Lys Pro Met Ser Lys Glu Pro Lys Pro Asp Ser Asn Leu Leu Thr Ile
260 265 270

Thr Ser Gly Gln Asp Lys Lys Ala Pro Ser Lys Arg Pro Pro Ile Ser
275 280 285

Asp Ser Glu Glu Leu Ser Ala Lys Lys Arg Lys Lys Ser Ser Ser Glu
290 295 300

Ala Leu Phe Lys Ser Phe Ser Ser Ala Pro Pro Leu Ile Leu Thr Cys
305 310 315 320

Ser Ala Asp Lys Lys Gln Ile Lys Asp Lys Ser His Val Lys Met Gly
325 330 335

```
Lys Val Lys Ile Glu Ser Glu Thr Ser Glu Lys Lys Lys Ser Thr Leu
            340                 345                 350

Pro Pro Phe Asp Asp Ile Val Asp Pro Asn Asp Ser Asp Val Glu Glu
        355                 360                 365

Asn Ile Ser Ser Lys Ser Asp Ser Glu Gln Pro Ser Pro Ala Ser Ser
    370                 375                 380

Ser Ser Ser Ser Ser Ser Ser Phe Thr Pro Ser Gln Thr Arg Gln Gln
385                 390                 395                 400

Gly Pro Leu Arg Ser Ile Met Lys Asp Leu His Ser Asp Asp Asn Glu
                405                 410                 415

Glu Glu Ser Asp Glu Val Glu Asp Asn Asp Asn Asp Ser Glu Met Glu
            420                 425                 430

Arg Pro Val Asn Arg Gly Gly Ser Arg Ser Arg Arg Val Ser Leu Ser
        435                 440                 445

Asp Gly Ser Asp Ser Glu Ser Ser Ser Ala Ser Ser Pro Leu His His
    450                 455                 460

Glu Pro Pro Pro Pro Leu Leu Lys Thr Asn Asn Asn Gln Ile Leu Glu
465                 470                 475                 480

Val Lys Ser Pro Ile Lys Gln Ser Lys Ser Asp Lys Gln Ile Lys Asn
                485                 490                 495

Gly Glu Cys Asp Lys Ala Tyr Leu Asp Glu Leu Val Glu Leu His Arg
            500                 505                 510

Arg Leu Met Thr Leu Arg Glu Arg His Ile Leu Gln Gln Ile Val Asn
        515                 520                 525

Leu Ile Glu Glu Thr Gly His Phe His Ile Thr Asn Thr Thr Phe Asp
    530                 535                 540

Phe Asp Leu Cys Ser Leu Asp Lys Thr Thr Val Arg Lys Leu Gln Ser
545                 550                 555                 560

Tyr Leu Glu Thr Ser Gly Thr Ser
                565


<210> SEQ ID NO 99
<211> LENGTH: 373
<212> TYPE: PRT
<213> ORGANISM: Homo sapiens

<400> SEQUENCE: 99

Met Leu Leu Gly Leu Ala Ala Met Glu Leu Lys Val Trp Val Asp Gly
 1               5                  10                  15

Ile Gln Arg Val Val Cys Gly Val Ser Glu Gln Thr Thr Cys Gln Glu
            20                  25                  30

Val Val Ile Ala Leu Ala Gln Ala Ile Gly Gln Thr Gly Arg Phe Val
        35                  40                  45

Leu Val Gln Arg Leu Arg Glu Lys Glu Arg Gln Leu Leu Pro Gln Glu
    50                  55                  60

Cys Pro Val Gly Ala Gln Ala Thr Cys Gly Gln Phe Ala Ser Asp Val
65                  70                  75                  80

Gln Phe Val Leu Arg Arg Thr Gly Pro Ser Leu Ala Gly Arg Pro Ser
                85                  90                  95

Ser Asp Ser Cys Pro Pro Pro Glu Arg Cys Leu Ile Arg Ala Ser Leu
            100                 105                 110

Pro Val Lys Pro Arg Ala Ala Leu Gly Cys Glu Pro Arg Lys Thr Leu
        115                 120                 125

Thr Pro Glu Pro Ala Pro Ser Leu Ser Arg Pro Gly Pro Ala Ala Pro
    130                 135                 140
```

Val Thr Pro Thr Pro Gly Cys Cys Thr Asp Leu Arg Gly Leu Glu Leu
145 150 155 160

Arg Val Gln Arg Asn Ala Glu Glu Leu Gly His Glu Ala Phe Trp Glu
165 170 175

Gln Glu Leu Arg Arg Glu Gln Ala Arg Glu Arg Glu Gly Gln Ala Arg
180 185 190

Leu Gln Ala Leu Ser Ala Ala Thr Ala Glu His Ala Ala Arg Leu Gln
195 200 205

Ala Leu Asp Ala Gln Ala Arg Ala Leu Glu Ala Glu Leu Gln Leu Ala
210 215 220

Ala Glu Ala Pro Gly Pro Pro Ser Pro Met Ala Ser Ala Thr Glu Arg
225 230 235 240

Leu His Gln Asp Leu Ala Val Gln Glu Arg Gln Ser Ala Glu Val Gln
245 250 255

Gly Ser Leu Ala Leu Val Ser Arg Ala Leu Glu Ala Ala Glu Arg Ala
260 265 270

Leu Gln Ala Gln Ala Gln Glu Leu Glu Glu Leu Asn Arg Glu Leu Arg
275 280 285

Gln Cys Asn Leu Gln Gln Phe Ile Gln Gln Thr Gly Ala Ala Leu Pro
290 295 300

Pro Pro Pro Arg Pro Asp Arg Gly Pro Pro Gly Thr Gln Gly Pro Leu
305 310 315 320

Pro Pro Ala Arg Glu Glu Ser Leu Leu Gly Ala Pro Ser Glu Ser His
325 330 335

Ala Gly Ala Gln Pro Arg Pro Arg Gly Gly Pro His Asp Ala Glu Leu
340 345 350

Leu Glu Val Ala Ala Ala Pro Ala Pro Glu Trp Cys Pro Leu Ala Ala
355 360 365

Gln Pro Gln Ala Leu
370

<210> SEQ ID NO 100
<211> LENGTH: 334
<212> TYPE: PRT
<213> ORGANISM: Homo sapiens

<400> SEQUENCE: 100

Met Lys Pro Pro Pro Arg Arg Arg Ala Ala Pro Ala Arg Tyr Leu Gly
1 5 10 15

Glu Val Thr Gly Pro Ala Thr Trp Ser Ala Arg Glu Lys Arg Gln Leu
20 25 30

Val Arg Leu Leu Gln Ala Arg Gln Gly Gln Pro Glu Pro Asp Ala Thr
35 40 45

Glu Leu Ala Arg Glu Leu Arg Gly Arg Ser Glu Ala Glu Ile Arg Val
50 55 60

Phe Leu Gln Gln Leu Lys Gly Arg Val Ala Arg Glu Ala Ile Gln Lys
65 70 75 80

Val His Pro Gly Gly Leu Gln Gly Pro Arg Arg Arg Glu Ala Gln Pro
85 90 95

Pro Ala Pro Ile Glu Val Trp Thr Asp Leu Ala Glu Lys Ile Thr Gly
100 105 110

Pro Leu Glu Glu Ala Leu Ala Val Ala Phe Ser Gln Val Leu Thr Ile
115 120 125

Ala Ala Thr Glu Pro Val Thr Leu Leu His Ser Lys Pro Pro Lys Pro 130 135 140

Thr Gln Ala Arg Gly Lys Pro Leu Leu Leu Ser Ala Pro Gly Gly Gln
145 150 155 160

Glu Asp Pro Ala Pro Glu Ile Pro Ser Ser Ala Pro Ala Ala Pro Ser
165 170 175

Ser Ala Pro Arg Thr Pro Asp Pro Ala Pro Glu Lys Pro Ser Glu Ser
180 185 190

Ser Ala Gly Pro Ser Thr Glu Glu Asp Phe Ala Val Asp Phe Glu Lys
195 200 205

Ile Tyr Lys Tyr Leu Ser Ser Val Ser Arg Ser Gly Arg Ser Pro Glu
210 215 220

Leu Ser Ala Ala Glu Ser Ala Val Val Leu Asp Leu Leu Met Ser Leu
225 230 235 240

Pro Glu Glu Leu Pro Leu Leu Pro Cys Thr Ala Leu Val Glu His Met
245 250 255

Thr Glu Thr Tyr Leu Arg Leu Thr Ala Pro Gln Pro Ile Pro Ala Gly
260 265 270

Gly Ser Leu Gly Pro Ala Ala Glu Gly Asp Gly Ala Gly Ser Lys Ala
275 280 285

Pro Glu Glu Thr Pro Pro Ala Thr Glu Lys Ala Glu His Ser Glu Leu
290 295 300

Lys Ser Pro Trp Gln Ala Ala Gly Ile Cys Pro Leu Asn Pro Phe Leu
305 310 315 320

Val Pro Leu Glu Leu Leu Gly Arg Ala Ala Thr Pro Ala Arg
325 330

<210> SEQ ID NO 101
<211> LENGTH: 1233
<212> TYPE: PRT
<213> ORGANISM: Homo sapiens

<400> SEQUENCE: 101

Met Gly Phe Leu Lys Leu Ile Glu Ile Glu Asn Phe Lys Ser Tyr Lys
1 5 10 15

Gly Arg Gln Ile Ile Gly Pro Phe Gln Arg Phe Thr Ala Ile Ile Gly
20 25 30

Pro Asn Gly Ser Gly Lys Ser Asn Leu Met Asp Ala Ile Ser Phe Val
35 40 45

Leu Gly Glu Lys Thr Ser Asn Leu Arg Val Lys Thr Leu Arg Asp Leu
50 55 60

Ile His Gly Ala Pro Val Gly Lys Pro Ala Ala Asn Arg Ala Phe Val
65 70 75 80

Ser Met Val Tyr Ser Glu Glu Gly Ala Glu Asp Arg Thr Phe Ala Arg
85 90 95

Val Ile Val Gly Gly Ser Ser Glu Tyr Lys Ile Asn Asn Lys Val Val
100 105 110

Gln Leu His Glu Tyr Ser Glu Glu Leu Glu Lys Leu Gly Ile Leu Ile
115 120 125

Lys Ala Arg Asn Phe Leu Val Phe Gln Gly Ala Val Glu Ser Ile Ala
130 135 140

Met Lys Asn Pro Lys Glu Arg Thr Ala Leu Phe Glu Glu Ile Ser Arg
145 150 155 160

Ser Gly Glu Leu Ala Gln Glu Tyr Asp Lys Arg Lys Lys Glu Met Val
165 170 175

```
Lys Ala Glu Glu Asp Thr Gln Phe Asn Tyr His Arg Lys Lys Asn Ile
            180                 185                 190

Ala Ala Glu Arg Lys Glu Ala Lys Gln Glu Lys Glu Glu Ala Asp Arg
        195                 200                 205

Tyr Gln Arg Leu Lys Asp Glu Val Val Arg Ala Gln Val Gln Leu Gln
    210                 215                 220

Leu Phe Lys Leu Tyr His Asn Glu Val Glu Ile Glu Lys Leu Asn Lys
225                 230                 235                 240

Glu Leu Ala Ser Lys Asn Lys Glu Ile Glu Lys Asp Lys Lys Arg Met
                245                 250                 255

Asp Lys Val Glu Asp Glu Leu Lys Glu Lys Lys Lys Glu Leu Gly Lys
            260                 265                 270

Met Met Arg Glu Gln Gln Gln Ile Glu Lys Glu Ile Lys Glu Lys Asp
        275                 280                 285

Ser Glu Leu Asn Gln Lys Arg Pro Gln Tyr Ile Lys Ala Lys Glu Asn
    290                 295                 300

Thr Ser His Lys Ile Lys Lys Leu Glu Ala Ala Lys Lys Ser Leu Gln
305                 310                 315                 320

Asn Ala Gln Lys His Tyr Lys Lys Arg Lys Gly Asp Met Asp Glu Leu
                325                 330                 335

Glu Lys Glu Met Leu Ser Val Glu Lys Ala Arg Gln Glu Phe Glu Glu
            340                 345                 350

Arg Met Glu Glu Glu Ser Gln Ser Gln Gly Arg Asp Leu Thr Leu Glu
        355                 360                 365

Glu Asn Gln Val Lys Lys Tyr His Arg Leu Lys Glu Glu Ala Ser Lys
    370                 375                 380

Arg Ala Ala Thr Leu Ala Gln Glu Leu Glu Lys Phe Asn Arg Asp Gln
385                 390                 395                 400

Lys Ala Asp Gln Asp Arg Leu Asp Leu Glu Glu Arg Lys Lys Val Glu
                405                 410                 415

Thr Glu Ala Lys Ile Lys Gln Lys Leu Arg Glu Ile Glu Glu Asn Gln
            420                 425                 430

Lys Arg Ile Glu Lys Leu Glu Glu Tyr Ile Thr Thr Ser Lys Gln Ser
        435                 440                 445

Leu Glu Glu Gln Lys Lys Leu Glu Gly Glu Leu Thr Glu Glu Val Glu
    450                 455                 460

Met Ala Lys Arg Arg Ile Asp Glu Ile Asn Lys Glu Leu Asn Gln Val
465                 470                 475                 480

Met Glu Gln Leu Gly Asp Ala Arg Ile Asp Arg Gln Glu Ser Ser Arg
                485                 490                 495

Gln Gln Arg Lys Ala Glu Ile Met Glu Ser Ile Lys Arg Leu Tyr Pro
            500                 505                 510

Gly Ser Val Tyr Gly Arg Leu Ile Asp Leu Cys Gln Pro Thr Gln Lys
        515                 520                 525

Lys Tyr Gln Ile Ala Val Thr Lys Val Leu Gly Lys Asn Met Asp Ala
    530                 535                 540

Ile Ile Val Asp Ser Glu Lys Thr Gly Arg Asp Cys Ile Gln Tyr Ile
545                 550                 555                 560

Lys Glu Gln Arg Gly Glu Pro Glu Thr Phe Leu Pro Leu Asp Tyr Leu
                565                 570                 575

Glu Val Lys Pro Thr Asp Glu Lys Leu Arg Glu Leu Lys Gly Ala Lys
            580                 585                 590

Leu Val Ile Asp Val Ile Arg Tyr Glu Pro Pro His Ile Lys Lys Ala
```

-continued

```
        595                 600                 605

Leu Gln Tyr Ala Cys Gly Asn Ala Leu Val Cys Asp Asn Val Glu Asp
    610                 615                 620

Ala Arg Arg Ile Ala Phe Gly Gly His Gln Arg His Lys Thr Val Ala
625                 630                 635                 640

Leu Asp Gly Thr Leu Phe Gln Lys Ser Gly Val Ile Ser Gly Gly Ala
                645                 650                 655

Ser Asp Leu Lys Ala Lys Ala Arg Arg Trp Asp Glu Lys Ala Val Asp
            660                 665                 670

Lys Leu Lys Glu Lys Lys Glu Arg Leu Thr Glu Glu Leu Lys Glu Gln
        675                 680                 685

Met Lys Ala Lys Arg Lys Glu Ala Glu Leu Arg Gln Val Gln Ser Gln
    690                 695                 700

Ala His Gly Leu Gln Met Arg Leu Lys Tyr Ser Gln Ser Asp Leu Glu
705                 710                 715                 720

Gln Thr Lys Thr Arg His Leu Ala Leu Asn Leu Gln Glu Lys Ser Lys
                725                 730                 735

Leu Glu Ser Glu Leu Ala Asn Phe Gly Pro Arg Ile Asn Asp Ile Lys
            740                 745                 750

Arg Ile Ile Gln Ser Arg Glu Arg Glu Met Lys Asp Leu Lys Glu Lys
        755                 760                 765

Met Asn Gln Val Glu Asp Glu Val Phe Glu Glu Phe Cys Arg Glu Ile
    770                 775                 780

Gly Val Arg Asn Ile Arg Glu Phe Glu Glu Glu Lys Val Lys Arg Gln
785                 790                 795                 800

Asn Glu Ile Ala Lys Lys Arg Leu Glu Phe Glu Asn Gln Lys Thr Arg
                805                 810                 815

Leu Gly Ile Gln Leu Asp Phe Glu Lys Asn Gln Leu Lys Glu Asp Gln
            820                 825                 830

Asp Lys Val His Met Trp Glu Gln Thr Val Lys Lys Asp Glu Asn Glu
        835                 840                 845

Ile Glu Lys Leu Lys Lys Glu Glu Gln Arg His Met Lys Ile Ile Asp
    850                 855                 860

Glu Thr Met Ala Gln Leu Gln Asp Leu Lys Asn Gln His Leu Ala Lys
865                 870                 875                 880

Lys Ser Glu Val Asn Asp Lys Asn His Glu Met Glu Glu Ile Arg Lys
                885                 890                 895

Lys Leu Gly Gly Ala Asn Lys Glu Met Thr His Leu Gln Lys Glu Val
            900                 905                 910

Thr Ala Ile Glu Thr Lys Leu Glu Gln Lys Arg Ser Asp Arg His Asn
        915                 920                 925

Leu Leu Gln Ala Cys Lys Met Gln Asp Ile Lys Leu Pro Leu Ser Lys
    930                 935                 940

Gly Thr Met Asp Asp Ile Ser Gln Glu Glu Gly Ser Ser Gln Gly Glu
945                 950                 955                 960

Asp Ser Val Ser Gly Ser Gln Arg Ile Ser Ser Ile Tyr Ala Arg Glu
                965                 970                 975

Ala Leu Ile Glu Ile Asp Tyr Gly Asp Leu Cys Glu Asp Leu Lys Asp
            980                 985                 990

Ala Gln Ala Glu Glu Glu Ile Lys Gln Glu Met Asn Thr Leu Gln Gln
        995                1000                1005

Lys Leu Asn Glu Gln Gln Ser Val Leu Gln Arg Ile Ala Ala Pro Asn
   1010                1015                1020
```

Met Lys Ala Met Glu Lys Leu Glu Ser Val Arg Asp Lys Phe Gln Glu
1025 1030 1035 1040

Thr Ser Asp Glu Phe Glu Ala Ala Arg Lys Arg Ala Lys Lys Ala Lys
1045 1050 1055

Gln Ala Phe Glu Gln Ile Lys Lys Glu Arg Phe Asp Arg Phe Asn Ala
1060 1065 1070

Cys Phe Glu Ser Val Ala Thr Asn Ile Asp Glu Ile Tyr Lys Ala Leu
1075 1080 1085

Ser Arg Asn Ser Ser Ala Gln Ala Phe Leu Gly Pro Glu Asn Pro Glu
1090 1095 1100

Glu Pro Tyr Leu Asp Gly Ile Asn Tyr Asn Cys Val Ala Pro Gly Lys
1105 1110 1115 1120

Arg Phe Arg Pro Met Asp Asn Leu Ser Gly Gly Glu Lys Thr Val Ala
1125 1130 1135

Ala Leu Ala Leu Leu Phe Ala Ile His Ser Tyr Lys Pro Ala Pro Phe
1140 1145 1150

Phe Val Leu Asp Glu Ile Asp Ala Ala Leu Asp Asn Thr Asn Ile Gly
1155 1160 1165

Lys Val Ala Asn Tyr Ile Lys Glu Gln Ser Thr Cys Asn Phe Gln Ala
1170 1175 1180

Ile Val Ile Ser Leu Lys Glu Glu Phe Tyr Thr Lys Ala Glu Ser Leu
1185 1190 1195 1200

Ile Gly Val Tyr Pro Glu Gln Gly Asp Cys Val Ile Ser Lys Val Leu
1205 1210 1215

Thr Phe Asp Leu Thr Lys Tyr Pro Asp Ala Asn Pro Asn Pro Asn Glu
1220 1225 1230

Gln

<210> SEQ ID NO 102
<211> LENGTH: 749
<212> TYPE: PRT
<213> ORGANISM: Homo sapiens

<400> SEQUENCE: 102

Met Ala Arg Lys Leu Ser Val Ile Leu Ile Leu Thr Phe Ala Leu Ser
1 5 10 15

Val Thr Asn Pro Leu His Glu Leu Lys Ala Ala Ala Phe Pro Gln Thr
20 25 30

Thr Glu Lys Ile Ser Pro Asn Trp Glu Ser Gly Ile Asn Val Asp Leu
35 40 45

Ala Ile Ser Thr Arg Gln Tyr His Leu Gln Gln Leu Phe Tyr Arg Tyr
50 55 60

Gly Glu Asn Asn Ser Leu Ser Val Glu Gly Phe Arg Lys Leu Leu Gln
65 70 75 80

Asn Ile Gly Ile Asp Lys Ile Lys Arg Ile His Ile His His Asp His
85 90 95

Asp His His Ser Asp His Glu His His Ser Asp His Glu Arg His Ser
100 105 110

Asp His Glu His His Ser Asp His Glu His His Ser Asp His Asn His
115 120 125

Ala Ala Ser Gly Lys Asn Lys Arg Lys Ala Leu Cys Pro Asp His Asp
130 135 140

Ser Asp Ser Ser Gly Lys Asp Pro Arg Asn Ser Gln Gly Lys Gly Ala
145 150 155 160

-continued

```
His Arg Pro Glu His Ala Ser Gly Arg Arg Asn Val Lys Asp Ser Val
                165                 170                 175

Ser Ala Ser Glu Val Thr Ser Thr Val Tyr Asn Thr Val Ser Glu Gly
            180                 185                 190

Thr His Phe Leu Glu Thr Ile Glu Thr Pro Arg Pro Gly Lys Leu Phe
        195                 200                 205

Pro Lys Asp Val Ser Ser Ser Thr Pro Pro Ser Val Thr Ser Lys Ser
    210                 215                 220

Arg Val Ser Arg Leu Ala Gly Arg Lys Thr Asn Glu Ser Val Ser Glu
225                 230                 235                 240

Pro Arg Lys Gly Phe Met Tyr Ser Arg Asn Thr Asn Glu Asn Pro Gln
                245                 250                 255

Glu Cys Phe Asn Ala Ser Lys Leu Leu Thr Ser His Gly Met Gly Ile
            260                 265                 270

Gln Val Pro Leu Asn Ala Thr Glu Phe Asn Tyr Leu Cys Pro Ala Ile
        275                 280                 285

Ile Asn Gln Ile Asp Ala Arg Ser Cys Leu Ile His Thr Ser Glu Lys
    290                 295                 300

Lys Ala Glu Ile Pro Pro Lys Thr Tyr Ser Leu Gln Ile Ala Trp Val
305                 310                 315                 320

Gly Gly Phe Ile Ala Ile Ser Ile Ile Ser Phe Leu Ser Leu Leu Gly
                325                 330                 335

Val Ile Leu Val Pro Leu Met Asn Arg Val Phe Phe Lys Phe Leu Leu
            340                 345                 350

Ser Phe Leu Val Ala Leu Ala Val Gly Thr Leu Ser Gly Asp Ala Phe
        355                 360                 365

Leu His Leu Leu Pro His Ser His Ala Ser His His His Ser His Ser
    370                 375                 380

His Glu Glu Pro Ala Met Glu Met Lys Arg Gly Pro Leu Phe Ser His
385                 390                 395                 400

Leu Ser Ser Gln Asn Ile Glu Glu Ser Ala Tyr Phe Asp Ser Thr Trp
                405                 410                 415

Lys Gly Leu Thr Ala Leu Gly Gly Leu Tyr Phe Met Phe Leu Val Glu
            420                 425                 430

His Val Leu Thr Leu Ile Lys Gln Phe Lys Asp Lys Lys Lys Lys Asn
        435                 440                 445

Gln Lys Lys Pro Glu Asn Asp Asp Asp Val Glu Ile Lys Lys Gln Leu
    450                 455                 460

Ser Lys Tyr Glu Ser Gln Leu Ser Thr Asn Glu Glu Lys Val Asp Thr
465                 470                 475                 480

Asp Asp Arg Thr Glu Gly Tyr Leu Arg Ala Asp Ser Gln Glu Pro Ser
                485                 490                 495

His Phe Asp Ser Gln Gln Pro Ala Val Leu Glu Glu Glu Glu Val Met
            500                 505                 510

Ile Ala His Ala His Pro Gln Glu Val Tyr Asn Glu Tyr Val Pro Arg
        515                 520                 525

Gly Cys Lys Asn Lys Cys His Ser His Phe His Asp Thr Leu Gly Gln
    530                 535                 540

Ser Asp Asp Leu Ile His His His His Asp Tyr His His Ile Leu His
545                 550                 555                 560

His His His His Gln Asn His His Pro His Ser His Ser Gln Arg Tyr
                565                 570                 575
```

Ser Arg Glu Glu Leu Lys Asp Ala Gly Val Ala Thr Leu Ala Trp Met
580 585 590

Val Ile Met Gly Asp Gly Leu His Asn Phe Ser Asp Gly Leu Ala Ile
595 600 605

Gly Ala Ala Phe Thr Glu Gly Leu Ser Ser Gly Leu Ser Thr Ser Val
610 615 620

Ala Val Phe Cys His Glu Leu Pro His Glu Leu Gly Asp Phe Ala Val
625 630 635 640

Leu Leu Lys Ala Gly Met Thr Val Lys Gln Ala Val Leu Tyr Asn Ala
645 650 655

Leu Ser Ala Met Leu Ala Tyr Leu Gly Met Ala Thr Gly Ile Phe Ile
660 665 670

Gly His Tyr Ala Glu Asn Val Ser Met Trp Ile Phe Ala Leu Thr Ala
675 680 685

Gly Leu Phe Met Tyr Val Ala Leu Val Asp Met Val Pro Glu Met Leu
690 695 700

His Asn Asp Ala Ser Asp His Gly Cys Ser Arg Trp Gly Tyr Phe Phe
705 710 715 720

Leu Gln Asn Ala Gly Met Leu Leu Gly Phe Gly Ile Met Leu Leu Ile
725 730 735

Ser Ile Phe Glu His Lys Ile Val Phe Arg Ile Asn Phe
740 745

<210> SEQ ID NO 103
<211> LENGTH: 519
<212> TYPE: PRT
<213> ORGANISM: Homo sapiens

<400> SEQUENCE: 103

Met Ile Pro Val Ser Leu Val Val Val Val Val Gly Gly Trp Thr Val
1 5 10 15

Val Tyr Leu Thr Asp Leu Val Leu Lys Ser Ser Val Tyr Phe Lys His
20 25 30

Ser Tyr Glu Asp Trp Leu Glu Asn Asn Gly Leu Ser Ile Ser Pro Phe
35 40 45

His Ile Arg Trp Gln Thr Ala Val Phe Asn Arg Ala Phe Tyr Ser Trp
50 55 60

Gly Arg Arg Lys Ala Arg Met Leu Tyr Gln Trp Phe Asn Phe Gly Met
65 70 75 80

Val Phe Gly Val Ile Ala Met Phe Ser Ser Phe Phe Leu Leu Gly Lys
85 90 95

Thr Leu Met Gln Thr Leu Ala Gln Met Met Ala Asp Ser Pro Ser Ser
100 105 110

Tyr Ser Ser Ser Ser Ser Ser Ser Ser Ser Ser Ser Ser Ser Ser Ser
115 120 125

Ser Ser Ser Ser Ser Ser Ser Ser Leu His Asn Glu Gln Val Leu Gln
130 135 140

Val Val Val Pro Gly Ile Asn Leu Pro Val Asn Gln Leu Thr Tyr Phe
145 150 155 160

Phe Thr Ala Val Leu Ile Ser Gly Val Val His Glu Ile Gly His Gly
165 170 175

Ile Ala Ala Ile Arg Glu Gln Val Arg Phe Asn Gly Phe Gly Ile Phe
180 185 190

Leu Phe Ile Ile Tyr Pro Gly Ala Phe Val Asp Leu Phe Thr Thr His
195 200 205

Leu Gln Leu Ile Ser Pro Val Gln Gln Leu Arg Ile Phe Cys Ala Gly
    210                 215                 220

Ile Trp His Asn Phe Val Leu Ala Leu Leu Gly Ile Leu Ala Leu Val
225                 230                 235                 240

Leu Leu Pro Val Ile Leu Leu Pro Phe Tyr Tyr Thr Gly Val Gly Val
                245                 250                 255

Leu Ile Thr Glu Val Ala Glu Asp Ser Pro Ala Ile Gly Pro Arg Gly
            260                 265                 270

Leu Phe Val Gly Asp Leu Val Thr His Leu Gln Asp Cys Pro Val Thr
        275                 280                 285

Asn Val Gln Asp Trp Asn Glu Cys Leu Asp Thr Ile Ala Tyr Glu Pro
    290                 295                 300

Gln Ile Gly Tyr Cys Ile Ser Ala Ser Thr Leu Gln Gln Leu Ser Phe
305                 310                 315                 320

Pro Val Arg Ala Tyr Lys Arg Leu Asp Gly Ser Thr Glu Cys Cys Asn
                325                 330                 335

Asn His Ser Leu Thr Asp Val Cys Phe Ser Tyr Arg Asn Asn Phe Asn
            340                 345                 350

Lys Arg Leu His Thr Cys Leu Pro Ala Arg Lys Ala Val Glu Ala Thr
        355                 360                 365

Gln Val Cys Arg Thr Asn Lys Asp Cys Lys Lys Ser Ser Ser Ser Ser
    370                 375                 380

Phe Cys Ile Ile Pro Ser Leu Glu Thr His Thr Arg Leu Ile Lys Val
385                 390                 395                 400

Lys His Pro Pro Gln Ile Asp Met Leu Tyr Val Gly His Pro Leu His
                405                 410                 415

Leu His Tyr Thr Val Ser Ile Thr Ser Phe Ile Pro Arg Phe Asn Phe
            420                 425                 430

Leu Ser Ile Asp Leu Pro Val Val Val Glu Thr Phe Val Lys Tyr Leu
        435                 440                 445

Ile Ser Leu Ser Gly Ala Leu Ala Ile Val Asn Ala Val Pro Cys Phe
    450                 455                 460

Ala Leu Asp Gly Gln Trp Ile Leu Asn Ser Phe Leu Asp Ala Thr Leu
465                 470                 475                 480

Thr Ser Val Ile Gly Asp Asn Asp Val Lys Asp Leu Ile Gly Phe Phe
                485                 490                 495

Ile Leu Leu Gly Gly Ser Val Leu Leu Ala Ala Asn Val Thr Leu Gly
            500                 505                 510

Leu Trp Met Val Thr Ala Arg
        515

<210> SEQ ID NO 104
<211> LENGTH: 274
<212> TYPE: PRT
<213> ORGANISM: Homo sapiens

<400> SEQUENCE: 104

Met Gly Thr Asp Ser Arg Ala Ala Lys Ala Leu Leu Ala Arg Ala Arg
 1               5                  10                  15

Thr Leu His Leu Gln Thr Gly Asn Leu Leu Asn Trp Gly Arg Leu Arg
            20                  25                  30

Lys Lys Cys Pro Ser Thr His Ser Glu Glu Leu His Asp Cys Ile Gln
        35                  40                  45

Lys Thr Leu Asn Glu Trp Ser Ser Gln Ile Asn Pro Asp Leu Val Arg 50                  55                  60

Glu Phe Pro Asp Val Leu Glu Cys Thr Val Ser His Ala Val Glu Lys
65                  70                  75                  80

Ile Asn Pro Asp Glu Arg Glu Glu Met Lys Val Ser Ala Lys Leu Phe
                85                  90                  95

Ile Val Glu Ser Asn Ser Ser Ser Ser Thr Arg Ser Ala Val Asp Met
            100                 105                 110

Ala Cys Ser Val Leu Gly Val Ala Gln Leu Asp Ser Val Ile Ile Ala
        115                 120                 125

Ser Pro Pro Ile Glu Asp Gly Val Asn Leu Ser Leu Glu His Leu Gln
    130                 135                 140

Pro Tyr Trp Glu Glu Leu Glu Asn Leu Val Gln Ser Lys Lys Ile Val
145                 150                 155                 160

Ala Ile Gly Thr Ser Asp Leu Asp Lys Thr Gln Leu Glu Gln Leu Tyr
                165                 170                 175

Gln Trp Ala Gln Val Lys Pro Asn Ser Asn Gln Val Asn Leu Ala Ser
            180                 185                 190

Cys Cys Val Met Pro Pro Asp Leu Thr Ala Phe Ala Lys Gln Phe Asp
        195                 200                 205

Ile Gln Leu Leu Thr His Asn Asp Pro Lys Glu Leu Leu Ser Glu Ala
    210                 215                 220

Ser Phe Gln Glu Ala Leu Gln Glu Ser Ile Pro Asp Ile Gln Ala His
225                 230                 235                 240

Glu Trp Val Pro Leu Trp Leu Leu Arg Tyr Ser Val Ile Val Lys Ser
                245                 250                 255

Arg Gly Ile Ile Lys Ser Lys Gly Tyr Ile Leu Gln Ala Lys Arg Arg
            260                 265                 270

Gly Ser

<210> SEQ ID NO 105
<211> LENGTH: 257
<212> TYPE: PRT
<213> ORGANISM: Homo sapiens

<400> SEQUENCE: 105

Met Ala Ala Asp Gly Val Asp Glu Arg Ser Pro Leu Leu Ser Ala Ser
1               5                   10                  15

His Ser Gly Asn Val Thr Pro Thr Ala Pro Pro Tyr Leu Gln Glu Ser
            20                  25                  30

Ser Pro Arg Ala Glu Leu Pro Pro Pro Tyr Thr Ala Ile Ala Ser Pro
        35                  40                  45

Asp Ala Ser Gly Ile Pro Val Ile Asn Cys Arg Val Cys Gln Ser Leu
    50                  55                  60

Ile Asn Leu Asp Gly Lys Leu His Gln His Val Val Lys Cys Thr Val
65                  70                  75                  80

Cys Asn Glu Ala Thr Pro Ile Lys Asn Pro Pro Thr Gly Lys Lys Tyr
                85                  90                  95

Val Arg Cys Pro Cys Asn Cys Leu Leu Ile Cys Lys Asp Thr Ser Arg
            100                 105                 110

Arg Ile Gly Cys Pro Arg Pro Asn Cys Arg Arg Ile Ile Asn Leu Gly
        115                 120                 125

Pro Val Met Leu Ile Ser Glu Glu Gln Pro Ala Gln Pro Ala Leu Pro
    130                 135                 140

Ile Gln Pro Glu Gly Thr Arg Val Val Cys Gly His Cys Gly Asn Thr

```
145                 150                 155                 160

Phe Leu Trp Met Glu Leu Arg Phe Asn Thr Leu Ala Lys Cys Pro His
                165                 170                 175

Cys Lys Lys Ile Ser Ser Val Gly Ser Ala Leu Pro Arg Arg Arg Cys
            180                 185                 190

Cys Ala Tyr Ile Thr Ile Gly Met Ile Cys Ile Phe Ile Gly Val Gly
        195                 200                 205

Leu Thr Val Gly Thr Pro Asp Phe Ala Arg Arg Phe Arg Ala Thr Tyr
    210                 215                 220

Val Ser Trp Ala Ile Ala Tyr Leu Leu Gly Leu Ile Cys Leu Ile Arg
225                 230                 235                 240

Ala Cys Tyr Trp Gly Ala Ile Arg Val Ser Tyr Pro Glu His Ser Phe
                245                 250                 255

Ala


<210> SEQ ID NO 106
<211> LENGTH: 619
<212> TYPE: PRT
<213> ORGANISM: Homo sapiens

<400> SEQUENCE: 106

Met Tyr Gly Phe Val Asn His Ala Leu Glu Leu Leu Val Ile Arg Asn
 1               5                  10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Glu Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Asn Cys Ser Leu Leu Ser Val Phe Ser Leu
                245                 250                 255

Val Arg Pro His Ile Asp Ile Ser Phe His Gly Ile Leu Ser His Ile
```

```
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Thr Glu Ile Ser Cys Leu
    290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350

Val Leu Leu Gly Glu Gln Phe Arg Glu Glu Tyr Lys Leu Thr Gln Glu
        355                 360                 365

Leu Glu Ile Leu Thr Asp Arg Leu Gln Leu Thr Leu Arg Ala Leu Glu
    370                 375                 380

Asp Glu Lys Lys Lys Thr Asp Thr Leu Leu Tyr Ser Val Leu Pro Pro
385                 390                 395                 400

Ser Val Ala Asn Glu Leu Arg His Lys Arg Pro Val Pro Ala Lys Arg
                405                 410                 415

Tyr Asp Asn Val Thr Ile Leu Phe Ser Gly Ile Val Gly Phe Asn Ala
            420                 425                 430

Phe Cys Ser Lys His Ala Ser Gly Glu Gly Ala Met Lys Ile Val Asn
        435                 440                 445

Leu Leu Asn Asp Leu Tyr Thr Arg Phe Asp Thr Leu Thr Asp Ser Arg
    450                 455                 460

Lys Asn Pro Phe Val Tyr Lys Val Glu Thr Val Gly Asp Lys Tyr Met
465                 470                 475                 480

Thr Val Ser Gly Leu Pro Glu Pro Cys Ile His His Ala Arg Ser Ile
                485                 490                 495

Cys His Leu Ala Leu Asp Met Met Glu Ile Ala Gly Gln Val Gln Val
            500                 505                 510

Asp Gly Glu Ser Val Gln Ile Thr Ile Gly Ile His Thr Gly Glu Val
        515                 520                 525

Val Thr Gly Val Ile Gly Gln Arg Met Pro Arg Tyr Cys Leu Phe Gly
    530                 535                 540

Asn Thr Val Asn Leu Thr Ser Arg Thr Glu Thr Thr Gly Glu Lys Gly
545                 550                 555                 560

Lys Ile Asn Val Ser Glu Tyr Thr Tyr Arg Cys Leu Met Ser Pro Glu
                565                 570                 575

Asn Ser Asp Pro Gln Phe His Leu Glu His Arg Gly Pro Val Ser Met
            580                 585                 590

Lys Gly Lys Lys Glu Pro Met Gln Val Trp Phe Leu Ser Arg Lys Asn
        595                 600                 605

Thr Gly Thr Glu Glu Thr Lys Gln Asp Asp Asp
    610                 615


<210> SEQ ID NO 107
<211> LENGTH: 153
<212> TYPE: PRT
<213> ORGANISM: Homo sapiens

<400> SEQUENCE: 107

Met Ala Asp Glu Ile Asp Phe Thr Thr Gly Asp Ala Gly Ala Ser Ser
 1               5                  10                  15
```

```
Thr Tyr Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Tyr Gln Leu Ile Cys Ile Gln Asp
                85                  90                  95

Gly Tyr Leu Ser Leu Leu Thr Glu Thr Gly Glu Val Arg Glu Asp Leu
            100                 105                 110

Lys Leu Pro Glu Gly Glu Leu Gly Lys Glu Ile Glu Gly Lys Tyr Asn
        115                 120                 125

Ala Gly Glu Asp Val Gln Val Ser Val Met Cys Ala Met Ser Glu Glu
    130                 135                 140

Tyr Ala Val Ala Ile Lys Pro Cys Lys
145                 150
```

<210> SEQ ID NO 108
<211> LENGTH: 253
<212> TYPE: PRT
<213> ORGANISM: Homo sapiens

<400> SEQUENCE: 108

```
Met Trp Pro Pro Gly Ser Ala Ser Gln Pro Pro Pro Ser Pro Ala Ala
 1               5                  10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240
```

```
Val Thr Ile Asp Arg Val Met Ser Tyr Leu Asn Ala Ser
                245                 250


<210> SEQ ID NO 109
<211> LENGTH: 518
<212> TYPE: PRT
<213> ORGANISM: Homo sapiens

<400> SEQUENCE: 109

Met Ala Glu Asn His Ala Gln Asn Lys Ala Lys Leu Ile Ser Glu Thr
 1               5                  10                  15

Arg Arg Arg Phe Glu Ala Glu Tyr Val Thr Asp Lys Ser Asp Lys Tyr
            20                  25                  30

Asp Ala Arg Asp Val Glu Arg Leu Gln Gln Asp Asp Asn Trp Val Glu
        35                  40                  45

Ser Tyr Leu Ser Trp Arg His Asn Ile Val Asp Glu Thr Leu Lys Met
    50                  55                  60

Leu Asp Glu Ser Phe Gln Trp Arg Lys Glu Ile Ser Val Asn Asp Leu
65                  70                  75                  80

Asn Glu Ser Ser Ile Pro Arg Trp Leu Leu Glu Ile Gly Val Ile Tyr
                85                  90                  95

Leu His Gly Tyr Asp Lys Glu Gly Asn Lys Leu Phe Trp Ile Arg Val
            100                 105                 110

Lys Tyr His Val Lys Asp Gln Lys Thr Ile Leu Asp Lys Lys Lys Leu
        115                 120                 125

Ile Ala Phe Trp Leu Glu Arg Tyr Ala Lys Arg Glu Asn Gly Lys Pro
    130                 135                 140

Val Thr Val Met Phe Asp Leu Ser Glu Thr Gly Ile Asn Ser Ile Asp
145                 150                 155                 160

Met Asp Phe Val Arg Phe Ile Ile Asn Cys Phe Lys Val Tyr Tyr Pro
                165                 170                 175

Lys Tyr Leu Ser Lys Ile Val Ile Phe Asp Met Pro Trp Leu Met Asn
            180                 185                 190

Ala Ala Phe Lys Ile Val Lys Thr Trp Leu Gly Pro Glu Ala Val Ser
        195                 200                 205

Leu Leu Lys Phe Thr Ser Lys Asn Glu Val Gln Asp Tyr Val Ser Val
    210                 215                 220

Glu Tyr Leu Pro Pro His Met Gly Gly Thr Asp Pro Phe Lys Tyr Ser
225                 230                 235                 240

Tyr Pro Pro Leu Val Asp Asp Asp Phe Gln Thr Pro Leu Cys Glu Asn
                245                 250                 255

Gly Pro Ile Thr Ser Glu Asp Glu Thr Ser Ser Lys Glu Asp Ile Glu
            260                 265                 270

Ser Asp Gly Lys Glu Thr Leu Glu Thr Ile Ser Asn Glu Glu Gln Thr
        275                 280                 285

Pro Leu Leu Lys Lys Ile Asn Pro Thr Glu Ser Thr Ser Lys Ala Glu
    290                 295                 300

Glu Asn Glu Lys Val Asp Ser Lys Val Lys Ala Phe Lys Lys Pro Leu
305                 310                 315                 320

Ser Val Phe Lys Gly Pro Leu Leu His Ile Ser Pro Ala Glu Glu Leu
                325                 330                 335

Tyr Phe Gly Ser Thr Glu Ser Gly Glu Lys Lys Thr Leu Ile Val Leu
            340                 345                 350

Thr Asn Val Thr Lys Asn Ile Val Ala Phe Lys Val Arg Thr Thr Ala
```

```
        355                 360                 365

Pro Glu Lys Tyr Arg Val Lys Pro Ser Asn Ser Ser Cys Asp Pro Gly
    370                 375                 380

Ala Ser Val Asp Ile Val Val Ser Pro His Gly Gly Leu Thr Val Ser
385                 390                 395                 400

Ala Gln Asp Arg Phe Leu Ile Met Ala Ala Glu Met Glu Gln Ser Ser
                405                 410                 415

Gly Thr Gly Pro Ala Glu Leu Thr Gln Phe Trp Lys Glu Val Pro Arg
            420                 425                 430

Asn Lys Val Met Glu His Arg Leu Arg Cys His Thr Val Glu Ser Ser
        435                 440                 445

Lys Pro Asn Thr Leu Thr Leu Lys Asp Asn Ala Phe Asn Met Ser Asp
    450                 455                 460

Lys Thr Ser Glu Asp Ile Cys Leu Gln Leu Ser Arg Leu Leu Glu Ser
465                 470                 475                 480

Asn Arg Lys Leu Glu Asp Gln Val Gln Arg Cys Ile Trp Phe Gln Gln
                485                 490                 495

Leu Leu Leu Ser Leu Thr Met Leu Leu Leu Ala Phe Val Thr Ser Phe
            500                 505                 510

Phe Tyr Leu Leu Tyr Ser
        515
```

<210> SEQ ID NO 110
<211> LENGTH: 542
<212> TYPE: PRT
<213> ORGANISM: Homo sapiens

<400> SEQUENCE: 110

```
Met Thr Lys Ser Asn Gly Glu Glu Pro Lys Met Gly Gly Arg Met Glu
 1               5                  10                  15

Arg Phe Gln Gln Gly Val Arg Lys Arg Thr Leu Leu Ala Lys Lys Lys
            20                  25                  30

Val Gln Asn Ile Thr Lys Glu Asp Val Lys Ser Tyr Leu Phe Arg Asn
        35                  40                  45

Ala Phe Val Leu Leu Thr Val Thr Ala Val Ile Val Gly Thr Ile Leu
    50                  55                  60

Gly Phe Thr Leu Arg Pro Tyr Arg Met Ser Tyr Arg Glu Val Lys Tyr
65                  70                  75                  80

Phe Ser Phe Pro Gly Glu Leu Leu Met Arg Met Leu Gln Met Leu Val
                85                  90                  95

Leu Pro Leu Ile Ile Ser Ser Leu Val Thr Gly Met Ala Ala Leu Asp
            100                 105                 110

Ser Lys Ala Ser Gly Lys Met Gly Met Arg Ala Val Val Tyr Tyr Met
        115                 120                 125

Thr Thr Thr Ile Ile Ala Val Val Ile Gly Ile Ile Ile Val Ile Ile
    130                 135                 140

Ile His Pro Gly Lys Gly Thr Lys Glu Asn Met His Arg Glu Gly Lys
145                 150                 155                 160

Ile Val Arg Val Thr Ala Ala Asp Ala Phe Leu Asp Leu Ile Arg Asn
                165                 170                 175

Met Phe Pro Pro Asn Leu Val Glu Ala Cys Phe Lys Gln Phe Lys Thr
            180                 185                 190

Asn Tyr Glu Lys Arg Ser Phe Lys Val Pro Ile Gln Ala Asn Glu Thr
        195                 200                 205
```

Leu Val Gly Ala Val Ile Asn Asn Val Ser Glu Ala Met Glu Thr Leu
    210                 215                 220

Thr Arg Ile Thr Glu Glu Leu Val Pro Val Pro Gly Ser Val Asn Gly
225                 230                 235                 240

Val Asn Ala Leu Gly Leu Val Val Phe Ser Met Cys Phe Gly Phe Val
                245                 250                 255

Ile Gly Asn Met Lys Glu Gln Gly Gln Ala Leu Arg Glu Phe Phe Asp
            260                 265                 270

Ser Leu Asn Glu Ala Ile Met Arg Leu Val Ala Val Ile Met Trp Tyr
        275                 280                 285

Ala Pro Val Gly Ile Leu Phe Leu Ile Ala Gly Lys Ile Val Glu Met
    290                 295                 300

Glu Asp Met Gly Val Ile Gly Gly Gln Leu Ala Met Tyr Thr Val Thr
305                 310                 315                 320

Val Ile Val Gly Leu Leu Ile His Ala Val Ile Val Leu Pro Leu Leu
                325                 330                 335

Tyr Phe Leu Val Thr Arg Lys Asn Pro Trp Val Phe Ile Gly Gly Leu
            340                 345                 350

Leu Gln Ala Leu Ile Thr Ala Leu Gly Thr Ser Ser Ser Ser Ala Thr
        355                 360                 365

Leu Pro Ile Thr Phe Lys Cys Leu Glu Glu Asn Asn Gly Val Asp Lys
    370                 375                 380

Arg Val Thr Arg Phe Val Leu Pro Val Gly Ala Thr Ile Asn Met Asp
385                 390                 395                 400

Gly Thr Ala Leu Tyr Glu Ala Leu Ala Ala Ile Phe Ile Ala Gln Val
                405                 410                 415

Asn Asn Phe Glu Leu Asn Phe Gly Gln Ile Ile Thr Ile Ser Ile Thr
            420                 425                 430

Ala Thr Ala Ala Ser Ile Gly Ala Ala Gly Ile Pro Gln Ala Gly Leu
        435                 440                 445

Val Thr Met Val Ile Val Leu Thr Ser Val Gly Leu Pro Thr Asp Asp
    450                 455                 460

Ile Thr Leu Ile Ile Ala Val Asp Trp Phe Leu Asp Arg Leu Arg Thr
465                 470                 475                 480

Thr Thr Asn Val Leu Gly Asp Ser Leu Gly Ala Gly Ile Val Glu His
                485                 490                 495

Leu Ser Arg His Glu Leu Lys Asn Arg Asp Val Glu Met Gly Asn Ser
            500                 505                 510

Val Ile Glu Glu Asn Glu Met Lys Lys Pro Tyr Gln Leu Ile Ala Gln
        515                 520                 525

Asp Asn Glu Thr Glu Lys Pro Ile Asp Ser Glu Thr Lys Met
    530                 535                 540

<210> SEQ ID NO 111
<211> LENGTH: 970
<212> TYPE: PRT
<213> ORGANISM: Homo sapiens

<400> SEQUENCE: 111

Met Ala Thr Cys Ile Gly Glu Lys Ile Glu Asp Phe Lys Val Gly Asn
1               5                   10                  15

Leu Leu Gly Lys Gly Ser Phe Ala Gly Val Tyr Arg Ala Glu Ser Ile
            20                  25                  30

His Ser Gly Leu Glu Val Ala Ile Lys Met Ile Asp Lys Lys Ala Met
        35                  40                  45

```
Tyr Lys Ala Gly Met Val Gln Arg Val Gln Asn Glu Val Lys Ile His
    50                  55                  60

Cys Gln Leu Lys His Pro Ser Ile Leu Glu Leu Tyr Asn Tyr Phe Glu
65                  70                  75                  80

Asp Ser Asn Tyr Val Tyr Leu Val Leu Glu Met Cys His Asn Gly Glu
                85                  90                  95

Met Asn Arg Tyr Leu Lys Asn Arg Val Lys Pro Phe Ser Glu Asn Glu
            100                 105                 110

Ala Arg His Phe Met His Gln Ile Ile Thr Gly Met Leu Tyr Leu His
        115                 120                 125

Ser His Gly Ile Leu His Arg Asp Leu Thr Leu Ser Asn Leu Leu Leu
    130                 135                 140

Thr Arg Asn Met Asn Ile Lys Ile Ala Asp Phe Gly Leu Ala Thr Gln
145                 150                 155                 160

Leu Lys Met Pro His Glu Lys His Tyr Thr Leu Cys Gly Thr Pro Asn
                165                 170                 175

Tyr Ile Ser Pro Glu Ile Ala Thr Arg Ser Ala His Gly Leu Glu Ser
            180                 185                 190

Asp Val Trp Ser Leu Gly Cys Met Phe Tyr Thr Leu Leu Ile Gly Arg
        195                 200                 205

Pro Pro Phe Asp Thr Asp Thr Val Lys Asn Thr Leu Asn Lys Val Val
    210                 215                 220

Leu Ala Asp Tyr Glu Met Pro Thr Phe Leu Ser Ile Glu Ala Lys Asp
225                 230                 235                 240

Leu Ile His Gln Leu Leu Arg Arg Asn Pro Ala Asp Arg Leu Ser Leu
                245                 250                 255

Ser Ser Val Leu Asp His Pro Phe Met Ser Arg Asn Ser Ser Thr Lys
            260                 265                 270

Ser Lys Asp Leu Gly Thr Val Glu Asp Ser Ile Asp Ser Gly His Ala
        275                 280                 285

Thr Ile Ser Thr Ala Ile Thr Ala Ser Ser Ser Thr Ser Ile Ser Gly
    290                 295                 300

Ser Leu Phe Asp Lys Arg Arg Leu Leu Ile Gly Gln Pro Leu Pro Asn
305                 310                 315                 320

Lys Met Thr Val Phe Pro Lys Asn Lys Ser Ser Thr Asp Phe Ser Ser
                325                 330                 335

Ser Gly Asp Gly Asn Ser Phe Tyr Thr Gln Trp Gly Asn Gln Glu Thr
            340                 345                 350

Ser Asn Ser Gly Arg Gly Arg Val Ile Gln Asp Ala Glu Glu Arg Pro
        355                 360                 365

His Ser Arg Tyr Leu Arg Arg Ala Tyr Ser Ser Asp Arg Ser Gly Thr
    370                 375                 380

Ser Asn Arg Gln Ser Gln Ala Lys Thr Tyr Thr Met Glu Arg Cys His
385                 390                 395                 400

Ser Ala Glu Met Leu Ser Val Ser Lys Arg Ser Gly Gly Gly Glu Asn
                405                 410                 415

Glu Glu Arg Tyr Ser Pro Thr Asp Asn Asn Ala Asn Ile Phe Asn Phe
            420                 425                 430

Phe Lys Glu Lys Thr Ser Ser Ser Ser Gly Ser Phe Glu Arg Pro Asp
        435                 440                 445

Asn Asn Gln Ala Leu Ser Asn His Leu Cys Pro Gly Lys Thr Pro Phe
    450                 455                 460
```

-continued

```
Pro Phe Ala Asp Pro Thr Pro Gln Thr Glu Thr Val Gln Gln Trp Phe
465                 470                 475                 480

Gly Asn Leu Gln Ile Asn Ala His Leu Arg Lys Thr Thr Glu Tyr Asp
                485                 490                 495

Ser Ile Ser Pro Asn Arg Asp Phe Gln Gly His Pro Asp Leu Gln Lys
            500                 505                 510

Asp Thr Ser Lys Asn Ala Trp Thr Asp Thr Lys Val Lys Lys Asn Ser
        515                 520                 525

Asp Ala Ser Asp Asn Ala His Ser Val Lys Gln Gln Asn Thr Met Lys
    530                 535                 540

Tyr Met Thr Ala Leu His Ser Lys Pro Glu Ile Ile Gln Gln Glu Cys
545                 550                 555                 560

Val Phe Gly Ser Asp Pro Leu Ser Glu Gln Ser Lys Thr Arg Gly Met
                565                 570                 575

Glu Pro Pro Trp Gly Tyr Gln Asn Arg Thr Leu Arg Ser Ile Thr Ser
            580                 585                 590

Pro Leu Val Ala His Arg Leu Lys Pro Ile Arg Gln Lys Thr Lys Lys
        595                 600                 605

Ala Val Val Ser Ile Leu Asp Ser Glu Glu Val Cys Val Glu Leu Val
    610                 615                 620

Lys Glu Tyr Ala Ser Gln Glu Tyr Val Lys Glu Val Leu Gln Ile Ser
625                 630                 635                 640

Ser Asp Gly Asn Thr Ile Thr Ile Tyr Tyr Pro Asn Gly Gly Arg Gly
                645                 650                 655

Phe Pro Leu Ala Asp Arg Pro Pro Ser Pro Thr Asp Asn Ile Ser Arg
            660                 665                 670

Tyr Ser Phe Asp Asn Leu Pro Glu Lys Tyr Trp Arg Lys Tyr Gln Tyr
        675                 680                 685

Ala Ser Arg Phe Val Gln Leu Leu Arg Ser Lys Ser Pro Lys Ile Thr
    690                 695                 700

Tyr Phe Thr Arg Tyr Ala Lys Cys Ile Leu Met Glu Asn Ser Pro Gly
705                 710                 715                 720

Ala Asp Phe Glu Val Trp Phe Tyr Asp Gly Val Lys Ile His Lys Thr
                725                 730                 735

Glu Asp Phe Ile Gln Val Ile Glu Lys Thr Gly Lys Ser Tyr Thr Leu
            740                 745                 750

Lys Ser Glu Ser Glu Val Asn Ser Leu Lys Glu Glu Ile Lys Met Tyr
        755                 760                 765

Met Asp His Ala Asn Glu Gly His Arg Ile Cys Leu Ala Leu Glu Ser
    770                 775                 780

Ile Ile Ser Glu Glu Glu Arg Lys Thr Arg Ser Ala Pro Phe Phe Pro
785                 790                 795                 800

Ile Ile Ile Gly Arg Lys Pro Gly Ser Thr Ser Ser Pro Lys Ala Leu
                805                 810                 815

Ser Pro Pro Pro Ser Val Asp Ser Asn Tyr Pro Thr Arg Asp Arg Ala
            820                 825                 830

Ser Phe Asn Arg Met Val Met His Ser Asp Ala Ser Pro Thr Gln Ala
        835                 840                 845

Pro Ile Leu Asn Pro Ser Met Val Thr Asn Glu Gly Leu Gly Leu Thr
    850                 855                 860

Thr Thr Ala Ser Gly Thr Asp Ile Ser Ser Asn Ser Leu Lys Asp Cys
865                 870                 875                 880

Leu Pro Lys Ser Ala Gln Leu Leu Lys Ser Val Phe Val Lys Asn Val
```

```
                885                 890                 895

Gly Trp Ala Thr Gln Leu Thr Ser Gly Ala Val Trp Val Gln Phe Asn
            900                 905                 910

Asp Gly Ser Gln Leu Val Val Gln Ala Gly Val Ser Ser Ile Ser Tyr
        915                 920                 925

Thr Ser Pro Asn Gly Gln Thr Thr Arg Tyr Gly Glu Asn Glu Lys Leu
    930                 935                 940

Pro Asp Tyr Ile Lys Gln Lys Leu Gln Cys Leu Ser Ser Ile Leu Leu
945                 950                 955                 960

Met Phe Ser Asn Pro Thr Pro Asn Phe His
                965                 970


<210> SEQ ID NO 112
<211> LENGTH: 345
<212> TYPE: PRT
<213> ORGANISM: Homo sapiens

<400> SEQUENCE: 112

Met Ser Leu Phe Gly Leu Leu Leu Leu Thr Ser Ala Leu Ala Gly Gln
 1               5                  10                  15

Arg Gln Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
    130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
    210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285
```

His Asn Cys Asn Glu Cys Gln Cys Val Pro Ser Lys Val Thr Lys Lys
    290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345

<210> SEQ ID NO 113
<211> LENGTH: 309
<212> TYPE: DNA
<213> ORGANISM: Homo sapiens

<400> SEQUENCE: 113
tgctttcttt ttatctgttt tggtaggaat aagcttttgt tctcttttct gttttgcaag 60
aacttcatca tataatgttt ctttcatgaa aagccagaag aagaggaaaa ttactgtaat 120
aactattgaa ggaataagaa caataaaata tgctgactca taaaactcca tggtactttt 180
gtcaatgtga tcctataaaa ccctgtgcgg ccgggaaagg agaccgggaa gacgcggcgg 240
cgccggcact acagcccggg ccgcccgctc cgaggcgccg ccgccgccgc cgccgccgcc 300
gcagtcgct 309

<210> SEQ ID NO 114
<211> LENGTH: 390
<212> TYPE: DNA
<213> ORGANISM: Homo sapiens
<220> FEATURE:
<221> NAME/KEY: misc_feature
<222> LOCATION: (221)..(221)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t

<400> SEQUENCE: 114
gccaagtgat aaagccacaa ccttgtgttt gctttccctc ccaatcccag aactcaggac 60
tggagcccat gtggtttgca gttaaaggcc aaaagtcctg cacctatttt ataaaactat 120
gactgtgttt atcactgtgt tggggtcggt tccatttttg aggttccatc tttatgaaaa 180
gataacctgt cttctaacct gcttggatgg ctggtagtca natgtgaacg aacacctacc 240
gtgtgcctgg ccatgttcta tgttctaggc tgcagcaatc aacaagatgg gccatacaac 300
acccacccgg tgaagttcaa gtcnagtagc tgttagctta aggaaagagt attcccttat 360
cccactacac cttaaaatgt attgctgtcc 390

<210> SEQ ID NO 115
<211> LENGTH: 404
<212> TYPE: DNA
<213> ORGANISM: Homo sapiens

<400> SEQUENCE: 115
tttttttttc caacagcaga tagattcttt atgttcaaga cagcaaattc agatacaaaa 60
acccaccgcc atcgtccctc cctccctcct gctctgggcc agggatgggc ctggaaggag 120
agatgggagg tggggaggag gttgcggggt tcacagcaga ctcgtgtcaa atgcggaggt 180
aacaggctcc acagggaggg ggctcctctc aggaggggtg agggcattat tgcatttgct 240
ggggggaagg acaaccctct cccctgtatt ccctgcgtca ggaaactagg aaggtcatga 300
cccccaaaca gaacccaagg ccccagggag acagagggac cagtttggca gctgatggtg 360
gaaagtggtg gaggcggggg tggccgccaa tttggctgat cctc 404

<210> SEQ ID NO 116
<211> LENGTH: 499
<212> TYPE: DNA
<213> ORGANISM: Homo sapiens

<400> SEQUENCE: 116
tttttttttt ttcctggggt gagaatcaaa ttcctgtgag ggggcattta gctcactgga 60
gtattcacga attaaaactt caatagcccc tttaatcatc tgatctctcc tctttgtttc 120
ttcatccaag gcttcttcat cgtcattagt gacagtttct ggccttgcat tcccattaga 180
agctttcttc tttgctttcc attcatccag ctgtgccttt gtctttgcat caactttaac 240
gagtagcttt ttctctccaa tttgcaggtc atgtaataat ctgagtgcac ggagggtaga 300
ttctggctcc ttgtactcac agaatccgaa ggcttgaagc tttccggaag caccttgtac 360
tctcttccag ctcaaaacca aaccacattt agctaagagt tgtcttataa gcatgtctga 420
agctttctcg gaaatgttgc caacaaaaac agtggtagta ggaccacaat tttcatcatt 480
ttctttagcc tttaagcct 499

<210> SEQ ID NO 117
<211> LENGTH: 493
<212> TYPE: DNA
<213> ORGANISM: Homo sapiens
<220> FEATURE:
<221> NAME/KEY: misc_feature
<222> LOCATION: (335)..(335)
<223> OTHER INFORMATION: n is a, c, g, or t

<400> SEQUENCE: 117
ttttgtggtc taaaataaac ttttaattgc acatttgtgt cttgggttat ctgtggggtg 60
agaaacctcc tcacttccaa tcccagctat ctgggtacaa tctggtgttg tggtctggct 120
gtcggcgagg ggtagaggtg ggtgcaggac tggcccccga gtctgcaccg acctcttcag 180
ggcagggagc tcagaccatg gtagtacttg cactgcttca gggcctcgct gaagccctca 240
cacagggaca ggtcactctg agtggtggaa cagtccagga actgcctgat ctcataggcg 300
cagggcccca tctgcagggg ctggggggca gcggnggtgg gggcctgctg gacagcaggc 360
tgggagggct ccgagctccc cccgctgaag gctccggtca gggcgctgcc catgacgtgt 420
cccacagccg agcccacggc tacccctgcg gccgtggtcg ccatctgagc catgagcccc 480
ggctggcccg aag 493

<210> SEQ ID NO 118
<211> LENGTH: 513
<212> TYPE: DNA
<213> ORGANISM: Homo sapiens
<220> FEATURE:
<221> NAME/KEY: misc_feature
<222> LOCATION: (484)..(484)
<223> OTHER INFORMATION: n is a, c, g, or t

<400> SEQUENCE: 118
gtcaaattgt atccgttaag ggttttctaa cttttgctat cccccccgcg accaaaaaaa 60
gggggggttt ataatttaaa gaaaaggaaa agaggcgtgg gttggtagtt gtgtccttaa 120
catttaggaa tgacatagcc tctggagtct acaaactgaa gaaactttca tctgatcagc 180

-continued

```
cttggaaatc caaagttaaa gagcctatgt gtctcttgag gcgggggtta gaggattcaa    240

atttgggatg atgctcattg attcctgacc atagcagtga gaggccattt tttgtgcagg    300

aaatgtgctt aggactcagt cttgttttcg gattatccac cacagaaacc ctgagacaca    360

gagcagctta gaagtctcta cccaggcgta aatagagctc cctactccag acccatagcc    420

agtgagaagg cccatttttt tggtgcagga aatgtgctta gggactcagt ccttggtttt    480

cgantatcca ccacaggaaa ccctggagac tag                                 513


<210> SEQ ID NO 119
<211> LENGTH: 415
<212> TYPE: DNA
<213> ORGANISM: Homo sapiens

<400> SEQUENCE: 119

tgctttctct tctctttcat gatatccttg gtgtcctgca gcatcttctc cttccaaaga     60

tcaaagaagt atgaagggtc tgtgtagaat ttgagtgcct cttttccatc gtccctgtaa    120

ggggtaagat tgttgagagg gggaggagta tcacaggtat tgtatgtttc taagacaggc    180

actgggagag agtttctgtc aaaaagcttc tggtcttgaa tggtggaact tctgaaggct    240

tttcgggtgt tgattccttg cagtgacact tcttcttcct tgggatccag ctgagtgact    300

ttaacctgta gtcggtcgac cctctcagca agggagctta cccgaggagc aaaggtattt    360

tcctgagtag aggactcccg aagaatgtct ctgcatattt actcaggctg ccgac         415


<210> SEQ ID NO 120
<211> LENGTH: 426
<212> TYPE: DNA
<213> ORGANISM: Homo sapiens

<400> SEQUENCE: 120

ttatgatttg gatgttttta aattattaat ttattttcaa atcatactca gtttgagttc     60

aaatagttca aaaatcaata taatgcttca ggatgcttcc agctattgaa acaacccaat    120

taaaaaatat acaactcaca ctttatttta gttaaattca taatgtaggt aatattaaaa    180

attattataa acatttaata atgctttata atttgctatt atagtacacc actacagaca    240

cataaaaagt tgacttatct aattaaaaca ttttcccttc ctatgtttct aattctgaaa    300

actataaaaa tattaaagtc atgttacata tttttcaaaa ataaaactgc catatcccat    360

tgccaacttt acatgaaaaa ggtatatgtt ctggtatatt aggaagttaa tgatgaaaaa    420

tatagg                                                               426


<210> SEQ ID NO 121
<211> LENGTH: 444
<212> TYPE: DNA
<213> ORGANISM: Homo sapiens

<400> SEQUENCE: 121

tttttttttc tcttttaaaa acttttatta cgcattgcta aataacattg catgatgtat     60

tgcacacatc atgtggtaaa cagcactcca cagtaatcca tacaatagct cgtacaatga    120

ccatcaaaat agtttgaaaa ccgttatagt tttcatccga gtgagtgtct ttatattctt    180

ccatgcaatc tgatttcata attaagatta ctcttccatt ctacaacaac caaccgaaaa    240

taatttttta taaaagccca accacaacaa aaggtcattg ggacattacg aaaagtcgga    300

aattagactc caaaatatca caaggtgtcc gtcttttgaa agacttgtcc ctaaaatttg    360

tgtgatctga cacttgggtt gcttttaccg ccagcagcat gtgacactgt acttactgag    420
```

aaggaacagt acattgacat atcg 444

<210> SEQ ID NO 122
<211> LENGTH: 474
<212> TYPE: DNA
<213> ORGANISM: Homo sapiens
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (467)..(467)
<223> OTHER INFORMATION: n is a, c, g, or t

<400> SEQUENCE: 122
caattaaggg tgtacaaatt ataataatgc atctctatct tcatactttg aatggcaaac 60
gctatttatg cataaatatt ttcattttaa gtaatatatg aagtgtaaat actcgatata 120
taagtataga ttttaaagat atgggacttt attttcacat aagtcaatag atgtttctct 180
agaacaaaat atttagtaaa gctttataaa ttatattaaa aggaagcggg gaacatgtat 240
tttttaacat agaacagaag tgacttcatt ctttttagac atcagaaatg ttaaagttga 300
ttcccaatat ttgttgtact tttttgtagc aaatgttaaa aatcaccgag ttaccatgta 360
tagaatgtgg actgtcatgt tgatatcatt ggtacagtgg ataagcccat ttttaaccng 420
tatacatttc nccaatttaa ttaacngggg tgaataattt ggtttcnttt taga 474

<210> SEQ ID NO 123
<211> LENGTH: 474
<212> TYPE: DNA
<213> ORGANISM: Homo sapiens
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (467)..(467)
<223> OTHER INFORMATION: n is a, c, g, or t

<400> SEQUENCE: 123
caattaaggg tgtacaaatt ataataatgc atctctatct tcatactttg aatggcaaac 60
gctatttatg cataaatatt ttcattttaa gtaatatatg aagtgtaaat actcgatata 120
taagtataga ttttaaagat atgggacttt attttcacat aagtcaatag atgtttctct 180
agaacaaaat atttagtaaa gctttataaa ttatattaaa aggaagcggg gaacatgtat 240
tttttaacat agaacagaag tgacttcatt ctttttagac atcagaaatg ttaaagttga 300
ttcccaatat ttgttgtact tttttgtagc aaatgttaaa aatcaccgag ttaccatgta 360

-continued

```
tagaatgtgg actgtcatgt tgatatcatt ggtacagtgg ataagcccat ttttaaccng    420

tatacatttc nccaatttaa ttaacngggg tgaataattt ggtttcnttt taga          474
```